(12) United States Patent
Schneider et al.

(10) Patent No.: US 12,390,498 B2
(45) Date of Patent: *Aug. 19, 2025

(54) TREATMENT OF CLOSTRIDIUM DIFFICILE INFECTION

(71) Applicant: Vedanta Biosciences, Inc., Cambridge, MA (US)

(72) Inventors: Jessica Schneider, Cambridge, MA (US); Yun-Gi Kim, Watertown, MA (US); Bernat Olle, Cambridge, MA (US); Shilpa Reddy, Watertown, MA (US); Jason Norman, North Weymouth, MA (US); Juan Patarroyo, Lexington, MA (US)

(73) Assignee: Vedanta Biosciences, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/326,511

(22) Filed: May 31, 2023

(65) Prior Publication Data

US 2024/0123000 A1 Apr. 18, 2024

Related U.S. Application Data

(63) Continuation of application No. 16/702,659, filed on Dec. 4, 2019, now Pat. No. 11,701,396, which is a continuation of application No. 16/423,487, filed on May 28, 2019, now Pat. No. 10,555,980, which is a continuation of application No. 16/157,640, filed on Oct. 11, 2018, now Pat. No. 10,456,431, which is a continuation of application No. 15/993,037, filed on May 30, 2018, now Pat. No. 10,350,250, which is a continuation of application No. 15/630,088, filed on Jun. 22, 2017, now Pat. No. 9,999,641, which is a continuation of application No. PCT/US2017/037498, filed on Jun. 14, 2017.

(60) Provisional application No. 62/349,914, filed on Jun. 14, 2016.

(51) Int. Cl.

| | | |
|---|---|---|
| *A61K 35/747* | (2015.01) | |
| *A23L 5/00* | (2016.01) | |
| *A23L 33/135* | (2016.01) | |
| *A61K 9/00* | (2006.01) | |
| *A61K 9/48* | (2006.01) | |
| *A61K 35/74* | (2015.01) | |
| *A61K 35/742* | (2015.01) | |
| *A61K 38/14* | (2006.01) | |
| *C12N 1/20* | (2006.01) | |
| *A23K 10/18* | (2016.01) | |
| *A23K 50/30* | (2016.01) | |

(52) U.S. Cl.
CPC .............. *A61K 35/747* (2013.01); *A23L 5/00* (2016.08); *A23L 33/135* (2016.08); *A61K 9/0053* (2013.01); *A61K 9/48* (2013.01); *A61K 35/74* (2013.01); *A61K 35/742* (2013.01); *A61K 38/14* (2013.01); *C12N 1/20* (2013.01); *A23K 10/18* (2016.05); *A23K 50/30* (2016.05); *A61K 9/0031* (2013.01)

(58) Field of Classification Search
CPC ................................. A23L 5/00; A23L 33/135
See application file for complete search history.

(56) References Cited

U.S. PATENT DOCUMENTS

| | | | |
|---|---|---|---|
| 6,635,260 B1 | 10/2003 | Gerding | |
| 8,460,648 B2 | 6/2013 | Borody | |
| 9,386,793 B2 | 7/2016 | Blaser et al. | |
| 9,642,881 B2 | 5/2017 | Honda et al. | |
| 9,649,345 B2 | 5/2017 | Honda et al. | |
| 9,999,641 B2 * | 6/2018 | Schneider | ............... A23L 5/00 |
| 10,064,904 B2 * | 9/2018 | Schneider | ............... C12N 1/20 |
| 10,350,250 B2 * | 7/2019 | Schneider | ............... A23L 5/00 |
| 10,456,431 B2 * | 10/2019 | Schneider | ............... A61K 35/74 |
| 10,555,980 B2 * | 2/2020 | Schneider | ............... A61K 38/14 |
| 11,701,396 B2 * | 7/2023 | Schneider | ............. A23L 33/135 |
| | | | 424/93.3 |
| 2004/0028689 A1 | 2/2004 | Borody | |
| 2009/0269321 A1 | 10/2009 | Sashihara et al. | |
| 2010/0074872 A1 | 3/2010 | Blaser et al. | |
| 2013/0045274 A1 | 2/2013 | Hlavka | |
| 2013/0195804 A1 | 8/2013 | Borody | |
| 2014/0199281 A1 | 7/2014 | Henn et al. | |
| 2014/0328803 A1 | 11/2014 | McKenzie et al. | |
| 2014/0341921 A1 | 11/2014 | Honda et al. | |
| 2015/0037476 A1 | 2/2015 | Dhingra et al. | |
| 2015/0079209 A1 | 3/2015 | Kameyama et al. | |
| 2016/0022745 A1 | 1/2016 | Wang | |

(Continued)

FOREIGN PATENT DOCUMENTS

| | | |
|---|---|---|
| EP | 3052111 B1 | 12/2020 |
| JP | 2015-500792 A | 1/2015 |

(Continued)

OTHER PUBLICATIONS

Drancourt et al. 2000 (16S Ribosomal DNA Sequence Analysis of a Large Collection of Environmental and Clinical Unidentifiable Bacterial Isolates; Journal of Clinical Microbiology, vol. 38, No. 10: 3623-3630; (Year: 2000).*
Reigadas et al. 2021 (How to: prophylactic interventions for prevention of Clostridiolides difficile infection; Clinical Microbiology and Infection 27: 1777-1783) (Year: 2021).*
Smits et al. 2016 (Clostridium difficile infection; Nature Reviews Disease Primers, vol. 2, p. 1-20) (Year: 2016).*
Mounsey et al. 2020 (Clostridioides difficile Infection: Update on Management; https://familydoctor.org/condition/clostridium-difficile-cdiff-infection) (Year: 2020).*

(Continued)

*Primary Examiner* — Mary Maille Lyons
(74) *Attorney, Agent, or Firm* — Wolf, Greenfield & Sacks, P.C.

(57) ABSTRACT

Provided herein are compositions and methods for the treatment or prevention of pathogenic infections.

20 Claims, 41 Drawing Sheets
Specification includes a Sequence Listing.

(56) References Cited

U.S. PATENT DOCUMENTS

| | | |
|---|---|---|
| 2016/0022746 A1 | 1/2016 | Lawley et al. |
| 2016/0040215 A1 | 2/2016 | Henn et al. |
| 2016/0113971 A1 | 4/2016 | Kaplan et al. |
| 2016/0193256 A1 | 7/2016 | Honda et al. |
| 2016/0193257 A1 | 7/2016 | Honda et al. |
| 2016/0228476 A1 | 8/2016 | Cutcliffe et al. |
| 2017/0143772 A1 | 5/2017 | Mulder et al. |
| 2017/0209502 A1 | 7/2017 | Honda et al. |
| 2017/0216378 A1 | 8/2017 | Honda et al. |
| 2017/0290889 A1 | 10/2017 | Loke et al. |
| 2017/0354697 A1 | 12/2017 | Schneider et al. |
| 2018/0169153 A1 | 6/2018 | Berry et al. |
| 2018/0169157 A1 | 6/2018 | Schneider et al. |
| 2018/0221286 A1 | 8/2018 | Kabadi et al. |
| 2018/0264056 A1 | 9/2018 | Schneider et al. |
| 2019/0030098 A1 | 1/2019 | Schneider et al. |
| 2019/0134106 A1 | 5/2019 | Borody |
| 2019/0275090 A1 | 9/2019 | Schneider et al. |
| 2020/0206284 A1 | 7/2020 | Schneider et al. |
| 2022/0143108 A1 | 5/2022 | Norman et al. |
| 2024/0100103 A1 | 3/2024 | Olle et al. |

FOREIGN PATENT DOCUMENTS

| | | | |
|---|---|---|---|
| JP | 2016-509002 A | | 3/2016 |
| WO | WO 2002/007741 A1 | | 1/2002 |
| WO | WO 2006/050479 A1 | | 5/2006 |
| WO | WO 2011/033310 A1 | | 3/2011 |
| WO | WO 2011/152566 A2 | | 12/2011 |
| WO | WO 2013/037067 A1 | | 3/2013 |
| WO | WO 2013/037068 A1 | | 3/2013 |
| WO | WO 2013/080561 A1 | | 6/2013 |
| WO | WO 2013/182038 A1 | | 12/2013 |
| WO | WO 2014/082050 A1 | | 5/2014 |
| WO | WO 2014/121298 A2 | | 8/2014 |
| WO | WO 2014/121301 A1 | | 8/2014 |
| WO | WO 2014/121302 A2 | | 8/2014 |
| WO | WO 2014/145958 A2 | | 9/2014 |
| WO | WO 2014/153194 A2 | | 9/2014 |
| WO | WO 2015/006355 A2 | | 1/2015 |
| WO | WO 2015/051323 A1 | | 4/2015 |
| WO | WO 2015/077794 A1 | | 5/2015 |
| WO | WO 2015/095241 A2 | | 6/2015 |
| WO | WO 2015/156419 A1 | | 10/2015 |
| WO | WO 2015/164555 A1 | | 10/2015 |
| WO | WO 2015/179437 A1 | | 11/2015 |
| WO | WO 2016/086161 A1 | | 6/2016 |
| WO | WO 2016/086205 A2 | | 6/2016 |
| WO | WO 2016/086206 A1 | | 6/2016 |
| WO | WO 2016/086208 A1 | | 6/2016 |
| WO | WO 2016/086209 A1 | | 6/2016 |
| WO | WO 2016/086210 A1 | | 6/2016 |
| WO | WO 2016/185469 A1 | | 11/2016 |
| WO | WO 2016/201053 A1 | | 12/2016 |
| WO | WO 2016/203217 A1 | | 12/2016 |
| WO | WO 2016/203218 A1 | | 12/2016 |
| WO | WO 2016/203220 A1 | | 12/2016 |
| WO | WO 2016/203221 A1 | | 12/2016 |
| WO | WO 2016/203223 A1 | | 12/2016 |
| WO | WO 2016/209806 A1 | | 12/2016 |
| WO | WO 2017/008026 A1 | | 1/2017 |
| WO | WO 2017/035188 A1 | | 3/2017 |
| WO | WO 2017/075098 A1 | | 5/2017 |
| WO | WO 2017/085518 A1 | | 5/2017 |
| WO | WO 2017/085520 A1 | | 5/2017 |
| WO | WO 2017/089794 A1 | | 6/2017 |
| WO | WO 2017/089795 A1 | | 6/2017 |
| WO | WO 2017/091783 A2 | | 6/2017 |
| WO | WO 2017/148596 A1 | | 9/2017 |
| WO | WO 2017/218680 A1 | | 12/2017 |
| WO | WO 2018/005606 A1 | | 1/2018 |
| WO | WO 2018/080477 A1 | | 5/2018 |
| WO | WO 2019/227085 A1 | | 11/2019 |
| WO | WO 2020/037271 A1 | | 2/2020 |

OTHER PUBLICATIONS

Dsouza et al., Colonization of the live biotherapeutic product VE303 and modulation of the microbiota and metabolites in healthy volunteers. Cell Host Microbe. Apr. 13, 2022;30(4):583-598.e8. doi: 10.1016/j.chom.2022.03.016.

Martiny et al., Phylogenetic conservatism of functional traits in microorganisms. ISME J. Apr. 2013;7(4):830-8. doi: 10.1038/ismej.2012.160. Epub Dec. 13, 2012.

Stackebrandt et al., Authors need to be prudent when assigning names to microbial isolates. Antonie Van Leeuwenhoek. Jan. 2022;115(1):1-5. doi: 10.1007/s10482-021-01675-8.

[No Author Listed], [Clostridium] innocuum strain I46 16S ribosomal RNA gene, partial sequence. GenBank Accession No. KR364751.1. Nov. 28, 2016. 2 pages.

[No Author Listed], [Clostridium] symbiosum gene for 16S ribosomal RNA, partial sequence, strain: JCM 1297. GenBank Accession No. LC036311.1. Mar. 20, 2015. 1 page.

Alang et al., Weight gain after fecal microbiota transplantation. Open Forum Infect Dis. Feb. 4, 2015;2(1):ofv004. doi: 10.1093/ofid/ofv004. eCollection Jan. 2015.

Apisarnthanarak et al., Adjunctive intracolonic vancomycin for severe *Clostridium difficile* colitis: case series and review of the literature. Clin Infect Dis. Sep. 15, 2002;35(6):690-6. Epub Aug. 26, 2002.

Bajaj et al., Fecal microbiota transplant from a rational stool donor improves hepatic encephalopathy: A randomized clinical trial. Hepatology. Dec. 2017;66(6):1727-1738. doi: 10.1002/hep.29306. Epub Oct. 30, 2017.

Blaser, The microbiome revolution. J Clin Invest. Oct. 2014;124(10):4162-5. doi: 10.1172/JCI78366. Epub Oct. 1, 2014.

Bloom et al., Microbiome therapeutics for hepatic encephalopathy. J Hepatol. Dec. 2021;75(6):1452-1464. doi: 10.1016/j.jhep.2021.08.004. Epub Aug. 25, 2021.

Bobilev et al., 1953. VE303, a Rationally Designed Bacterial Consortium for Prevention of Recurrent Clostridioides difficile (*C. difficile*) infection (rCDI), Stably Restores the Gut Microbiota After Vancomycin (vanco)-Induced Dysbiosis in Adult Healthy Volunteers (HV). Open Forum Infect Dis. Oct. 2019; 6(Suppl 2): S60. EPub Oct. 23, 2019. doi: 10.1093/ofid/ofz359.130.

Borody et al., Therapeutic faecal microbiota transplantation: current status and future developments. Curr Opin Gastroenterol.Jan. 2014;30(1):97-105. doi: 10.1097/MOG.0000000000000027.

Bucci et al., MDSINE: Microbial Dynamical Systems INference Engine for microbiome time-series analyses. Genome Biol. Jun. 3, 2016;17(1):121. doi: 10.1186/s13059-016-0980-6.

Buffie et al., Precision microbiome reconstitution restores bile acid mediated resistance to *Clostridium difficile*. Nature. Jan. 8, 2015;517(7533):205-8. doi: 10.1038/nature13828. Epub Oct. 22, 2014.

Burns et al., Donor Recruitment and Eligibility for Fecal Microbiota Transplantation: Results From an International Public Stool Bank. Gastro. Apr. 2015;148(4):S96-S97.

Calfee, *Clostridium difficile*: a reemerging pathogen. Geriatrics. Sep. 1, 2008;63(9):10-21.

Cammarota et al., Randomised clinical trial: faecal microbiota transplantation by colonoscopy vs. vancomycin for the treatment of recurrent *Clostridium difficile* infection. Aliment Pharmacol Ther. May 2015;41(9):835-43. doi: 10.1111/apt.13144. Epub Mar. 1, 2015.

Cash et al., Current concepts in the assessment and treatment of hepatic encephalopathy. QJM. Jan. 2010;103(1):9-16. doi: 10.1093/qjmed/hcp152. Epub Nov. 10, 2009.

Demorrow, Bile Acids in Hepatic Encephalopathy. J Clin Exp Hepatol. Jan.-Feb. 2019;9(1):117-124. doi: 10.1016/j.jceh.2018.04.011. Epub May 4, 2018.

Drancourt et al., 16S ribosomal DNA sequence analysis of a large collection of environmental and clinical unidentifiable bacterial isolates. J Clin Microbiol. Oct. 2000;38(10):3623-30. doi: 10.1128/JCM.38.10.3623-3630.2000.

Eyre et al., Whole-genome sequencing demonstrates that fidaxomicin is superior to vancomycin for preventing reinfection and relapse of

(56) References Cited

OTHER PUBLICATIONS infection with *Clostridium difficile*. J Infect Dis. May 1, 2014;209(9):1446-51. doi:10.1093/infdis/jit598. Epub Nov. 11, 2013.
Ferenci et al., Hepatic encephalopathy—definition, nomenclature, diagnosis, and quantification: final report of the working party at the 11th World Congresses of Gastroenterology, Vienna, 1998. Hepatology. Mar. 2002;35(3):716-21. doi: 10.1053/jhep.2002.31250.
Genbank Accession No. NR_104687.1. NCBI. Sakamoto. Feb. 3, 2015.
Hooper et al., Interactions between the microbiota and the immune system. Science. Jun. 8, 2012;336(6086):1268-73. doi: 10.1126/science.1223490. Epub Jun. 6, 2012.
Hughes et al., Immune activation in irritable bowel syndrome: can neuroimmune interactions explain symptoms? AmJ Gastroenterol. Jul. 2013;108(7):1066-74. doi: 10.1038/ajg.2013.120. Epub May 7, 2013.
Janda et al., 16S rRNA gene sequencing for bacterial identification in the diagnostic laboratory: pluses, perils, and pitfalls. J Clin Microbiol. Sep. 2007;45(9):2761-4. doi: 10.1128/JCM.01228-07. Epub Jul. 11, 2007.
Kakihana et al., Fecal microbiota transplantation for patients with steroid-resistant acute graft-versus-host disease of the gut. Blood. Oct. 20, 2016;128(16):2083-2088. doi: 10.1182/blood-2016-05-717652. Epub Jul. 26, 2016.
Kassam et al., Fecal microbiota transplantation for *Clostridium difficile* infection: systematic review and meta-analysis. Am J Gastroenterol. Apr. 2013;108(4):500-8. doi: 10.1038/ajg.2013.59. Epub Mar. 19, 2013.
Khoruts et al., Emergence of fecal microbiota transplantation as an approach to repair disrupted microbial gut ecology. Immunol Lett. Dec. 2014;162(2 Pt A):77-81. doi: 10.1016/j.imlet.2014.07.016. Epub Aug. 10, 2014.
Leblanc et al., Bacteria as vitamin suppliers to their host: a gut microbiota perspective. Curr Opin Biotechnol. Apr. 2013;24(2):160-8. doi: 10.1016/j.copbio.2012.08.005. Epub; Aug. 30, 2012.
Lessa et al., Burden of *Clostridium difficile* infection in the United States. N Engl J Med. Feb. 26, 2015;372(9):825-34. doi:10.1056/NEJMoa1408913.
Louie et al., Fidaxomicin preserves the intestinal microbiome during and after treatment of *Clostridium difficile* infection (CDI) and reduces both toxin reexpression and recurrence of CDI. Clin Infect Dis. Aug. 2012;55 Suppl 2:S132-42. doi: 10.1093/cid/cis338.
Marvola et al., Enteric polymers as binders and coating materials in multiple-unit site-specific drug delivery systems. Eur J Pharm Sci. Feb. 1999;7(3):259-67.
Miller, Fidaxomicin (OPT-80) for the treatment of *Clostridium difficile* infection. Expert Opin Pharmacother. Jun. 2010;11(9):1569-78. doi:10.1517/14656566.2010.485614.

Mullane, Fidaxomicin in *Clostridium difficile* infection: latest evidence and clinical guidance. Ther Adv Chronic Dis. Mar. 2014;5(2):69-84. doi:10.1177/2040622313511285.
Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.
Paramsothy et al., Donor Recruitment for Fecal Microbiota Transplantation. Inflamm Bowel Dis. Jul. 2015;21(7):1600-6. doi: 10.1097/MIB.0000000000000405.
Rose et al., Hepatic encephalopathy: Novel insights into classification, pathophysiology and therapy. J Hepatol. Dec. 2020;73(6):1526-1547. doi: 10.1016/j.jhep.2020.07.013. Epub Oct. 21, 2020.
Rossi-Tamisier et al., Cautionary tale of using 16S rRNA gene sequence similarity values in identification of human-associated bacterial species. Int J Syst Evol Microbiol. Jun. 2015;65(Pt 6):1929-34. doi:10.1099/ijs.0.000161. Epub Mar. 3, 2015.
Shannon-Lowe et al., Prevention and medical management of *Clostridium difficile* infection. BMJ. Mar. 12, 2010;340:c1296. doi:10.1136/bmj.c1296.
Surawicz, Fecal microbiota transplantation: what we know and what we need to know. Ann Intern Med. May 5, 2015;162(9):662-3. doi: 10.7326/M15-0609.
Tannock et al., A new macrocyclic antibiotic, fidaxomicin (OPT-80), causes less alteration to the bowel microbiota of *Clostridium difficile*-infected patients than does vancomycin. Microbiology. Nov. 2010;156(Pt 11):3354-9. doi: 10.1099/mic.0.042010-0. Epub Aug. 19, 2010.
Van Nood et al., Duodenal infusion of donor feces for recurrent *Clostridium difficile*. N Engl J Med. Jan. 31, 2013;368(5):407-15. doi: 10.1056/NEJMoa1205037. Epub Jan. 16, 2013.
Wang et al., Microbiota-derived butyrate dynamically regulates intestinal homeostasis through regulation of actin-associated protein synaptopodin. Proc Natl Acad Sci U S A. May 26, 2020;117(21):11648-11657. doi: 10.1073/pnas.1917597117. Epub May 12, 2020.
Wei et al., Fecal microbiota transplantation restores dysbiosis in patients with methicillin resistant *Staphylococcus aureus* enterocolitis. BMC Infect Dis. Jul. 11, 2015;15:265. doi: 10.1186/s12879-015-0973-1.
Xiao et al., Bacterial diversity and community structure of supragingival plaques in adults with dental health or caries revealed by 16S pyrosequencing. Frontiers in microbiology. Jul. 22, 2016;7:1145. 15 pages.
Xie et al., Fecal Microbiota Transplantation for Treating Hepatic Encephalopathy: Experimental and Clinical Evidence and Possible Underlying Mechanisms. Journal of Exploratory Research in Pharmacology 2018;3(4):119-124. doi: 10.14218/JERP.2018.00017.
Youngster et al., Fecal microbiota transplant for relapsing Clostridium difficile infection using a frozen inoculum from unrelated donors: a randomized, open-label, controlled pilot study. Clin Infect Dis. Jun. 2014;58(11):1515-22. doi: 10.1093/cid/ciu135. Epub Apr. 23, 2014.

\* cited by examiner

Figure 1

| Composition A | Composition B | Composition C | Composition D |
|---|---|---|---|
| SEQ_03 - 5 - Clostridium_hathewayi (XIVa)* | SEQ_10 - 211 - Flavonifractor_plautii (IV) | SEQ_12 - VE202-26 - Clostridium_scindens (XIVa)* | SEQ_12 - VE202-26 - Clostridium_scindens (XIVa)* |
| SEQ_04 - 7 - Blautia_hansenii (XIVa)* | SEQ_14 - VE202-13 - Anaerotruncus_colihominis (IV) | SEQ_03 - 5 - Clostridium_hathewayi (XIVa)* | SEQ_03 - 5 - Clostridium_hathewayi (XIVa)* |
| SEQ_05 - 10 - Blautia_hansenii (XIVa)* | SEQ_15 - VE202-14 - Eubacterium_fissicatena (XIVa) | SEQ_05 - 10 - Blautia_hansenii (XIVa)* | SEQ_05 - 10 - Blautia_hansenii (XIVa)* |
| SEQ_07 - 59 - Blautia_producta / Blautia_coccoides (XIVa) | SEQ_16 - VE202-16 - Clostridium_symbiosum (XIVa) | SEQ_01 - 71 - Blautia_wexlerae (XIVa)* | SEQ_01 - 71 - Blautia_wexlerae (XIVa)* |
| SEQ_08 - 79 - Blautia_hansenii (XIVa)* | SEQ_17 - VE202-7 - Clostridium_boteae (XIVa) | SEQ_07 - 59 - Blautia_producta/Blautia_coccoides (XIVa) | SEQ_14 - VE202-13 - Anaerotruncus_colihominis (IV) |
| SEQ_09 - VE202-21 - Eubacterium_contortum / Eubacterium_fissicatena (XIVa)* | SEQ_20 - 170 - Dorea longicatena (XIVa) | SEQ_18 - 148 - Dorea_longicatena (XIVa) | SEQ_18 - 148 - Dorea_longicatena (XIVa) |
| SEQ_11 - VE202-9 - Anaerostipes_caccae (XIVa) | SEQ_19 - 16 - Blautia_producta (XIVa) | SEQ_21 - 189 - Clostridium_innocuum (XVII) | SEQ_21 - 189 - Clostridium_innocuum (XVII) |
| SEQ_12 - VE202-26 - Clostridium_scindens (XIVa)* | SEQ_21 - 189 - Clostridium_innocuum (XVII) | SEQ_10 - 211 - Flavonifractor_plautii (IV) / | SEQ_10 - 211 - Flavonifractor_plautii (IV) / |
| SEQ_13 - 136 - Marvinbryantia_formatexgens (XIVa)* | | SEQ_14 - VE202-13 - Anaerotruncus_colihominis (IV) | SEQ_02 - 102 - Turicibacter_sanguinis (non-Clostridium) |
| SEQ_23 - VE202-29 - Eisenbergiella_tayi (XIVa)* | | SEQ_16 - VE202-16 - Clostridium_symbiosum (XIVa) | SEQ_06 - 40 - Lactobacillus_mucosae (non-Clostridium) |

* = BaiCD+       bolding indicates strains other than Clostridium cluster XIVa

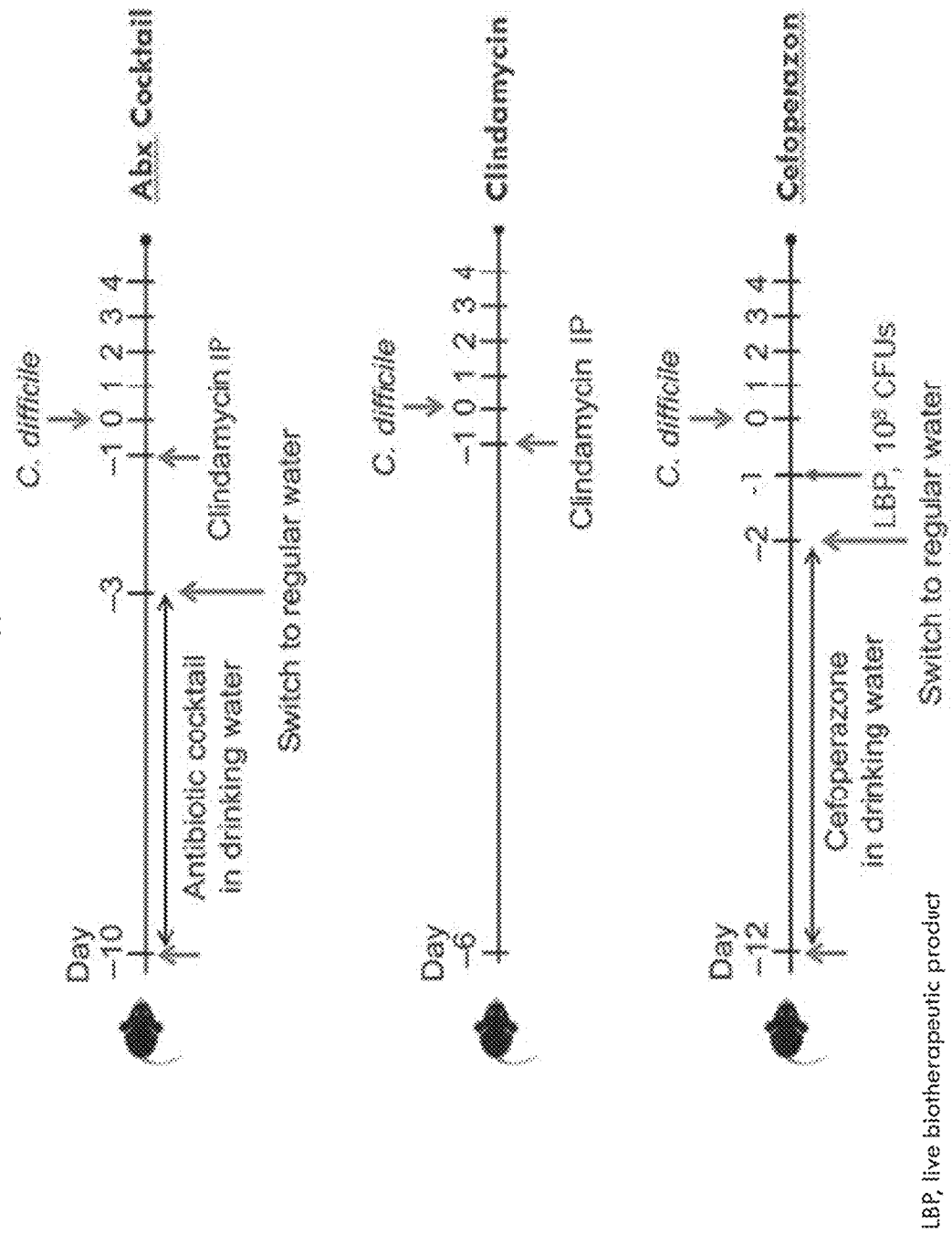

Figure 3

| Groups | # of animals | Abx | C. difficile Spores |
|---|---|---|---|
| (1) Control | 5 | - | $10^1$ |
| (2) Control | 5 | - | $10^4$ |
| (3) Abx cocktail | 5 | + | $10^1$ |
| (4) Abx cocktail | 5 | + | $10^4$ |
| (5) Clindamycin | 5 | + | $10^1$ |
| (6) Clindamycin | 5 | + | $10^4$ |
| (7) Cefoperazone | 5 | + | $10^1$ |
| (8) Cefoperazone | 5 | + | $10^4$ |

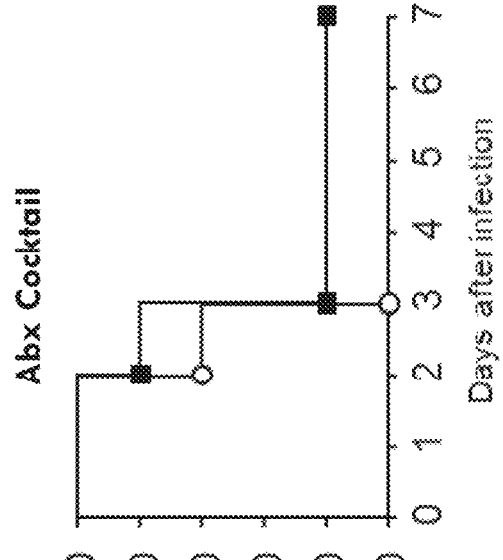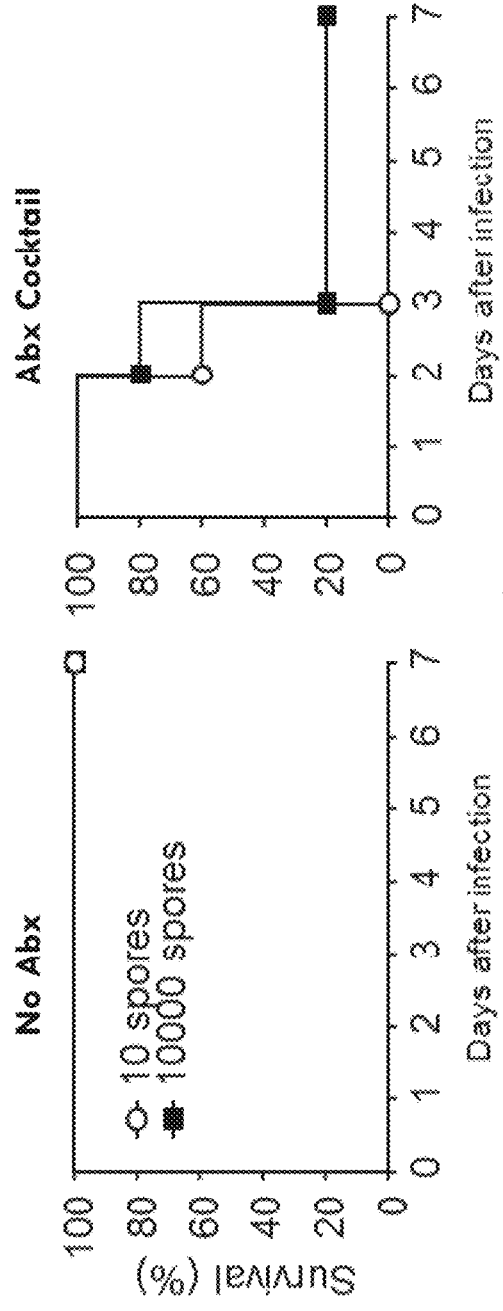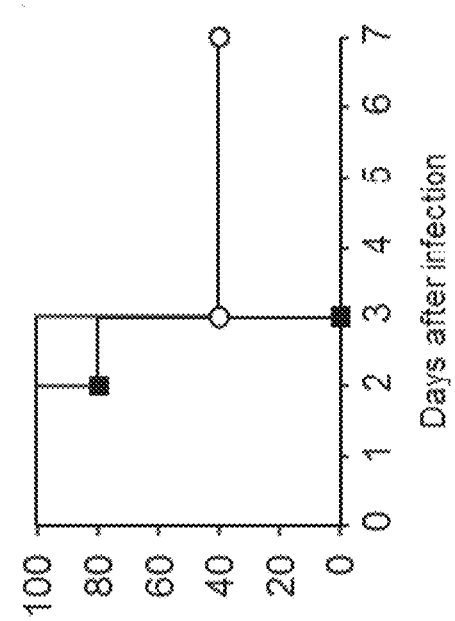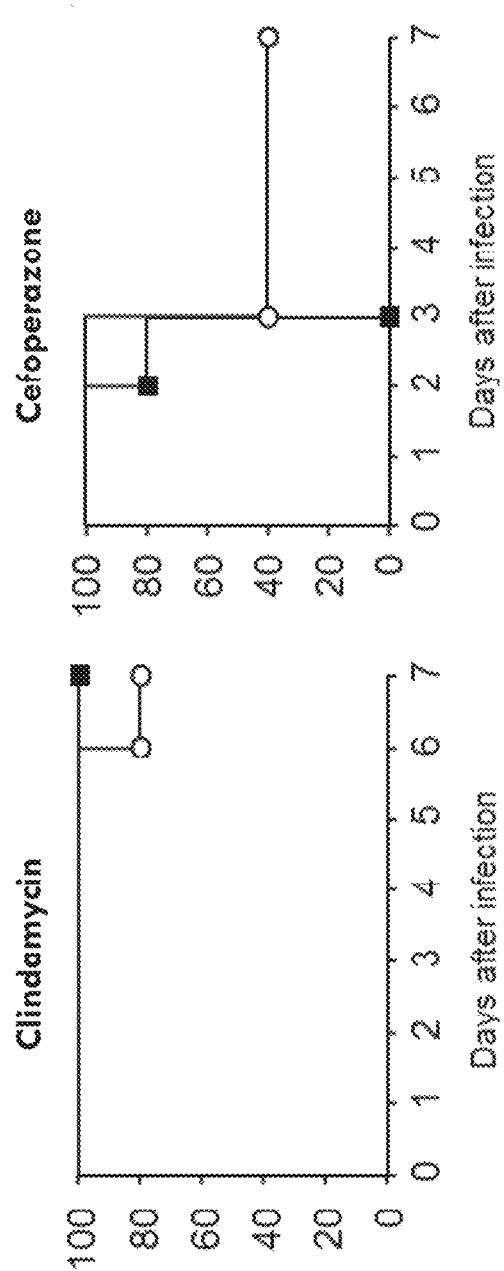

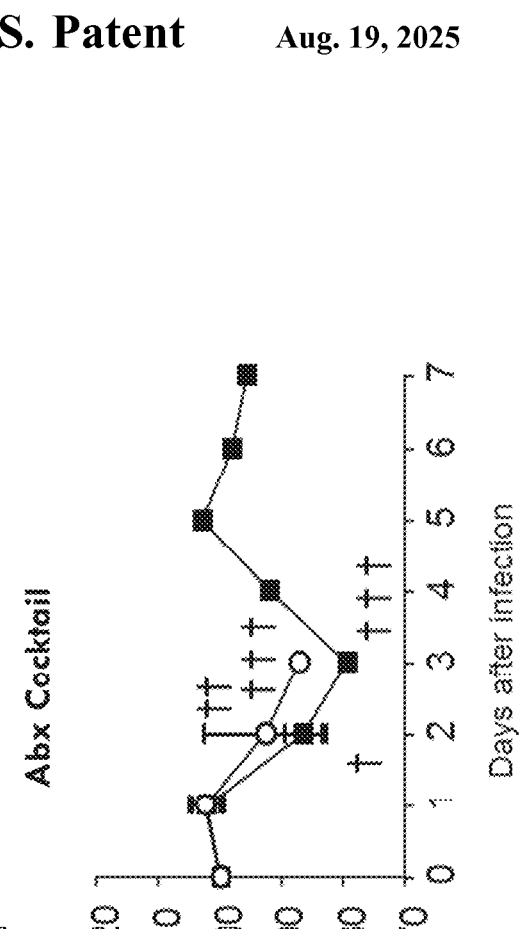
Figure 4E — No Abx
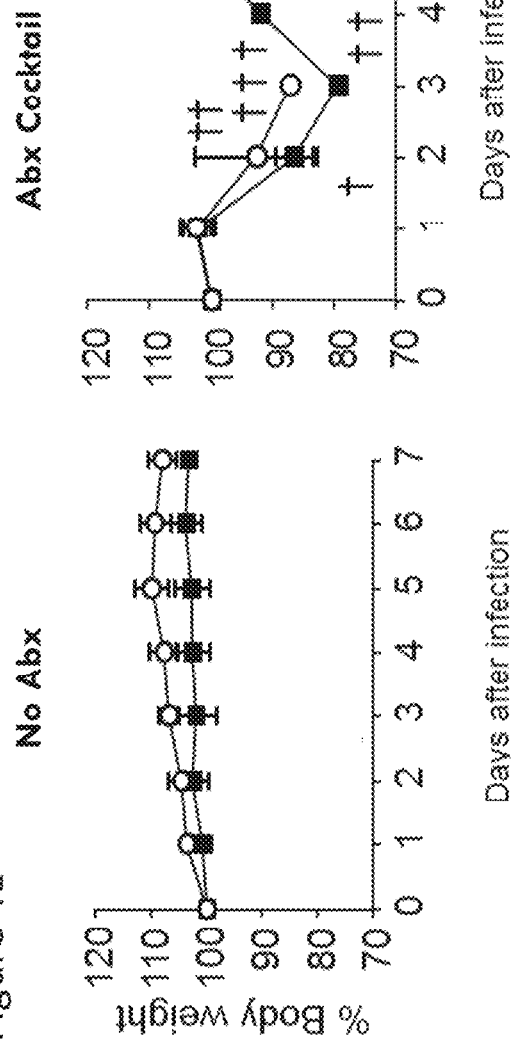
Figure 4F — Abx Cocktail
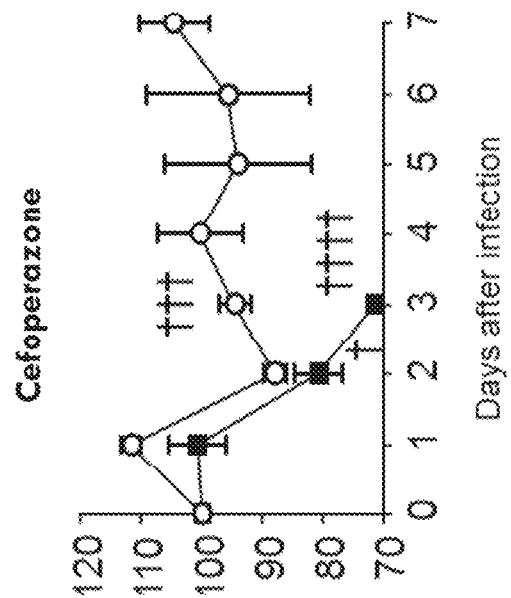
Figure 4G — Clindamycin
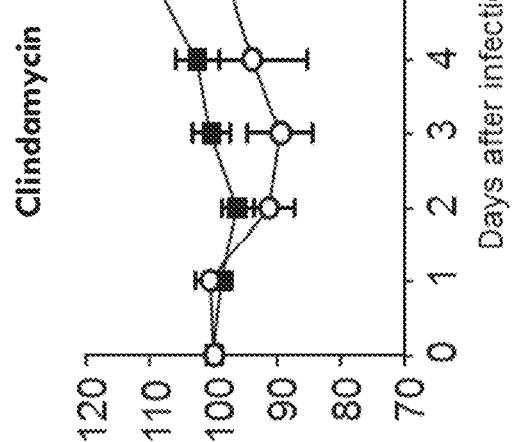
Figure 4H — Cefoperazone

Figure 5

| Groups | # of animals | Abx | CFUs (Spores) |
|---|---|---|---|
| (1) Control- | 5 | - | $10^4$ |
| (2) Control+ | 5 | + | $10^4$ |
| (3) Van | 5 | + | $10^4$ |
| (4) Composition E | 5 | + | $10^4$ |
| (5) Composition I | 5 | + | $10^4$ |
| (6) Composition A | 5 | + | $10^4$ |
| (7) Composition B | 5 | + | $10^4$ |
| (8) Composition C | 5 | + | $10^4$ |
| (9) Composition D | 5 | + | $10^4$ |

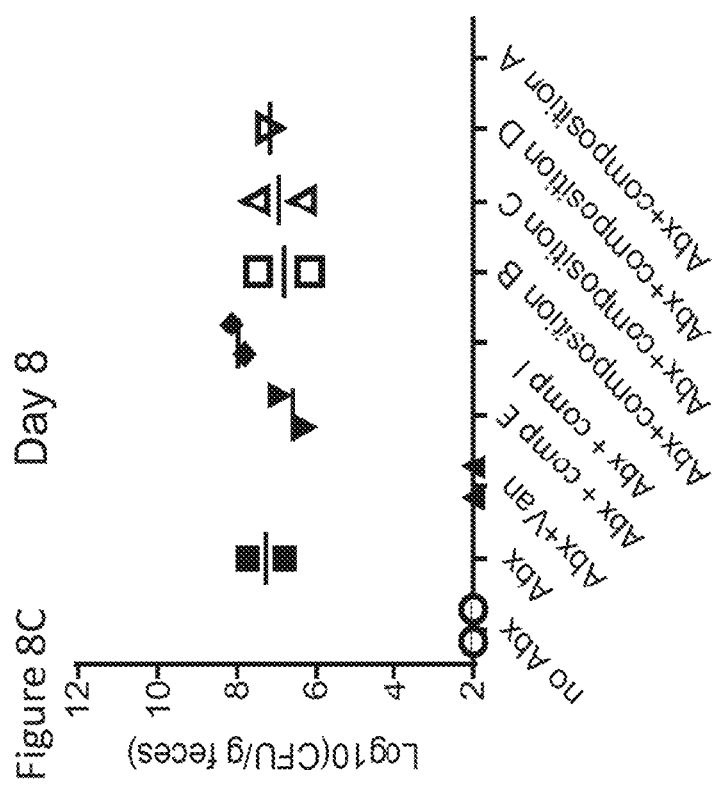

Figure 9

| Groups | # of animals | Abx | C. difficile spore | CFUs LBPs |
|---|---|---|---|---|
| (1) Control | 7 | + | $10^4$ | - |
| (2) Composition B | 8 | + | $10^4$ | $10^8$/mouse |

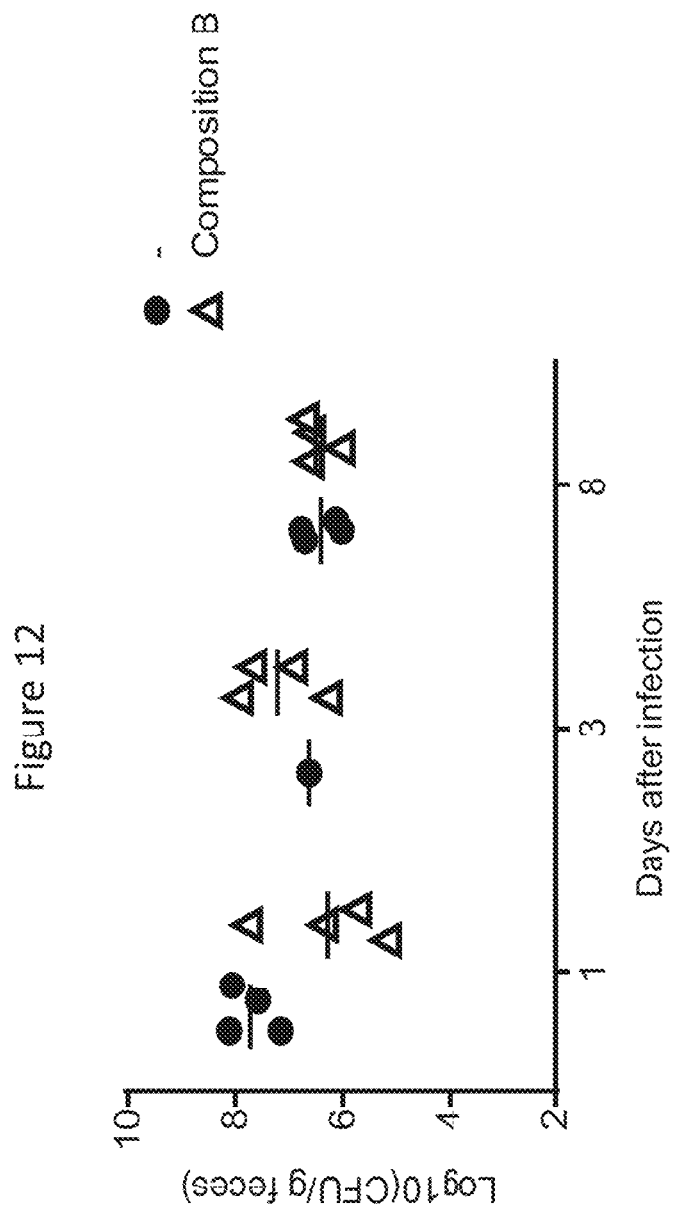

Figure 13

Composition F

| SEQ_NO | StrainID | Genus_species | SEQ_NO | StrainID | Genus_species |
|---|---|---|---|---|---|
| SEQ_24 | YK96 | Dorea_longicatena | SEQ_52 | YK51 | Eubacterium_rectale |
| SEQ_25 | YK101 | Ruminococcus_obeum | SEQ_53 | YK52 | Eubacterium_rectale |
| SEQ_26 | YK110 | Megasphaera_elsdenii | SEQ_54 | YK54 | Anaerostipes_hadrus |
| SEQ_27 | YK149 | Acdamirococcus_fermentans / Acdamirococcus_intestini | SEQ_55 | YK56 | Ruminococcus_faecis |
| SEQ_28 | YK154 | Megasphaera_elsdenii | SEQ_56 | YK57 | Ruminococcus_faecis |
| SEQ_29 | YK36 | Ruminococcus_faecis | SEQ_57 | YK58 | Dorea_longicatena |
| SEQ_30 | YK95 | Bacteroides_cellulosilyticus | SEQ_58 | YK65 | Roseburia_faecis |
| SEQ_31 | YK32 | Anaerostipes_hadrus | SEQ_59 | YK67 | Blautia_luti |
| SEQ_32 | YK64 | Ruminococcus_obeum | SEQ_60 | YK69 | Fusicatenibacter_saccharivorans |
| SEQ_33 | YK73 | Flavonifractor_plautii | SEQ_61 | YK70 | Fusicatenibacter_saccharivorans |
| SEQ_34 | YK87 | Eubacterium_rectale | SEQ_62 | YK71 | Roseburia_faecis |
| SEQ_35 | YK105 | Flavonifractor_plautii | SEQ_63 | YK74 | Megasphaera_elsdenii |
| SEQ_36 | YK153 | Megasphaera_elsdenii | SEQ_64 | YK88 | Eubacterium_rectale |
| SEQ_37 | YK163 | Eubacterium_rectale | SEQ_65 | YK89 | Eubacterium_rectale |
| SEQ_38 | YK191 | Ruminococcus_albus | SEQ_66 | YK97 | Roseburia_faecis |
| SEQ_39 | YK99 | Ruminococcus_champanellensis / Ruminococcus_champanellensis | SEQ_67 | YK98 | Blautia_faecis |
| SEQ_40 | YK55 | Ruminococcus_faecis | SEQ_68 | YK139 | Fusicatenibacter_saccharivorans |
| SEQ_41 | YK75 | Bifidobacterium_bifidum | SEQ_69 | YK141 | Dorea_formicigenerans |
| SEQ_42 | YK90 | Anaerostipes_hadrus | SEQ_70 | YK142 | Ruminococcus_faecis |
| SEQ_43 | YK30 | Anaerostipes_hadrus | SEQ_71 | YK152 | Blautia_hansenii |
| SEQ_44 | YK31 | Anaerostipes_hadrus | SEQ_72 | YK155 | Blautia_hansenii |
| SEQ_45 | YK12 | Eubacterium_rectale | SEQ_73 | YK157 | Eubacterium_rectale |
| SEQ_46 | YK27 | Ruminococcus_faecis | SEQ_74 | YK160 | Roseburia_faecis |
| SEQ_47 | YK28 | Blautia_luti | SEQ_75 | YK166 | Eubacterium_rectale |
| SEQ_48 | YK29 | Ruminococcus_faecis | SEQ_76 | YK168 | Eubacterium_rectale |
| SEQ_49 | YK33 | Anaerostipes_hadrus | SEQ_77 | YK169 | Eubacterium_rectale |
| SEQ_50 | YK34 | Anaerostipes_hadrus | SEQ_78 | YK171 | Eubacterium_rectale |
| SEQ_51 | YK35 | Ruminococcus_faecis | SEQ_79 | YK192 | Roseburia_faecis |

Figure 14

| Cluster | Composition F | SCFAs |
|---|---|---|
| XIVa | Eubacterium rectale 12 | A, B, L |
| | Ruminococcus faecis 8 | A, L |
| | Ruminococcus obeum 2 | A, L |
| | Blautia faecis 1 | A, L |
| | Blautia hansenii 2 | A, L |
| | Blautia luti 2 | A, L |
| | Anaerostipes hadrus 7 | B |
| | Roseburia faecis 5 | A, B |
| | Fusicatenibacter saccharivorans 3 | A, L |
| | Dorea formicigenerans 1 | A |
| | Dorea longicatena 2 | A |
| IV | Flavonifractor plautii 2 | A, B |
| | Ruminococcus champanellensis 2 | A |
| IX | Acidaminococcus fermentans 1 | A, B, P |
| | Megasphaera elsdenii 4 | P |
| other | Bacteroides cellulosilyticus 1 | A, S |
| | Bifidobacterium Bifidum | L, A |

A, acetate;
B, Butyrate;
L, lactate;
P, propionate;
S, succinate

Figure 15

| Groups | # of animals | Abx | *C. difficile* spore | CFUs LBPs |
|---|---|---|---|---|
| (1) Control | 10 | + | $10^4$ | - |
| (2) Composition B dosed at day -1 | 10 | + | $10^4$ | $10^8$/mouse |
| (3) Composition B dosed at day -2 and -1 | 10 | + | $10^4$ | $10^8$/mouse |
| (4) Composition B dosed at day -2, -1, 1, 2, and 3 | 10 | + | $10^4$ | $10^9$/mouse |
| (5) Composition F dosed at day -1 | 5 | + | $10^4$ | OD Normalized |
| (6) Composition F dosed at day -2, -1, 1, 2, and 3 | 5 | + | $10^4$ | OD Normalized |
| (7) FMT mouse | 5 | + | $10^4$ | 200ul of 10% fecal samples/mouse |
| (8) FMT human | 5 | + | $10^4$ | 200ul of 10% fecal samples/mouse |

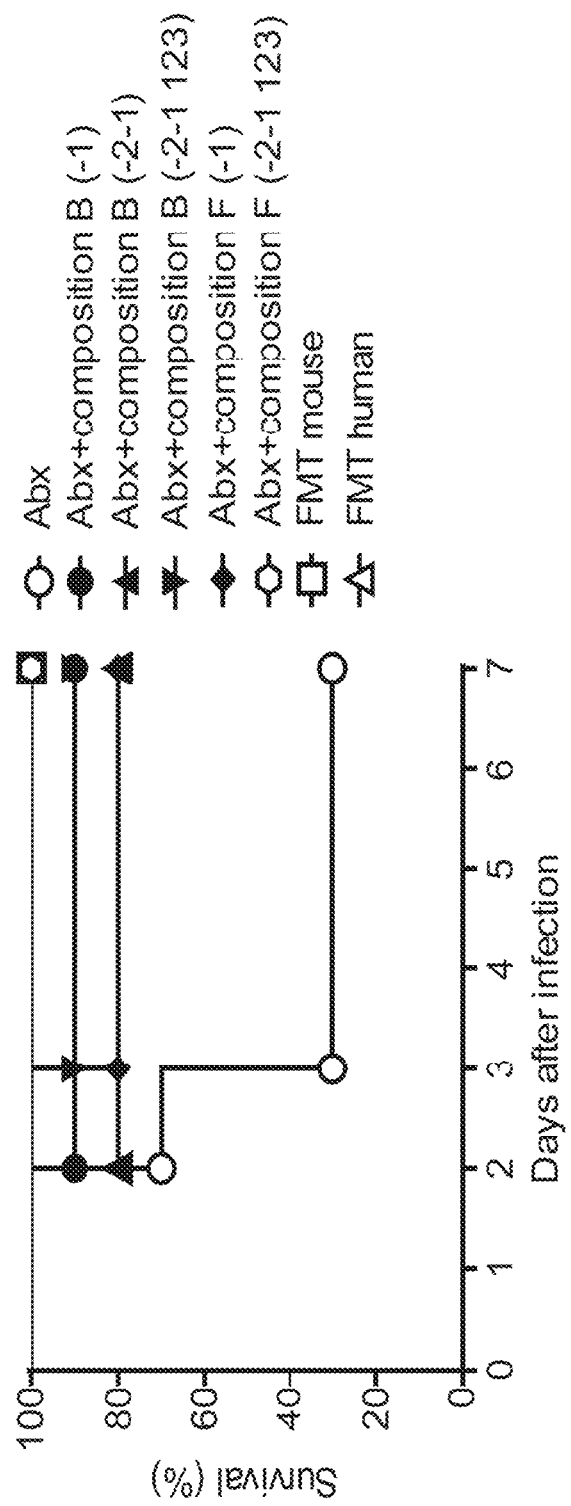

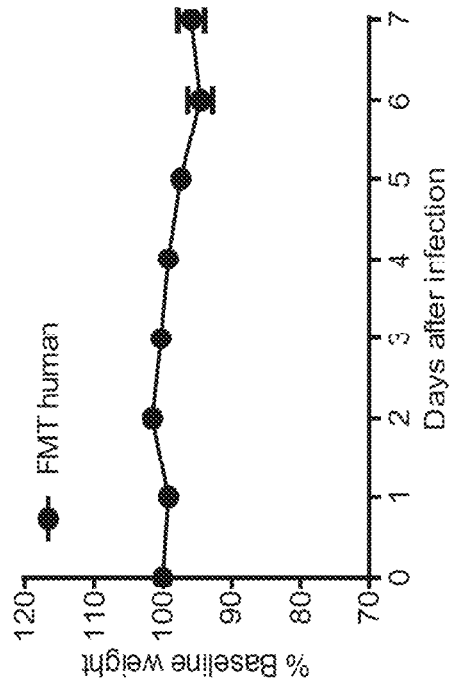
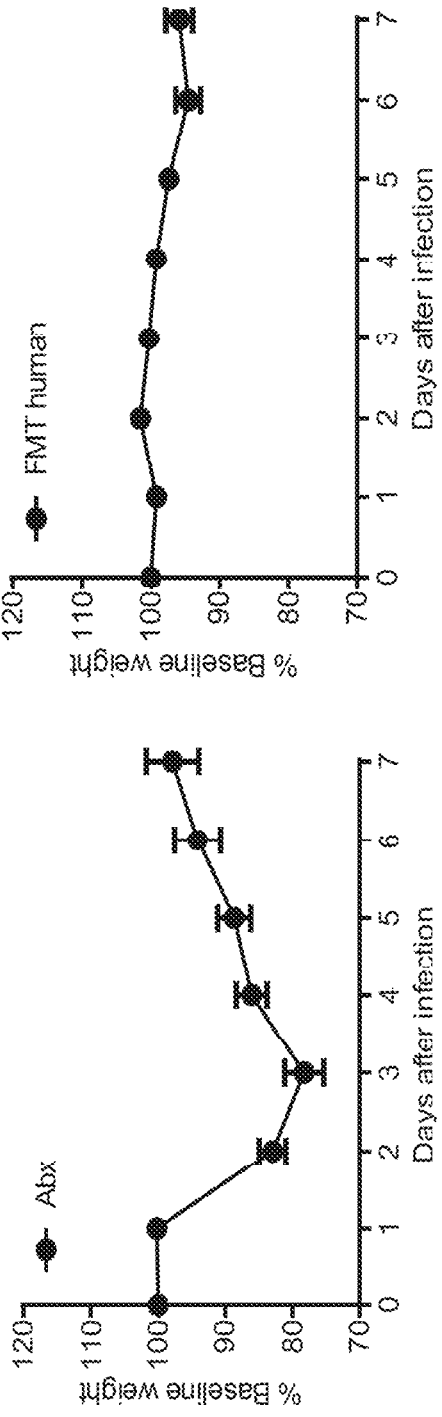
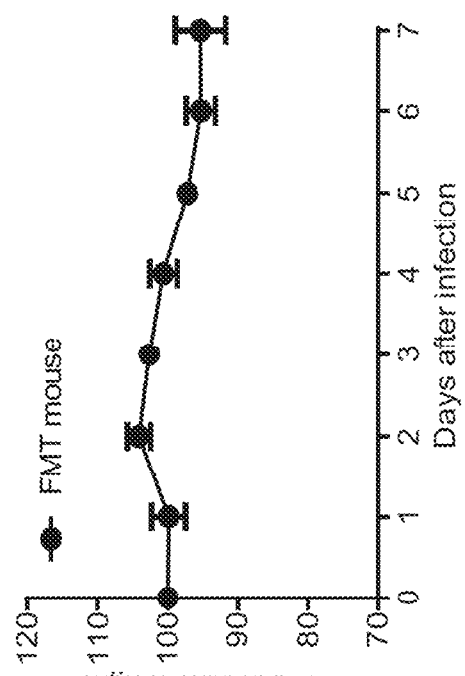
Figure 17A
Figure 17B
Figure 17C

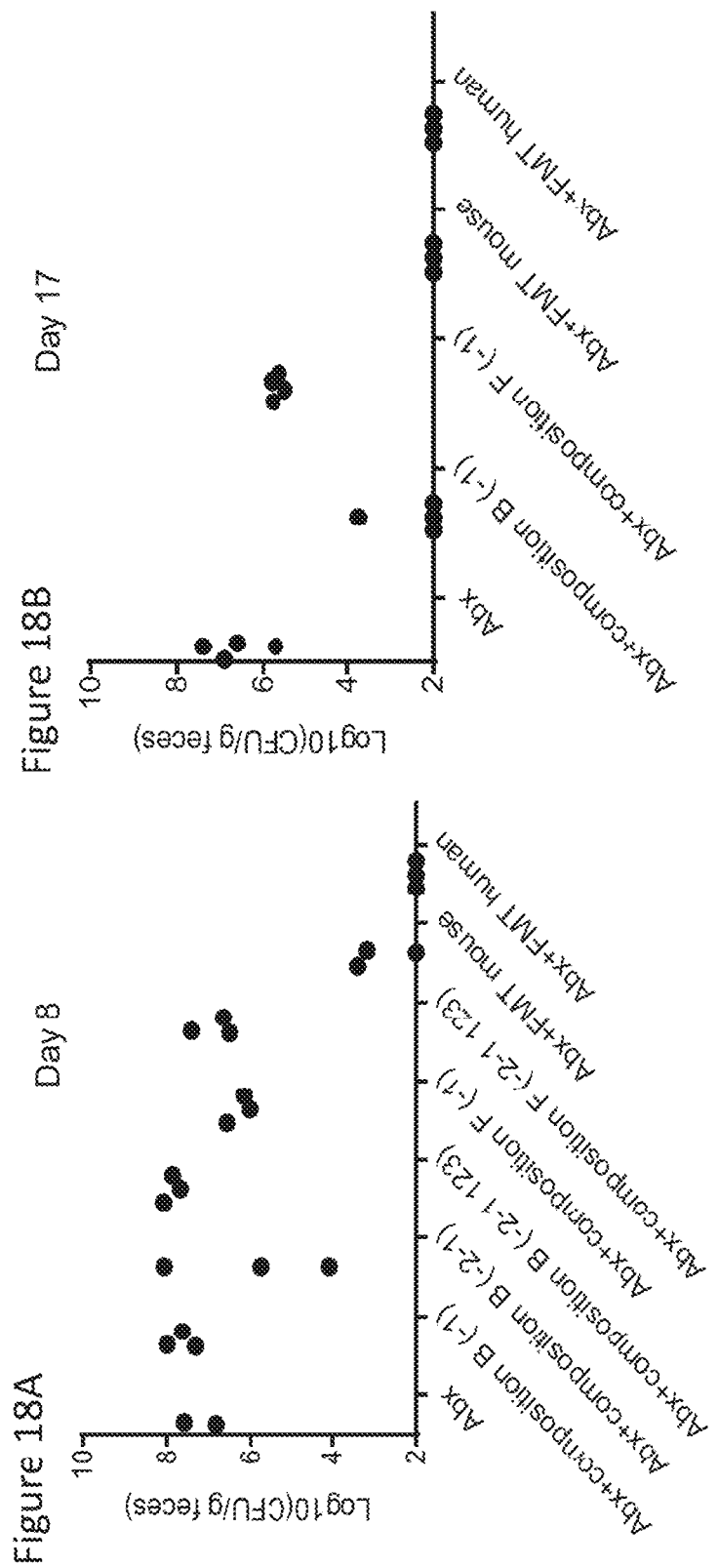

Figure 19

Composition G

| | | |
|---|---|---|
| SEQ_27 | YK149 | Acidaminococcus_fermentans/Acidaminococcus_intesti |
| SEQ_43 | YK90 | Anaerostipes_hadrus |
| SEQ_44 | YK30 | Anaerostipes_hadrus |
| SEQ_51 | YK34 | Anaerostipes_hadrus |
| SEQ_55 | YK54 | Anaerostipes_hadrus |
| SEQ_68 | YK98 | Blautia_faecis |
| SEQ_72 | YK152 | Blautia_hansenii |
| SEQ_70 | YK141 | Dorea_formicigenerans |
| SEQ_24 | YK96 | Dorea_longicatena |
| SEQ_34 | YK87 | Eubacterium_rectale |
| SEQ_37 | YK163 | Eubacterium_rectale |
| SEQ_46 | YK12 | Eubacterium_rectale |
| SEQ_76 | YK166 | Eubacterium_rectale |
| SEQ_77 | YK168 | Eubacterium_rectale |
| SEQ_35 | YK105 | Flavonifractor_plautii |
| SEQ_52 | YK70 | Fusicatenibacter_saccharivorans |
| SEQ_26 | YK110 | Megasphaera_elsdenii |
| SEQ_63 | YK71 | Roseburia_faecis |
| SEQ_67 | YK97 | Roseburia_faecis |
| SEQ_40 | YK99 | Ruminococcus_champanellensis |
| SEQ_38 | YK191 | Ruminococcus_champanellensis/Ruminococcus_albus |
| SEQ_47 | YK27 | Ruminococcus_faecis |
| SEQ_56 | YK56 | Ruminococcus_faecis |
| SEQ_25 | YK101 | Ruminococcus_obeum |
| SEQ_32 | YK64 | Ruminococcus_obeum |

Figure 20

| Groups | N | Abx | CFUs *C. difficile* | CFUs LBPs |
|---|---|---|---|---|
| (1) Vehicle | 7 | + | $10^4$ | 200ul of PBS |
| (2) Composition B | 8 | + | $10^4$ | $10^8$/mouse |
| (3) Composition B1 | 8 | + | $10^4$ | $10^8$/mouse |
| (4) Composition B2 | 8 | + | $10^4$ | $10^8$/mouse |
| (5) Composition F | 7 | + | $10^4$ | OD Normalized |
| (6) Composition G | 7 | + | $10^4$ | OD Normalized |
| (7) EtOH treated Human fecal samples | 5 | + | $10^4$ | 200ul of 10% fecal samples/mouse |
| (8) EtOH treated Composition B | 5 | + | $10^4$ | $10^8$/mouse |
| (9) Frozen Composition B | 5 | + | $10^4$ | $10^8$/mouse |
| (10) EtOH treated Composition J | 5 | + | $10^4$ | colony scrapes |

Figure 25

| Groups | N | Abx | CFUs *C. difficile* | CFUs LBPs |
|---|---|---|---|---|
| (1) Vehicle | 10 | + | $10^4$ | 200ul of PBS |
| (2) human FMT | 10 | + | $10^4$ | 200ul of 10% fecal samples/mouse |
| (3) Composition B | 10 | + | $10^4$ | $10^8$/mouse |
| (4) Composition B + 4 spores* | 10 | + | $10^4$ | $10^8$ live bacteria+spores/mouse |
| (5) Composition H** | 10 | + | $10^4$ | $10^8$/mouse |

*Composition B + 4 spores = The strains of Composition B plus the following four strains in spore form: *Clostrodium bolteae, Anaerotruncus colihominis, Clostridium symbiosum,* and *Clostridium innocuum*

**Composition H contains the following six strains in spore form: *Clostrodium bolteae, Anaerotruncus colihominis, Clostridium symbiosum, Clostridium innocuum, Clostridium disporicum,* and *Erysipelatoclostridium ramosum*

Figure 26
Composition H

**Composition H = The following six strains in spore form Clostrodium boiteae, An

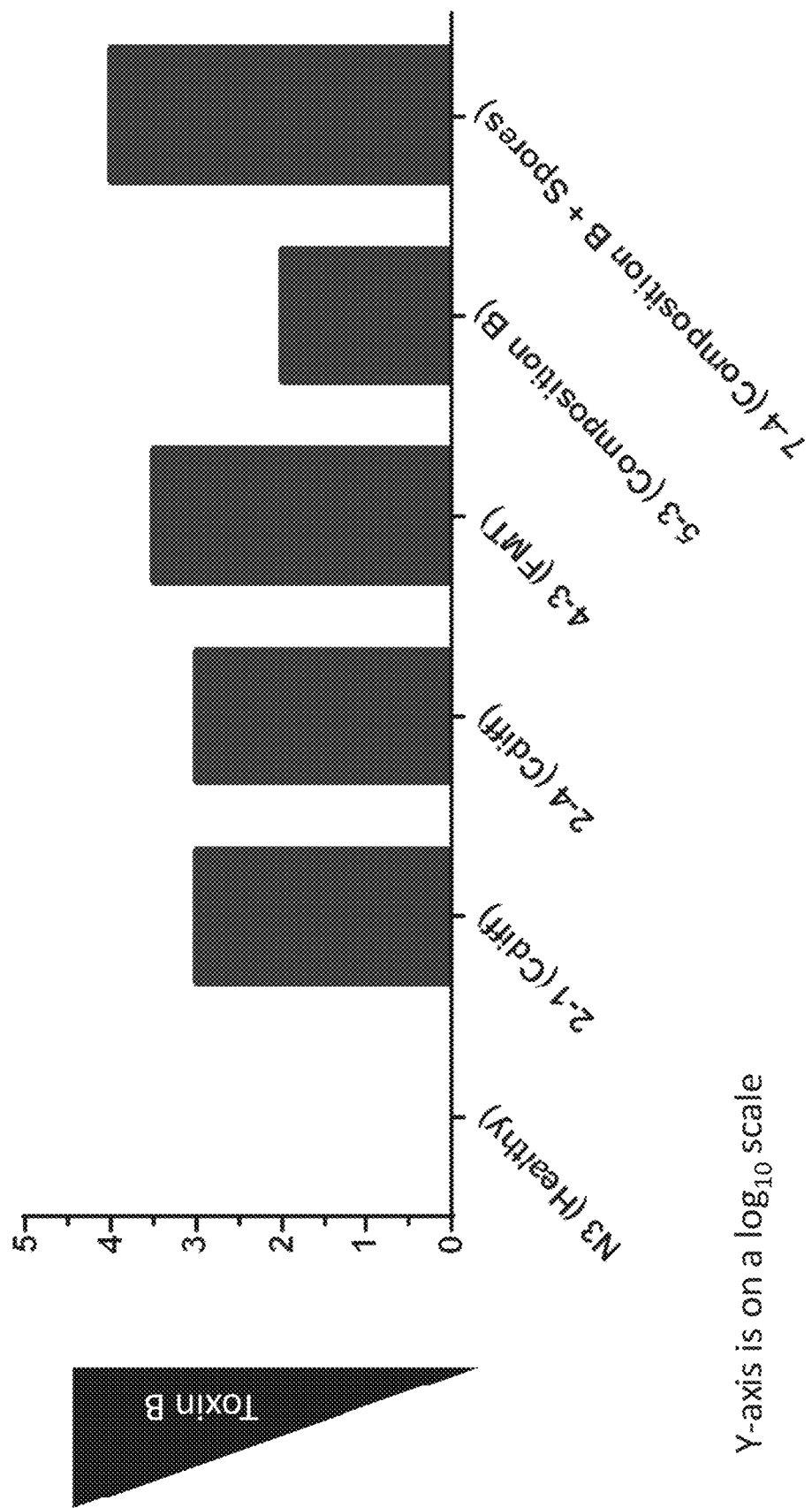

TREATMENT OF CLOSTRIDIUM DIFFICILE INFECTION

RELATED APPLICATIONS

This application is a continuation of U.S. application Ser. No. 16/702,659, filed Dec. 4, 2019, which is a continuation of U.S. application Ser. No. 16/423,487, filed May 28, 2019, now issued as U.S. Pat. No. 10,555,980, which is a continuation of U.S. application Ser. No. 16/157,640, filed Oct. 11, 2018, now issued as U.S. Pat. No. 10,456,431, which is a continuation of U.S. application Ser. No. 15/993,037, filed May 30, 2018, now issued as U.S. Pat. No. 10,350,250, which is a continuation of U.S. application Ser. No. 15/630,088, filed Jun. 22, 2017, now issued as U.S. Pat. No. 9,999,641, which is a continuation of international application number PCT/US2017/037498, filed Jun. 14, 2017, which claims the benefit under 35 U.S.C. § 119(e) of U.S. provisional application No. 62/349,914, filed Jun. 14, 2016, each of which is incorporated by reference herein in its entirety.

REFERENCE TO AN ELECTRONIC SEQUENCE LISTING

The contents of the electronic sequence listing (P074570006US07-SEQ-NTJ.xml; Size: 340,528 bytes; and Date of Creation: May 15, 2023) is herein incorporated by reference in its entirety.

FIELD OF INVENTION

The disclosure relates to compositions of purified bacterial strains, and methods for treating pathogenic infections, such as *Clostridium difficile* infections, by administering the compositions to a subject having a pathogenic infection.

BACKGROUND OF THE INVENTION

The collection of bacterial, viral, and fungal commensal microorganisms that reside within and on the human body are collectively known as the human microbiome. The bacterial subset of the human microbiome plays an important role in host nutrient acquisition, development, immunological homeostasis, neurological health, and protection against pathogens (LeBlanc et al. *Curr. Opin. Biotechnol.* (2013) 24(2): 160-168; Hooper et al. *Science* (2012) 336 (6086): 1268-1273; Hughes et al. *Am. J. Gastroenterol.* (2013) 108(7): 1066-1074). As the largest reservoir of mammalian commensals, bacteria residing in the gastrointestinal (GI) tract influence nearly all of these aspects of human biology (Blaser *J. Clin. Invest.* (2014) 124(10): 4162-4165). Consequently, perturbation of the normal bacterial populations within the GI niche, a state known as dysbiosis, can predispose humans to a variety of diseases.

*Clostridium difficile* infection (CDI) arises after intestinal colonization by the anaerobic spore-forming Gram-positive pathogen *Clostridium difficile*. Upon colonization of the GI tract, *C. difficile* produces toxins which causes diarrhea and may ultimately lead to death. This illness is the most common identifiable cause of nosocomial diarrhea and is thought to arise as a direct result of dysbiosis (Calfee *Geriatrics* (2008) 63: 10-21; Shannon-Lowe et al *BMJ* (2010) 340: c1296). Not surprisingly, usage of nearly all classes of antibiotics has been associated with CDI, presumably by inducing dysbiosis in the GI tract and thereby enabling *C. difficile* outgrowth. The Center for Disease Control currently classifies CDI as a public health threat requiring immediate and aggressive action because of its natural resistance to many drugs and the emergence of a fluoroquinolone-resistant strain that is now prevalent throughout North America and Europe. *C. difficile* was responsible for almost half a million infections and was associated with approximately 29,000 deaths in 2011 (Lessa et al. *NEJM* 2015 372: 825-834).

The antibiotics metronidazole, vancomycin, and fidaxomicin are the current therapeutic options for treatment of CDI. However, metronidazole is inadequate because of decreased response rates and neither metronidazole nor vancomycin prevent disease recurrence, with up to 30% of patients initially responding experiencing a clinical recurrence after antibiotic cessation (Miller *Expert Opin. Pharmacother.* (2010) 11: 1569-1578). Fidaxomicin has been shown to be superior to vancomycin in preventing recurrent CDI (Mullane *Ther. Adv. Chronic Dis.* (2014) 5(2): 69-84). Because of its narrow spectrum of activity, fidaxomicin is thought to enable normal microbiome repopulation of the gut following dysbiosis and CDI, thereby lowering the likelihood of recurrent disease (Tannock et al. *Microbiology* (2010) 156 (Pt 11): 3354-3359; Louie et al. *Clin. Infect. Dis.* (2012) 55 Suppl. 2: S132-142). Nonetheless, 14% of fidaxomicin-treated patients experience CDI relapse and mutations conferring reduced sensitivity have already been reported (Eyre et al. *J. Infect. Dis.* (2014) 209(9): 1446-1451).

Because the risk of recurrent CDI is heightened by antibiotic use and *C. difficile* spores are inherently recalcitrant to the available chemotherapeutic arsenal, alternative therapeutic modalities are being pursued for the treatment of CDI. Fecal microbiota transplantation (FMT) is one such modality that has shown efficacy against CDI (Khoruts et al. *Immunol. Lett.* (2014) 162(2): 77-81; van Nood et al. *N. Engl. J. Med.* (2013) 368(5): 407-415). To date, results of FMT studies for the treatment of CDI, have reported cure rates up to 90% in three randomized controlled studies (Cammarota et al. *Alimen. Pharmacol. Therap.* (2015) 41(9): 835-843; Kassam et al. *Am. J. Gastroenterol.* (2013) 108(4): 500-508; van Nood et al. *N. Engl. J. Med.* (2013) 368(5): 407-415; Youngster et al. *Infec. Dis. Soc. Am.* (2014) 58(11): 1515-1522).

Despite the success of FMT, this therapeutic approach is not without risks and logistical concerns. Selection of FMT donors is critical and challenging. When FMT donor recruitment is performed with stringent screening and standardization protocols, most prospective donors fail this process. Only 6-10% of prospective FMT donors qualify, with the majority of failures arising from asymptomatic carriage of GI pathogens (Paramsothy et al. *Inflamm. Bowel Dis.* (2015) 21(7): 1600-1606; Borody et al. *Curr. Opin. Gastroenterol.* (2014) 30(10): 97-105; Burns et al. *Gastroenterology* (2015) 148: S96-S97; Surawicz *Ann. Intern. Med.* (2015) 162(9): 662-663). Furthermore, variation between donors may lead to variation in FMT efficacy. In addition, the risk of transmission of even non-infectious illnesses may be heightened by FMT. Indeed, significant weight gain has been reported in a patient who received an FMT from an overweight stool donor (Alang et al. *Open Forum Infect. Dis.* (Winter 2015) 2(1)).

SUMMARY OF THE INVENTION

Provided herein are compositions and methods for the treatment or prevention of pathogenic infections including *C. difficile*.

In one aspect, the disclosure provides compositions comprising two or more purified bacterial strains of species selected from the group consisting of: *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimonas intestinalis, Dracourtella massiliensis, Dracourtella massilinesis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50 AFAA, *Lachnospiraceae bacterium* 7_1_58 FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostridium bolteae* 90A9, *Dorea longicatena, Dorea longicatena* CAG:42, *Clostridium innocuum, Erysipelotrichaceae_bacterium_21-3, Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellnsis, Ruminococcus albus, Bifidobacterium bifidum, Blautia luti, Roseburia faecis, Fusicatenibacter saccharivorans, Roseburia faecis, Blautia faecis, Dorea formicigenerans* and *Bacteroides ovatus*.

In some embodiments of the compositions provided herein, the composition comprises two or more purified bacterial strains of species selected from the group consisting of: *Clostridium hathewayi, Blautia hansenii, Blautia producta, Blautia producta* ATCC 27340, *Clostridium bacterium* UC5.1-1D4, *Blautia coccoides, Eubacterium contortum, Eubacterium fissicatena, Sellimonas intestinalis, Dracourtella massiliensis, Dracourtella massilinesis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50 AFAA, *Lachnospiraceae bacterium* 7_1_58 FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostridium bolteae* 90A9, *Dorea longicatena, Dorea longicatena* CAG:42, *Clostridium innocuum, Erysipelotrichaceae_bacterium_21-3, Blautia wexlerae, Turicibacter sanguinis, Lactobacillus mucosae,* and *Bacteroides ovatus*.

In some embodiments of the compositions provided herein, the composition comprises two or more purified bacterial strains of species selected from the group consisting of: *Clostridium hathewayi, Blautia hansenii, Blautia producta, Blautia coccoides, Eubacterium contortum, Eubacterium fissicatena, Anaerostipes caccae, Clostridium scindens, Marvinbryanta formatexigens,* and *Eisenbergiella tayi*.

In some embodiments of the compositions provided herein, the composition comprises two or more purified bacterial strains of species selected from the group consisting of: *Flavinofractor plautii, Clostridium orbiscindens* 1_3_50 AFAA, *Lachnospiraceae bacterium* 7_1_58 FAA, *Subdoligranulum, Anaerotruncus colihominis, Anaerotruncus colihominis* DSM 17241, *Eubacterium fissicatena, Sellimonas intestinalis, Dracourtella massiliensis, Dracourtella massilinesis* GD1, *Ruminococcus torques, Clostridium symbiosum, Clostridium symbiosum* WAL-14163, *Clostridium bolteae, Clostridium bolteae* 90A9, *Dorea longicatena, Dorea longicatena* CAG:42, *Blautia producta, Blautia producta* ATCC 27340, *Clostridium bacterium* UC5.1-1D4, *Clostridium innocuum,* and *Erysipelotrichaceae_bacterium_21-3*.

In some embodiments of the compositions provided herein, the composition comprises two or more purified bacterial strains of species selected from the group consisting of: *Clostridium orbiscindens* 1_3_50 AFAA, *Anaerotruncus colihominis* DSM 17241, *Dracourtella massilinesis* GD1, *Clostridium symbiosum* WAL-14163, *Clostridium bolteae* 90A9, *Dorea longicatena* CAG:42, *Clostridium bacterium* UC5.1-1D4, and *Erysipelotrichaceae_bacterium_21-3*.

In some embodiments of the compositions provided herein, the composition comprises two or more purified bacterial strains of species selected from the group consisting of: *Clostridium orbiscindens* 1_3_50 AFAA, *Anaerotruncus colihominis* DSM 17241, *Sellimonas intestinalis, Clostridium symbiosum* WAL-14163, *Clostridium bolteae* 90A9, *Dorea longicatena* CAG:42, *Clostridium bacterium* UC5.1-1D4, and *Erysipelotrichaceae_bacterium_21_3*.

In some embodiments of the compositions provided herein, the composition comprises purified bacterial strains *Clostridium orbiscindens* 1_3_50 AFAA, *Anaerotruncus colihominis* DSM 17241, *Dracourtella massilinesis* GD1, *Clostridium symbiosum* WAL-14163, *Clostridium bolteae* 90A9, *Dorea longicatena* CAG:42, *Clostridium bacterium* UC5.1-1D4, and *Erysipelotrichaceae_bacterium_21-3*.

In some embodiments of the compositions provided herein, the composition comprises purified bacterial strains *Clostridium orbiscindens* 1_3_50 AFAA, *Anaerotruncus colihominis* DSM 17241, *Sellimonas intestinalis* GD1, *Clostridium symbiosum* WAL-14163, *Clostridium bolteae* 90A9, *Dorea longicatena* CAG:42, *Clostridium bacterium* UC5.1-1D4, and *Erysipelotrichaceae_bacterium_21_3*.

In some embodiments of the compositions provided herein, the composition comprises two or more purified bacterial strains of species selected from the group consisting of: *Flavinofractor plautii, Anaerotruncus colihominis, Dracourtella massiliensis, Clostridium symbiosum, Clostridium bolteae, Dorea longicatena, Blautia producta,* and *Clostridium innocuum*.

In some embodiments of the compositions provided herein, the composition comprises purified bacterial strains *Flavinofractor plautii, Anaerotruncus colihominis, Dracourtella massiliensis, Clostridium symbiosum, Clostridium bolteae, Dorea longicatena, Blautia producta,* and *Clostridium innocuum*.

In some embodiments of the compositions provided herein, the composition comprises two or more purified bacterial strains of species selected from the group consisting of: *Flavinofractor plautii, Anaerotruncus colihominis, Eubacterium fissicatena, Clostridium symbiosum, Clostridium bolteae, Dorea longicatena, Blautia producta,* and *Clostridium innocuum*.

In some embodiments of the compositions provided herein, the composition comprises purified bacterial strains *Flavinofractor plautii, Anaerotruncus colihominis, Eubacterium fissicatena, Clostridium symbiosum, Clostridium bolteae, Dorea longicatena, Blautia producta,* and *Clostridium innocuum*.

In some embodiments of the compositions provided herein, the composition comprises two or more purified bacterial strains of species selected from the group consisting of: *Flavinofractor plautii, Lachnospiraceae bacterium* 7_1_58 FAA, *Subdoligranulum, Anaerotruncus colihominis, Eubacterium fissicatena, Ruminococcus torques,*

*Clostridium symbiosum, Clostridium bolteae, Dorea longicatena, Blautia producta, Clostridium innocuum, Erysipelotrichaceae_bacterium_21-3*, and *Bacteroides ovatus*.

In some embodiments of the compositions provided herein, the composition comprises two or more purified bacterial strains of species selected from the group consisting of: *Clostridium orbiscindens* 1_3_50 AFAA, *Anaerotruncus colihominis* DSM 17241, *Dracourtella massiliensis* GD1, *Clostridium symbiosum* WAL-14163, *Clostridium bolteae* 90A9, *Dorea longicatena* CAG:42, *Clostridium bacterium* UC5.1-1D4, *Erysipelotrichaceae_bacterium_21-3*, and *Bacteroides ovatus*.

In some embodiments of the compositions provided herein, the composition comprises two or more purified bacterial strains of species selected from the group consisting of: *Clostridium orbiscindens* 1_3_50 AFAA, *Anaerotruncus colihominis* DSM 17241, *Sellimonas intestinalis, Clostridium symbiosum* WAL-14163, *Clostridium bolteae* 90A9, *Dorea longicatena* CAG:42, *Clostridium bacterium* UC5.1-1D4, *Erysipelotrichaceae_bacterium_21-3*, and *Bacteroides ovatus*.

In some embodiments of the compositions provided herein, the composition does not include a bacterial strain of the species *Flavinofractor plautii, Subdoligranulum*, or *Lachnospiraceae bacterium* 7_1_58 FAA. In some embodiments of the compositions provided herein, the composition does not include a bacterial strain of the species *Bacteroides ovatus*. The composition of any one of claims 4-12, wherein the composition does not include a bacterial strain of the species *Flavinofractor plautii, Subdoligranulum, Clostridium orbiscindens* 1_3_50 AFAA, or *Lachnospiraceae bacterium* 7¬_1_58 FAA.

In some embodiments of the compositions provided herein, the composition comprises two or more purified bacterial strains of species selected from the group consisting of: *Clostridium scindens, Clostridium hathewayi, Blautia hansenii, Blautia wexlerae, Blautia producta, Blautia coccoides, Dorea longicatena, Clostridium innocuum, Erysipelotrichaceae_bacterium_21-3, Flavinofractor plautii, Lachnospiraceae bacterium* 7-_1_58 FAA, *Subdoligranulum, Anaerotruncus colihominis*, and *Clostridium symbiosum*. In some embodiments of the compositions provided herein, the composition does not include a bacterial strain of the species *Flavinofractor plautii, Subdoligranulum*, or *Lachnospiraceae bacterium* 7_1_58 FAA.

In some embodiments of the compositions provided herein, the composition comprises two or more purified bacterial strains of species selected from the group consisting of: *Clostridium scindens, Clostridium hathewayi, Blautia hansenii, Blautia wexlerae, Anaerotruncus colihominis, Dorea longicatena, Clostridium innocuum, Erysipelotrichaceae_bacterium_21-3, Flavinofractor plautii, Lachnospiraceae bacterium* 7-_1_58 FAA, *Subdoligranulum, Turicibacter sanguinis*, and *Lactobacillus mucosae*. In some embodiments of the compositions provided herein, the composition does not include a bacterial strain of the species *Flavinofractor plautii, Subdoligranulum* or *Lachnospiraceae bacterium* 7_1_58 FAA.

In some embodiments of the compositions provided herein, the composition comprises two or more purified bacterial strains of species selected from the group consisting of: *Dorea longicatena, Ruminococcus obeum, Megasphaera elsdenii, Acidaminococcus fermentans, Acidaminococcus intestine, Ruminococcus faecis, Bacteroides cellulosilyticus, Anaerostipes hadrus, Flavinofractor plautii, Eubacterium rectale, Ruminococcus champanellensis, Ruminococcus albus, Bifidobacterium bifidum, Ruminococcus faecis, Blautia luti, Roseburia faecis, Fusicatenibacter saccharivorans, Blautia faecis, Dorea formicigenerans*, and *Blautia hansenii*.

In some embodiments of the compositions provided herein, the composition comprises two or more purified bacterial strains of species selected from the group consisting of: *Acidaminococcus fermentans, Acidaminococcus intestine, Anaerostipes hadrus, Blautia faecis, Blautia hansenii, Dorea formicigenerans, Dorea longicatena, Eubacterium rectale, Flavinofractor plautii, Fusicatenibacter saccharivorans, Megasphaera elsdenii, Roseburia faecis, Ruminococcus champanellensis, Ruminococcus albus, Ruminococcus faecis*, and *Ruminococcus obeum*.

In one aspect the disclosure provides compositions comprising two or more purified bacterial strains, wherein the two or more purified bacterial strains comprise 16S rDNA sequences having at least 97% homology with nucleic acid sequences selected from the group consisting of SEQ ID NOs:1-83 and 124-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:1-23, SEQ ID NO:83, SEQ ID NOs: 124-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21. In some embodiments of the compositions provided herein, the composition comprises purified bacterial strains that comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124, SEQ ID NO: 129, SEQ ID NO: 132, SEQ ID NO: 137, SEQ ID NO: 141, SEQ ID NO: 146, SEQ ID NO: 152, and SEQ ID NO: 157. In some embodiments of the compositions provided herein, the composition comprises purified bacterial strains that comprise 16S rDNA sequences having at least 97% homology with nucleic acid sequences selected from the group consisting of SEQ ID NO: 124, SEQ ID NO: 129, SEQ ID NO: 132, SEQ ID NO: 137, SEQ ID NO: 141, SEQ ID NO: 146, SEQ ID NO: 152, and SEQ ID NO: 157.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20 and SEQ ID NO:21, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:124-156, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21 and SEQ ID NO:22. In some embodiments of the compositions provided herein, the composition comprises two or more purified bacterial strains, wherein the two or more purified bacterial strains comprise 16S rDNA sequences having at least 97% homology with nucleic acid sequence selected from the group consisting of SEQ ID NO: 124-145, SEQ ID NO: 152-159, SEQ ID NO: 18, and SEQ ID NO: 22.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21 and SEQ ID NO:22, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124-145 and SEQ ID NO: 152-156, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10 and SEQ ID NOs:14-22. In some embodiments of the compositions provided herein, the composition comprises two or more purified bacterial strains, wherein the two or more purified bacterial strains comprise 16S rDNA sequences having at least 97% homology with nucleic acid sequence selected from the group consisting of SEQ ID NOs: 124-159, SEQ ID NO: 18, and SEQ ID NO: 22.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:14-22 and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 129-156, SEQ ID NO: 18, SEQ ID NO: 22, and wherein the composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21 and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID Nos: 124-159 and SEQ ID NO: 83.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-156 and SEQ ID NO: 83, and wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22 and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159, SEQ ID NO: 22, and SEQ ID NO: 83, In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-145, SEQ ID NOs: 152-156, SEQ ID NO: 22, and SEQ ID NO: 83, wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:10, SEQ ID NOs:14-22, and SEQ ID NO:83. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs: 124-159, SEQ ID NO: 18, SEQ ID NO:22, and SEQ ID NO: 83.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:14-22 and SEQ ID NO:83, and wherein the composition does not include a bacterial strain comprising a 16S rDNA sequence having at least 97% homology with a nucleic acid sequence of SEQ ID NO:10. In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO: 124-15, SEQ ID NO: 18, SEQ ID NO:22, and SEQ ID NO: 83, wherein composition does not include a bacterial strain comprising a 16S rDNA sequence having at least 97% homology with a nucleic acid sequence selected from the group consisting of SEQ ID NOs:157-159.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:1, SEQ ID NO:3, SEQ ID NO:5, SEQ ID NO:7, SEQ ID NO:10, SEQ ID NO:12, SEQ ID NO:14, SEQ ID NO:16, SEQ ID NO:18, and SEQ ID NO:21.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:1, SEQ ID NO:2, SEQ ID NO:3, SEQ ID NO:5, SEQ ID NO:6, SEQ ID NO:10, SEQ ID NO:12, SEQ ID NO:14, SEQ ID NO:18, and SEQ ID NO:21.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:24-79.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NOs:24-27, SEQ ID NO:32, SEQ ID NO:34, SEQ ID NO:35, SEQ ID NO:37, SEQ ID NO:38, SEQ ID NO:40, SEQ ID NO:43, SEQ ID NO:44, SEQ ID NO:46, SEQ ID NO:47, SEQ ID NO:51, SEQ ID NO:55, SEQ ID NO:56, SEQ ID NO:62, SEQ ID NO:63, SEQ ID NO:67, SEQ ID NO:68, SEQ ID NO:70, SEQ ID NO:72, SEQ ID NO:76 and SEQ ID NO:77.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:14, SEQ ID NO:16, SEQ ID NO:21, and SEQ ID NOs:80-82.

In one aspect the disclosure provides compositions comprising two or more purified bacterial strains, wherein the two or more purified bacterial strains comprise 16S rDNA sequences having at least 97% homology with nucleic acid sequences selected from the group consisting of SEQ ID NOs:84-123.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:97, SEQ ID NO:98, SEQ ID NO:99, SEQ ID NO:101, SEQ ID NO:102, SEQ ID NO:103, SEQ ID NO:105, SEQ ID NO:106, SEQ ID NO:108, SEQ ID NO:109, SEQ ID NO:110, SEQ ID NO:121, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:88, SEQ ID NO:89, SEQ ID NO:99, SEQ ID NO:103, SEQ ID NO:105, SEQ ID NO:106, SEQ ID NO:108, SEQ ID NO:109, and SEQ ID NO:121.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:102, SEQ ID NO:106, SEQ ID NO:110, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:95, SEQ ID NO:97, SEQ ID NO:98, SEQ ID NO:102, SEQ ID NO:106, SEQ ID NO:110, and SEQ ID NO:122, and wherein the composition does not include a bacterial strain comprising a 16S rDNA sequence having at least 97% homology with a nucleic acid sequence of SEQ ID NO:93.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:101, SEQ ID NO:102, SEQ ID NO:106, SEQ ID NO:110, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:95, SEQ ID NO:97, SEQ ID NO:98, SEQ ID NO:101, SEQ ID NO:102, SEQ ID NO:106, SEQ ID NO:110, and SEQ ID NO:122, and wherein the composition does not include a bacterial strain comprising a 16S rDNA sequence having at least 97% homology with a nucleic acid sequence of SEQ ID NO:93.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:93, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:87, SEQ ID NO:90, SEQ ID NO:91, SEQ ID NO:93, SEQ ID NO:94, SEQ ID NO:95, SEQ ID NO:97, SEQ ID NO:98, SEQ ID NO:99, and SEQ ID NO:105.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:100, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, and SEQ ID NO:120.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, and SEQ ID NO:119.

In some embodiments of the compositions provided herein, the composition comprises two or more purified bacterial strains, wherein the two or more purified bacterial strains comprise 16S rDNA sequences having at least 97% homology with nucleic acid sequences selected from the group consisting of SEQ ID NO:86, SEQ ID NO:95, SEQ ID NO:98, SEQ ID NO:110, SEQ ID NO:122, and SEQ ID NO:123.

In some embodiments of the compositions provided herein, the composition comprises at least one bacterial strain from *Clostridium* cluster XIVa and at least one bacterial strain from *Clostridium* cluster XVII. In some embodiments of the compositions provided herein, the composition comprises at least one bacterial strain from *Clostridium* cluster IV and at least one bacterial strain from *Clostridium* cluster XVII. In some embodiments of the compositions provided herein, the composition comprises at least one bacterial strain from *Clostridium* cluster XIVa, at least one strain from *Clostridium* cluster IV and at least one bacterial strain from *Clostridium* cluster XVII.

In some embodiments of the compositions provided herein, the composition comprises at least one *Bacteroides* strain. In some embodiments of the compositions provided herein, the composition does not include *Clostridium scindens*.

In some embodiments of the compositions provided herein, the composition comprises at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 purified bacterial strains.

In some embodiments of the compositions provided herein, one or more of the bacterial strains are spore formers. In some embodiments of the compositions provided herein, one or more of the bacterial strains are in spore form. In some embodiments of the compositions provided herein, each of the bacterial strains is in spore form.

In some embodiments of the compositions provided herein, one or more of the bacterial strains is in vegetative form. In some embodiments of the compositions provided herein, each of the bacterial strains is in vegetative form.

In some embodiments of the compositions provided herein, the composition comprises only obligate anaerobic bacterial strains. In some embodiments of the compositions provided herein, the composition comprises bacterial strains that originate from more than one human donor.

In some embodiments of the compositions provided herein, one or more of the bacterial strains are baiCD−. In some embodiments of the compositions provided herein, each of the bacterial strains is baiCD−. In some embodiments of the compositions provided herein, the composition does not mediate bile acid 7-alpha-dehydroxylation. In some embodiments of the compositions provided herein, the composition inhibits *C. difficile* toxin production. In some embodiments of the compositions provided herein, the composition inhibits *C. difficile* replication and/or survival.

In some embodiments of the compositions provided herein, the bacterial strains are lyophilized.

In some embodiments of the compositions provided herein, the composition induces the proliferation and/or accumulation of regulatory T cells (Tregs).

In one aspect, the disclosure provides compositions comprising two or more purified bacterial strains, wherein the composition comprises at least one bacterial strain from *Clostridium* cluster XIVa and at least one bacterial strain from *Clostridium* cluster XVII. In one aspect, the disclosure provides compositions comprising two or more purified bacterial strains, wherein the composition comprises at least one bacterial strain from *Clostridium* cluster IV and at least one bacterial strain from *Clostridium* cluster XVII. In one aspect, the disclosure provides compositions comprising two or more purified bacterial strains, wherein the composition comprises at least one bacterial strain from *Clostridium* cluster IV, at least one bacterial strain from *Clostridium* cluster XIVa and at least one bacterial strain from *Clostridium* cluster XVII.

In some embodiments of the compositions provided herein, the composition comprises at least one *Bacteroides* strain. In some embodiments of the compositions provided herein, the composition does not include *Clostridium scindens*.

In some embodiments of the compositions provided herein, the composition comprises at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 purified bacterial strains.

In some embodiments of the compositions provided herein, one or more of the bacterial strains are spore formers. In some embodiments of the compositions provided herein, one or more of the bacterial strains are in spore form. In some embodiments of the compositions provided herein, each of the bacterial strains is in spore form.

In some embodiments of the compositions provided herein, one or more of the bacterial strains is in vegetative form. In some embodiments of the compositions provided herein, each of the bacterial strains is in vegetative form.

In some embodiments of the compositions provided herein, the composition comprises only obligate anaerobic bacterial strains.

In some embodiments of the compositions provided herein, the composition comprises bacterial strains that originate from more than one human donor.

In some embodiments of the compositions provided herein, one or more of the bacterial strains are baiCD−. In some embodiments of the compositions provided herein, each of the bacterial strains is baiCD−. In some embodiments of the compositions provided herein, the composition does not mediate bile acid 7-alpha-dehydroxylation. In some embodiments of the compositions provided herein, the composition inhibits *C. difficile* toxin production. In some embodiments of the compositions provided herein, the composition inhibits *C. difficile* replication and/or survival.

In some embodiments of the compositions provided herein, the bacterial strains are lyophilized.

In some embodiments of the compositions provided herein, the composition induces the proliferation and/or accumulation of regulatory T cells (Tregs).

In one aspect, the disclosure provides a pharmaceutical composition comprising any of the compositions provided herein further comprising a pharmaceutically acceptable excipient. In some embodiments of the pharmaceutical compositions provided herein, the pharmaceutical composition is formulated for oral delivery. In some embodiments of the pharmaceutical compositions provided herein, the pharmaceutical composition is formulated for rectal delivery. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon.

In one aspect, the disclosure provides a food product comprising any of the compositions provided herein further comprising a nutrient.

In one aspect, the disclosure provides a method of treating a pathogenic infection in a subject, comprising administering to the subject a therapeutically effective amount of any of the compositions or food products provided herein to treat the pathogenic infection.

In some embodiments of the methods provided herein, the pathogenic infection is *C. difficile*, Vancomycin Resistant Enterococci (VRE), Carbapenem Resistant Enterobacteriaceae (CRE), *Neisseria gonorrheae*, Multidrug Resistant *Acinetobacter*, *Campylobacter*, Extended spectrum beta-lactamese (ESBL) producing Enterobacteriaceae, Multidrug Resistant *Pseudomonas aeruginosa*, *Salmonella*, Drug resistant non-typhoid *Salmonella*, Drug resistant *Salmonella typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, Clindamycin resistant Group B *Streptococcus*, and combinations thereof. In some embodiments of the methods provided herein, the pathogenic infection is *C. difficile*. In some embodiments of the methods provided herein, the pathogenic infection is Vancomycin-Resistant Enterococci.

In some embodiments of the methods provided herein, the subject is human. In some embodiments of the methods provided herein, the subject is an asymptotic carrier.

In some embodiments of the methods provided herein, the subject is administered a dose of an antibiotic prior to administration of the composition. In some embodiments of the methods provided herein, the subject is administered more than one dose of the antibiotic prior to administration of the composition. In some embodiments of the methods provided herein, the subject has not been administered an antibiotic prior to administration of the composition.

In some embodiments of the methods provided herein, the composition is administered to the subject by oral administration. In some embodiments of the methods provided herein, the composition is administered to the subject by rectal administration.

In some embodiments of the methods provided herein, the administering results in proliferation and/or accumulation of regulatory T cells (Tregs).

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 1 shows the strains of Compositions A-D. Each entry includes the SEQ ID NO of the 16S rDNA sequence of the strain, a strain identifier, and the species with the closest known homology (can be more than one species). The bracketed roman numeral indicates the *Clostridium* cluster classification of each strain based on the closest species homology. Strains that are not classified in Cluster XIVa are highlighted in bold. The two non-clostridial strains (SEQ ID NO:2, closest known species *Turicibacter sanguinis*, and SEQ ID NO:6, closest known species *Lactobacillus mucosae*) do not belong to the *Clostridium* genus.

FIG. 2 shows various *Clostridium difficile* infection models. Timelines indicate antibiotic type, duration of treatment, as well as exposure to *C. difficile* spores. The top panel shows an antibiotic cocktail treatment model in which the antibiotic cocktail is provided in the drinking water from day −10 to day −3 followed by intraperitoneal clindamycin on day −1. The middle panel shows a clindamycin IP injection model, in which clindamycin is administered by intraperitoneal injection on day −1. The bottom panel shows the cefoperazone treatment model, in which cefoperazone is provided in the drinking water from day −12 to day −2, followed by administration of a live biotherapeutic product (LBP) on day −1.

FIG. 3 shows the experimental conditions described in Example 1. The groups of mice were divided based on the antibiotic regimen received prior to administration of the indicated amount of *C. difficile* spores. "Abx" refers to treatment with any of the antibiotic regimens.

FIGS. 4A-4L show data obtained in Example 1. FIGS. 4A-4D show survival of mice that received no treatment (FIG. 4A), antibiotic cocktail (FIG. 4B), clindamycin (FIG. 4C), or cefoperazone (FIG. 4D) prior to *C. difficile* infection. FIGS. 4E-4H show body weight of mice that received no treatment (FIG. 4E), antibiotic cocktail (FIG. 4F), clindamycin (FIG. 4G), or cefoperazone (FIG. 4H) prior to *C. difficile* infection. FIGS. 4I-4L show *C. difficile* burden (CFU) per gram of feces from mice that received no treatment (FIG. 4I), antibiotic cocktail (FIG. 4J), clindamycin (FIG. 4K), or cefoperazone (FIG. 4L) prior to *C. difficile* infection. Open circles indicate infection with 10 *C. difficile* spores; closed squares indicate infection with 10,000 *C. difficile* spores. Black triangles in FIG. 4J indicate an additional experimental arm in which mice were treated with vancomycin following *C. difficile* infection.

FIG. 5 shows experimental conditions evaluated in Example 2, the results for which are presented in FIGS. 7-9. Composition E corresponds to a mixture of 17 bacterial strains (See e.g., Narushima et al., Gut Microbes 5: 3, 333-339). Composition I corresponds to a mixture of *Clostridium scindens, Pseudoflavonifractor capillosus*, and *Blautia hansenii*. "Abx" refers to treatment with any of the antibiotic regimens.

FIG. 7A shows weight of the mice that received no antibiotic treatment. FIG. 7B shows weight of the mice that received cefoperazone treatment. FIG. 7C shows weight of the mice that received cefoperazone treatment followed by vancomycin. FIG. 7D shows weight of the mice that received cefoperazone treatment followed by Composition I. FIG. 7E shows weight of the mice that received cefoperazone treatment followed by Composition E. FIG. 7F shows weight of the mice that received cefoperazone treatment followed by composition A. FIG. 7G shows weight of the mice that received cefoperazone treatment followed by composition B. FIG. 7H shows weight of the mice that received cefoperazone treatment followed by composition C. FIG. 7I shows weight of the mice that received cefoperazone treatment followed by composition D.

FIGS. 8A-8C show the load of *C. difficile* in colony forming units (CFUs) in fecal pellets at various times post infection with *C. difficile*. FIG. 8A shows *C. difficile* CFU/g feces one-day post infection. FIG. 8B shows *C. difficile* CFU/g feces 3 days post infection. FIG. 8C shows *C. difficile* CFU/g feces 8 days post infection.

FIG. 9 shows experimental conditions evaluated in Example 3, the results for which are presented in FIGS. 10-12.

FIG. 12 shows the *C. difficile* burden in colony forming units (CFUs) in fecal pellets collected from mice 1, 3, and 8 days post infection with *C. difficile*.

FIG. 13 shows the strains of Composition F. The genus-species notation indicates the closest species based on the sequence of the isolated strain.

FIG. 14 shows the classification by *Clostridium* cluster of the strains in Composition F and their short-chain fatty acid producing abilities.

FIG. 15 shows experimental conditions evaluated in Example 4, the results for which are presented in FIGS. 16-18. The dosing days are relative to *C. difficile* infection. FMT refers to Fecal Matter Transplant with fecal matter isolated from mice or from humans.

FIG. 16 shows survival of the mice over time post infection with *C. difficile* spores, according to the experimental conditions shown in FIG. 15. Mice losing >20% body weight of baseline were included in mortality numbers in survival curves.

FIGS. 17A-17H show weight of the mice at various times post infection with *C. difficile* spores. Groups of mice received cefoperazone (Abx) treatment followed by the indicated composition, then were administered *C. difficile* spores. FIG. 17A shows weight of the mice that received cefoperazone treatment. FIG. 17B shows weight of the mice that received cefoperazone treatment followed by FMT with fecal matter from a human. FIG. 17C shows weight of the mice that received cefoperazone treatment followed by FMT with fecal matter from a mouse. FIG. 17D shows weight of the mice that received cefoperazone treatment followed by Composition B on day −1. FIG. 17E shows weight of the mice that received cefoperazone treatment followed by Composition B on days −2 and −1. FIG. 17F shows weight of the mice that received cefoperazone treatment followed by Composition B on days −2, −1, 1, 2, and 3. FIG. 17G shows weight of the mice that received cefoperazone treatment followed by Composition F on day −1. FIG. 17H shows weight of the mice that received cefoperazone treatment followed by Composition F on days −2, −1, 1, 2, and 3.

FIGS. 18A-18B show the load of *C. difficile* in colony forming units (CFUs) in fecal pellets at various times post infection with *C. difficile*. FIG. 18A shows *C. difficile* CFU/g feces 8 days post infection. FIG. 18B shows *C. difficile* CFU/g feces 17 days post infection.

FIG. 19 shows the strains of Composition G. The genus-species notation indicates the closest species based on the sequence of the isolated strain.

FIG. 20 shows experimental conditions evaluated in Example 5, the results for which are presented in FIGS. 21-23. Composition B1=Composition B with *Bacteroides*; Composition B2=Composition B with *Bacteroides* but without *Flavonifractor plautii*.

FIG. 22A shows weight of the mice that received vehicle control. FIG. 22B shows weight of the mice that received Composition F. FIG. 22C shows weight of the mice that received Composition G. FIG. 22D shows weight of the mice that received cefoperazone treatment followed by Composition B. FIG. 22E shows weight of the mice that received cefoperazone treatment followed by Composition B2 (=Composition B without *Flavonifractor plautii* and with added *Bacteroides*). FIG. 22F shows weight of the mice that received cefoperazone treatment followed by Composition B1 (=Composition B with *Bacteroides* added). FIG. 22G shows weight of the mice that received cefoperazone treatment followed by frozen Composition B. FIG. 22H shows weight of the mice that received cefoperazone treatment followed by ethanol treated human fecal samples. FIG. 22I shows weight of the mice that received cefoperazone treatment followed by ethanol treated Composition B. FIG. 22J shows weight of the mice that received cefoperazone treatment followed by Composition J.

FIG. 25 shows experimental conditions evaluated in Example 6, the results of which are presented in FIGS. 27-29.

FIG. 26 shows the strains in Composition H (SEQ ID NO:14—VE202-13—*Anaerotruncus colihominis* (Cluster IV); SEQ ID NO:16—VE202-16—*Clostridium symbiosum* (Cluster XIVa); SEQ ID NO:21-189—*Clostridium innocuum* (Cluster XVII); SEQ ID NO:82—PE9—*Clostridium disporicum* (Cluster I); SEQ ID NO:81—PE5—*Clostridium bolteae* (Cluster XIVa); SEQ ID NO:80—VE202-18—*Erysipelatoclostridium ramosum* (Cluster XVIII).

FIG. 28A shows survival/mortality of mice that received the indicated treatment prior to *C. difficile* infection. FIG. 28B shows the weight over time of mice that received the indicated treatment prior to *C. difficile* infection.

FIGS. 29A and 29B show the *C. difficile* burden in CFU/gram feces collected from mice that received the indicated treatment prior to *C. difficile*. FIG. 29A shows *C. difficile* burden at one-day post *C. difficile* infection. FIG. 29B shows *C. difficile* burden at 4 days post *C. difficile* infection.

FIG. 30 shows that Composition B reduced the amount of *C. difficile* Toxin B compared to no treatment controls: "2-1 (Cdiff)" and "2-4 (Cdiff)" and FMT. In addition, Composition B reduced the amount of *C. difficile* Toxin B compared to Composition B with additional spores.

DETAILED DESCRIPTION OF THE INVENTION

Figure 4I:
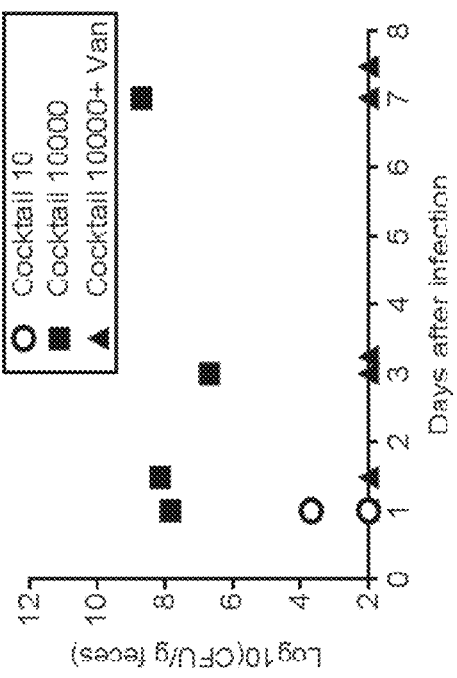

Disclosed herein are compositions comprising purified bacterial strains and pharmaceutical compositions and food products containing such compositions and bacterial strains. Also disclosed are methods of treating a pathogenic infection, such as *Clostridium difficile* (*C. difficile*) infection, in a subject by administering said compositions to the subject.

Various factors including antibiotic usage can induce dysbiosis of the gastrointestinal tract, which may allow for colonization by pathogenic microorganisms, such as *C. difficile*. Such colonization or pathogenic infection can lead to a variety of adverse effects in the subject including diarrhea, which is one of the primary symptoms characteristic of *C. difficile* infection (CDI). In the case of CDI, diarrhea is thought to be a result of *C. difficile* production of Toxin B (also referred to as cytotoxin TcdB), which results in opening of the tight junctions between intestinal epithelial cells, increasing vascular permeability, hemorrhage, and inflammation.

The compositions described herein are effective in the treatment of *C. difficile* infection. As shown herein, the disclosed compositions are effective in suppressing the pathogenic effects of *C. difficile* infection. The compositions provided herein reduce the amount of *C. difficile* after infection and thereby provide an effective method for eliminating *C. difficile* from the body (e.g., the gut). The compositions provided herein induce the proliferation and/or accumulation of regulatory T cells (Tregs), for example when administered to a subject. Remarkably, the compositions disclosed herein have been found to reduce or inhibit production or activity of *C. difficile* Toxin B and thereby represent effective compositions for the treatment or prevention of CDI. The compositions disclosed herein have also been found to inhibit the growth and/or survival of *C. difficile*.

The present disclosure provides compositions comprising purified bacterial strains that can be administered to subjects experiencing or having experienced a pathogenic infection to treat the infection. In some embodiments, the compositions may be administered to subjects who may be at risk for a pathogenic infection. Such subjects include subjects who previously had pathogenic infections, subjects who have been treated with antibiotics and subjects who will undergo a procedure that will put them at an increased risk for a pathogenic infection (e.g., surgery and/or hospitalization). In some embodiments, the pathogenic infection, is infection by a pathogen that is present predominantly in the gut or the intestine. In some embodiments, the pathogen that is present predominantly in the gut or the intestine is *Clostridium difficile*.

In some embodiments, the one or more of the bacterial strains of the compositions provided herein colonize or recolonize the intestinal tract or parts of the intestinal tract (e.g., the colon or the cecum) of the subject. Such colonization or recolonization may also be referred to as grafting. In some embodiments, the one or more of the bacterial strains of the compositions recolonize the intestinal tract (e.g., the colon or the cecum) of the subject after the naturally present microbiome has been partially or completely removed, e.g., because of administration of antibiotics. In some embodiments, the one or more of the bacterial strains of the compositions colonize a dysbiotic gastrointestinal tract.

In some embodiments, the one or more of the bacterial strains of the compositions can "outgrow" a pathogen, such as *C. difficile*. Thus, in some embodiments, if a pathogen (e.g., *C. difficile*) and one or more bacteria of compositions provided herein are both present in the intestinal tract (e.g., the colon or the cecum), the one or more bacteria of compositions provided herein grow faster (e.g., have a shorter doubling time) than the pathogen, thereby preventing the pathogen from accumulating in the intestinal tract (e.g., the colon or the cecum). In some embodiments, the faster growth results because the one or more bacteria of the compositions provided herein are better at grafting in the intestinal tract (e.g., the colon or the cecum). In some embodiments, the faster growth results because the one or more bacteria of the compositions provided herein are better at metabolizing nutrients present in the intestinal tract (e.g., the colon or the cecum). In some embodiments, the compositions of bacterial strains provided herein prevent or inhibit production of bacterial toxins by the pathogenic infection, or prevent or inhibit the cytopathic or cytotoxic effects of such bacterial toxins. In some embodiments, the bacterial strains of the compositions provided herein can treat pathogenic infections, because of the synergy between the bacterial strains. Thus, without being limiting, in some embodiments, the combination of the bacterial strains of the compositions provided herein act synergistically because the combination of the strains is particularly well-suited to use nutrients in the intestinal tract (e.g., the colon or the cecum), or instance through metabolic interactions, and/or because the combination is superior in grafting (e.g., by providing a favorable microenvironment).

In some embodiments, a pathogenic infection such as *C. difficile* is treated because the combination of bacterial strains of the compositions provided herein is superior in the use of nutrients when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein is superior in the use of nutrients and in grafting when compared to the pathogen such as *C. difficile*, thereby suppressing the growth of the pathogen such as *C. difficile*. In some embodiments, a pathogenic infection such as *C. difficile* is treated because the combination of bacterial strains of the compositions provided herein inhibits the growth and/or survival of the pathogen such as *C. difficile*. In some embodiments, a pathogenic infection such as *C. difficile* is treated because the combination of bacterial strains of the compositions provided herein induces regulatory T cells (Tregs) in the subject that results in reduction or elimination of the pathogen such as *C. difficile*. In some embodiments, a pathogenic infection such as *C. difficile* is treated because the combination of bacterial strains of the compositions provided herein inhibits the growth and/or survival of the pathogen and induces regulatory T cells (Tregs) in the subject that results in reduction or elimination of the pathogen such as *C. difficile*.

In some embodiments, the synergistic effect is provided by the capacity of the combination to colonize specific niches in the intestinal tract (e.g., the colon or the cecum). In some embodiments, the synergistic effect is provided by the capacity of the combination to metabolize specific nutrients. In some embodiments, the synergistic effect is provided by the capacity of the combination to provide specific metabolites to the environment. Such specific metabolites may suppress growth of the pathogen and/or stimulate growth of non-pathogens. In some embodiments, the synergistic effect is provided by the capacity of the combination to provide short-chain fatty acids to the environment. In some embodiments, the synergistic effect is provided by the capacity of the combination to provide specific short-chain fatty acids to the environment. In some embodiments, the synergistic effect is provided by the capacity of the combination to produce butyrate. In some embodiments, the synergistic effect is provided by the capacity of the combination to produce acetate. In some embodiments, the synergistic effect is provided by the capacity of the combination to produce lactate. In some embodiments, the synergistic effect is provided by the capacity of the combination to produce propionate. In some embodiments, the synergistic effect is provided by the capacity of the combination to produce succinate. In some embodiments, the synergistic effect is provided by the capacity of the combination to produce multiple metabolites. In some embodiments, the synergistic effect is provided by the capacity of the combination to produce multiple short-chain fatty acids. In some embodiments, the synergistic effect is provided by the capacity of the combination to produce both butyrate and acetate. In some embodiments, the synergistic effect is provided by the capacity of the combination to produce both butyrate and lactate. In some embodiments, the synergistic effect is provided by the capacity of the combination to produce both butyrate and propionate. In some embodiments, the synergistic effect is provided by the capacity of the combination to produce both butyrate and succinate. In some embodiments, the synergistic effect is provided by the capacity of the combination to produce butyrate, acetate and additional short-chain fatty acids.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments, the bacteria of the compositions provided herein are anaerobic bacteria. In some embodiments, the bacteria of the compositions provided herein are obligate anaerobic bacteria. In some embodiments, the bacteria of the compositions provided herein are clostridia. Clostridia may be classified into phylogenetic clusters with other closely related strains and species. (See e.g., Rajilic-Stojanovic, M., and de Vos, W. M. *FEMS Microbiol Rev* 38, (2014) 996-1047). In general, clostridia are classified as belonging to a specific cluster based on their 16S rRNA (or 16S rDNA) nucleic acid sequence. Methods for determining the identity of specific bacterial species based on their 16S rRNA (or 16S rDNA) nucleic acid sequence are well known in the art (See e.g., *Jumpstart Consortium Human Microbiome Project Data Generation Working, G. PLoS One* (2012) 7, e39315).

Provided herein are compositions comprising bacterial strains belonging to specific *Clostridium* clusters that have been found to be effective in treating and/or preventing pathogenic infection (e.g., *C. difficile* infection). In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster XVII. In some embodiments, at least one of the bacterial strains of the composition belongs to *Clostridium* cluster I. In some embodiments, at least one of the bacterial strains of the composition belongs to *Clostridium* cluster IX. In some embodiments, at least one of the bacterial strains of the composition belongs to *Clostridium* cluster XIVa and at least one of the bacterial strains belongs to *Clostridium* cluster XVII. In some embodiments, at least one of the bacterial strains of the composition belongs to *Clostridium* cluster IV and at least one of the bacterial strains belongs to *Clostridium* cluster XVII. In some embodiments, at least one of the bacterial strains of the composition belongs to *Clostridium* cluster IV, at least one of the bacterial strains belongs to *Clostridium* cluster XIVa, and at least one of the bacterial strains belongs to *Clostridium* cluster XVII.

In some embodiments, the composition has at least twice as many bacterial strains that belong to *Clostridium* cluster XIVa when compared to the bacterial strains that belong to *Clostridium* cluster IV. In some embodiments, at least two of the bacterial strains of the composition belong to *Clostridium* cluster IV and at least five of the bacterial strains belong to *Clostridium* cluster XIVa. In some embodiments, the composition has at least twice as many bacterial strains that belong to *Clostridium* cluster XIVa when compared to the bacterial strains that belong to *Clostridium* cluster IV, and the composition has at least one strain that belongs to *Clostridium* cluster XVII. In some embodiments, at least two of the bacterial strains of the composition belong to *Clostridium* cluster IV, at least five of the bacterial strains belongs to *Clostridium* cluster XIVa, and at least one of the bacterial strains belongs to *Clostridium* cluster XVII.

In some embodiments, the compositions provided herein do not include bacterial strains belonging to *Clostridium* cluster XVIII. In some embodiments, the compositions provided herein do not include bacterial strains belonging to *Clostridium* cluster XVI. In some embodiments, the compositions provided herein do not include bacterial strains belonging to *Clostridium* cluster XI. In some embodiments, the compositions provided herein do not include bacterial strains belonging to *Clostridium* cluster I.

In one aspect, the disclosure provides bacterial strains comprising a 16S rDNA sequence with a nucleic acid sequence selected from the group consisting of SEQ ID NOs: 1-83 and 124-159. It should be appreciated that SEQ ID NOs: 1-83 and 124-159 may include both full length and partial 16S rDNA sequences.

In one aspect, the disclosure provides compositions comprising a bacterial strain comprising a 16S rDNA sequence with a nucleic acid sequence selected from the group consisting of SEQ ID NOs: 1-83 and 124-159. In one aspect, the disclosure provides compositions comprising as an active ingredient a bacterial strain comprising a 16S rDNA sequence with a nucleic acid sequence selected from the group consisting of SEQ ID NOs: 1-83 and 124-159. It should be appreciated that for all compositions provided herein, in some embodiments, the bacterial strain or the bacterial strains are the active ingredient of the composition.

It should be appreciated that for all compositions provided herein, in some embodiments, the bacterial strains are purified. Thus, for example the disclosure provides purified bacterial strains comprising a 16S rDNA sequence with a nucleic acid sequence selected from the group consisting of SEQ ID NOs: 1-83 and 124-159. In addition, for example, the disclosure provides compositions comprising purified bacterial strains comprising a 16S rDNA sequence with a nucleic acid sequence selected from the group consisting of SEQ ID NOs: 1-83 and 124-159. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides compositions comprising one or more bacterial strains, wherein the one or more bacterial strains comprise a 16S rDNA sequence with a nucleic acid sequence selected from the group consisting of SEQ ID NOs:1-83 and 124-159. In one aspect, the disclosure provides compositions comprising one or more bacterial strains wherein the one or more bacterial strains comprise 16S rDNA sequences having at least 97% homology with nucleic acid sequences selected from the group consisting of SEQ ID NOs:1-83 and 124-159. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% homology with nucleic acid sequences selected from the group consisting of SEQ ID NOs:1-83 and 124-159.

In one aspect, the disclosure provides compositions comprising two or more purified bacterial strains wherein the two or more purified bacterial strains comprise 16S rDNA sequences having at least 97% homology with nucleic acid sequences selected from the group consisting of SEQ ID NOs:1-83 and 124-159. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% homology with nucleic acid sequences selected from the group consisting of SEQ ID NOs:1-83 and 124-159.

In one aspect, the disclosure provides bacterial strains and combinations of bacterial strains that are homologous or have a high percent of homology with bacterial strains comprising 16S rDNA sequences selected from the group consisting of SEQ ID NOs:1-83 and 124-159. As discussed previously, in some embodiments, the bacterial strains are purified. The bacterial strains disclosed herein that have a 16S rDNA sequence with a nucleic acid sequence selected from the group consisting of SEQ ID NOs:1-83 and 124-159 have a high percent of homology (e.g., greater than 90%) with 16S rDNA sequences of bacterial strains that have been described in various databases (See e.g., the National Center for Biotechnology Information). Table 1 and Table 3 provides the closest known species by homology when the 16S rDNA sequences comprising SEQ ID NOs:1-83 and 124-159 are compared to 16S rDNA sequences of bacterial species available in public databases. By way of example, the bacterial strain comprising a 16S rDNA sequence with SEQ ID NO:1 (also referred to herein as "Strain 71") disclosed herein has the highest homology with a bacterial strain of the species *Blautia wexlerae* as defined by Accession #NR_044054 (having 16S rDNA sequence SEQ ID NO:94). While the bacterial strain with SEQ ID NO:1 has homology with other published bacterial strains as well, the highest homology is with a bacterial strain of the species *Blautia wexlerae* as defined by Accession #NR_044054. In this particular example the homology of SEQ ID NO:1 is 96.6% with SEQ ID NO:94 (corresponding to *Blautia wexlerae*). It should be appreciated that multiple bacterial strains disclosed herein may have the highest homology with the same species. (e.g., both SEQ ID NO:4 and SEQ ID NO:5 have the highest homology with a 16S rDNA sequence of a strain of the species *Blautia hansenii*).

It should further be appreciated that the bacterial strains disclosed herein that have a 16S rDNA sequence with a nucleic acid sequence selected from the group consisting of SEQ ID NOs:1-83 and 124-159, are also homologous to other strains based on their whole genome sequence, or subset of their whole genome sequence. Homologies based on whole genome analysis are provided in Table 2 and Table 3.

In one aspect, the disclosure provides compositions comprising one or more bacterial strains wherein the one or more bacterial strains are of species selected from the group consisting of *Clostridium hathewayi*, *Blautia hansenii*, *Blautia producta*, *Blautia producta* ATCC 27340, *Clostridium bacterium* UC5.1-1D4, *Blautia coccoides*, *Eubacterium contortum*, *Eubacterium fissicatena*, *Sellimona intestinalis*, *Dracourtella massiliensis*, *Dracourtella massiliensis* GD1, *Ruminococcus torques*, *Anaerostipes caccae*, *Clostridium scindens*, *Marvinbryanta formatexigens*, *Eisenbergiella tayi*, *Flavinofractor plautii*, *Clostridium orbiscindens* 1_3_50 AFAA, *Lachnospiraceae bacterium* 7_1_58 FAA, *Subdoligranulum*, *Anaerotruncus colihominis*, *Anaerotruncus colihominis* DSM 17241, *Clostridium symbiosum*, *Clostridium symbiosum* WAL-14163, *Clostridium bolteae*, *Clostrdium bolteae* 90A9, *Dorea longicatena*, *Dorea longicatena* CAG:42, *Clostridium innocuum*, *Erysipelotrichaceae_bacterium_21-3*, *Blautia wexlerae*, *Clostridium disporicum*, *Erysipelatoclostridium ramosum*, *Pseudoflavinofractor capillosus*, *Turicibacter sanguinis*, *Lactobacillus mucosae*, *Ruminococcus obeum*, *Megasphaera elsdenii*, *Acidaminococcus fermentans*, *Acidaminococcus intestine*, *Ruminococcus faecis*, *Bacteroides cellulosilyticus*, *Anaerostipes hadrus*, *Eubacterium rectale*, *Ruminococcus champanellensis*, *Ruminococcus albus*, *Bifidobacterium bifidum*, *Blautia luti*, *Roseburia faecis*, *Fusicatenibacter saccharivorans*, *Roseburia faecis*, *Blautia faecis*, *Dorea formicigenerans* and *Bacteroides ovatus*.

In some embodiments, the disclosure provides compositions comprising two or more bacterial strains, wherein the two or more bacterial strains are of species selected from the group consisting of *Clostridium hathewayi*, *Blautia hansenii*, *Blautia producta*, *Blautia producta* ATCC 27340, *Clostridium bacterium* UC5.1-1D4, *Blautia coccoides*, *Eubacterium contortum*, *Eubacterium fissicatena*, *Sellimona intestinalis*, *Dracourtella massiliensis*, *Dracourtella massiliensis* GD1, *Ruminococcus torques*, *Anaerostipes caccae*, *Clostridium scindens*, *Marvinbryanta formatexigens*, *Eisenbergiella tayi*, *Flavinofractor plautii*, *Clostridium orbiscindens* 1_3_50 AFAA, *Lachnospiraceae bacterium* 7_1_58 FAA, *Subdoligranulum*, *Anaerotruncus colihominis*, *Anaerotruncus colihominis* DSM 17241, *Clostridium symbiosum*, *Clostridium symbiosum* WAL-14163, *Clostridium bolteae*, *Clostrdium bolteae* 90A9, *Dorea longicatena*, *Dorea longicatena* CAG:42, *Clostridium innocuum*, *Erysipelotrichaceae_bacterium_21-3*, *Blautia wexlerae*, *Clostridium disporicum*, *Erysipelatoclostridium ramosum*, *Pseudoflavinofractor capillosus*, *Turicibacter sanguinis*, *Lactobacillus mucosae*, *Ruminococcus obeum*, *Megasphaera elsdenii*, *Acidaminococcus fermentans*, *Acidaminococcus intestine*, *Ruminococcus faecis*, *Bacteroides cellulosilyticus*, *Anaerostipes hadrus*, *Eubacterium rectale*, *Ruminococcus champanellensis*, *Ruminococcus albus*, *Bifidobacterium bifidum*, *Blautia luti*, *Roseburia faecis*, *Fusicatenibacter saccharivorans*, *Roseburia faecis*, *Blautia faecis*, *Dorea formicigenerans* and *Bacteroides ovatus*.

It should be appreciated that the compositions may include multiple strains of a particular species. Thus, for illustration, a non-limiting example of the compositions disclosed herein, comprises one strain of *Clostridium hathewayi* and two strains of *Blautia hansenii*.

The invention also encompasses compositions comprising bacterial strains that are close in homology to and/or fall within the species *Clostridium hathewayi*, *Blautia hansenii*,

*Blautia producta, Blautia producta* ATCC 27340, Clostridia bacteria UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50 AFAA, *Lachnospiraceae bacterium* 7_1_58 FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium*_21-3, *Blautia wexlerae, Clostridium disporicum, Erysipelatoclostridium ramosum, Pseudoflavinofractor capillosus, Turicibacter sanguinis, Lactobacillus mucosae, Ruminococcus obeum, Megasphaera elsdenii, Acidaminococcus fermentans, Acidaminococcus intestine, Ruminococcus faecis, Bacteroides cellulosilyticus, Anaerostipes hadrus, Eubacterium rectale, Ruminococcus champanellensis, Ruminococcus albus, Bifidobacterium bifidum, Blautia luti, Roseburia faecis, Fusicatenibacter saccharivorans, Roseburia faecis, Blautia faecis, Dorea formicigenerans* and *Bacteroides ovatus*. Thus, in one embodiment, the compositions of the disclosure include one or more bacterial strains comprising 16S rDNA sequences having at least 97% homology with nucleic acid sequences selected from the group consisting of SEQ ID NOs: 84-123. In some embodiments, the compositions of the disclosure include two or more bacterial strains comprising 16S rDNA sequences having at least 97% homology with nucleic acid sequences selected from the group consisting of SEQ ID NOs:84-123.

In one aspect, the compositions of the disclosure include two or more purified bacterial strains comprising 16S rDNA sequences having at least 97% homology with nucleic acid sequences selected from the group consisting of SEQ ID NOs:1-23 and 124-159. In some embodiments, the compositions of the disclosure include two or more bacterial strains of species selected from the group consisting of *Clostridium hathewayi, Blautia hansenii, Blautia producta, Blautia producta* ATCC 27340, Clostridia bacteria UC5.1-1D4, *Blautia coccoides, Eubacterium contortum, Eubacterium fissicatena, Sellimona intestinalis, Dracourtella massiliensis, Dracourtella massiliensis* GD1, *Ruminococcus torques, Anaerostipes caccae, Clostridium scindens, Marvinbryanta formatexigens, Eisenbergiella tayi, Flavinofractor plautii, Clostridium orbiscindens* 1_3_50 AFAA, *Lachnospiraceae bacterium* 7_1_58 FAA, *Subdoligranulum, Anaerotruncus colihominis, Anaerotruncus colihominis* DSM 17241, *Clostridium symbiosum, Clostridium symbiosum* WAL-14163, *Clostridium bolteae, Clostrdium bolteae* 90A9, *Dorea longicatena, Dorea longicatena* CAG:42, *Clostridium innocuum, Erysipelotrichaceae_bacterium*_21-3, *Blautia wexlerae, Turicibacter sanguinis, Lactobacillus mucosae*, and *Bacteroides ovatus*. In some embodiments, the compositions of the disclosure include two or more purified bacterial strains comprising 16S rDNA sequences having at least 97% homology with nucleic acid sequences selected from the group consisting of SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:97, SEQ ID NO:98, SEQ ID NO:99, SEQ ID NO:102, SEQ ID NO:103, SEQ ID NO:105, SEQ ID NO:106, SEQ ID NO:108, SEQ ID NO:109, SEQ ID NO:110, SEQ ID NO:121, and SEQ ID NO:122.

In one aspect, the disclosure provides Composition A (See e.g., FIG. 1, Table A). As shown in FIG. 1, Composition A contains bacterial strains that comprise 16S rDNA sequences with nucleic acid sequences: SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with two or more purified bacterial strains that comprise 16S rDNA sequences with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with five or more purified bacterial strains that comprise 16S rDNA sequences with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with at least ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition consisting of ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition essentially consisting of ten purified bacterial strains, wherein the bacterial strains comprise 16S rDNA sequences with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. As used herein, essentially consisting of refers to a composition that includes no additional bacterial strains.

In some embodiments, the disclosure provides compositions with bacterial strains that comprise 16S rDNA sequences having at least 97% homology with nucleic acid sequences selected from the group consisting of: SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with two or more purified bacterial strains that comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with five or more purified bacterial strains that comprise 16S rDNA having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the disclosure provides compositions with at least ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition consisting of ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively. In some embodiments, the disclosure provides a composition essentially consisting of ten purified bacterial strains, wherein the bacterial strains comprise 16S rDNA sequences having at least 97% homology with nucleic acid sequences SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, respectively.

The bacterial strains in Composition A are related to the following bacterial species: *Clostridium hathewayi, Blautia hansenii, Blautia producta, Blautia coccoides, Eubacterium contortum, Eubacterium fissicatena, Anaerostipes caccae, Clostridium scindens, Marvinbryanta formatexigens*, and *Eisenbergiella tayi* (See e.g., Table 1). It should be appreciated that multiple bacterial strains of the compositions disclosed herein can have the same related bacterial species. For instance, the bacterial strains having 16S rDNA sequences with nucleic acid sequences SEQ ID NO:4, SEQ ID NO:5 and SEQ ID NO:7 all have *Blautia hansenii* as related species. In some embodiments, the disclosure provides compositions with two or more bacteria of species selected from the group consisting of *Clostridium hathewayi, Blautia hansenii, Blautia producta, Blautia coccoides, Eubacterium contortum, Eubacterium fissicatena, Anaerostipes caccae, Clostridium scindens, Marvinbryanta formatexigens*, and *Eisenbergiella tayi*. In some embodiments, the disclosure provides compositions with two or more purified bacterial strains comprising 16S rDNA sequences having at least 97% homology with nucleic acid sequences selected from the group consisting of SEQ ID NO:87, SEQ ID NO:88, SEQ ID NO:89, SEQ ID NO:99, SEQ ID NO:103, SEQ ID NO:105, SEQ ID NO:106, SEQ ID NO:108, SEQ ID NO:109, and SEQ ID NO:121.

In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:5, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:5, SEQ ID NO:7, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:7, SEQ ID NO:8, SEQ ID NO:9, SEQ ID NO:11, SEQ ID NO:12, SEQ ID NO:13, and SEQ ID NO:23. In some embodiments, the composition comprises two or more purified bacterial strains comprising 16S rDNA sequences having at least 97% homology with nucleic acid sequences selected from the group consisting of SEQ ID NO:3, SEQ ID NO:4, SEQ ID NO:5; SEQ ID NO:7, SEQ ID NO:8, and SEQ ID NO:13.

Each of the bacterial strains of Composition A are BaiCD+, meaning that the bacterial strains encode, or are predicted to encode, the bile inducible operon gene BaiCD and/or a protein with stereospecific NAD(H)-dependent 3-oxo-$\Delta^4$-cholenoic acid oxidoreductase activity. The BaiCD status of a bacterial strain can be determined for instance by PCR (See e.g., Wells et al. *Clin Chim Acta* (2003) May; 331(1-2):127-34). Furthermore, each of the strains of Composition A are classified as belonging to *Clostridium* cluster XIVa. In some embodiments, the disclosure provides compositions comprising two or more bacterial strains, wherein the bacterial strains are BaiCD+ strains. In some embodiments, the disclosure provides compositions comprising two or more bacterial strains, wherein the bacterial strains are BaiCD+ and belong to *Clostridium* cluster XIVa. In some embodiments of the compositions comprising two or more bacterial strains that are BaiCD+ strains and that belong to *Clostridium* cluster XIVa, the compositions do not include bacterial strains that belong to *Clostridium* cluster IV.

In some embodiments, the disclosure provides compositions with two or more purified bacterial strains that comprise 16S rDNA sequences having at least 97% homology with nucleic acid sequences selected from the group consisting of SEQ ID NO:3, SEQ ID NO:4, SEQ ID NO:5, SEQ ID NO:7, SEQ ID NO:8, SEQ ID NO:9, SEQ ID NO:11, SEQ ID NO:12, SEQ ID NO:13, and SEQ ID NO:23, wherein all the bacterial strains belong to *Clostridium* cluster XIVa.

TABLE A

Composition A

SEQ_03 - 5 - *Clostridium_hathewayi* (XIVa)*
SEQ_04 - 7 - *Blautia_hansenii* (XIVa)*
SEQ_05 - 10 - *Blautia_hansenii* (XIVa)*
SEQ_07 - 59 - *Blautia_producta/Blautia_coccoides* (XIVa)
SEQ_08 - 79 - *Blautia_hansenii* (XIVa)*
SEQ_09 - VE202-21 - *Eubacterium_contortum/Eubacterium_fissicatena* (XIVa)*
SEQ_11 - VE202-9 - *Anaerostipes_caccae* (XIVa)*
SEQ_12 - VE202-26 - *Clostridium_scindens* (XIVa)*
SEQ_13 - 136 - *Marvinbryantia_formatexigens* (XIVa)*
SEQ_23 - VE202-29 - *Eisenbergiella_tayi* (XIVa)*

*= BaiCD+

In one aspect, the disclosure provides Composition B (See e.g., FIG. 1, Table B). As shown in FIG. 1, Composition B contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include two or more purified bacterial strains comprising 16S rDNA sequences with nucleic acid sequences selected from the group consisting of SEQ ID NOs: 124-159. In some embodiments, the compositions include two or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include five or more purified bacterial strains comprising 16S rDNA sequences with nucleic acid sequences selected from the group consisting of SEQ ID NOs: 124-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include at least eight purified bacterial strains comprising 16S rDNA sequences with nucleic acid sequences selected from the group consisting of SEQ ID NOs: 124-159, respectively. In some embodiments, the compositions include at least eight purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of eight purified bacterial strains comprising 16S rDNA sequences with nucleic acid sequences selected from the group consisting of SEQ ID NOs:124-159, respectively. In some embodiments, the compositions consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition essentially consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of at least eight purified bacterial strains comprising 16S rDNA sequences with nucleic acid sequences selected from the group consisting of SEQ ID NOs:124-159, respectively. In some embodiments, the composition essentially consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the compositions include eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include eight purified bacterial strains comprising 16S rDNA sequences with nucleic acid sequences selected from the group consisting of SEQ ID NOs: 124-159, respectively. In some embodiments, the compositions include eight purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of eight purified bacterial strains comprising 16S rDNA sequences with nucleic acid sequences selected from the group consisting of SEQ ID NOs:124-159, respectively. In some embodiments, the compositions consists of eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition essentially consists of eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of eight purified bacterial strains comprising 16S rDNA sequences with nucleic acid sequences selected from the group consisting of SEQ ID NOs:124-159, respectively. In some embodiments, the composition essentially consists of eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-159. In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In one aspect, the disclosure provides a composition that contains bacterial strains that comprise 16S rDNA sequences with nucleic acid sequences: SEQ ID NOs: 124-159. In one aspect, the disclosure provides a composition that contains bacterial strains that comprise 16S rDNA sequences with nucleic acid sequences: SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159. In some embodiments, the compositions include two or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include two or more purified bacterial strains comprising 16S rDNA sequences with nucleic acid sequences selected from the group consisting of SEQ ID NO:22, SEQ ID NOs: 124-145, and SEQ ID NOs: 152-159. In some embodiments, the compositions include two or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include five or more purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the compositions include at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the compositions include at least eight purified bacterial strains comprising 16S rDNA sequences with nucleic acid sequences selected from the group consisting of SEQ ID NO:22, SEQ ID NOs: 124-145, and SEQ ID NOs: 152-159. In some embodiments, the compositions include five or more purified bacterial strains comprising 16S rDNA sequences with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the composition consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition consists of at least eight purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the composition consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NOs: 124-145, and SEQ ID NOs: 152-159, respectively. In some embodiments, the composition essentially consists of at least eight purified bacterial strains comprising 16S rDNA sequences with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition essentially consists of at least eight purified bacterial strains comprising 16S rDNA sequences with nucleic acid sequences selected from the group consisting of SEQ ID NO: 22, SEQ ID NOs: 124-145, and SEQ ID NOs: 152-159. In some embodiments, the composition essentially consists of at least eight purified bacterial strains comprising 16S rDNA sequences with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In one aspect, the disclosure provides compositions that contain bacterial strains that comprise 16S rDNA sequences having at least 97% homology with nucleic acid sequences selected from the group consisting of: SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159. In one aspect, the disclosure provides compositions that contain bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In one aspect, the disclosure provides compositions that contain bacterial strains that comprise 16S rDNA sequences having at least 97% homology with nucleic acid sequences selected from the group consisting of: SEQ ID NOs: 124-159. In one aspect, the disclosure provides compositions that contain bacterial strains that comprise 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include two or more purified bacterial strains comprising 16S rDNA sequences having at least 97% homology with nucleic acid sequences selected from the group consisting of SEQ ID NOs: 124-159. In some embodiments, the compositions include two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the compositions include five or more purified bacterial strains comprising 16S rDNA sequences having at least 97% homology with nucleic acid sequences selected from the group consisting of SEQ ID NOs: 124-159. In some embodiments, the compositions include five or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159, respectively. In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the compositions include at least eight purified bacterial strains comprising 16S rDNA sequences having at least 97% homology with nucleic acid sequences selected from the group consisting of SEQ ID NOs: 124-159. In some embodiments, the compositions include at least eight purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition consists of at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NOs: 124-159, respectively. In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition consists of at least eight purified bacterial strains comprising 16S rDNA sequences having at least 97% homology with nucleic acid sequences selected from the group consisting of SEQ ID NOs:124-159, respectively. In some embodiments, the composition consists of at least eight purified bacterial strains comprising 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition essentially consists of at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159, respectively. In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:20, and SEQ ID NO:21, respectively. In some embodiments, the composition essentially consists of at least eight purified bacterial strains comprising 16S rDNA sequences having at least 97% homology with nucleic acid sequences selected from the group consisting of SEQ ID NOs: 124-159, respectively. In some embodiments, the composition essentially consists of at least eight purified bacterial strains comprising 16S rDNA sequences having at least 97% homology with nucleic acid sequences SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In one aspect, the disclosure provides a composition that contains bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159. In one aspect, the disclosure provides a composition that contains bacterial strains that comprise 16S rDNA sequences having at least 97% homology with nucleic acid sequences: SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In one aspect, the disclosure provides a composition that contains bacterial strains that comprise 16S rDNA sequences having at least 97% homology with nucleic acid sequences: SEQ ID NO:22, SEQ ID NO: 124-145, and SEQ ID NOs: 152-159.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO: 124-145, and SEQ ID NOs: 152-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include two or more purified bacterial strains comprising 16S rDNA sequences having at least 97% homology with nucleic acid sequences selected from the group consisting of SEQ ID NO: 22, SEQ ID NO: 124-145, and SEQ ID NOs: 152-159.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the compositions include five or more purified bacterial strains comprising 16S rDNA sequences having at least 97% homology with nucleic acid sequences selected from the group consisting of SEQ ID NO: 20, SEQ ID NO: 124-145, and SEQ ID NOs: 152-159.

In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the compositions include at least eight purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the compositions include at least eight purified bacterial strains comprising 16S rDNA sequences having at least 97% homology with nucleic acid sequences selected from the group consisting of SEQ ID NO: 22, SEQ ID NO: 124-145, and SEQ ID NOs: 152-159.

In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the composition consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition consists of at least eight purified bacterial strains comprising 16S rDNA sequences having at least 97% homology with nucleic acid sequences SEQ ID NO: 22, SEQ ID NO: 124-145, and SEQ ID NOs: 152-159.

In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, and SEQ ID NOs: 152-159, respectively. In some embodiments, the composition essentially consists of at least eight purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:19, SEQ ID NO:21, and SEQ ID NO:22, respectively. In some embodiments, the composition essentially consists of at least eight purified bacterial strains comprising 16S rDNA sequences having at least 97% homology with nucleic acid sequences SEQ ID NO: 22, SEQ ID NO: 124-145, and SEQ ID NOs: 152-159.

In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159. In one aspect, the disclosure provides a composition that contains bacterial strains that comprise 16S rDNA sequences with nucleic acid sequences: SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In one aspect, the disclosure provides a composition that contains bacterial strains that comprise 16S rDNA sequences with nucleic acid sequences: SEQ ID NO:18, SEQ ID NO:22, and SEQ ID NO: 124-159.

In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159. In some embodiments, the compositions include two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In some embodiments, the compositions include two or more purified bacterial strains comprising 16S rDNA sequences having at least 97% homology with nucleic acid sequences selected from the group consisting of SEQ ID NO:18, SEQ ID NO:22, and SEQ ID NO: 124-159.

In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-159. In some embodiments, the compositions include five or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In some embodiments, the compositions include five or more purified bacterial strains comprising 16S rDNA sequences having at least 97% homology with nucleic acid sequences selected from the group consisting of SEQ ID NO:18, SEQ ID NO:22, and SEQ ID NOs: 124-159.

In some embodiments, the compositions include at least ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-159, respectively. In some embodiments, the compositions include at least ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the compositions include at least ten purified bacterial strains comprising 16S rDNA sequences having at least 97% homology with nucleic acid sequences selected from the group consisting of SEQ ID NO: 18, SEQ ID NO: 22, and SEQ ID NOs: 124-159.

In some embodiments, the composition consists of ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159, respectively. In some embodiments, the composition consists of ten purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the composition consists of ten purified bacterial strains comprising 16S rDNA sequences having at least 97% homology with nucleic acid sequences selected from the group consisting of SEQ ID NO:18, SEQ ID NO:22, SEQ ID NOs: 124-159, respectively.

In some embodiments, the composition essentially consists of ten purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO: 124-159, respectively. In some embodiments, the composition essentially consists of ten purified bacterial strains comprising 16S rDNA sequences having at least 97% homology with nucleic acid sequences SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively. In some embodiments, the composition essentially consists of ten purified bacterial strains comprising 16S rDNA sequences having at least 97% homology with nucleic acid sequences selected from the group consisting of SEQ ID NO:18, SEQ ID NO:22, and SEQ ID NO: 124-159, respectively.

The bacterial strains in Composition B are related to the following bacterial species: *Flavinofractor plautii, Lachnospiraceae, bacterium 7_1_58 FAA, Subdoligranulum Anaerotruncus colihominis, Eubacterium fissicatena, Ruminococcus torques Clostridium symbiosum, Clostridium bolteae, Dorea longicatena, Blautia producta, Clostridium innocuum*, and *Erysipelotrichaceae_bacterium_21-3* (See e.g., Table 2).

Selected strains were subjected to whole genome sequencing using a PacBio Biosciences platform (Menlo Park, CA) and sequences were assembled into whole genomes (Table 3). The 16S rDNA sequences were identified using Prokka and Barrnap. It was found that several strains contained more than one 16S sequence. All identified 16S rRNA gene nucleotide sequences for each strain were then clustered at 97% identity using the usearch (v 5.2.236) algorithm and the cluster seed sequence was selected as the representative sequence for each Composition B strain (The Consensus 16S sequence: column labeled "*Consensus SEQ ID # of 16S region as determined by WGS" in Table 3). Table 3 provides identification of the indicated strains included in Composition B based on Sanger sequencing of the 16S region as well as on whole genome sequencing (WGS). The closest species of the bacterial strains were identified both by comparison to a 16S database (column labeled: "Closest species based on Consensus SEQ ID # of 16S region as compared with 16S database") and to whole genome databases (column labeled: "Closest species based on WGS compared versus WG databases").

Based on identification of 16S sequences through whole genome sequencing, and by comparing these sequences with 16S databases, the bacterial strains in Composition B are related to the following bacterial species: *Clostridium bolteae, Anaerotruncus colihominis, Dracourtella massiliensis, Clostridium symbiosum Blautia producta, Dorea longicatena Clostridium innocuum* and *Flavinofractor plautii* (see, e.g., Table 3).

Based on whole genome sequencing and comparing of the whole genome to whole genome databases, the bacterial strains in Composition B are most closely related to the following bacterial species: *Clostridium bolteae* 90A9, *Anaerotruncus colihominis* DSM 17241, *Dracourtella massiliensis* GD1, *Clostridium symbiosum* WAL-14163, *Clostridium bacterium* UC5.1-1D4, *Dorea longicatena* CAG:42, *Erysipelotrichaceae bacterium* 21_3, and *Clostridium orbiscindens* 1_3_50 AFAA (see, e.g., Table 3).

It should be appreciated that multiple strains of the compositions disclosed herein can have the same related bacterial species. For instance, the bacterial strains comprising 16S rDNA sequences with nucleic acid sequences SEQ ID NO 18, SEQ ID NO:20 and SEQ ID NO:22 all have *Dorea longicatena* as related bacterial species. In some embodiments, the disclosure provides compositions with two or more bacteria selected from the group consisting of *Flavinofractor plautii, Lachnospiraceae, bacterium 7_1_58 FAA, Subdoligranulum Anaerotruncus colihominis, Eubacterium fissicatena, Ruminococcus torques Clostridium symbiosum, Clostridium bolteae, Dorea longicatena, Blautia producta, Clostridium innocuum* and *Erysipelotrichaceae_ bacterium_21-3*. In some embodiments, the disclosure provides compositions with two or more bacteria selected from the group consisting of *Flavinofractor plautii, Anaerotruncus colihominis, Eubacterium fissicatena, Clostridium symbiosum, Clostridium bolteae, Dorea longicatena, Blautia producta*, and *Clostridium innocuum*. In some embodiments, the disclosure provides compositions that include two or more purified bacterial strains comprising 16S rDNA sequences having at least 97% homology with nucleic acid sequences selected from the group consisting of SEQ ID NO:93, SEQ ID NO:95, SEQ ID NO:97, SEQ ID NO:98, SEQ ID NO:102, SEQ ID NO:106, SEQ ID NO:110, and SEQ ID NO:122.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, SEQ ID NO:22, and SEQ ID NOs: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NOs: 124-159. In some embodiments, the composition comprises two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:146, SEQ ID NO:152 and SEQ ID NO:157.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, SEQ ID NO:22, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:18, SEQ ID NO:22, and SEQ ID NO: 124-159. In some embodiments, the composition comprises two or more purified bacterial strains comprising 16S rDNA sequences having at least 97% homology with nucleic acid sequences selected from the group consisting of SEQ ID NO:18, SEQ ID NO:22, SEQ ID NO: 124, SEQ ID NO:129, SEQ ID NO:132, SEQ ID NO:137, SEQ ID NO:141, SEQ ID NO:146, SEQ ID NO:152, and SEQ ID NO:157.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments, the composition comprises two or more purified bacterial strains comprising 16S rDNA sequences having at least 97% homology with nucleic acid sequences selected from the group consisting of SEQ ID NO:18 and SEQ ID NO: 124-159. In some embodiments, the composition comprises two or more purified bacterial strains comprising 16S rDNA sequences having at least 97% homology with nucleic acid sequences selected from the group consisting of SEQ ID NO:18, SEQ ID NO: 124, SEQ ID NO:129, SEQ ID NO:132, SEQ ID NO:137, SEQ ID NO:141, SEQ ID NO:146, SEQ ID NO:152, and SEQ ID NO:157

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO: 124-145, and SEQ ID NO: 151-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:22, SEQ ID NO: 124-145, and SEQ ID NO: 151-159. In some embodiments, the composition comprises two or more purified bacterial strains comprising 16S rDNA sequences having at least 97% homology with nucleic acid sequences selected from the group consisting of SEQ ID NO: 124, SEQ ID NO:129, SEQ ID NO:132, SEQ ID NO:137, SEQ ID NO:141, SEQ ID NO:152, and SEQ ID NO:157

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO: 124-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some embodiments, the composition comprises two or more purified bacterial strains comprising 16S rDNA sequences having at least 97% homology with nucleic acid sequences selected from the group consisting of SEQ ID NOs: 124-159.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:21, SEQ ID NOs: 124-145, and SEQ ID NOs: 152-159. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, and SEQ ID NO:21. In some embodiments, the composition comprises two or more purified bacterial strains comprising 16S rDNA sequences having at least 97% homology with nucleic acid sequences selected from the group consisting of SEQ ID NO: 18, SEQ ID NOs: 124-145, and SEQ ID NOs: 152-159.

In some embodiments, the composition comprises two or more purified bacterial strains comprising 16S rDNA sequences having at least 97% homology with nucleic acid sequences selected from the group consisting of SEQ ID NO:10, SEQ ID NO:18, SEQ ID NO:19, SEQ ID NO:20, SEQ ID NO:21, SEQ ID NO:22, SEQ ID NOs: 157-159, and SEQ ID NOs:141-156. In some embodiments, the composition comprises two or more purified bacterial strains comprising 16S rDNA sequences having at least 97% homology with nucleic acid sequences selected from the group consisting of SEQ ID NO:10, SEQ ID NO:18, SEQ ID NO:19, SEQ ID NO:20, SEQ ID NO:21, and SEQ ID NO:22. In some embodiments, the composition comprises two or more purified bacterial strains comprising 16S rDNA sequences having at least 97% homology with nucleic acid sequences selected from the group consisting of SEQ ID NO:18, SEQ ID NO:22, SEQ ID NOs: 157-159, and SEQ ID NO:141-156.

Each of the bacteria of Composition B are BaiCD– strains, meaning that the strains do not encode and/or are not predicted to encode the bile inducible operon gene baiCD and/or a protein with stereospecific NAD(H)-dependent 3-oxo-$\Delta^4$-cholenoic acid oxidoreductase activity. In some embodiments, the disclosure provides compositions comprising two or more bacteria, wherein the bacteria are BaiCD– strains. The strains of Composition B are classified as belonging to *Clostridium* clusters IV, XIVa, and XVII. In some embodiments, the disclosure provides two or more bacterial strains, wherein the bacteria are BaiCD– strains and belong to *Clostridium* clusters IV, XIVa, or XVII. In some embodiments, the disclosure provides two or more bacterial strains, wherein the bacteria are BaiCD– strains and belong to *Clostridium* clusters IV or XVII. In some embodiments, the disclosure provides two or more bacterial strains, wherein the bacteria are BaiCD– strains and belong to *Clostridium* clusters XIVa or XVII. In some embodiments, the disclosure provides two or more bacterial strains, wherein the bacteria are BaiCD– strains and belong to *Clostridium* clusters IV or XIVa. In some embodiments, the disclosure provides two or more bacterial strains, wherein the bacteria are BaiCD– strains and belong to *Clostridium* cluster IV. In some embodiments, the disclosure provides two or more bacterial strains, wherein the bacteria are BaiCD– strains and belong to *Clostridium* cluster XIVa. In some embodiments, the disclosure provides two or more bacterial strains, wherein the bacteria are BaiCD– strains and belong to *Clostridium* clusters XVII. In some embodiments, the disclosure provides two or more bacterial strains, wherein the bacteria are BaiCD– strains and belong to *Clostridium* clusters IV, XIVa, and XVII and do not belong to *Clostridium* clusters XVI or XVIII.

In some embodiments, the disclosure provides two or more bacterial strains wherein the bacterial strains are spore forming bacterial strains. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NO:14, SEQ ID NO:16, SEQ ID NO:17, SEQ ID NO:21, SEQ ID NOs 124-140, and SEQ ID NO: 152-156. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NO:14, SEQ ID NO:16, SEQ ID NO:17, and SEQ ID NO:21. In some embodiments, the disclosure provides two or more bacterial strains wherein the bacteria are spore formers and wherein the bacterial strains comprise 16S rDNA sequences having at least 97% homology with nucleic acid sequences selected from the group consisting of SEQ ID NOs: 124-140, and SEQ ID NOs: 152-156.

In some embodiments, the disclosure provides two or more bacterial strains wherein the bacteria include both spore formers and non-spore formers. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NO:14, SEQ ID NO:16, SEQ ID NO:17, SEQ ID NO:21, SEQ ID NOs: 124-140, and SEQ ID NOs: 152-156. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NO:14, SEQ ID NO:16, SEQ ID NO:17, and SEQ ID NO:21. In some embodiments, the disclosure provides two or more bacterial strains wherein the bacteria include both spore formers and non-spore formers, and wherein the spore forming bacterial strains comprise two or more purified bacterial strains comprising 16S rDNA sequences having at least 97% homology with nucleic acid sequences selected from the group consisting of SEQ ID NOs: 124-140 and SEQ ID NO: 152-156.

TABLE B

Composition B

SEQ_10 - 211 - Flavonifractor_plautii (IV)
SEQ_14 - VE202-13 - Anaerotruncus_colihominis (IV)
SEQ_15 - VE202-14 - Eubacterium_fissicatena (XIVa)
SEQ_16 - VE202-16 - Clostridium_symbiosum (XIVa)
SEQ_17 - VE202-7 - Clostridium_bolteae (XIVa)
SEQ_19 - 16 - Blautia_producta (XIVa)
SEQ_20 - 170 - Dorea_longicatena (XIVa)
SEQ_21 - 189 - Clostridium_innocuum (XVII)

In some embodiments, the compositions include one or more bacterial species from the *Bacteroides* genus. In some embodiments, the compositions include one or more bacterial species selected from the group consisting of *B. acidifaciens, B. caccae, B. coprocola, B. coprosuis, B. eggerthii, B. finegoldii, B. fragilis, B. helcogenes, B. intestinalis, B. massiliensis, B. nordii, B. ovatus, B. thetaiotaomicron, B. vulgatus, B. plebeius, B. uniformis B. salyersai, B. pyogenes, B. goldsteinii, B. dorei*, and *B. johnsonii*. In some embodiments, the compositions include *Bacteroides ovatus*. In some embodiments, the *Bacteroides ovatus* has a 16S rDNA sequence comprising SEQ ID NO:83. In some embodiments, the *Bacteroides ovatus* has a 16S rDNA sequence having at least 97% homology with a nucleic acid sequence comprising SEQ ID NO:83. In some embodiments, the *Bacteroides ovatus* has a 16S rDNA sequence having at least 97% homology with a nucleic acid sequence comprising SEQ ID NO:101.

While not being limited to a specific mechanism it is thought that the inclusion of a *Bacteroides* species in the bacterial compositions disclosed herein increases the ability to sense and adapt to nutrient availability or influence the host immune system so that it becomes more effective in fighting pathogens (e.g., *C. difficile*). In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, SEQ ID NO: 124-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:20, SEQ ID NO:21, and SEQ ID NO:83. (Composition B1, See e.g., Table B1). In some embodiments, the composition comprises two or more purified bacterial strains comprising 16S rDNA sequences having at least 97% homology with nucleic acid sequences selected from the group consisting of SEQ ID NOs: 124-159, and SEQ ID NO: 83.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, SEQ ID NO: 124-145, SEQ ID NO: 152-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:19, SEQ ID NO:21, SEQ ID NO:22, and SEQ ID NO:83. In some embodiments, the composition comprises two or more purified bacterial strains comprising 16S rDNA sequences having at least 97% homology with nucleic acid sequences selected from the group consisting of SEQ ID NOs: 124-145, SEQ ID NO: 152-159, and SEQ ID NO: 83.

In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO: 124-159, and SEQ ID NO:83. In some embodiments, the composition comprises two or more purified bacterial strains comprising 16S rDNA sequences having at least 97% homology with nucleic acid sequences selected from the group consisting of SEQ ID NO:10, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:83. In some embodiments, the composition comprises two or more purified bacterial strains comprising 16S rDNA sequences having at least 97% homology with nucleic acid sequences selected from the group consisting of SEQ ID NOs: 124-159, SEQ ID NO: 18, SEQ ID NO: 22, and SEQ ID NO: 83.

In some embodiments, the composition comprises two or more purified bacterial strains comprising 16s rDNA sequences having at least 97% homology with nucleic acid sequences selected from the group consisting of SEQ ID NO:93, SEQ ID NO:95, SEQ ID NO:97, SEQ ID NO:98, SEQ ID NO:101, SEQ ID NO:102, SEQ ID NO:106, SEQ ID NO:110, and SEQ ID NO:122. It should also be appreciated that in some embodiments, the compositions disclosed herein do not include bacterial species from the *Bacteroides* genus.

TABLE B1

Composition B1

SEQ_10 - 211 - *Flavonifractor_plautii* (IV)
SEQ_14 - VE202-13 - *Anaerotruncus_colihominis* (IV)
SEQ_15 - VE202-14 - *Eubacterium_fissicatena* (XIVa)
SEQ_16 - VE202-16 - *Clostridium_symbiosum* (XIVa)
SEQ_17 - VE202-7 - *Clostridium_bolteae* (XIVa)
SEQ_20 - 170 - *Dorea_longicatena* (XIVa)
SEQ_19 - 16 - *Blautia_producta* (XIVa)
SEQ_21 - 189 - *Clostridium_innocuum* (XVII)
SEQ_83 *Bacteroides ovatus*

In some embodiments, the compositions disclosed herein do not include *Clostridium orbiscindens* 1_3_50 AFAA, *Flavinofractor plautii, Subdoligranulum* or *Lachnospiraceae bacterium* 7_1_58 FAA. In some embodiments, the compositions disclosed herein do not include *Clostridium orbiscindens* 1_3_50 AFAA. In some embodiments, the compositions disclosed herein do not include *Flavinofractor plautii*. In some embodiments, the compositions disclosed herein do not include *Subdoligranulum*. In some embodiments, the compositions disclosed herein do not include *Lachnospiraceae bacterium* 7_1_58 FAA.

In some embodiments, the composition comprises two or more purified bacterial strains comprising 16S rDNA sequences having at least 97% homology with nucleic acid sequences selected from the group consisting of SEQ ID NO:14, SEQ ID NO: 15, SEQ ID NO:16, SEQ ID NO:17, SEQ ID NO:19, SEQ ID NO:20, SEQ ID NO:21, and SEQ ID NO: 124-156, wherein the composition does not include a bacterial strain comprising a 16s rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO: 15, SEQ ID NO:16, SEQ ID NO:17, SEQ ID NO:19, SEQ ID NO:20, and SEQ ID NO:21, wherein the composition does not include a bacterial strain comprising a 16s rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NOs: 124-156, wherein the composition does not include a bacterial strain comprising a 16S rDNA sequence having at least 97% homology with a nucleic acid sequence of SEQ ID NOs:157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22, and SEQ ID NOs: 124-146 and SEQ ID NO: 152-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, and SEQ ID NO:22, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22, SEQ ID NOs: 124-146, and SEQ ID NOs: 152-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NOs: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:18, SEQ ID NO:22, and SEQ ID NOs: 124-159, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:95, SEQ ID NO:97, SEQ ID NO:98, SEQ ID NO:102, SEQ ID NO:106, SEQ ID NO:110, and SEQ ID NO:122, wherein the composition does not include a bacterial strain comprising a 16S rDNA sequence having at least 97% homology with a nucleic acid sequence of SEQ ID NO:93.

In some embodiments, the compositions include one or more bacterial species from the *Bacteroides* genus and do not include *Clostridium orbiscindens* 1_3_50 AFAA, *Flavinofractor plautii, Subdoligranulum* or *Lachnospiraceae bacterium* 7_1_58 FAA. (Composition B2, See e.g., Table B2). In some embodiments, the compositions include *Bacteroides ovatus* and do not include *Clostridium orbiscindens* 1_3_50 AFAA, *Flavinofractor plautii, Subdoligranulum* or *Lachnospiraceae bacterium* 7_1_58 FAA.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 SEQ ID NO:83, and SEQ ID NOs: 124-156, wherein the composition does not include a bacterial strain comprising a 16S rDNA sequence having at least 97% homology with a nucleic acid sequence of SEQ ID NO:10 and SEQ ID NOs:

157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:20, SEQ ID NO:21 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:83 and SEQ ID NOs: 124-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22, SEQ ID NO:83, SEQ ID NOs: 124-145, and SEQ ID NOs: 152-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:19, SEQ ID NO:21, SEQ ID NO:22 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22 SEQ ID NO:83, SEQ ID NOs: 124-145, and SEQ ID NOs: 152-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:83, and SEQ ID NO: 124-156, wherein the composition does not include a bacterial strain comprising a 16S rDNA sequence having at least 97% homology with a nucleic acid sequence of SEQ ID NO:10 and SEQ ID NOs: 157-159. In some embodiments, the composition comprises two or more purified bacterial strains comprising 16S rDNA sequences having at least 97% homology with nucleic acid sequences selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:83, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:22, SEQ ID NO:83, and SEQ ID NO: 124-156, wherein the composition does not include a bacterial strain comprising a 16S rDNA sequence having at least 97% homology with a nucleic acid sequence of SEQ ID NOs: 157-159.

In some embodiments, the composition comprises two or more purified bacterial strains comprising 16S rDNA sequences having at least 97% homology with nucleic acid sequences selected from the group consisting of SEQ ID NO:95, SEQ ID NO:97, SEQ ID NO:98, SEQ ID NO:101, SEQ ID NO:102, SEQ ID NO:106, SEQ ID NO:110, and SEQ ID NO:122, wherein the composition does not include a bacterial strain comprising a 16S rDNA sequence having at least 97% homology with a nucleic acid sequence of SEQ ID NO:93.

TABLE B2

Composition B2

SEQ_14 - VE202-13 - *Anaerotruncus_colihominis* (IV)
SEQ_15 - VE202-14 - *Eubacterium_fissicatena* (XIVa)
SEQ_16 - VE202-16 - *Clostridium_symbiosum* (XIVa)
SEQ_17 - VE202-7 - *Clostridium_bolteae* (XIVa)
SEQ_20 - 170 - *Dorea_longicatena* (XIVa)
SEQ_19 - 16 - *Blautia_producta* (XIVa)
SEQ_21 - 189 - *Clostridium_innocuum* (XVII)
SEQ_ 83 *Bacteroides ovatus*

In one aspect, the disclosure provides Composition C (See e.g., FIG. 1, Table C). As shown in FIG. 1, Composition C contains bacteria that have the following 16S rDNA sequences: SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the disclosure provides compositions with two or more purified bacterial strains that have 16S rDNA sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include four or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include at least ten purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the composition consists of ten purified bacterial strains comprising 16S rDNA sequences with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively. In some embodiments, the composition consists essentially of ten purified bacterial strains comprising 16S rDNA sequences with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively.

In some embodiments, the compositions include two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include four or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the compositions include at least ten purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16. In some embodiments, the composition consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively. In some embodiments, the composition essentially consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:7, SEQ ID NO:18, SEQ ID NO:21, SEQ ID NO:10, SEQ ID NO:14, and SEQ ID NO:16, respectively.

The bacterial strains in Composition C are related to the following species: *Clostridium scindens, Clostridium hathewayi, Blautia hansenii, Blautia wexlerae, Blautia producta, Blautia coccoides, Dorea longicatena, Clostridium innocuum, Flavonifractor plautii, Lachnospiraceae bacterium 7_1_58 FAA, Subdoligranulum, Anaerotruncus colihominis,* and *Clostridium symbiosum.* In some embodiments, the disclosure provides compositions with two or more bacterial strains of species selected from the group consisting of *Clostridium scindens, Clostridium hathewayi, Blautia hansenii, Blautia wexlerae, Blautia product, Blautia coccoides, Dorea longicatena, Clostridium innocuum, Flavonifractor plautii, Lachnospiraceae bacterium 7_1_58 FAA, Subdoligranulum, Anaerotruncus colihominis,* and *Clostridium symbiosum.* In some embodiments, the disclosure provides compositions that include two or more purified bacterial strains comprising 16S rDNA sequences having at least 97% homology with nucleic acid sequences selected from the group consisting of SEQ ID NO:87, SEQ ID NO:93, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122.

In some embodiments, the compositions disclosed herein do not include *Flavinofractor plautii, Subdoligranulum* or *Lachnospiraceae bacterium 7_1_58 FAA.* In some embodiments, the composition comprises two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:7, SEQ ID NO:18, SEQ ID NO:21, SEQ ID NO:14, and SEQ ID NO:16, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:87, SEQ ID NO:94, SEQ ID NO:95, SEQ ID NO:97, SEQ ID NO:98, SEQ ID NO:99, SEQ ID NO:103, SEQ ID NO:105, SEQ ID NO:106, and SEQ ID NO:122, wherein the composition does not include a bacterial strain comprising a 16S rDNA sequence having at least 97% homology with a nucleic acid sequence of SEQ ID NO:93.

The strains of Composition C include both BaiCD⁺ strains and Bai CD− strains. In some embodiments, the disclosure provides compositions comprising two or more bacteria, wherein one or more bacteria are BaiCD+ strains and one or more bacteria are BaiCD− strains. In some embodiments of the one or more bacteria that are BaiCD+ strains are selected from bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, and SEQ ID NO:7. In some embodiments the one or more bacteria that are BaiCD− strains are selected from bacterial strains comprising 16S rDNA sequences having at least 97% homology with nucleic acid sequences selected from the group consisting of SEQ ID NO:18, SEQ ID NO:21, SEQ ID NO:10, SEQ ID NO:14, and SEQ ID NO:16. In some embodiments of the one or more bacteria that are BaiCD+ strains are selected from the bacterial species *Clostridium scindens, Clostridium hathewayi, Blautia hansenii, Blautia wexlerae, Blautia product,* and *Blautia coccoides.* In some embodiments of the one or more bacteria that are BaiCD− strains are selected from the bacterial species *Dorea longicatena, Clostridium innocuum, Flavonifractor plautii,* or *Lachnospiraceae bacterium 7_1_58 FAA, Anaerotruncus colihominis,* and *Clostridium symbiosum.* The clostridial strains of Composition C are classified as belonging to *Clostridium* clusters IV, XIVa, and XVII. In some embodiments, the disclosure provides two or more bacterial strains, wherein the bacteria are BaiCD− strains and BaiCD+ strains and belong to *Clostridium* clusters IV, XIVa, or XVII. In some embodiments, the disclosure provides two or more bacterial strains, wherein the bacteria are BaiCD− strains and BaiCD+ strains and belong to *Clostridium* clusters XIVa or XVII. In some embodiments, the disclosure provides two or more bacterial strains, wherein the bacteria are BaiCD− strains and BaiCD+ strains and belong to *Clostridium* clusters IV or XIVa.

TABLE C

| Composition C |
|---|
| SEQ_12 - VE202-26 - *Clostridium_scindens* (XIVa)* |
| SEQ_03 - 5 - *Clostridium_hathewayi* (XIVa)* |
| SEQ_05 - 10 - *Blautia_hansenii* (XIVa)* |
| SEQ_01 - 71 - *Blautia_wexlerae* (XIVa)* |
| SEQ_07 - 59 - *Blautia_producta/Blautia_coccoides* (XIVa)* |
| SEQ_18 - 148 - *Dorea_longicatena* (XIVa) |
| SEQ_21 - 189 - *Clostridium_innocuum* (XVII) |
| SEQ_10 - 211 - *Flavonifractor_plautii* (IV) |
| SEQ_14 - VE202-13 - *Anaerotruncus_colihominis* (IV) |
| SEQ_16 - VE202-16 - *Clostridium_symbiosum*) (XIVa) |

*= BaiCD+

In one aspect, the disclosure provides Composition D (See e.g., FIG. 1, Table D). As shown in FIG. 1, Composition D contains bacteria that have the following 16S rDNA sequences: SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions with two or more purified bacterial strains that have 16S rDNA sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include three or more purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include at least ten purified bacterial strains comprising 16S rDNA sequences with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides a composition that consists of ten purified bacterial strains comprising 16S rDNA sequences with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively. In some embodiments, the disclosure provides a composition that consists essentially of ten purified bacterial strains comprising 16S rDNA sequences with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively In some embodiments, the disclosure provides compositions that include two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include three or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides compositions that include at least ten more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6. In some embodiments, the disclosure provides a composition that consists of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively. In some embodiments, the disclosure provides a composition that consists essentially of ten purified bacterial strains comprising 16S rDNA sequences having at least 97% homology with nucleic acid sequences SEQ ID NO:12, SEQ ID NO:3, SEQ ID NO:5, SEQ ID NO:1, SEQ ID NO:14, SEQ ID NO:18, SEQ ID NO:21, SEQ ID NO:10, SEQ ID NO:2, and SEQ ID NO:6, respectively.

The bacterial strains in Composition D are related to the following bacteria: *Clostridium scindens, Clostridium hathewayi, Blautia hansenii, Blautia wexlerae, Anaerotruncus colihominis, Dorea longicatena, Clostridium innocuum, Flavonifractor plautii, Lachnospiraceae bacterium 7_1_58 FAA, Subdoligranulum, Turicibacter sanguinis*, and *Lactobacillus mucosae*. In some embodiments, the disclosure provides compositions with two or more bacterial strains of species selected from the group consisting of *Clostridium scindens, Clostridium hathewayi, Blautia hansenii, Blautia wexlerae, Anaerotruncus colihominis, Dorea longicatena, Clostridium innocuum, Erysipelotrichaceae_bacterium_21-3, Flavonifractor plautii, Lachnospiraceae bacterium 7_1_58 FAA, Turicibacter sanguinis*, and *Lactobacillus mucosae*. In some embodiments, the disclosure provides compositions that include two or more purified bacterial strains comprise 16S rDNA sequences having at least 97% homology with nucleic acid sequences selected from the group consisting of SEQ ID NO:87, SEQ ID NO:90, SEQ ID NO:91, SEQ ID NO:93, SEQ ID NO:94, SEQ ID NO:95, SEQ ID NO:97, SEQ ID NO:98, SEQ ID NO:99, and SEQ ID NO:105.

In some embodiments, the compositions disclosed herein do not include *Flavinofractor plautii, Subdoligranulum* or *Lachnospiraceae bacterium 7_1_58 FAA*. In some embodiments, the composition comprises two or more purified bacterial strains comprising 16S rDNA sequences having at least 97% homology with nucleic acid sequences selected from the group consisting of SEQ ID NO:12, SEQ ID NO:3, SEQ ID NO:5, SEQ ID NO:1, SEQ ID NO:14, SEQ ID NO:18, SEQ ID NO:21, SEQ ID NO:2, and SEQ ID NO:6, wherein the composition does not include a bacterial strain comprising a 16S rDNA sequence having at least 97% homology with a nucleic acid sequence of SEQ ID NO:10. In some embodiments, the composition comprises two or more purified bacterial strains comprising 16S rDNA sequences having at least 97% homology with nucleic acid sequences selected from the group consisting of SEQ ID NO:87, SEQ ID NO:90, SEQ ID NO:91, SEQ ID NO:94, SEQ ID NO:95, SEQ ID NO:97, SEQ ID NO:98, SEQ ID NO:99, and SEQ ID NO:105, wherein the composition does not include a bacterial strain comprising a 16S rDNA sequence having at least 97% homology with a nucleic acid sequence of SEQ ID NO:93.

The strains of Composition D include both BaiCD+ strains and Bai CD− strains. In some embodiments, the disclosure provides compositions comprising two or more bacteria, wherein one or more bacteria are BaiCD+ strains and one or more bacteria are BaiCD− strains. In some embodiments of the one or more bacteria that are BaiCD+ strains are selected from bacterial strains comprising 16S rDNA sequences having at least 97% homology with nucleic acid sequences selected from the group consisting of SEQ ID NO:12, SEQ ID NO:3, SEQ ID NO:5, and SEQ ID NO:1. In some embodiments the one or more bacteria that are BaiCD− strains are selected from bacterial strains comprising 16S rDNA sequences having at least 97% homology with nucleic acid sequences selected from the group consisting of SEQ ID NO:18, SEQ ID NO:21, SEQ ID NO:10, and SEQ ID NO:14. In some embodiments of the one or more bacteria that are BaiCD+ strains are selected from the bacterial species *Clostridium scindens, Clostridium hathewayi, Blautia hansenii*, and *Blautia wexlerae*. In some embodiments of the one or more bacteria that are BaiCD− strains are selected from the bacterial species *Dorea longicatena, Clostridium innocuum, Flavonifractor plautii*, and *Anaerotruncus colihominis*. The Clostridial strains of Composition D are classified as belonging to *Clostridium* clusters IV, XIVa, and XVII. In some embodiments, the disclosure provides two or more bacterial strains, wherein the bacteria are BaiCD− strains and BaiCD+ strains and belong to Clostridium clusters IV, XIVa, or XVII. In some embodiments, the disclosure provides two or more bacterial strains, wherein the bacteria are BaiCD− strains and BaiCD+ strains and belong to Clostridium clusters XIVa or XVII. In some embodiments, the disclosure provides two or more bacterial strains, wherein the bacteria are BaiCD− strains and BaiCD+ strains and belong to Clostridium clusters IV or XIVa.

Composition D includes the non-Clostridium strains Turicibacter sanguinis and Lactobacillus mucosae. In some embodiments, the disclosure provides compositions comprising two or more bacteria, wherein the composition includes both Clostridium strains and non-Clostridium strains. In some embodiments, the non-Clostridium strains are the members of the genus Lactobacillus. Members of the genus Lactobacillus include, without limitation L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii subsp. bulgaricus, L. delbrueckii subsp. delbrueckii, L. delbrueckii subsp. lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamsteri, L. harbinensis, L. hayakitensis, L. helveticus, L. hilgardii, L. homohiochii, L. iners, L. ingluviei, L. intestinalis, L. jensenii, L. johnsonii, L. kalixensis, L. kefiranofaciens, L. kefiri, L. kimchii, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracasei, L. paracollinoides, L. parafarraginis, L. parakefiri, L. paralimentarius, L. paraplantarum, L. pentosus, L. perolens, L. plantarum, L. pontis, L. protectus, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae, and L. zymae. In some embodiments, the non-Clostridium strain is Lactobacillus mucosae. In some embodiments, the non-Clostridium strain is Lactobacillus mucosae. In some embodiments, the Lactobacillus mucosae has a 16S rDNA sequence comprising SEQ ID NO:2. In some embodiments, the Lactobacillus mucosae has a 16S rDNA sequence having at least 97% homology with a nucleic acid comprising SEQ ID NO:2. In some embodiments, the Lactobacillus mucosae has a 16S rDNA sequence having at least 97% homology with a nucleic acid comprising SEQ ID NO:91.

In some embodiments, the disclosure provides compositions comprising two or more bacteria, wherein the composition includes both Clostridium strains and non-Clostridium strains. In some embodiments, the non-Clostridium strains are members of the genus Turicibacter. In some embodiments, the non-Clostridium strain is Turicibacter sanguinis. In some embodiments, the Turicibacter sanguinis has a 16S rDNA sequence comprising SEQ ID NO:6. In some embodiments, the Turicibacter sanguinis has a 16S rDNA sequence having at least 97% homology with a nucleic acid comprising SEQ ID NO:6. In some embodiments, the Turicibacter sanguinis has a 16S rDNA sequence having at least 97% homology with a nucleic acid comprising SEQ ID NO:90.

In some embodiments, the disclosure provides compositions comprising two or more bacteria, wherein the composition includes both Clostridium strains and non-Clostridium strains. In some embodiments, the non-Clostridium strains are Lactobacillus mucosae and Turicibacter sanguinis.

In some embodiments, the disclosure provides compositions comprising two or more bacteria, wherein the composition does not include Lactobacillus. In some embodiments, the disclosure provides compositions comprising two or more bacteria, wherein the composition does not include Turicibacter. In some embodiments, the disclosure provides compositions comprising two or more bacteria, wherein the composition does not include Lactobacillus or Turicibacter. In some embodiments, the disclosure provides compositions comprising two or more bacteria, wherein the composition only includes clostridia strains. In some embodiments, the disclosure provides compositions comprising two or more bacteria, wherein the composition only includes clostridia strains belonging to Clostridium cluster IV, XIVa or XVII strains. In some embodiments, the disclosure provides compositions comprising two or more bacteria, wherein the composition does not include Clostridium cluster XI strains.

In some embodiments, the disclosure provides compositions comprising two or more purified bacterial strains selected from the group consisting of: Clostridium scindens, Pseudoflavonifractor capillosus, and Blautia hansenii. In some embodiments, the compositions disclosed herein do not include Clostridium scindens, Pseudoflavonifractor capillosus, or Blautia hansenii.

TABLE D

| Composition D |
|---|
| SEQ_12 - VE202-26 - Clostridium_scindens (XIVa)* |
| SEQ_03 - 5 - Clostridium_hathewayi (XIVa)* |
| SEQ_05 - 10 - Blautia_hansenii (XIVa)* |
| SEQ_01 - 71 - Blautia_wexlerae (XIVa)* |
| SEQ_14 - VE202-13 - Anaerotruncus_colihominis (IV) |
| SEQ_18 - 148 - Dorea_longicatena (XIVa) |
| SEQ_21 - 189 - Clostridium_innocuum (XVII) |
| SEQ_10 - 211 - Flavonifractor_plautii (IV) |
| SEQ_02 - 102 - Turicibacter_sanguinis (non-Clostridium) |
| SEQ_06 - 40 - Lactobacillus_mucosae (non-Clostridium) |

*= BaiCD+

In one aspect, the disclosure provides Composition F (See e.g., FIGS. 13 and 14, and Tables F1 and F2). As shown in FIG. 13, Composition F contains bacteria that have the following 16S rDNA sequences: SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

In some embodiments, the disclosure provides compositions with two or more purified bacterial strains that have 16S rDNA sequences selected from the group consisting of SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

In some embodiments, the compositions include two or more purified bacterial strains comprising 16S rDNA sequences having at least 97% homology with nucleic acid sequences selected from the group consisting of SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, and SEQ ID NO:79.

The bacterial strains in Composition F are related to the following bacteria: *Dorea longicatena, Ruminococcus obeum, Megasphaera elsdenii, Acidaminococcus fermentans, Acidaminococcus intestine, Megasphaera elsdenii, Ruminococcus faecis, Bacteroides cellulosilyticus, Anaerostipes hadrus, Ruminococcus obeum, Flavonifractor plautii, Eubacterium rectale, Flavonifractor plautii, Megasphaera elsdenii, Eubacterium rectale, Ruminococcus champanellensis, Ruminococcus albus, Ruminococcus champanellensis, Ruminococcus faecis, Bifidobacterium bifidum, Anaerostipes hadrus, Anaerostipes hadrus, Anaerostipes hadrus, Eubacterium rectale, Ruminococcus faecis, Blautia luti, Ruminococcus faecis, Anaerostipes hadrus, Anaerostipes hadrus, Ruminococcus faecis, Eubacterium rectale, Eubacterium rectale, Anaerostipes hadrus, Ruminococcus faecis, Ruminococcus faecis, Dorea longicatena, Roseburia faecis, Blautia luti, Fusicatenibacter saccharivorans, Fusicatenibacter saccharivorans, Roseburia faecis, Megasphaera elsdenii, Eubacterium rectale, Eubacterium rectale, Roseburia faecis, Blautia faecis, Fusicatenibacter saccharivorans*, and *Dorea formicigenerans*.

In some embodiments, the disclosure provides compositions with two or more bacterial strains of species selected from the group consisting of *Dorea longicatena, Ruminococcus obeum, Megasphaera elsdenii, Acidaminococcus fermentans, Acidaminococcus intestine, Megasphaera elsdenii, Ruminococcus faecis, Bacteroides cellulosilyticus, Anaerostipes hadrus, Ruminococcus obeum, Flavonifractor plautii, Eubacterium rectale, Flavonifractor plautii, Megasphaera elsdenii, Eubacterium rectale, Ruminococcus champanellensis, Ruminococcus albus, Ruminococcus champanellensis, Ruminococcus faecis, Bifidobacterium bifidum, Anaerostipes hadrus, Anaerostipes hadrus, Anaerostipes hadrus, Eubacterium rectale, Ruminococcus faecis, Blautia luti, Ruminococcus faecis, Anaerostipes hadrus, Anaerostipes hadrus, Ruminococcus faecis, Eubacterium rectale, Eubacterium rectale, Anaerostipes hadrus, Ruminococcus faecis, Ruminococcus faecis, Dorea longicatena, Roseburia faecis, Blautia luti, Fusicatenibacter saccharivorans, Fusicatenibacter saccharivorans, Roseburia faecis, Megasphaera elsdenii, Eubacterium rectale, Eubacterium rectale, Roseburia faecis, Blautia faecis, Fusicatenibacter saccharivorans*, and *Dorea formicigenerans*.

In some embodiments, the disclosure provides compositions that include two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:100, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, and SEQ ID NO:120. It should be appreciated that multiple strains of the compositions disclosed herein can have the same related bacterial species. For instance, Composition F includes 12 strains that have *Eubacterium rectale* as the closest related species.

In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster IX. In some embodiments, at least one of the bacterial strains of the composition belongs to *Clostridium* cluster IV. In some embodiments, at least one of the bacterial strains of the composition belongs to *Clostridium* cluster XIVa and at least one of the bacterial strains belongs to *Clostridium* cluster IX. In some embodiments, at least one of the bacterial strains of the composition belongs to *Clostridium* cluster IV and at least one of the bacterial strains belongs to *Clostridium* cluster IX. In some embodiments, at least one of the bacterial strains of the composition belongs to *Clostridium* cluster IV, at least one of the bacterial strains belongs to *Clostridium* cluster XIVa, and at least one of the bacterial strains belongs to *Clostridium* cluster IX. In some embodiments, the compositions provided herein do not include bacterial strains belonging to *Clostridium* cluster XVIII. In some embodiments, the compositions provided herein do not include bacterial strains belonging to *Clostridium* cluster XVI or XVIII.

Composition F includes non-*Clostridium* bacterial strains. In some embodiments, the disclosure provides compositions comprising two or more bacteria, wherein the composition includes both *Clostridium* strains and non-*Clostridium* strains. In some embodiments, the non-*Clostridium* strains are the members of the genus *Bacteroides*. In some embodiments, the non-*Clostridium* strain is *Bacteroides cellulosilyticus*. In some embodiments, the non-*Clostridium* strains are the members of the genus *Bifidobacterium*. In some embodiments, the non-*Clostridium* strain is *Bifidobacterium bifidum*. In some embodiments, the disclosure provides compositions comprising two or more bacteria, wherein the composition includes both *Clostridium* strains and non-*Clostridium* strains, and wherein the non-*Clostridium* strains are *Bacteroides cellulosilyticus* and *Bifidobacterium bifidum*.

In some embodiments, the disclosure provides compositions comprising two or more bacteria, wherein the composition does not include *Bacteroides*. In some embodiments, the disclosure provides compositions comprising two or more bacteria, wherein the composition does not include *Bifidobacterium*. In some embodiments, the disclosure provides compositions comprising two or more bacteria, wherein the composition does not include *Bacteroides* and does not include *Bifidobacterium*. In some embodiments, the disclosure provides compositions comprising two or more bacteria, wherein the composition does not include non-*Clostridium* strains. In some embodiments, the disclosure provides compositions comprising two or more bacteria, wherein the composition only includes clostridia strains belonging to *Clostridium* cluster IV, XIVa or XVII strains. In some embodiments, the disclosure provides compositions comprising two or more bacteria, wherein the composition does not include *Clostridium* cluster XI strains.

TABLE F2-continued

Composition F, strain groupings

| Cluster | Composition F | *SCFAs |
|---|---|---|
| IV | *Dorea formicigenerans* 1 | A |
|  | *Dorea longicatena* 2 | A |
|  | *Flavomfractor_plautii* 2 | A, B |
|  | *Ruminococcus champanellensis* 2 | A |
| IX | *Acidaminococcus fermentans* 1 | A, B, P |
|  | *Megasphaera elsdeni* 4 | P |
| other | *Bacteroides cellulosilyticus* 1 | A, S |
|  | *Bifiidobacterium Bifidum* | L, A |

*Short chain fatty acid legend:
A, acetate;
B, Butyrate;
L, lactate;
P, propionate;
S, succinate

TABLE F1

Composition F

| SEQ_NO | StrainID | Genus_species | SEQ_NO | StrainID | Genus_species |
|---|---|---|---|---|---|
| SEQ_24 | YK96 | *Dorea_longicatena* | SEQ_52 | YK51 | *Eubacterium_rectale* |
| SEQ_25 | YK101 | *Ruminococcus_obeum* | SEQ_53 | YK52 | *Eubacterium_rectale* |
| SEQ_26 | YK110 | *Megasphaera_elsdenii* | SEQ_54 | YK54 | *Anaerostipes_hadrus* |
| SEQ_27 | YK149 | *Acidaminococcus_fermentans/ Acidaminococcus_intestini* | SEQ_55 | YK56 | *Ruminococcus_faecis* |
| SEQ_28 | YK154 | *Megasphaera_elsdenii* | SEQ_56 | YK57 | *Ruminococcus_faecis* |
| SEQ_29 | YK36 | *Ruminococcus_faecis* | SEQ_57 | YK58 | *Dorea_longicatena* |
| SEQ_30 | YK95 | *Bacteroides_cellulosilyticus* | SEQ_58 | YK65 | *Roseburia_faecis* |
| SEQ_31 | YK32 | *Anaerostipes_hadrus* | SEQ_59 | YK67 | *Blautia_luti* |
| SEQ_32 | YK64 | *Ruminococcus_obeum* | SEQ_60 | YK69 | *Fusicatenibacter_saccharivorans* |
| SEQ_33 | YK73 | *Flavonifractor_plautii* | SEQ_61 | YK70 | *Fusicatenibacter_saccharivorans* |
| SEQ_34 | YK87 | *Eubacterium_rectale* | SEQ_62 | YK71 | *Roseburia_faecis* |
| SEQ_35 | YK105 | *Flavonifractor_plautii* | SEQ_63 | YK74 | *Megasphaera_elsdenii* |
| SEQ_36 | YK153 | *Megasphaera_elsdenii* | SEQ_64 | YK88 | *Eubacterium_rectale* |
| SEQ_37 | YK163 | *Eubacterium_rectale* | SEQ_65 | YK89 | *Eubacterium_rectale* |
| SEQ_38 | YK191 | *Ruminococcus_champanellensis/ Ruminococcus_albus* | SEQ_66 | YK97 | *Roseburia_faecis* |
| SEQ_39 | YK99 | *Ruminococcus_champanellensis* | SEQ_67 | YK98 | *Blautia_faecis* |
| SEQ_40 | YK55 | *Ruminococcus_faecis* | SEQ_68 | YK139 | *Fusicatenibacter_saccharivorans* |
| SEQ_41 | YK75 | *Bifidobacterium_bifidum* | SEQ_69 | YK141 | *Dorea_formicigenerans* |
| SEQ_42 | YK90 | *Anaerostipes_hadrus* | SEQ_70 | YK142 | *Ruminococcus_faecis* |
| SEQ_43 | YK30 | *Anaerostipes_hadrus* | SEQ_71 | YK152 | *Blautia_hansenii* |
| SEQ_44 | YK31 | *Anaerostipes_hadrus* | SEQ_72 | YK155 | *Blautia_hansenii* |
| SEQ_45 | YK12 | *Eubacterium_rectale* | SEQ_73 | YK157 | *Eubacterium_rectale* |
| SEQ_46 | YK27 | *Ruminococcus_faecis* | SEQ_74 | YK160 | *Roseburia_faecis* |
| SEQ_47 | YK28 | *Blautia_luti* | SEQ_75 | YK166 | *Eubacterium_rectale* |
| SEQ_48 | YK29 | *Ruminococcus_faecis* | SEQ_76 | YK168 | *Eubacterium_rectale* |
| SEQ_49 | YK33 | *Anaerostipes_hadrus* | SEQ_77 | YK169 | *Eubacterium_rectale* |
| SEQ_50 | YK34 | *Anaerostipes_hadrus* | SEQ_78 | YK171 | *Eubacterium_rectale* |
| SEQ_51 | YK35 | *Ruminococcus_faecis* | SEQ_79 | YK192 | *Roseburia_faecis* |

TABLE F2

Composition F, strain groupings

| Cluster | Composition F | *SCFAs |
|---|---|---|
| XIVa | *Eubacterium rectale* 12 | A, B, L |
|  | *Ruminococcus faecis* 8 | A, L |
|  | *Ruminococcus obeum* 2 | A, L |
|  | *Blautia faecis* 1 | A, L |
|  | *Blautia hansenii* 2 | A, L |
|  | *Blautia luti* 2 | A, L |
|  | *Anaerostipes hadrus* 7 | B |
|  | *Roseburia faecis* 5 | A, B |
|  | *Fusicatenibacter saccharivorans* 3 | A, L |

In one aspect, the disclosure provides Composition G (See e.g., FIG. 19; Table G). As shown in FIG. 19, Composition G contains bacteria that have the following 16S rDNA sequences: SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

In some embodiments, the disclosure provides compositions with two or more purified bacterial strains that have 16S rDNA sequences selected from the group consisting of SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

In some embodiments, the compositions include two or more purified bacterial strains comprising 16S rDNA sequences having at least 97% homology with nucleic acid sequences selected from the group consisting of SEQ ID NO:27, SEQ ID NO:43, SEQ ID NO:44, SEQ ID NO:51, SEQ ID NO:55, SEQ ID NO:68, SEQ ID NO:72, SEQ ID NO:70, SEQ ID NO:24, SEQ ID NO:34, SEQ ID NO:37, SEQ ID NO:46, SEQ ID NO:76, SEQ ID NO:77, SEQ ID NO:35, SEQ ID NO:62, SEQ ID NO:26, SEQ ID NO:63, SEQ ID NO:67, SEQ ID NO:40, SEQ ID NO:38, SEQ ID NO:47, SEQ ID NO:56, SEQ ID NO:25, and SEQ ID NO: 32.

The bacterial strains in Composition G are related to the following bacteria: *Acidaminococcus fermentans, Acidaminococcus intestine, Anaerostipes hadrus, Blautia faecis, Blautia hansenii, Dorea formicigenerans, Dorea longicatena, Eubacterium rectale, Flavonifractor plautii, Fusicatenibacter saccharivorans, Megasphaera elsdenii, Roseburia faecis, Ruminococcus champanellensis, Ruminococcus albus, Ruminococcus faecis,* and *Ruminococcus obeum.*

In some embodiments, the disclosure provides compositions with two or more bacterial strains of species selected from the group consisting of *Acidaminococcus fermentans, Acidaminococcus intestine, Anaerostipes hadrus, Blautia faecis, Blautia hansenii, Dorea formicigenerans, Dorea longicatena, Eubacterium rectale, Flavonifractor plautii, Fusicatenibacter saccharivorans, Megasphaera elsdenii, Roseburia faecis, Ruminococcus champanellensis, Ruminococcus albus, Ruminococcus faecis,* and *Ruminococcus obeum.*

In some embodiments, the disclosure provides compositions that include two or more purified bacterial strains comprise 16S rDNA sequences having at least 97% homology with nucleic acid sequences selected from the group consisting of SEQ ID NO:84, SEQ ID NO:85, SEQ ID NO:92, SEQ ID NO:93, SEQ ID NO:96, SEQ ID NO:97, SEQ ID NO:99, SEQ ID NO:104, SEQ ID NO:107, SEQ ID NO:111, SEQ ID NO:112, SEQ ID NO:113, SEQ ID NO:114, SEQ ID NO:115, SEQ ID NO:116, SEQ ID NO:117, and SEQ ID NO:119.

TABLE G

| Composition G | | |
|---|---|---|
| SEQ_27 | YK149 | *Acidaminococcus_fermentans/Acidaminococcus*_intesti |
| SEQ_43 | YK90 | *Anaerostipes_hadrus* |
| SEQ_44 | YK30 | *Anaerostipes_hadrus* |
| SEQ_51 | YK34 | *Anaerostipes_hadrus* |
| SEQ_55 | YK54 | *Anaerostipes_hadrus* |
| SEQ_68 | YK98 | *Blautia _faecis* |
| SEQ_72 | YK152 | *Blautia _hansenii* |
| SEQ_70 | YK141 | *Dorea_formicigenerans* |
| SEQ_24 | YK96 | *Dorea_longicatena* |
| SEQ_34 | YK87 | *Eubacterium_rectale* |
| SEQ_37 | YK163 | *Eubacterium_rectale* |
| SEQ_46 | YK12 | *Eubacterium_rectale* |
| SEQ_76 | YK166 | *Eubacterium_rectale* |
| SEQ_77 | YK168 | *Eubacterium_rectale* |
| SEQ_35 | YK105 | *Flavonifractor_plautii* |

TABLE G-continued

| Composition G | | |
|---|---|---|
| SEQ_62 | YK70 | *Fusicatenibacter_saccharivorans* |
| SEQ_26 | YK110 | *Megasphaera_elsdenii* |
| SEQ_63 | YK71 | *Roseburia_faecis* |
| SEQ_67 | YK97 | *Roseburia_faecis* |
| SEQ_40 | YK99 | *Ruminococcus_champanellensis* |
| SEQ_38 | YK191 | *Ruminococcus_champanellensis/Ruminococcus_albus* |
| SEQ_47 | YK27 | *Ruminococcus _faecis* |
| SEQ_56 | YK56 | *Ruminococcus _faecis* |
| SEQ_25 | YK101 | *Ruminococcus_obeum* |
| SEQ_32 | YK64 | *Ruminococcus_obeum* |

Figure 26:
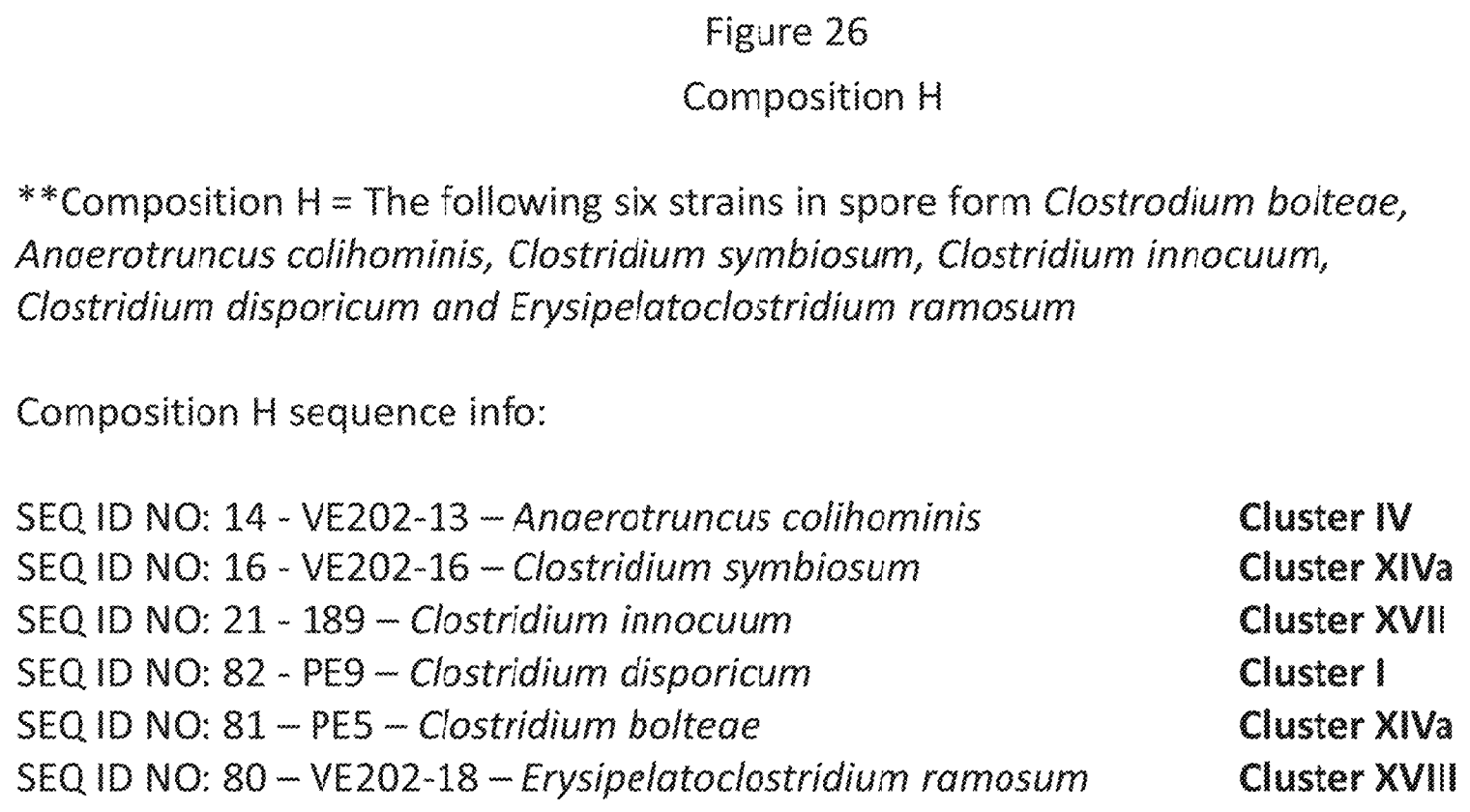

In one aspect, the disclosure provides Composition H (See e.g., FIG. 26, Table H). As shown in FIG. 26, Composition H contains bacteria that have the following 16S rDNA sequences: SEQ ID NO:14, SEQ ID NO:16, SEQ ID NO:21, SEQ ID NO:82, SEQ ID NO:81, and SEQ ID NO:80. In some embodiments, the disclosure provides compositions with two or more purified bacterial strains that have 16S rDNA sequences selected from the group consisting of SEQ ID NO:14, SEQ ID NO:16, SEQ ID NO:21, SEQ ID NO:82, SEQ ID NO:81, and SEQ ID NO:80.

In some embodiments, the compositions include two or more purified bacterial strains comprising 16S rDNA sequences having at least 97% homology with nucleic acid sequences selected from the group consisting of SEQ ID NO:14, SEQ ID NO:16, SEQ ID NO:21, SEQ ID NO:82, SEQ ID NO:81, and SEQ ID NO:80. In some embodiments, the compositions include four or more purified bacterial strains comprising 16S rDNA sequences having at least 97% homology with nucleic acid sequences selected from the group consisting of SEQ ID NO:14, SEQ ID NO:16, SEQ ID NO:21, SEQ ID NO:82, SEQ ID NO:81, and SEQ ID NO:80.

The bacterial strains in Composition H are related to the following bacteria: *Anaerotruncus colihominis, Clostridium symbiosum, Clostridium innocuum, Erysipelotrichaceae_bacterium_21-3, Clostridium disporicum, Clostridium bolteae,* and *Erysipelatoclostridium ramosum.* In some embodiments, the disclosure provides compositions with two or more bacterial strains selected from the group consisting of *Anaerotruncus colihominis, Clostridium symbiosum, Clostridium innocuum, Erysipelotrichaceae_bacterium_21-3, Clostridium disporicum, Clostridium bolteae,* and *Erysipelatoclostridium* ramosum.

In some embodiments, the disclosure provides compositions that include two or more purified bacterial strains comprise 16S rDNA sequences having at least 97% homology with nucleic acid sequences selected from the group consisting of SEQ ID NO:86, SEQ ID NO:95, SEQ ID NO:98, SEQ ID NO:110, SEQ ID NO:122, and SEQ ID NO:123.

Composition H includes bacteria from *Clostridium* cluster I, IV, XIVa, XVII and XVIII. In some embodiments, the disclosure provides compositions that include two or more purified bacterial strains from *Clostridium* cluster I, IV, XIVa, XVII and XVIII. In some embodiments, at least one of the bacterial strains of the composition belongs to *Clostridium* cluster IV. In some embodiments, at least one of the bacterial strains of the composition belongs to *Clostridium* cluster XIVa. In some embodiments, at least one of the bacterial strains of the composition belongs to *Clostridium* cluster XVII. In some embodiments, at least one of the bacterial strains of the composition belongs to *Clostridium* cluster I. In some embodiments, at least one of the bacterial strains of the composition belongs to

*Clostridium* cluster XVIII. In some embodiments, at least one of the bacterial strains of the composition belongs to *Clostridium* cluster XIVa and at least one of the bacterial strains belongs to *Clostridium* cluster IV. In some embodiments, at least one of the bacterial strains of the composition belongs to *Clostridium* cluster XIVa and at least one of the bacterial strains belongs to *Clostridium* cluster XVII.

TABLE H

Composition H

| SEQ ID NO | Strain | Closest species | Cluster |
|---|---|---|---|
| SEQ ID NO: 14 | VE202-13 | *Anaerotruncus colihominis* | Cluster IV |
| SEQ ID NO: 16 | VE202-16 | *Clostridium symbiosum* WAL-14163 | Cluster XIVa |
| SEQ ID NO: 21 | 189 | *Clostridium innocuum* | Cluster XVII |
| SEQ ID NO: 82 | PE9 | *Clostridium disporicum* | Cluster I |
| SEQ ID NO: 81 | PE5 | *Clostridium bolteae* | Cluster XIVa |
| SEQ ID NO: 80 | VE202-18 | *Erysipelatoclostridium ramosum* | Cluster XVIII |

In some embodiments, the disclosure provides compositions comprising two or more bacteria, wherein the composition does not include bacteria from *Clostridium* cluster I. In some embodiments, the disclosure provides compositions comprising two or more bacteria, wherein the composition does not include bacteria from *Clostridium* cluster XVIII. In some embodiments, the disclosure provides compositions comprising two or more bacteria, wherein the composition does not include bacteria from *Clostridium* cluster I and does not include bacteria from *Clostridium* cluster XVIII.

In some embodiments, the disclosure provides compositions comprising two or more bacteria, wherein all the bacteria are anaerobic bacteria. In some embodiments, the disclosure provides compositions comprising two or more bacteria, wherein all the bacteria are obligate anaerobic bacteria.

In some embodiments, the disclosure provides compositions comprising two or more bacteria (e.g., purified bacterial strains), wherein the composition does not include *Clostridium scindens*. In some embodiments, the disclosure provides compositions comprising two or more bacteria, wherein the composition does not include *Flavonifractor plautii*. In some embodiments, the disclosure provides compositions comprising two or more bacteria, wherein the composition does not include Parabacteroides. In some embodiments, the disclosure provides compositions comprising two or more bacteria, wherein the composition does not include *Lactobacillus*. In some embodiments, the disclosure provides compositions comprising two or more bacteria, wherein the composition does not include Colinsella. In some embodiments, the disclosure provides compositions comprising two or more bacteria, wherein the composition does not include Dialister. In some embodiments, the disclosure provides compositions comprising two or more bacteria, wherein the composition does not include Raoultella. In some embodiments, the disclosure provides compositions comprising two or more bacteria, wherein the composition does not include *Streptococcus*. In some embodiments, the disclosure provides compositions comprising two or more bacteria, wherein the composition does not include *Staphylococcus*. In some embodiments, the disclosure provides compositions comprising two or more bacteria, wherein the composition does not include *Microbacterium*. In some embodiments, the disclosure provides compositions comprising two or more bacteria, wherein the composition does not include Proteobacteria. In some embodiments, the disclosure provides compositions comprising two or more bacteria, wherein the composition does not include Peptostreptococcaceae. In some embodiments, the disclosure provides compositions comprising two or more bacteria, wherein the composition does not include Oscillospiraceae.

In one aspect, the disclosure provides bacterial strains with 16S rDNA sequences that have homology to a nucleic acid sequence of any one of the sequences of the bacterial strains or species described herein. In some embodiments, the bacterial strain has at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8% or 99.9% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) *Adv. Appl. Math.* 2:482c, by the homology alignment algorithm of Needleman and Wunsch, *J. Mol. Biol.* (1970) 48:443, by the search for similarity method of Pearson and Lipman. *Proc. Natl. Acad. Sci. USA* (1998) 85:2444, by computerized implementations of these algorithms (GAP, BESTFIT, FASTA, and TFASTA in the Wisconsin Genetics Software Package, Genetics Computer Group. Madison. WI), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res.* (1977) 25:3389-3402, and Altschul et al., *J. Mol. Biol.* (1990) 215:403-410, respectively.

In one aspect, the disclosure provides compositions comprising multiple purified bacterial strains (e.g., Compositions A-J). For instance, FIGS. 1, 13, 19, and 26 present several example compositions comprising multiple bacterial strains. In one aspect, the 16S rDNA sequences of purified bacterial strains of the compositions were compared to 16S rDNA sequences of known bacterial species/strains in a bacterial genome database to identify the closest known related bacterial species to the bacterial strains disclosed herein (See e.g., Table 1). It should be appreciated that multiple bacterial strains of the compositions disclosed herein may have the same closest related bacterial species. In one aspect, the disclosure provides compositions comprising one or more bacterial strains or species with 16S rDNA sequences that have homology to a nucleic acid sequence of any one of the sequences provided by SEQ ID NOs:1-83 and 124-159. In some embodiments, the species with 16S rDNA sequences with homology to a nucleic acid sequence of any one of the closest related species to any of the strains described herein, correspond to bacterial strains with 16S rDNA sequences provided by SEQ ID NOs:84-123.

In some embodiments, the compositions disclosed herein provide at least one of the bacterial strains (e.g., purified bacterial strains) described herein. In some embodiments, the compositions that comprise at least one bacterial strain, comprise at least one bacterial strain with a 16S rDNA sequence selected from any one of SEQ ID NOs:1-122 and 124-159. In some embodiments, the compositions that comprise at least one bacterial strain, comprise at least one bacterial strain with a 97% homology to 16S rDNA sequence selected from any one of SEQ ID NOs:1-122 and 124-159.

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more bacterial strains (e.g., purified bacterial strains).

It should be appreciated the compositions and methods provided herein can be distinguished from compositions and methods associated with the treatment of *C. difficile* infection that are available. For instance, it has been proposed that non-toxigenic *C. difficile* strains, i.e., strains that do not produce *C. difficile* toxins, may be used to treat *C. difficile* infection (See, e.g., U.S. Pat. No. 6,635,260). The compositions disclosed herein can be distinguished at least because the compositions described herein do not comprise non-toxigenic strains of *C. difficile*. Thus, in some embodiments, the compositions herein do not include comprise non-toxigenic strains of *C. difficile*. *C. difficile* belongs to *Clostridium* cluster XI. In some embodiments, the compositions herein do not include bacterial strains belonging to *Clostridium* cluster XI.

It is also considered in the art that bacterial strains expressing a bile inducible 7α/β-dehydroxylation operon can be used in the treatment of *C. difficile* (see, e.g., Buffie et al. *Nature* (2015) 517:205-208). The catalysis of bile acid 7α dihydroxylation is mediated by a stereo-specific NAD (H)-dependent 3-oxo-$\Delta^4$-cholenoic acid oxidoreductase encoded by the gene baiCD. In some embodiments, the compositions provided herein do not mediate bile acid 7-alpha-dehydroxylation.

In contrast to the findings in the art, in some embodiments, as shown herein, combinations of bacterial strains that do not encode baiCD (or a homolog thereof), or encode a baiCD that comprises one or more mutations that result in a non-functional BaiCD protein ("baiCD−"), are more effective at treating *C. difficile* infection and/or reducing or inhibiting production of Toxin B by *C. difficile* than combinations of bacterial strains that have a functional BaiCD protein ("baiCD+"). Thus, in some embodiments, the compositions of bacterial strains provided herein are baiCD− (i.e., the combination of the bacteria has no effective baiCD+ function). In some embodiments, all of bacterial strains in the compositions provided herein are baiCD−. In some embodiments, the majority (i.e., 50% or greater) of the bacterial strains in the compositions are baiCD−. In some embodiments, the majority (i.e., 50% or greater) of the bacterial strains in the compositions are baiCD− and the composition has no effective BaiCD function. In some embodiments, the minority (i.e., 50% or less) of the bacterial strains in the compositions are baiCD− and the composition has no effective BaiCD function. In some embodiments, bacterial strains for the compositions are selected based on the absence (or presence) of a baiCD gene or a predicted baiCD gene. In some embodiments, bacterial strains may be modified (e.g., genetically engineered) to prevent or reduce expression of a baiCD gene and/or to reduce or eliminate NAD(H)-dependent 3-oxo-$\Delta^4$-cholenoic acid oxidoreductase activity of BaiCD protein. The NAD(H)-dependent 3-oxo-$\Delta^4$-cholenoic acid oxidoreductase activity of a bacterial strain may be assessed by methods such as measuring the amount of 7α-dehydroxylated bile acid. In some embodiments, the compositions described herein comprise bacterial strains without the baiCD operon (baiCD⁻) or baiCD function.

In some embodiments, the compositions described herein do not include *Clostridium scindens*. In some embodiments, the compositions described herein do not include *Barnesiella intestihominis*. In some embodiments, the compositions described herein do not include *Blautia hansenii*. In some embodiments, the compositions described herein do not include *Pseudoflavinofractor capillosus*. In some embodiments, the compositions described herein do not include *Clostridium scindens. Barnesiella intestihominis, Blautia hansenii* or *Pseudoflavinofractor capillosus*.

In some embodiments, the compositions provided herein do not include Colinsella aerofaciens. In some embodiments, the compositions provided herein do not include *Acetovibrio ethanolgignens*. In some embodiments, the compositions provided herein do not bacterial strains belonging to *Clostridium* cluster I. In some embodiments, the compositions provided herein do not include *Clostridium butyricum*. In some embodiments, the compositions provided herein do not include *Clostridium dispori-*

*cum.* In some embodiments, the compositions provided herein do not include strains belonging to *Clostridium* cluster XI. In some embodiments, the compositions provided herein do not include *Clostridium glycolicum*. In some embodiments, the compositions provided herein do not include *Faecalibacterium prausnitzii*. In some embodiments, the compositions provided herein do not include *Turicibacter sanguinis*. In some embodiments, the compositions provided herein do not include *Eubacterium rectale*. In some embodiments, the compositions provided herein do not include *Eubacterium ventriosum*. In some embodiments, the compositions provided herein do not include *Ruminococcus obeum*. In some embodiments, the compositions provided herein do not include *Pseudobutyrivibrio*. In some embodiments, the compositions provided herein do not include *Christensenellaceae*. In some embodiments, the compositions do not comprise gram-negative bacteria. In some embodiments, the compositions do not comprise *E. coli*. In some embodiments, the compositions do not comprise fungi, such as *Monilla* species.

In some embodiments of the compositions provided herein, the compositions do not include bacterial strains that are resistant to one or more antibiotics. It should be appreciated that it may be desirable to have a mechanism to remove the bacterial compositions provided herein from the body of the subject after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, vancomycin, imipenem, meropenem, metronidazole and clindamycin. In some embodiments, the compositions do not include bacterial strains that are resistant to vancomycin.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. As used herein, an "antibiotic that is efficacious in a human" refers to an antibiotic that has been used to successfully treat bacterial infections in a human.

In some embodiments, the compositions described herein comprise spore forming and non-spore forming bacterial strains. In some embodiments, the compositions described herein comprise spore forming bacterial strains. In some embodiments, the compositions described herein comprise only spore forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (As discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

In some embodiments, the disclosure provides compositions wherein the compositions comprise bacterial strains that are spore forming bacterial strains. In some embodiments, the disclosure provides compositions wherein the compositions comprise bacterial strains that are non-spore forming bacterial strains. In some embodiments, the disclosure provides compositions wherein the compositions comprise bacterial strains that are spore forming bacterial strains and bacterial strains that are non-spore forming bacterial strains. In some embodiments, the disclosure provides compositions, wherein the compositions comprise a mixture of bacterial strains wherein at least 10% of the bacterial strains are spore forming bacterial strains, at least 20% of the bacterial strains are spore forming bacterial strains, at least 30% of the bacterial strains are spore forming bacterial strains, at least 40% of the bacterial strains are spore forming bacterial strains, at least 50% of the bacterial strains are spore forming bacterial strains, at least 60% of the bacterial strains are spore forming bacterial strains, at least 70% of the bacterial strains are spore forming bacterial strains, at least 80% of the bacterial strains are spore forming bacterial strains, at least 90% of the bacterial strains are spore forming bacterial strains bacteria up to 100% spore forming bacterial strains. Whether a bacterial strain is a spore forming strain can be determined for instance by evaluating the genome of the bacterial strain for the presence of sporulation genes. However, it should be appreciated that not all bacteria that are predicted to encode spore forming genes can be made to sporulate. In addition, whether a bacterial strain is a spore forming strain can be determined by exposing the bacterial strain to stress conditions, e.g., heat or exposure to chemicals (e.g., ethanol or chloroform), that are known to induce sporulation.

It should be appreciated that spore forming bacteria can be in spore form or in vegetative form. In some embodiments of the compositions provided herein, the spore forming bacteria are in spore form. In some embodiments of the compositions provided herein, the spore forming bacteria are in vegetative form. In some embodiments of the compositions provided herein, the spore forming bacteria are both present in spore form and in vegetative form. In some embodiments, the disclosure provides compositions, wherein the compositions comprise spore forming bacteria at least 10% of the spore forming bacteria are in spore format, at least 20% of the spore forming bacteria are in spore format, at least 30% of the spore forming bacteria are in spore format, at least 40% of the spore forming bacteria are in spore format, at least 50% of the spore forming bacteria are in spore format, at least 60% of the spore forming bacteria are in spore format, at least 70% of the spore forming bacteria are in spore format, at least 80% of the spore forming bacteria are in spore format, at least 90% of the spore forming bacteria are in spore format, up to 100% in spore format.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

Methods of inducing sporulation of spore-forming bacterial strains are well known in the art (See e.g., Paredes-Sabja et al., *Trends Microbiol.* (2011) 19(2):85-94). Generally, bacterial strains that are spore-formers can be made to go into spore form by stressing the bacterial strains. Non-limiting examples of stresses that can induce sporulation are an increase in temperature, change in the nutrients available and/or exposure to chemicals (e.g., ethanol or chloroform). It should be noted that bacteria that are non-spore formers, for instance because they are missing sporulation genes, cannot be made to sporulate by stress. To prepare compositions in which all the bacterial strains are in the spore form, the composition or bacterial cultures used to prepare the composition may be subjected to treatment to kill any bacteria not in spore form (e.g., in vegetative form), for example by exposing the composition to heat and are chemically breaking down the non-spore bacteria. The bacteria in spore format can subsequently be separated from the non-spore bacteria for instance by filtration.

The amount of spores can be quantified using techniques know in the art. These techniques include phase contrast microscopy for enumerating spores using a hemocytometer. In addition, the viability of spores can be determined by plating the spores and growing the spores. For instance, spores can be plated in appropriate media and incubated in the anaerobic chamber for a period of time (e.g., 48-96 hrs.). Viability can subsequently be determined by quantifying the colony forming units which correspond to spores that germinated. For instance, spores can be plated on TCCFA plates (Taurocholate, cycloserine, cefoxintin, fructose agar plates), in which taurocholate helps the spores to germinate. In addition, spores can be quantified using the dipicolinic assay (DPA assay). DPA is an agent that allows for spore selection and is a clear indicator of endospores. When complexed with terbium, bright green luminescence is observed.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals.

As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected.

As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In some embodiments, the bacterial strains of the compositions provided herein are obligate anaerobes. In some embodiments, the bacterial strains of the compositions provided herein are facultative anaerobes.

Aspects of the present disclosure are related to methods for treating a pathogenic infection in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject. In some embodiments, the subject is a pig.

In some embodiments, the subject is a carrier of a pathogenic organism and is suffering from the effects of the infection (e.g., diarrhea caused by *C. difficile* toxins). In some embodiments the subject is an asymptomatic carrier of a pathogen. In some embodiments, the subject is a carrier of *C. difficile*. In some embodiments the subject is an asymptomatic *C. difficile* carrier. In some embodiments, the subject has experienced recurrent or chronic pathogenic infections. In some embodiments, the subject is suffering from a first occurrence of a particular pathogenic infection. In some embodiments, the subject has been treated with antibiotics which resulted in the recurrence of the pathogenic infection. In some embodiments, the subject has been treated with antibiotics which resulted in a first occurrence of a pathogenic infection. In some embodiments, the subject is to undergo a procedure that puts the subject at a higher risk of infection. In some embodiments, the compositions provided herein are administered to a subject to lower the risk of becoming infected by a pathogen.

In some embodiments, the compositions provided herein are administered to a subject if the subject has a dysbiosis (e.g., has as microbiome associated with a disease state). In some embodiments, treatment with the compositions provided herein results in the change in the microbiome of the subject. In some embodiments, treatment with the compositions provided herein removes the dysbiosis in the subject resulting in a healthy microbiome. In some embodiments, treatment with the compositions provided herein removes the dysbiosis in the subject resulting in microbiome refractory or less susceptible to infection by a pathogen.

As used herein, the term "pathogen" in regard to a pathogenic infection refers to a microorganism (e.g., a bacterium) that causes a disease or a disease state in a subject. In some embodiments, the disease or disease state of the subject may include symptoms such as colitis, diarrhea, watery diarrhea, abdominal cramping, fever, blood or pus in the stool, nausea, dehydration, loss of appetite, chills, weight loss, and/or kidney failure. In some embodiments, the pathogenic infection may be diagnosed, for example, by detecting a pathogen (or protein or nucleic acid associated with a pathogen) in a fecal sample collected from the subject. In some embodiments, the pathogenic infection may be diagnosed, for example, by comparing the microbiota of a fecal sample of the subject with the microbiota in a fecal sample of a healthy subject.

In some embodiments, the pathogenic infection is *C. difficile; Clostridium perfringens; Clostridium botulinum; Clostridium tributrycum; Clostridium sporogenes; Escherichia coli; Pseudomonas aeruginosa*, such as Multidrug Resistant *Pseudomonas aeruginosa*; Vancomycin Resistant Enterococci (VRE); Carbapenem Resistant Enterobacteriaceae (CRE); *Neisseria gonorrheae; Acinetobacter*; Multidrug Resistant *Acinetobacter; Campylobacter*; Multi-drug resistant *Campylobacter; Candida*; Fluconazole-resistant *Candida*; Extended spectrum beta-lactamese (ESBL) producing Enterobacteriaceae; *Salmonella, Salmonella Typhimurium*, Drug resistant non-typhoid *Salmonella* spp.; Drug resistant *Salmonella Typhi*; Drug resistant *Shigella; Staphylococcus aureus*, such as Methicillin Resistant *S. aureus* or vancomycin resistant *S. aureus*; Drug resistant *Streptococcus pneumoniae*; Drug resistant Tuberculosis; Erythromycin Resistant Group A *Streptococcus*; Clindamycin resistant Group B *Streptococcus*, and any combinations thereof. In some embodiments, the pathogenic infection is *C. difficile*. In some embodiments, the *C. difficile* is an antibiotic-resistant *C. difficile*, e.g., fluoroquinolone resistant *C. difficile*. In some embodiments, the pathogenic infection is vancomycin-resistant Enterococci.

Additional non-limiting examples of pathogens responsible for pathogenic infection that can be treated according to the methods provided herein are *Leishmania, Staphylococcus epidermis, Staphylococcus saprophyticus, Streptococcus pyogenes, Streptococcus pneumoniae, Streptococcus agalactiae, Enterococcus faecalis, Corynebacterium diptheriae, Bacillus anthracis, Listeria monocytogenes, Clostridium perfringens, Clostridium tetanus, Clostridium botulinum, Clostridium difficile, Neisseria meningitidis, Neisseria gonorrhoeae, Escherichia coli, Salmonella typhimurium, Salmonella cholerasuis, Salmonella enterica, Salmonella enteriditis, Yersinia pestis, Yersinia pseudotuberculosis, Yersinia enterocolitica, Vibrio cholerae, Campylobacter jejuni, Campylobacter fetus, Helicobacter pylori, Pseudomonas aeruginosa, Pseudomonas mallei, Haemophilus influenzae, Bordetella pertussis, Mycoplasma pneumoniae, Ureaplasma urealyticum, Legionella pneumophila, Treponema pallidum, Leptospira interrogans, Borrelia burgdorferi, Mycobacterium tuberculosis, Mycobacterium leprae, Chlamydia psittaci, Chlamydia trachomatis, Chlamydia pneumoniae, Rickettsia ricketsii, Rickettsia akari, Rickettsia prowazekii, Brucella abortus, Brucella melitens, Brucella suis*, and *Francisella tularensis*. In general, any *bacterium* that is capable of inducing a disease in a subject and/or that is not present in healthy individual is considered a pathogen herein. It should be appreciated that a subject may carry multiple pathogens and/or have multiple pathogenic infections.

Any of the compositions described herein may be administered to a subject in a therapeutically effective amount or a dose of a therapeutically effective amount to treat or prevent a pathogenic infection (e.g., one or more pathogenic infections). The terms "treat" or "treatment" refer to reducing or alleviating one or more of the symptoms associated with a pathogenic infection, reducing the amount of bacterial toxin produced by the pathogenic infection, and/or reducing the bacterial load of the pathogenic infection. The terms "prevent" or "prevention" encompass prophylactic administration and may reduce the incidence or likelihood of pathogenic infection or a recurrent or chronic pathogenic infection. For instance, in some embodiments, administration of the compositions provided herein result in a healthy microbiome that is refractory to pathogenic infection, thereby preventing the pathogenic infection.

As used herein, a "therapeutically effective amount" of composition, such as a pharmaceutical composition, is any amount that results in a desired response or outcome in a subject, such as those described herein, including but not limited to prevention of infection, an immune response or an enhanced immune response to the pathogenic infection, prevention or reduction of symptoms associated with pathogenic infection, and/or a reduction or inhibition of toxin production by the pathogenic infection. It should be appreciated that the term effective amount may be expressed in number of bacteria or bacterial spores to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to enhance survival of the subject, reduce the bacterial burden of the pathogenic infection in the subject, and/or reduce or inhibit toxin production by the pathogenic infection. In some embodiments, the therapeutically effective amount is an amount sufficient to reduce the bacterial burden of the pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the bacterial burden in a subject with a pathogenic infection that has not received any of the compositions described herein, or as compared to a fecal sample from the same subject that was collected prior to administration of any of the compositions.

In some embodiments, the compositions provided herein inhibit the production of a bacterial toxin, e.g., *C. difficile* Toxin B. In some embodiments, the therapeutically effective amount is an amount sufficient to reduce or inhibit the amount of bacterial toxin (e.g., *C. difficile* Toxin B) produced by pathogenic infection in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of the bacterial toxin in a subject with a pathogenic infection that has not received any of the compositions described herein or as compared to a fecal sample from the same subject that was collected prior to administration of any of the compositions.

In some embodiments, the compositions provided herein induce the proliferation and/or accumulation of regulatory T cells in the subject. As will be evident to one of ordinary skill in the art, regulatory T cells, also referred to as "Tregs," are a subset of T lymphocytes that are generally thought to suppress an abnormal or excessive immune response and play a role in immune tolerance. Regulatory T cells may be identified based expression of the markers Foxp3 and CD4 (Foxp3+ CD4+). The term regulatory T cells may also include Foxp3-negative regulatory T cells that are IL-10-producing CD4-positive T cells.

In some embodiments, the therapeutically effective amount is an amount sufficient to induce the proliferation and/or accumulation of Tregs in the subject (or in a sample obtained from a subject) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the amount of Tregs in a subject (e.g., a subject with a pathogenic infection) that has not received any of the compositions described herein or as compared to a fecal sample from the same subject that was collected prior to administration of any of the compositions.

As used herein, the phrase "induces proliferation and/or accumulation of regulatory T cells" refers to an effect of inducing the differentiation of immature T cells into regulatory T cells, which differentiation leads to the proliferation and/or the accumulation of regulatory T cells. Further, the meaning of "induces proliferation and/or accumulation of regulatory T cells" includes in vivo effects, in vitro effects, and ex vivo effects. In some embodiments, the proliferation and/or accumulation of regulatory T cells may be assessed by detecting and/or quantifying the number of cells that express markers of regulatory T cells (e.g., Foxp3 and CD4), for example by flow cytometry. In some embodiments, the proliferation and/or accumulation of regulatory T cells may be assessed by determining the activity of the regulatory T cells, such as the production of cytokines (e.g., IL-10).

In some embodiments, the therapeutically effective amount is an amount sufficient to recolonize or repopulate the gastrointestinal tract of the subject with non-pathogenic bacteria. In some embodiments, the therapeutically effective amount is an amount sufficient to graft one or more of the bacterial strains of the composition in the gastrointestinal tract of the subject. In some embodiments, a fecal sample is obtained from the subject to assess the bacterial burden of the pathogenic infection and/or evaluate the efficacy of administration of the bacterial compositions described herein. In some embodiments, the microbiota of the subject (e.g., the identity and abundance of strains and/or species of the microbiota) may be assessed to determine a disease state of the subject and/or assess progress of the treatment. In some embodiments, the microbiota of the subject having a pathogenic infection is compared to the microbiota of a healthy subject, such as a subject that is not experiencing or has not experienced the pathogenic infection. In some embodiments, the microbiota of the subject having a pathogenic infection is compared to the microbiota of the same subject from a fecal sample obtained from the subject prior to the pathogenic infection.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions of the invention can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution.

Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coating that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, *AAPS PharmSciTech*, (2016) 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., *Int J Pharm* 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions of the present invention can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions of the present invention, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacteria per dosage amount.

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ CFUs of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined per dosage amount.

Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein. In some embodiments, the person has not been administered and antibiotic to treat the pathogenic infection. In some embodiments, the compositions provided herein comprise the first treatment of the pathogenic infection.

In some embodiments, the subject may be administered one or more doses of an antibiotic prior to or concurrently with a bacterial composition. Generally, the first line of defense in the treatment of a pathogenic infection is the administration of an antibiotic. In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, vancomycin, clindamycin, fidaxomicin, and cefoperazone.

Table 1 below provides sequence identifier numbers (SEQ ID NOs) used in the compositions of the experiments disclosed herein, along with the accompanying strain identification number (Strain ID). The closest bacterial species to the indicated strain is presented by genus-species. The 16S rDNA sequence associated with each genus species identified as the closest related genus species is also provided. The percent alignment presents the percent identity between the sequence of the indicated strain with the sequence from the closest genus species and the length of the alignment. The GenBank Accession Number of the closest related species is provided in the last column.

TABLE 1

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 01 | 71 | Blautia_wexlerae | SEQ_94 | 96.62 | 207 | NR_044054 |
| SEQ ID NO: 02 | 102 | Turicibacter_sanguinis | SEQ_91 | 97.81 | 183 | NR_028816 |
| SEQ ID NO: 03 | 5 | Clostridium_hathewayi | SEQ_105 | 92.42 | 198 | NR_036928 |
| SEQ ID NO: 04 | 7 | Blautia_hansenii | SEQ_99 | 96.62 | 207 | NR_104687 |
| SEQ ID NO: 05 | 10 | Blautia_hansenii | SEQ_99 | 98.06 | 206 | NR_104687 |
| SEQ ID NO: 06 | 40 | Lactobacillus_mucosae | SEQ_90 | 87.57 | 185 | NR_024994 |
| SEQ ID NO: 07 | 59 | Blautia_producta | SEQ_106 | 98.54 | 206 | NR_113270 |
| SEQ ID NO: 07 | 59 | Blautia_coccoides | SEQ_103 | 98.54 | 206 | NR_104700 |
| SEQ ID NO: 08 | 79 | Blautia_hansenii | SEQ_99 | 100 | 194 | NR_104687 |
| SEQ ID NO: 09 | VE202-21 | Eubacterium_contortum | SEQ_109 | 94.59 | 296 | NR_117147 |
| SEQ ID NO: 09 | VE202-21 | Eubacterium_fissicatena | SEQ_108 | 94.59 | 296 | NR_117142 |
| SEQ ID NO: 10 | 211 | Flavonifractor_plautii | SEQ_93 | 98.49 | 199 | NR_043142 |
| SEQ ID NO: 11 | VE202-9 | Anaerostipes_caccae | SEQ_88 | 99.5 | 399 | NR_028915 |
| SEQ ID NO: 12 | VE202-26 | Clostridium_scindens | SEQ_87 | 95.76 | 354 | NR_028785 |
| SEQ ID NO: 13 | 136 | Marvinbryantia_formatexigens | SEQ_89 | 94.66 | 131 | NR_042152 |

TABLE 1-continued

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 14 | VE202-13 | Anaerotruncus_colihominis | SEQ_95 | 99.34 | 1365 | NR_027558 |
| SEQ ID NO: 15 | VE202-14 | Eubacterium_fissicatena | SEQ_102 | 93.33 | 1530 | NR_117563 |
| SEQ ID NO: 16 | VE202-16 | Clostridium_symbiosum | SEQ_122 | 98.43 | 1469 | NR_118730 |
| SEQ ID NO: 17 | VE202-7 | Clostridium_bolteae | SEQ_110 | 99.86 | 1390 | NR_113410 |
| SEQ ID NO: 18 | 148 | Dorea_longicatena | SEQ_97 | 99.7 | 1318 | NR_028883 |
| SEQ ID NO: 19 | 16 | Blautia_producta | SEQ_106 | 98.33 | 1493 | NR_113270 |
| SEQ ID NO: 20 | 170 | Dorea_longicatena | SEQ_97 | 99.7 | 1318 | NR_028883 |
| SEQ ID NO: 21 | 189 | Clostridium_innocuum | SEQ_98 | 98.64 | 1476 | NR_029164 |
| SEQ ID NO: 22 | 169 | Dorea_longicatena | SEQ_97 | 99.58 | 475 | NR_028883 |
| SEQ ID NO: 23 | VE202-29 | Eisenbergiella_tayi | SEQ_121 | 100 | 354 | NR_118643 |
| SEQ ID NO: 24 | YK96 | Dorea_longicatena | SEQ_97 | 99.48 | 191 | NR_028883 |
| SEQ ID NO: 25 | YK101 | Ruminococcus_obeum | SEQ_85 | 96.81 | 188 | NR_118692 |
| SEQ ID NO: 26 | YK110 | Megasphaera_elsdenii | SEQ_119 | 96.62 | 207 | NR_102980 |
| SEQ ID NO: 27 | YK149 | Acidaminococcus_fermentans | SEQ_115 | 99.48 | 192 | NR_074928 |
| SEQ ID NO: 27 | YK149 | Acidaminococcus_intestini | SEQ_112 | 99.48 | 192 | NR_074306 |
| SEQ ID NO: 28 | YK154 | Megasphaera_elsdenii | SEQ_119 | 96.12 | 206 | NR_102980 |
| SEQ ID NO: 29 | YK36 | Ruminococcus_faecis | SEQ_96 | 99.29 | 425 | NR_116747 |
| SEQ ID NO: 30 | YK95 | Bacteroides_cellulosilyticus | SEQ_100 | 99.54 | 437 | NR_112933 |
| SEQ ID NO: 31 | YK32 | Anaerostipes_hadrus | SEQ_107 | 98.8 | 415 | NR_104799 |
| SEQ ID NO: 32 | YK64 | Ruminococcus_obeum | SEQ_84 | 99.04 | 415 | NR_119185 |
| SEQ ID NO: 33 | YK73 | Flavonifractor_plautii | SEQ_93 | 98.56 | 418 | NR_043142 |
| SEQ ID NO: 34 | YK87 | Eubacterium_rectale | SEQ_114 | 99.52 | 416 | NR_074634 |
| SEQ ID NO: 35 | YK105 | Flavonifractor_plautii | SEQ_93 | 99.26 | 407 | NR_043142 |
| SEQ ID NO: 36 | YK153 | Megasphaera_elsdenii | SEQ_119 | 96.04 | 429 | NR_102980 |
| SEQ ID NO: 37 | YK163 | Eubacterium_rectale | SEQ_114 | 99.76 | 415 | NR_074634 |
| SEQ ID NO: 38 | YK191 | Ruminococcus_champanellensis | SEQ_117 | 94.47 | 416 | NR_102884 |
| SEQ ID NO: 38 | YK191 | Ruminococcus_albus | SEQ_113 | 94.47 | 416 | NR_074399 |
| SEQ ID NO: 39 | YK99 | Ruminococcus_champanellensis | SEQ_117 | 97.28 | 184 | NR_102884 |
| SEQ ID NO: 40 | YK55 | Ruminococcus_faecis | SEQ_96 | 99.02 | 408 | NR_116747 |
| SEQ ID NO: 41 | YK75 | Bifidobacterium_bifidum | SEQ_118 | 99.45 | 183 | NR_102971 |
| SEQ ID NO: 42 | YK90 | Anaerostipes_hadrus | SEQ_107 | 98.97 | 194 | NR_104799 |
| SEQ ID NO: 43 | YK30 | Anaerostipes_hadrus | SEQ_107 | 99.48 | 191 | NR_104799 |
| SEQ ID NO: 44 | YK31 | Anaerostipes_hadrus | SEQ_107 | 98.97 | 194 | NR_104799 |
| SEQ ID NO: 45 | YK12 | Eubacterium_rectale | SEQ_114 | 99.27 | 412 | NR_074634 |
| SEQ ID NO: 46 | YK27 | Ruminococcus_faecis | SEQ_96 | 99.51 | 412 | NR_116747 |
| SEQ ID NO: 47 | YK28 | Blautia_luti | SEQ_111 | 99.5 | 400 | NR_041960 |
| SEQ ID NO: 48 | YK29 | Ruminococcus_faecis | SEQ_96 | 99.03 | 413 | NR_116747 |

TABLE 1-continued

Closest bacterial species to the strains described herein

| SEQ ID | Strain ID | Closest Genus_species | SEQ ID NO. of closest species | Percent alignment | Alignment length | Accession # of closest species |
|---|---|---|---|---|---|---|
| SEQ ID NO: 49 | YK33 | *Anaerostipes_hadrus* | SEQ_107 | 99.27 | 413 | NR_104799 |
| SEQ ID NO: 50 | YK34 | *Anaerostipes_hadrus* | SEQ_107 | 99.51 | 410 | NR_104799 |
| SEQ ID NO: 51 | YK35 | *Ruminococcus_faecis* | SEQ_96 | 99.51 | 409 | NR_116747 |
| SEQ ID NO: 52 | YK51 | *Eubacterium_rectale* | SEQ_114 | 99.27 | 413 | NR_074634 |
| SEQ ID NO: 53 | YK52 | *Eubacterium_rectale* | SEQ_114 | 99.03 | 413 | NR_074634 |
| SEQ ID NO: 54 | YK54 | *Anaerostipes_hadrus* | SEQ_107 | 85.82 | 409 | NR_104799 |
| SEQ ID NO: 55 | YK56 | *Ruminococcus_faecis* | SEQ_96 | 99.03 | 413 | NR_116747 |
| SEQ ID NO: 56 | YK57 | *Ruminococcus_faecis* | SEQ_96 | 98.79 | 413 | NR_116747 |
| SEQ ID NO: 57 | YK58 | *Dorea_longicatena* | SEQ_97 | 98.8 | 417 | NR_028883 |
| SEQ ID NO: 58 | YK65 | *Roseburia_faecis* | SEQ_92 | 99.27 | 413 | NR_042832 |
| SEQ ID NO: 59 | YK67 | *Blautia_luti* | SEQ_111 | 98.57 | 419 | NR_041960 |
| SEQ ID NO: 60 | YK69 | *Fusicatenibacter_saccharivorans* | SEQ_116 | 99.27 | 413 | NR_114326 |
| SEQ ID NO: 61 | YK70 | *Fusicatenibacter_saccharivorans* | SEQ_116 | 98.79 | 414 | NR_114326 |
| SEQ ID NO: 62 | YK71 | *Roseburia_faecis* | SEQ_92 | 99.28 | 414 | NR_042832 |
| SEQ ID NO: 63 | YK74 | *Megasphaera_elsdenii* | SEQ_119 | 96.06 | 431 | NR_102980 |
| SEQ ID NO: 64 | YK88 | *Eubacterium_rectale* | SEQ_114 | 99.28 | 415 | NR_074634 |
| SEQ ID NO: 65 | YK89 | *Eubacterium_rectale* | SEQ_114 | 99.27 | 413 | NR_074634 |
| SEQ ID NO: 66 | YK97 | *Roseburia_faecis* | SEQ_92 | 99.28 | 414 | NR_042832 |
| SEQ ID NO: 67 | YK98 | *Blautia_faecis* | SEQ_104 | 98.02 | 405 | NR_109014 |
| SEQ ID NO: 68 | YK139 | *Fusicatenibacter_saccharivorans* | SEQ_116 | 99.03 | 412 | NR_114326 |
| SEQ ID NO: 69 | YK141 | *Dorea_formicigenerans* | SEQ_120 | 98.51 | 402 | NR_044645 |
| SEQ ID NO: 70 | YK142 | *Ruminococcus_faecis* | SEQ_96 | 98.79 | 413 | NR_116747 |
| SEQ ID NO: 71 | YK152 | *Blautia_hansenii* | SEQ_99 | 99.5 | 401 | NR_104687 |
| SEQ ID NO: 72 | YK155 | *Blautia_hansenii* | SEQ_99 | 98.79 | 413 | NR_104687 |
| SEQ ID NO: 73 | YK157 | *Eubacterium_rectale* | SEQ_114 | 99.27 | 413 | NR_074634 |
| SEQ ID NO: 74 | YK160 | *Roseburia_faecis* | SEQ_92 | 99.03 | 414 | NR_042832 |
| SEQ ID NO: 75 | YK166 | *Eubacterium_rectale* | SEQ_114 | 99.27 | 409 | NR_074634 |
| SEQ ID NO: 76 | YK168 | *Eubacterium_rectale* | SEQ_114 | 99.27 | 413 | NR_074634 |
| SEQ ID NO: 77 | YK169 | *Eubacterium_rectale* | SEQ_114 | 99.28 | 416 | NR_074634 |
| SEQ ID NO: 78 | YK171 | *Eubacterium_rectale* | SEQ_114 | 97.87 | 188 | NR_074634 |
| SEQ ID NO: 79 | YK192 | *Roseburia_faecis* | SEQ_92 | 99.03 | 414 | NR_042832 |
| SEQ ID NO: 80 | VE202-18 | *Erysipelatoclostridium_ramosum* | SEQ_123 | 100 | 1485 | NR_113243 |
| SEQ ID NO: 81 | PE5 | *Clostridium_bolteae* | SEQ_110 | 100 | 1385 | NR_113410 |
| SEQ ID NO: 82 | PE9 | *Clostridium_disporicum* | SEQ_86 | 99.21 | 382 | NR_026491 |
| SEQ ID NO: 83 | 211-B | *Bacteroides_ovatus* | SEQ_101 | 95.64 | 436 | NR_112940 |

TABLE 2

Bacterial species with a high degree of homology based on whole genome analysis:

| Strain | Whole genome homology |
| --- | --- |
| SEQ_10 - 211 | *Lachnospiraceae bacterium 7_1_58FAA* |
| | *Subdoligranulum* |
| | *Flavinofractor plautii* |
| SEQ_14 - VE202-13 | *Anaerotruncus_colihominis* |
| SEQ_15 - VE202-14 | *Eubacterium_fissicatena* |
| | *Ruminococcus torques* |
| SEQ_16 - VE202-16 | *Clostridium_symbiosum* |
| SEQ_17 - VE202-7 | *Clostridium_bolteae* |
| SEQ_22 - 169/SEQ_20 - 170 | *Dorea_longicatena* |
| SEQ_19 - 16 | *Blautia_producta* |
| SEQ_21 - 189 | *Clostridium_innocuum* |
| | *Erysipelotrichaceae_bacterium_21_3* |

TABLE 3

Bacterial species with highest degree of homology based on whole genome analysis

| Composition B strain number | Strain identifier | SEQ ID # of 16S region as determined by Sanger sequencing | Closest species based on Sanger sequencing of 16S region | SEQ ID # of 16S regions as determined by WGS^ | *Consensus SEQ ID # of 16S region as determined by WGS |
| --- | --- | --- | --- | --- | --- |
| 1 | VE202-7 | 17 | *Clostridium bolteae* | 124, 125, 126, 127, 128 | 124 |
| 2 | VE202-13 | 14 | *Anaerotruncus colihominis* | 129, 130, 131 | 129 |
| 3 | VE202-14 | 15 | *Eubacterium fissicatena* | 132, 133, 134, 135, 136 | 132 |
| 4 | VE202-16 | 16 | *Clostridium symbiosum* | 137, 138, 139, 140 | 137 |
| 5 | strain #16 | 19 | *Blautia producta* | 141, 142, 143, 144, 145 | 141 |
| 6 | strain #170 | 20 | *Dorea longicatena* | 146, 147, 148, 149, 150, 151 | 146 |
| 7 | strain #189 | 21 | *Clostridium innocuum* | 152, 153, 154, 155, 156 | 152 |
| 8 | strain #211 | 10 | *Flavinofractor plautii* | 157, 158, 159 | 157 |

| Composition B strain number | Closest species based on Concensus SEQ ID # of 16S region as compared with 16S database | Closest species based on WGS compared versus WG databases | Additional closely related sequences | *Clostridium* cluster |
| --- | --- | --- | --- | --- |
| 1 | *Clostridium bolteae* | *Clostridium bolteae* 90A9 | | XIVa |
| 2 | *Anaerotruncus colihominis* | *Anaerotruncus colihominis* DSM 17241 | | IV |
| 3 | *Dracourtella massiliensis* | *Dracourtella massiliensis* GD1 | *Ruminococcus torques*; *Sellimonas intestinalis* | XIVa |
| 4 | *Clostridium symbiosum* | *Clostridium symbiosum* WAL-14163 | | XIVa |
| 5 | *Blautia producta* | *Clostridium bacterium* UC5.1-1D4 | *Blautia product* ATCC 27340 | XIVa |
| 6 | *Dorea longicatena* | *Dorea longicatena* CAG: 42 | | XIVa |
| 7 | *Clostridium innocuum* | *Erysipelotrichaceae bacterium* 21_3 | | XVII |

TABLE 3-continued

Bacterial species with highest degree of homology based on whole genome analysis

| 8 | *Flavinofractor plautii* | *Clostridium orbiscindens* 1_3_50AFAA | Subdolinogranulum | IV |

ʷWGS refers to Whole Genome Sequencing performed on a PacBio Biosciences platform (Menlo Park, CA).
*Consensus sequence is defined as the 16S sequence that has the most overlap with all other identified 16S sequences.

In some embodiments, in any of the compositions described herein, *Clostridium bolteae* can be replaced with *Clostridium bolteae* 90A9. In some embodiments, in any of the compositions described herein, *Anaerotruncus colihominis* can be replaced with *Anaerotruncus colihominis* DSM 17241. In some embodiments, in any of the compositions described herein, *Eubacterium fissicatena* can be replaced with *Sellimonas instestinalis, Drancourtella massiliensis* or *Drancourtella massiliensis* GPI. In some embodiments, in any of the compositions described herein, *Clostridium symbiosum* can be replaced with *Clostridium symbiosum* WAL-14163. In some embodiments, in any of the compositions described herein, *Blautia producta* can be replaced with *Clostridium bacterium* CD5.1-1D4 or *Blautia product* ATCC27340. In some embodiments, in any of the compositions described herein, *Dorea longicatena* can be replaced with *Dorea longicatena* CAG:42. In some embodiments, in any of the compositions described herein, *Clostridium innocuum* can be replaced with *Erysipelotrichaceae bacterium* 21_3. In some embodiments, in any of the compositions described herein, *Flavonifractor plautii* can be replaced with *Clostridium orbiscindens* 1_3_50 AFAA.

Aspects described herein provide pharmaceutical composition comprising a purified bacterial mixture consisting of bacterial strains comprising 16S rDNA sequences of at least 95% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 97% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 98% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 99% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21.

In some aspects, at least a portion of the bacteria of the pharmaceutical composition are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture consisting of bacterial strains comprising 16S rDNA sequences of at least 95% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 97% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 98% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 99% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising bacterial strains comprising 16S rDNA sequences of at least 95% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 97% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 98% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21. In some aspects, the bacterial strains have at least 99% homology to SEQ ID NO:10, SEQ ID NO:14, SEQ ID NO:15, SEQ ID NO:16, SEQ ID NO:17, SEQ ID NO:19, SEQ ID NO:20, and SEQ ID NO:21.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising bacterial strains comprising 16S rDNA sequences of at least 95% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 97% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 98% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, the bacterial strains have at least 99% homology to SEQ ID NO:124, SEQ ID NO:129, SEQ ID NO:132, SEQ ID NO:137, SEQ ID NO:141, SEQ ID NO:146, SEQ ID NO:152, and SEQ ID NO:157. In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture consisting of the following bacterial strains: *Clostridium bolteae, Anaerostruncus colihominis, Sellimonas intestinalis, Clostridium symbiosum, Blautia producta, Dorea Longicatena, Erysipelotrichaceae bacterium*, and *Clostridium orbiscindens*.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide pharmaceutical compositions comprising a purified bacterial mixture comprising the following bacterial strains: *Clostridium bolteae, Anaerostruncus colihominis, Sellimonas intestinalis, Clostridium symbiosum, Blautia producta, Dorea Longicatena, Erysipelotrichaceae bacterium*, and *Clostridium orbiscindens*.

In some aspects, at least a portion of the bacterial strains are in spore-form. In some aspects, the pharmaceutical composition further comprises a pharmaceutically acceptable excipient.

In some aspects, the pharmaceutical composition is formulated for oral administration. In some aspects, the pharmaceutical composition is in the form of a capsule. In some aspects, the pharmaceutical composition is formulated for delivery to the colon. In some aspects, the pharmaceutical composition further comprises a pH sensitive composition comprising one or more enteric polymers.

Aspects described herein provide methods of treating an infectious disease in a subject, the method comprising administering the pharmaceutical composition of any of the aspects described herein to the subject in an amount sufficient to treat the infectious disease. In some aspects, the infectious disease is *Clostridium difficile* infection.

The nucleic acid sequences of the 16S rDNA, or portion thereof, for the bacterial strains described herein are provided below:

```
>SEQ ID NO: 01|71|
GCCCGGAGCAGTTGATGTGAAGGATGGGTCACCTGTGGACTGCATTGGAACTGTCATACTTGAGTGCCGGAGGGTAA

GCGGAATTCCTAGTGTAGCGGTGAAATGCGTAGATATTAGGAGGAACACCAGTGGCGAAGGCGGCTTACTGGACGGT

AACTGACGTTGAGGCTCGAAAGCGTGGGGAGCAAACAGGATTAGATACCCTGGTAA

>SEQ ID NO: 02|102|
CTAACCGTGGAGGTCATTGGAAACTGGTCAACTTGAGTGCAGAAGAGGGAAGTGGAATTCCATGTGTAGCGGTGAAA

TGCGTAGAGATATGGAGGAACACCAGTGGCGAAGGCGGCTTCCTGGTCTGTAACTGACACTGAGGCGCGAAAGCGTG

GGGGGCAAACAGGATTAGATCCCCCGGTAA

>SEQ ID NO: 03|5|
ATGAAAGCCGGGGCTCAACCCCGGTACTGCTTTGGAAACTGTTTGACTTGAGTGCTTGAGAGGTAAGTGGAATTCCT

AGTGTAGCGGGAAATGTTTAGATATTAGGAGGACACCAGTGGCGAAGGCGGCTTACTGGACTGTAACTGACGTTGTG

GCTCGATTTGTGGGGAGCAAACAGGATTATATCCCCTGGTAA

>SEQ ID NO: 04|7|
CGGAAGGTCTGATGTGAAGGTTGGGGCTTACCCCGGACTGCATTGGAAACTGTTTTTCTAGAGTGCCCGAGAGGTAA

GCGGAATTCCTAGTGTAGCGGTGAAATGCTTTAGATATTAGGAGGAACACCAGTGGCGAAGGCGGCTTACTGGACGG

TAACTGACGTTGAGGCTCGAAAGCGTGGGGAGCAAACAGGATTAGATACCCTGGTAA

>SEQ ID NO: 05|10|
CGATGTCTGAGTGAAGGCTGGGGCTTACCCCAGGACTGCATTGGAACTGTTTTTCTAGAGTGCCGGAGAGGTAAGCG

GAATTCCTAGTGTAGCGGTGAAATGCGTAGATATTAGGAGGAACACCAGTGGCGAAGGCGGCTTACTGGACGGTAAC

TGACGTTGAGGCTCGAAAGCGTGGGGAGCAAACAGGATTAGATACCCTGGTAA
```

>SEQ ID NO: 06|40|
TTAACCAAGAAGTGCATTGGAACTGTCAGACTTGGGGGAAAAAAAGACAGTGCAACTCCATGTGTAGCGGTGGAATG

CTCCATATATATGGAAGAACACCAGTGGCGAAGGCGGCTGTCTGGTCTGCAACTGACGCTGAGGCTCGAATTCATGG

GTAAGAAAGTATTAGTCCCTTGTAA

>SEQ ID NO: 07|59|
ACCCGCTTGGTCTGAGGTGAGGCTGGGGCTTAACCCCAGGACTGCATTGGAAACTGTTGTTCTAGAGTGCCGGAGAG

GTAAGCGGAATTCCTAGTGTAGCGGTGAAATGCGTAGATATTAGGAGGAACACCAGTGGCGAAGGCGGCTTACTGGA

CGGTAACTGACGTTGAGGCTCGAAAGCGTGGGGAGCAAACAGGATTAGATACCCTGGTAA

>SEQ ID NO: 08|79|
TAGGCTGGGGCTTAACCCCAGGACTGCATTGGAAACTGTTTTTCTAGAGTGCCGGAGAGGTAAGCGGAATTCCTAGT

GTAGCGGTGAAATGCGTAGATATTAGGAGGAACACCAGTGGCGAAGGCGGCTTACTGGACGGTAACTGACGTTGAGG

CTCGAAAGCGTGGGGAGCAAACAGGATTAGATACCCTGGTAA

>SEQ ID NO: 09|VE202-21|
TTGCATTGGACACTATGTCAGCTGAGTGTCGGAGAGGTAAGTGGAATTCCTAGTGTAGCGGTGAAATGCGTAGATAT

TAGGAGGAACACCAGTGGCGAAGGCGGCTTACTGCACGTTTTCTGACGTTGAGGCTCGAAATCGTGGGGAGCAAACA

AAAATAGATACCCTGGTAGTCCACGCCGTAAACGATGCATACTAGGTGTCGGGTGGCAAAGCCATTCGGTGCCGCAG

CAAACGCAATAAGTATGCCACCTGGGGAGTACGTTCGCAAGAATGAAACTCAAATAAATTGACGGA

>SEQ ID NO: 10|211|
CCCGTCGTAGATGTGAACTGGGGGCTCACCTCCAGCCTGCATTTGAAACTGTAGTTCTTGAGTGCTGGAGAGGCAAT

CGGAATTCCGTGTGTAGCGGTGAAATGCGTAGATATACGGAGGAACACCAGTGGCGAAGGCGGATTGCTGGACAGTA

ACTGACGCTGAGGCGCGAAAGCGTGGGGAGCAAACAGGATTAGATACCCTCATAA

>SEQ ID NO: 11|VE202-9|
ACCTGATGCAGCGACGCCGCGTGAGTGAAGAAGTATTTCGGTATGTAAAGCTCTATCAGCAGGGAAGAAAAAAGACG

GTACCTGACTAAGAAGCCCCGGCTAACTACGTGCCAGCAGCCGCGGTAATACGTAGGGGGCAAGCGTTATCCGGAAT

TACTGGGTGTAAAGGGTGCGTAGGTGGCATGGTAAGTCAGAAGTGAAAGCCCGGGGCTTAACCCCGGGACTGCTTTT

GAAACTGTCATGCTGGAGTGCAGGAGAGGTAAGCGGAATTCCTAGTGTAGCGGTGAAATGCGTAGATATTAGGAGGA

ACACCAGTGGCGAAGGCGGCTTACTGGACTGTCACTGACACTGATGCACGAAAGCGTGGGGAGCAAACAGGATTAGA

TACCCTGGAAGTCCAT

>SEQ ID NO: 12|VE202-26|
ATGGGAGCGTAGATGGCGACTGGGCCATATGTGACAGCCCTGGTCTCAACCCCTTAACTGCATTTGGAACTGAGTGG

CTGGAGTGTCGGAGAGGCAGGCGGAATTCCTAGTGTAGCGGTGAAATGCGTAGATATTAGGAGGAACACCAGTGGCG

AAGGCGGCCTGCTGGACGATGACTGACGTTGAGGCTCGAAAGCGTGGGGAGCAAACAGGATTAGATACCCTGGTAGT

CCACGCCGTAAACGATGACTACTAGGTGTCGGGTGGCAAGGACATTCGGTGCCGCAGCAAACGCAATAAGTAGTCCA

CCTGGGGAGTACGTTCGCAAGAATGAAACTCAAAGGAAATTGACGGA

>SEQ ID NO: 13|136|
CGCAGCGGAGTGTATCCTAGGCTCACCTGGCTGCTTTCGAACTGGTTTTCTAGATCGTGTAGAGGGGGAGATTCCTG

GTGTAGCGTGAAATGCGTAGATATCTGGAGGAACACCAGTGGCGAAGGCGGCCTCCTGGACGGCAACTGACGTTGAG

GCTCGAAAGTGTGGGGAGCAAACAGGATTAGATACCCTGGTAA

>SEQ ID NO: 14|VE202-13|
TCAAAGAGTTTGATCCTGGCTCAGGACGAACGCTGGCGGCGCGCCTAACACATGCAAGTCGAACGGAGCTTACGTTT

TGAAGTTTTCGGATGGACGAATGTAAGCTTAGTGGCGGACGGGTGAGTAACACGTGAGCAACCTGCCTTTCAGAGGG

GGATAACAGCCGGAAACGGCTGCTAATACCGCATGATGTTGCGGGGGCACATGCCCCTGCAACCAAAGGAGCAATCC

GCTGAAAGATGGGCTCGCGTCCGATTAGCCAGTTGGCGGGGTAACGGCCCACCAAAGCGACGATCGGTAGCCGGACT

GAGAGGTTGAACGGCCACATTGGGACTGAGACACGGCCCAGACTCCTACGGGAGGCAGCAGTGGGGGATATTGCACA

```
ATGGGCGAAAGCCTGATGCAGCGACGCCGCGTGAGGGAAGACGGTCTTCGGATTGTAAACCTCTGTCTTTGGGGAAG
AAAATGACGGTACCCAAAGAGGAAGCTCCGGCTAACTACGTGCCAGCAGCCGCGGTAATACGTAGGGAGCAAGCGTT
GTCCGGAATTACTGGGTGTAAAGGGAGCGTAGGCGGGATGGCAAGTAGAATGTTAAATCCATCGGCTCAACCGGTGG
CTGCGTTCTAAACTGCCGTTCTTGAGTGAAGTAGAGGCAGGCGGAATTCCTAGTGTAGCGGTGAAATGCGTAGATAT
TAGGAGGAACACCAGTGGCGAAGGCGGCCTGCTGGGCTTTAACTGACGCTGAGGCTCGAAAGCGTGGGGAGCAAACA
GGATTAGATACCCTGGTAGTCCACGCCGTAAACGATGATTACTAGGTGTGGGGGACTGACCCCTTCCGTGCCGCAG
TTAACACAATAAGTAATCCACCTGGGGAGTACGGCCGCAAGGTTGAAACTCAAAGGAATTGACGGGGGCCCGCACAA
GCAGTGGAGTATGTGGTTTAATTCGAAGCAACGCGAAGAACCTTACCAGGTCTTGACATCGGATGCATAGCCTAGAG
ATAGGTGAAGCCCTTCGGGGCATCCAGACAGGTGGTGCATGGTTGTCGTCAGCTCGTGTCGTGAGATGTTGGGTTAA
GTCCCGCAACGAGCGCAACCCTTATTATTAGTTGCTACGCAAGAGCACTCTAATGAGACTGCCGTTGACAAAACGGA
GGAAGGTGGGGATGACGTCAAATCATCATGCCCCTTATGACCTGGGCTACACACGTACTACAATGGCACTAAAACAG
AGGGCGGCGACACCGCGAGGTGAAGCGAATCCCGAAAAAGTGTCTCAGTTCAGATTGCAGGCTGCAACCCGCCTGCA
TGAAGTCGGAATTGCTAGTAATCGCGGATCAGCATGCCGCGGTGAATACGTTCCCGGGCCTTGTACACACCGCCCGT
CACACCATGGGAGTCGGTAACACCCGAAGCCAGTAGCCTAACCGCAAGGGGGCGCTGTCGAAGGTGGGATTGATGA
CTGGGGTGAAGTCGTAACAAGGTAGCCGTATCGGAAGGTGCGGCTGGATCACCTCCTTT
>SEQ ID NO: 15|VE202-14|
TACGAGAGTTTGATCCTGGCTCAGGATGAACGCTGGCGGCGTGCCTAACACATGCAAGTCGAGCGAAGCGCTGTTTT
CAGAATCTTCGGAGGAAGAGGACAGTGACTGAGCGGCGGACGGGTGAGTAACGCGTGGGCAACCTGCCTCATACAGG
GGGATAACAGTTAGAAATGACTGCTAATACCGCATAAGCGCACAGGACCGCATGGTGTAGTGTGAAAAACTCCGGTG
GTATGAGATGGACCCGCGTCTGATTAGGTAGTTGGTGGGTAAAGGCCTACCAAGCCGACGATCAGTAGCCGACCTG
AGAGGGTGACCGGCCACATTGGGACTGAGACACGGCCCAAACTCCTACGGGAGGCAGCAGTGGGGAATATTGCACAA
TGGGGGAAACCCTGATGCAGCGACGCCGCGTGAAGGAAGAAGTATTTCGGTATGTAAACTTCTATCAGCAGGGAAGA
AGATGACGGTACCTGAGTAAGAAGCACCGGCTAAATACGTGCCAGCAGCCGCGGTAATACGTATGGTGCAAGCGTTA
TCCGGATTTACTGGGTGTAAAGGGAGCGTAGACGGATAGGCAAGTCTGGAGTGAAAACCCAGGGCTCAACCCTGGGA
CTGCTTTGGAAACTGCAGATCTGGAGTGCCGGAGAGGTAAGCGGAATTCCTAGTGTAGCGGTGAAATGCGTAGATAT
TAGGAGGAACACCAGTGGCGAAGGCGGCTTACTGGACGGTGACTGACGTTGAGGCTCGAAAGCGTGGGGAGCAAACA
GGATTAGATACCCTGGTAGTCCACGCCGTAAACGATGACTACTAGGTGTCGGTGTGCAAAGCACATCGGTGCCGCAG
CAAACGCAATAAGTAGTCCACCTGGGGAGTACGTTCGCAAGAATGAAACTCAAAGGAATTGACGGGACCCGCACAA
GCGGTGGAGCATGTGGTTTAATTCGAAGCAACGCGAAGAACCTTACCTGGTCTTGACATCCGGATGACGGGCGAGTA
ATGTCGCCGTCCCTTCGGGGCATCCGAGACAGGTGGTGCATGGTTGTCGTCAGCTCGTGTCGTGAGATGTTGGGTTA
AGTCCCGCAACGAGCGCAACCCTTATCTTCAGTAGCCAGCATATAAGGTGGGCACTCTGGAGAGACTGCCAGGGAGA
ACCTGGAGGAAGGTGGGGATGACGTCAAATCATCATGCCCCTTATGGCCAGGGCTACACACGTGCTACAATGGCGTA
AACAAAGGGAAGCGAGAGGGTGACCTGGAGCGAATCCCAAAAATAACGTCTCAGTTCGGATTGTAGTCTGCAACTCG
ACTACATGAAGCTGGAATCGCTAGTAATCGCGGATCAGCATGCCGCGGTGAATACGTTCCCGGGTCTTGTACACACC
GCCCGTCACACCATGGGAGTCAGTAACGCCCGAAGCCAGTGACCCAACCTTAGAGGAGGGAGCTGTCGAAGGCGGGA
CGGATAACTGGGGTGAAGTCGTAACAAGGTAGCCGTATCGGAAGGTGCGGCTGGATCACCTCCTTT
>SEQ ID NO: 16|VE202-16|
ATGAGAGTTTGATCCTGGCTCAGGATGAACGCTGGCGGCGTGCCTAACACATGCAAGTCGAACGAAGCGATTTAACG
GAAGTTTTCGGATGAAGTTGAATTGACTGAGTGGCGGACGGGTGAGTAACGCGTGGGTAACCTGCCTTGTACTGGG
GGACAACAGTTAGAAATGACTGCTAATACCGCATAAGCGCACAGTATCGCATGATACAGTGTGAAAAACTCCGGTGG
```

```
TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 17|VE202-7|
ATGAGAGTTTGATCCTGGCTCAGGATGAACGCTGGCGGCGTGCCTAACACATGCAAGTCGAACGAAGCAATTAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

GATTAGATACCCTGGTAGTCCACGCCGTAAACGATGAATGCTAGGTGTTGGGGGCAAAGCCCTTCGGTGCCGTCGC

AAACGCAGTAAGCATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAAGTCTTGACATCCTCTTGACCGGCGTGTAA

CGGCGCCTTCCCTTCGGGGCAAGAGAGACAGGTGGTGCATGGTTGTCGTCAGCTCGTGTCGTGAGATGTTGGGTTAA

GTCCCGCAACGAGCGCAACCCTTATCCTTAGTAGCCAGCAGGTAAAGCTGGGCACTCTAGGGAGACTGCCAGGGATA

ACCTGGAGGAAGGTGGGGATGACGTCAAATCATCATGCCCCTTATGATTTGGGCTACACACGTGCTACAATGGCGTA

AACAAAGGGAAGCAAGACAGTGATGTGGAGCAAATCCCAAAAATAACGTCCCAGTTCGGACTGTAGTCTGCAACCCG

ACTACACGAAGCTGGAATCGCTAGTAATCGCGAATCAGAATGTCGCGGTGAATACGTTCCCGGGTCTTGTACACACC

GCCCGTCACACCATGGGAGTCAGCAACGCCCGAAGTCAGTGACCCAACTCGCAAGAGAGGGAGCTGCCGAAGGCGGG

GCAGGTAACTGGGGTGAAGTCGTAACAAGGTAGCCGTATCGGAAGGTGCGGCTGGATCACCTCCTTT

>SEQ ID NO: 18|148|
AACGAGAGTTTGATCCTGGCTCAGGATGAACGCTGGCGGCGTGCTTAACACATGCAAGTCGAGCGAAGCACTTTGGA

AGATTCTTCGGATGAAGACTTTTGTGACTGAGCGGCGGACGGGTGAGTAACGCGTGGGTAACCTGCCTCATACAGGG
```

```
GGATAACAGTTAGAAATGACTGCTAATACCGCATAAGACCACGGTACCGCATGGTACAGTGGTAAAAACTCCGGTGG
TATGAGATGGACCCGCGTCTGATTAGGTAGTTGGTGGGGTAACGGCCTACCAAGCCGACGATCAGTAGCCGACCTGA
GAGGGTGACCGGCCACATTGGGACTGAGACACGGCCCAGACTCCTACGGGAGGCAGCAGTGGGGAATATTGCACAAT
GGAGGAAACTCTGATGCAGCGACGCCGCGTGAAGGATGAAGTATTTCGGTATGTAAACTTCTATCAGCAGGGAAGAA
AATGACGGTACCTGACTAAGAAGCCCCGGCTAACTACGTGCCAGCAGCCGCGGTAATACGTAGGGGGCAAGCGTTAT
CCGGATTTACTGGGTGTAAAGGGAGCGTAGACGGCACGGCAAGCCAGATGTGAAAGCCCGGGGCTCAACCCCGGGAC
TGCATTTGGAACTGCTGAGCTAGAGTGTCGGAGAGGCAAGTGGAATTCCTAGTGTAGCGGTGAAATGCGTAGATATT
AGGAGGAACACCAGTGGCGAAGGCGGCTTGCTGGACGATGACTGACGTTGAGGCTCGAAAGCGTGGGGAGCAAACAG
GATTAGATACCCTGGTAGTCCACGCCGTAAACGATGACTGCTAGGTGTCGGGTGGCAAAGCCATTCGGTGCCGCAGC
TAACGCAATAAGCAGTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCTGATCTTGACATCCCGATGACCGCTTCGTAA
TGGAAGCTTTTCTTCGGAACATCGGTGACAGGTGGTGCATGGTTGTCGTCAGCTCGTGTCGTGAGATGTTGGGTTAA
GTCCCGCAACGAGCGCAACCCCTATCTTCAGTAGCCAGCAGGTTAAGCTGGGCACTCTGGAGAGACTGCCAGGGATA
ACCTGGAGGAAGGTGGGGATGACGTCAAATCATCATGCCCCTTATGACCAGGGCTACACACGTGCTACAATGGCGTA
AACAAAGAGAAGCGAACTCGCGAGGGTAAGCAAATCTCAAAAATAACGTCTCAGTTCGGATTGTAGTCTGCAACTCG
ACTACATGAAGCTGGAATCGCTAGTAATCGCAGATCAGAATGCTGCGGTGAATACGTTCCCGGGTCTTGTACACACC
GCCCGTCACACCATGGGAGTCAGTAACGCCCGAAGTCAGTGACCCAACCGTAAGGAGGGAGCTGCCGAAGGTGGGAC
CGATAACTGGGGTGAAGTCGTAACAAGGTAGCCGTATCGGAAGGTGCGGCTGGATCACCTCCTTT

>SEQ ID NO: 19|16|
ATCAGAGAGTTTGATCCTGGCTCAGGATGAACGCTGGCGGCGTGCTTAACACATGCAAGTCGAGCGAAGCACTTAAG
TGGATCTCTTCGGATTGAAACTTATTTGACTGAGCGGCGGACGGGTGAGTAACGCGTGGGTAACCTGCCTCATACAG
GGGGATAACAGTTAGAAATGGCTGCTAATACCGCATAAGCGCACAGGACCGCATGGTCTGGTGTGAAAAACTCCGGT
GGTATGAGATGGACCCGCGTCTGATTAGCTAGTTGGAGGGGTAACGGCCCACCAAGGCGACGATCAGTAGCCGGCCT
GAGAGGGTGAACGGCCACATTGGGACTGAGACACGGCCCAGACTCCTACGGGAGGCAGCAGTGGGGAATATTGCACA
ATGGGGGAAACCCTGATGCAGCGACGCCGCGTGAAGGAAGAAGTATCTCGGTATGTAAACTTCTATCAGCAGGGAAG
AAAATGACGGTACCTGACTAAGAAGCCCCGGCTAACTACGTGCCAGCAGCCGCGGTAATACGTAGGGGGCAAGCGTT
ATCCGGATTTACTGGGTGTAAAGGGAGCGTAGACGGAAGAGCAAGTCTGATGTGAAAGGCTGGGGCTTAACCCCAGG
ACTGCATTGGAAACTGTTTTTCTAGAGTGCCGGAGAGGTAAGCGGAATTCCTAGTGTAGCGGTGAAATGCGTAGATA
TTAGGAGGAACACCAGTGGCGAAGGCGGCTTACTGGACGGTAACTGACGTTGAGGCTCGAAAGCGTGGGGAGCAAAC
AGGATTAGATACCCTGGTAGTCCACGCCGTAAACGATGAATACTAGGTGTCGGGTGGCAAAGCCATTCGGTGCCGCA
GCAAACGCAATAAGTATTCCACCTGGGGAGTACGTTCGCAAGAATGAAACTCAAAGGAATTGACGGGACCCGCACA
AGCGGTGGAGCATGTGGTTTAATTCGAAGCAACGCGAAGAACCTTACCAAGTCTTGACATCCCTCTGACCGGCCCGT
AACGGGGCCTTCCCTTCGGGGCAGAGGAGACAGGTGGTGCATGGTTGTCGTCAGCTCGTGTCGTGAGATGTTGGGTT
AAGTCCCGCAACGAGCGCAACCCCTATCCTTAGTAGCCAGCAGGTGAAGCTGGGCACTCTAGGGAGACTGCCGGGGA
TAACCCGGAGGAAGGCGGGGACGACGTCAAATCATCATGCCCCTTATGATTTGGGCTACACACGTGCTACAATGGCG
TAAACAAAGGGAAGCGAGACAGCGATGTTGAGCAAATCCCAAAAATAACGTCCCAGTTCGGACTGCAGTCTGCAACT
CGACTGCACGAAGCTGGAATCGCTAGTAATCGCGAATCAGAATGTCGCGGTGAATACGTTCCCGGGTCTTGTACACA
CCGCCCGTCACACCATGGGAGTCAGTAACGCCCGAAGTCAGTGACCCAACCTTACAGGAGGGAGCTGCCGAAGGCGG
GACCGATAACTGGGGTGAAGTCGTAACAAGGTAGCCGTATCGGAAGGTGCGGCTGGATCACCTCCTTT
```

>SEQ ID NO: 20|170|
AACGAGAGTTTGATCCTGGCTCAGGATGAACGCTGGCGGCGTGCTTAACACATGCAAGTCGAGCGAAGCACTTTGGA
AGATTCTTCGGATGATTTCCTTTGTGACTGAGCGGCGGACGGGTGAGTAACGCGTGGGTAACCTGCCTCATACAGGG
GGATAACAGTTAGAAATGACTGCTAATACCGCATAAGACCACGGTACCGCATGGTACAGTGGTAAAAACTCCGGTGG
TATGAGATGGACCCGCGTCTGATTAGGTAGTTGGTGGGGTAACGGCCTACCAAGCCGACGATCAGTAGCCGACCTGA
GAGGGTGACCGGCCACATTGGGACTGAGACACGGCCCAGACTCCTACGGGAGGCAGCAGTGGGGAATATTGCACAAT
GGAGGAAACTCTGATGCAGCGACGCCGCGTGAAGGATGAAGTATTTCGGTATGTAAACTTCTATCAGCAGGGAAGAA
AATGACGGTACCTGACTAAGAAGCCCCGGCTAACTACGTGCCAGCAGCCGCGGTAATACGTAGGGGGCAAGCGTTAT
CCGGATTTACTGGGTGTAAAGGGAGCGTAGACGGCACGGCAAGCCAGATGTGAAAGCCCGGGGCTCAACCCCGGGAC
TGCATTTGGAACTGCTGAGCTAGAGTGTCGGAGAGGCAAGTGGAATTCCTAGTGTAGCGGTGAAATGCGTAGATATT
AGGAGGAACACCAGTGGCGAAGGCGGCTTGCTGGACGATGACTGACGTTGAGGCTCGAAAGCGTGGGGAGCAAACAG
GATTAGATACCCTGGTAGTCCACGCCGTAAACGATGACTGCTAGGTGTCGGGTGGCAAAGCCATTCGGTGCCGCAGC
TAACGCAATAAGCAGTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCTGATCTTGACATCCCGATGACCGCTTCGTAA
TGGAAGCTTTTCTTCGGAACATCGGTGACAGGTGGTGCATGGTTGTCGTCAGCTCGTGTCGTGAGATGTTGGGTTAA
GTCCCGCAACGAGCGCAACCCCTATCTTCAGTAGCCAGCAGGTTAAGCTGGGCACTCTGGAGAGACTGCCAGGGATA
ACCTGGAGGAAGGTGGGGATGACGTCAAATCATCATGCCCCTTATGACCAGGGCTACACACGTGCTACAATGGCGTA
AACAAAGAGAAGCGAACTCGCGAGGGTAAGCAAATCTCAAAAATAACGTCTCAGTTCGGATTGTAGTCTGCAACTCG
ACTACATGAAGCTGGAATCGCTAGTAATCGCAGATCAGAATGCTGCGGTGAATACGTTCCCGGGTCTTGTACACACC
GCCCGTCACACCATGGGAGTCAGTAACGCCCGAAGTCAGTGACCCAACCGTAAGGAGGGAGCTGCCGAAGGTGGGAC
CGATAACTGGGGTGAAGTCGTAACAAGGTAGCCGTATCGGAAGGTGCGGCTGGATCACCTCCTTT

>SEQ ID NO: 21|189|
ATGGAGAGTTTGATCCTGGCTCAGGATGAACGCTGGCGGCATGCCTAATACATGCAAGTCGAACGAAGTTTCGAGGA
AGCTTGCTTCCAAAGAGACTTAGTGGCGAACGGGTGAGTAACACGTAGGTAACCTGCCCATGTGTCCGGGATAACTG
CTGGAAACGGTAGCTAAAACCGGATAGGTATACAGAGCGCATGCTCAGTATATTAAAGCGCCCATCAAGGCGTGAAC
ATGGATGGACCTGCGGCGCATTAGCTAGTTGGTGAGGTAACGGCCCACCAAGGCGATGATGCGTAGCCGGCCTGAGA
GGGTAAACGGCCACATTGGGACTGAGACACGGCCCAAACTCCTACGGGAGGCAGCAGTAGGGAATTTTCGTCAATGG
GGGAAACCCTGAACGAGCAATGCCGCGTGAGTGAAGAAGGTCTTCGGATCGTAAAGCTCTGTTGTAAGTGAAGAACG
GCTCATAGAGGAAATGCTATGGGAGTGACGGTAGCTTACCAGAAAGCCACGGCTAACTACGTGCCAGCAGCCGCGGT
AATACGTAGGTGGCAAGCGTTATCCGGAATCATTGGGCGTAAAGGGTGCGTAGGTGGCGTACTAAGTCTGTAGTAAA
AGGCAATGGCTCAACCATTGTAAGCTATGGAAACTGGTATGCTGGAGTGCAGAAGAGGGCGATGGAATTCCATGTGT
AGCGGTAAAATGCGTAGATATATGGAGGAACACCAGTGGCGAAGGCGGTCGCCTGGTCTGTAACTGACACTGAGGCA
CGAAAGCGTGGGGAGCAAATAGGATTAGATACCCTAGTAGTCCACGCCGTAAACGATGAGAACTAAGTGTTGGAGGA
ATTCAGTGCTGCAGTTAACGCAATAAGTTCTCCGCCTGGGGAGTATGCACGCAAGTGTGAAACTCAAAGGAATTGAC
GGGGGCCCGCACAAGCGGTGGAGTATGTGGTTTAATTCGAAGCAACGCGAAGAACCTTACCAGGCCTTGACATGGAA
ACAAATACCCTAGAGATAGGGGGATAATTATGGATCACACAGGTGGTGCATGGTTGTCGTCAGCTCGTGTCGTGAGA
TGTTGGGTTAAGTCCCGCAACGAGCGCAACCCTTGTCGCATGTTACCAGCATCAAGTTGGGGACTCATGCGAGACTG
CCGGTGACAAACCGGAGGAAGGTGGGGATGACGTCAAATCATCATGCCCCTTATGGCCTGGGCTACACACGTACTAC
AATGGCGGCCACAAAGAGCAGCGACACAGTGATGTGAAGCGAATCTCATAAAGGTCGTCTCAGTTCGGATTGAAGTC
TGCAACTCGACTTCATGAAGTCGGAATCGCTAGTAATCGCAGATCAGCATGCTGCGGTGAATACGTTCTCGGGCCTT

```
GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT
```

>SEQ ID NO: 22|169|
```
AGTAACGCGTGGGTAACCTGCCTCATACAGGGGGATAACAGTTAGAAATGACTGCTAATACCGCATAAGACCACGGT

ACCGCATGGTACAGTGGTAAAAACTCCGGTGGTATGAGATGGACCCGCGTCTGATTAGGTAGTTGGTGGGGTAACGG

CCTACCAAGCCGACGATCAGTAGCCGACCTGAGAGGGTGACCGGCCACATTGGGACTGAGACACGGCCCAGACTCCT

ACGGGAGGCAGCAGTGGGGAATATTGCACAATGGAGGAAACTCTGATGCAGCGACGCCGCGTGAAGGATGAAGTATT

TCGGTATGTAAACTTCTATCAGCAGGGAAGAAAATGACGGTACCTGACTAAGAAGCCCCGGCTAACTACGTGCCAGC

AGCCGCGGTAATACGTAGGGGGCAAGCGTTATCCGGATTTACTGGGTGTAAAGGGAGCGTAGACGGCACGGCAAGCC

AGATGTGAAAGCCC
```

>SEQ ID NO: 23|VE202-29|
```
CAGGCTGGAGTGCAGGAGAGGTAAGCGGAATTCCTAGTGTAGCGGTGAAATGCGTAGATATTAGGAGGAACACCAGT

GGCGAAGGCGGCTTACTGGACTGTAACTGACGTTGAGGCTCGAAAGCGTGGGGAGCAAACAGGATTAGATACCCTGG

TAGTCCACGCGGTAAACGATGATTGCTAGGTGTAGGTGGGTATGGACCCATCGGTGCCGCAGCTAACGCAATAAGCA

ATCCACCTGGGGAGTACGTTCGCAAGAATGAAACTCAAAGGAATTGACGGGGACCCGCACAAGCGGTGGAGCATGTG

GTTTAATTCGAAGCAACGCGAAGAACCTTACCAAGTCTTGACATCC
```

>SEQ ID NO: 24|YK96|
```
CCGGGGCTCACCCCGGGACTGCATTTGGAACTGCTGAGCTAGAGTGTCGGAGAGGCAAGTGGAATTCCTAGTGTAGC

GGTGAAATGCGTAGATATTAGGAGGAACACCAGTGGCGAAGGCGGCTTGCTGGACGATGACTGACGTTGAGGCTCGA

AAGCGTGGGGAGCAAACAGGATTAGATACCCTGGTA
```

>SEQ ID NO: 25|YK101|
```
AGGGTCAACCCCTGGACTGCATTGGAAACTGTCAGGCTGGAGTGCCGGAGAGGTAAGCGGAATTCCTAGTGTAGCGG

TGAAATGCGTAGATATTAGGAGGAACACCAGTGGCGAAGGCGGCTTACTGGACGGTAACTGACGTTGATGCTCGAAA

GCGTGGGGAGCAAACAGGATTAGATAACCTGGTAAA
```

>SEQ ID NO: 26|YK110|
```
GGGAAGTCGGTCTTAAGTGCGGGGCTTAACCCCGTGAGGGGACCGAAACTGTGAAGCTCGAGTGTCGGAGAGGAAAG

CGGAATTCCTAGTGTAGCGGTGAAATGCGTAGATATTAGGAGGAACACCAGTGGCGAAAGCGGCTTTCTGGACGACA

ACTGACGCTGAGGCGCGAAAGCCAGGGGAGCAAACGGGATTAGATACCCCAGTAA
```

>SEQ ID NO: 27|YK149|
```
TAGTCTGAGTGATGCGGGGCTTAACCCCGTATGGCGTTGGATACTGGAAGTCTTGAGTGCAGGAGAGGAAAGGGGAA

TTCCCAGTGTAGCGGTGAAATGCGTAGATATTGGGAGGAACACCAGTGGCGAAGGCGCCTTTCTGGACTGTGTCTGA

CGCTGAGATGCGAAAGCCAGGGTAGCAAACGGGATTAGATACCACGGTA
```

>SEQ ID NO: 28|YK154|
```
GATAGTCGGTCTTAAGTGCGGGGCTTACCCCGTGAGGGGACCGAAACTGTGAAGCTCGAGTGTCGGAGAGGAAAGCG

GAATTCCTAGTGTAGCGGTGAAATGCGTAGATATTAGGAGGAACACCAGTGGCGAAAGCGGCTTTCTGGACGACAAC

TGACGCTGAGGCGCGAAAGCCAGGGGAGCAAACGGGATTAGATACCACGGTAA
```

>SEQ ID NO: 29|YK36|
```
CGTTTGCTCCACGCTTTCGAGCCTCACGTCAGTTACCGTCCAGTAAGCCGCCTTCGCCACTGGTGTTCCTCCTAATA

TCTACGCATTTCACCGCTACACTAGGAATTCCGCTTACCTCTCCGGTACTCTAGATTGACAGTTTCCAATGCAGTCC

CGGGGTTGAGCCCCGGGTTTTCACATCAGACTTGCCACTCCGTCTACGCTCCCTTTACACCCAGTAAATCCGGATAA

CGCTTGCACCATACGTATTACCGCGGCTGCTGGCACGTATTTAGCCGGTGCTTCTTAGTCAGGTACCGTCATTTTCT

TCCCTGCTGATAGAGCTTTACATACCGAAATACTTCATCGCTCACGCGGCGTCGCTGCATCAGGGTTTCCCCCATTG

TGCAATATTCCCCACTGCTGCCTCCCGTAGGAGTTTGGA
```

>SEQ ID NO: 30|YK95|
TGTCACACTTTCGAGCATCAGCGTCAGTTACAGTCCAGTAAGCTGCCTTCGCAATCGGAGTTCTTCGTGATATCTAA

GCATTTCACCGCTACACCACGAATTCCGCCTACCTCTACTGCACTCAAGACGACCAGTATCAACTGCAATTTTACGG

TTGAGCCGCAAACTTTCACAGCTGACTTAATAGTCCGCCTACGCTCCCTTTAAACCCAATAAATCCGGATAACGCTT

GGATCCTCCGTATTACCGCGGCTGCTGGCACGGAGTTAGCCGATCCTTATTCGTATGGTACATACAAAAAGCCACAC

GTGGCTCACTTTATTCCCATATAAAAGAAGTTTACAACCCATAGGGCAGTCATCCTTCACGCTACTTGGCTGGTTCA

GACTCTCGTCCATTGACCAATATTCCTCACTGCTGCCTCCCGTAGGTAGTTTGGAA

>SEQ ID NO: 31|YK32|
CCGTTGTCACGCTTTCGTGCTCAGTGTCAGTTTCAGTCCAGTAAGCCGCCTTCGCCACTGATGTTCCTCCTAATATC

TACGCATTTCACCGCTACACTAGGAATTCCGCTTACCTCTCCTGCACTCCAGTCTGACAGTTTCAAAAGCAGTCCCA

GAGTTAAGCCCTGGGTTTTCACTTCTGACTTGCCATACCACCTACGCACCCTTTACACCCAGTAATTCCGGATAACG

CTTGCCCCCTACGTATTACCGCGGCTGCTGGCACGTAGTTAGCCGGGGCTTCTTAGTCAGGTACCGTCATTTTCTTC

CCTGCTGATAGAGCTTTACATACCGAAATACTTCTTCACTCACGCGGCGTCGCTGCATCAGGGTTCCCCCCATTGTG

CAATATTCCCCACTGCTGCCTCCCGTGGAAGTTTGGA

>SEQ ID NO: 32|YK64|
GCGAATGTCACGCATTCGAGCCTCACGTCAGTTACCGTCCAGTAAGCCGCCTTCGCCACTGGTGTTCCTCCTAATAT

CTACGCATTTCACCGCTACACTAGGAATTCCGCTTACCTCTCCGGCACTCAAGACTAACAGTTTCCAATGCAGTCCA

GGGGTTGAGCCCCCGCCTTTCACATCAGACTTGCCAGTCCGTCTACGCTCCCTTTACACCCAGTAAATCCGGATAAC

GCTTGCCCCCTACGTATTACCGCGGCTGCTGGCACGTAGTTAGCCGGGGCTTCTTAGTCAGGTACCGTCACTATCTT

CCCTGCTGATAGAAGTTTACATACCGAGATACTTCTTCCTTCACGCGGCGTCGCTGCATCAGGGTTTCCCCCATTGT

GCAATATTCCCCACTGCTGCCTCCCGTGGGAGTTTGGAA

>SEQ ID NO: 33|YK73|
TGCTCACGCTTTCGCGCTCAGCGTCAGTTACTGTCCAGCAATCCGCCTTCGCCACTGGTGTTCCTCCGTATATCTAC

GCATTTCACCGCTACACACGGAATTCCGCGATTGCCTCTCCAGCACTCAAGAACTACAGTTTCAAATGCAGGCTGGAGG

TTGAGCCCCCAGTTTTCACATCTGACTTGCAATCCCGCCTACACGCCCTTTACACCCAGTAAATCCGGATAACGCTT

GCCACCTACGTATTACCGCGGCTGCTGGCACGTAGTTAGCCGTGGCTTATTCGTCAGGTACCGTCATTTGTTTCGTC

CCTGACAAAAGAAGTTTACAACCCGAAAGCCTTCTTCCTTCACGCGGCGTTGCTGGGTCAGGCTTGCGCCCATTGCC

CAATATTCCCCACTGCTGCCTCCCGTGGTAGTTTGGA

>SEQ ID NO: 34|YK87|
TGTCCACGCTTTCGAGCTCAGCGTCAGTTATCGTCCAGTAAGCCGCCTTCGCCACTGGTGTTCCTCCTAATATCTAC

GCATTTCACCGCTACACTAGGAATTCCGCTTACCCCTCCGACACTCTAGTACGACAGTTTCCAATGCAGTACCGGGG

TTGAGCCCCGGGCTTTCACATCAGACTTGCCGCACCGCCTGCGCTCCCTTTACACCCAGTAAATCCGGATAACGCTT

GCACCATACGTATTACCGCGGCTGCTGGCACGTATTTAGCCGGTGCTTCTTAGTCAGGTACCGTCATTATCTTCCCT

GCTGATAGAGCTTTACATACCGAAATACTTCTTCGCTCACGCGGCGTCGCTGCATCAGGCTTTCGCCCATTGTGCAA

TATTCCCCACTGCTGACTCCCGTAGGAGTTTGGA

>SEQ ID NO: 35|YK105|
CGTTTCTCCACGCTTCGCGCTCAGCGTCAGTTACTGTCCAGCAATCCGCCTTCGCCACTGGTGTTCCTCCGTATATC

TACGCATTTCACCGCTACACACGAATTCCGCGATTGCCTCTCCAGCACTCAAGAACTACAGTTTCAAATGCAGGCTGG

AGGTTGAGCCCCCAGTTTTCACATCTGACTTGCAATCCCGCCTACACGCCCTTTACACCCAGTAAATCCGGATAACG

CTTGCCACCTACGTATTACCGCGGCTGCTGGCACGTAGTTAGCCGTGGCTTATTCGTCAGGTACCGTCATTTGTTTC

GTCCCCGACAAAAGAAGTTTACAACCCGAAAGCCTTCTTCCTTCACGCGGCGTTGCTGGGTCAGGCTTGCGCCCATT

GCCCAATATTCCCCACTGCTGCCTCCCTGGGAAGTTTGG

```
>SEQ ID NO: 36|YK153|
ATGTCCTGACTTCGCGCCTCAGCGTCAGTTGTCGTCCAGAAAGCCGCTTTCGCCACTGGTGTTCCTCCTAATATCTA
CGCATTTCACCGCTACACTAGGAATTCCGCTTTCCTCTCCGACACTCGAGCTTCACAGTTTCGGTCCCCTCACGGGG
TTAAGCCCCGCACTTTTAAGACCGACTTGCGATGCCGCCTGCGCGCCCTTTACGCCCAATAATTCCGGACAACGCTT
GCCACCTACGTATTACCGCGGCTGCTGGCACGTAGTTAGCCGTGCTTTCTCTTACGGTACCGTCAGGGATAACGGG
TATTGACCGCTATCCTGTTCGTCCCATATAACAGAACTTTACAACCCGAAGGCCGTCATCGTTCACGCGGCGTTGCT
CCGTCAGACTTTCGTCCATTGCGGAAGATTCCCCACTGCTGCCTCCCTGGGAAGTTTGGA

>SEQ ID NO: 37|YK163|
GTTTGCTCACGCTTTCGAGCTCAGCGTCAGTTATCGTCCAGTAAGCCGCCTTCGCCACTGGTGTTCCTCCTAATATC
TACGCATTTCACCGCTACACTAGGAATTCCGCTTACCCCTCCGACACTCTAGTACGACAGTTTCCAATGCAGTACCG
GGGTTGAGCCCCGGGCTTTCACATCAGACTTGCCGCACCGCCTGCGCTCCCTTTACACCCAGTAAATCCGGATAACG
CTTGCACCATACGTATTACCGCGGCTGCTGGCACGTATTTAGCCGGTGCTTCTTAGTCAGGTACCGTCATTATCTTC
CCTGCTGATAGAGCTTTACATACCGAAATACTTCTTCGCTCACGCGGCGTCGCTGCATCAGGCTTTCGCCCATTGTG
CAATATTCCCCACTGCTGCCTCCCGTAGGAGTTTGG

>SEQ ID NO: 38|YK191|
CGTTGCTCACGCATTCGAGCCTCAGCGTCAGTTAAGCCCAGTAAGCCGCCTTCGCCACTGATGTTCCTCCTAATATC
TACGCATTTCACCGCTACACTAGGAATTCCGCTTACCTCTACTTCACTCAAGAACCACAGTTTCAAATGCAGTTTAT
GGGTTAAGCCCATAGTTTTCACATCTGACTTGCGATCCCGCCTACGCTCCCTTTACACCCAGTAATTCCGGACAACG
CTCGCTCCCTACGTATTACCGCGGCTGCTGGCACGTAGTTAGCCGGAGCTTCCTCCTCAGGTACCGTCTTTTTTCGT
CCCTGAAGACAGAGGTTTACAATCCTAAAACCTTCTTCCCTCACGCGGCATCGCTGCATCAGAGTTTCCTCCATTGT
GCAATATTCCCCACTGCTGCCTCCCGTAGGAGTTTGGAA

>SEQ ID NO: 39|YK99|
TGGGCTTACCCATAAACTGCATTTGAAACTGTGGTTCTTGAGTGAAGTAGAGGTAAGCGGAATTCCTAGTGTAGCGG
TGAAATGCGTAGATATTAGGAGGAACATCAGTGGCGAAGGCGGCTTACTGGGCTTTAACTGACGCTGAGGCTCGAAA
GCGTGGGGAGCAAACAGGATTAGATACCCAAGTAA

>SEQ ID NO: 40|YK55|
GTCAGCATCGAGCTCACGTCAGTTACCGTCCAGTAAGCCGCCTTCGCCACTGGTGTTCCTCCTAATATCTACGCATT
TCACCGCTACACTAGGAATTCCGCTTACCTCTCCGGTACTCTAGATTGACAGTTTCCAATGCAGTCCCGGGGTTGAG
CCCCGGGTTTTCACATCAGACTTGCCACTCCGTCTACGCTCCCTTTACACCCAGTAAATCCGGATAACGCTTGCACC
ATACGTATTACCGCGGCTGCTGGCACGTATTTAGCCGGTGCTTCTTAGTCAGGTACCGTCATTTTCTTCCCTGCTGA
TAGAGCTTTACATACCGAAATACTTCATCGCTCACGCGGCGTCGCTGCATCAGGGTTTCCCCCATTGTGCAATATTC
CCCACTGCTGCCTCCCGAGGGAGTTTGGA

>SEQ ID NO: 41|YK75|
TCATCGCTTACGGTGGATCTGCGCCGGGTACGGGCGGCTGGAGTGCGGTAGGGGAGACTGGAATTCCCGGTGTAAC
GGTGGAATGTGTAGATATCGGGAAGAACACCGATGGCGAAGGCAGGTCTCTGGGCCGTCACTGACGCTGAGGAGCGA
AAGCGTGGGGAGCGAACAGGATTAGATACAACGGTAA

>SEQ ID NO: 42|YK90|
TGAACCCAGGGCTTAACTCTGGGACTGCTTTTGAACTGTCAGACTGGAGTGCAGGAGAGGTAAGCGGAATTCCTAGT
GTAGCGGTGAAATGCGTAGATATTAGGAGGAACATCAGTGGCGAAGGCGGCTTACTGGACTGAAACTGACACTGAGG
CACGAAAGCGTGGGGAGCAAACAGGATTAGATACCATGGTAA

>SEQ ID NO: 43|YK30|
ACCAGGGCTTAACTCTGGGACTGCTTTTGAACTGTCAGACTGGAGTGCAGGAGAGGTAAGCGGAATTCCTAGTGTAG
CGGTGAAATGCGTAGATATTAGGAGGAACATCAGTGGCGAAGGCGGCTTACTGGACTGAAACTGACACTGAGGCACG
AAAGCGTGGGGAGCAAACAGGATTAGATACCCTGGTAA
```

>SEQ ID NO: 44|YK31|
GAACCCAGGGCTTAACTCTGGGACTGCTTTTGAACTGTCAGACTGGAGTGCAGGAGAGGTAAGCGGAATTCCTAGTG

TAGCGGTGAAATGCGTAGATATTAGGAGGAACATCAGTGGCGAAGGCGGCTTACTGGACTGAAACTGACACTGAGGC

ACGAAAGCGTGGGGAGCAAACAGGATTAGATACCCCGGTAA

>SEQ ID NO: 45|YK12|
GAGTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAGGGAGTTTGGA

>SEQ ID NO: 46|YK27|
TGTCAGCTTTCGAGCTCACGTCAGTTACCGTCCAGTAAGCCGCCTTCGCCACTGGTGTTCCTCCTAATATCTACGCA

TTTCACCGCTACACTAGGAATTCCGCTTACCTCTCCGGTACTCTAGATTGACAGTTTCCAATGCAGTCCCGGGGTTG

AGCCCCGGGTTTTCACATCAGACTTGCCACTCCGTCTACGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTTTCTTCCCTGCT

GATAGAGCTTTACATACCGAAATACTTCATCGCTCACGCGGCGTCGCTGCATCAGGGTTTCCCCCATTGTGCAATAT

TCCCCACTGCTGCCTCCCGTAGGAGTTTGGA

>SEQ ID NO: 47|YK28|
CACGTCAGTTACCGTCCAGTAAGCCGCCTTCGCCACTGGTGTTCCTCCTAATATCTACGCATTTCACCGCTACACTA

GGAATTCCGCTTACCTCTCCGGCACTCAAGACGGGCAGTTTCCAATGCAGTCCCGGGGTTGAGCCCCAGCCTTTCAC

ATCAGACTTGTCCATCCGTCTACGCTCCCTTTACACCCAGTAAATCCGGATAACGCTTGCCCCCTACGTATTACCGC

GGCTGCTGGCACGTAGTTAGCCGGGGCTTCTTAGTCAGGTACCGTCATTTTCTTCCCTGCTGATAGAAGTTTACATA

CCGAGATACTTCTTCCTTCACGCGGCGTCGCTGCATCAGGGTTTCCCCCATTGTGCAATATTCCCCACTGCTGCCTC

CCGTAGGAGTTTGGG

>SEQ ID NO: 48|YK29|
GTCAGCTTTCGAGCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCCCGTGGGAGTTTGGA

>SEQ ID NO: 49|YK33|
GATGCTCAGCTTTCGTGCTCAGTGTCAGTTTCAGTCCAGTAAGCCGCCTTCGCCACTGATGTTCCTCCTAATATCTA

CGCATTTCACCGCTACACTAGGAATTCCGCTTACCTCTCCTGCACTCCAGTCTGACAGTTTCAAAAGCAGTCCCAGA

GTTAAGCCCTGGGTTTTCACTTCTGACTTGCCATACCACCTACGCACCCTTTACACCCAGTAATTCCGGATAACGCT

TGCCCCCTACGTATTACCGCGGCTGCTGGCACGTAGTTAGCCGGGGCTTCTTAGTCAGGTACCGTCATTTTCTTCCC

TGCTGATAGAGCTTTACATACCGAGATACTTCTTCACTCACGCGGCGTCGCTGCATCAGGGTTTCCCCCATTGTGCA

ATATTCCCCACTGCTGCCTCCCGAAGGAAGTTTGGA

>SEQ ID NO: 50|YK34|70A_009_YK34_A1_A02
GTGTCAGCTTCGTGCTCAGTGTCAGTTTCAGTCCAGTAAGCCGCCTTCGCCACTGATGTTCCTCCTAATATCTACGC

ATTTCACCGCTACACTAGGAATTCCGCTTACCTCTCCTGCACTCCAGTCTGACAGTTTCAAAAGCAGTCCCAGAGTT

AAGCCCTGGGTTTTCACTTCTGACTTGCCATACCACCTACGCACCCTTTACACCCAGTAATTCCGGATAACGCTTGC

CCCCTACGTATTACCGCGGCTGCTGGCACGTAGTTAGCCGGGGCTTCTTAGTCAGGTACCGTCATTTTCTTCCCTGC

TGATAGAGCTTTACATACCGAGATACTTCTTCACTCACGCGGCGTCGCTGCATCAGGGTTTCCCCCATTGTGCAATA

TTCCCCACTGCTGCCTCCCGTAGGGAGTTTGGA

>SEQ ID NO: 51|YK35|
GTCAGCTTCGAGCCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCGCGTAGGAGTTTGGA

>SEQ ID NO: 52|YK51|
TGTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTGCCTCCCGAAGGGAGTTTGGA

>SEQ ID NO: 53|YK52|
TTCAGCTTTCGAGCTCAGCGTCAGTTATCGTCCAGTAAGCCGCCTTCGCCACTGGTGTTCCTCCTAATATCTACGCA

TTTCACCGCTACACTAGGAATTCCGCTTACCCCTCCGACACTCTAGTACGACAGTTTCCAATGCAGTACCGGGGTTG

AGCCCCGGGCTTTCACATCAGACTTGCCGCACCGCCTGCGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTATCTTCCCTGCT

GATAGAGCTTTACATACCGAAATACTTCTTCGCTCACGCGGCGTCGCTGCATCAGGCTTTCGCCCATTGTGCAATAT

TCCCCACTGCTGCCTCCCGAGGGGAGTTTGG

>SEQ ID NO: 54|YK54|
TTCGGTCTGCTTTCCCCTTCTCGCGCCTCAGTGTCAGTTTCTGTCTAGTAAGCCGCCTTCGCCACTGATGTTCCTCC

TAATATCTACGCACTTCACCGCTCCACAATGAATTCCGCTTACCCCTCCCGCGCTCTAGTCTGACAGTTTTAAAAAA

ACTCCCCGAGAGAAACCCTGGGTTTTTTCTTCTGACATGCGATATCCCACCCCCACCCTTTATACACCCAAAAATCG

GATAAAAGGTGCGACCTACGTATTATACCGGCTGCTGGGGCGTAGATAGCCGGGGGTTCTTATACAGGGACCGTCAT

TTTCTTTCCCGCTGATACAGCTTTACATACCGAAATACTTCTTTCTCACGCGGCGTCGCTGCATCAGGGTTTCCCCC

ATTGTGCAATATTCCCCACTGCTGCCTCCCGAAGGGGAAGTTGGGGGAAA

>SEQ ID NO: 55|YK56|
GTTCAGCTTTCGAGCCTCACGTCAGTTACCGTCCAGTAAGCCGCCTTCGCCACTGGTGTTCCTCCTAATATCTACGC

ATTTCACCGCTACACTAGGAATTCCGCTTACCTCTCCGGTACTCTAGATTGACAGTTTCCAATGCAGTCCCGGGGTT

GAGCCCCGGGTTTTCACATCAGACTTGCCACTCCGTCTACGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTTTCTTCCCTGC

TGATAGAGCTTTACATACCGAAATACTTCATCGCTCACGCGGCGTCGCTGCATCAGGGTTTCCCCCATTGTGCAATA

TTCCCCACTGCTGCCTCCCGAGGGGAGTTTGGA

>SEQ ID NO: 56|YK57|
GTCAGCTTTCGAGCTCACGTCAGTTACCGTCCAGTAAGCCGCCTTCGCCACTGGTGTTCCTCCTAATATCTACGCAT

TTCACCGCTACACTAGGAATTCCGCTTACCTCTCCGGTACTCTAGATTGACAGTTTCCAATGCAGTCCCGGGGTTGA

GCCCCGGGTTTTCACATCAGACTTGCCACTCCGTCTACGCTCCCTTTACACCCAGTAAATCCGGATAACGCTTGCAC

CATACGTATTACCGCGGCTGCTGGCACGTATTTAGCCGGTGCTTCTTAGTCAGGTACCGTCATTTTCTTCCCTGCTG

ATAGAGCTTTACATACCGAAATACTTCATCGCTCACGCGGCGTCGCTGCATCAGGGTTTCCCCCATTGTGCAATATT

CCCCACTGCTGCCTCCCGAGGGGAGTTTGGA

>SEQ ID NO: 57|YK58|
TCTCACGCTTTCGAGCTCACGTCAGTCATCGTCCAGCAAGCCGCCTTCGCCACTGGTGTTCCTCCTAATATCTACGC

ATTTCACCGCTACACTAGGAATTCCACTTGCCTCTCCGACACTCTAGCTCAGCAGTTCCAAATGCAGTCCCGGGGTT

GAGCCCCGGGCTTTCACATCTGGCTTGCCGTGCCGTCTACGCTCCCTTTACACCCAGTAAATCCGGATAACGCTTGC

CCCCTACGTATTACCGCGGCTGCTGGCACGTAGTTAGCCGGGGCTTCTTAGTCAGGTACCGTCATTTTCTTCCCTGC

TGATAGAAGTTTACATACCGAAATACTTCATCCTTCACGCGGCGTCGCTGCATCAGAGTTTCCTCCATTGTGCAATA

TTCCCCACTGCTGCCTCCCGTAGGGAGTTTGG

>SEQ ID NO: 58|YK65|
GTCAGCTTTCGAGCTCAGCGTCAGTTATCGTCCAGTAAGCCGCCTTCGCCACTGGTGTTCCTCCTAATATCTACGCA

TTTCACCGCTACACTAGGAATTCCACTTACCCCTCCGACACTCTAGTACGACAGTTTCCAATGCAGTACCGGGGTTG

AGCCCCGGGCTTTCACATCAGACTTGCCGCACCGCCTGCGCTCCCTTTACACCCAGTAAATCCGGATAACGCTTGCA

CCATACGTATTACCGCGGCTGCTGGCACGTATTTAGCCGGTGCTTCTTAGTCAGGTACCGTCATTCTTCTTCCCTGC

TGATAGAGCTTTACATACCGAAATACTTCTTCGCTCACGCGGCGTCGCTGCATCAGGGTTTCCCCCATTGTGCAATA

TTCCCCACTGCTGCCTCCCGAGGGAGTTTGGA

>SEQ ID NO: 59|YK67|
AGCCCCGCTTTCGAGCCTCACGTCAGTTACCGTCCAGTAAGCCGCCTTCGCCACTGGTGTTCCTCCTAATATCTACG

CATTTCACCGCTACACTAGGAATTCCGCTTACCTCTCCGGCACTCAAGACGGGCAGTTTCCAATGCAGTCCCGGGGT

TGAGCCCCAGCCTTTCACATCAGACTTGTCCATCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTTTCTTCCCTG

CTGATAGAAGTTTACATACCGAGATACTTCTTCCTTCACGCGGCGTCGCTGCATCAGGGTTTCCCCCATTGTGCAAT

ATTCCCCACTGCTGCCTCCCGAAGGAAGTTTGGA

>SEQ ID NO: 60|YK69|
TGCTCAGCTTTCGAGCCTCACGTCAGTTACCGTCCAGTAAGCCGCCTTCGCCACTGGTGTTCTTCCTAATATCTACG

CATTTCACCGCTACACTAGGAATTCCGCTTACCTCTCCGGCACTCGAGCCAGACAGTTTCCAATGCAGTCCCAGGGT

TAAGCCCTGGGTTTTCACATCAGACTTGCCTTGCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTATCTTCCCTG

CTGATAGAGCTTTACATACCGAAATACTTCTTCGCTCACGCGGCGTCGCTGCATCAGGGTTTCCCCCATTGTGCAAT

ATTCCCCACTGCTGCCTCCCGAAGGGAGTTTGGA

>SEQ ID NO: 61|YK70|
GTTGCTCAGCTTTCGAGCTCACGTCAGTTACCGTCCAGTAAGCCGCCTTCGCCACTGGTGTTCTTCCTAATATCTAC

GCATTTCACCGCTACACTAGGAATTCCGCTTACCTCTCCGGCACTCGAGCCAGACAGTTTCCAATGCAGTCCCAGGG

TTAAGCCCTGGGTTTTCACATCAGACTTGCCTTGCCGTCTACGCTCCCTTTACACCCAGTAAATCCGGATAACGCTT

GCCCCCTACGTATTACCGCGGCTGCTGGCACGTAGTTAGCCGGGGCTTCTTAGTCAGGTACCGTCATTATCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGAAAGTTTGGA

>SEQ ID NO: 62|YK71|
TGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCACTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTCTTCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGGAGTTTGGA

>SEQ ID NO: 63|YK74|
GATGCCCTGGCTTCGCGCTCAGCGTCAGTTGTCGTCCAGAAAGCCGCTTTCGCCACTGGTGTTCCTCCTAATATCTA

CGCATTTCACCGCTACACTAGGAATTCCGCTTTCCTCTCCGACACTCGAGCTTCACAGTTTCGGTCCCCTCACGGGG

TTAAGCCCCGCACTTTTAAGACCGACTTGCGATGCCGCCTGCGCGCCCTTTACGCCCAATAATTCCGGACAACGCTT

GCCACCTACGTATTACCGCGGCTGCTGGCACGTAGTTAGCCGTGGCTTTCTCTTACGGTACCGTCAGGGATAACGGG

TATTGACCGCTATCCTGTTCGTCCCATATAACAGAACTTTACAACCCGAAGGCCGTCATCGTTCACGCGGCGTTGCT

CCGTCAGACTTTCGTCCATTGCGGAAGATTCCCCACTGCTGCCTCCCGGGGGAGTTTGGA

>SEQ ID NO: 64|YK88|
GTCCCGCTTTCGAGCCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAAGGGAAGTTTGG

>SEQ ID NO: 65|YK89|
TGTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTGCCTCCCGAAGGGAGTTTGGA

>SEQ ID NO: 66|YK97|
TGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCACTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTCTTCTTCCCT

GCTGATAGAGCTTTACATACCGAAATACTTCTTCGCTCACGCGGCGTCGCTGCATCAGGGTTTCCCCCATTGTGCAA

TATTCCCCACTGCTGCCTCCCGAAGGGAGTTTGGA

>SEQ ID NO: 67|YK98|
ATTCAGCTTTCGAGCTCACGTCAGTTACCGTCCAGTAAGCCGCCTTCGCCACTGGTGTTCCTCCTAATATCTACGCA

TTTCACCGCTACACTAGGAATTCCGCTTACCCCTCCGGCACTCAAGCATACCAGTTTCCAATGCAGTCCAGGGGTTA

AGCCCCTGCCTTTCACATCAGACTTGATACGCCGTCTACGCTCCCTTTACACCCAGTAAATCCGGATAACGCTCGCC

CCCTACGTATTACCGCGGCTGCTGGCACGTAGTTAGCCGGGGCTTCTTAGTCAGGTACCGTCATTATCTTCCCTGCT

GATAGAAGTTTACATACCGAGATACTTCTTCCTTCACGCGGCGTCGCTGCATCAGGGTTTCCCCCATTGTGCAATAT

TCCCCACTGCTGCCTCCCGAGGGAAGTTTGGA

>SEQ ID NO: 68|YK139|
GTGTCAGCTTTCGAGCTCACGTCAGTTACCGTCCAGTAAGCCGCCTTCGCCACTGGTGTTCTTCCTAATATCTACGC

ATTTCACCGCTACACTAGGAATTCCGCTTACCTCTCCGGCACTCGAGCCAGACAGTTTCCAATGCAGTCCCAGGGTT

AAGCCCTGGGTTTTCACATCAGACTTGCCTTGCCGTCTACGCTCCCTTTACACCCAGTAAATCCGGATAACGCTTGC

CCCCTACGTATTACCGCGGCTGCTGGCACGTAGTTAGCCGGGGCTTCTTAGTCAGGTACCGTCATTATCTTCCCTGC

TGATAGAGCTTTACATACCGAAATACTTCTTCGCTCACGCGGCGTCGCTGCATCAGGGTTTCCCCCATTGTGCAATA

TTCCCCACTGCTGCCTCCCGAGGGAGTTTGG

>SEQ ID NO: 69|YK141|
GCCAGCTTCGAGCCTCACGTCAGTCATCGTCCAGTAAGCCGCCTTCGCCACTGGTGTTCCTCCTAATATCTACGCAT

TTCACCGCTACACTAGGAATTCCACTTACCTCTCCGACACTCTAGCTGCACAGTTTCCAAAGCAGTCCACAGGTTGA

GCCCATGCCTTTCACTTCAGACTTGCACAGCCGTCTACGCTCCCTTTACACCCAGTAAATCCGGATAACGCTTGCCC

CCTACGTATTACCGCGGCTGCTGGCACGTAGTTAGCCGGGGCTTCTTAGTCAGGTACCGTCATTTTCTTCCCTGCTG

ATAGAAGTTTACATACCGAAATACTTCATCCTTCACGCGGCGTCGCTGCATCAGGCTTTCGCCCATTGTGCAATATT

CCCCACTGCTGCCTCCCGAGGGAAGTTTGGA

>SEQ ID NO: 70|YK142|
TGATCAGCTTTCGAGCTCACGTCAGTTACCGTCCAGTAAGCCGCCTTCGCCACTGGTGTTCCTCCTAATATCTACGC

ATTTCACCGCTACACTAGGAATTCCGCTTACCTCTCCGGTACTCTAGATTGACAGTTTCCAATGCAGTCCCGGGGTT

GAGCCCCGGGTTTTCACATCAGACTTGCCACTCCGTCTACGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTTTCTTCCCTGC

TGATAGAGCTTTACATACCGAAATACTTCATCGCTCACGCGGCGTCGCTGCATCAGGGTTTCCCCCATTGTGCAATA

TTCCCCACTGCTGCCTCCCGGGGGAGTTTGGA

>SEQ ID NO: 71|YK152|
GATGATCAGCTTTCGAGCTCACGTCAGTTACCGTCCAGTAAGCCGCCTTCGCCACTGGTGTTCCTCCTAATATCTAC

GCATTTCACCGCTACACTAGGAATTCCGCTTACCTCTCCGGCACTCTAGAAAAACAGTTTCCAATGCAGTCCTGGGG

TTAAGCCCCAGCCTTTCACATCAGACTTGCTCTTCCGTCTACGCTCCCTTTACACCCAGTAAATCCGGATAACGCTT

GCCCCCTACGTATTACCGCGGCTGCTGGCACGTAGTTAGCCGGGGCTTCTTAGTCAGGTACCGTCATTTTCTTCCCT

GCTGATAGAAGTTTACATACCGAGATACTTCTTCCTTCACGCGGCGTCGCTGCATCAGGGTTTCCCCCATTGTGCAA

TATTCCCCACTGCTGCCTCCCGGGGGAAGTTTGGA

>SEQ ID NO: 72|YK155|
TTGATCAGCTTTCGAGCTCACGTCAGTTACCGTCCAGTAAGCCGCCTTCGCCACTGGTGTTCCTCCTAATATCTACG

CATTTCACCGCTACACTAGGAATTCCGCTTACCTCTCCGGCACTCTAGAAAAACAGTTTCCAATGCAGTCCTGGGGT

TAAGCCCCAGCCTTTCACATCAGACTTGCTCTTCCGTCTACGCTCCCTTTACACCCAGTAAATCCGGATAACGCTTG

CCCCCTACGTATTACCGCGGCTGCTGGCACGTAGTTAGCCGGGGCTTCTTAGTCAGGTACCGTCATTTTCTTCCCTG

CTGATAGAAGTTTACATACCGAGATACTTCTTCCTTCACGCGGCGTCGCTGCATCAGGGTTTCCCCCATTGTGCAAT

ATTCCCCACTGCTGCCTCCCGAAGGGAGTTTGG

>SEQ ID NO: 73|YK157|
GTATTTCAGCTTTCGAGCTCAGCGTCAGTTATCGTCCAGTAAGCCGCCTTCGCCACTGGTGTTCCTCCTAATATCTA

CGCATTTCACCGCTACACTAGGAATTCCGCTTACCCCTCCGACACTCTAGTACGACAGTTTCCAATGCAGTACCGGG

GTTGAGCCCCGGGCTTTCACATCAGACTTGCCGCACCGCCTGCGCTCCCTTTACACCCAGTAAATCCGGATAACGCT

TGCACCATACGTATTACCGCGGCTGCTGGCACGTATTTAGCCGGTGCTTCTTAGTCAGGTACCGTCATTATCTTCCC

TGCTGATAGAGCTTTACATACCGAAATACTTCTTCGCTCACGCGGCGTCGCTGCATCAGGCTTTCGCCCATTGTGCA

ATATTCCCCACTGCTGCCTCCCGAAGGGAGTTTGGA

>SEQ ID NO: 74|YK160|
GCTCAGCTTTCGAGCTCAGCGTCAGTTATCGTCCAGTAAGCCGCCTTCGCCACTGGTGTTCCTCCTAATATCTACGC

ATTTCACCGCTACACTAGGAATTCCACTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTCTTCTTCCCTG

CTGATAGAGCTTTACATACCGAAATACTTCTTCGCTCACGCGGCGTCGCTGCATCAGGGTTTCCCCCATTGTGCAAT

ATTCCCCACTGCTGCCTCCCGAGGGGAGTTTGGA

>SEQ ID NO: 75|YK166|
TTTCAGCTTCGAGCCTCAGCGTCAGTTATCGTCCAGTAAGCCGCCTTCGCCACTGGTGTTCCTCCTAATATCTACGC

ATTTCACCGCTACACTAGGAATTCCGCTTACCCCTCCGACACTCTAGTACGACAGTTTCCAATGCAGTACCGGGGTT

GAGCCCCGGGCTTTCACATCAGACTTGCCGCACCGCCTGCGCTCCCTTTACACCCAGTAAATCCGGATAACGCTTGC

ACCATACGTATTACCGCGGCTGCTGGCACGTATTTAGCCGGTGCTTCTTAGTCAGGTACCGTCATTATCTTCCCTGC

TGATAGAGCTTTACATACCGAAATACTTCTTCGCTCACGCGGCGTCGCTGCATCAGGCTTTCGCCCATTGTGCAATA

TTCCCCACTGCTAGCTCCCGAAGGAGTTTGGA

>SEQ ID NO: 76|YK168|
AGCTCAGCTTTCGAGCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAAGGGAGTTTGGA

>SEQ ID NO: 77|YK169|
GTCCAGCTTTCGAGCCTCAGCGTCAGTTATCGTCCAGTAAGCCGCCTTCGCCACTGGTGTTCCTCCTAATATCTACG

CATTTCACCGCTACACTAGGAATTCCGCTTACCCCTCCGACACTCTAGTACGACAGTTTCCAATGCAGTACCGGGGT

TGAGCCCCGGGCTTTCACATCAGACTTGCCGCACCGCCTGCGCTCCCTTTACACCCAGTAAATCCGGATAACGCTTG

CACCATACGTATTACCGCGGCTGCTGGCACGTATTTAGCCGGTGCTTCTTAGTCAGGTACCGTCATTATCTTCCCTG

CTGATAGAGCTTTACATACCGAAATACTTCTTCGCTCACGCGGCGTCGCTGCATCAGGCTTTCGCCCATTGTGCAAT

ATTCCCCACTGCTGCCTCCCGAGGGGAGTTTGGA

>SEQ ID NO: 78|YK171|
TGAGCCGGGCTCACCCCGGTACTGCATTGGAACTGTCGTACTAGAGTGTCGGAGGGGTAAGCGGAATTCCTAGTGTA

GCGGTGAAATGCGTAGATATTAGGAGGAACACCAGTGGCGAAGGCGGCTTACTGGACGATAACTGACGCTGAGGCTC

GAAAGCGTGGGGAGCAAACAGGATTAGATACACCGGTAA

>SEQ ID NO: 79|YK192|
CACGATGTCAGCTTTCGAGCTCAGCGTCAGTTATCGTCCAGTAAGCCGCCTTCGCCACTGGTGTTCCTCCTAATATC

TACGCATTTCACCGCTACACTAGGAATTCCACTTACCCCTCCGACACTCTAGTACGACAGTTTCCAATGCAGTACCG

GGGTTGAGCCCCGGGCTTTCACATCAGACTTGCCGCACCGCCTGCGCTCCCTTTACACCCAGTAAATCCGGATAACG

CTTGCACCATACGTATTACCGCGGCTGCTGGCACGTATTTAGCCGGTGCTTCTTAGTCAGGTACCGTCATTCTTCTT

CCCTGCTGATAGAGCTTTACATACCGAAATACTTCTTCGCTCACGCGGCGTCGCTGCATCAGGGTTTCCCCCATTGT

GCAATATTCCCCACTGCTGCCTCCCGAGGGGAGTTTGGA

>SEQ ID NO: 80|VE202-18|
ATGGAGAGTTTGATCCTGGCTCAGGATGAACGCTGGCGGCGTGCCTAATACATGCAAGTCGAACGCGAGCACTTGTG

CTCGAGTGGCGAACGGGTGAGTAATACATAAGTAACCTGCCCTAGACAGGGGGATAACTATTGGAAACGATAGCTAA

GACCGCATAGGTACGGACACTGCATGGTGACCGTATTAAAAGTGCCTCAAAGCACTGGTAGAGGATGGACTTATGG

CGCATTAGCTGGTTGGCGGGTAACGGCCCACCAAGGCGACGATGCGTAGCCGACCTGAGAGGGTGACCGGCCACAC

TGGGACTGAGACACGGCCCAGACTCCTACGGGAGGCAGCAGTAGGGAATTTTCGGCAATGGGGGAAACCCTGACCGA

GCAACGCCGCGTGAAGGAAGAAGGTTTTCGGATTGTAAACTTCTGTTATAAAGGAAGAACGGCGGCTACAGGAAAT

GGTAGCCGAGTGACGGTACTTTATTAGAAAGCCACGGCTAACTACGTGCCAGCAGCCGCGGTAATACGTAGGTGGCA

```
AGCGTTATCCGGAATTATTGGGCGTAAAGAGGGAGCAGGCGGCAGCAAGGGTCTGTGGTGAAAGCCTGAAGCTTAAC

TTCAGTAAGCCATAGAAACCAGGCAGCTAGAGTGCAGGAGAGGATCGTGGAATTCCATGTGTAGCGGTGAAATGCG

TAGATATATGGAGGAACACCAGTGGCGAAGGCGACGATCTGGCCTGCAACTGACGCTCAGTCCCGAAAGCGTGGGA

GCAAATAGGATTAGATACCCTAGTAGTCCACGCCGTAAACGATGAGTACTAAGTGTTGGATGTCAAAGTTCAGTGCT

GCAGTTAACGCAATAAGTACTCCGCCTGAGTAGTACGTTCGCAAGAATGAAACTCAAAGGAATTGACGGGGGCCCG

CACAAGCGGTGGAGCATGTGGTTTAATTCGAAGCAACGCGAAGAACCTTACCAGGTCTTGACATACTCATAAAGGCT

CCAGAGATGGAGAGATAGCTATATGAGATACAGGTGGTGCATGGTTGTCGTCAGCTCGTGTCGTGAGATGTTGGGTT

AAGTCCCGCAACGAGCGCAACCCTTATCGTTAGTTACCATCATTAAGTTGGGGACTCTAGCGAGACTGCCAGTGAC

AAGCTGGAGGAAGGCGGGGATGACGTCAAATCATCATGCCCCTTATGACCTGGGCTACACACGTGCTACAATGGATG

GTGCAGAGGGAAGCGAAGCCGCGAGGTGAAGCAAAACCCATAAAACCATTCTCAGTTCGGATTGTAGTCTGCAACTC

GACTACATGAAGTTGGAATCGCTAGTAATCGCGAATCAGCATGTCGCGGTGAATACGTTCTCGGGCCTTGTACACA

CCGCCCGTCACACCACGAGAGTTGATAACACCCGAAGCCGGTGGCCTAACCGCAAGGAAGGAGCTGTCTAAGGTGGG

ATTGATGATTGGGGTGAAGTCGTAACAAGGTATCCCTACGGGAACGTGGGGATGGATCACCTCCTTT

>SEQ ID NO: 81|PE5|
ATGAGAGTTTGATCCTGGCTCAGGATGAACGCTGGCGGCGTGCCTAACACATGCAAGTCGAACGAAGCAATTGAAGG

AAGTTTTCGGATGGAATTCGATTGACTGAGTGGCGGACGGGTGAGTAACGCGTGGATAACCTGCCTCACACTGGGGG

ATAACAGTTAGAAATGACTGCTAATACCGCATAAGCGCACAGTACCGCATGGTACAGTGTGAAAAACTCCGGTGGT

GTGAGATGGATCCGCGTCTGATTAGCCAGTTGGCGGGGTAACGGCCCACCAAAGCGACGATCAGTAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATAT

TAGGAGGAACACCAGTGGCGAAGGCGGCTTACTGGACGATAACTGACGTTGAGGCTCGAAAGCGTGGGGAGCAAACA

GGATTAGATACCCTGGTAGTCCACGCCGTAAACGATGAATGCTAGGTGTTGGGGGGCAAAGCCCTTCGGTGCCGTCG

CAAACGCAGTAAGCATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCTCTTGACCGGCGTGT

AACGGCGCCTTCCCTTCGGGGCAAGAGAGACAGGTGGTGCATGGTTGTCGTCAGCTCGTGTCGTGAGATGTTGGGTT

AAGTCCCGCAACGAGCGCAACCCTTATCCTTAGTAGCCAGCAGGTAAAGCTGGGCACTCTAGGGAGACTGCCAGGG

ATAACCTGGAGGAAGGTGGGGATGACGTCAAATCATCATGCCCCTTATGATTTGGGCTACACACGTGCTACAATGGC

GTAAACAAAGGGAAGCAAGACAGTGATGTGGAGCAAATCCCAAAAATAACGTCCCAGTTCGGACTGTAGTCTGCAAC

CCGACTACACGAAGCTGGAATCGCTAGTAATCGCGAATCAGAATGTCGCGGTGAATACGTTCCCGGGTCTTGTACA

CACCGCCCGTCACACCATGGGAGTCAGCAACGCCCGAAGTCAGTGACCCAACTCGCAAGAGAGGGAGCTGCCGAAGG

CGGGGCAGGTAACTGGGGTGAAGTCGTAACAAGGTAGCCGTATCGGAAGGTGCGGCTGGATCACCTCCTTT

>SEQ ID NO: 82|PE9|
AATTCGACGTTGTCCGGATTACTGGGCGTAAAGGGAGCGTAGGCGGACTTTTAAGTGAGATGTGAAATACCCGGGCT

CAACTTGGGTGCTGCATTTCAAACTGGAAGTCTAGAGTGCAGGAGAGGAGAATGGAATTCCTAGTGTAGCGGTGAAA

TGCGTAGAGATTAGGAAGAACACCAGTGGCGAAGGCGATTCTCTGGACTGTAACTGACGCTGAGGCTCGAAAGCGTG

GGGAGCAAACAGGATTAGATACCCTGGTAGTCCACGCCGTAAACGATGAATACTAGGTGTAGGGGTTGTCATGACCT

CTGTGCCGCCGCTAACGCATTAAGTATTCCGCCTGGGGAGTACGGTCGCAAGATTAAAACTCAAAGAAATTGACGGA
```

>SEQ ID NO: 83|211-B|
ACGAGCGTATCGGATTATTGGGTTTAAGGGAGCGTAGGTGGATTGTTAAGTCAGTTGTGAAAGTTTGCGGCTCAACC

GTAAAATTGCAGTTGAAACTGGCAGTCTTGAGTACAGTAGAGGTGGGCGGAATTCGTGGTGTAGCGGTGAAATGCTT

AGATATCACGAAGAACTCCGATTGCGAAGGCAGCTCACTAGACTGTCACTGACACTGATGCTCGAAAGTGTGGGTAT

CAAACAGGATTAGATACCCTGGTAGTCCACACAGTAAACGATGAATACTCGCTGTTTGCGATATACAGTAAGCGGCC

AAGCGAAAGCATTAAGTATTCCACCTGGGGAGTACGCCGGCAACGGTGAAACTCAAAGAAATTGACGGAAGCCCGCC

CAGGGGGGAAAAACATGGGGTTTAGTTGGATGATACGGGGAGGAACCTC

>SEQ ID NO: 84|NR_119185.1|Ruminococcus obeum 16S ribosomal RNA gene,
complete sequence
GGCGGCGTGCTTAACACATGCAAGTCGAACGGGAAACCTTTCATTGAAGCTTCGGCAGATTTGGNNTGTTTCTAGTG

GCGGACGGGTGAGTAACGCGTGGGTAACCTGCCTTATACAGGGGGATAACAACCAGAAATGGTTGCTAATACCGCAT

AAGCGCACAGGACCGCATGGTCTGGTGTGAAAAACTCCGGTGGTATAAGATGGACCCGCGTTGGATTAGCTAGTTGG

CAGGGTAACGGCCTACCAAGGCGACGATCCATAGCCGGCCTGAGAGGGTGAACGGCCACATTGGGACTGAGACACGG

CCCAGACTCCTACGGGAGGCAGCAGTGGGGAATATTGCACAATGGGGGAAACCCTGATGCAGCGACGCCGCGTGAAG

GAAGAAGTATCTCGGTATGTAAACTTCTATCAGCAGGGAAGATAGTGACGGTACCTGACTAAGAAGCCCCGGCTAAC

TACGTGCCAGCAGCCGCGGTAATACGTAGGGGGCAAGCGTTATCCGGATTTACTGGGTGTAAAGGGAGCGTAGACGG

ACTGGCAAGTCTGATGTGAAAGGCGGGGGCTCAACCCCTGGACTGCATTGGAAACTGTTAGTCTTGAGTGCCGGAGA

GGTAAGCGGAATTCCTAGTGTAGCGGTGAAATGCGTAGATATTAGGAGGAACACCAGTGGCGAAGGCGGCTTACTGG

ACGGTAACTGACGTTGAGGCTCGAAAGCGTGGGGAGCAAACAGGATTAGATACCCTGGTAGTCCACGCCGTAAACGA

TGATTACTAGGTGTTGGGGAGCAAAGCTCTTCGGTGCCGCCGCAAACGCATTAAGTATTCCACCTGGGGAGTACGTT

CGCAAGAATGAAACTCAAAGGAATTGACGGGACCCGCACAAGCGGTGGAGCATGTGGTTTAATTCGAAGCAACGCG

AAGAACCTTACCAAGTCTTGACATCCCTCTGACCGNCCCTTAACCGGATCTTTCCTTCGGGACAGGGGAGACAGGTG

GTGCATGGTTGTCGTCAGCTCGTGTCGTGAGATGTTGGGTTAAGTCCCGCAACGAGCGCAACCCCTATCCCCAGTAG

CCAGCAGTCCGGCTGGGCACTCTGAGGAGACTGCCAGGGATAACCTGGAGGAAGGCGGGGATGACGTCAAATCATCA

TGCCCCTTATGATTTGGGCTACACACGTGCTACAATGGCGTAAACAAAGGGAAGCAAGCCTGCGAAGGTAAGCAAAT

CCCAAAAATAACGTCCCAGTTCGGACTGCAGTCTGCAACTCGACTGCACGAAGCTGGAATCGCTAGTAATCGCGGAT

CAGAATGCCGCGGTGAATACGTTCCCGGGTCTTGTACACACCGCCCGTCACACCATGGGAGTCAGTAACGCCCGAAG

TCAGTGACCTAACTGCAAAGAAGGAGCTGCCGAAGGCGGGACCGATGACTGGGGTGAAGTCGTAACAAGGT

>SEQ ID NO: 85|NR_118692.1|Ruminococcus obeum strain ATCC 29174 16S
ribosomal RNA gene, complete sequence
GGCGTGCTTAACACATGCAAGTCGAACGGGAAACTTTTCATTGAAGCTTCGGCAGATTTGGTCTGTTTCTAGTGGCG

GACGGGTGAGTAACGCGTGGGTAACCTGCCTTATACAGGGGGATAACAACCAGAAATGGTTGCTAATACCGCATAAG

CGCACAGGACCGCATGGTCTGGTGTGAAAAACTCCGGTGGTATAAGATGGACCCGCGTTGGATTAGCTAGTTGGCAG

GGTAACGGCCTACCAAGGCGACGATCCATAGCCGGCCTGAGAGGGTGAACGGCCACATTGGGACTGAGACACGCCCC

AGACTCCTCGGAGGCAGCAGTGGGGAATATTGCACAATGGGGGAAACCCTGATGCAGCGACGCCGCGTGAAGGAAG

AAGTATCTCGGTATGTAAACTTCTATCAGCAGGGAAGATAGTGACGGTACCTGACTAAGAAGCCCCGKCTAACTACG

TGCCAGCAGCCGCGGTAATACGTAGGGGGCAAGCGTTATCCGGATTTACTGGGTGTAAAGGGAGCGTAGACGGACTG

GCAAGTCTGATGTGAAAGGCGGGGGCTCAACCCCTGGACTGCATTGGAAACTGTTAGTCTTGAGTGCCGGAGAGGTA

AGCGGAATTCCTAGTGTAGCGGTGAAATGCGTAGATATTAGGAGGAACACCAGTGGCGAAGGCGGCTTACTGGACGG

TAACTGACGTTGAGGCTCGAAAGCGTGGGGAGCAAACAGGATTAGATACCCTGGTAGTCCACGCCGCAAACGATGAA

TACTAGGTGTTGGGGAGCAAAGCTCTTCGGTGCCGCCGCAAACGCATTAAGTATTCCACCTGGGGAGTACGTTCGCA

AGAATGAAACTCAAAGGAATTGACGGGACCCGCACAAGCGGTGGAGCATGTGGTTTAATTCGAAGCAACGCGAAGA

ACCTTACCAAGTCTTGACATCCCTCTGACCGTCCCTTAACCGGATCTTTCCTTCGGGACAGGGGAGACAGGTGGTGC

ATGGTTGTCGTCAGCTCGTGTCGTGAGATGTTGGGTTAAGTCCCGCAACGAGCGCAACCCCTATCCCCAGTAGCCAG

CAGTNCGGCTGGGCACTCTGAGGAGACTGCCAGGGATAACCTGGAGGAAGGCGGGGATGACGTCAAATCATCATGCC

CCTTATGATTTGGGCTACACACGTGCTACAATGGCGTAAACAAAGGGAAGCNAGCCTKCGRAGGTAAGCAAATCCCA

NAAATAACGTCCCAGTTCGGACTGCAGTCTGCAACTCGACTGCACGAAGCTGGAATCGCTAGTAATCGCGGATCAGA

ATGCCGCGGTGAATACGTTCCCGGGTCTTGTACACACCGCCCGTCACACCATGGGAGTCAGTAACGCCCGAAGTCAG

TGACCTAACTGC

>SEQ ID NO: 86|NR_026491.1|*Clostridium disporicum* strain DS1 16S ribosomal
RNA gene, partial sequence
GCTCAGGACGAACGCTGGCGGCGTGCCTAACACATGCAAGTCGAGCGAGTTGATTCTCTTCGGAGATGAAGCTAGCG

GCGGACGGGTGAGTAACACGTGGGCAACCTGCCTCATAGAGGGGAATAGCCTCCCGAAAGGGAGATTAATACCGCAT

AAGATTGTAGCTTCGCATGAAGTAGCAATTAAAGGAGCAATCCGCTATGAGATGGGCCCGCGGCGCATTAGCTAGTT

GGTGAGGTAACGGCTCACCAAGGCGACGATGCGTAGCCGACCTGAGAGGGTGATCGGCCACATTGGGACTGAGACAC

GGCCCAGACTCCTACGGGAGGCAGCAGTGGGGAATATTGCACAATGGGGGAAACCCTGATGCAGCAACGCCGCGTGA

GTGATGACGGCCTTCGGGTTGTAAAGCTCTGTCTTCAGGGACGATAATGACGGTACCTGAGGAGGAAGCCACGGCTA

ACTACGTGCCAGCAGCCGCGGTAATACGTAGGTGGCGAGCGTTGTCCGGATTTACTGGGCGTAAAGGGAGCGTAGGC

GGACTTTTAAGTGAGATGTGAAATACCCGGGCTCAACTTGGGTGCTGCATTTCAAACTGGAAGTCTAGAGTGCAGGA

GAGGAGAATGGAATTCCTAGTGTAGCGGTGAAATGCGTAGAGATTAGGAAGAACACCAGTGGCGAAGGCGATTCTCT

GGACTGTAACTGACGCTGAGGCTCGAAAGCGTGGGGAGCAAACAGGATTAGATACCCTGGTAGTCCACGCCGTAAAC

GATGAATACTAGGTGTAGGGGTTGTCATGACCTCTGTGCCGCCGCTAACGCATTAAGTATTCCGCCTGGGGAGTACG

GTCGCAAGATTAAAACTCAAAGGAATTGACGGGGGCCCGCACAAGCAGCGGAGCATGTGGTTTAATTCGAAGCAACG

CGAAGAACCTTACCTAGACTTGACATCTCCTGAATTACCCGTAACTGGGGAAGCCACTTCGGTGGCAGGAAGACAGG

TGGTGCATGGTTGTCGTCAGCTCGTGTCGTGAGATGTTGGGTTAAGTCCCGCAACGAGCGCAACCCTTATTGTTAGT

TGCTACCATTTAGTTGAGCACTCTAGCGAGACTGCCCGGGTTAACCGGGAGGAAGGTGGGGATGACGTCAAATCATC

ATGCCCCTTATGTCTAGGGCTACACACGTGCTACAATGGCAAGTACAAAGAGAAGCAAGACCGCGAGGTGGAGCAAA

ACTCAAAAACTTGTCTCAGTTCGGATTGTAGGCTGAAACTCGCCTACATGAAGCTGGAGTTGCTAGTAATCGCGAAT

CAGCATGTCGCGGTGAATACGTTCCCGGGCCTTGTACACACCGCCCGTCACACCATGAGAGTTGGCAATACCCAACG

TACGTGATCTAACCCGCAAGGGAGGAAGCGTCCTAAGGTAGGGTCAGCGATTGGGGTGAAGTCGTAACAAGGTAGCC

GTAGGAGAA

>SEQ ID NO: 87|NR_028785.1|*Clostridium scindens* strain ATCC 35704 16S
ribosomal RNA gene, complete sequence
GAGAGTTTGATCCTGGCTCAGGATGAACGCTGGCGGCGTGCCTAACACATGCAAGTCGAACGAAGCGCCTGGCCCCG

ACTTCTTCGGAACGAGGAGCCTTGCGACTGAGTGGCGGACGGGTGAGTAACGCGTGGGCAACCTGCCTTGCACTGGG

GGATAACAGCCAGAAATGGCTGCTAATACCGCATAAGACCGAAGCGCCGCATGGCGCGGCGGCCAAAGCCCCGGCGG

TGCAAGATGGGCCCGCGTCTGATTAGGTAGTTGGCGGGGTAACGGCCCACCAAGCCGACGATCAGTAGCCGACCTGA

GAGGGTGACCGGCCACATTGGGACTGAGACACGGCCCAGACTCCTACGGGAGGCAGCAGTGGGGAATATTGCACAAT

GGGGGAAACCCTGATGCAGCGACGCCGCGTGAAGGATGAAGTATTTCGGTATGTAAACTTCTATCAGCAGGGAAGAA

GATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGATGCAAGCCAGATGTGAAAGCCCGGGGCTCAACCCCGGGAC

TGCATTTGGAACTGCGTGGCTGGAGTGTCGGAGAGGCAGGCGGAATTCCTAGTGTAGCGGTGAAATGCGTAGATATT

AGGAGGAACACCAGTGGCGAAGGCGGCCTGCTGGACGATGACTGACGTTGAGGCTCGAAAGCGTGGGGAGCAAACAG

GATTAGATACCCTGGTAGTCCACGCCGTAAACGATGACTACTAGGTGTCGGGTGGCAAGGCCATTCGGTGCCGCAGC

AAACGCAATAAGTAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGCCAAAGCGCGTA

ACGCGCTCTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCATTTTGGATGGGCACTCTGGAGAGACTGCCAGGGAGAA

CCTGGAGGAAGGTGGGGATGACGTCAAATCATCATGCCCCTTATGACCAGGGCTACACACGTGCTACAATGGCGTAA

ACAAAGGGAGGCGAACCCGCGAGGGTGGGCAAATCCCAAAATAACGTCTCAGTTCGGATTGTAGTCTGCAACTCGA

CTACATGAAGTTGGAATCGCTAGTAATCGCGAATCAGAATGTCGCGGTGAATACGTTCCCGGGTCTTGTACACACCG

CCCGTCACACCATGGGAGTCAGTAACGCCCGAAGCCGGTGACCCAACCCGTAAGGGAGGGAGCCGTCGAAGGTGGGA

CCGATAACTGGGGTGAAGTCGTAACAAGGTAGCCGTATCGGAAGGTGCGGCTGGATCACCTCCTTC

>SEQ ID NO: 88|NR_028915.1|Anaerostipes caccae strain L1-92 16S ribosomal
RNA gene, partial sequence
GCGCTTAATACATGTCAAGTCGAACGAAGCATTTAGGATTGAAGTTTTCGGATGGATTTCCTATATGACTGAGTGGC

GGACGGGTGAGTAACGCGTGGGAACCTGCCCTATACAGGGGGATAACAGCTGGAAACGGCTGCTAATACCGCATAA

GCGCACAGAATCGCATGATTCAGTGTGAAAAGCCCTGGCAGTATAGGATGGTCCCGCGTCTGATTAGCTGGTTGGTG

AGGTAACGGCTCACCAAGGCGACGATCAGTAGCCGGCTTGAGAGAGTGAACGGCCACATTGGGACTGAGACACGGCC

CAAACTCCTACGGGAGGCAGCAGTGGGGAATATTGCACAATGGGGGTAAACCCTGATGCAGCGACGCCGCGTGAGTG

AAGAAGTATTTCGGTATGTAAAGCTCTATCAGCAGGGAAGAAAACAGACGGTACCTGACTAAGAAGCCCCGGCTAAC

TACGTGCCAGCAGCCGCGGTAATACGTAGGGGGCAAGCGTTATCCGGAATTACTGGGTGTAAAGGGTGCGTAGGTGG

CATGGTAAGTCAGAAGTGAAAGCCCGGGGCTTAACCCCGGGACTGCTTTTGAAACTGTCATGCTGGAGTGCAGGAGA

GGTAAGCGGAATTCCTAGTGTAGCGGTGAAATGCGTAGATATTAGGAGGAACACCAGTGGCGAAGGCGGCTTACTGG

ACTGTCACTGACACTGATGCACGAAAGCGTGGGGAGCAAACAGGATTAGATACCCTGGTAGTCCACGCCGTAAACGA

TGAATACTAGGTGTCGGGGCCGTAGAGGCTTCGGTGCCGCAGCAAACGCAGTAAGTATTCCACCTGGGGAGTACGTT

CGCAAGAATGAAACTCAAAGGAATTGACGGGACCCGCACAAGCGGTGGAGCATGTGGTTTAATTCGAAGCAACGCG

AAGAACCTTACCTGGTCTTGACATCCCAATGACCGAACCTTAACCGGTTTTTTCTTTCGAGACATTGGAGACAGGTG

GTGCATGGTTGTCGTCAGCTCGTGTCGTGAGATGTTGGGTTAAGTCCCGCAACGAGCGCAACCCCTATCTTTAGTAG

CCAGCATTTAAGGTGGGCACTCTAGAGAGACTGCCAGGGATAACCTGGAGGAAGGTGGGGACGACGTCAAATCATCA

TGCCCCTTATGGCCAGGGCTACACACGTGCTACAATGGCGTAAACAAAGGGAAGCGAAGTCGTGAGGCGAAGCAAAT

CCCAGAAATAACGTCTCAGTTCGGATTGTAGTCTGCAACTCGACTACATGAAGCTGGAATCGCTAGTAATCGTGAAT

CAGAATGTCACGGTGAATACGTTCCCGGGTCTTGTACACACCGCCCGTCACACCATGGGAGTCAGTAACGCCCGAAG

TCAGTGACCCAACCGCAAGGAGGGAGCTGCCGAAGGTGGGACCGATAACTGGGGTGAAGTCGTAACAAGG

>SEQ ID NO: 89|NR_042152.1|Marvinbryantia formatexigens strain I-52 16S
ribosomal RNA gene, partial sequence >gi|636558750|ref|NR_114807.1|
Marvinbryantia formatexigens strain I-52 16S ribosomal RNA gene, complete
sequence
TGGCGGCGTGCTTAACACATGCAAGTCGAGCGAAGCATTTTAAATGAAGTTTTCGGACGAATTTAAAATGACTGAG

CGGCGGACGGGTGAGTAACGCGTGGATAACCTGCCTTATACAGGGGGATAACAGCCAGAAATGGCTGCTAATACCGC

ATAAGCGCACGGTACCGCATGGTACAGTGTGAAAAACTCCGGTGGTATAAGATGGGTCCGCGTTGGATTAGGCAGTT

GGCGGGGTAAAGGCCCACCAAACCGACGATCCATAGCCGGCCTGAGAGGGTGGACGGCCACATTGGGACTGAGACAC

GGCCCAGACTCCTACGGGAGGCAGCAGTGGGGAATATTGCACAATGGGGGAAACCCTGATGCAGCGACGCCGCGTGG

GTGAAGAAGTATTTCGGTATGTAAAGCCCTATCAGCAGGGAAGAAAATGACGGTACCTGACCAAGAAGCCCCGGCTA

ACTACGTGCCAGCAGCCGCGGTAATACGTAGGGGGCAAGCGTTATCCGGATTTACTGGGTGTAAAGGGAGCGTAGAC

GGCCATGCAAGTCTGGTGTGAAAGGCGGGGGCTCAACCCCCGGACTGCATTGGAAACTGTATGGCTTGAGTGCCGGA

GAGGTAAGCGGAATTCCTGGTGTAGCGGTGAAATGCGTAGATATCAGGAGGAACACCAGTGGCGAAGGCGGCTTACT

GGACGGTAACTGACGTTGAGGCTCGAAAGCGTGGGGAGCAAACAGGATTAGATACCCTGGTAGTCCACGCCGTAAAC

GATGAATACCAGGTGTCGGGGGACACGGTCCTTCGGTGCCGCAGCAAACGCACTAAGTATTCCACCTGGGGAGTACG

TTCGCAAGAATGAAACTCAAAGGAATTGACGGGGACCCGCACAAGCGGTGGAGCATGTGGTTTAATTCGAAGCAACG

CGAAGAACCTTACCAGGTCTTGACATCCGGACGACCGGACAGTAACGTGTCCTTCCCTTCGGGGCGTCCGAGACAGG

TGGTGCATGGTTGTCGTCAGCTCGTGTCGTGAGATGTTGGGTTAAGTCCCGCAACGAGCGCAACCCCTGTTCCCAGT

AGCCAGCATTCAGGATGGGCACTCTGGGGAGACTGCCAGGGATAACCTGGAGGAAGGCGGGGATGACGTCAAATCAT

CATGCCCCTTATGATCTGGGCTACACACGTGCTACAATGGCGTGAACAGAGGGAAGCGAACCCGCGAGGGGGAGCAA

ATCCCAGAAATAACGTCCCAGTTCGGATTGTAGTCTGCAACCCGGCTACATGAAGCTGGAATCGCTAGTAATCGCGG

ATCAGCATGCCGCGGTGAATACGTTCCCGGGTCTTGTACACACCGCCCGTCACACCATGGGAGTCGGAAATGCCCGA

AGTCAGTGACCCAACCGGAAGGAGGGAGCTGCCGAAGGCGGGGCCGGTAACTGGGGTGAAGTCGTAACAA

>SEQ ID NO: 90|NR_024994.1|Lactobacillus mucosae strain S32 16S ribosomal
RNA gene, complete sequence
AGAGTTTGATCCTGGCTCAGGATGAACGCCGGCGGTGTGCCTAATACATGCAAGTCGAACGCGTTGGCCCAACTGAT

TGAACGTGCTTGCACGGACTTGACGTTGGTTTACCAGCGAGTGGCGGACGGGTGAGTAACACGTAGGTAACCTGCCC

CAAAGCGGGGGATAACATTTGGAAACAGATGCTAATACCGCATAACAATTTGAATCGCATGATTCAAATTTAAAAGA

TGGCTTCGGCTATCACTTTGGGATGGACCTGCGGCGCATTAGCTTGTTGGTAGGGTAACGGCCTACCAAGGCTGTGA

TGCGTAGCCGAGTTGAGAGACTGATCGGCCACAATGGAACTGAGACACGGTCCATACTCCTACGGGAGGCAGCAGTA

GGGAATCTTCCACAATGGGCGCAAGCCTGATGGAGCAACACCGCGTGAGTGAAGAAGGGTTTCGGCTCGTAAAGCTC

TGTTGTTAGAGAAGAACGTGCGTGAGAGCAACTGTTCACGCAGTGACGGTATCTAACCAGAAAGTCACGGCTAACTA

CGTGCCAGCAGCCGCGGTAATACGTAGGTGGCAAGCGTTATCCGGATTTATTGGGCGTAAAGCGAGCGCAGGCGGTT

TGATAAGTCTGATGTGAAAGCCTTTGGCTTAACCAAAGAAGTGCATCGGAAACTGTCAGACTTGAGTGCAGAAGAGG

ACAGTGGAACTCCATGTGTAGCGGTGGAATGCGTAGATATATGGAAGAACACCAGTGGCGAAGGCGGCTGTCTGGTC

TGCAACTGACGCTGAGGCTCGAAAGCATGGGTAGCGAACAGGATTAGATACCCTGGTAGTCCATGCCGTAAACGATG

AGTGCTAGGTGTTGGAGGGTTTCCGCCCTTCAGTGCCGCAGCTAACGCATTAAGCACTCCGCCTGGGGAGTACGACC

GCAAGGTTGAAACTCAAAGGAATTGACGGGGGCCCGCACAAGCGGTGGAGCATGTGGTTTAATTCGAAGCTACGCGA

AGAACCTTACCAGGTCTTGACATCTTGCGCCAACCCTAGAGATAGGGCGTTTCCTTCGGAACGCAATGACAGGTGG

TGCATGGTCGTCGTCAGCTCGTGTCGTGAGATGTTGGGTTAAGTCCCGCAACGAGCGCAACCCTTGTTACTAGTTGC

CAGCATTCAGTTGGGCACTCTAGTGAGACTGCCGGTGACAAACCGGAGGAAGGTGGGGACGACGTCAGATCATCATG

CCCCTTATGACCTGGGCTACACACGTGCTACAATGGACGGTACAACGAGTCGCGAACTCGCGAGGGCAAGCTAATCT

CTTAAAACCGTTCTCAGTTCGGACTGCAGGCTGCAACTCGCCTGCACGAAGTCGGAATCGCTAGTAATCGCGGATCA

GCATGCCGCGGTGAATACGTTCCCGGGCCTTGTACACACCGCCCGTCACACCATGAGAGTTTGCAACACCCAAAGTC

GGTGGGGTAACCCTTCGGGGAGCTAGCCGCCTAAGGTGGGGCAGATGATTAGGGTGAAGTCGTAACAAGGTAGCCGT

AGGAGAACCTGCGGCTGGATCACCTCCT

>SEQ ID NO: 91|NR_028816.1|Turicibacter sanguinis strain MOL361 16S
ribosomal RNA gene, complete sequence
AGAGTTTGATCATGGCTCAGGATGAACGCTGGCGGCGTGCCTAATACATGCAAGTCGAGCGAACCACTTCGGTGGTG

AGCGGCGAACGGGTGAGTAACACGTAGGTTATCTGCCCATCAGACGGGGACAACGATTGGAAACGATCGCTAATACC

GGATAGGACGAAAGTTTAAAGGTGCTTCGGCACCACTGATGGATGAGCCTGCGGCGCATTAGCTAGTTGGTAGGGTA

AAGGCCTACCAAGGCGACGATGCGTAGCCGACCTGAGAGGGTGAACGGCCACACTGGGACTGAGACACGGCCCAGAC

TCCTACGGGAGGCAGCAGTAGGGAATCTTCGGCAATGGGCGAAAGCCTGACCGAGCAACGCCGCGTGAATGATGAAG

```
GCCTTCGGGTTGTAAAATTCTGTTATAAGGGAAGAATGGCTCTAGTAGGAAATGGCTAGAGTGTGACGGTACCTTAT

GAGAAAGCCACGGCTAACTACGTGCCAGCAGCCGCGGTAATACGTAGGTGGCGAGCGTTATCCGGAATTATTGGGCG

TAAAGAGCGCGCAGGTGGTTGATTAAGTCTGATGTGAAAGCCCACGGCTTAACCGTGGAGGGTCATTGGAAACTGGT

CAACTTGAGTGCAGAAGAGGGAAGTGGAATTCCATGTGTAGCGGTGAAATGCGTAGAGATATGGAGGAACACCAGTG

GCGAAGGCGGCTTCCTGGTCTGTAACTGACACTGAGGCGCGAAAGCGTGGGGAGCAAACAGGATTAGATACCCTGGT

AGTCCACGCCGTAAACGATGAGTGCTAAGTGTTGGGGGTCGAACCTCAGTGCTGAAGTTAACGCATTAAGCACTCCG

CCTGGGGAGTACGGTCGCAAGACTGAAACTCAAAGGAATTGACGGGACCCGCACAAGCGGTGGAGCATGTGGTTTA

ATTCGAAGCAACGCGAAGAACCTTACCAGGTCTTGACATACCAGTGACCGTCCTAGAGATAGGATTTTCCCTTCGGG

GACAATGGATACAGGTGGTGCATGGTTGTCGTCAGCTCGTGTCGTGAGATGTTGGGTTAAGTCCCGCAACGAGCGCA

ACCCCTGTCGTTAGTTGCCAGCATTCAGTTGGGGACTCTAACGAGACTGCCAGTGACAAACTGGAGGAAGGTGGGGA

TGACGTCAAATCATCATGCCCCTTATGACCTGGGCTACACACGTGCTACAATGGTTGGTACAAAGAGAAGCGAAGCG

GTGACGTGGAGCAAACCTCATAAAGCCAATCTCAGTTCGGATTGTAGGCTGCAACTCGCCTACATGAAGTTGGAATC

GCTAGTAATCGCGAATCAGCATGTCGCGGTGAATACGTTCCCGGGTCTTGTACACACCGCCCGTCACACCACGAGAG

TTTACAACACCCGAAGTCAGTGGCCTAACCGCAAGGAGGGAGCTGCCTAAGGTGGGGTAGATGATTGGGGTGAAGTC

GTAACAAGGTATCCCTACCGGAAGGTGGGGTTGGATCACCTCCTT
```

>SEQ ID NO: 92|NR_042832.1|*Roseburia faecis* strain M72/1 16S ribosomal RNA gene, partial sequence
```
GATGAACGCTGGCGGCGTGCTTAACACATGCAAGTCGAACGAAGCACTCTATTTGATTTTCTTCGGAAATGAAGATT

TTGTGACTGAGTGGCGGACGGGTGAGTAACGCGTGGGTAACCTGCCTCATACAGGGGGATAACAGTTGGAAACGACT

GCTAATACCGCATAAGCGCACAGGATCGCATGATCCGGTGTGAAAAACTCCGGTGGTATGAGATGGACCCGCGTCTG

ATTAGCCAGTTGGCAGGGTAACGGCCTACCAAAGCGACGATCAGTAGCCGACCTGAGAGGGTGACCGGCCACATTGG

GACTGAGACACGGCCCAAACTCCTACGGGAGGCAGCAGTGGGGAATATTGCACAATGGGGGAAACCCTGATGCAGCG

ACGCCGCGTGAGCGAAGAAGTATTTCGGTATGTAAAGCTCTATCAGCAGGGAAGAAGAATGACGGTACCTGACTAAG

AAGCACCGGCTAAATACGTGCCAGCAGCCGCGGTAATACGTATGGTGCAAGCGTTATCCGGATTTACTGGGTGTAAA

GGGAGCGCAGGCGGTGCGGCAAGTCTGATGTGAAAGCCCGGGGCTCAACCCCGGTACTGCATTGGAAACTGTCGTAC

TAGAGTGTCGGAGGGGTAAGTGGAATTCCTAGTGTAGCGGTGAAATGCGTAGATATTAGGAGGAACACCAGTGGCGA

AGGCGGCTTACTGGACGATAACTGACGCTGAGGCTCGAAAGCGTGGGGAGCAAACAGGATTAGATACCCTGGTAGTC

CACGCCGTAAACGATGAATACTAGGTGTCGGGAGCATTGCTCTTCGGTGCCGCAGCAAACGCAATAAGTATTCCAC

CTGGGGAGTACGTTCGCAAGAATGAAACTCAAAGGAATTGACGGGACCCGCACAAGCGGTGGAGCATGTGGTTTAA

TTCGAAGCAACGCGAAGAACCTTACCAAGTCTTGACATCCCGATGACAGAGTATGTAATGTACYTTCTCTTCGGAGC

ATCGGTGACAGGTGGTGCATGGTTGTCGTCAGCTCGTGTCGTGAGATGTTGGGTTAAGTCCCGCAACGAGCGCAACC

CCTGTCCTTAGTAGCCAGCGGTTCGGCCGGGCACTCTAGGGAGACTGCCAGGGATAACCTGGAGGAAGGCGGGGATG

ACGTCAAATCATCATGCCCCTTATGACTTGGGCTACACACGTGCTACAATGGCGTAAACAAAGGGAAGCGGAGCCGT

GAGGCCGAGCAAATCTCAAAAATAACGTCTCAGTTCGGACTGTAGTCTGCAACCCGACTACACGAAGCTGGAATCGC

TAGTAATCGCAGATCAGAATGCTGCGGTGAATACGTTCCCGGGTCTTGTACACACCGCCCGTCACACCATGGGAGTT

GGAAATGCCCGAAGTCAGTGACCCAACCGCAAGGAGGGAGCTGCCGAAGGCAGGTTCGATAACTGGGGTG
```

>SEQ ID NO: 93|NR_043142.1|*Flavonifractor plautii* strain Prevot S1 16S ribosomal RNA gene, partial sequence
```
CGCTGGCGGCGTGCTTAACACATGCAAGTCGAACGGGGTGCTCATGACGGAGGATTCGTCCAATGGATTGAGTTACC

TAGTGGCGGACGGGTGAGTAACGCGTGAGGAACCTGCCTTGGAGAGGGGAATAACACTCCGAAAGGAGTGCTAATAC

CGCATGAAGCAGTTGGGTCGCATGGCTCTGACTGCCAAAGATTTATCGCTCTGAGATGGCCTCGCGTCTGATTAGCT

AGTAGGCGGGGTAACGGCCCACCTAGGCGACGATCAGTAGCCGGACTGAGAGGTTGACCGGCCACATTGGGACTGAG
```

ACACGGCCCAGACTCCTACGGGAGGCAGCAGTGGGGAATATTGGGCAATGGGCGCAAGCCTGACCCAGCAACGCCGC

GTGAAGGAAGAAGGCTTTCGGGTTGTAAACTTCTTTTGTCGGGGACGAAACAAATGACGGTACCCGACGAATAAGCC

ACGGCTAACTACGTGCCAGCAGCCGCGGTAATACGTAGGTGGCAAGCGTTATCCGGATTTACTGGGTGTAAAGGGCG

TGTAGGCGGGATTGCAAGTCAGATGTGAAAACTGGGGGCTCAACCTCCAGCCTGCATTTGAAACTGTAGTTCTTGAG

TGCTGGAGAGGCAATCGGAATTCCGTGTGTAGCGGTGAAATGCGTAGATATACGGAGGAACACCAGTGGCGAAGGCG

GATTGCTGGACAGTAACTGACGCTGAGGCGCGAAAGCGTGGGGAGCAAACAGGATTAGATACCCTGGTAGTCCACGC

CGTAAACGATGGATACTAGGTGTGGGGGGTCTGACCCCCTCCGTGCCGCAGTTAACACAATAAGTATCCCACCTGGG

GAGTACGATCGCAAGGTTGAAACTCAAAGGAATTGACGGGGGCCCGCACAAGCGGTGGAGTATGTGGTTTAATTCGA

AGCAACGCGAAGAACCTTACCAGGGCTTGACATCCCACTAACGAGGCAGAGATGCGTTAGGTGCCCTTCGGGGAAAG

TGGAGACAGGTGGTGCATGGTTGTCGTCAGCTCGTGTCGTGAGATGTTGGGTTAAGTCCCGCAACGAGCGCAACCCT

TATTGTTAGTTGCTACGCAAGAGCACTCTAGCGAGACTGCCGTTGACAAAACGGAGGAAGGTGGGGACGACGTCAAA

TCATCATGCCCCTTATGTCCTGGGCCACACACGTACTACAATGGTGGTTAACAGAGGGAGGCAATACCGCGAGGTGG

AGCAAATCCCTAAAAGCCATCCCAGTTCGGATTGCAGGCTGAAACCCGCCTGTATGAAGTTGGAATCGCTAGTAATC

GCGGATCAGCATGCCGCGGTGAATACGTTCCCGGGCCTTGTACACACCGCCCGTCACACCATGAGAGTCGGGAACAC

CCGAAGTCCGTAGCCTAACCGCAAGGAGGGCGCGGCCGAAGGTGGGTTCGATAATTGGGGTGAAGTCGTAACAAGGT

AG

>SEQ ID NO: 94|NR_044054.1|Blautia wexlerae strain DSM 19850 16S ribosomal
RNA gene, partial sequence
CAAGTCGAACGGGAATTANTTTATTGAAACTTCGGTCGATTTAATTTAATTCTAGTGGCGGACGGGTGAGTAACGCG

TGGGTAACCTGCCTTATACAGGGGGATAACAGTCAGAAATGGCTGCTAATACCGCATAAGCGCACAGAGCTGCATGG

CTCAGTGTGAAAAACTCCGGTGGTATAAGATGGACCCGCGTTGGATTAGCTTGTTGGTGGGGTAACGGCCCACCAAG

GCGACGATCCATAGCCGGCCTGAGAGGGTGAACGGCCACATTGGGACTGAGACACGGCCCAGACTCCTACGGGAGGC

AGCAGTGGGGAATATTGCACAATGGGGGAAACCCTGATGCAGCGACGCCGCGTGAAGGAAGAAGTATCTCGGTATGT

AAACTTCTATCAGCAGGGAAGATAGTGACGGTACCTGACTAAGAAGCCCCGGCTAACTACGTGCCAGCAGCCGCGGT

AATACGTAGGGGGCAAGCGTTATCCGGATTTACTGGGTGTAAAGGGAGCGTAGACGGTGTGGCAAGTCTGATGTGAA

AGGCATGGGCTCAACCTGTGGACTGCATTGGAAACTGTCATACTTGAGTGCCGGAGGGGTAAGCGGAATTCCTAGTG

TAGCGGTGAAATGCGTAGATATTAGGAGGAACACCAGTGGCGAAGGCGGCTTACTGGACGGTAACTGACGTTGAGGC

TCGAAAGCGTGGGGAGCAAACAGGATTAGATACCCTGGTAGTCCACGCCGTAAACGATGAATAACTAGGTGTCGGGT

GGCAAAGCCATTCGGTGCCGTCGCAAACGCAGTAAGTATTCCACCTGGGGAGTACGTTCGCAAGAATGAAACTCAAA

GGAATTGACGGGGACCCGCACAAGCGGTGGAGCATGTGGTTTAATTCGAAGCAACGCGAAGAACCTTACCAAGTCTT

GACATCCGCCTGACCGATCCTTAACCGGATCTTTCCTTCGGGACAGGCGAGACAGGTGGTGCATGGTTGTCGTCAGC

TCGTGTCGTGAGATGTTGGGTTAAGTCCCGCAACGAGCGCAACCCCTATCCTCAGTAGCCAGCATTTAAGGTGGGCA

CTCTGGGGAGACTGCCAGGGATAACCTGGAGGAAGGCGGGGATGACGTCAAATCATCATGCCCCTTATGATTTGGGC

TACACACGTGCTACAATGGCGTAAACAAAGGGAAGCGAGATTGTGAGATGGAGCAAATCCCAAAAATAACGTCCCAG

TTCGGACTGTAGTCTGCAACCCGACTACACGAAGCTGGAATCGCTAGTAATCGCGGATCAGAATGCCGCGGTGAATA

CGTTCCCGGGTCTTGTACACACCGCCCGTCACACCATGGGAGTCAGTAACGCCCGAAGTCAGTGACCTAACTGCAAA

GAAGGAGCTGCCGAAGGCGGGACCGATGACTGGGGTGAAGTCGTAACAAGGT

>SEQ ID NO: 95|NR_027558.1|Anaerotruncus colihominis strain WAL 14565 16S
ribosomal RNA gene, partial sequence
AACGGAGCTTACGTTTTGAAGTTTTCGGATGGATGAATGTAAGCTTAGTGGCGGACGGGTGAGTAACACGTGAGCAA

CCTGCCTTTCAGAGGGGGATAACAGCCGGAAACGGCTGCTAATACCGCATGATGTTGCGGGGGCACATGCCCCTGCA

```
ACCAAAGGAGCAATCCGCTGAAAGATGGGCTCGCGTCCGATTAGCCAGTTGGCGGGGTAACGGCCCACCAAAGCGAC
GATCGGTAGCCGGACTGAGAGGTTGAACGGCCACATTGGGACTGAGACACGGCCCAGACTCCTACGGGAGGCAGCAG
TGGGGGATATTGCACAATGGGCGAAAGCCTGATGCAGCGACGCCGCGTGAGGGAAGACGGTCTTCGGATTGTAAACC
TCTGTCTTTGGGGAAGAAAATGACGGTACCCAAAGAGGAAGCTCCGGCTAACTACGTGCCAGCAGCCGCGGTAATAC
GTAGGGAGCAAGCGTTGTCCGGAATTACTGGGTGTAAAGGGAGCGTAGGCGGGATGGCAAGTAGAATGTTAAATCCA
TCGGCTCAACCGGTGGCTGCGTTCTAAACTGCCGTTCTTGAGTGAAGTAGAGGCAGGCGGAATTCCTAGTGTAGCGG
TGAAATGCGTAGATATTAGGAGGAACACCAGTGGCGAAGGCGGCCTGCTGGGCTTTAACTGACGCTGAGGCTCGAAA
GCGTGGGGAGCAAACAGGATTAGATACCCTGGTAGTCCACGCCGTAAACGATGATTACTAGGTGTGGGGGGACTGAC
CCCTTCCGTGCCGCAGTTAACACAATAAGTAATCCACCTGGGGAGTACGGCCGCAAGGTTGAAACTCAAAGGAATTG
ACGGGGCCCGCACAAGCAGTGGAGTATGTGGTTTAATTCGAAGCAACGCGAAGAACCTTACCAGGTCTTGACATCG
GCGTAATAGCCTAGAGAGTAGGTGAAGCCCTTCGGGGCATCCAGACAGGTGGTGCATGGTTGTCGTCAGCTCGTGTC
GTGAGATGTTGGGTTAAGTCCCGCAACGAGCGCAACCCTTATTATTAGTTGCTACGCAAGAGCACTCTAATGAGACT
GCCGTTGACAAAACGGAGGAAGGTGGGGATGACGTCAAATCATCATGCCCCTTATGACCTGGGCTACACACGTACTA
CAATGGCACTAAAACAGAGGGCGGCGACACCGCGAGGTGAAGCGAATCCCAGAAAAAGTGTCTCAGTTCAGATTGCA
GGCTGCAACCCGCCTGCATGAAGTCGGAATTGCTAGTAATCGCGGATCAGCATGCCGCGGTGAATACGTTCCCGGGC
CTTGTACACACCGCCCGTCACACCATGGGAGTCCGGGTAACACCCGAAGCCAGTAG
```

>SEQ ID NO: 96|NR_116747.1|*Ruminococcus faecis* strain Eg2 16S ribosomal RNA gene, partial sequence
```
ATGCAAGTCGAACGAAGCACCTTGATTTGATTCTTCGGATGAAGATCTTGGTGACTGAGTGGCGGACGGGTGAGTAA
CGCGTGGGTAACCTGCCTCATACAGGGGGATAACAGTTAGAAATGACTGCTAATACCGCATAAGACCACAGCACCGC
ATGGTGCAGGGGTAAAAACTCCGGTGGTATGAGATGGACCCGCGTCTGATTAGGTAGTTGGTGGGGTAACGGCCTAC
CAAGCCGACGATCAGTAGCCGACCTGAGAGGGTGACCGGCCACATTGGGACTGAGACACGGCCCAAACTCCTACGGG
AGGCAGCAGTGGGGAATATTGCACAATGGGGGAAACCCTGATGCAGCGACGCCGCGTGAGCGATGAAGTATTTCGGT
ATGTAAAGCTCTATCAGCAGGGAAGAAAATGACGGTACCTGACTAAGAAGCACCGGCTAAATACGTGCCAGCAGCCG
CGGTAATACGTATGGTGCAAGCGTTATCCGGATTTACTGGGTGTAAAGGGAGCGTAGACGGAGTGGCAAGTCTGATG
TGAAAACCCGGGGCTCAACCCCGGGACTGCATTGGAAACTGTCAATCTAGAGTACCGGAGAGGTAAGCGGAATTCCT
AGTGTAGCGGTGAAATGCGTAGATATTAGGAGGAACACCAGTGGCGAAGGCGGCTTACTGGACGGTAACTGACGTTG
AGGCTCGAAAGCGTGGGGAGCAAACAGGATTAGATACCCTGGTAGTCCACGCCGTAAACGATGACTACTAGGTGTCG
GGCAGCAAAGCTGTTCGGTGCCGCAGCAAACGCAATAAGTAGTCCACCTGGGGAGTACGTTCGCAAGAATGAAACTC
AAAGGAATTGACGGGGACCCGCACAAGCGGTGGAGCATGTGGTTTAATTCGAAGCAACGCGAAGAACCTTACCTGCT
CTTGACATCTCCCTGACCGGCAAGTAATGTTGCCTTTCCTTCGGGACAGGGATGACAGGTGGTGCATGGTTGTCGTC
AGCTCGTGTCGTGAGATGTTGGGTTAAGTCCCGCAACGAGCGCAACCCCTATCTTTAGTAGCCAGCGGTTTGGCCGG
GCACTCTAGAGAGACTGCCAGGGATAACCTGGAGGAAGGTGGGGATGACGTCAAATCATCATGCCCCTTATGAGCAG
GGCTACACACGTGCTACAATGGCGTAAACAAAGGGAGGCAGAACCGCGAGGTCGAGCAAATCCCAAAAATAACGTCT
CAGTTCGGATTGTAGTCTGCAACTCGACTACATGAAGCTGGAATCGCTAGTAATCGCGAATCAGAATGTCGCGGTGA
ATACGTTCCCGGGTCTTGTACACACCGCCCGTCACACCATGGGAGTCAGTAACGCCCGAAGTCAGTGACCCAACCGT
AAGGAGGAGCTGCCGAAG
```

>SEQ ID NO: 97|NR_028883.1|*Dorea longicatena* strain 111-35 16S ribosomal RNA gene, partial sequence
```
TAACGCGTGGGTAACCTGCCTCATACAGGGGGATAACAGTTAGAAATGACTGCTAATACCGCATAAGACCACGTACC
GCATGGTACAGTGGTAAAAACTCCGGTGGTATGAGATGGACCCGCGTCTGATTAGGTAGTTGGTGGGGTAACGGCCT
ACCAAGCCGACGATCAGTAGCCGACCTGAGAGGGTGACCGGCCACATTGGGACTGAGACACGGCCCAGACTCCTACG
```

GGAGGCAGCAGTGGGGAATATTGCACAATGGAGGAAACTCTGATGCAGCGACGCCGCGTGAAGGATGAAGTATTTCG

GTATGTAAACTTCTATCAGCAGGGAAGAAAATGACGGTACCTGACTAAGAAGCCCCGGCTAACTACGTGCCAGCAGC

CGCGGTAATACGTAGGGGGCAAGCGTTATCCGGATTTACTGGGTGTAAAGGGAGCGTAGACGGCACGGCAAGCCAGA

TGTGAAAAGCCCGGGGCTCAACCCCGGGACTGCATTTGGAACTGCTGAGCTAGAGTGTCGGAGAGGCAAGTGGAATT

CCTAGTGTAGCGGTGAAATGCGTAGATATTAGGAGGAACACCAGTGGCGAAGGCGGCTTGCTGGACGATGACTGACG

TTGAGGCTCGAAAGCGTGGGGAGCAAACAGGATTAGATACCCTGGTAGTCCACGCCGTAAACGATGACTGCTAGGTG

TCGGGTGGCAAAGCCATTCGGTGCCGCAGCTAACGCAATAAGCAGTCCACCTGGGGAGTACGTTCGCAAGAATGAAA

CTCAAAGGAATTGACGGGGACCCGCACAAGCGGTGGAGCATGTGGTTTAATTCGAAGCAACGCGAAGAACCTTACCT

GATCTTGACATCCCGATGACCGCTTCGTAATGGAAGTTTTTCTTCGGAACATCGGTGACAGGTGGTGCATGGTTGTC

GTCAGCTCGTGTCGTGAGATGTTGGGTTAAGTCCCGCAACGAGCGCAACCCCTATCTTCAGTAGCCAGCAGGTTAAG

CTGGGCACTCTGGAGAGACTGCCAGGGATAACCTGGAGGAAGGTGGGGATGACGTCAAATCATCATGCCCCTTATGA

CCAGGGCTACACACGTGCTACAATGGCGTAAACAAAGAGAAGCGAACTCGCGAGGGTAAGCAAATCTCAAAAATAAC

GTCTCAGTTCGGATTGTAGTCTGCAACTCGACTACATGAAGCTGGAATCGCTAGTAATCGCAGATCAGAATGCTGCG

GTGAATACGTTCCCGGGTCTTGTACACACCGCCCGTCACACCATGGGAGTCATAACGCCCGAAGTCAGTGACCCAAC

CGTAAGG

>SEQ ID NO: 98|NR_029164.1|*Clostridium innocuum* strain B-3 16S ribosomal RNA gene, partial sequence
ATGGAGAGTTTGATCCTGGCTCAGGATGAACGCTGGCGGCATGCCTAATACATGCAAGTCGAACGAAGTCTTCAGGA

AGCTTGCTTCCAAAAAGACTTAGTGGCGAACGGGTGAGTAACACGTAGGTAACCTGCCCATGTGTCCGGGATAACTG

CTGGAAACGGTAGCTAAAACCGGATAGGTATACGGAGCGCATGCTCTGTATATTAAAGCGCCCTTCAAGGCGTGAAC

ATGGATGGACCTGCGACGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGYAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGAA

ATTCAGTGCTGCAGTTAACGCAATAAGTTCTCCGCCTGGGGAGTATGCACGCAAGTTNGAAACTCAAAGGAATTGAC

GGGGGCCCGCACAAGCGNTGGAGTATGTGGTTTAATTCGAAGCAACGCGAAGAACCTTACCAGGCCTTGACATGAAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGACCACAAAGAGCAGCGACTTGGTGACAAGAAGCGAATCTCATAAAGATCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGA

>SEQ ID NO: 99|NR_104687.1|*Blautia hansenii* strain JCM 14655 16S ribosomal RNA gene, partial sequence
AGAGTTTGATCCTGGCTCAGGATGAACGCTGGCGGCGTGCTTAACACATGCAAGTCGAGCGAAGCACTTATCATTGA

CTCTTCGGAAGATTTGATATTTGACTGAGCGGCGGACGGGTGAGTAACGCGTGGGTAACCTGCCTCATACAGGGGAA

```
TAACAGTTAGAAATGGCTGCTAATGCCGCATAAGCGCACAGGACCGCATGGTCTGGTGTGAAAAACTGAGGTGGTAT

GAGATGGACCCGCGTCTGATTAGGTAGTTGGTGGGGTAACGGCCTACCAAGCCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTTTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGGTGCAAAGCAGTTCGGTGCCGCAGCAAA

CGCAATAAGTATTCCACCTGGGGAGTACGTTCGCAAGAATGAAACTCAAAGGAATTGACGGGGACCCGCACAAGCGG

TGGAGCATGTGGTTTAATTCGAAGCAACGCGAAGAACCTTACCAAGTCTTGACATCTGCCTGACCGTTCCTTAACCG

GAGCTTTCCTTCGGGACAGGCAAGACAGGTGGTGCATGGTTGTCGTCAGCTCGTGTCGTGAGATGTTGGGTTAAGTC

CCGCAACGAGCGCAACCCCTATCCTTAGTAGCCAGCAGTCCGGCTGGGCACTCTAGGGAGACTGCCGGGGATAACCC

GGAGGAAGGCGGGGACGACGTCAAATCATCATGCCCCTTATGATTTGGGCTACACACGTGCTACAATGGCGTAAACA

AAGGGAAGCGAAGCGGTGACGCTTAGCAAATCTCAAAAATAACGTCCCAGTTCGGACTGCAGTCTGCAACTCGACTG

CACGAAGCTGGAATCGCTAGTAATCGCGAATCAGAATGTCGCGGTGAATACGTTCCCGGGTCTTGTACACACCGCCC

GTCACACCATGGGAGTCAGTAACGCCCGAAGTCAGTGACCCAACCTTATGGAGGGAGCTGCCGAAGGCGGGACCGAT

AACTGGGGTGAAGTCGTAACAAGGTAACC

>SEQ ID NO: 100|NR_112933.1|Bacteroides cellulosilyticus strain JCM 15632
16S ribosomal RNA gene, partial sequence
AGAGTTTGATCCTGGCTCAGGATGAACGCTAGCTACAGGCTTAACACATGCAAGTCGAGGGGCAGCATGACCTAGCA

ATAGGTTGATGGCGACCGGCGCACGGGTGAGTAACACGTATCCAACCTACCGGTTATTCCGGGATAGCCTTTCGAAA

GAAAGATTAATACCGGATAGTATAACGAGAAGGCATCTTTTTGTTATTAAAGAATTTCGATAACCGATGGGGATGCG

TTCCATTAGTTTGTTGGCGGGGTAACGGCCCACCAAGACATCGATGGATAGGGGTTCTGAGAGGAAGGTCCCCCACA

TTGGAACTGAGACACGGTCCAAACTCCTACGGGAGGCAGCAGTGAGGAATATTGGTCAATGGACGAGAGTCTGAACC

AGCCAAGTAGCGTGAAGGATGACTGCCCTATGGGTTGTAAACTTCTTTTATATGGGAATAAAGTGAGCCACGTGTGG

CTTTTTGTATGTACCATACGAATAAGGATCGGCTAACTCCGTGCCAGCAGCCGCGGTAATACGGAGGATCCGAGCGT

TATCCGGATTTATTGGGTTTAAAGGGAGCGTAGGCGGACTATTAAGTCAGCTGTGAAAGTTTGCGGCTCAACCGTAA

AATTGCAGTTGATACTGGTCGTCTTGAGTGCAGTAGAGGTAGGCGGAATTCGTGGTGTAGCGGTGAAATGCTTAGAT

ATCACGAAGAACTCCGATTGCGAAGGCAGCTTACTGGACTGTAACTGACGCTGATGCTCGAAAGTGTGGGTATCAAA

CAGGATTAGATACCCTGGTAGTCCACACAGTAAACGATGAATACTCGCTGTTTGCGATATACAGCAAGCGGCCAAGC

GAAAGCATTAAGTATTCCACCTGGGGAGTACGCCGGCAACGGTGAAACTCAAAGGAATTGACGGGGCCCGCACAAG

CGGAGGAACATGTGGTTTAATTCGATGATACGCGAGGAACCTTACCCGGGCTTAAATTGCATCTGAATAATTTGGAA

ACAGATTAGCCGCAAGGCAGATGTGAAGGTGCTGCATGGTTGTCGTCAGCTCGTGCCGTGAGGTGTCGGCTTAAGTG

CCATAACGAGCGCAACCCTTATCTTTAGTTACTAACAGGTCATGCTGAGGACTCTAGAGAGACTGCCGTCGTAAGAT

GTGAGGAAGGTGGGGATGACGTCAAATCAGCACGGCCCTTACGTCCGGGGCTACACACGTGTTACAATGGGGGGTAC

AGAAGGCAGCTACACAGCGATGTGATGCTAATCCCAAAAGCCTCTCTCAGTTCGGATTGGAGTCTGCAACCCGACTC

CATGAAGCTGGATTCGCTAGTAATCGCGCATCAGCCACGGCGCGGTGAATACGTTCCCGGGCCTTGTACACACCGCC

CGTCAAGCCATGAAAGCCGGGGGTACCTGAAGTCCGTAACCGCAAGGAGCGGCCTAGGGTAAAACTGGTAATTGGGG

CTAAGTCGTA
```

>SEQ ID NO: 101|NR_112940.1|*Bacteroides ovatus* strain JCM 5824 16S ribosomal RNA gene, partial sequence
GGCTCAGGATGAACGCTAGCTACAGGCTTAACACATGCAAGTCGAGGGGCAGCATTTTAGTTTGCTTGCAAACTGAA
GATGGCGACCGGCGCACGGGTGAGTAACACGTATCCAACCTGCCGATAACTCCGGAATAGCCTTTCGAAAGAAAGAT
TAATACCGGATAGCATACGAATATCGCATGATATTTTTATTAAAGAATTTCGGTTATCGATGGGGATGCGTTCCATT
AGTTTGTTGGCGGGGTAACGGCCCACCAAGACTACGATGGATAGGGGTTCTGAGAGGAAGGTCCCCCACATTGGAAC
TGAGACACGGTCCAAACTCCTACGGGAGGCAGCAGTGAGGAATATTGGTCAATGGGCGAGAGCCTGAACCAGCCAAG
TAGCGTGAAGGATGAAGGCTCTATGGGTCGTAAACTTCTTTTATATGGGAATAAAGTTTTCCACGTGTGGAATTTTG
TATGTACCATATGAATAAGGATCGGCTAACTCCGTGCCAGCAGCCGCGGTAATACGGAGGATCCGAGCGTTATCCGG
ATTTATTGGGTTTAAAGGGAGCGTAGGTGGATTGTTAAGTCAGTTGTGAAAGTTTGCGGCTCAACCGTAAAATTGCA
GTTGAAACTGGCAGTCTTGAGTACAGTAGAGGTGGGCGGAATTCGTGGTGTAGCGGTGAAATGCTTAGATATCACGA
AGAACTCCGATTGCGAAGGCAGCTCACTAGACTGTTACTGACACTGATGCTCGAAAGTGTGGGTATCAAACAGGATT
AGATACCCTGGTAGTCCACACAGTAAACGATGAATACTCGCTGTTTGCGATATACAGTAAGCGGCCAAGCGAAAGCA
TTAAGTATTCCACCTGGGGAGTACGCCGGCAACGGTGAAACTCAAAGGAATTGACGGGGGCCCGCACAAGCGGAGGA
ACATGTGGTTTAATTCGATGATACGCGAGGAACCTTACCCGGGCTTAAATTGCAACAGAATATATTGGAAACAGTAT
AGCCGTAAGGCTGTTGTGAAGGTGCTGCATGGTTGTCGTCAGCTCGTGCCGTGAGGTGTCGGCTTAAGTGCCATAAC
GAGCGCAACCCTTATCTTTAGTTACTAACAGGTTATGCTGAGGACTCTAGAGAGACTGCCGTCGTAAGATGTGAGGA
AGGTGGGGATGACGTCAAATCAGCACGGCCCTTACGTCCGGGGCTACACACGTGTTACAATGGGGGGTACAGAAGGC
AGCTACCTGGCGACAGGATGCTAATCCCAAAAACCTCTCTCAGTTCGGATCGAAGTCTGCAACCCGACTTCGTGAAG
CTGGATTCGCTAGTAATCGCGCATCAGCCATGGCGCGGTGAATACGTTCCCGGGCCTTGTACACACCGCCCGTCAAG
CCATGAAAGCCGGGGGTACCTGAAGTACGTAACCGCAAGGAGCGTCCTAGGGTAAAACTGGTAATTGGGCTA >SEQ ID NO: 102|NR_117563.1|*Eubacterium fissicatena* 16S ribosomal RNA gene, partial sequence
TAGAGTTTGATCCTGGCTCAGGATGAACGCTGGCGGCGTGCTTAACACATGCAAGTCGAGCGAAGCGCTTTACTTAG
ATTTCTTCGGATTGAAGAGTTTTGCGACTGAGCGGCGGACGGGTGAGTAACGCGTGGGTAACCTGCCTCATACAGGG
GGATAACAGTTAGAAATGACTGCTAATACCGCATAAGACCACAGTACCGCATGGTACAGTGGGAAAAACTCCGGTGG
TATGAGATGGACCCGCGTCTGATTAGCTAGTTGGTAAGGTAACGGCTTACCAAGGCGACGATCAGTAGCCGACCTGA
GAGGGTGACCGGCCACATTGGGACTGAGACACGGCCCAAACTCCTACGGGAGGCAGCAGTGGGGAATATTGCACAAT
GGGGGAAACCCTGATGCAGCGACGCCGCGTGAAGGATGAAGTATTTCGGTATGTAAACTTCTATCAGCAGGGAAGAA
AATGACGGTACCTGACTAAGAAGCCCCGGCTAACTACGTGCCAGCAGCCGCGGTAATACGTAGGGGGCAAGCGTTAT
CCGGATTTACTGGGTGTAAAGGGAGCGTAGACGGTTATGTAAGTCTGATGTGAAAACCCGGGGCTCAACCCCGGGAC
TGCATTGGAAACTATGTAACTAGAGTGTCGGAGAGGTAAGTGGAATTCCTAGTGTAGCGGTGAAATGCGTAGATATT
AGGAGGAACACCAGTGGCGAAGGCGGCTTACTGGACGATCACTGACGTTGAGGCTCGAAAGCGTGGGGAGCAAACAG
GATTAGATACCCTGGTAGTCCACGCCGTAAACGATGAATACTAGGTGTCGGGTGGCAAAGCCATTCGGTGCCGCAGC
AAACGCAATAAGTATTCCACCTGGGGAGTACGTTCGCAAGAATGAAACTCAAAGGAATTGACGGGGACCCGCACAAG
CGGTGGAGCATGTGGTTTAATTCGAAGCAACGCGAAGAACCTTACCTGCTCTTGACATCCCACTGACCGGCGTGTAA
TGGCGCCTTCCCTTCGGGGCAGTGGAGACAGGTGGTGCATGGTTGTCGTCAGCTCGTGTCGTGAGATGTTGGGTTAA
GTCCCGCAACGAGCGCAACCCTTATCTTTAGTAGCCAGCGGTTTGGCCGGGCACTCTAGAGAGACTGCCAGGGATAA
CCTGGAGGAAGGTGGGGATGACGTCAAATCATCATGCCCCTTATGAGCAGGGCTACACACGTGCTACAATGGCGTAA
ACAAAGGGAGGCAATACCGCGAGGTTGAGCAAATCCCAAAAATAACGTCTCAGTTCGGATTGTAGTCTGCAACTCGA
CTACATGAAGCTGGAATCGCTAGTAATCGCGAATCAGAATGTCGCGGTGAATACGTTCCCGGGTCTTGTACACACCG

CCCGTCACACCATGGGAGTTGGTAACGCCCGAAGTCAGTGACCCAACCGTAAGGAGGGAGCTGCCGAAGGCGGGATC

GATAACTGGGGTGAAGTCGTAACAAGGTAGCCGTATCGGAAGGTGCGGCTGGATCACCTCCTT

>SEQ ID NO: 103|NR_104700.1|Blautia coccoides strain JCM 1395 16S ribosomal
RNA gene, partial sequence
AGAGTTTGATCCTGGCTCAGGATGAACGCTGGCGGCGTGCTTAACACATGCAAGTCGAGCGAAGCGCTAAGACAGAT

TTCTTCGGATTGAAGTCTTTGTGACTGAGCGGCGGACGGGTGAGTAACGCGTGGGTAACCTGCCTCATACAGGGGGA

TAACAGTTAGAAATGACTGCTAATACCGCATAAGCGCACAGGACCGCATGGTCTGGTGTGAAAAACTCCGGTGGTAT

GAGATGGACCCGCGTCTGATTAGCTAGTTGGAGGGGTAACGGCCCACCAAGGCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTGTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGTGGCAAAGCCATTCGGTGCCGCAGCAAA

CGCAATAAGTATTCCACCTGGGGAGTACGTTCGCAAGAATGAAACTCAAAGGAATTGACGGGGACCCGCACAAGCGG

TGGAGCATGTGGTTTAATTCGAAGCAACGCGAAGAACCTTACCAAGTCTTGACATCCCTCTGACCGTCCCGTAACGG

GGGCTTCCCTTCGGGGCAGAGGAGACAGGTGGTGCATGGTTGTCGTCAGCTCGTGTCGTGAGATGTTGGGTTAAGTC

CCGCAACGAGCGCAACCCTTATCCTTAGTAGCCAGCACATGATGGTGGGCACTCTAGGGAGACTGCCGGGGATAACC

CGGAGGAAGGCGGGGACGACGTCAAATCATCATGCCCCTTATGATTTGGGCTACACACGTGCTACAATGGCGTAAAC

AAAGGGAAGCGAGACAGCGATGTTGAGCGAATCCCAAAAATAACGTCCCAGTTCGGACTGCAGTCTGCAACTCGACT

GCACGAAGCTGGAATCGCTAGTAATCGCGGATCAGAATGCCGCGGTGAATACGTTCCCGGGTCTTGTACACACCGCC

CGTCACACCATGGGAGTCAGTAACGCCCGAAGTCAGTGACCTAACCGAAAGGAAGGAGCTGCCGAAGGCGGGACCGA

TAACTGGGGTGAAGTCGTAACAAGGTAACC

>SEQ ID NO: 104|NR_109014.1|Blautia faecis strain M25 16S ribosomal RNA
gene, partial sequence
ATAACAGCCAGAAATGACTGCTAATACCGCATAAGCGCACAGAACCGCATGGTTCGGTGTGAAAAACTCCGGTGGTA

TAAGATGGACCCGCGTTGGATTAGCTAGTTGGCAGGGCAGCGGCCTACCAAGGCGACGATCCATAGCCGGCCTGAGA

GGGTGAACGGCCACATTGGGACTGAGACACGCCCAGACTCCTACGGGAGGCAGCAGTGGGGAATATTGCACAATGG

GGGAAACCCTGATGCAGCGACGCCGCGTGAAGGAAGAAGTATCTCGGTATGTAAACTTCTATCAGCAGGGAAGATAA

TGACGGTACCTGACTAAGAAGCCCCGGCTAACTACGTGCCAGCAGCCGCGGTAATACGTAGGGGGCAAGCGTTATCC

GGATTTACTGGGTGTAAAGGGAGCGTAGACGGCGCAGCAAGTCTGATGTGAAAGGCAGGGGCTTAACCCCTGGACTG

CATTGGAAACTGCTGTGCTTGAGTGCCGGAGGGGTAAGCGGAATTCCTAGTGTAGCGGTGAAATGCGTAGATATTAG

GAGGAACACCAGTGGCGAAGGCGGCTTACTGGACGGTAACTGACGTTGAGGCTCGAAAGCGTGGGGAGCAAACAGGA

TTAGATACCCTGGTAGTCCACGCCGTAAACGATGAATACTAGGTGTCAGGGAGCACAGCTCTTTGGTGCCGCCGCAA

ACGCATTAAGTATTCCACCTGGGGAGTACGTTCGCAAGAATGAAACTCAAAGGAATTGACGGGACCCGCACAAGCG

GTGGAGCATGTGGTTTAATTCGAAGCAACGCGAAGAACCTTACCAAATCTTGACATCCCTCTGACCGGGACTTAACC

GTCCCTTTCCTTCGGGACAGGGGAGACAGGTGGTGCATGGTTGTCGTCAGCTCGTGTCGTGAGATGTTGGGTTAAGT

CCCGCAACGAGCGCAACCCCTATCCTTAGTAGCCAGCACGCARTGGTGGGCACTCTGAGGAGACTGCCAGGGATAAC

CTGGAGGAAGGCGGGGATGACGTCAAATCATCATGCCCCTTATGATTTGGGCTACACACGTGCTACAATGGCGTAAA

CAAAGGGAAGCGAACCCGCGAGGGTGGGCAAATCTCAAAAATAACGTCCCAGTTCGGACTGCAGTCTGCAACTCGAC

```
TGCACGAAGCTGGAATCGCTAGTAATCGCGGATCAGAATGCCGCGGTGAATACGTTCCCGGGTCTTGTACACACCGC

CCGTCACACCATGGGAGTCAGTAACGCCCG
```

>SEQ ID NO: 105|NR_036928.1|*Clostridium hathewayi* strain 1313 16S ribosomal RNA gene, partial sequence
```
CTCAGGATGAACGCTGGCGGCGTGCTTAACACATGCAAGTCGAGCGAAGCGGTTTCAATGAAGTTTTCGGATGGATT

TGAAATTGACTTAGCGGCGGACGGGTGAGTAACGCGTGGGTAACCTGCCTTACACTGGGGGATAACAGTTAGAAATG

ACTGCTAATACCGCATAAGCGCACAGGGCCGCATGGNCTGGTGTGAAAAACTCCGGNGGTGTAAGATGGACCCGCGT

CTGATTAGGTAGTTGGNGGGGTAACGGCCCACCAAGCCGACGATCAGTAGCCGACCTGAGAGGGTGACCGGCCACAT

TGGGACTGAGACACGGCCCAAACTCCTACGGGAGGCAGCAGTGGGGAATATTGGACAATGGGCGAAAGCCTGATCCA

GCGACGCCGCGTGAGTGAAGAAGTATTTCGGTATGTAAAGCTCTATCAGCAGGGAAGAAAATGACGGTACCTGACTA

AGAAGCCCCGGCTAACTACGTGCCAGCAGCCGCGGTAATACGTAGGGGGCAAGCGTTATCCGGATTTACTGGGTGTA

AAGGGAGCGTAGACGGTTTAGCAAGTCTGAAGTGAAAGCCCGGGGCTCAACCCCGGTACTGCTTTGGAAACTGTTAG

ACTTGAGTGCAGGAGAGGTAAGTGGAATTCCTAGTGTAGCGGTGAAATGCGTAGATATTAGGAGGAACACCAGTGGC

GAAGGCGGCTTACTGGACTGTAACTGACGTTGAGGCTCGAAAGCGTGGGGAGCAAACAGGATTAGATACCCTGGTAG

TCCACGCCGTAAACGATGAATACTAGGTGTCGGGGGGCAAAGCCCTTCGGTGCCGCCGCAAACGCAATAAGTATTCC

ACCTGGGGAGTACGTTCGCAAGAATGAAACTCAAAGGAATTGACGGGACCCGCACAAGCGGTGGAGCATGTGGTTT

AATTCGAAGCAACGCGAAGAACCTTACCAAGTCTTGACATCCCACTGAAAACACNTTAACCGTGATCCCTCTTCGGA

GCAGTGGAGACAGGTGGTGCATGGTTGTCGTCAGCTCGTGTCGTGAGATGTTGGGTTAAGTCCCGCAACGAGCGCAA

CCCTTATCCTTAGTAGCCAGCGAGTAGAGTCGGGCACTCTGGGGAGACTGCCAGGGATAACCTGGAGGAAGGTGGGG

ATGACGTCAAATCATCATGCCCCTTATGATTTGGGCTACACACGTGCTACAATGGCGTAAACAAAGGGAGGCAAAGG

AGCGATCTGGAGCAAACCCCAAAAATAACGTCTCAGTTCGGATTGCAGGCTGCAACTCGCCTGCATGAAGCTGGAAT

CGCTAGTAATCGCGAATCAGAATGTCGCGGTGAATACGTTCCCGGGTCTTGTACACACCGCCCGTCACACCATGGGA

GTTGGTAACGCCCGAAGTCAGTGACCCAACCGAAAGGAGGGAGCT
```

>SEQ ID NO: 106|NR_113270.1|*Blautia producta* strain JCM 1471 16S ribosomal RNA gene, partial sequence
```
AGAGTTTGATCCTGGCTCAGGATGAACGCTGGCGGCGTGCTTAACACATGCAAGTCGAGCGAAGCACTAAGACGGAT

TTCTTCGGATTGAAGTCTTTGTGACTGAGCGGCGGACGGGTGAGTAACGCGTGGGTAACCTGCCTCATACAGGGGGA

TAACAGTTAGAAATGACTGCTAATACCGCATAAGCGCACAGGACCGCATGGTCTGGTGTGAAAAACTCCGGTGGTAT

GAGATGGACCCGCGTCTGATTAGCTAGTTGGAGGGGTAACGGCCCACCAAGGCGACGATCAGTAGCCGGCCTGAGAG

GGTGAACGGCCACATTGGGACTGAGACACGGCCCAGACTCCTACGGGAGGCAGCAGTGGGGAATATTGCACAATGGG

GGAAACCCTGATGCAGCGACGCCGCGTGAAGGAAGAAGTATCTCGGTATGTAAACTTCTATCAGCAGGGAAGAAAT

GACGGTACCTGACTAAGAAGCCCCGGCTAACTACGTGCCAGCAGCCGCGGTAATACGTAGGGGGCAAGCGTTATCCG

GATTTACTGGGTGTAAAGGGAGCGTAGACGGAAGAGCAAGTCTGATGTGAAAGGCTGGGGCTTAACCCCAGGACTGC

ATTGGAAACTGTTGTTCTAGAGTGCCGGAGAGGTAAGCGGAATTCCTAGTGTAGCGGTGAAATGCGTAGATATTAGG

AGGAACACCAGTGGCGAAGGCGGCTTACTGGACGGTAACTGACGTTGAGGCTCGAAAGCGTGGGGAGCAAACAGGAT

TAGATACCCTGGTAGTCCACGCCGTAAACGATGAATACTAGGTGTCGGGTGGCAAAGCCATTCGGTGCCGCAGCAAA

CGCAATAAGTATTCCACCTGGGGAGTACGTTCGCAAGAATGAAACTCAAAGGAATTGACGGGACCCGCACAAGCGG

TGGAGCATGTGGTTTAATTCGAAGCAACGCGAAGAACCTTACCAAGTCTTGACATCCCTCTGACCGTCCCGTAACGG

GGACTTCCCTTCGGGGCAGAGGAGACAGGTGGTGCATGGTTGTCGTCAGCTCGTGTCGTGAGATGTTGGGTTAAGTC

CCGCAACGAGCGCAACCCTTATCCTTAGTAGCCAGCACATGATGGTGGGCACTCTAGGGAGACTGCCGGGGATAACC

CGGAGGAAGGCGGGGACGACGTCAAATCATCATGCCCCTTATGATTTGGGCTACACACGTGCTACAATGGCGTAAAC
```

AAAGGGAAGCGAGACAGCGATGTTGAGCGAATCCCAAAAATAACGTCCCAGTTCGGACTGCAGTCTGCAACTCGACT

GCACGAAGCTGGAATCGCTAGTAATCGCGGATCAGAATGCCGCGGTGAATACGTTCCCGGGTCTTGTACACACCGCC

CGTCACACCATGGGAGTCAGTAACGCCCGAAGTCAGTGACCTAACCGAAAGGAAGGAGCTGCCGAAGGCGGGACCGA

TAACTGGGGTGAAGTCGTAACAAGGTAACC

>SEQ ID NO: 107|NR_104799.1|*Anaerostipes hadrus* strain DSM 3319 16S
ribosomal RNA gene, partial sequence
TGGCTCAGGATGAACGCTGGCGGCGTGCTTAACACATGCAAGTCGAACGAAGCTGCTTAACTGATCTTCTTCGGAAT

TGACGTTTTGTAGACTGAGTGGCGGACGGGTGAGTAACGCGTGGGCAACCTGCCCTGTACAGGGGGATAACAGTCAG

AAATGACTGCTAATACCGCATAAGACCACAGCACCGCATGGTGCAGGGGTAAAAACTCCGGTGGTACAGGATGGACC

CGCGTCTGATTAGCTGGTTGGTGAGGTAACGGCTCACCAAGGCGACGATCAGTAGCCGGCTTGAGAGAGTGAACGGC

CACATTGGGACTGAGACACGGCCCAAACTCCTACGGGAGGCAGCAGTGGGGAATATTGCACAATGGGGGAAACCCTG

ATGCAGCGACGCCGCGTGAGTGAAGAAGTATCTCGGTATGTAAAGCTCTATCAGCAGGGAAGAAAATGACGGTACCT

GACTAAGAAGCCCCGGCTAACTACGTGCCAGCAGCCGCGGTAATACGTAGGGGGCAAGCGTTATCCGGAATTACTGG

GTGTAAAGGGTGCGTAGGTGGTATGGCAAGTCAGAAGTGAAAACCCAGGGCTTAACTCTGGGACTGCTTTTGAAACT

GTCAGACTGGAGTGCAGGAGAGGTAAGCGGAATTCCTAGTGTAGCGGTGAAATGCGTAGATATTAGGAGGAACATCA

GTGGCGAAGGCGGCTTACTGGACTGAAACTGACACTGAGGCACGAAAGCGTGGGGAGCAAACAGGATTAGATACCCT

GGTAGTCCACGCCGTAAACGATGAATACTAGGTGTCGGGGCCGTAGAGGCTTCGGTGCCGCAGCCAACGCAGTAAGT

ATTCCACCTGGGGAGTACGTTCGCAAGAATGAAACTCAAAGGAATTGACGGGGACCCGCACAAGCGGTGGAGCATGT

GGTTTAATTCGAAGCAACGCGAAGAACCTTACCTGGTCTTGACATCCTTCTGACCGGTCCTTAACCGGACCTTTCCT

TCGGGACAGGAGAGACAGGTGGTGCATGGTTGTCGTCAGCTCGTGTCGTGAGATGTTGGGTTAAGTCCCGCAACGAG

CGCAACCCCTATCTTTAGTAGCCAGCATTTCAGGTGGGCACTCTAGAGAGACTGCCAGGGATAACCTGGAGGAAGGT

GGGGACGACGTCAAATCATCATGCCCCTTATGACCAGGGCTACACACGTGCTACAATGGCGTAAACAGAGGGAAGCA

GCCTCGTGAGAGTGAGCAAATCCCAAAAATAACGTCTCAGTTCGGATTGTAGTCTGCAACTCGACTACATGAAGCTG

GAATCGCTAGTAATCGCGAATCAGAATGTCGCGGTGAATACGTTCCCGGGTCTTGTACACACCGCCCGTCACACCAT

GGGAGTCAGTAACGCCCGAAGTCAGTGACCCAACCGTAAGGAGGGAGCTGCCGAAGGCGGGACCGATAACTGGGTG

AAGTCGTAACAAGGTAGCCGTATCGGAAGGTGCGGCTGGATCACCTCCTTTC

>SEQ ID NO: 108|NR_117142.1|*Eubacterium fissicatena* strain DSM 3598 16S
ribosomal RNA gene, partial sequence
GTTTGATCCTGGCTCAGGATGAACGCTGGCGGCGTGCTTAACACATGCAAGTCGAGCGAAGCGCTTTACTTAGATTT

CTTCGGATTGAAGAGTTTTGCGACTGAGCGGCGGACGGGTGAGTAACGCGTGGGTAACCTGCCTCATACAGGGGGAT

AACAGTTAGAAATGACTGCTAATACCGCATAAGACCACAGTACCGCATGGTACAGTGGGAAAAACTCCGGTGGTATG

AGATGGACCCGCGTCTGATTAGCTAGTTGGTAAGGTAACGGCTTACCAAGGCAACGATCAGTAGCCGACCTGAGAGG

GTGACCGGCCACATTGGGACTGAGACACGGCCCAAACTCCTACGGGAGGCAGCAGTGGGGAATATTGCACAATGGG

GAAACCCTGATGCAGCGACGCCGCGTGAAGGATGAAGTATTTCGGTATGTAAACTTCTATCAGCAGGGAAGAAATG

ACGGTACCTGACTAAGAAGCCCCGGCTAACTACGTGCCAGCAGCCGCGGTAATACGTAGGGGGCAAGCGTTATCCGG

ATTTACTGGGTGTAAAGGGAGCGTAGACGGTTATGTAAGTCTGATGTGAAAACCCGGGGCTCAACCCCGGGACTGCA

TTGGAAACTATGTAACTAGAGTGTCGGAGAGGTAAGTGGAATTCCTAGTGTAGCGGTGAAATGCGTAGATATTAGGA

GGAACACCAGTGGCGAAGGCGGCTTACTGGACGATCACTGACGTTGAGGCTCGAAAGCGTGGGGAGCAAACAGGATT

AGATACCCTGGTAGTCCACGCCGTAAACGATGAATACTAGGTGTCGGGTGGCAAAGCCATTCGGTGCCGCAGCAAAC

GCAATAAGTATTCCACCTGGGGAGTACGTTCGCAAGAATGAAACTCAAAGGAATTGACGGGGACCCGCACAAGCGGT

GGAGCATGTGGTTTAATTCGAAGCAACGCGAAGAACCTTACCTGCTCTTGACATCCCACTGACCGGCGTGTAATGGC

GCCTTCCCTTCGGGGCAGTGGAGACAGGTGGTGCATGGTTGTCGTCAGCTCGTGTCGTGAGATGTTGGGTTAAGTCC

CGCAACGAGCGCAACCCTTATCTTTAGTAGCCAGCGGTTTGGCCGGGCACTCTAGAGACTGCCAGGGATAACCTG

GAGGAAGGTGGGGATGACGTCAAATCATCATGCCCCTTATGAGCAGGGCTACACACGTGCTACAATGGCGTAAACAA

AGGGAGGCAATACCGCGAGGTTGAGCAAATCCCAAAAATAACGTCTCAGTTCGGATTGTAGTCTGCAACTCGACTAC

ATGAAGCTGGAATCGCTAGTAATCGCGAATCAGAATGTCGCGGTGAATACGTTCCCGGGTCTTGTACACACCGCCCG

TCACACCATGGGAGTTGGTAACGCCCGAAGTCAGTGACCCAACCGTAAGGAGGGAGCTGCCGAAGGCGGGATCGATA

ACTGGGGTGAAGTCGTAACAAGGTAGCCGTATCGGAAGGTGCGGCTGGATCACCTCCTTT

>SEQ ID NO: 109|NR_117147.1|Eubacterium contortum strain DSM 3982 16S
ribosomal RNA gene, partial sequence
TTTGATCCTGGCTCAGGATGAACGCTGGCGACGTGCTTAACACATGCAAGTCGAGCGAAGCACTTTACTTTGATTTC

TTCGGAATGAAAGGTTTTGTGACTGAGCGGCGGACGGGTGAGTAACGCGTGGGTAACCTGCCTCATACAGGGGGATA

ACAGTTAGAAATGACTGCTAATACCGCATAAGACCACAGTACCGCATGGTACAGTGGGAAAAACTCCGGTGGTATGA

GATGGACCCGCGTCTGATTAGCTAGTTGGTAAGGTAACGGCTTACCAAGGCGACGATCAGTAGCCGACCTGAGAGGG

TGACCGGCCACATTGGGACTGAGACACGGCCCAAACTCCTACGGGAGGCAGCAGTGGGGAATATTGCACAATGGGGG

AAACCCTGATGCAGCGACGCCGCGTGAAGGATGAAGTATTTCGGTATGTAAACTTCTATCAGCAGGGAAGAAAATGA

CGGTACCTGACTAAGAAGCCCCGGCTAACTACGTGCCAGCAGCCGCGGTAATACGTAGGGGGCAAGCGTTATCCGGA

TTTACTGGGTGTAAAGGGAGCGTAGACGGTTATGTAAGTCTGATGTGAAAACCCGGGGCTCAACCCCGGGACTGCAT

TGGAAACTATGTAACTAGAGTGTCGGAGAGGTAAGTGGAATTCCTAGTGTAGCGGTGAAATGCGTAGATATTAGGAG

GAACACCAGTGGCGAAGGCGGCTTACTGGACGATGACTGACGTTGAGGCTCGAAAGCGTGGGGAGCAAACAGGATTA

GATACCCTGGTAGTCCACGCCGTAAACGATGAATACTAGGTGTCGGGTGGCAAAGCCATTCGGTGCCGCAGCAAACG

CAATAAGTATTCCACCTGGGGAGTACGTTCGCAAGAATGAAACTCAAAGGAATTGACGGGGACCCGCACAAGCGGTG

GAGCATGTGGTTTAATTCGAAGCAACGCGAAGAACCTTACCTGCTCTTGACATCCCCCTGACCGGCGTGTAATGGTG

CCTTTCCTTCGGGACAGGGGAGACAGGTGGTGCATGGTTGTCGTCAGCTCGTGTCGTGAGATGTTGGGTTAAGTCCC

GCAACGAGCGCAACCCTTATCTTTAGTAGCCAGCGGTTTGGCCGGGCACTCTAGAGAGACTGCCAGGGATAACCTGG

AGGAAGGTGGGGATGACGTCAAATCATCATGCCCCTTATGAGCAGGGCTACACACGTGCTACAATGGCGTAAACAAA

GGGAGGCGAAGCCGTGAGGTGGAGCAAATCCCAAAAATAACGTCTCAGTTCGGATTGTAGTCTGCAACTCGACTACA

TGAAGCTGGAATCGCTAGTAATCGCGAATCAGAATGTCGCGGTGAATACGTTCCCGGGTCTTGTACACACCGCCCGT

CACACCATGGGAGTTGGTAACGCCCGAAGTCAGTGACCCAACCGCAAGGAGGGAGCTGCCGAGGGTGGGACCGATAA

CTGGGGTGAAGTCGTAACAAGGTAGCCGTATCGGAAGGTGCGGCTGGATCACCTCCTTTCT

>SEQ ID NO: 110|NR_113410.1|Clostridium bolteae strain JCM 12243 16S
ribosomal RNA gene, partial sequence
TTTTAATTGACTGAGTGGCGGACGGGTGAGTAACGCGTGGATAACCTGCCTCACACTGGGGGATAACAGTTAGAAAT

GACTGCTAATACCGCATAAGCGCACAGTACCGCATGGTACAGTGTGAAAAACTCCGGTGGTGTGAGATGGATCCGCG

TCTGATTAGCCAGTTGGCGGGGTAACGGCCCACCAAAGCGACGATCAGTAGCCGACCTGAGAGGGTGACCGGCCACA

TTGGGACTGAGACACGGCCCAAACTCCTACGGGAGGCAGCAGTGGGGAATATTGCACAATGGGCGAAAGCCTGATGC

AGCGACGCCGCGTGAGTGAAGAAGTATTTCGGTATGTAAAGCTCTATCAGCAGGGAAGAAAATGACGGTACCTGACT

AAGAAGCCCCGGCTAACTACGTGCCAGCAGCCGCGGTAATACGTAGGGGGCAAGCGTTATCCGGATTTACTGGGTGT

AAAGGGAGCGTAGACGGCGAAGCAAGTCTGAAGTGAAAACCCAGGGCTCAACCCTGGGACTGCTTTGGAAACTGTTT

TGCTAGAGTGTCGGAGAGGTAAGTGGAATTCCTAGTGTAGCGGTGAAATGCGTAGATATTAGGAGGAACACCAGTGG

CGAAGGCGGCTTACTGGACGATAACTGACGTTGAGGCTCGAAAGCGTGGGGAGCAAACAGGATTAGATACCCTGGTA

GTCCACGCCGTAAACGATGAATGCTAGGTGTTGGGGGGCAAAGCCCTTCGGTGCCGTCGCAAACGCAGTAAGCATTC

CACCTGGGGAGTACGTTCGCAAGAATGAAACTCAAAGGAATTGACGGGGACCCGCACAAGCGGTGGAGCATGTGGTT

```
TAATTCGAAGCAACGCGAAGAACCTTACCAAGTCTTGACATCCTCTTGACCGGCGTGTAACGGCGCCTTCCCTTCGG

GGCAAGAGAGACAGGTGGTGCATGGTTGTCGTCAGCTCGTGTCGTGAGATGTTGGGTTAAGTCCCGCAACGAGCGCA

ACCCTTATCCTTAGTAGCCAGCAGGTAAAGCTGGGCACTCTAGGGAGACTGCCAGGGATAACCTGGAGGAAGGTGGG

GATGACGTCAAATCATCATGCCCCTTATGATTTGGGCTACACACGTGCTACAATGGCGTAAACAAAGGGAAGCAAGA

CAGTGATGTGGAGCAAATCCCAAAAATAACGTCCCAGTTCGGACTGTAGTCTGCAACCCGACTACACGAAGCTGGAA

TCGCTAGTAATCGCGAATCAGAATGTCGCGGTGAATACGTTCCCGGGTCTTGTACACACCGCCCGTCACACCATGGG

AGTCAGCAACGCCCGAAGTCAGTGACCCAACTCGCAAGAGAGGGAGCTGCCGAAGGCGGGGCAGGTAACTGGGGTGA

AGTC
```

>SEQ ID NO: 111|NR_041960.1|Blautia luti strain BInIX 16S ribosomal RNA
gene, complete sequence

```
GTGGGTAACCTGCCTTATACAGGGGGATAACAGTCAGAAATGACTGCTAATACCGCATAAGCGCACAGAGCTGCATG

GCTCCGGTGTGAAAAACTCCGGTGGTATAAGATGGACCCGCGTTGGATTAGCTAGTTGGTGAGGTAACGGCCCACCA

AGGCGACGATCCATAGCCGGCCTGAGAGGGTGAACGGCCACATTGGGACTGAGACACGGCCCAGACTCCTACGGGAG

GCAGCAGTGGGGAATATTGCACAATGGGGGAAACCCTGATGCAGCGACGCCGCGTGAAGGAAGAAGTATCTCGGTAT

GTAAACTTCTATCAGCAGGGAAGAAAATGACGGTACCTGACTAAGAAGCCCCGGCTAACTACGTGCCAGCAGCCGCG

GTAATACGTAGGGGGCAAGCGTTATCCGGATTTACTGGGTGTAAAGGGAGCGTAGACGGCATGGACAAGTCTGATGT

GAAAGGCTGGGGCTCAACCCCGGGACTGCATTGGAAACTGCCCGTCTTGAGTGCCGGAGAGGTAAGCGGAATTCCTA

GTGTAGCGGTGAAATGCGTAGATATTAGGAGGAACACCAGTGGCGAAGGCGGCTTACTGGACGGTAACTGACGTTGA

GGCTCGAAAGCGTGGGGAGCAAACAGGATTAGATACCCTGGTAGTCCACGCCGTAAACGATGAATCCTAGGTGTCGG

GGAGCAAANNNNTTCGGTGCCGCCGCAAACGCATTAAGCATTCCACCTGGGGAGTACGTTCGCAAGAATGAAACTCA

AAGGAATTGACGGGGACCCGCACAAGCGGTGGAGCATGTGGTTTAATTCGAAGCAACGCGAAGAACCTTACCAAGTC

TTGACATCCCTCTGACCGAGTATGTATGGTACTTTTCCTTCGGGAGAGAGAGGAGACAGGTGGTGCATGGTTGTCGT

CAGCTCGTGTCGTGAGATGTTGGGTTAAGTCCCGCAACGAGCGCAACCCCTATCCCCAGTAGCCAGCGGTTCGGCCG

GGCACTCTGAGGAGACTGCCAGGGATAACCTGGAGGAAGGCGGGGATGACGTCAAATCATCATGCCCCTTATGATTT

GGGCTACACACGTGCTACAATGGCGTAAACAAAGGGAAGCAAGCCTGCGAGGGTGGGCAAATCCCAAAAATAACGTC

CCAGTTCGGACTGTAGTCTGCAACCCGACTACACGAAGCTGGAATCGCTAGTAATCGCGGATCAGAATGCCGCGGTG

AATACGTTCCCGGGTCTTGTACACACCGCCCGTCACACCATGGGAGTCAGTAACGCCCGAAGTCAGTGACCTAACT
```

>SEQ ID NO: 112|NR_074306.1|Acidaminococcus intestini RyC-MR95 strain
RyC-MR95 16S ribosomal RNA, complete sequence

```
CTGGCGGCGTGCTTAACACATGCAAGTCGAACGGAGAACTTATTTCGGTAAGTTCTTAGTGGCGAACGGGTGAGTAA

CGCGTGGGCAACCTGCCCTCCAGTTGGGGACAACATTCCGAAAGGGATGCTAATACCGAATGTCCTCCCTCCTCCGC

ATGGAGGAGGGAGGAAAGATGGCCTCTGCTTGCAAGCTATCGCTGGAAGATGGGCCCGCGTCTGATTAGCTAGTTGG

TGGGGTAACGGCTCACCAAGGCGATGATCAGTAGCCGGTCTGAGAGGATGAACGGCCACATTGGGACTGAGACACGG

CCCAAACTCCTACGGGAGGCAGCAGTGGGGAATCTTCCGCAATGGACGAAAGTCTGACGGAGCAACGCCGCGTGAGT

GATGAAGGTCTTCGGATTGTAAAACTCTGTTGTTAGGGACGAAAGCACCGTGTTCGAACAGGTCATGGTGTTGACGG

TACCTAACGAGGAAGCCACGGCTAACTACGTGCCAGCAGCCGCGGTAATACGTAGGTGGCAAGCGTTGTCCGGAATT

ATTGGGCGTAAAGAGCATGTAGGCGGGCTTTTAAGTCTGACGTGAAAATGCGGGGCTTAACCCCGTATGGCGTTGGA

TACTGGAAGTCTTGAGTGCAGGAGAGGAAAGGGGAATTCCCAGTGTAGCGGTGAAATGCGTAGATATTGGGAGGAAC

ACCAGTGGCGAAGGCGCCTTTCTGGACTGTGTCTGACGCTGAGATGCGAAAGCCAGGGTAGCAAACGGGATTAGATA

CCCCGGTAGTCCTGGCCGTAAACGATGGATACTAGGTGTAGGAGGTATCGACCCCTTCTGTGCCGGAGTTAACGCAA

TAAGTATCCCGCCTGGGGACTACGATCGCAAGATTGAAACTCAAAGGAATTGACGGGGGCCCGCACAAGCGGTGGAG

TATGTGGTTTAATTCGACGCAACGCGAAGAACCTTACCAAGGCTTGACATTGAGTGAAAGACCTAGAGATAGGTCCC
```

TCCCTTCGGGGACACGAAAACAGGTGGTGCATGGCTGTCGTCAGCTCGTGTCGTGAGATGTTGGGTTAAGTCCCGCA

ACGAGCGCAACCCCTATCCTATGTTACCAGCGCGTAAAGGCGGGGACTCATAGGAGACTGCCAGGGATAACTTGGAG

GAAGGCGGGGATGACGTCAAGTCATCATGCCCCTTATGTCTTGGGCTACACACGTACTACAATGGTCGGCAACAAAG

GGCAGCGAAACCGCGAGGTGGAGCAAATCCCAGAAACCCGACCCCAGTTCGGATCGTAGGCTGCAACCCGCCTACGT

GAAGTTGGAATCGCTAGTAATCGCAGGTCAGCATACTGCGGTGAATACGTTCCCGGGCCTTGTACACACCGCCCGTC

ACACCACGAAAGTTGGTAACACCCGAAGCCGGTGAGATAACCTTTTAGGAGTCAGCTGTCTAAGGTGGGGCCGATGA

TTGGGGTGAAGTCGTAACAAGGTAGC

>SEQ ID NO: 113|NR_074399.1|*Ruminococcus albus* strain 7 16S ribosomal RNA
gene, complete sequence
AGAGTTTGATCCTGGCTCAGGACGAACGCTGGCGGCACGCTTAACACATGCAAGTCGAACGAGCGAAAGAGTGCTTG

CACTCTCTAGCTAGTGGCGGACGGGTGAGTAACACGTGAGCAATCTGCCTTTCGGAGAGGGATACCAATTGGAAACG

ATTGTTAATACCTCATAACATAACGAAGCCGCATGACTTTGTTATCAAATGAATTTCGCCGAAAGATGAGCTCGCGT

CTGATTAGGTAGTTGGTGAGGTAACGGCCCACCAAGCCGACGATCAGTAGCCGGACTGAGAGGTTGAACGGCCACAT

TGGGACTGAGACACGGCCCAGACTCCTACGGGAGGCAGCAGTGGGGAATATTGCACAATGGGCGAAAGCCTGATGCA

GCGATGCCGCGTGAGGGAAGAAGGTTTTAGGATTGTAAACCTCTGTCTTTGGGGACGATAATGACGGTACCCAAGGA

GGAAGCTCCGGCTAACTACGTGCCAGCAGCCGCGGTAATACGTAGGGAGCGAGCGTTGTCCGGAATTACTGGGTGTA

AAGGGAGCGTAGGCGGGATTGCAAGTCAGGTGTGAAATTTAGGGGCTTAACCCCTGAACTGCACTTGAAACTGTAGT

TCTTGAGTGAAGTAGAGGTAAGCGGAATTCCTAGTGTAGCGGTGAAATGCGTAGATATTAGGAGGAACATCAGTGGC

GAAGGCGGCTTACTGGGCTTTAACTGACGCTGAGGCTCGAAAGCGTGGGGAGCAAACAGGATTAGATACCCTGGTAG

TCCACGCCGTAAACGATGATTACTAGGTGTGGGGGACTGACCCCTTCCGTGCCGCAGTTAACACAATAAGTAATCC

ACCTGGGGAGTACGGCCGCAAGGCTGAAACTCAAAGGAATTGACGGGGACCCGCACAAGCAGTGGAGTATGTGGTTT

AATTCGAAGCAACGCGAAGAACCTTACCAGGTCTTGACATCGTACGCATAGCATAGAGATATGTGAAATCCCTTCGG

GGACGTATAGACAGGTGGTGCATGGTTGTCGTCAGCTCGTGTCGTGAGATGTTGGGTTAAGTCCCGCAACGAGCGC

AACCCTTACTGTTAGTTGCTACGCAAGAGCACTCTAGCAGGACTGCCGTTGACAAAACGGAGGAAGGTGGGGATGAC

GTCAAATCATCATGCCCCTTATGACCTGGGCTACACACGTACTACAATGGCTGTTAACAGAGGGAAGCAAAACAGTG

ATGTGGAGCAAAACCCTAAAAGCAGTCTTAGTTCGGATTGTAGGCTGCAACCCGCCTACATGAAGTCGGAATTGCTA

GTAATCGCGGATCAGCATGCCGCGGTGAATACGTTCCCGGGCCTTGTACACACCGCCCGTCACGCCATGGGAGTCGG

TAACACCCGAAGCCTGTGTTCTAACCGCAAGGAGGAAGCAGTCGAAGGTGGGATTGATGACTGGGGTGAAGTCGTAA

CAAGGTAGCCGTATCGGAAGGTGCGGCTGGATCACCT

>SEQ ID NO: 114|NR_074634.1|*Eubacterium rectale* strain ATCC 33656 16S
ribosomal RNA gene, complete sequence
AGAGTTTGATCCTGGCTCAGGATGAACGCTGGCGGCGTGCTTAACACATGCAAGTCGAACGAAGCACTTTATTTGAT

TTCCTTCGGGACTGATTATTTTGTGACTGAGTGGCGGACGGGTGAGTAACGCGTGGGTAACCTGCCTTGTACAGGGG

GATAACAGTTGGAAACGGCTGCTAATACCGCATAAGCGCACGGCATCGCATGATGCAGTGTGAAAAACTCCGGTGGT

ATAAGATGGACCCGCGTTGGATTAGCTAGTTGGTGAGGTAACGGCCCACCAAGGCGACGATCCATAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGCGAAGAAGTATTTCGGTATGTAAAGCTCTATCAGCAGGGAAGATA

ATGACGGTACCTGACTAAGAAGCACCGGCTAAATACGTGCCAGCAGCCGCGGTAATACGTATGGTGCAAGCGTTATC

CGGATTTACTGGGTGTAAAGGGAGCGCAGGCGGTGCGGCAAGTCTGATGTGAAAGCCCGGGGCTCAACCCCGGTACT

GCATTGGAAACTGTCGTACTAGAGTGTCGGAGGGGTAAGCGGAATTCCTAGTGTAGCGGTGAAATGCGTAGATATTA

GGAGGAACACCAGTGGCGAAGGCGGCTTACTGGACGATAACTGACGCTGAGGCTCGAAAGCGTGGGGAGCAAACAGG

ATTAGATACCCTGGTAGTCCACGCCGTAAACGATGAATACTAGGTGTTGGGAAGCATTGCTTCTCGGTGCCGTCGCA

AACGCAGTAAGTATTCCACCTGGGGAGTACGTTCGCAAGAATGAAACTCAAAGGAATTGACGGGGACCCGCACAAGC

GGTGGAGCATGTGGTTTAATTCGAAGCAACGCGAAGAACCTTACCAAGTCTTGACATCCTTCTGACCGGTACTTAAC

CGTACCTTCTCTTCGGAGCAGGAGTGACAGGTGGTGCATGGTTGTCGTCAGCTCGTGTCGTGAGATGTTGGGTTAAG

TCCCGCAACGAGCGCAACCCTTATCTTTAGTAGCCAGCGGTTCGGCCGGGCACTCTAGAGAGACTGCCAGGGATAAC

CTGGAGGAAGGCGGGGATGACGTCAAATCATCATGCCCCTTATGACTTGGGCTACACACGTGCTACAATGGCGTAAA

CAAAGGGAAGCAAAGCTGTGAAGCCGAGCAAATCTCAAAAATAACGTCTCAGTTCGGACTGTAGTCTGCAACCCGAC

TACACGAAGCTGGAATCGCTAGTAATCGCAGATCAGAATGCTGCGGTGAATACGTTCCCGGGTCTTGTACACACCGC

CCGTCACACCATGGGAGTTGGGAATGCCCGAAGCCAGTGACCTAACCGAAAGGAAGGAGCTGTCGAAGGCAGGCTCG

ATAACTGGGGTGAAGTCGTAACAAGGTAGCCGTATCGGAAGGTGCGGCTGGATCACCT

>SEQ ID NO: 115|NR_074928.1|Acidaminococcus fermentans strain DSM 20731 16S
ribosomal RNA gene, complete sequence
AGAGTTTGATCCTGGCTCAGGACGAACGCTGGCGGCGTGCTTAACACATGCAAGTCGAACGGAGAACTTTCTTCGGA

ATGTTCTTAGTGGCGAACGGGTGAGTAACGCGTAGGCAACCTGCCCTCTGGTTGGGGACAACATTCCGAAAGGGATG

CTAATACCGAATGAGATCCTCTTTCCGCATGGAGAGAGGATGAAAGATGGCCTCTACTTGTAAGCTATCGCCAGAAG

ATGGGCCTGCGTCTGATTAGCTAGTAGGTGAGGTAACGGCTCACCTAGGCGATGATCAGTAGCCGGTCTGAGAGGAT

GAACGGCCACATTGGGACTGAGACACGGCCCAAACTCCTACGGGAGGCAGCAGTGGGGAATCTTCCGCAATGGACGA

AAGTCTGACGGAGCAACGCCGCGTGAGTGATGAAGGCCTTCGGGTTGTAAAACTCTGTTGTCAGGGACGAAAGCACC

GATCTATAATACATTTTGGTGTTGACGGTACCTGACGAGGAAGCCACGGCTAACTACGTGCCAGCAGCCGCGGTAAT

ACGTAGGTGGCAAGCGTTGTCCGGAATTATTGGGCGTAAAGAGCATGTAGGCGGCTTTTAAGTCCGACGTGAAAAT

GCGGGGCTTAACCCCGTATGGCGTTGGATACTGGAAGTCTTGAGTGCAGGAGAGGAAAGGGGAATTCCCAGTGTAGC

GGTGAAATGCGTAGATATTGGGAGGAACACCAGTGGCGAAGGCGCCTTTCTGGACTGTGTCTGACGCTGAGATGCGA

AAGCCAGGGTAGCAAACGGGATTAGATACCCCGGTAGTCCTGGCCGTAAACGATGGGTACTAGGTGTAGGAGGTATC

GACCCCTTCTGTGCCGGAGTTAACGCAATAAGTACCCCGCCTGGGGACTACGATCGCAAGATTGAAACTCAAAGGAA

TTGACGGGGCCCGCACAAGCGGTGGAGTATGTGGTTTAATTCGACGCAACGCGAAGAACCTTACCAAGGCTTGACA

TTGAGTGAAAGACCCAGAGATGGGTCCCCTTCTTCGGAAGCACGAAAACAGGTGGTGCATGGCTGTCGTCAGCTCGT

GTCGTGAGATGTTGGGTTAAGTCCCGCAACGAGCGCAACCCTTATCCTATGTTACCAGCACGTAATGGTGGGGACTC

ATAGGAGACTGCCAGGGATAACCTGGAGGAAGGCGGGGATGACGTCAAGTCATCATGCCCCTTATGTCTTGGGCTAC

ACACGTACTACAATGGTCGGCAACAAAGGGCAGCGAAGCCGCGAGGCGGAGCCAATCCCAGAAACCCGACCCCAGTT

CGGATCGCAGGCTGCAACCCGCCTGCGTGAAGTTGGAATCGCTAGTAATCGCAGGTCAGCATACTGCGGTGAATACG

TTCCCGGGCCTTGTACACACCGCCCGTCACACCACGAAAGTTGGTAACACCCGAAGCCGGTGAGATAACCTTTTAGG

AGTCAGCTGTCTAAGGTGGGGCCGATGATTGGGGTGAAGTCGTAACAAGGTAGCCGTTCGAGAACGAGCGGCTGGAT

CACCT

>SEQ ID NO: 116|NR_114326.1|Fusicatenibacter saccharivorans strain HT03-11
16S ribosomal RNA gene, partial sequence
TGGCTCAGGATGAACGCTGGCGGCGTGCTTAACACATGCAAGTCGAGCGAAGCAGTTAAGAAGATTYTTCGGATGAT

TCTTGACTGACTGAGCGGCGGACGGGTGAGTAACGCGTGGGTGACCTGCCCCATACCGGGGGATAACAGCTGGAAAC

GGCTGCTAATACCGCATAAGCGCACAGAGCTGCATGGCTCGGTGTGAAAAACTCCGGTGGTATGGGATGGGCCCGCG

TCTGATTAGGCAGTTGGCGGGGTAACGGCCCACCAAACCGACGATCAGTAGCCGGCCTGAGAGGGCGACCGGCCACA

TTGGGACTGAGACACGGCCCAAACTCCTACGGGAGGCAGCAGTGGGGAATATTGCACAATGGGGGAAACCCTGATGC

AGCGACGCCGCGTGAGCGAAGAAGTATTTCGGTATGTAAAGCTCTATCAGCAGGGAAGATAATGACGGTACCTGACT

AAGAAGCCCCGGCTAACTACGTGCCAGCAGCCGCGGTAATACGTAGGGGGCAAGCGTTATCCGGATTTACTGGGTGT

AAAGGGAGCGTAGACGGCAAGGCAAGTCTGATGTGAAAACCCAGGGCTTAACCCTGGGACTGCATTGGAAACTGTCT

GGCTCGAGTGCCGGAGAGGTAAGCGGAATTCCTAGTGTAGCGGTGAAATGCGTAGATATTAGGAAGAACACCAGTGG

CGAAGGCGGCTTACTGGACGGTAACTGACGTTGAGGCTCGAAAGCGTGGGGAGCAAACAGGATTAGATACCCTGGTA

GTCCACGCCGTAAACGATGAATGCTAGGTGTTGGGGAGCAAAGCTCTTCGGTGCCGCCGCAAACGCATTAAGCATTC

CACCTGGGGAGTACGTTCGCAAGAATGAAACTCAAAGGAATTGACGGGGACCCGCACAAGCGGTGGAGCATGTGGTT

TAATTCGAAGCAACGCGAAGAACCTTACCAGGTCTTGACATCCCGATGACCGGCCCGTAACGGGCCTTCTCTTCGG

AGCATTGGAGACAGGTGGTGCATGGTTGTCGTCAGCTCGTGTCGTGAGATGTTGGGTTAAGTCCCGCAACGAGCGCA

ACCCTTATCCTCAGTAGCCAGCAGGTAAAGCTGGGCACTCTGTGGAGACTGCCAGGGATAACCTGGAGGAAGGTGGG

GATGACGTCAAATCATCATGCCCCTTATGATCTGGGCTACACACGTGCTACAATGGCGTAAACAAAGGGAGGCAAAG

CCGCGAGGTGGAGCAAATCCCAAAAATAACGTCTCAGTTCGGACTGCAGTCTGCAACTCGACTGCACGAAGCTGGAA

TCGCTAGTAATCGCGAATCAGAATGTCGCGGTGAATACGTTCCCGGGTCTTGTACACACCGCCCGTCACACCATGGG

AGTTGGTAACGCCCGAAGTCAGTGACCCAACCTTTTA

>SEQ ID NO: 117|NR_102884.1|Ruminococcus champanellensis strain 18P13 16S
ribosomal RNA gene, complete sequence
AGAGTTTGATCCTGGCTCAGGACGAACGCTGGCGGCACGCCTAACACATGCAAGTCGAACGGAGATAAAGACTTCGG

TTTTTATCTTAGTGGCGGACGGGTGAGTAACACGTGAGCAACCTGCCTCTGAGAGAGGGATAGCTTCTGGAAACGGA

TGGTAATACCTCATAACATAGCGGTACCGCATGATACTGCTATCAAAGATTTATCGCTCAGAGATGGGCTCGCGTCT

GATTAGCTAGATGGTGAGGTAACGGCTCACCATGGCGACGATCAGTAGCCGGACTGAGAGGTTGAACGGCCACATTG

GGACTGAGACACGGCCCAGACTCCTACGGGAGGCAGCAGTGGGGAATATTGCACAATGGGCGCAAGCCTGATGCAGC

GATGCCGCGTGGAGGAAGAAGGTTTTCGGATTGTAAACTCCTGTCTTAAGGGACGATAATGACGGTACCTTAGGAGG

AAGCTCCGGCTAACTACGTGCCAGCAGCCGCGGTAATACGTAGGGAGCGAGCGTTGTCCGGAATTACTGGGTGTAAA

GGGAGCGTAGGCGGGATTGCAAGTCAGATGTGAAAACTATGGGCTTAACCCATAGACTGCATTTGAAACTGTAGTTC

TTGAGTGAAGTAGAGGTAAGCGGAATTCCTAGTGTAGCGGTGAAATGCGTAGATATTAGGAGGAACATCGGTGGCGA

AGGCGGCTTACTGGGCTTTTACTGACGCTGAGGCTCGAAAGCGTGGGGAGCAAACAGGATTAGATACCCTGGTAGTC

CACGCTGTAAACGATGATTACTAGGTGTGGGGGGACTGACCCCTTCCGTGCCGCAGTTAACACAATAAGTAATCCAC

CTGGGGAGTACGGCCGCAAGGTTGAAACTCAAAGGAATTGACGGGGGCCCGCACAAGCAGTGGAGTATGTGGTTTAA

TTCGAAGCAACGCGAAAAACCTTACCAGGTCTTGACATCGAGTGAATGATCTAGAGATAGATCAGTCCTTCGGGACA

CAAAGACAGGTGGTGCATGGTTGTCGTCAGCTCGTGTCGTGAGATGTTGGGTTAAGTCCCGCAACGAGCGCAACCCT

TACCTTTAGTTGCTACGCAAGAGCACTCTAGAGGGACTGCCGTTGACAAAACGGAGGAAGGTGGGGATGACGTCAAA

TCATCATGCCCCTTATGACCTGGGCTACACACGTACTACAATGGCAATGAACAGAGGGAAGCAATACAGTGATGTGG

AGCAAATCCCCAAAATTGTCCCAGTTCAGATTGTAGGCTGCAACTCGCCTACATGAAGTCGGAATTGCTAGTAATC

GCAGATCAGCATGCTGCGGTGAATACGTTCCCGGGCCTTGTACACACCGCCCGTCACACCATGGGAGTCGGTAACAC

CCGAAGCCAGTAGCCTAACCGCAAGGAGGGCGCTGTCGAAGGTGGGATTGATGACTGGGGTGAAGTCGTAACAAGGT

AGCCGTATCGGAAGGTGCGGCTGGATCACCT

>SEQ ID NO: 118|NR_102971.1|Bifidobacterium bifidum S17 strain S17 16S
ribosomal RNA, complete sequence
TTTTTGTGGAGGGTTCGATTCTGGCTCAGGATGAACGCTGGCGGCGTGCTTAACACATGCAAGTCGAACGGGATCCA

TCGGGCTTTGCTTGGTGGTGAGAGTGGCGAACGGGTGAGTAATGCGTGACCGACCTGCCCCATGCTCCGGAATAGCT

CCTGGAAACGGGTGGTAATGCCGGATGTTCCACATGATCGCATGTGATTGTGGGAAAGATTCTATCGGCGTGGGATG

GGGTCGCGTCCTATCAGCTTGTTGGTGAGGTAACGGCTCACCAAGGCTTCGACGGGTAGCCGGCCTGAGAGGGCGAC

CGGCCACATTGGGACTGAGATACGGCCCAGACTCCTACGGGAGGCAGCAGTGGGGAATATTGCACAATGGGCGCAAG

CCTGATGCAGCGACGCCGCGTGAGGGATGGAGGCCTTCGGGTTGTAAACCTCTTTTGTTTGGGAGCAAGCCTTCGGG

TGAGTGTACCTTTCGAATAAGCGCCGGCTAACTACGTGCCAGCAGCCGCGGTAATACGTAGGGCGCAAGCGTTATCC

GGATTTATTGGGCGTAAAGGGCTCGTAGGCGGCTCGTCGCGTCCGGTGTGAAAGTCCATCGCTTAACGTGGATCTG

CGCCGGGTACGGGCGGGCTGGAGTGCGGTAGGGGAGACTGGAATTCCCGGTGTAACGGTGGAATGTGTAGATATCGG

GAAGAACACCGATGGCGAAGGCAGGTCTCTGGGCCGTCACTGACGCTGAGGAGCGAAAGCGTGGGGAGCGAACAGGA

TTAGATACCCTGGTAGTCCACGCCGTAAACGGTGGACGCTGGATGTGGGGCACGTTCCACGTGTTCCGTGTCGGAGC

TAACGCGTTAAGCGTCCCGCCTGGGGAGTACGGCCGCAAGGCTAAAACTCAAAGAAATTGACGGGGGCCCGCACAAG

CGGCGGAGCATGCGGATTAATTCGATGCAACGCGAAGAACCTTACCTGGGCTTGACATGTTCCCGACGACGCCAGAG

ATGGCGTTTCCCTTCGGGGCGGGTTCACAGGTGGTGCATGGTCGTCGTCAGCTCGTGTCGTGAGATGTTGGGTTAAG

TCCCGCAACGAGCGCAACCCTCGCCCCGTGTTGCCAGCACGTTATGGTGGGAACTCACGGGGGACCGCCGGGGTTAA

CTCGGAGGAAGGTGGGGATGACGTCAGATCATCATGCCCCTTACGTCCAGGGCTTCACGCATGCTACAATGGCCGGT

ACAGCGGGATGCGACATGGCGACATGGAGCGGATCCCTGAAAACCGGTCTCAGTTCGGATCGGAGCCTGCAACCCGG

CTCCGTGAAGGCGGAGTCGCTAGTAATCGCGGATCAGCAACGCCGCGGTGAATGCGTTCCCGGGCCTTGTACACACC

GCCCGTCAAGTCATGAAAGTGGGCAGCACCCGAAGCCGGTGGCCTAACCCCTTGTGGGATGGAGCCGTCTAAGGTGA

GGCTCGTGATTGGGACTAAGTCGTAACAAGGTAGCCGTACCGGAAGGTGCGGCTGGATCACCTCCTTTCT

>SEQ ID NO: 119|NR_102980.1|*Megasphaera elsdenii* strain DSM 20460 16S
ribosomal RNA gene, complete sequence
AGAGTTTGATCCTGGCTCAGGACGAACGCTGGCGGCGTGCTTAACACATGCAAGTCGAACGAGAAGAGATGAGAAGC

TTGCTTCTTATCAATTCGAGTGGCAAACGGGTGAGTAACGCGTAAGCAACCTGCCCTTCAGATGGGGACAACAGCTG

GAAACGGCTGCTAATACCGAATACGTTCTTTTTGTCGCATGGCAGAGGGAAGAAAGGGAGGCTCTTCGGAGCTTTCG

CTGAAGGAGGGGCTTGCGTCTGATTAGCTAGTTGGAGGGGTAACGGCCCACCAAGGCGACGATCAGTAGCCGGTCTG

AGAGGATGAACGGCCACATTGGGACTGAGACACGGCCCAGACTCCTACGGGAGGCAGCAGTGGGGAATCTTCCGCAA

TGGACGAAAGTCTGACGGAGCAACGCCGCGTGAACGATGACGGCCTTCGGGTTGTAAAGTTCTGTTATACGGGACGA

ATGGCGTAGCGGTCAATACCCGTTACGAGTGACGGTACCGTAAGAGAAAGCCACGGCTAACTACGTGCCAGCAGCCG

CGGTAATACGTAGGTGGCAAGCGTTGTCCGGAATTATTGGGCGTAAAGGGCGCGCAGGCGGCGTCGTAAGTCGGTCT

TAAAAGTGCGGGGCTTAACCCCGTGAGGGGACCGAAACTGCGATGCTAGAGTATCGGAGAGGAAAGCGGAATTCCTA

GTGTAGCGGTGAAATGCGTAGATATTAGGAGGAACACCAGTGGCGAAAGCGGCTTTCTGGACGACAACTGACGCTGA

GGCGCGAAAGCCAGGGGAGCAAACGGGATTAGATACCCCGGTAGTCCTGGCCGTAAACGATGGATACTAGGTGTAGG

AGGTATCGACCCCTTCTGTGCCGGAGTTAACGCAATAAGTATCCCGCCTGGGGAGTACGGCCGCAAGGCTGAAACTC

AAAGGAATTGACGGGGGCCCGCACAAGCGGTGGAGTATGTGGTTTAATTCGACGCAACGCGAAGAACCTTACCAAGC

CTTGACATTGATTGCTATGGATAGAGATATCCAGTTCCTCTTCGGAGGACAAGAAAACAGGTGGTGCACGGCTGTCG

TCAGCTCGTGTCGTGAGATGTTGGGTTAAGTCCCGCAACGAGCGCAACCCCTATCTTCTGTTACCAGCGGTTCGGCC

GGGGACTCAGGAGAGACTGCCGCAGACAATGCGGAGGAAGGCGGGGATGACGTCAAGTCATCATGCCCCTTATGGCT

TGGGCTACACACGTACTACAATGGCTCTTAATAGAGGGAAGCGAAGGAGCGATCCGGAGCAAACCCCAAAAACAGAG

TCCCAGTTCGGATTGCAGGCTGCAACTCGCCTGCATGAAGCAGGAATCGCTAGTAATCGCAGGTCAGCATACTGCGG

TGAATACGTTCCCGGGCCTTGTACACACCGCCCGTCACACCACGAAAGTCATTCACACCCGAAGCCGGTGAGGTAAC

CTTTTGGAGCCAGCCGTCGAAGGTGGGGGCGATGATTGGGGTGAAGTCGTAACAAGGTAGCCGTATCGGAAGGTGCG

GCTGGATCACCT

>SEQ ID NO: 120|NR_044645.2|*Dorea formicigenerans* strain ATCC 27755 16S
ribosomal RNA gene, complete sequence
TTAAACGAGAGTTTGATCCTGGCTCAGGATGAACGCTGGCGGCGTGCTTAACACATGCAAGTCGAGCGAAGCACATA

AGTTTGATTCTTCGGATGAAGACTTTTGTGACTGAGCGGCGGACGNNNGAGTAACGCGTGGGTAACCTGCCTCATAC

AGGGGGATAACAGYTAGAAATGGCTGCTAATACCGCATAAGACCACAGTACTGCATGGTACAGTGNNNAAAACTCCG

GTGGTATGAGATGGACCCGCGTCTGATTAGGTAGTTGGTGAGGTAACGGCCCACCNAGCCGACGATCAGTAGCCGAC

CTGAGAGGGTGACCGGCCACATTGGGACTGAGACACGGCCNNGACTCCTACGGGAGGCAGCAGTGGGGAATATTGCA

CAATGGGCGAAAGCCTGATGCAGCGACGCCGCGTGAAGGATGAAGTATTTCGGTATGTAAACTTCTATCAGCAGGGA

AGAAAATGACGGTACCTGACTAAGAAGCCCCGGCTAACTACGTGCCAGCAGCCGNGGTAATACGTAGGGGGNNAGCG

TTATCCGGATTTACTGGGTGTAAAGGGAGCGTAGACGGCTGTGCAAGTCTGAAGTGAAAGGCATGGGCTCAACCTGT

GGACTGCTTTGGAAACTGTGCAGCTAGAGTGTCGGAGAGGTAAGTGGAATTCCTAGTGTAGCGGTGAAATGCGTAGA

TATTAGGAGGAACACCAGTGGCGAAGGCGGCNTACTGGACGATGACTGACGTTGAGGCTCGAAAGCGTGGGGAGCAA

ACAGGATTAGATACCCTGGTAGTCCACGCCGTAAACGATGACTGCTAGGTGTCGGGTAGCAAAGCTATTCGGTGCCG

CAGCTAACGCAATAAGCAGTCCACCTGGGGAGTACGTTCGCAAGAATGAAACTCAAAGGAATTGACGGGGNCCNGCA

CAAGCGGTGGAGCATGTGGTTTAATTCGAANNAACGCGAAGAACCTTACCTGATCTTGACATCCCGATGACCGCTTC

GTAATGGAAGYTTTTCTTCGGAACATCGGTGACAGGTGGTGCATGGTTGTCGTCAGCTCGTGTCGTGAGATGTTGGG

TTAAGTCCCGCAACGAGCGCAACCCTTATCTTCAGTAGCCAGCATTTAGGATGGGCACTCTGGAGAGACTGCCAGGG

ATAACCTGGAGGAAGGTGGGGATGACGTNNAATCATCATGCCCCTTATGACCAGGGCTACACACGTGCTACAATGGC

GTAAACAGAGGGAGGCAGAGCCGCGAGGCCGAGCAAATCTCAAAAATAACGTCTCAGTTCGGATTGTAGTCTGCAAC

TCGACTACATGAAGCTGGAATCGCTAGTAATCGCAGATCAGAATGCTGCGGTGAATACGTTCCCGGGTCTTGTACAC

ACCGCCCGTCACACCATGGGAGTCAGTAACGCCCGAAGTCAGTGACCCAACCGAAAGGAGGGAGCTGCCGAAGGTGG

GACCGATAACTGGGGT

>SEQ ID NO: 121|NR_118643.1|*Eisenbergiella tayi* strain B086562 16S ribosomal
RNA gene, partial sequence
GGTATAACTTAGTGGCGGACGGGTGAGTAACGCGTGGGAAACCTGCCCTGTACCGGGGATAACACTTAGAAATAGG

TGCTAATACCGCATAAGCGCACGGAACCGCATGGTTCCGTGTGAAAAACTCCGGTGGTACAGGATGGTCCCGCGTCT

GATTAGCCAGTTGGCAGGGTAACGGCCTACCAAAGCGACGATCAGTAGCCGGCCTGAGAGGGTGAACGGCCACATTG

GGACTGAGACACGGCCCAAACTCCTACGGGAGGCAGCAGTGGGGAATATTGCACAATGGGGGAAACCCTGATGCAGC

GACGCCGCGTGAGTGAAGAAGTATTTCGGTATGTAAAGCTCTATCAGCAGGGAAGAAAATGACGGTACCTGACTAAG

AAGCCCCGGCTAACTACGTGCCAGCAGCCGCGGTAATACGTAGGGGGCAAGCGTTATCCGGATTTACTGGGTGTAAA

GGGAGCGTAGACGGCATGGCAAGCCAGATGTGAAAACCCAGGGCTCAACCTTGGGATTGCATTTGGAACTGCCAGGC

TGGAGTGCAGGAGAGGTAAGCGGAATTCCTAGTGTAGCGGTGAAATGCGTAGATATTAGGAGGAACACCAGTGGCGA

AGGCGGCTTACTGGACTGTAACTGACGTTGAGGCTCGAAAGCGTGGGGAGCAAACAGGATTAGATACCCTGGTAGTC

CACGCGGTAAACGATGATTGCTAGGTGTAGGTGGGTATGACCCATCGGTGCCGCAGCTAACGCAATAAGCAATCCA

CCTGGGGAGTACGTTCGCAAGAATGAAACTCAAAGGAATTGACGGGACCCGCACAAGCGGTGGAGCATGTGGTTTA

ATTCGAAGCAACGCGAAGAACCTTACCAAGTCTTGACATCCCAATGACGCACCTGTAAAGAGGTGTTCCCTTCGGGG

CATTGGAGACAGGTGGTGCATGGTTGTCGTCAGCTCGTGTCGTGAGATGTTGGGTTAAGTCCCGCAACGAGCGCAAC

CCTTATTCTTAGTAGCCAGCAGGTAAAGCTGGGCACTCTAAGGAGACTGCCGGGGATAACCCGGAGGAAGGCGGGGA

TGACGTCAAATCATCATGCCCCTTATGATTTGGGCTACACACGTGCTACAATGGCGTAAACAAAGGGAAGCGAGACA

GTGATGTGGAGCAAATCYCAGAAATAACGTCTCAGTTCGGATTGTAGTCTGCAACTCGACTACATGAAGCTGGAATC

GCTAGTAATCGCGAATCAGCATGTCGCGGTGAATACGTTCCCGGGTCTTGTACACACCGCCCGTCACACCATGGGAG

TTGGAAATGCCCGAAGTCTGTGACCTAACCGAAAGGGAGGAGCAGCCGAAGGCAGGTCTGATAACTGGGGTGAAGTC

GTAA

>SEQ ID NO: 122|NR_118730.1|*Clostridium symbiosum* strain ATCC 14940 16S
ribosomal RNA gene, partial sequence
AAACATGAGAGTTTGATCCTGGCTCAGGATGAACGCTGGCGGCGTGCCTAACACATGCAAGTCGAACGAAGCGATTT

AACGGAAGTTTTCGGATGGAAGTTGAATTGACTGAGTGGCGGACGGGTGAGTAACGCGTGGGTAACCTGCCTTGTAC

TGGGGGACAACAGTTAGAAATGACTGCTAATACCGCATAAGCGCACAGTATTGCATGATACAGTGTGAAAAACTCCG

GTGGTACAAGATGGACCCGCGTCTGATTAGCTAGTTGGTAAGGTAACGGCTTACCAAGGCGACGATCAGTAGCCGAC

CTGAGAGGGTGACCGGCCACATTGGGACTGAGACACGGCCNNAACTCCTACGGGAGGCAGCAGTGGGGAATATTGCA

CAATGGGCGAAAGCCTGATGCAGCGACGCCGCGTGAGTGAAGAAGTATTTCGGTATGTAAAGCTCTATCAGCAGGGA

AGAAAATGACGGTACCTGACTAAGAAGCCCCGGCTAACTACGTGCCAGCAGCCGCGGTAATACGTAGGGGGNNAGCG

TTATCCGGATTTACTGGGTGTAAAGGGAGCGTAGACGGTAAAGCAAGTCTGAAGTGAAAGCCCGCGNCTCAACTGCG

GNNCTGCTTTGGAAACTGTTTAACTGGAGTGTCGGAGAGGTAAGTGGAATTCCTAGTGTAGCGGTGAAATGCGTAGA

TATTAGGAGGAACACNAGTGGCGAAGGCGACTTACTGGACGATAACTGACGTTGAGGCTCGAAAGCGTGGGGAGCAA

ACAGGATTAGATACCCTGGTAGTCCACGCCGTAAACGATGAATACTAGGTGTTGGGGAGCAAAGCTCTTCGGTGCCG

TCGCAAACGCAGTAAGTATTCCACCTGGGGAGTACGTTCGCAAGAATGAAACTCAAAGGAATTGACGGGGACCNGCA

CAAGCGGTGGAGCATGTGGTTTAATTCGAANNAACGCGAAGAACCTTACCAGGTCTTGACATCGACTCGACGGGGGA

GTAACGTCCCNNTNCCTTCGGGGCGGAGAAGACAGGTGGTGCATGGTTGTCGTCAGCTCGTGTCGTGAGATGTTGGG

TTNAGTCCCGCAACGAGCGCAACCCTTATTCTAAGTAGCCAGCGGTTCGGCCGGGAACTCTTGGGAGACTGCCAGGG

ATAACCTGGAGGAAGGTGGGGATGACGTCNAATCATCATGCCCCTTATGATCTGGGCTACACACGTGCTACAATGGC

GTAAACANAGAGAAGCAAGACCGCGAGGTGGAGCAAATCTCAAAAATAACGTCTCAGTTCGGACTGCAGGCTGCAAC

TCGCCTGCACGAAGCTGGAATCGCTAGTAATCGCGAATCAGAATGTCGCGGTGAATACGTTCCCGGGTCTTGTACAC

ACCGNNCGTCACACCATGGGAGTCAGTAACGCCCGAAGTCAGTGACCCAACCGCAAGGAGGGAGCTGCCGAAGGCGG

GACCGANAACNNGGG

>SEQ ID NO: 123|NR_113243.1|*Erysipelatoclostridium ramosum* strain JCM 1298
16S ribosomal RNA gene, partial sequence
AGAGTTTGATCCTGGCTCAGGATGAACGCTGGCGGCGTGCCTAATACATGCAAGTCGAACGCGAGCACTTGTGCTCG

AGTGGCGAACGGGTGAGTAATACATAAGTAACCTGCCCTAGACAGGGGGATAACTATTGGAAACGATAGCTAAGACC

GCATAGGTACGGACACTGCATGGTGACCGTATTAAAAGTGCCTCAAAGCACTGGTAGAGGATGGACTTATGGCGCAT

TAGCTGGTTGGCGGGTAACGGCCCACCAAGGCGACGATGCGTAGCCGACCTGAGAGGGTGACCGGCCACACTGGGA

CTGAGACACGGCCCAGACTCCTACGGGAGGCAGCAGTAGGGAATTTTCGGCAATGGGGGAAACCCTGACCGAGCAAC

GCCGCGTGAAGGAAGAAGGTTTTCGGATTGTAAACTTCTGTTATAAAGGAAGAACGGCGGCTACAGGAAATGGTAGC

CGAGTGACGGTACTTTATTAGAAAGCCACGGCTAACTACGTGCCAGCAGCCGCGGTAATACGTAGGTGGCAAGCGTT

ATCCGGAATTATTGGGCGTAAAGAGGGAGCAGGCGGCAGCAAGGGTCTGTGGTGAAAGCCTGAAGCTTAACTTCAGT

AAGCCATAGAAACCAGGCAGCTAGAGTGCAGGAGAGGATCGTGGAATTCCATGTGTAGCGGTGAAATGCGTAGATAT

ATGGAGGAACACCAGTGGCGAAGGCGACGATCTGGCCTGCAACTGACGCTCAGTCCCGAAAGCGTGGGGAGCAAATA

GGATTAGATACCCTAGTAGTCCACGCCGTAAACGATGAGTACTAAGTGTTGGATGTCAAAGTTCAGTGCTGCAGTTA

ACGCAATAAGTACTCCGCCTGAGTAGTACGTTCGCAAGAATGAAACTCAAAGGAATTGACGGGGCCCGCACAAGCG

GTGGAGCATGTGGTTTAATTCGAAGCAACGCGAAGAACCTTACCAGGTCTTGACATACTCATAAAGGCTCCAGAGAT

GGAGAGATAGCTATATGAGATACAGGTGGTGCATGGTTGTCGTCAGCTCGTGTCGTGAGATGTTGGGTTAAGTCCCG

CAACGAGCGCAACCCTTATCGTTAGTTACCATCATTAAGTTGGGGACTCTAGCGAGACTGCCAGTGACAAGCTGGAG

GAAGGCGGGGATGACGTCAAATCATCATGCCCCTTATGACCTGGGCTACACACGTGCTACAATGGATGGTGCAGAGG

GAAGCGAAGCCGCGAGGTGAAGCAAAACCCATAAAACCATTCTCAGTTCGGATTGTAGTCTGCAACTCGACTACATG

AAGTTGGAATCGCTAGTAATCGCGAATCAGCATGTCGCGGTGAATACGTTCTCGGGCCTTGTACACACCGCCCGTCA

CACCACGAGAGTTGATAACACCCGAAGCCGGTGGCCTAACCGCAAGGAAGGAGCTGTCTAAGGTGGGATTGATGATT

GGGGTGAAGTCGTAACAAGGTAACC

>SEQ ID NO: 124 |PROKKA_00507 16S ribosomal RNA gene | VE202-7
ATGAGAGTTTGATCCTGGCTCAGGATGAACGCTGGCGGCGTGCCTAACACATGCAAGTCGAACGAAGCAATTAAAGG

AAGTTTTCGGATGGAATTTGATTGACTGAGTGGCGGACGGGTGAGTAACGCGTGGATAACCTGCCTCACACTGGGGG

ATAACAGTTAGAAATGACTGCTAATACCGCATAAGCGCACAGTACCGCATGGTACGGTGTGAAAAACTCCGGTGGTG

TGAGATGGATCCGCGTCTGATTAGCCAGTTGGCGGGGTAACGGCCCACCAAAGCGACGATCAGTAGCCGACCTGAGA

GGGTGACCGGCCACATTGGGACTGAGACACGGCCCAAACTCCTACGGGAGGCAGCAGTGGGGAATATTGCACAATGG

GCGAAAGCCTGATGCAGCGACGCCGCGTGAGTGAAGAAGTATTTCGGTATGTAAAGCTCTATCAGCAGGGAAGAAAA

TGACGGTACCTGACTAAGAAGCCCCGGCTAACTACGTGCCAGCAGCCGCGGTAATACGTAGGGGGCAAGCGTTATCC

GGATTCACTGGGTGTAAAGGGAGCGTAGACGGCGAAGCAAGTCTGAAGTGAAAACCCAGGGCTCAACCCTGGGACTG

CTTTGGAAACTGTTTTGCTAGAGTGTCGGAGAGGTAAGTGGAATTCCTAGTGTAGCGGTGAAATGCGTAGATATTAG

GAGGAACACCAGTGGCGAAGGCGGCTTACTGGACGATAACTGACGTTGAGGCTCGAAAGCGTGGGGAGCAAACAGGA

TTAGATACCCTGGTAGTCCACGCCGTAAACGATGAATGCTAGGTGTTGGGGGCAAAGCCCTTCGGTGCCGTCGCAA

ACGCAGTAAGCATTCCACCTGGGGAGTACGTTCGCAAGAATGAAACTCAAAGGAATTGACGGGGACCCGCACAAGCG

GTGGAGCATGTGGTTTAATTCGAAGCAACGCGAAGAACCTTACCAAGTCTTGACATCCTCTTGACCGGCGTGTAACG

GCGCCTTCCCTTCGGGGCAAGAGAGACAGGTGGTGCATGGTTGTCGTCAGCTCGTGTCGTGAGATGTTGGGTTAAGT

CCCGCAACGAGCGCAACCCTTATCCTTAGTAGCCAGCAGGTAGAGCTGGGCACTCTAGGGAGACTGCCAGGGATAAC

CTGGAGGAAGGTGGGGATGACGTCAAATCATCATGCCCCTTATGATTTGGGCTACACACGTGCTACAATGGCGTAAA

CAAAGGGAAGCAAGACAGTGATGTGGAGCAAATCCCAAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 125 |PROKKA_00709 16S ribosomal RNA gene | VE202-7
ATGAGAGTTTGATCCTGGCTCAGGATGAACGCTGGCGGCGTGCCTAACACATGCAAGTCGAACGAAGCAATTAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGGGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

GATTAGATACCCTGGTAGTCCACGCCGTAAACGATGAATGCTAGGTGTTGGGGGCAAAGCCCTTCGGTGCCGTCGC

AAACGCAGTAAGCATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAAGTCTTGACATCCTCTTGACCGGCGTGTAA

CGGCGCCTTCCCTTCGGGGCAAGAGAGACAGGTGGTGCATGGTTGTCGTCAGCTCGTGTCGTGAGATGTTGGGTTAA

GTCCCGCAACGAGCGCAACCCTTATCCTTAGTAGCCAGCAGGTAAAGCTGGGCACTCTAGGGAGACTGCCAGGGATA

ACCTGGAGGAAGGTGGGGATGACGTCAAATCATCATGCCCCTTATGATTTGGGCTACACACGTGCTACAATGGCGTA

AACAAAGGGAAGCAAGACAGTGATGTGGAGCAAATCCCAAAAATAACGTCCCAGTTCGGACTGTAGTCTGCAACCCG

ACTACACGAAGCTGGAATCGCTAGTAATCGCGAATCAGAATGTCGCGGTGAATACGTTCCCGGGTCTTGTACACACC

GCCCGTCACACCATGGGAGTCAGCAACGCCCGAAGTCAGTGACCCAACTCGCAAGAGAGGGAGCTGCCGAAGGCGGG

GCAGGTAACTGGGGTGAAGTCGTAACAAGGTAGCCGTATCGGAAGGTGCGGCTGGATCACCTCCTTT

>SEQ ID NO: 126 |PROKKA_01766 16S ribosomal RNA gene | VE202-7
ATGAGAGTTTGATCCTGGCTCAGGATGAACGCTGGCGGCGTGCCTAACACATGCAAGTCGAACGAAGCAATTAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

ATGACGGTACCTGACTAAGAAGCCCCGGCTAACTACGTGCCAGCAGCCGCGGTAATACGTAGGGGGCAAGCGTTATC

CGGATTTACTGGGTGTAAAGGGAGCGTAGACGGCGAAGCAAGTCTGAAGTGAAAACCCAGGGCTCAACCCTGGGACT

GCTTTGGAAACTGTTTTGCTAGAGTGTCGGAGAGGTAAGTGGAATTCCTAGTGTAGCGGTGAAATGCGTAGATATTA

GGAGGAACACCAGTGGCGAAGGCGGCTTACTGGACGATAACTGACGTTGAGGCTCGAAAGCGTGGGGAGCAAACAGG

ATTAGATACCCTGGTAGTCCACGCCGTAAACGATGAATGCTAGGTGTTGGGGGCAAAGCCCTTCGGTGCCGTCGCAA

ACGCAGTAAGCATTCCACCTGGGGAGTACGTTCGCAAGAATGAAACTCAAAGGAATTGACGGGGACCCGCACAAGCG

GTGGAGCATGTGGTTTAATTCGAAGCAACGCGAAGAACCTTACCAAGTCTTGACATCCTCTTGACCGGCGTGTAACG

GCGCCTTCCCTTCGGGGCAAGAGAGACAGGTGGTGCATGGTTGTCGTCAGCTCGTGTCGTGAGATGTTGGGTTAAGT

CCCGCAACGAGCGCAACCCTTATCCTTAGTAGCCAGCAGGTAAAGCTGGGCACTCTAGGGAGACTGCCAGGGATAAC

CTGGAGGAAGGTGGGGATGACGTCAAATCATCATGCCCCTTATGATTTGGGCTACACACGTGCTACAATGGCGTAAA

CAAAGGGAAGCAAGACAGTGATGTGGAGCAAATCCCAAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 127 |PROKKA_01779 16S ribosomal RNA gene | VE202-7
ATGAGAGTTTGATCCTGGCTCAGGATGAACGCTGGCGGCGTGCCTAACACATGCAAGTCGAACGAAGCAATTAAAT

GAAGTTTTCGGATGGATTTTTGATTGACTGAGTGGCGGACGGGTGAGTAACGCGTGGATAACCTGCCTCACACTGGG

GGATAACAGTTAGAAATGACTGCTAATACCGCATAAGCGCACAGTACCGCATGGTACGGTGTGAAAAACTCCGGTGG

TGTGAGATGGATCCGCGTCTGATTAGCCAGTTGGCGGGGTAACGGCCCACCAAAGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGCGAAGCAAGTCTGAAGTGAAAACCCAGGGCTCAACCCTGGGAC

TGCTTTGGAAACTGTTTTGCTAGAGTGTCGGAGAGGTAAGTGGAATTCCTAGTGTAGCGGTGAAATGCGTAGATATT

AGGAGGAACACCAGTGGCGAAGGCGGCTTACTGGACGATAACTGACGTTGAGGCTCGAAAGCGTGGGGAGCAAACAG

GATTAGATACCCTGGTAGTCCACGCCGTAAACGATGAATGCTAGGTGTTGGGGGCAAAGCCCTTCGGTGCCGTCGCA

AACGCAGTAAGCATTCCACCTGGGGAGTACGTTCGCAAGAATGAAACTCAAAGGAATTGACGGGGACCCGCACAAGC

GGTGGAGCATGTGGTTTAATTCGAAGCAACGCGAAGAACCTTACCAAGTCTTGACATCCTCTTGACCGGCGTGTAAC

GGCGCCTTCCCTTCGGGGCAGGAGAGACAGGTGGTGCATGGTTGTCGTCAGCTCGTGTCGTGAGATGTTGGGTTAAG

TCCCGCAACGAGCGCAACCCTTATCCTTAGTAGCCAGCAGGTAGAGCTGGGCACTCTAGGGAGACTGCCAGGGATAA

CCTGGAGGAAGGTGGGGATGACGTCAAATCATCATGCCCCTTATGATTTGGGCTACACACGTGCTACAATGGCGTAA

ACAAAGGGAAGCAAGACAGTGATGTGGAGCAAATCCCAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 128 |PROKKA_05926 16S ribosomal RNA gene | VE202-7
ATGAGAGTTTGATCCTGGCTCAGGATGAACGCTGGCGGCGTGCCTAACACATGCAAGTCGAACGAAGCAATTAAAAT

GAAGTTTTCGGATGGATTTTAATTGACTGAGTGGCGGACGGGTGAGTAACGCGTGGATAACCTGCCTCACACTGGGG

GATAACAGTTAGAAATGACTGCTAATACCGCATAAGCGCACAGTACCGCATGGTACGGTGTGAAAAACTCCGGTGGT

GTGAGATGGATCCGCGTCTGATTAGCCAGTTGGCGGGGTAACGGCCCACCAAAGCGACGATCAGTAGCCGACCTGAG

AGGGTGACCGGCCACATTGGGACTGAGACACGGCCCAAACTCCTACGGGAGGCAGCAGTGGGGAATATTGCACAATG

GGCGAAAGCCTGATGCAGCGACGCCGCGTGAGTGAAGAAGTATTTCGGTATGTAAAGCTCTATCAGCAGGGAAGAA

ATGACGGTACCTGACTAAGAAGCCCCGGCTAACTACGTGCCAGCAGCCGCGGTAATACGTAGGGGGCAAGCGTTATC

CGGATTTACTGGGTGTAAAGGGAGCGTAGACGGCGAAGCAAGTCTGAAGTGAAAACCCAGGGCTCAACCCTGGGACT

GCTTTGGAAACTGTTTTGCTAGAGTGTCGGAGAGGTAAGTGGAATTCCTAGTGTAGCGGTGAAATGCGTAGATATTA

GGAGGAACACCAGTGGCGAAGGCGGCTTACTGGACGATAACTGACGTTGAGGCTCGAAAGCGTGGGGAGCAAACAGG

ATTAGATACCCTGGTAGTCCACGCCGTAAACGATGAATGCTAGGTGTTGGGGGGCAAAGCCCTTCGGTGCCGTCGCA

AACGCAGTAAGCATTCCACCTGGGGAGTACGTTCGCAAGAATGAAACTCAAAGGAATTGACGGGACCCGCACAAGC

GGTGGAGCATGTGGTTTAATTCGAAGCAACGCGAAGAACCTTACCAAGTCTTGACATCCTCTTGACCGGCGTGTAAC

GGCGCCTTCCCTTCGGGGCAAGAGAGACAGGTGGTGCATGGTTGTCGTCAGCTCGTGTCGTGAGATGTTGGGTTAAG

TCCCGCAACGAGCGCAACCCTTATCCTTAGTAGCCAGCAGGTAAAGCTGGGCACTCTAGGGAGACTGCCAGGGATAA

CCTGGAGGAAGGTGGGGATGACGTCAAATCATCATGCCCCTTATGATTTGGGCTACACACGTGCTACAATGGCGTAA

ACAAAGGGAAGCAAGACAGTGATGTGGAGCAAATCCCAAAATAACGTCCCAGTTCGGACTGTAGTCTGCAACCCGAC

TACACGAAGCTGGAATCGCTAGTAATCGCGAATCAGAATGTCGCGGTGAATACGTTCCCGGGTCTTGTACACACCGC

CCGTCACACCATGGGAGTCAGCAACGCCCGAAGTCAGTGACCCAACTCGCAAGAGAGGGAGCTGCCGAAGGCGGGGC

AGGTAACTGGGGTGAAGTCGTAACAAGGTAGCCGTATCGGAAGGTGCGGCTGGATCACCTCCTTT

>SEQ ID NO: 129 | PROKKA_01784 16S ribosomal RNA gene
TCAAAGAGTTTGATCCTGGCTCAGGACGAACGCTGGCGGCGCGCCTAACACATGCAAGTCGAACGGAGCTTACGTTT

TGAAGTTTTCGGATGGATGAATGTAAGCTTAGTGGCGGACGGGTGAGTAACACGTGAGCAACCTGCCTTTCAGAGGG

GGATAACAGCCGGAAACGGCTGCTAATACCGCATGATGTTGCGGGGCACATGCCCCTGCAACCAAAGGAGCAATCC

GCTGAAAGATGGGCTCGCGTCCGATTAGCCAGTTGGCGGGGTAACGGCCCACCAAAGCGACGATCGGTAGCCGGACT

GAGAGGTTGAACGGCCACATTGGGACTGAGACACGGCCCAGACTCCTACGGGAGGCAGCAGTGGGGGATATTGCACA

ATGGGCGAAAGCCTGATGCAGCGACGCCGCGTGAGGGAAGACGGTCTTCGGATTGTAAACCTCTGTCTTTGGGGAAG

AAAATGACGGTACCCAAAGAGGAAGCTCCGGCTAACTACGTGCCAGCAGCCGCGGTAATACGTAGGGAGCAAGCGTT

GTCCGGAATTACTGGGTGTAAAGGGAGCGTAGGCGGGATGGCAAGTAGAATGTTAAATCCATCGGCTCAACCGGTGG

CTGCGTTCTAAACTGCCGTTCTTGAGTGAAGTAGAGGCAGGCGGAATTCCTAGTGTAGCGGTGAAATGCGTAGATAT

TAGGAGGAACACCAGTGGCGAAGGCGGCCTGCTGGGCTTTAACTGACGCTGAGGCTCGAAAGCGTGGGGAGCAAACA

GGATTAGATACCCTGGTAGTCCACGCCGTAAACGATGATTACTAGGTGTGGGGGACTGACCCCTTCCGTGCCGCAG

TTAACACAATAAGTAATCCACCTGGGGAGTACGGCCGCAAGGTTGAAACTCAAAGGAATTGACGGGGCCCGCACAA

GCAGTGGAGTATGTGGTTTAATTCGAAGCAACGCGAAGAACCTTACCAGGTCTTGACATCGGATGCATAGCCTAGAG

ATAGGTGAAGCCCTTCGGGGCATCCAGACAGGTGGTGCATGGTTGTCGTCAGCTCGTGTCGTGAGATGTTGGGTTAA

GTCCCGCAACGAGCGCAACCCTTATTATTAGTTGCTACGCAAGAGCACTCTAATGAGACTGCCGTTGACAAAACGGA

GGAAGGTGGGGATGACGTCAAATCATCATGCCCCTTATGACCTGGGCTACACACGTACTACAATGGCACTAAAACAG

AGGGCGGCGACACCGCGAGGTGAAGCGAATCCCGAAAAAGTGTCTCAGTTCAGATTGCAGGCTGCAACCCGCCTGCA

TGAAGTCGGAATTGCTAGTAATCGCGGATCAGCATGCCGCGGTGAATACGTTCCCGGGCCTTGTACACACCGCCCGT

CACACCATGGGAGTCGGTAACACCCGAAGCCAGTAGCCTAACCGCAAGGGGGCGCTGTCGAAGGTGGGATTGATGA

CTGGGGTGAAGTCGTAACAAGGTAGCCGTATCGGAAGGTGCGGCTGGATCACCTCCTTT

>SEQ ID NO: 130 | PROKKA_01864 16S ribosomal RNA gene
TCAAAGAGTTTGATCCTGGCTCAGGACGAACGCTGGCGGCGCGCCTAACACATGCAAGTCGAACGGAGCTTACGTTT

TGAAGTTTTCGGATGGACGAATGTAAGCTTAGTGGCGGACGGGTGAGTAACACGTGAGCAACCTGCCTTTCAGAGGG

GATAACAGCCGGAAACGGCTGCTAATACCGCATGATGTTGCGGGGCACATGCCCCTGCAACCAAAGGAGCAATCCG

CTGAAAGATGGGCTCGCGTCCGATTAGCCAGTTGGCGGGTAACGGCCCACCAAAGCGACGATCGGTAGCCGGACTG

AGAGGTTGAACGGCCACATTGGGACTGAGACACGGCCCAGACTCCTACGGGAGGCAGCAGTGGGGATATTGCACAA

TGGGCGAAAGCCTGATGCAGCGACGCCGCGTGAGGGAAGACGGTCTTCGGATTGTAAACCTCTGTCTTTGGGGAAGA

AAATGACGGTACCCAAAGAGGAAGCTCCGGCTAACTACGTGCCAGCAGCCGCGGTAATACGTAGGGAGCAAGCGTTG

TCCGGAATTACTGGGTGTAAAGGGAGCGTAGGCGGGATGGCAAGTAGAATGTTAAATCCATCGGCTCAACCGGTGGC

TGCGTTCTAAACTGCCGTTCTTGAGTGAAGTAGAGGCAGGCGGAATTCCTAGTGTAGCGGTGAAATGCGTAGATATT

AGGAGGAACACCAGTGGCGAAGGCGGCCTGCTGGGCTTTAACTGACGCTGAGGCTCGAAAGCGTGGGGAGCAAACAG

GATTAGATACCCTGGTAGTCCACGCCGTAAACGATGATTACTAGGTGTGGGGGACTGACCCCTTCCGTGCCGCAGT

TAACACAATAAGTAATCCACCTGGGGAGTACGGCCGCAAGGTTGAAACTCAAAGGAATTGACGGGGGCCCGCACAAG

CAGTGGAGTATGTGGTTTAATTCGAAGCAACGCGAAGAACCTTACCAGGTCTTGACATCGGATGCATAGCCTAGAGA

TAGGTGAAGCCCTTCGGGGCATCCAGACAGGTGGTGCATGGTTGTCGTCAGCTCGTGTCGTGAGATGTTGGGTTAAG

TCCCGCAACGAGCGCAACCCTTATTATTAGTTGCTACGCAAGAGCACTCTAATGAGACTGCCGTTGACAAAACGGAG

GAAGGTGGGGATGACGTCAAATCATCATGCCCCTTATGACCTGGGCTACACACGTACTACAATGGCACTAAAACAGA

GGGCGGCGACACCGCGAGGTGAAGCGAATCCCGAAAAAGTGTCTCAGTTCAGATTGCAGGCTGCAACCCGCCTGCAT

GAAGTCGGAATTGCTAGTAATCGCGGATCAGCATGCCGCGGTGAATACGTTCCCGGGCCTTGTACACACCGCCCGTC

ACACCATGGGAGTCGGTAACACCCGAAGCCAGTAGCCTAACCGCAAGGGGGCGCTGTCGAAGGTGGGATTGATGAC

TGGGGTGAAGTCGTAACAAGGTAGCCGTATCGGAAGGTGCGGCTGGATCACCTCCTTT

>SEQ ID NO: 131 | PROKKA_02671 16S ribosomal RNA gene
TCAAAGAGTTTGATCCTGGCTCAGGACGAACGCTGGCGGCGCGCCTAACACATGCAAGTCGAACGGAGCTTACGTTT

TGAAGTTTTCGGATGGATGAATGTAAGCTTAGTGGCGGACGGGTGAGTAACACGTGAGCAACCTGCCTTTCAGAGGG

GGATAACAGCCGGAAACGGCTGCTAATACCGCATGATGTTGCGGGGGCACATGCCCCTGCAACCAAAGGAGCAATCC

GCTGAAAGATGGGCTCGCGTCCGATTAGCCAGTTGGCGGGTAACGGCCCACCAAAGCGACGATCGGTAGCCGGACT

GAGAGGTTGAACGGCCACATTGGGACTGAGACACGGCCCAGACTCCTACGGGAGGCAGCAGTGGGGATATTGCACA

ATGGGCGAAAGCCTGATGCAGCGACGCCGCGTGAGGGAAGACGGTCTTCGGATTGTAAACCTCTGTCTTTGGGGAAG

AAAATGACGGTACCCAAAGAGGAAGCTCCGGCTAACTACGTGCCAGCAGCCGCGGTAATACGTAGGGAGCAAGCGTT

GTCCGGAATTACTGGGTGTAAAGGGAGCGTAGGCGGGATGGCAAGTAGAATGTTAAATCCATCGGCTCAACCGGTGG

CTGCGTTCTAAACTGCCGTTCTTGAGTGAAGTAGAGGCAGGCGGAATTCCTAGTGTAGCGGTGAAATGCGTAGATAT

TAGGAGGAACACCAGTGGCGAAGGCGGCCTGCTGGGCTTTAACTGACGCTGAGGCTCGAAAGCGTGGGGAGCAAACA

GGATTAGATACCCTGGTAGTCCACGCCGTAAACGATGATTACTAGGTGTGGGGGACTGACCCCTTCCGTGCCGCAG

```
TTAACACAATAAGTAATCCACCTGGGGAGTACGGCCGCAAGGTTGAAACTCAAAGGAATTGACGGGGGCCCGCACAA
GCAGTGGAGTATGTGGTTTAATTCGAAGCAACGCGAAGAACCTTACCAGGTCTTGACATCGGATGCATAGCCTAGAG
ATAGGTGAAGCCCTTCGGGGCATCCAGACAGGTGGTGCATGGTTGTCGTCAGCTCGTGTCGTGAGATGTTGGGTTAA
GTCCCGCAACGAGCGCAACCCTTATTATTAGTTGCTACGCAAGAGCACTCTAATGAGACTGCCGTTGACAAAACGGA
GGAAGGTGGGGATGACGTCAAATCATCATGCCCCTTATGACCTGGGCTACACACGTACTACAATGGCACTAAAACAG
AGGGCGGCGACACCGCGAGGTGAAGCGAATCCCGAAAAAGTGTCTCAGTTCAGATTGCAGGCTGCAACCCGCCTGCA
TGAAGTCGGAATTGCTAGTAATCGCGGATCAGCATGCCGCGGTGAATACGTTCCCGGGCCTTGTACACACCGCCCGT
CACACCATGGGAGTCGGTAACACCCGAAGCCAGTAGCCTAACCGCAAGGGGGCGCTGTCGAAGGTGGGATTGATGA
CTGGGGTGAAGTCGTAACAAGGTAGCCGTATCGGAAGGTGCGGCTGGATCACCTCCTTT

>SEQ ID NO: 132 | PROKKA_00690 16S ribosomal RNA gene
TACGAGAGTTTGATCCTGGCTCAGGATGAACGCTGGCGGCGTGCCTAACACATGCAAGTCGAGCGAAGCGCTGTTTT
CAGAATCTTCGGAGGAAGAGGACAGTGACTGAGCGGCGGACGGGTGAGTAACGCGTGGGCAACCTGCCTCATACAGG
GGGATAACAGTTAGAAATGACTGCTAATACCGCATAAGCGCACAGGACCGCATGGTGTAGTGTGAAAAACTCCGGTG
GTATGAGATGGACCCGCGTCTGATTAGGTAGTTGGTGGGGTAAAGGCCTACCAAGCCGACGATCAGTAGCCGACCTG
AGAGGGTGACCGGCCACATTGGGACTGAGACACGGCCCAAACTCCTACGGGAGGCAGCAGTGGGGAATATTGCACAA
TGGGGGAAACCCTGATGCAGCGACGCCGCGTGAAGGAAGAAGTATTTCGGTATGTAAACTTCTATCAGCAGGGAAGA
AAATGACGGTACCTGAGTAAGAAGCACCGGCTAAATACGTGCCAGCAGCCGCGGTAATACGTATGGTGCAAGCGTTA
TCCGGATTTACTGGGTGTAAAGGGAGCGTAGACGGATAGGCAAGTCTGGAGTGAAAACCCAGGGCTCAACCCTGGGA
CTGCTTTGGAAACTGCAGATCTGGAGTGCCGGAGAGGTAAGCGGAATTCCTAGTGTAGCGGTGAAATGCGTAGATAT
TAGGAGGAACACCAGTGGCGAAGGCGGCTTACTGGACGGTGACTGACGTTGAGGCTCGAAAGCGTGGGGAGCAAACA
GGATTAGATACCCTGGTAGTCCACGCCGTAAACGATGACTACTAGGTGTCGGTGTGCAAAGCACATCGGTGCCGCAG
CAAACGCAATAAGTAGTCCACCTGGGGAGTACGTTCGCAAGAATGAAACTCAAAGGAATTGACGGGGACCCGCACAA
GCGGTGGAGCATGTGGTTTAATTCGAAGCAACGCGAAGAACCTTACCTGGTCTTGACATCCGGATGACGGGCGAGTA
ATGTCGCCGTCCCTTCGGGGCGTCCGAGACAGGTGGTGCATGGTTGTCGTCAGCTCGTGTCGTGAGATGTTGGGTTA
AGTCCCGCAACGAGCGCAACCCTTATCTTCAGTAGCCAGCATATAAGGTGGGCACTCTGGAGAGACTGCCAGGGAGA
ACCTGGAGGAAGGTGGGGATGACGTCAAATCATCATGCCCCTTATGGCCAGGGCTACACACGTGCTACAATGGCGTA
AACAAAGGGAAGCGAGAGGGTGACCTGGAGCGAATCCCAAAAATAACGTCTCAGTTCGGATTGTAGTCTGCAACTCG
ACTACATGAAGCTGGAATCGCTAGTAATCGCGGATCAGCATGCCGCGGTGAATACGTTCCCGGGTCTTGTACACACC
GCCCGTCACACCATGGGAGTCAGTAACGCCCGAAGCCAGTGACCCAACCTTAGAGGAGGGAGCTGTCGAAGGCGGGA
CGGATAACTGGGGTGAAGTCGTAACAAGGTAGCCGTATCGGAAGGTGCGGCTGGATCACCTCCTTT >SEQ ID NO: 133 | PROKKA_00991 16S ribosomal RNA gene
TACGAGAGTTTGATCCTGGCTCAGGATGAACGCTGGCGGCGTGCCTAACACATGCAAGTCGAGCGAAGCGCTGTTTT
CAGAATCTTCGGAGGAAGAGGACAGTGACTGAGCGGCGGACGGGTGAGTAACGCGTGGGCAACCTGCCTCATACAGG
GGGATAACAGTTAGAAATGACTGCTAATACCGCATAAGCGCACAGGACCGCATGGTGTAGTGTGAAAAACTCCGGTG
GTATGAGATGGACCCGCGTCTGATTAGGTAGTTGGTGGGGTAAAGGCCTACCAAGCCGACGATCAGTAGCCGACCTG
AGAGGGTGACCGGCCACATTGGGACTGAGACACGGCCCAAACTCCTACGGGAGGCAGCAGTGGGGAATATTGCACAA
TGGGGGAAACCCTGATGCAGCGACGCCGCGTGAAGGAAGAAGTATTTCGGTATGTAAACTTCTATCAGCAGGGAAGA
AGATGACGGTACCTGAGTAAGAAGCACCGGCTAAATACGTGCCAGCAGCCGCGGTAATACGTATGGTGCAAGCGTTA
TCCGGATTTACTGGGTGTAAAGGGAGCGTAGACGGATAGGCAAGTCTGGAGTGAAAACCCAGGGCTCAACCCTGGGA
CTGCTTTGGAAACTGCAGATCTGGAGTGCCGGAGAGGTAAGCGGAATTCCTAGTGTAGCGGTGAAATGCGTAGATAT
TAGGAGGAACACCAGTGGCGAAGGCGGCTTACTGGACGGTGACTGACGTTGAGGCTCGAAAGCGTGGGGAGCAAACA
```

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGAAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 134 | PROKKA_01948 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

CTGCTTTGGAAACTGCAGATCTGGAGTGCCGGAGAGGTAAGCGGAATTCCTAGTGTAGCGGTGAAATGCGTAGATAT

TAGGAGGAACACCAGTGGCGAAGGCGGCTTACTGGACGGTGACTGACGTTGAGGCTCGAAAGCGTGGGGAGCAAACA

GGATTAGATACCCTGGTAGTCCACGCCGTAAACGATGACTACTAGGTGTCGGTGTGCAAAGCACATCGGTGCCGCAG

CAAACGCAATAAGTAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGGTCTTGACATCCGGATGACGGGCGAGTA

ATGTCGCCGTCCCTTCGGGGCATCCGAGACAGGTGGTGCATGGTTGTCGTCAGCTCGTGTCGTGAGATGTTGGGTTA

AGTCCCGCAACGAGCGCAACCCTTATCTTCAGTAGCCAGCATATAAGGTGGGCACTCTGGAGAGACTGCCAGGGAGA

ACCTGGAGGAAGGTGGGGATGACGTCAAATCATCATGCCCCTTATGGCCAGGGCTACACACGTGCTACAATGGCGTA

AACAAAGGGAAGCGAGAGGGTGACCTGGAGCGAATCCCAAAAATAACGTCTCAGTTCGGATTGTAGTCTGCAACTCG

ACTACATGAAGCTGGAATCGCTAGTAATCGCGGATCAGCATGCCGCGGTGAATACGTTCCCGGGTCTTGTACACACC

GCCCGTCACACCATGGGAGTCAGTAACGCCCGAAGCCAGTGACCCAACCTTAGAGGAGGGAGCTGTCGAAGGCGGGA

CGGATAACTGGGGTGAAGTCGTAACAAGGTAGCCGTATCGGAAGGTGCGGCTGGATCACCTCCTTT

>SEQ ID NO: 135 | PROKKA_02310 16S ribosomal RNA gene
TACGAGAGTTTGATCCTGGCTCAGGATGAACGCTGGCGGCGTGCCTAACACATGCAAGTCGAGCGAAGCGCTGTTTT

CAGAATCTTCGGAGGAAGAGGACAGTGACTGAGCGGCGGACGGGTGAGTAACGCGTGGGCAACCTGCCTCATACAGG

GGGATAACAGTTAGAAATGACTGCTAATACCGCATAAGCGCACAGGACCGCATGGTGTAGTGTGAAAAACTCCGGTG

GTATGAGATGGACCCGCGTCTGATTAGGTAGTTGGTGGGTAAAGGCCTACCAAGCCGACGATCAGTAGCCGACCTG

AGAGGGTGACCGGCCACATTGGGACTGAGACACGGCCCAAACTCCTACGGGAGGCAGCAGTGGGGAATATTGCACAA

TGGGGGAAACCCTGATGCAGCGACGCCGCGTGAAGGAAGAAGTATTTCGGTATGTAAACTTCTATCAGCAGGGAAGA

AGATGACGGTACCTGAGTAAGAAGCACCGGCTAAATACGTGCCAGCAGCCGCGGTAATACGTATGGTGCAAGCGTTA

TCCGGATTTACTGGGTGTAAAGGGAGCGTAGACGGATAGGCAAGTCTGGAGTGAAAACCCAGGGCTCAACCCTGGGA

```
CTGCTTTGGAAACTGCAGATCTGGAGTGCCGGAGAGGTAAGCGGAATTCCTAGTGTAGCGGTGAAATGCGTAGATAT
TAGGAGGAACACCAGTGGCGAAGGCGGCTTACTGGACGGTGACTGACGTTGAGGCTCGAAAGCGTGGGGAGCAAACA
GGATTAGATACCCTGGTAGTCCACGCCGTAAACGATGACTACTAGGTGTCGGTGTGCAAAGCACATCGGTGCCGCAG
CAAACGCAATAAGTAGTCCACCTGGGGAGTACGTTCGCAAGAATGAAACTCAAAGGAATTGACGGGGACCCGCACAA
GCGGTGGAGCATGTGGTTTAATTCGAAGCAACGCGAAGAACCTTACCTGGTCTTGACATCCGGATGACGGGCGAGTA
ATGTCGCCGTCCCTTCGGGGCATCCGAGACAGGTGGTGCATGGTTGTCGTCAGCTCGTGTCGTGAGATGTTGGGTTA
AGTCCCGCAACGAGCGCAACCCTTATCTTCAGTAGCCAGCATATAAGGTGGGCACTCTGGAGAGACTGCCAGGGAGA
ACCTGGAGGAAGGTGGGGATGACGTCAAATCATCATGCCCCTTATGGCCAGGGCTACACACGTGCTACAATGGCGTA
AACAAAGGGAAGCGAGAGGGTGACCTGAAGCGAATCCCAAAAATAACGTCTCAGTTCGGATTGTAGTCTGCAACTCG
ACTACATGAAGCTGGAATCGCTAGTAATCGCGGATCAGCATGCCGCGGTGAATACGTTCCCGGGTCTTGTACACACC
GCCCGTCACACCATGGGAGTCAGTAACGCCCGAAGCCAGTGACCCAACCTTAGAGGAGGGAGCTGTCGAAGGCGGGA
CGGATAACTGGGGTGAAGTCGTAACAAGGTAGCCGTATCGGAAGGTGCGGCTGGATCACCTCCTTT
>SEQ ID NO: 136 | PROKKA_02993 16S ribosomal RNA gene
TACGAGAGTTTGATCCTGGCTCAGGATGAACGCTGGCGGCGTGCCTAACACATGCAAGTCGAGCGAAGCGCTGTTTT
CAGAATCTTCGGAGGAAGAGGACAGTGACTGAGCGGCGGACGGGTGAGTAACGCGTGGGCAACCTGCCTCATACAGG
GGGATAACAGTTAGAAATGACTGCTAATACCGCATAAGCGCACAGGACCGCATGGTGTAGTGTGAAAAACTCCGGTG
GTATGAGATGGACCCGCGTCTGATTAGGTAGTTGGTGGGGTAAAGGCCTACCAAGCCGACGATCAGTAGCCGACCTG
AGAGGGTGACCGGCCACATTGGGACTGAGACACGGCCCAAACTCCTACGGGAGGCAGCAGTGGGGAATATTGCACAA
TGGGGGAAACCCTGATGCAGCGACGCCGCGTGAAGGAAGAAGTATTTCGGTATGTAAACTTCTATCAGCAGGGAAGA
AGATGACGGTACCTGAGTAAGAAGCACCGGCTAAATACGTGCCAGCAGCCGCGGTAATACGTATGGTGCAAGCGTTA
TCCGGATTTACTGGGTGTAAAGGGAGCGTAGACGGATAGGCAAGTCTGGAGTGAAAACCCAGGGCTCAACCCTGGGA
CTGCTTTGGAAACTGCAGATCTGGAGTGCCGGAGAGGTAAGCGGAATTCCTAGTGTAGCGGTGAAATGCGTAGATAT
TAGGAGGAACACCAGTGGCGAAGGCGGCTTACTGGACGGTGACTGACGTTGAGGCTCGAAAGCGTGGGGAGCAAACA
GGATTAGATACCCTGGTAGTCCACGCCGTAAACGATGACTACTAGGTGTCGGTGTGCAAAGCACATCGGTGCCGCAG
CAAACGCAATAAGTAGTCCACCTGGGGAGTACGTTCGCAAGAATGAAACTCAAAGGAATTGACGGGGACCCGCACAA
GCGGTGGAGCATGTGGTTTAATTCGAAGCAACGCGAAGAACCTTACCTGGTCTTGACATCCGGATGACGGGCGAGTA
ATGTCGCCGTCCCTTCGGGGCATCCGAGACAGGTGGTGCATGGTTGTCGTCAGCTCGTGTCGTGAGATGTTGGGTTA
AGTCCCGCAACGAGCGCAACCCTTATCTTCAGTAGCCAGCATATAAGGTGGGCACTCTGGAGAGACTGCCAGGGAGA
ACCTGGAGGAAGGTGGGGATGACGTCAAATCATCATGCCCCTTATGGCCAGGGCTACACACGTGCTACAATGGCGTA
AACAAAGGGAAGCGAGAGGGTGACCTGGAGCGAATCCCAAAAATAACGTCTCAGTTCGGATTGTAGTCTGCAACTCG
ACTACATGAAGCTGGAATCGCTAGTAATCGCGGATCAGCATGCCGCGGTGAATACGTTCCCGGGTCTTGTACACACC
GCCCGTCACACCATGGGAGTCAGTAACGCCCGAAGCCAGTGACCCAACCTTAGAGGAGGGAGCTGTCGAAGGCGGGA
CGGATAACTGGGGTGAAGTCGTAACAAGGTAGCCGTATCGGAAGGTGCGGCTGGATCACCTCCTTT
>SEQ ID NO: 137 | PROKKA_00436 16S ribosomal RNA gene
ATGAGAGTTTGATCCTAGCTCAGGATGAACGCTGGCGGCGTGCCTAACACATGCAAGTCGAACGAAGCAATTTAACG
GAAGTTTTCGGATGGAAGTTGAATTGACTGAGTGGCGGACGGGTGAGTAACGCGTGGGTAACCTGCCTTGTACTGGG
GGACAACAGTTAGAAATGACTGCTAATACCGCATAAGCGCACAGTATCGCATGATACAGTGTGAAAAACTCCGGTGG
TACAAGATGGACCCGCGTCTGATTAGCTAGTTGGTAAGGTAACGGCTTACCAAGGCGACGATCAGTAGCCGACCTGA
GAGGGTGACCGGCCACATTGGGACTGAGACACGGCCCAAACTCCTACGGGAGGCAGCAGTGGGGAATATTGCACAAT
GGGCGAAAGCCTGATGCAGCGACGCCGCGTGAGTGAAGAAGTATTTCGGTATGTAAAGCTCTATCAGCAGGGAAGAA
AATGACGGTACCTGACTAAGAAGCCCCGGCTAACTACGTGCCAGCAGCCGCGGTAATACGTAGGGGGCAAGCGTTAT
```

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 138 | PROKKA_00685 16S ribosomal RNA gene
ATGAGAGTTTGATCCTGGCTCAGGATGAACGCTGGCGGCGTGCCTAACACATGCAAGTCGAACGAAGCGATTTAACG

GAAATTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 139 | PROKKA_01171 16S ribosomal RNA gene
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGAATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

```
GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 140 | PROKKA_05969 16S ribosomal RNA gene
ATGAGAGTTTGATCCTGGCTCAGGATGAACGCTGGCGGCGTGCCTAACACATGCAAGTCGAACGAAGCGATTTAACG

GAAGTTTTCGGATGGAAGTTGGATTGACTGAGTGGCGGACGGGTGAGTAACGCGTGGGTAACCTGCCTTGTACTGGG

GGACAACAGTTAGAAATGACTGCTAATACCGCATAAGCGCACAGTATCGCATGATACAGTGTGAAAAACTCCGGTGG

TACAAGATGGACCCGCGTCTGATTAGCTAGTTGGTAAGGTAACGGCTTACCAAGGCGACGATCAGTAGCCGACCTGA

GAGGGTGACCGGCCACATTGGGACTGAGACACGGCCCAAACTCCTACGGGAGGCAGCAGTGGGGAATATTGCACAAT

GGGCGAAAGCCTGATGCAGCGACGCCGCGTGAGTGAAGAAGTATTTCGGTATGTAAAGCTCTATCAGCAGGGAAGAA

AATGACGGTACCTGACTAAGAAGCCCCGGCTAACTACGTGCCAGCAGCCGCGGTAATACGTAGGGGGCAAGCGTTAT

CCGGATTTACTGGGTGTAAAGGGAGCGTAGACGGTAAAGCAAGTCTGAAGTGAAAGCCCGCGGCTCAACTGCGGGAC

TGCTTTGGAAACTGTTTAACTGGAGTGTCGGAGAGGTAAGTGGAATTCCTAGTGTAGCGGTGAAATGCGTAGATATT

AGGAGGAACACCAGTGGCGAAGGCGACTTACTGGACGATAACTGACGTTGAGGCTCGAAAGCGTGGGGAGCAAACAG

GATTAGATACCCTGGTAGTCCACGCCGTAAACGATGAATACTAGGTGTTGGGGAGCAAAGCTCTTCGGTGCCGTCGC

AAACGCAGTAAGTATTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCAGGTCTTGACATCGATCCGACGGGGGAGTAA

CGTCCCCTTCCCTTCGGGGCGGAGAAGACAGGTGGTGCATGGTTGTCGTCAGCTCGTGTCGTGAGATGTTGGGTTAA

GTCCCGCAACGAGCGCAACCCTTATTCTAAGTAGCCAGCGGTTCGGCCGGGAACTCTTGGGAGACTGCCAGGGATAA

CCTGGAGGAAGGTGGGGATGACGTCAAATCATCATGCCCCTTATGATCTGGGCTACACACGTGCTACAATGGCGTAA

ACAAAGAGAAGCAAGACCGCGAGGTGGAGCAAATCTCAAAAATAACGTCTCAGTTCGGACTGCAGGCTGCAACTCGC

CTGCACGAAGCTGGAATCGCTAGTAATCGCGAATCAGAATGTCGCGGTGAATACGTTCCCGGGTCTTGTACACACCG

CCCGTCACACCATGGGAGTCAGTAACGCCCGAAGTCAGTGACCCAACCGCAAGGAGGGAGCTGCCGAAGGCGGGACC

GATAACTGGGGTGAAGTCGTAACAAGGTAGCCGTATCGGAAGGTGCGGCTGGATCACCTCCTTT

>SEQ ID NO: 141 | PROKKA_00279 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT
```

```
GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTTTAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 142 | PROKKA_01221 16S ribosomal RNA gene
ATCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGTGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTGAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 143 | PROKKA_02318 16S ribosomal RNA gene
ATCAGAGAGTTTGATCCTGGCTCAGGATGAACGCTGGCGGCGTGCTTAACACATGCAAGTCGAGCGAAGCACTTAAG TGGATCTCTTCGGATTGAAGCTTATTTGACTGAGCGGCGGACGGGTGAGTAACGCGTGGGTAACCTGCCTCATACAG
```

```
GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT

>SEQ ID NO: 144 | PROKKA_02336 16S ribosomal RNA gene
ATCAGAGAGTTTGATCCTGGCTCAGGATGAACGCTGGCGGCGTGCTTAACACATGCAAGTCGAGCGAAGCACTTAAG

CGGATCTCTTCGGATTGAAACTTATTTGACTGAGCGGCGGACGGGTGAGTAACGCGTGGGTAACCTGCCTCATACAG

GGGGATAACAGTTAGAAATGGCTGCTAATACCGCATAAGCGCACAGGACCGCATGGTCTGGTGTGAAAAACTCCGGT

GGTATGAGATGGACCCGCGTCTGATTAGCTAGTTGGAGGGGTAACGGCCCACCAAGGCGACGATCAGTAGCCGGCCT

GAGAGGGTGAACGGCCACATTGGGACTGAGACACGGCCCAGACTCCTACGGGAGGCAGCAGTGGGGAATATTGCACA

ATGGGGGAAACCCTGATGCAGCGACGCCGCGTGAAGGAAGAAGTATCTCGGTATGTAAACTTCTATCAGCAGGGAAG

AAAATGACGGTACCTGACTAAGAAGCCCCGGCTAACTACGTGCCAGCAGCCGCGGTAATACGTAGGGGGCAAGCGTT

ATCCGGATTTACTGGGTGTAAAGGGAGCGTAGACGGAAGAGCAAGTCTGATGTGAAAGGCTGGGGCTTAACCCCAGG

ACTGCATTGGAAACTGTTTTTCTAGAGTGCCGGAGAGGTAAGCGGAATTCCTAGTGTAGCGGTGAAATGCGTAGATA

TTAGGAGGAACACCAGTGGCGAAGGCGGCTTACTGGACGGTAACTGACGTTGAGGCTCGAAAGCGTGGGGAGCAAAC

AGGATTAGATACCCTGGTAGTCCACGCCGTAAACGATGAATACTAGGTGTCGGGTGGCAAAGCCATTCGGTGCCGCA

GCAAACGCAATAAGTATTCCACCTGGGGAGTACGTTCGCAAGAATGAAACTCAAAGGAATTGACGGGGACCCGCACA

AGCGGTGGAGCATGTGGTTTAATTCGAAGCAACGCGAAGAACCTTACCAAGTCTTGACATCCCTCTGACCGGCCCGT

AACGGGGCCTTCCCTTCGGGGCAGAGGAGACAGGTGGTGCATGGTTGTCGTCAGCTCGTGTCGTGAGATGTTGGGTT

AAGTCCCGCAACGAGCGCAACCCCTATCCTTAGTAGCCAGCAGGTGAAGCTGGGCACTCTAGGGAGACTGCCGGGGA

TAACCCGGAGGAAGGCGGGGACGACGTCAAATCATCATGCCCCTTATGATTTGGGCTACACACGTGCTACAATGGCG

TAAACAAAGGGAAGCGAGACAGCGATGTTGAGCAAATCCCAAAAATAACGTCCCAGTTCGGACTGCAGTCTGCAACT

CGACTGCACGAAGCTGGAATCGCTAGTAATCGCGAATCAGAATGTCGCGGTAATACGTTCCCGGGTCTTGTACACA

CCGCCCGTCACACCATGGGAGTCAGTAACGCCCGAAGTCAGTGACCCAACCTTACAGGAGGGAGCTGCCGAAGGCGG

GACCGATAACTGGGGTGAAGTCGTAACAAGGTAGCCGTATCGGAAGGTGCGGCTGGATCACCTCCTTT
```

>SEQ ID NO: 145 | PROKKA_04947 16S ribosomal RNA gene
ATCAGAGAGTTTGATCCTGGCTCAGGATGAACGCTGGCGGCGTGCTTAACACATGCAAGTCGAGCGAAGCACTTAAG
TGGATCTCTTCGGATTGAAACTTATTTGACTGAGCGGCGGACGGGTGAGTAACGCGTGGGTAACCTGCCTCATACAG
GGGGATAACAGTTAGAAATGGCTGCTAATACCGCATAAGCGCACAGGACCGCATGGTCTGGTGTGAAAAACTCCGGT
GGTATGAGATGGACCCGCGTCTGATTAGCTAGTTGGAGGGGTAACGGCCCACCAAGGCGACGATCAGTAGCCGGCCT
GAGAGGGTGAACGGCCACATTGGGACTGAGACACGGCCCAGACTCCTACGGGAGGCAGCAGTGGGGAATATTGCACA
ATGGGGGAAACCCTGATGCAGCGACGCCGCGTGAAGGAAGAAGTATCTCGGTATGTAAACTTCTATCAGCAGGGAAG
AAAATGACGGTACCTGACTAAGAAGCCCCGGCTAACTACGTGCCAGCAGCCGCGGTAATACGTAGGGGGCAAGCGTT
ATCCGGATTTACTGGGTGTAAAGGGAGCGTAGACGGAAGAGCAAGTCTGATGTGAAAGGCTGGGGCTTAACCCCAGG
ACTGCATTGGAAACTGTTTTTCTAGAGTGCCGGAGAGGTAAGCGGAATTCCTAGTGTAGCGGTGAAATGCGTAGATA
TTAGGAGGAACATCAGTGGCGAAGGCGGCTTACTGGACGGTAACTGACGTTGAGGCTCGAAAGCGTGGGGAGCAAAC
AGGATTAGATACCCTGGTAGTCCACGCCGTAAACGATGAATACTAGGTGTCGGGTGGCAAAGCCATTCGGTGCCGCA
GCAAACGCAATAAGTATTCCACCTGGGGAGTACGTTCGCAAGAATGAAACTCAAAGGAATTGACGGGACCCGCACA
AGCGGTGGAGCATGTGGTTTAATTCGAAGCAACGCGAAGAACCTTACCAAGTCTTGACATCCCTCTGACCGGCCCGT
AACGGGGCCTTCCCTTCGGGGCAGAGGAGACAGGTGGTGCATGGTTGTCGTCAGCTCGTGTCGTGAGATGTTGGGTT
AAGTCCCGCAACGAGCGCAACCCCTATCCTTAGTAGCCAGCAGGTGAAGCTGGGCACTCTAGGGAGACTGCCGGGGA
TAACCCGGAGGAAGGCGGGGACGACGTCAAATCATCATGCCCCTTATGATTTGGGCTACACACGTGCTACAATGGCG
TAAACAAAGGGAAGCGAGACAGCGATGTTGAGCAAATCCCAAAAATAACGTCCTAGTTCGGACTGCAGTCTGCAACT
CGACTGCACGAAGCTGGAATCGCTAGTAATCGCGAATCAGAATGTCGCGGTGAATACGTTCCCGGGTCTTGTACACA
CCGCCCGTCACACCATGGGAGTCAGTAACGCCCGAAGTCAGTGACCCAACCTTACAGGAGGGAGCTGCCGAAGGCGG
GACCGATAACTGGGGTGAAGTCGTAACAAGGTAGCCGTATCGGAAGGTGCGGCTGGATCACCTCCTTT
>SEQ ID NO: 146 | PROKKA_00208 16S ribosomal RNA gene
AACGAGAGTTTGATCCTGGCTCAGGATGAACGCTGGCGGCGTGCTTAACACATGCAAGTCGAGCGAAGCACTTAAGT
TTGATTCTTCGGATGAAGACTTTTGTGACTGAGCGGCGGACGGGTGAGTAACGCGTGGGTAACCTGCCTCATACAGG
GGGATAACAGTTAGAAATGACTGCTAATACCGCATAAGACCACGGTACCGCATGGTACAGTGGTAAAAACTCCGGTG
GTATGAGATGGACCCGCGTCTGATTAGGTAGTTGGTGGGGTAACGGCCTACCAAGCCGACGATCAGTAGCCGACCTG
AGAGGGTGACCGGCCACATTGGGACTGAGACACGGCCCAGACTCCTACGGGAGGCAGCAGTGGGGAATATTGCACAA
TGGAGGAAACTCTGATGCAGCGACGCCGCGTGAAGGATGAAGTATTTCGGTATGTAAACTTCTATCAGCAGGGAAGA
AAATGACGGTACCTGACTAAGAAGCCCCGGCTAACTACGTGCCAGCAGCCGCGGTAATACGTAGGGGGCAAGCGTTA
TCCGGATTTACTGGGTGTAAAGGGAGCGTAGACGGCACGGCAAGCCAGATGTGAAAGCCCGGGGCTCAACCCCGGGA
CTGCATTTGGAACTGCTGAGCTAGAGTGTCGGAGAGGCAAGTGGAATTCCTAGTGTAGCGGTGAAATGCGTAGATAT
TAGGAGGAACACCAGTGGCGAAGGCGGCTTGCTGGACGATGACTGACGTTGAGGCTCGAAAGCGTGGGGAGCAAACA
GGATTAGATACCCTGGTAGTCCACGCCGTAAACGATGACTGCTAGGTGTCGGGTGGCAAAGCCATTCGGTGCCGCAG
CTAACGCAATAAGCAGTCCACCTGGGGAGTACGTTCGCAAGAATGAAACTCAAAGGAATTGACGGGACCCGCACAA
GCGGTGGAGCATGTGGTTTAATTCGAAGCAACGCGAAGAACCTTACCTGATCTTGACATCCCGATGACCGCTTCGTA
ATGGAAGTTTTTCTTCGGAACATCGGTGACAGGTGGTGCATGGTTGTCGTCAGCTCGTGTCGTGAGATGTTGGGTTA
AGTCCCGCAACGAGCGCAACCCCTATCTTCAGTAGCCAGCAGGTTAAGCTGGGCACTCTGGAGACTGCCAGGGAT
AACCTGGAGGAAGGTGGGGATGACGTCAAATCATCATGCCCCTTATGACCAGGGCTACACACGTGCTACAATGGCGT
AAACAAAGAGAAGCGAACTCGCGAGGGTAAGCAAATCTCAAAAATAACGTCTCAGTTCGGATTGTAGTCTGCAACTC
GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 147 | PROKKA_00340 16S ribosomal RNA gene
AACGAGAGTTTGATCCTGGCTCAGGATGAACGCTGGCGGCGTGCTTAACACATGCAAGTCGAGCGAAGCACTTTGGA

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGCTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

ACCTGGAGGAAGGTGGGGATGACGTCAAATCATCATGCCCCTTATGACCAGGGCTACACACGTGCTACAATGGCGTA

AACAAAGAGAAGCGAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT

>SEQ ID NO: 148 | PROKKA_01031 16S ribosomal RNA gene
AACGAGAGTTTGATCCTGGCTCAGGATGAACGCTGGCGGCGTGCTTAACACATGCAAGTCGAGCGAAGCACTTAAGT

TTGATTCTTCGGATGAAGACTTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGATCTTGACATCCCGATGACCGCTTCGTA

ATGGAAGCTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 149 | PROKKA_01840 16S ribosomal RNA gene
AACGAGAGTTTGATCCTGGCTCAGGATGAACGCTGGCGGCGTGCTTAACACATGCAAGTCGAGCGAAGCACTTTGGA

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGGACCCGCACAA

GCGGTGGAGCATGTGGTTTAATTCGAAGCAACGCGAAGAACCTTACCTGATCTTGACATCCCGATGACCGCTTCGTA

ATGGAAGCTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT

>SEQ ID NO: 150 | PROKKA_02944 16S ribosomal RNA gene
AACGAGAGTTTGATCCTGGCTCAGGATGAACGCTGGCGGCGTGCTTAACACATGCAAGTCGAGCGAAGCGCTTAAGT

TTGATTCTTCGGATGAAGACTTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTCTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGCTCAACCCCGGGAC

TGCATTTGGAACTGCTGAGCTAGAGTGTCGGAGAGGCAAGTGGAATTCCTAGTGTAGCGGTGAAATGCGTAGATATT

AGGAGGAACACCAGTGGCGAAGGCGGCTTGCTGGACGATGACTGACGTTGAGGCTCGAAAGCGTGGGGAGCAAACAG

GATTAGATACCCTGGTAGTCCACGCCGTAAACGATGACTGCTAGGTGTCGGGTGGCAAAGCCATTCGGTGCCGCAGC

TAACGCAATAAGCAGTCCACCTGGGGAGTACGTTCGCAAGAATGAAACTCAAAGGAATTGACGGGGACCCGCACAAG

CGGTGGAGCATGTGGTTTAATTCGAAGCAACGCGAAGAACCTTACCTGATCTTGACATCCCGATGACCGCTTCGTAA

TGGAAGTTTTTCTTCGGAACATCGGTGACAGGTGGTGCATGGTTGTCGTCAGCTCGTGTCGTGAGATGTTGGGTTAA

GTCCCGCAACGAGCGCAACCCCTATCTTCAGTAGCCAGCAGGTTAAGCTGGGCACTCTGGAGAGACTGCCAGGGATA

```
ACCTGGAGGAAGGTGGGGATGACGTCAAATCATCATGCCCCTTATGACCAGGGCTACACACGTGCTACAATGGCGTA

AACAAAGAGAGGCAAACTCGCGAGGGTAAGCAAATCTCAAAAATAACGTCTCAGTTCGGATTGTAGTCTGCAACTCG

ACTACATGAAGCTGGAATCGCTAGTAATCGCAGATCAGAATGCTGCGGTGAATACGTTCCCGGGTCTTGTACACACC

GCCCGTCACACCATGGGAGTCAGTAACGCCCGAAGTCAGTGACCCAACCGTAAGGAGGGAGCTGCCGAAGGTGGGAC

CGATAACTGGGGTGAAGTCGTAACAAGGTAGCCGTATCGGAAGGTGCGGCTGGATCACCTCCTTT
```

>SEQ ID NO: 151 | PROKKA_04036 16S ribosomal RNA gene
```
AACGAGAGTTTGATCCTGGCTCAGGATGAACGCTGGCGGCGTGCTTAACACATGCAAGTCGAGCGAAGCGCTTTGGG

AAGATTCTTCGGATGATTTCCTTTGTGACTGAGCGGCGGACGGGTGAGTAACGCGTGGGTAACCTGCCTCATACAGG

GGGATAACAGTTAGAAATGACTGCTAATACCGCATAAGACCACGGTACCGCATGGTACAGTGGTAAAAACTCCGGTG

GTATGAGATGGACCCGCGTTTGATTAGGTAGTTGGTGGGGTAACGGCCTACCAAGCCGACGATCAGTAGCCGACCTG

AGAGGGTGACCGGCCACATTGGGACTGAGACACGGCCCAGACTCCTACGGGAGGCAGCAGTGGGGAATATTGCACAA

TGGAGGAAACTCTGATGCAGCGACGCCGCGTGAAGGATGAAGTATTTCGGTATGTAAACTTCTATCAGCAGGGAAGA

AAATGACGGTACCTGACTAAGAAGCCCCGGCTAACTACGTGCCAGCAGCCGCGGTAATACGTAGGGGGCAAGCGTTA

TCCGGATTTACTGGGTGTAAAGGGAGCGTAGACGGCACGGCAAGCCAGATGTGAAAGCCCGGGGCTCAACCCCGGGA

CTGCATTTGGAACTGCTGAGCTAGAGTGTCGGAGAGGCAAGTGGAATTCCTAGTGTAGCGGTGAAATGCGTAGATAT

TAGGAGGAACACCAGTGGCGAAGGCGGCTTGCTGGACGATGACTGACGTTGAGGCTCGAAAGCGTGGGGAGCAAACA

GGATTAGATACCCTGGTAGTCCACGCCGTAAACGATGACTGCTAGGTGTCGGGTGGCAAAGCCATTCGGTGCCGCAG

CTAACGCAATAAGCAGTCCACCTGGGGAGTACGTTCGCAAGAATGAAACTCAAAGGAATTGACGGGACCCGCACAA

GCGGTGGAGCATGTGGTTTAATTCGAAGCAACGCGAAGAACCTTACCTGATCTTGACATCCCGATGACTGCTTCGTA

ATGGAAGTTTTTCTTCGGAACATCGGTGACAGGTGGTGCATGGTTGTCGTCAGCTCGTGTCGTGAGATGTTGGGTTA

AGTCCCGCAACGAGCGCAACCCCTATCTTCAGTAGCCAGCAGGTTAAGCTGGGCACTCTGGAGAGACTGCCAGGGAT

AACCTGGAGGAAGGTGGGGATGACGTCAAATCATCATGCCCCTTATGACCAGGGCTACACACGTGCTACAATGGCGT

AAACAAAGAGAAGCGAACTCGCGAGGGTAAGCAAATCTCAAAAATAACGTCTCAGTTCGGATTGTAGTCTGCAACTC

GACTACATGAAGCTGGAATCGCTAGTAATCGCAGATCAGAATGCTGCGGTGAATACGTTCCCGGGTCTTGTACACAC

CGCCCGTCACACCATGGGAGTCAGTAACGCCCGAAGTCAGTGACCCAACCGTAAGGAGGGAGCTGCCGAAGGTGGGA

CCGATAACTGGGGTGAAGTCGTAACAAGGTAGCCGTATCGGAAGGTGCGGCTGGATCACCTCCTTT
```

>SEQ ID NO: 152 | PROKKA_00437 16S ribosomal RNA gene
```
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCTCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGAA

ACAAATACCCTAGAGATAGGGGGATAATTATGGATCACACAGGTGGTGCATGGTTGTCGTCAGCTCGTGTCGTGAGA
```

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 153 | PROKKA_00896 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 154 | PROKKA_02845 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCTCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 155 | PROKKA_04164 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGACCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGCAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 156 | PROKKA_04921 16S ribosomal RNA gene
ATGGAGAGTTTGATCCTGGCTCAGGATGAACGCTGGCGGCATGCCTAATACATGCAAGTCGAACGAAGTTTCGAGGA

AGCTTGCTTCCAAAGAGACTTAGTGGCGAACGGGTGAGTAACACGTAGGTAACCTGCCCATGTGTCCGGATAACTG

CTGGAAACGGTAGCTAAAACCGGATAGGTATACAGAGCGCATGCTCAGTATATTAAAGCGCCCATCAAGGCGTGAAC

ATGGATGGACCTGCGGCGCATTAGCTAGTTGGTGAGGTAACGGCCCACCAAGGCGATGATGCGTAGCCGGCCTGAGA

GGGTAAACGGCCACATTGGGACTGAGACACGGCCCAAACTCCTACGGGAGGCAGCAGTAGGGAATTTTCGTCAATGG

GGGAAACCCTGAACGAGCAATGCCGCGTGAGTGAAGAAGGTCTTCGGATCGTAAAGCTCTGTTGTAAGTGAAGAACG

GCTCATAGAGGAAATGCTATGGGAGTGACGGTAGCTTACCAGAAAGCCACGGCTAACTACGTGCCAGCAGCCGCGGT

AATACGTAGGTGGCAAGCGTTATCCGGAATCATTGGGCGTAAAGGGTGCGTAGGTGGCGTACTAAGTCTGTAGTAAA

AGGCAATGGCTCAACCATTGTAAGCTATGGAAACTGGTATGCTGGAGTGCAGAAGAGGGCGATGGAATTCCATGTGT

AGCGGTAAAATGCGTAGATATATGGAGGAACACCAGTGGCGAAGGCGGTCGCCTGGTCTGTAACTGACACTGAGGCA

CGAAAGCGTGGGGAGCAAATAGGATTAGATACCCTAGTAGTCCACGCCGTAAACGATGAGAACTAAGTGTTGGAGGA

ATTCAGTGCTGCAGTTAACGCAATAAGTTCTCCGCCTGGGGAGTATGCACGCAAGTGTGAAACTCAAAGGAATTGAC

GGGGGCCCGCACAAGCGGTGGAGTATGTGGTTTAATTCGAAGCAACGCGAAGAACCTTACCAGGCCTTGACATGGAA

ACAAATACCCTAGAGATAGGGGGATAATTATGGATCACACAGGTGGTGCATGGTTGTCGTCAGCTCGTGTCGTGAGA

TGTTGGGTTAAGTCCCGCAACGAGCGCAACCCTTGTCGCATGTTACCAGCATCAAGTTGGGGACTCATGCGAGACTG

CCGGTGACAAACCGGAGGAAGGTGGGGATGACGTCAAATCATCATGCCCCTTATGGCCTGGGCTACACACGTACTAC

AATGGCGGCCACAAAGAGCAGCGACACAGTGATGTGAAGCGAATCTCATAAAGGTCGTCTCAGTTCGGATTGAAGTC

TGCAACTCGACTTCATGAAGTCGGAATCGCTAGTAATCGCAGATCAGCATGCTGCGGTGAATACGTTCTCGGGCCTT

GTACACACCGCCCGTCAAACCATGGGAGTCAGTAATACCCGAAGCCGGTGGCATAACCGTAAGGAGTGAGCCGTCGA

AGGTAGGACCGATGACTGGGGTTAAGTCGTAACAAGGTATCCCTACGGGAACGTGGGGATGGATCACCTCCTTT

>SEQ ID NO: 157 | PROKKA_00199 16S ribosomal RNA gene
TATTGAGAGTTTGATCCTGGCTCAGGATGAACGCTGGCGGCGTGCTTAACACATGCAAGTCGAACGGGGTGCTCATG

ACGGAGGATTCGTCCAACGGATTGAGTTACCTAGTGGCGGACGGGTGAGTAACGCGTGAGGAACCTGCCTTGGAGAG

GGGAATAACACTCCGAAAGGAGTGCTAATACCGCATGATGCAGTTGGGTCGCATGGCTCTGACTGCCAAAGATTTAT

CGCTCTGAGATGGCCTCGCGTCTGATTAGCTAGTAGGCGGGGTAACGGCCCACCTAGGCGACGATCAGTAGCCGGAC

TGAGAGGTTGACCGGCCACATTGGGACTGAGACACGGCCCAGACTCCTACGGGAGGCAGCAGTGGGGAATATTGGGC

AATGGGCGCAAGCCTGACCCAGCAACGCCGCGTGAAGGAAGAAGGCTTTCGGGTTGTAAACTTCTTTTGTCGGGGAC

GAAACAAATGACGGTACCCGACGAATAAGCCACGGCTAACTACGTGCCAGCAGCCGCGGTAATACGTAGGTGGCAAG

CGTTATCCGGATTTACTGGGTGTAAAGGGCGTGTAGGCGGGATTGCAAGTCAGATGTGAAAACTGGGGGCTCAACCT

CCAGCCTGCATTTGAAACTGTAGTTCTTGAGTGCTGGAGAGGCAATCGGAATTCCGTGTGTAGCGGTGAAATGCGTA

GATATACGGAGGAACACCAGTGGCGAAGGCGGATTGCTGGACAGTAACTGACGCTGAGGCGCGAAAGCGTGGGGAGC

AAACAGGATTAGATACCCTGGTAGTCCACGCCGTAAACGATGGATACTAGGTGTGGGGGTCTGACCCCCTCCGTGCC

GCAGTTAACACAATAAGTATCCCACCTGGGGAGTACGATCGCAAGGTTGAAACTCAAAGGAATTGACGGGGGCCCGC

ACAAGCGGTGGAGTATGTGGTTTAATTCGAAGCAACGCGAAGAACCTTACCAGGGCTTGACATCCCACTAACGAAGC

AGAGATGCATTAGGTGCCCTTCGGGGAAAGTGGAGACAGGTGGTGCATGGTTGTCGTCAGCTCGTGTCGTGAGATGT

TGGGTTAAGTCCCGCAACGAGCGCAACCCTTATTGTTAGTTGCTACGCAAGAGCACTCTAGCGAGACTGCCGTTGAC

AAAACGGAGGAAGGTGGGGACGACGTCAAATCATCATGCCCCTTATGTCCTGGGCCACACACGTACTACAATGGTGG

TTAACAGAGGGAGGCAATACCGCGAGGTGGAGCAAATCCCTAAAAGCCATCCCAGTTCGGATTGCAGGCTGAAACCC

GCCTGTATGAAGTTGGAATCGCTAGTAATCGCGGATCAGCATGCCGCGGTGAATACGTTCCCGGGCCTTGTACACAC

CGCCCGTCACACCATGAGAGTCGGGAACACCCGAAGTCCGTAGCCTAACCGCAAGGAGGGCGCGGCCGAAGGTGGGT

TCGATAATTGGGGTGAAGTCGTAACAAGGTAGCCGTATCGGAAGGTGCGGCTGGATCACCTCCTTT

>SEQ ID NO: 158 | PROKKA_00208 16S ribosomal RNA gene
TATTGAGAGTTTGATCCTGGCTCAGGATGAACGCTGGCGGCGTGCTTAACACATGCAAGTCGAACGGGGTGCTCATG

ACGGAGGATTCGTCCAACGGATTGAGTTACCTAGTGGCGGACGGGTGAGTAACGCGTGAGGAACCTGCCTTGGAGAG

GGGAATAACACTCCGAAAGGAGTGCTAATACCGCATGATGCAGTTGGGTCGCATGGCTCTGACTGCCAAAGATTTAT

CGCTCTGAGATGGCCTCGCGTCTGATTAGCTAGTAGGCGGGGTAACGGCCCACCTAGGCGACGATCAGTAGCCGGAC

TGAGAGGTTGACCGGCCACATTGGGACTGAGACACGGCCCAGACTCCTACGGGAGGCAGCAGTGGGGAATATTGGGC

AATGGGCGCAAGCCTGACCCAGCAACGCCGCGTGAAGGAAGAAGGCTTTCGGGTTGTAAACTTCTTTTGTCGGGGAC

GAAACAAATGACGGTACCCGACGAATAAGCCACGGCTAACTACGTGCCAGCAGCCGCGGTAATACGTAGGTGGCAAG

CGTTATCCGGATTTACTGGGTGTAAAGGGCGTGTAGGCGGGATTGCAAGTCAGATGTGAAAACTGGGGGCTCAACCT

CCAGCCTGCATTTGAAACTGTAGTTCTTGAGTGCTGGAGAGGCAATCGGAATTCCGTGTGTAGCGGTGAAATGCGTA

```
GATATACGGAGGAACACCAGTGGCGAAGGCGGATTGCTGGACAGTAACTGACGCTGAGGCGCGAAAGCGTGGGAGC

AAACAGGATTAGATACCCTGGTAGTCCACGCCGTAAACGATGGATACTAGGTGTGGGGGGTCTGACCCCCTCCGTGC

CGCAGTTAACACAATAAGTATCCCACCTGGGGAGTACGATCGCAAGGTTGAAACTCAAAGGAATTGACGGGGCCCG

CACAAGCGGTGGAGTATGTGGTTTAATTCGAAGCAACGCGAAGAACCTTACCAGGGCTTGACATCCCACTAACGAAG

CAGAGATGCATTAGGTGCCCTTCGGGGAAAGTGGAGACAGGTGGTGCATGGTTGTCGTCAGCTCGTGTCGTGAGATG

TTGGGTTAAGTCCCGCAACGAGCGCAACCCTTATTGTTAGTTGCTACGCAAGAGCACTCTAGCGAGACTGCCGTTGA

CAAAACGGAGGAAGGTGGGGACGACGTCAAATCATCATGCCCCTTATGTCCTGGGCCACACACGTACTACAATGGTG

GTTAACAGAGGGAGGCAATACCGCGAGGTGGAGCAAATCCCTAAAAGCCATCCCAGTTCGGATTGCAGGCTGAAACC

CGCCTGTATGAAGTTGGAATCGCTAGTAATCGCGGATCAGCATGCCGCGGTGAATACGTTCCCGGGCCTTGTACACA

CCGCCCGTCACACCATGAGAGTCGGGAACACCCGAAGTCCGTAGCCTAACCGCAAGGAGGGCGCGGCCGAAGGTGGG

TTCGATAATTGGGGTGAAGTCGTAACAAGGTAGCCGTATCGGAAGGTGCGGCTGGATCACCTCCTTT
>SEQ ID NO: 159 | PROKKA_04460 16S ribosomal RNA gene
TATTGAGAGTTTGATCCTGGCTCAGGATGAACGCTGGCGGCGTGCTTAACACATGCAAGTCGAACGGGGTGCTCATG

ACGGAGGATTCGTCCAACGGATTGAGTTACCTAGTGGCGGACGGGTGAGTAACGCGTGAGGAACCTGCCTTGGAGAG

GGGAATAACACTCCGAAAGGAGTGCTAATACCGCATAATGCAGTTGGGTCGCATGGCTCTGACTGCCAAAGATTTAT

CGCTCTGAGATGGCCTCGCGTCTGATTAGCTAGTAGGCGGGTAACGGCCCACCTAGGCGACGATCAGTAGCCGGAC

TGAGAGGTTGACCGGCCACATTGGGACTGAGACACGCCCAGACTCCTACGGGAGGCAGCAGTGGGGAATATTGGGC

AATGGGCGCAAGCCTGACCCAGCAACGCCGCGTGAAGGAAGAAGGCTTTCGGGTTGTAAACTTCTTTTGTCAGGGAC

GAAACAAATGACGGTACCTGACGAATAAGCCACGGCTAACTACGTGCCAGCAGCCGCGGTAATACGTAGGTGGCAAG

CGTTATCCGGATTTACTGGGTGTAAAGGGCGTGTAGGCGGGATTGCAAGTCAGATGTGAAAACTGGGGGCTCAACCT

CCAGCCTGCATTTGAAACTGTAGTTCTTGAGTGCTGGAGAGGCAATCGGAATTCCGTGTGTAGCGGTGAAATGCGTA

GATATACGGAGGAACACCAGTGGCGAAGGCGGATTGCTGGACAGTAACTGACGCTGAGGCGCGAAAGCGTGGGAGC

AAACAGGATTAGATACCCTGGTAGTCCACGCCGTAAACGATGGATACTAGGTGTGGGGGGTCTGACCCCTCCGTGCC

GCAGTTAACACAATAAGTATCCCACCTGGGGAGTACGATCGCAAGGTTGAAACTCAAAGGAATTGACGGGGCCCGC

ACAAGCGGTGGAGTATGTGGTTTAATTCGAAGCAACGCGAAGAACCTTACCAGGGCTTGACATCCCACTAACGAAGC

AGAGATGCATTAGGTGCCCTTCGGGGAAAGTGGAGACAGGTGGTGCATGGTTGTCGTCAGCTCGTGTCGTGAGATGT

TGGGTTAAGTCCCGCAACGAGCGCAACCCTTATTGTTAGTTGCTACGCAAGAGCACTCTAGCGAGACTGCCGTTGAC

AAAACGGAGGAAGGTGGGGACGACGTCAAATCATCATGCCCCTTATGTCCTGGGCCACACACGTACTACAATGGTGG

TTAACAGGGGAGGCAATACCGCGAGGTGGAGCAAATCCCTAAAAGCCATCCCAGTTCGGATTGCAGGCTGAAACCC

GCCTGTATGAAGTTGGAATCGCTAGTAATCGCGGATCAGCATGCCGCGGTGAATACGTTCCCGGGCCTTGTACACAC

CGCCCGTCACACCATGAGAGTCGGGAACACCCGAAGTCCGTAGCCTAACCGCAAGGAGGGCGCGGCCGAAGGTGGGT

TCGATAATTGGGGTGAAGTCGTAACAAGGTAGCCGTATCGGAAGGTGCGGCTGGATCACCTCCTTT
```

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Mouse Model of C. difficile Infection

Mouse Husbandry

Experiments were performed using C57BL/6J female mice purchased from Jackson Laboratories (Bar Harbor, ME) and housed in ventilated sterile cages. All animals were maintained in a specific-pathogen-free facility. Animals were acclimated to the vivarium for at least 3 days prior to study (i.e., commencing antibiotic courses). For experiments involving C. difficile infection, mice were administered $10$-$10^4$ C. difficile VPI 10463 spores in 200 µl PBS by oral gavage. Experiments were performed in compliance with institutional guidelines and approved by the institution's Institutional Animal Care and Use Committee. Sterile food and drinking water were provided to the animals Live Biotherapeutic Product (LBP) Preparation Individual bacterial strains were isolated from fecal material obtained from healthy donors. The individual strains were struck out from 15% glycerol freezer stocks onto EG (Eggerth Gagnon) agar plates containing 5% horse blood in an anaerobic chamber and incubated for 24-48 hours at 37° C. Colonies were inoculated into pre-reduced liquid Peptone Yeast Glucose (PYG) media and grown for 24-48 hours until dense (static in the anaerobic chamber). Optical density ($OD_{600}$) of the cultures was assessed and live biotherapeutic product (LBP) cocktails were prepared inside an anaerobic chamber adjusting inputs based upon $OD_{600}$ for equal CFU ratio cocktails in PBS (sterile, pre-treated).

C. difficile Colony Forming Unit (CFU) Determination

Fecal pellets were collected, transported to an anaerobic chamber (<2 hours), and manually homogenized in 500 µL of pre-reduced PBS using a pipette tip and through repeated pipetting. Serial dilutions of fecal homogenates were prepared in pre-reduced PBS, 100 µL of which was spread onto cycloserine-cefoxitin-fructose agar with sodium taurocholate (TCCFA) plates, and incubated anaerobically at 37° C. C. difficile CFUs were enumerated at 48 hours.

Murine Susceptibility to C. difficile Infection

Groups of mice were evaluated for susceptibility to C. difficile using three antibiotic regimen protocols: (1) an antibiotic cocktail, (2) clindamycin administration, or (3) cefoperazone administration (FIGS. 2 and 3). The antibiotic cocktail consisted of kanamycin (0.4 mg/ml), gentamicin (0.035 mg/ml), colistin (0.056 mg/ml), metronidazole (0.215 mg/ml), vancomycin (0.045 mg/ml) in the drinking water from day −10 to day −3, followed by a single intraperitoneal clindamycin injection (200 µg/mouse). The clindamycin administration involved a single intraperitoneal injection of clindamycin (200 µg/mouse) on day −1. The notation of days is relative to day 0, the day of C. difficile infection.

Figure 4J:
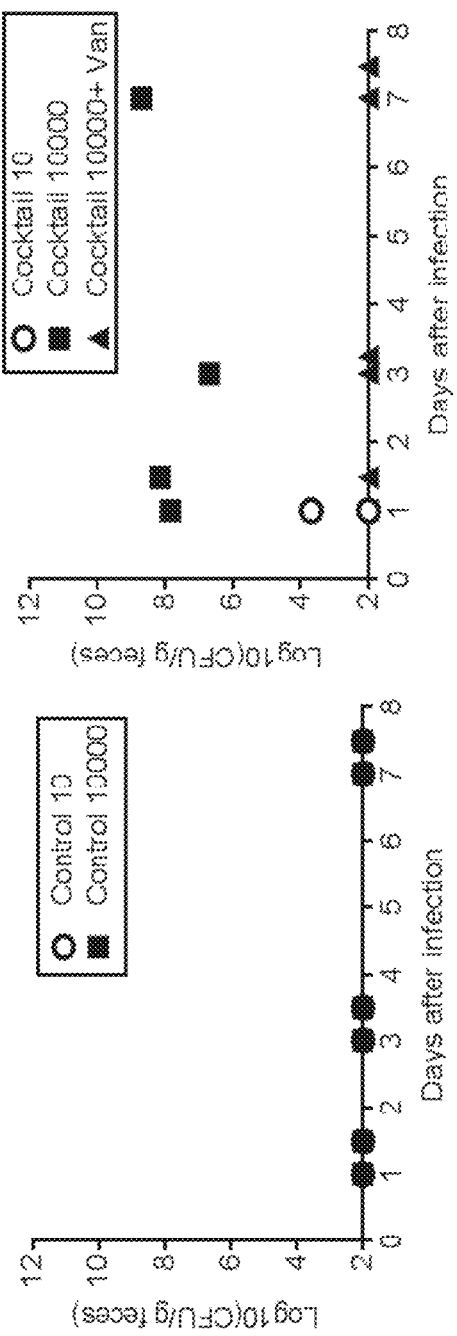
Figure 4K:
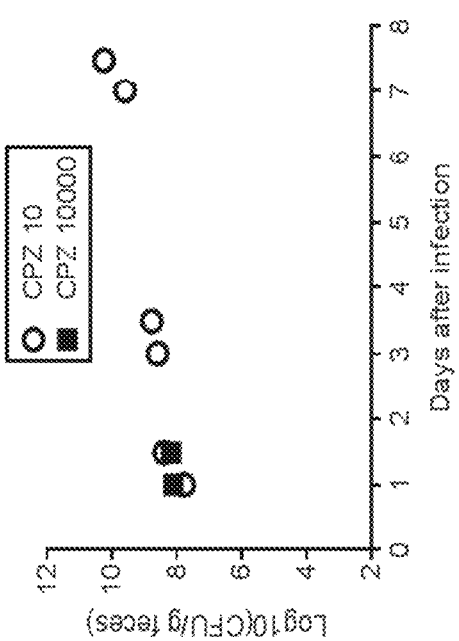
Figure 4L:
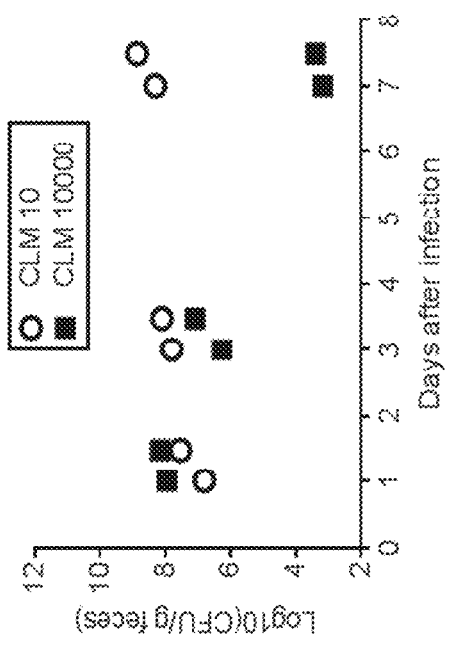

Mice were treated with the indicated antibiotic regimen as described above and then infected with either 10 or $10^4$ C. difficile spores by oral gavage on day 0 (FIGS. 2 and 3). An additional experimental arm was added to the antibiotic treatment model in which mice were treated with vancomycin after C. difficile infection (FIG. 4J; black triangles).

Mice were monitored daily following infection for mortality/survival (FIGS. 4A-4D) and weight (FIGS. 4E-4H). Fecal pellets were also collected daily and used for C. difficile CFU enumeration, presented as CFU/gram feces (FIGS. 4I-4L).

The groups of mice that received cefoperazone treatment had a significant change in weight (FIG. 4H) and substantial C. difficile bacterial load in the fecal pellets (FIG. 4L), even following administration with 10 C. difficile spores. These results indicated that the cefoperazone pre-treatment regimen provided a good model for C. difficile infection and for evaluating protection and/or treatment of C. difficile infection. In the absence of antibiotic treatment prior to infection, C. difficile infection was not established (FIG. 4I) and all mice survived (FIG. 4A) without significant change in body weight (FIG. 4E).

Example 2: Live Biotherapeutic Product (LBP) Preparations Protect Against C. difficile Infection The following LBP compositions were evaluated for their capacity to protect and/or treat C. difficile infection:
Composition A,
Composition B,
Composition C,
Composition D,
Composition E (See e.g., Narushima et al., Gut Microbes (2014) 5(3) 333-339), and
Composition I: a mixture of *Clostridium scindens*, *Pseudoflavonifractor capillosus* and *Blautia hansenii* (FIG. 5).

In general, LBP cocktails were mixed in PYG media, and each mouse was administered a dose by oral gavage in 250 µL pre-reduced PBS (media-free). For composition E, bacteria were mixed in equal volumes (not equal ratios/CFUs) and administered in a 250 µL dose. Each LBP of Compositions A-D contained $10^8$ CFUs total in a 250 µL dose, comprised of $10^7$ CFU of each of the bacterial strains (FIG. 1), for a total of $10^8$ CFU administered to each animal. Composition I contained a total of $10^6$ CFUs in a 250 µL dose (approximately 333,000 of each of the 3 bacteria mixed).

Figure 6:
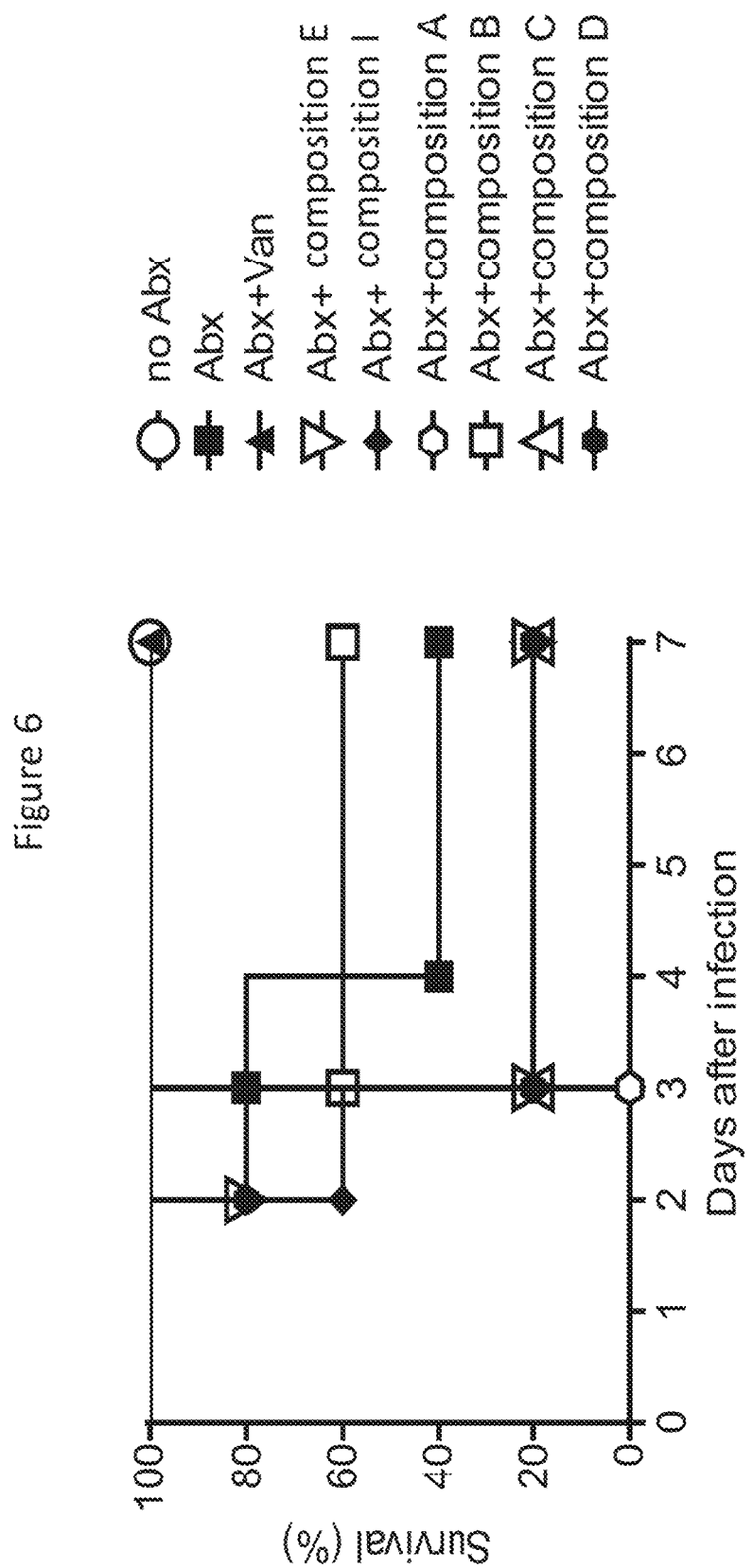
FIG. 6 shows survival of mice over time post infection with *C. difficile* spores, according to the experimental conditions shown in FIG. 5. Mice losing >20% body weight of baseline were included in mortality numbers in survival curves.
Figure 7A:
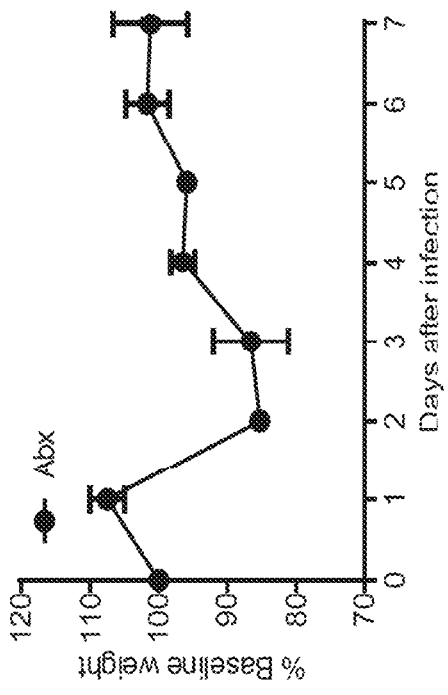
FIGS. 7A-7I show weight of the mice at various times post infection with *C. difficile* spores. Groups of mice received cefoperazone (Abx) treatment followed by the indicated composition, or no cefoperazone (no Abx), then were administered *C. difficile* spores.
Figure 7B:
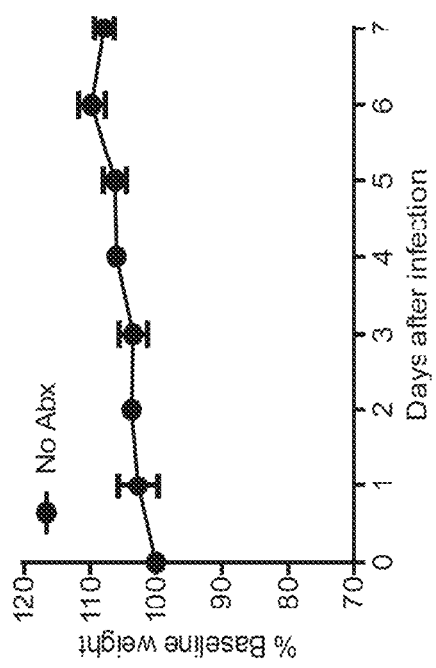
Figure 7C:
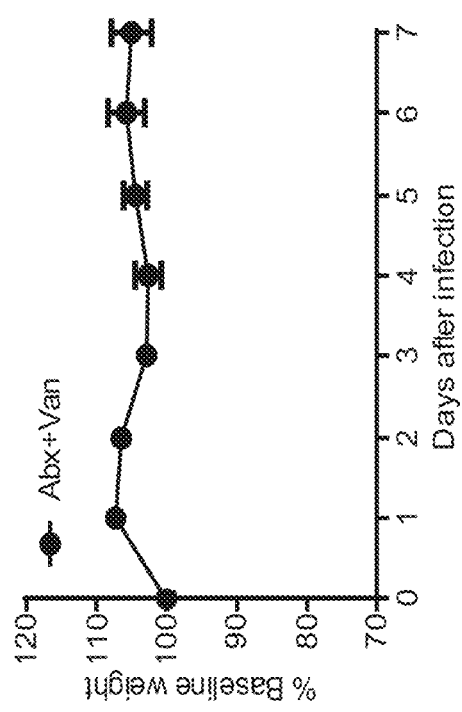
Figure 7E:
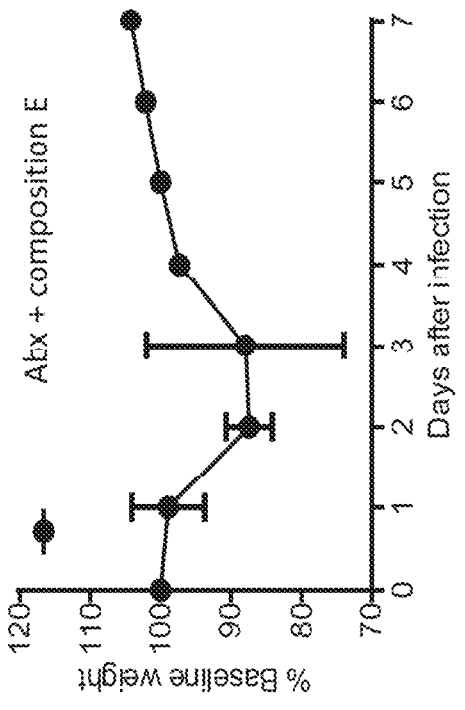
Figure 7D:
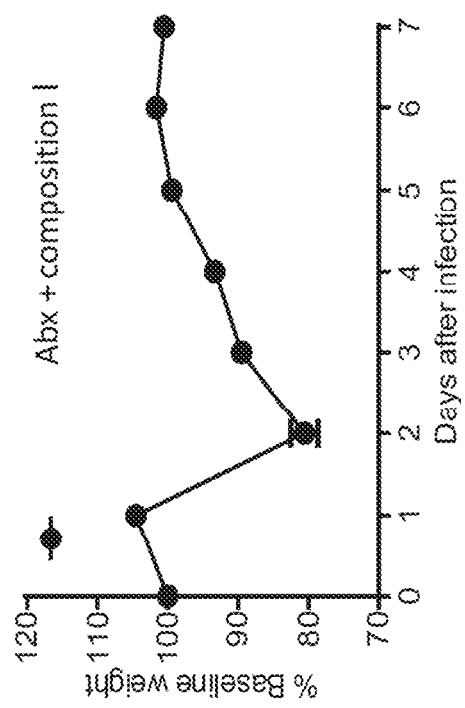
Figure 7F:
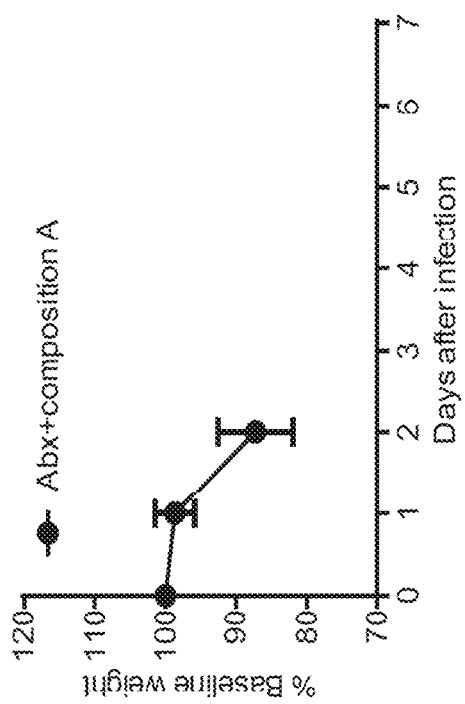
Figure 7G:
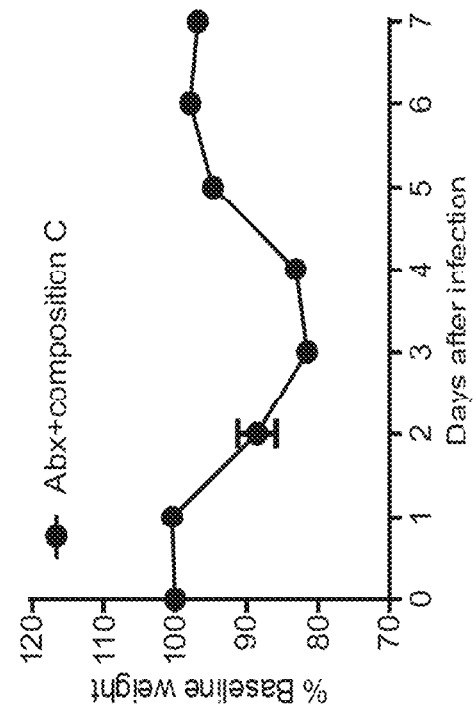
Figure 7H:
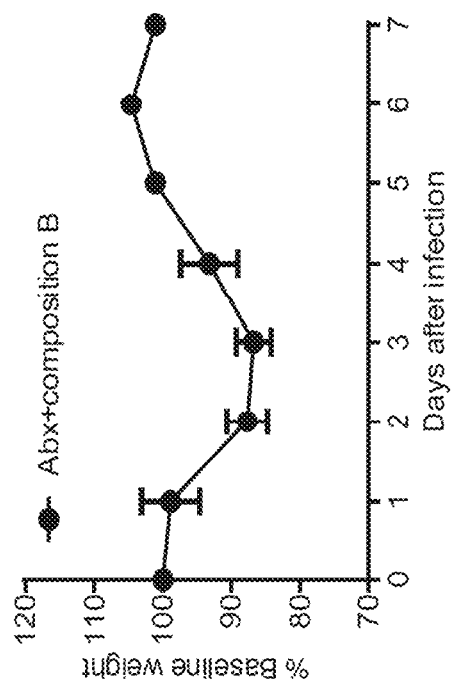
Figure 7I:
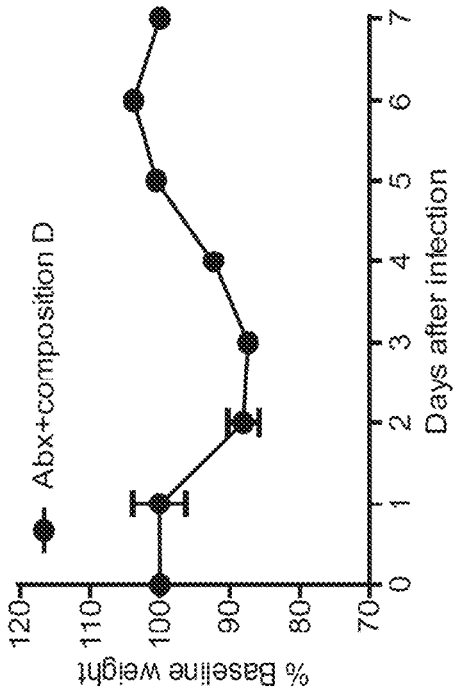
Figure 8A:
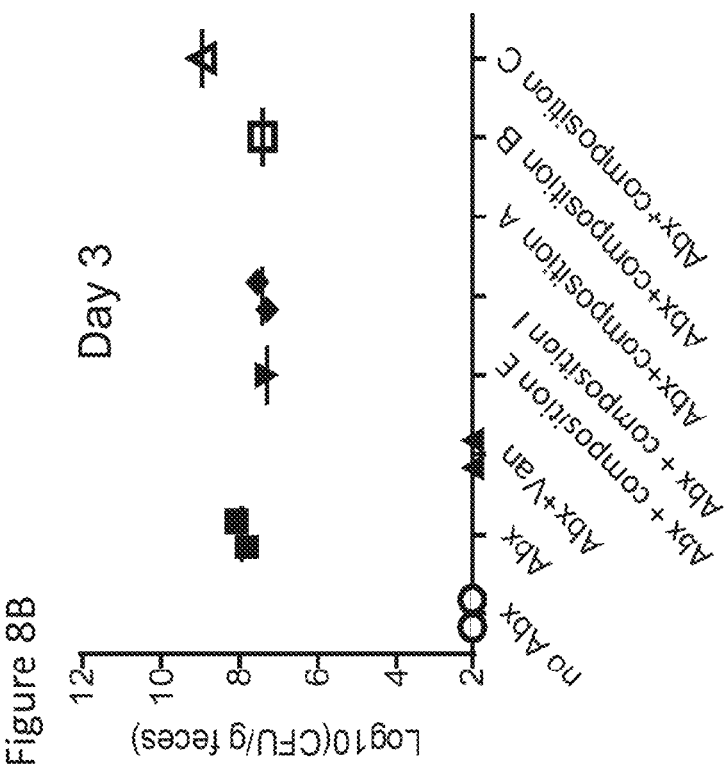
Figure 8B:
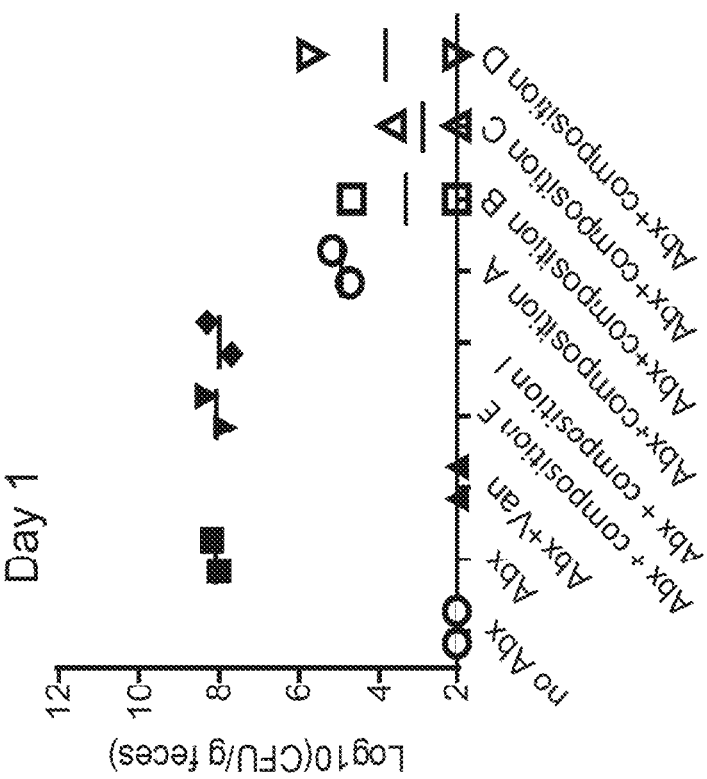

Groups of mice were subjected to cefoperazone treatment, as described in Example 1, and were administered the indicated composition by oral gavage 2 days after the cessation of cefoperazone treatment. Twenty-four hours later, the mice were subjected to infection with $10^4$ C. difficile spores (FIG. 5). Mice evaluated for survival/mortality (FIG. 6), weight (FIGS. 7A-7I, and C. difficile CFUs (FIGS. 8A-8C). The results show that administration of Composition B prior to C. difficile infection is an effective protection and/or treatment against C. difficile infection.

Figure 10:
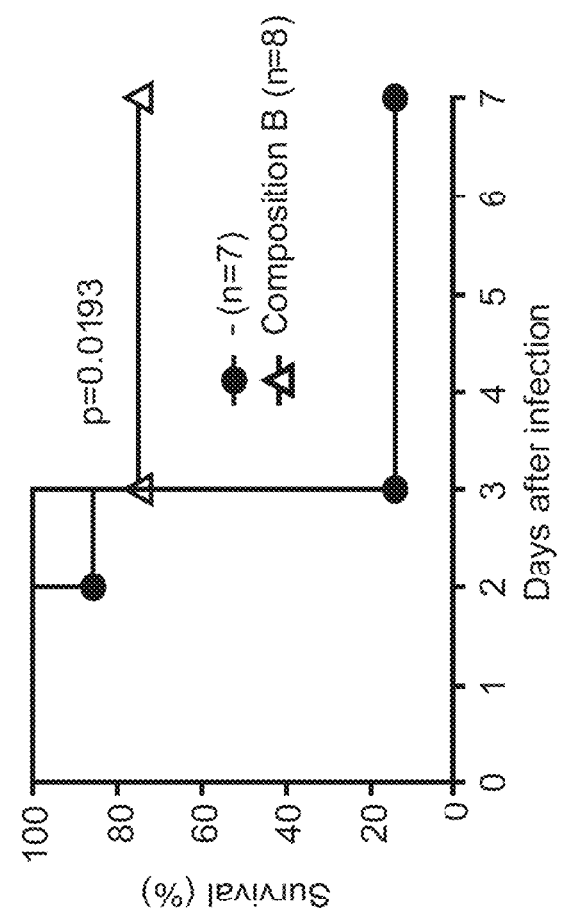
FIG. 10 shows survival of the mice over time post infection with *C. difficile* spores, according to the experimental conditions shown in FIG. 9. Mice losing >20% body weight of baseline were included in mortality numbers in survival curves.
Figure 11:
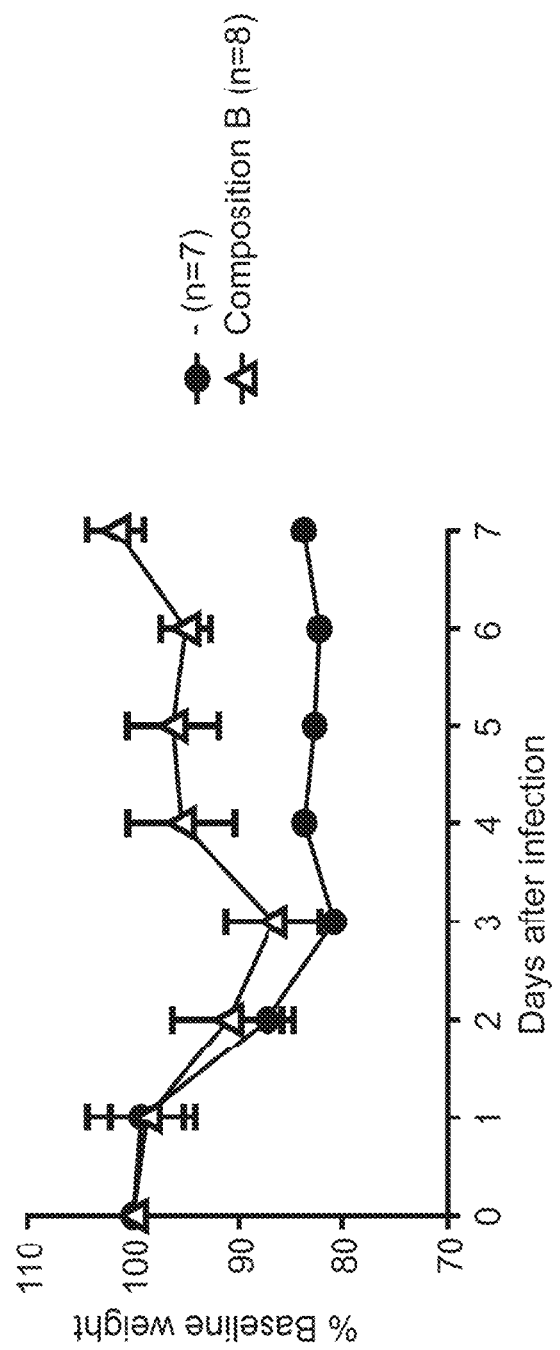
FIG. 11 shows weight of the mice at various times post infection with *C. difficile* spores.
Figure 17E:
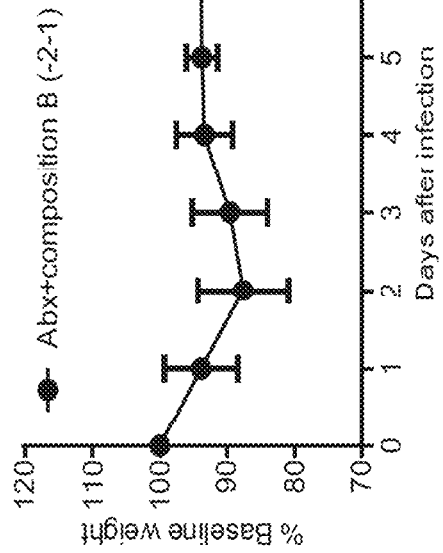
Figure 17D:
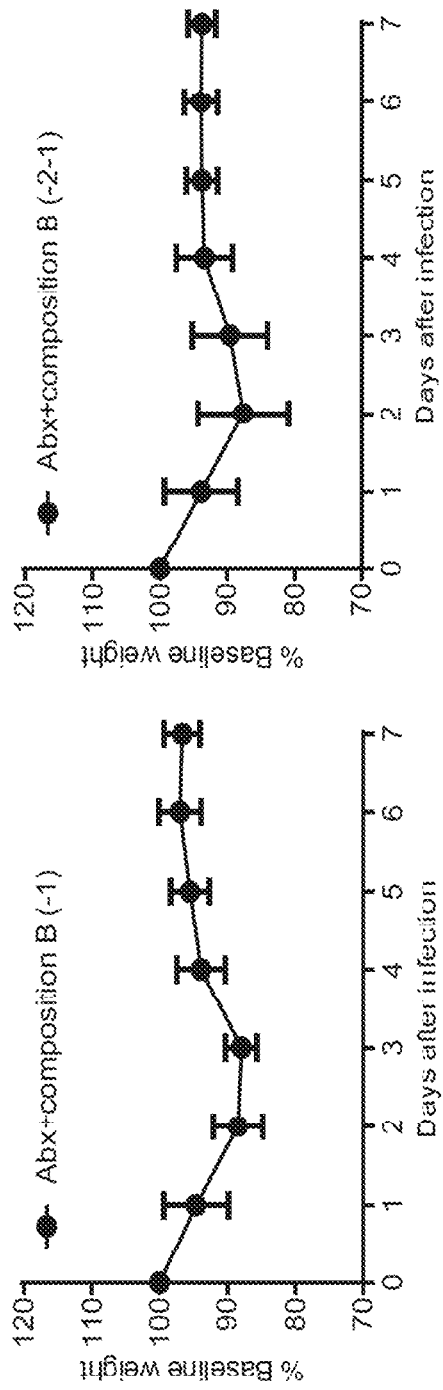
Figure 17F:
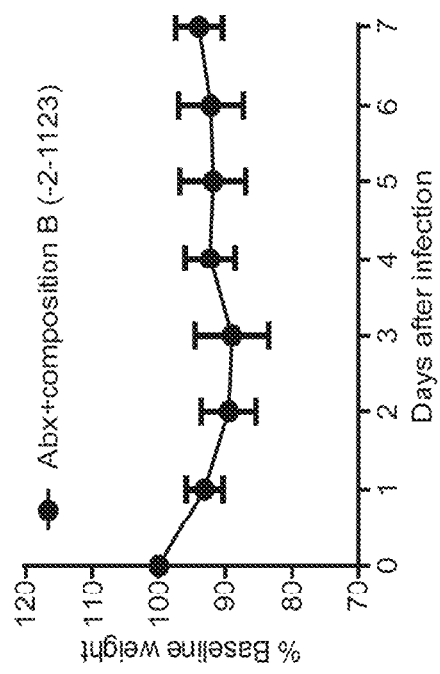
Figure 17G:
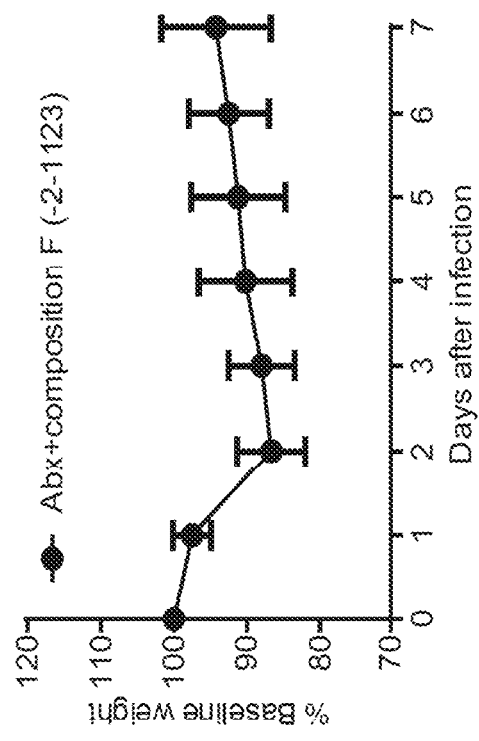
Figure 17H:
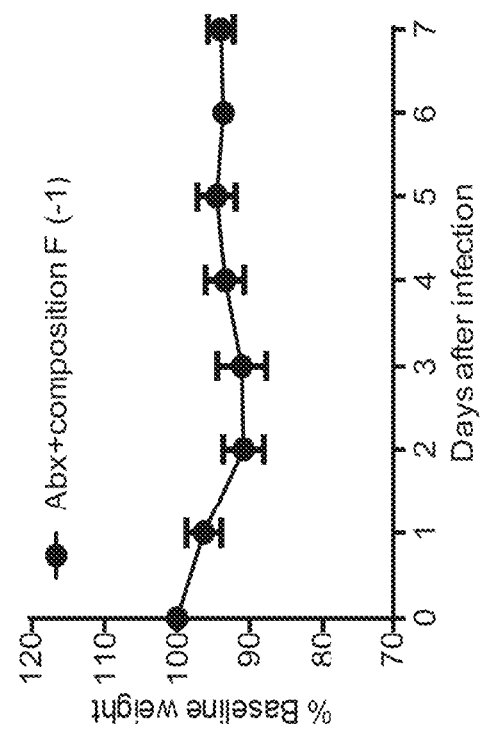

Example 3: Composition B Protects Against and/or Treats C. difficile Infection Groups of 10-12 week old mice were used in the C. difficile mouse model (FIG. 9). Mice were subjected to cefoperazone treatment as described in Example 1. One group of mice was then administered Composition B ($10^8$ CFU per mouse) administered by oral gavage, as described in Examples 1 and 2, 2 days after the cessation of cefoperazone treatment. The other group of mice did not receive a live biotherapeutic product after cefoperazone treatment (control). Twenty-four hours later, the mice were subjected to *C. difficile* infection ($10^4$ *C. difficile* spores) and then evaluated for survival/mortality (FIG. 10), weight (FIG. 11), and *C. difficile* burden (CFUs per gram feces; FIG. 12). These results confirm the results of Example 2 that demonstrate treatment with Composition B prior to *C. difficile* infection is an effective protection and/or treatment against *C. difficile* infection.

Example 4: LBP Composition F Protects Against and/or Treat *C. difficile* Infection FIG. 13 shows the strains of live biotherapeutic product (LBP) Composition F. The genus-species classification indicates the closest species based on the sequence of the isolated strain. FIG. 14 shows the classification by *Clostridium* cluster of the strains in Composition F.

Groups of mice were administered cefoperazone, as described in the Examples above, then administered LBPs or fecal matter transplant (FMT) from mice or human (FIG. 15). Composition B was administered to the indicated groups on day −1; days −2 and −1; or on days −2, −1, 1, 2, and 3, relative to infection with $10^4$ *C. difficile* spores. Composition F was administered to the indicated groups on day −1 or on days −2, −1, 1, 2, and 3, relative to administration of *C. difficile* spores. Additional groups received FMT from mice or from humans (200 µL of a 10% fecal sample s per mouse). Mice were then evaluated for survival/mortality (FIG. 16), weight (FIGS. 17A-17H), and *C. difficile* burden (CFU/gram feces) on days 1, 3, 8 and 17 after infection (FIGS. 18A and 18B). The data demonstrate that Composition B, Composition F, and FMT protect against and/or treat *C. difficile* infection.

Example 5: LBP Compositions Protect Against and/or Treat *C. difficile* Infection FIG. 19 shows the strains of LBP Composition G. The genus-species notation indicates the closest species based on the sequence of the isolated strain. Composition G includes a subset of the strains of Composition F. Groups of mice were administered cefoperazone, as described in the Examples above, then administered the LBP:
  Composition B;
  Composition B-1 (Composition B with *Bacteroides* added);
  Composition B-2 (Composition B from which *Flavonifractor plautii* was removed and *Bacteroides* added);
  Composition F;
  Composition G;
  Human fecal samples subjected to ethanol treatment;
  Composition B subjected to ethanol treatment;
  Composition B that had been frozen; or
  Composition J: *Clostridium innocuum, Clostridium bolteae* and *Clostridium symbiosum* subjected to ethanol treatment; (See also FIG. 20).
The *Bacteroides* strain used in Composition B-1 and B-2 was *Bacteroides ovatus* (strain identifier 211-B; SEQ ID NO: 83).

Figure 21:
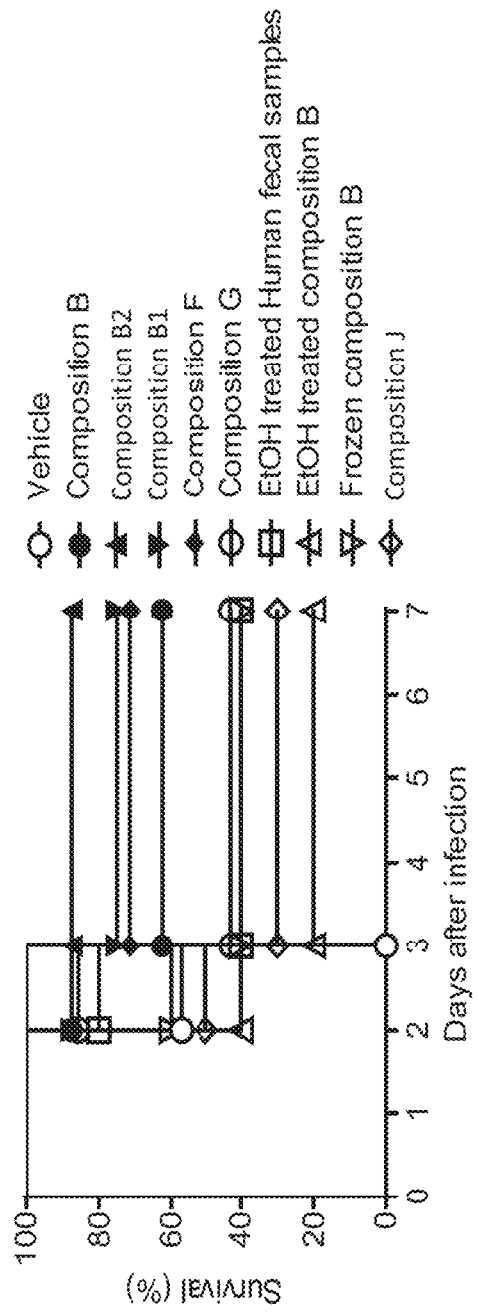
FIG. 21 shows survival of the mice over time post infection with *C. difficile* spores, according to the experimental conditions shown in FIG. 20. Mice losing >20% body weight of baseline were included in mortality numbers in survival curves.
Figure 22B:
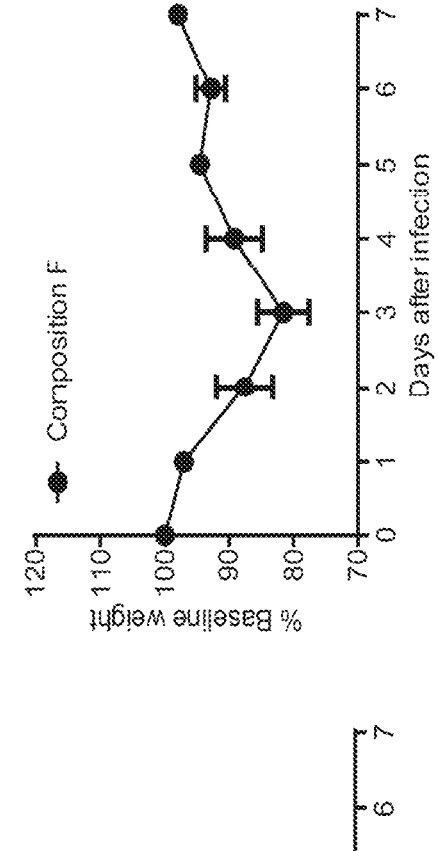
FIGS. 22A-22J show weight of the mice at various times post infection with *C. difficile* spores.
Figure 22A:
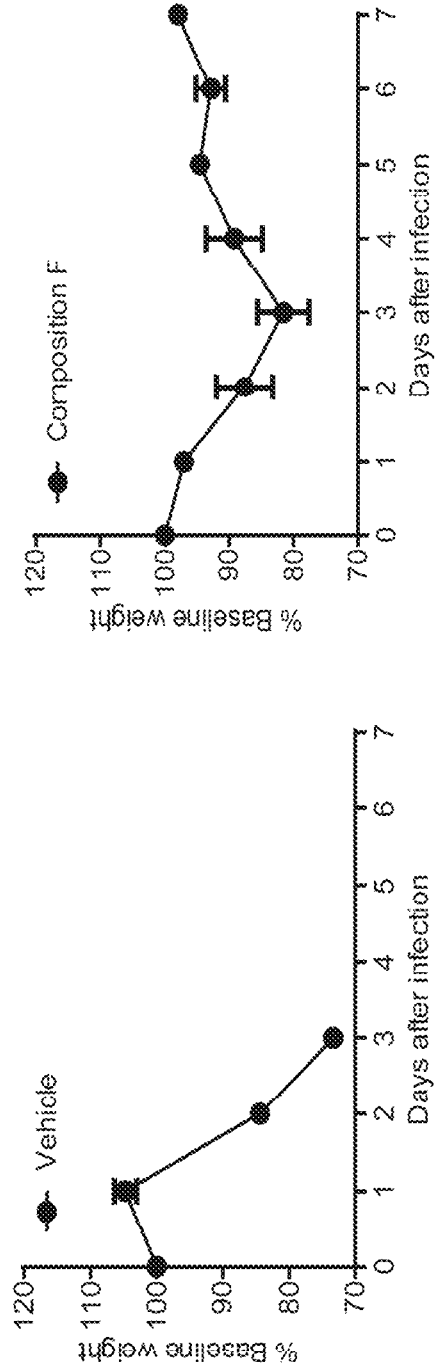
Figure 22C:
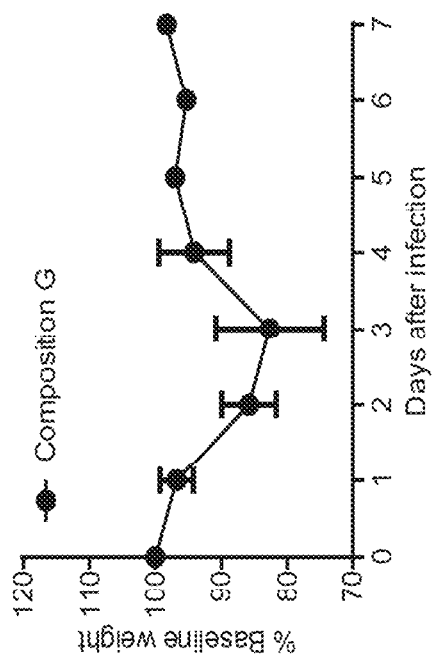
Figure 22D:
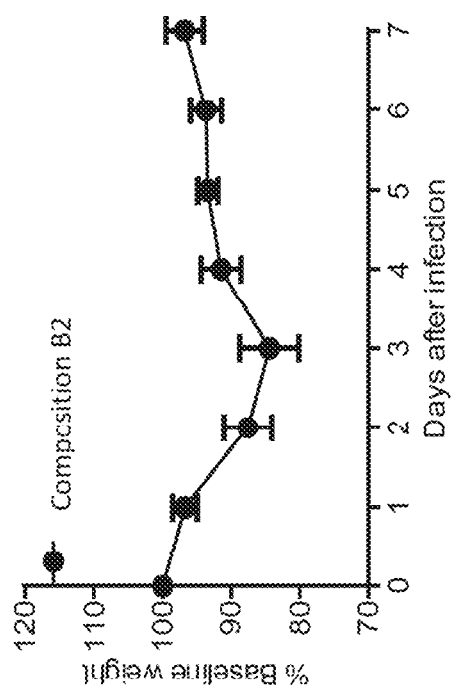
Figure 22F:
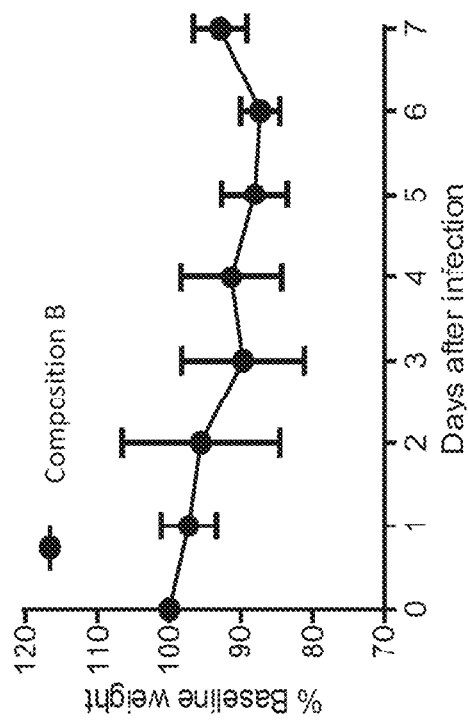
Figure 22E:
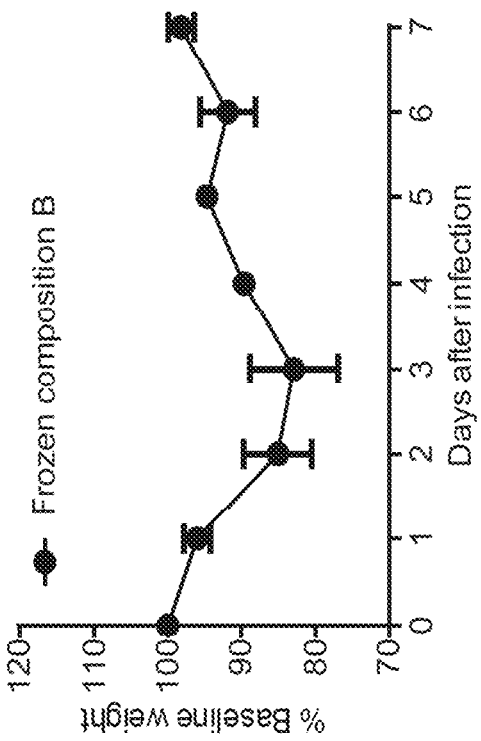
Figure 22G:
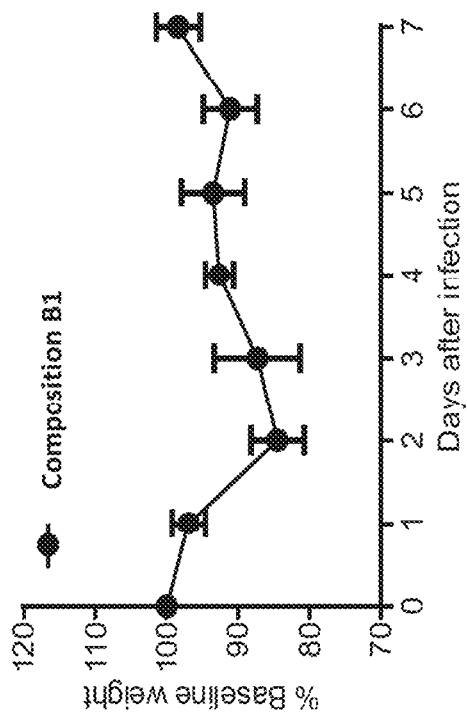
Figure 22I:
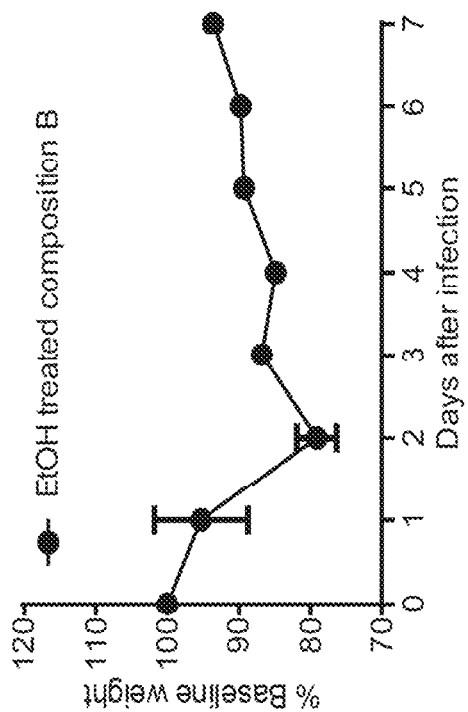
Figure 22H:
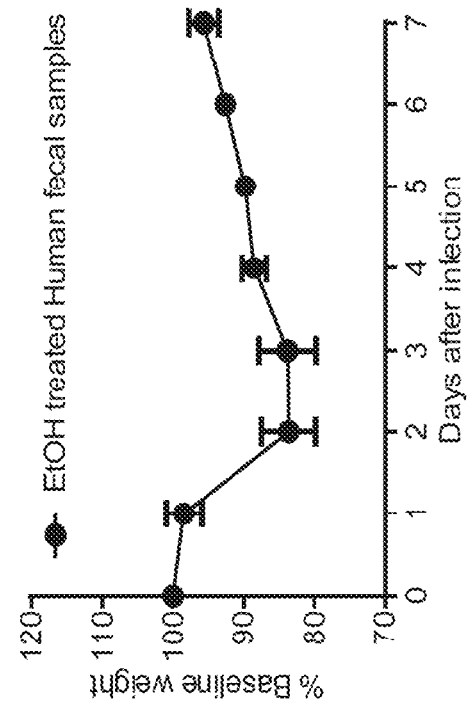
Figure 22J:
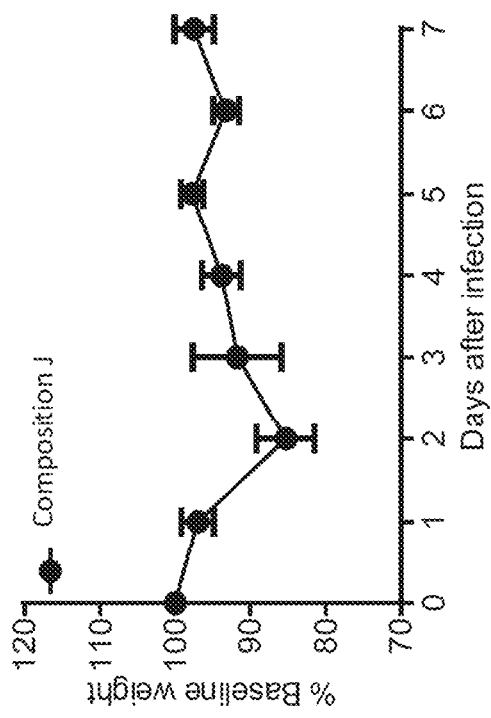
Figure 23:
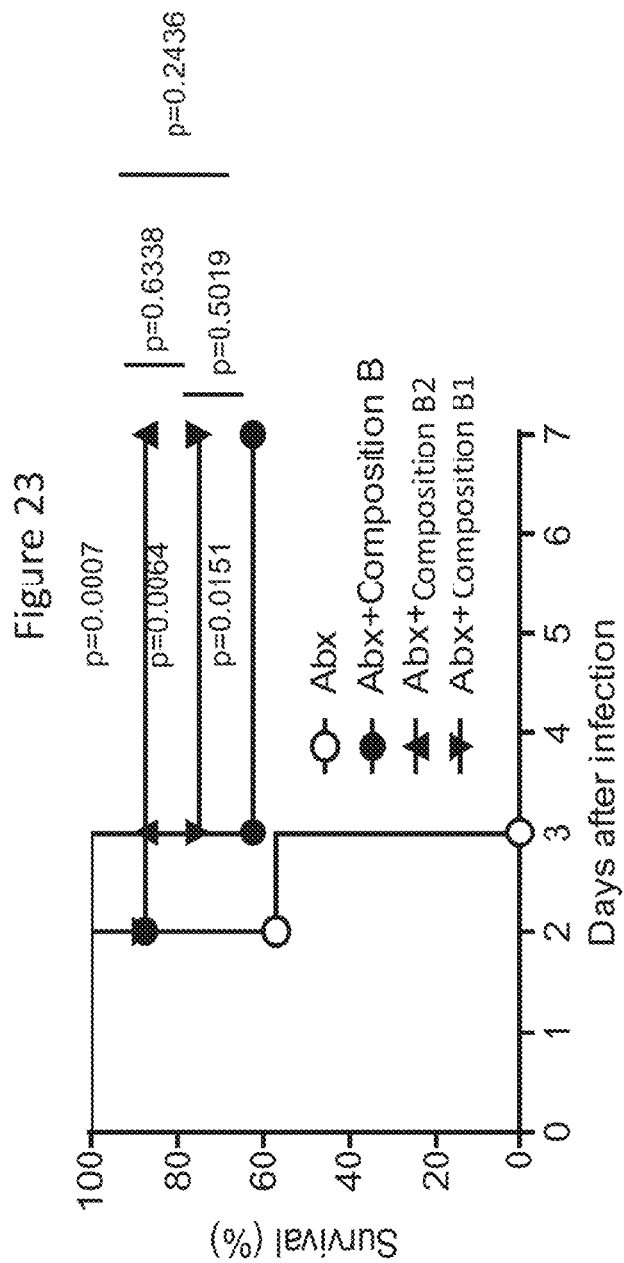
FIG. 23 shows the load of *C. difficile* in colony forming units (CFUs) in fecal pellets at various times post infection with *C. difficile*.
Figure 24:
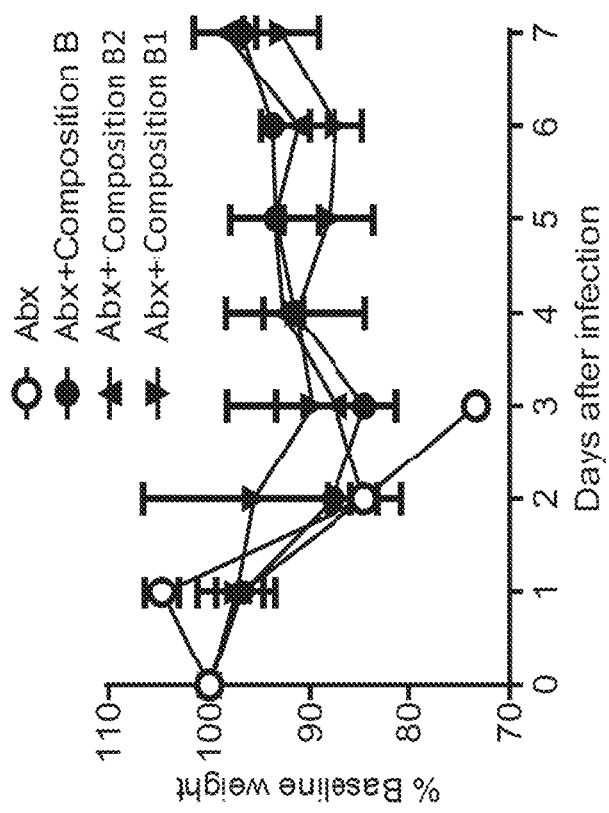
FIG. 24 shows weight of the indicated groups of mice at various times post infection with *C. difficile* spores.

Mice were challenged with *C. difficile* VPI 10463 spores ($10^4$) and monitored daily (Day 0 to Day 7 post *C. difficile* infection) for survival/mortality (FIGS. 21 and 23) and change in weight (FIGS. 22A-22J and 24). These data show that the compositions protect against and/or treat *C. difficile* infection.

Example 6: LBP Compositions Protect Against and/or Treat *C. difficile* Infection Groups of mice were subjected to cefoperazone treatment, as described above, then administered human fecal matter transplant, Composition B, Composition B+4 spores, or Composition H (FIG. 25). "Composition B+4 spores" refers to Composition B plus the following four strains in spore form: *Clostridium bolteae, Anaerotruncus colihominis, Clostridium symbiosum* and *Clostridium innocuum*. Composition H contains the following six strains in spore form: *Clostridium bolteae, Anaerotruncus colihominis, Clostridium symbiosum, Clostridium innocuum, Clostridium disporicum* and *Erysipelatoclostridium ramosum* (FIG. 26).

Figure 27A:
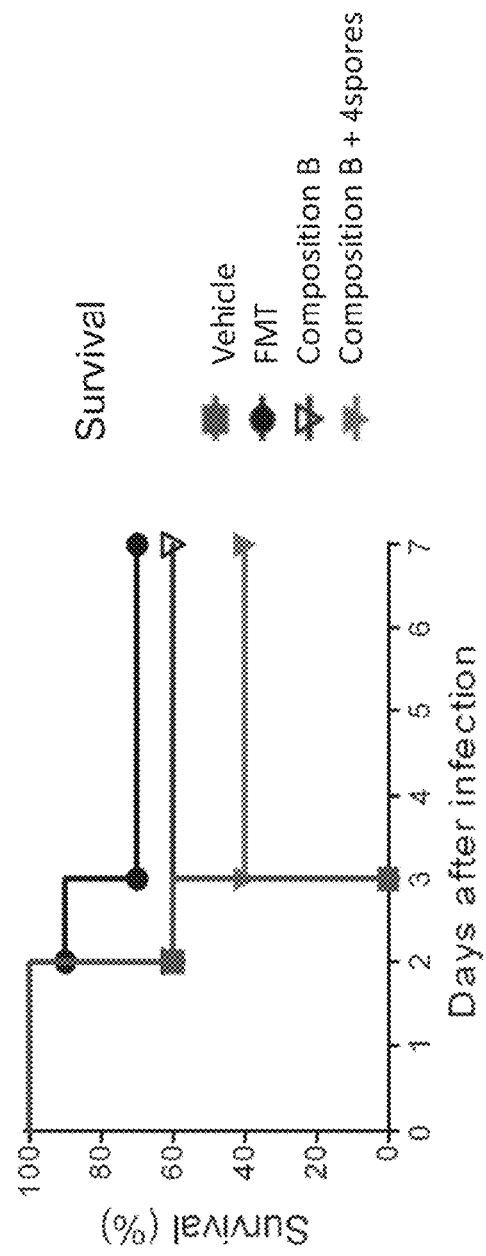
FIGS. 27A and 27B shows survival and weight loss of the mice over time post infection with *C. difficile* spores, according to the experimental conditions shown in FIG. 25. Mice losing >20% body weight of baseline were included in mortality numbers in survival curves.
Figure 27B:
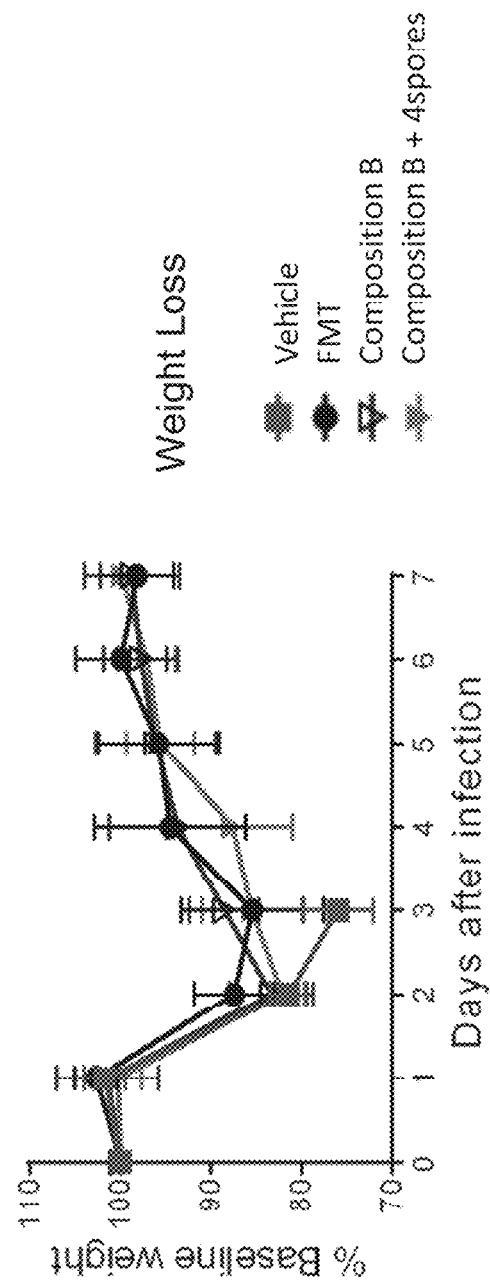
Figure 28A:
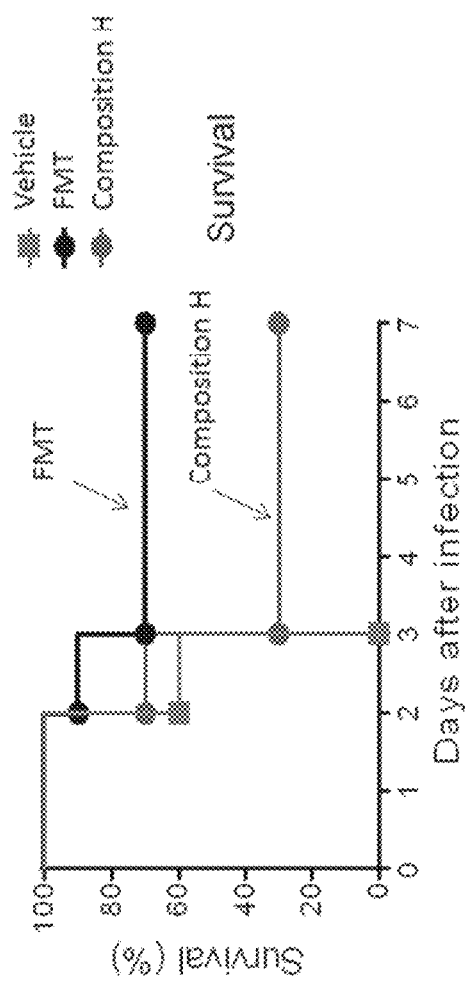
FIGS. 28A and 28B show results from the experimental conditions shown in FIG. 25.
Figure 28B:
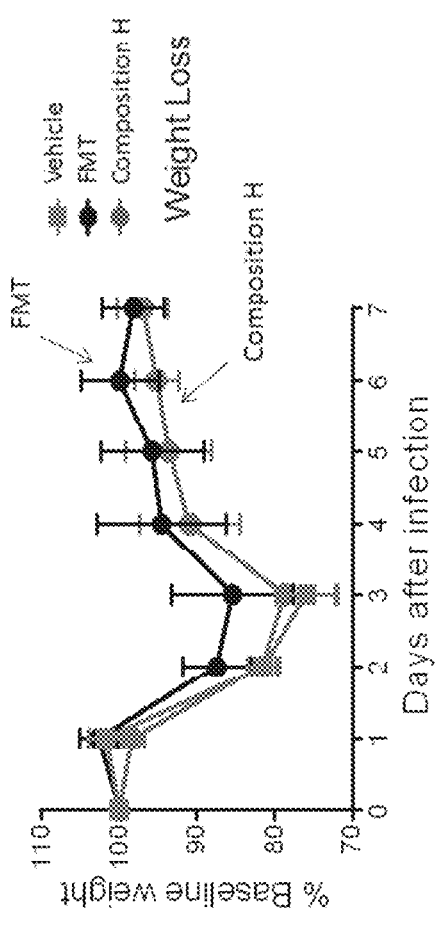
Figure 29A:
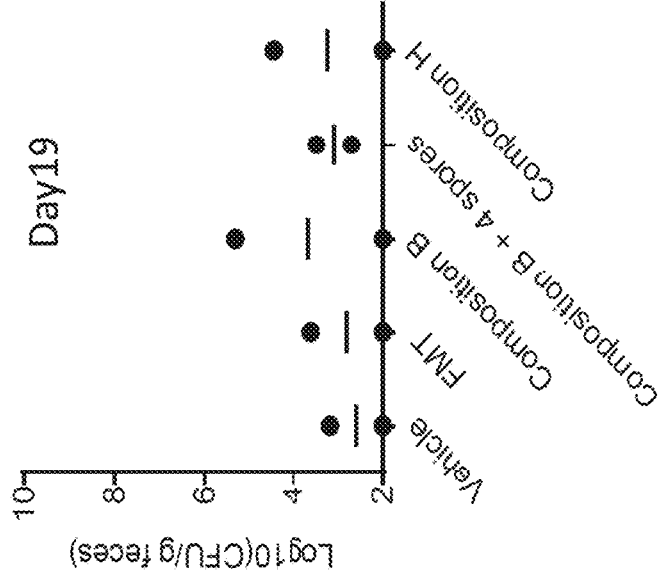
FIG. 29A shows survival/mortality of mice that received the indicated treatment prior to *C. difficile* infection.
Figure 29B:
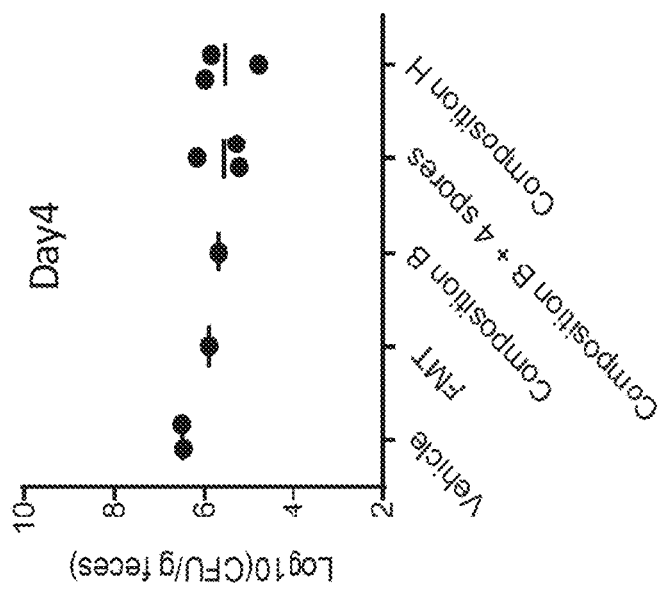
FIG. 29B shows the weight over time of mice that received the indicated treatment prior to *C. difficile* infection.
Figure 29C:
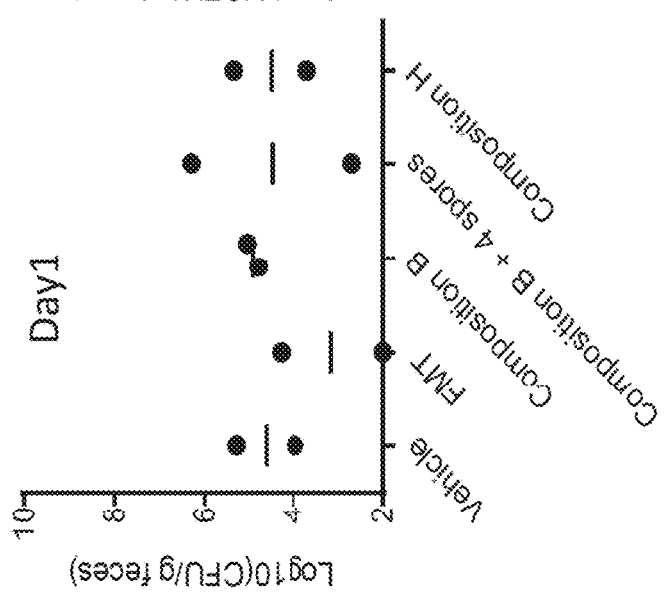
FIG. 29C shows *C. difficile* burden at 19 days post *C. difficile* infection.

Mice were then challenged with *C. difficile* infection with $10^4$ *C. difficile* VPI 10463 spores and monitored for survival/mortality (FIGS. 27A and 28A), weight (FIGS. 27B and 28B). Mice that lost more than 20% body weight relative to baseline were included in mortality numbers in survival curves. The *C. difficile* burden was assessed by CFU in fecal pellets on days 1, 4 and 19 after infection (FIGS. 29A-29C).

These data indicate that Composition B as well as other compositions can improve survival in the cefoperazone-induced *C. difficile* mouse model and protect against and/or treat *C. difficile* infection.

Example 7: *C. difficile* Toxin Experiment

Vero cells, epithelial cells derived from African Green Monkey kidney epithelium, are sensitive to a variety of bacterial toxins, including *C. difficile* Toxin B. Exposure of cells to *C. difficile* Toxin B results in inhibition of the function of Rho, Rac, and Cdc42 leading to a decline in F-actin, a change in cell morphology (e.g., cell rounding), and eventually apoptosis.

To determine whether administration of bacterial compositions described herein has an effect on the production or activity of *C. difficile* Toxin B, a cellular assay was performed. Briefly, groups of mice were treated with cefoperazone, as described above, and administered human fecal matter transplant (FMT) ("4-3"); Composition B ("5-3"); Composition B plus four strains in spore form: *Clostridium bolteae, Anaerotruncus colihominis, Clostridium symbiosum* and *Clostridium innocuum* ("7-4"), or no treatment. Each of the groups of mice were then exposed to *C. difficile* infection with $10^4$ *C. difficile* spores. The groups of mice that did not receive a treatment after cefoperazone administration and prior to *C. difficile* infection are referred to as "2-1 (Cdiff)" and "2-4 (Cdiff)." An additional group of mice was not exposed to *C. difficile* as indicated by "N3 (Healthy)".

Fecal pellets were collected from each of the groups of mice, weighed, and homogenized in PBS and normalized to a fixed concentration (~25 mg/mL). The samples were centrifuged to prepare a clarified supernatant, which was then diluted in 10-fold serial dilutions to produce a range from 1:10 to 1:10-6 dilutions of clarified pellet supernatant. Vero cell cultures were exposed to the diluted samples for approximately 18 hours, then visualized by phase contract microscopy to assess morphological changes (i.e., cell rounding) associated with *C. difficile* toxin exposure. The cells were scored based on the highest concentration of supernatant that did not yield a change in morphology (FIG.

30). The samples from mice that had been treated with Composition B prior to *C. difficile* infection had reduced amounts of *C. difficile* Toxin B, as compared to samples from control mice that did not receive a treatment after cefoperazone administration and prior to *C. difficile* infection ("2-1 (Cdiff)" and "2-4 (Cdiff)") as well as compared to samples from mice that received FMT. Notably, the samples from mice that had been treated with Composition B also had reduced amounts of *C. difficile* Toxin B, as compared to samples from mice that had been treated with Composition B with additional spores.

Example 8: In Vitro Competition Between Compositions B and *C. difficile*

Composition B was assessed for its ability to suppress *Clostridium difficile* growth by an in vitro mixed culture competition assay. From glycerol freezer stocks, individual strains of Composition B, *C. difficile* (Cdiff), *Clostridium bifermentans*, and *Bacteroides* thetaiotaomicron were struck out onto Eggerth-Gagnon agar plates with horse blood (EG+HB). Single colonies of each of the strains were subsequently inoculated into brain heart infusion (BHI) liquid media and allowed to grow in pure culture for 24-48 hours. Turbid cultures were sub-cultured then grown to exponential phase and finally diluted and combined to prepare a mixed culture with an optical density (0D600) of 0.1. Exponential phase Cdiff culture was added to the mixed culture at a final concentration with an OD of 0.1. After the cultures were combined and incubated for 2-3 hours, samples were collected, serially diluted, and plated on Taurocholate-Cycloserine-Cefoxitin-Fructose Agar (TCCFA) plates to select for Cdiff growth. After 48-72 hours, the colony forming units (CFUs) of Cdiff in each competition experiment were determined by manual colony counting.

EG+HB agar plates were prepared according to standard procedures and reduced in an anaerobic environment for at least 6-8 hours prior to use. Liquid BHI medium was obtained from BD Biosciences (Catalog #211059, San Jose, CA), prepared according to the manufacturer's instructions, and reduced in an anaerobic environment for at least 18-24 hours prior to use. TCCFA plates were prepared according to standard procedures and reduced in an anaerobic environment for at least 6-8 hours prior to use. *Clostridium difficile* strain used in the experiments: American Type Culture Collection (ATCC) 43255.

TABLE 4

Composition B strains

Composition B

VE202-7
VE202-13
VE202-14
VE202-16
Strain #16
Strain #170
Strain #189
Strain #211

Strains were struck out onto EG+HB agar plates from frozen glycerol stocks inside an anaerobic chamber for 48-72 hours. Single colonies were inoculated into 10 mL of BHI media and grown 24-48 hours at 37° C. in the anaerobic chamber. Turbid cultures were then diluted to an OD of 0.1 and grown for 2-3 hours at 37° C. in the anaerobic chamber. Exponential phase cultures were diluted and combined at equivalent ODs. For the competition assay, each of the strains of Combination B (Table 4) were combined in equal parts, based on $OD_{600}$, to reach a final consortium $OD_{600}$ of 0.1. *C. bifermentans* and *B. thetaiotaomicron* were setup to compete with Cdiff individually at an OD of 0.1. The $OD_{600}$ for Cdiff in each of the mixed culture competition experiments was 0.1. After combination, the cultures were incubated for 2-3 hours at 37° C. in the anaerobic chamber, then prepared for enumerations on Cdiff selective plates.

TCCFA plates are selective for Cdiff growth, and none of the Combination B strains, nor either of the control strains (*C. bifermentans* and *B. thetaiotaomicron*), grow on these plates. Inside an anaerobic chamber, a 100 µL sample of each competition culture was collected and serially diluted 1:10 to reach a final dilution of $1\times10^{-6}$. Plates for CFU enumeration were prepared by spreading 100 µL of each of the $1\times10^{-4}$ through $1\times10^{-6}$ dilutions on TCCFA plates using sterile spreading loops. CFU plates were incubated for 48-72 hours at 37° C. in the anaerobic chamber. CFU enumeration was completed by manually counting colonies.

Figure 31:
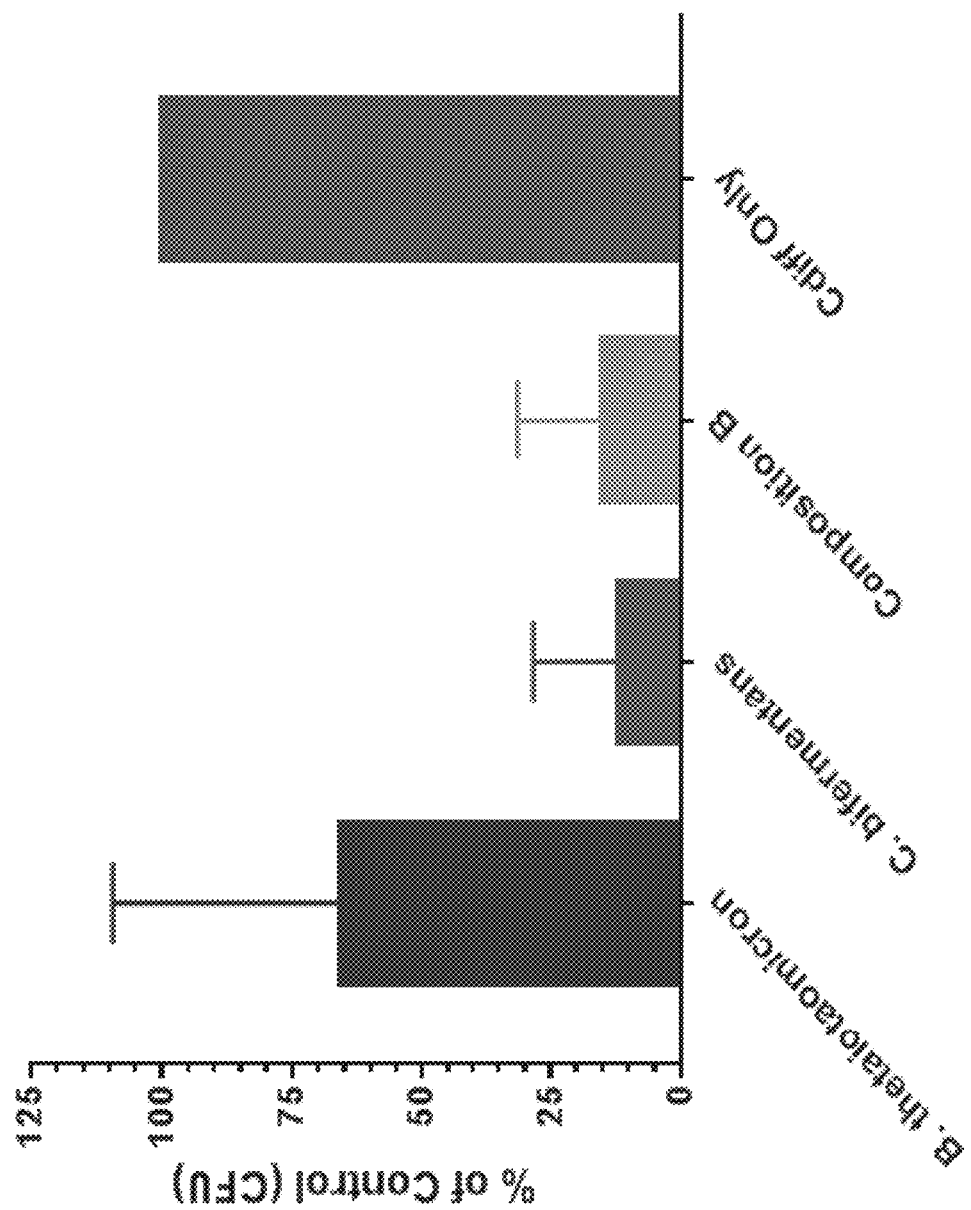
FIG. 31 shows Composition B reduced *C. difficile* growth in in vitro competition experiments. Cultures of *C. difficile* were incubated in the presence of *B. thetaiotaomicron*, *C. bifermentans*, or Composition B, or in the absence of a competing strain(s) (C. diff only). The quantity of *C. difficile* is presented as the percentage of the control (C. diff only).

To determine the effect of competition, the ratio of CFUs determined for the competition samples and Cdiff alone was calculated and expressed as a percentage. Inhibition of Cdiff growth by the Composition B cocktail was compared to the responses of *B. thetaiotaomicron* (negative control) and *C. bifermentans* (positive control). The results are shown in Table 5 and FIG. 31.

TABLE 5

Summary Results for In Vitro Competition

| Experiment Number | No Competing Strain(s) | Competition with B. thetaiotaomicron | Competition with C. bifermentans | Competition with Composition B |
|---|---|---|---|---|
| n = 1 | 100 | | | 33.8 |
| n = 2 | 100 | 9.90 | 0.1 | 0.5 |
| n = 3 | 100 | 115 | 39.5 | 33.1 |
| n = 4 | 100 | 41.3 | 0.7 | 0.7 |
| n = 5 | 100 | 105 | 14.1 | 20.9 |
| n = 6 | 100 | 57.4 | 4.1 | 1.6 |
| Mean | 100 | 65.6 | 11.7 | 15.1 |
| Std. Dev. | 0 | 43.8 | 16.5 | 16.2 |
| Total N | 6 | 5 | 5 | 6 |

Data is expressed as Cdiff CFU as a percentage of control. Each n is representative of a single biological replicate, independent of other measurements.

In in vitro competition, Composition B inhibited Cdiff growth to 15.1±16.2% of control (absence of competing strain(s)). This result is consistent with the inhibition observed by the positive control, *C. bifermentans*, of 11.7±16.5% of control. *B. thetaiotaomicron*, a negative control, yielded a negligible effect on Cdiff growth at 65.6±43.8% of control. Given the variability inherent in the assessment of CFU, inhibition of growth to <25% of control is considered to be significant inhibition and both the positive control and Composition B cocktail meet this threshold of activity. The Composition B consortium attenuated Cdiff growth in vitro comparable to the direct competition observed by *C. bifermentans*. Direct competition with *B. thetaiotaomicron* did not significantly inhibit Cdiff growth.

Example 9: Determination of In Vitro Short-Chain Fatty Acid Production

Each strain of Composition B was assessed for individual short-chain fatty acid (SCFA) production in vitro. Composition B strains were grown in pure cultures inside an anaerobic chamber. Spent supernatant from liquid media cultures was harvested by centrifugation, filter sterilized, and then stored at <−70° C. Frozen clarified supernatant specimens were analyzed for short-chain fatty acids (SCFAs).

EG+HB agar plates (Eggerth-Gagnon agar plates with horse blood) were prepared according to standard methods and reduced in an anaerobic environment for at least 6-8 hours prior to use. Liquid PYG medium (pre-formulated, pre-reduced) was obtained from Anaerobe Systems (Catalog #AS-822; Morgan Hill, CA).

Strains were struck out onto EG+HB agar plates from frozen 15% glycerol stocks inside an anaerobic chamber for 48-72 hours. Single colonies were inoculated into 7 mL PYG media and grown 24-48 hours at 37° C. in the anaerobic chamber. Unless otherwise noted, when the optical density (OD) was ≥0.2, samples were collected for CFU enumeration and filtration. Inside an anaerobic chamber, a 100 µL sample of turbid culture was collected and serially diluted 1:10 to reach a final dilution of $1 \times 10^{-6}$. Plates for CFU enumeration were prepared by spreading 100 µL/dilution for the $1 \times 10^{-4}$ through $1 \times 10^{-6}$ dilutions on EG+HB agar plates using sterile glass beads. CFU plates were incubated for 48-72 hours in the anaerobic chamber. CFU enumeration was completed using the EasyCount 2 (bioMérieux SA, Marcy-l'Étoile, France). Immediately after samples of turbid cultures were collected for CFU enumeration, the remaining turbid cultures were centrifuged at approximately 1000 RCF for 10 minutes to pellet cellular debris. The clarified supernatants were transferred to a 0.2 µm plate filter and vacuum filtered to remove any remaining particulates prior to bioanalysis. In the event of blockage in the filter plate, clarified supernatants were manually filtered using 0.2 µm syringe filters. Filtered supernatants were aliquoted and stored at <−70° C. prior to bioanalysis of SCFAs.

To facilitate easier comparisons between samples, raw SCFA data (µg/mL) was normalized by the login of corresponding determined/estimated CFU for the culture. The results are depicted in Table 6 and Table 7 below.

TABLE 6

Enumerated CFUs for Composition B Strains

| Sample ID | OD600 | Enumerated CFU (CFU/mL) |
|---|---|---|
| VE202-7 | >2 | 6.11E+08 |
| VE202-13 | 0.8 | 4.00E+08 |
| VE202-14 | >2 | 1.60E+09 |
| VE202-16 | 1.92 | 1.28E+09 |
| #16 | 1.97 | 1.69E+08 |
| #170 | 1.8 | 1.08E+08 |
| #189 | 1.03 | 1.74E+09 |
| #211 | 0.35 | 3.71E+08 |

TABLE 7

SFCAs produced by individual Composition B strains

| | Normalized (µg/Log(CFU/mL)*mL) | | | | | | | |
|---|---|---|---|---|---|---|---|---|
| Sample ID | Acetate | Propionate | Iso-butyrate | Butyrate | 2-Methyl-butyrate | Iso-valerate | Valerate | Hexanoate |
| VE202-7 | 123.7 | 0.077 | 0.102 | 0.208 | 0.015 | 0.056 | BLOQ | 0.031 |
| VE202-13 | 30.1 | 0.545 | 0.116 | 34.452 | 0.288 | 0.188 | 0.097 | 0.034 |
| VE202-14 | 110.5 | 0.054 | 0.022 | 0.248 | 0.011 | 0.014 | BLOQ | 0.009 |
| VE202-16 | 313.2 | 0.000 | 0.000 | 0.280 | 0.004 | 0.000 | BLOQ | 0.009 |
| #16 | 104.0 | 0.005 | 0.000 | 50.988 | 0.014 | 0.033 | BLOQ | 0.009 |
| #170 | 87.1 | 0.055 | 0.025 | 0.215 | 0.011 | 0.039 | BLOQ | 0.016 |
| #189 | 0.0 | BLOQ | 0.000 | 35.751 | 0.005 | 0.019 | 0.359 | 0.587 |
| #211 | 57.6 | 5.289 | 0.000 | 78.227 | 0.028 | 0.050 | 0.053 | 0.095 |

Seven strains of Composition B were found to produce significant quantities (>1 µg/Log(CFU/mL)*mL) of the 2-carbon SCFA, acetate. One strain, (#211), produced substantial quantities of the 3-carbon SCFA, propionate. Four strains of Composition B produced substantial quantities of the 4-carbon SCFA, butyrate. Trace quantities (<1 µg/Log (CFU/mL)*mL) of other SCFAs were also produced by the Composition B strains.

Example 10: Composition B Induces Regulatory T Cells (Tregs)

Each of the bacterial strains of Composition B were grown to log phase, combined to a total dose of ~$10^8$ cfu per mouse. Germ-free mice were inoculated with Composition B or a negative control by oral gavage and sacrificed following four weeks of colonization. Lamina propria leukocytes were isolated from colonic tissue of individual mice by standard procedures and assessed by flow cytometry. The regulatory T cell content was evaluated as the percentage of Foxp3-positive cells among CD4+ T cells.

Figure 32:
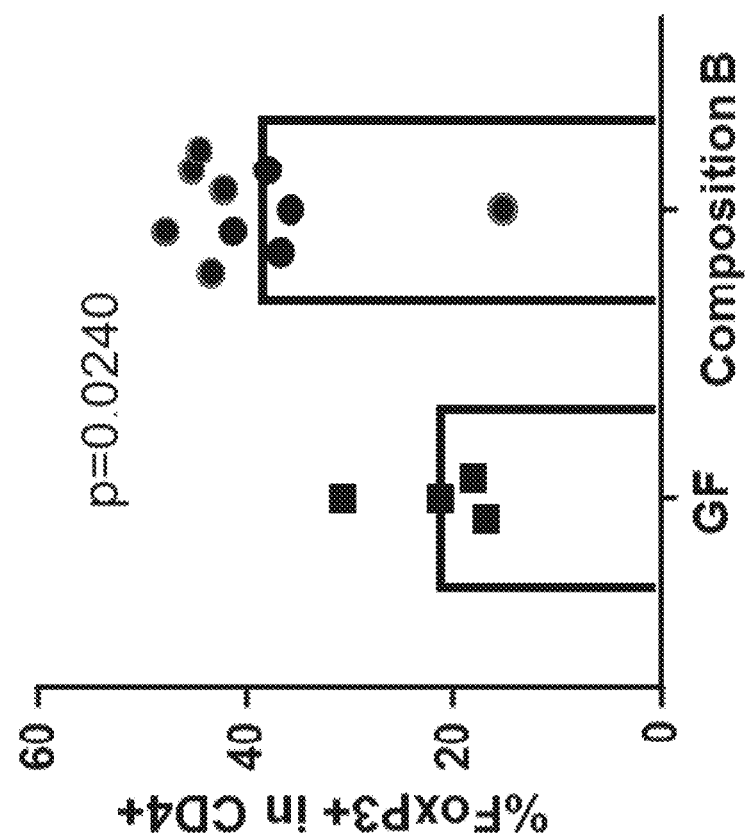
FIG. 32 shows that inoculation with Composition B induced the percentage of FoxP3+CD4+ cells (regulatory T cells) in the intestine of germ-free mice as compared to control mice ("GF").

As shown in FIG. 32, mice that were inoculated with Composition B were found to have significantly more regulatory T cells as compared to mice that were inoculated with the control.

What is claimed is:

1. A pharmaceutical composition comprising a purified bacterial mixture, wherein the purified bacterial mixture consists of 7 to 10 bacterial strains, wherein the purified bacterial mixture comprises at least 7 of:
   (i) a bacterial strain comprising a 16S rDNA sequence having at least 97% sequence identity to the nucleotide sequence of SEQ ID NO: 157;
   (ii) a bacterial strain comprising a 16S rDNA sequence having at least 97% sequence identity to the nucleotide sequence of SEQ ID NO: 129;
   (iii) a bacterial strain comprising a 16S rDNA sequence having at least 97% sequence identity to the nucleotide sequence of SEQ ID NO: 132;
   (iv) a bacterial strain comprising a 16S rDNA sequence having at least 97% sequence identity to the nucleotide sequence of SEQ ID NO: 137;
   (v) a bacterial strain comprising a 16S rDNA sequence having at least 97% sequence identity to the nucleotide sequence of SEQ ID NO: 124;
   (vi) a bacterial strain comprising a 16S rDNA sequence having at least 97% sequence identity to the nucleotide sequence of SEQ ID NO: 141;
   (vii) a bacterial strain comprising a 16S rDNA sequence having at least 97% sequence identity to the nucleotide sequence of SEQ ID NO: 146; and
   (viii) a bacterial strain comprising a 16S rDNA sequence having at least 97% sequence identity to the nucleotide sequence of SEQ ID NO: 152,
   wherein the bacterial strains are lyophilized.

2. The pharmaceutical composition of claim 1, wherein the purified bacterial mixture comprises:
   (i) a bacterial strain comprising a 16S rDNA sequence having at least 99% sequence identity to the nucleotide sequence of SEQ ID NO: 157;
   (ii) a bacterial strain comprising a 16S rDNA sequence having at least 99% sequence identity to the nucleotide sequence of SEQ ID NO: 129;
   (iii) a bacterial strain comprising a 16S rDNA sequence having at least 99% sequence identity to the nucleotide sequence of SEQ ID NO: 132;
   (iv) a bacterial strain comprising a 16S rDNA sequence having at least 99% sequence identity to the nucleotide sequence of SEQ ID NO: 137;
   (v) a bacterial strain comprising a 16S rDNA sequence having at least 99% sequence identity to the nucleotide sequence of SEQ ID NO: 124;
   (vi) a bacterial strain comprising a 16S rDNA sequence having at least 99% sequence identity to the nucleotide sequence of SEQ ID NO: 141;
   (vii) a bacterial strain comprising a 16S rDNA sequence having at least 99% sequence identity to the nucleotide sequence of SEQ ID NO: 146; and
   (viii) a bacterial strain comprising a 16S rDNA sequence having at least 99% sequence identity to the nucleotide sequence of SEQ ID NO: 152.

3. The pharmaceutical composition of claim 1, wherein the pharmaceutical composition comprises a pH-sensitive composition comprising one or more enteric polymers.

4. The pharmaceutical composition of claim 1, wherein the pharmaceutical composition is in the form of a capsule.

5. The pharmaceutical composition of claim 1, wherein the pharmaceutical composition comprises between $1 \times 10^7$ and $1 \times 10^{10}$ colony forming units (CFUs) per bacterial strain.

6. The pharmaceutical composition of claim 1, further comprising a pharmaceutically acceptable excipient.

7. The pharmaceutical composition of claim 1, wherein the pharmaceutical composition is formulated for oral administration.

8. The pharmaceutical composition of claim 1, wherein the pharmaceutical composition is formulated for rectal administration.

9. The pharmaceutical composition of claim 1, wherein the pharmaceutical composition is formulated for delivery to the intestine.

10. The pharmaceutical composition of claim 1, wherein the pharmaceutical composition is formulated for delivery to the colon.

11. A method of reducing the likelihood of a *Clostridium difficile* infection in a subject, the method comprising administering the pharmaceutical composition of claim 1 to the subject in a therapeutically effective amount to reduce the likelihood of the *Clostridium difficile* infection.

12. The method of claim 11, wherein the *Clostridium difficile* infection is a first occurrence of a *Clostridium difficile* infection.

13. The method of claim 11, wherein the *Clostridium difficile* infection is a recurrence of *Clostridium difficile* infection.

14. The method of claim 11, wherein the subject is administered one or more doses of an antibiotic prior to the pharmaceutical composition.

15. The method of claim 14, wherein the antibiotic is vancomycin, kanamycin, gentamicin, colistin, metronidazole, clindamycin, fidaxomicin, or cefoperazone.

16. The method of claim 14, wherein the antibiotic is vancomycin.

17. A method to suppress an abnormal or excessive immune response in a subject comprising administering the pharmaceutical composition of claim 1 to the subject in a therapeutically effective amount to suppress the abnormal or excessive immune response.

18. The method of claim 17, wherein the abnormal or excessive immune response is suppressed by inducing proliferation and/or accumulation of regulatory T cells.

19. The method of claim 17, wherein the subject is administered one or more doses of an antibiotic prior to the pharmaceutical composition.

20. The method of claim 19, wherein the antibiotic is vancomycin, kanamycin, gentamicin, colistin, metronidazole, clindamycin, fidaxomicin, or cefoperazone.

* * * * *

SEQUENCE LISTING

```
Sequence total quantity: 159
SEQ ID NO: 1                moltype = DNA   length = 210
FEATURE                     Location/Qualifiers
misc_feature                1..210
                            note = Synthetic Polynucleotide
source                      1..210
                            mol_type = other DNA
                            organism = synthetic construct
SEQUENCE: 1
gcccggagca gttgatgtga aggatgggtc acctgtggac tgcattggaa ctgtcatact    60
tgagtgccgg agggtaagcg gaattcctag tgtagcgtg aaatgcgtag atattaggag    120
gaacaccagt ggcgaaggcg gcttactgga cggtaactga cgttgaggct cgaaagcgtg   180
gggagcaaac aggattagat accctggtaa                                    210

SEQ ID NO: 2                moltype = DNA   length = 184
FEATURE                     Location/Qualifiers
misc_feature                1..184
                            note = Synthetic Polynucleotide
source                      1..184
                            mol_type = other DNA
                            organism = synthetic construct
SEQUENCE: 2
ctaaccgtgg aggtcattgg aaactggtca acttgagtgc agaagaggga agtggaattc    60
catgtgtagc ggtgaaatgc gtagagatat ggaggaacac cagtggcgaa ggcggcttcc   120
tggtctgtaa ctgacactga ggcgcgaaag cgtgggggc aaacaggatt agatcccccg    180
gtaa                                                                184

SEQ ID NO: 3                moltype = DNA   length = 196
FEATURE                     Location/Qualifiers
misc_feature                1..196
                            note = Synthetic Polynucleotide
source                      1..196
                            mol_type = other DNA
                            organism = synthetic construct
SEQUENCE: 3
atgaaagccg gggctcaacc ccggtactgc tttggaaact gtttgacttg agtgcttgag    60
aggtaagtgg aattcctagt gtagcgggaa atgtttagat attaggagga caccagtggc   120
gaaggcggct tactgdactg taactgacgt tgtggctcga tttgtgggga gcaaacagga   180
ttatatcccc tggtaa                                                   196

SEQ ID NO: 4                moltype = DNA   length = 211
FEATURE                     Location/Qualifiers
misc_feature                1..211
                            note = Synthetic Polynucleotide
source                      1..211
                            mol_type = other DNA
                            organism = synthetic construct
SEQUENCE: 4
cggaaggtct gatgtgaagg ttggggctta ccccggactg cattggaaac tgttttcta    60
gagtgcccga gaggtaagcg gaattcctag tgtagcggtg aaatgcttta gatattagga   120
ggaacaccag tggcgaaggc ggcttactgg acggtaactg acgttgaggc tcgaaagcgt   180
ggggagcaaa caggattaga taccctggta a                                  211

SEQ ID NO: 5                moltype = DNA   length = 207
FEATURE                     Location/Qualifiers
misc_feature                1..207
                            note = Synthetic Polynucleotide
source                      1..207
                            mol_type = other DNA
                            organism = synthetic construct
SEQUENCE: 5
cgatgtctga gtgaaggctg gggcttaccc caggactgca ttggaactgt ttttctagag    60
tgccggagag gtaagcggaa ttcctagtgt agcggtgaaa tgcgtagata ttaggaggaa   120
caccagtggc gaaggcggct tactggacgg taactgacgt tgaggctcga aagcgtgggg   180
agcaaacagg attagatacc ctggtaa                                       207

SEQ ID NO: 6                moltype = DNA   length = 179
FEATURE                     Location/Qualifiers
misc_feature                1..179
                            note = Synthetic Polynucleotide
source                      1..179
                            mol_type = other DNA
                            organism = synthetic construct
SEQUENCE: 6
ttaaccaaga agtgcattgg aactgtcaga cttgggggaa aaaagacag tgcaactcca    60
tgtgtagcgg tggaatgctc catatatatg gaagaacacc agtggcgaag gcggctgtct   120
ggtctgcaac tgacgctgag gctcgaattc atgggtaaga agtattagt cccttgtaa    179
```

```
SEQ ID NO: 7                 moltype = DNA   length = 214
FEATURE                      Location/Qualifiers
misc_feature                 1..214
                             note = Synthetic Polynucleotide
source                       1..214
                             mol_type = other DNA
                             organism = synthetic construct
SEQUENCE: 7
acccgcttgg tctgaggtga ggctggggct taaccccagg actgcattgg aaactgttgt      60
tctagagtgc cggagaggta agcggaattc ctagtgtagc ggtgaaatgc gtagatatta    120
ggaggaacac cagtggcgaa ggcggcttac tggacggtaa ctgacgttga ggctcgaaag    180
cgtggggagc aaacaggatt agataccctg gtaa                                214

SEQ ID NO: 8                 moltype = DNA   length = 196
FEATURE                      Location/Qualifiers
misc_feature                 1..196
                             note = Synthetic Polynucleotide
source                       1..196
                             mol_type = other DNA
                             organism = synthetic construct
SEQUENCE: 8
taggctgggg cttaacccca ggactgcatt ggaaactgtt tttctagagt gccggagagg      60
taagcggaat tcctagtgta gcggtgaaat gcgtagatat taggaggaac cagtggcg      120
aaggcggctt actggacggt aactgacgtt gaggctcgaa agcgtgggga gcaaacagga    180
ttagataccc tggtaa                                                    196

SEQ ID NO: 9                 moltype = DNA   length = 297
FEATURE                      Location/Qualifiers
misc_feature                 1..297
                             note = Synthetic Polynucleotide
source                       1..297
                             mol_type = other DNA
                             organism = synthetic construct
SEQUENCE: 9
ttgcattgga cactatgtca gctgagtgtc ggagaggtaa gtggaattcc tagtgtagcg      60
gtgaaatgcg tagatattag gaggaacacc agtggcgaag gcggcttact gcacgttttc    120
tgacgttgag gctcgaaatc gtggggagca aacaaaaata gatacctgg tagtccacgc     180
cgtaaacgat gcatactagg tgtcgggtgg caaagccatt cggtgccgca gcaaacgcaa    240
taagtatgcc acctggggag tacgttcgca agaatgaaac tcaaataaat tgacgga       297

SEQ ID NO: 10                moltype = DNA   length = 209
FEATURE                      Location/Qualifiers
misc_feature                 1..209
                             note = Synthetic Polynucleotide
source                       1..209
                             mol_type = other DNA
                             organism = synthetic construct
SEQUENCE: 10
cccgtcgtag atgtgaactg ggggctcacc tccagcctgc atttgaaact gtagttcttg      60
agtgctggaa aggcaatcgg aattccgtgt gtagcggtga aatgcgtaga tatacggagg    120
aacaccagtg gcgaaggcgg attgctggac agtaactgac gctgaggcgc gaaagcgtgg    180
ggagcaaaca ggattagata ccctcataa                                      209

SEQ ID NO: 11                moltype = DNA   length = 401
FEATURE                      Location/Qualifiers
misc_feature                 1..401
                             note = Synthetic Polynucleotide
source                       1..401
                             mol_type = other DNA
                             organism = synthetic construct
SEQUENCE: 11
acctgatgca gcgacgccgc gtgagtgaag aagtatttcg gtatgtaaag ctctatcagc      60
agggaagaaa aaagacggta cctgactaag aagcccccggc taactacgtg ccagcagccg   120
cggtaatacg taggggcaa gcgttatccg gaattactgg gtgtaaaggg tgcgtaggtg    180
gcatggtaag tcagaagtga aagcccgggg cttaacccccg ggactgcttt tgaaactgtc   240
atgctggagt gcaggagagg taagcggaat tcctagtgta gcggtgaaat gcgtagatat    300
taggaggaac accagtggcg aaggcggctt actggactgt cactgacact gatgcacgaa    360
agcgtgggga gcaaacagga ttagataccc tggaagtcca t                        401

SEQ ID NO: 12                moltype = DNA   length = 355
FEATURE                      Location/Qualifiers
misc_feature                 1..355
                             note = Synthetic Polynucleotide
source                       1..355
                             mol_type = other DNA
                             organism = synthetic construct
SEQUENCE: 12
atgggagcgt agatggcgac tgggccatat gtgacagccc tggtctcaac cccttaactg      60
catttggaac tgagtggctg gagtgtcgga gaggcaggcg gaattcctag tgtagcggtg    120
```

```
aaatgcgtag atattaggag gaacaccagt ggcgaaggcg gcctgctgga cgatgactga    180
cgttgaggct cgaaagcgtg gggagcaaac aggattagat accctggtag tccacgccgt    240
aaacgatgac tactaggtgt cgggtggcaa ggacattcgg tgccgcagca aacgcaataa    300
gtagtccacc tggggagtac gttcgcaaga atgaaactca aaggaaattg acgga         355

SEQ ID NO: 13            moltype = DNA   length = 197
FEATURE                  Location/Qualifiers
misc_feature             1..197
                         note = Synthetic Polynucleotide
source                   1..197
                         mol_type = other DNA
                         organism = synthetic construct
SEQUENCE: 13
cgcagcggag tgtatcctag gctcacctgg ctgctttcga actggttttc tagatcgtgt    60
agaggggggag attcctggtg tagcgtgaaa tgcgtagata tctggaggaa caccagtggc   120
gaaggcggcc tcctggacgg caactgacgt tgaggctcga agtgtgggg agcaaacagg    180
attagatacc ctggtaa                                                   197

SEQ ID NO: 14            moltype = DNA   length = 1522
FEATURE                  Location/Qualifiers
misc_feature             1..1522
                         note = Synthetic Polynucleotide
source                   1..1522
                         mol_type = other DNA
                         organism = synthetic construct
SEQUENCE: 14
tcaaagagtt tgatcctggc tcaggacgaa cgctggcggc gcgcctaaca catgcaagtc    60
gaacggagct tacgttttga agttttcgga tggacgaatg taagcttagt ggcggacggg    120
tgagtaacac gtgagcaacc tgcctttcag aggggggataa cagccggaaa cggctgctaa   180
taccgcatga tgttgcgggg gcacatgccc ctgcaaccaa ggagcaatc cgctgaaaga    240
tgggctcgcg tccgattagc cagttggcgg ggtaacggcc caccaaagcg acgatcggta    300
gccggactga gaggttgaac ggccacattg gactgagaca cgcccaga ctcctacggg    360
aggcagcagt gggggatatt gcacaatggg cgaaagcctg atgcagcgac gccgcgtgag    420
ggaagacggt cttcggattg taaacctctg tctttgggga agaaaatgac ggtacccaaa    480
gaggaagctc cggctaacta cgtgccagca gccgcggtaa tacgtaggga gcaagcgttg    540
tccggaatta ctgggtgtaa agggagcgta ggcgggatgg caagtagaat gttaaatcca    600
tcggctcaac cggtggctgc gttctaaact gccgttcttg agtgaagtag aggcaggcgg    660
aattcctagt gtagcggtga aatgcgtaga tattaggagg aacaccagtg gcgaaggcgg    720
cctgctgggc tttaactgac gctgaggctc gaaagcgtgg ggagcaaaca ggattagata    780
ccctggtagt ccacgccgta aacgatgatt actaggtgtg gggggactga cccccttccgt   840
gccgcagtta acacaataag taatccacct ggggagtacg gccgcaaggt tgaaactcaa    900
aggaattgac ggggccccgc acaagcagtg gagtatgtgg tttaattcga agcaacgcga    960
agaaccttac caggtcttga catcggatgc atagcctaga gataggtgaa gccctccggg    1020
gcatccagac aggtggtgca tggttgtcgt cagctcgtgt cgtgagatgt tgggttaagt    1080
cccgcaacga gcgcaaccct tattattagt tgctacgcaa gagcactcta atgagactgc    1140
cgttgacaaa acggaggaag gtggggatga cgtcaaatca tcatgcccct tatgacctgg    1200
gctacacacg tactacaatg gcactaaaac agagggcggc gacaccgcga ggtgaagcga    1260
atcccgaaaa agtgtctcag ttcagattgc aggctgcaac ccgcctgcat gaagtcgaaa    1320
ttgctagtaa tcgcggatca gcatgccgcg gtgaatacgt tcccgggcct tgtacacacc    1380
gcccgtcaca ccatggagat cggtaacacc cgaagccagt agcctaaccg caaggggggc    1440
gctgtcgaag gtgggattga tgactggggt gaagtcgtaa caaggtagcc gtatcggaag    1500
gtgcggctgg atcacctcct tt                                             1522

SEQ ID NO: 15            moltype = DNA   length = 1529
FEATURE                  Location/Qualifiers
misc_feature             1..1529
                         note = Synthetic Polynucleotide
source                   1..1529
                         mol_type = other DNA
                         organism = synthetic construct
SEQUENCE: 15
tacgagagtt tgatcctggc tcaggatgaa cgctggcggc gtgcctaaca catgcaagtc    60
gagcgaagcg ctgttttcag aatcttcgga ggaagaggac agtgactgag cggcggacgg    120
gtgagtaacg cgtgggcaac ctgcctcata caggggatag acagttagaa atgactgcta    180
ataccgcata agcgcacagg accgcatggt gtagtgtgaa aaactccggt ggtatgagat    240
ggacccgcgt ctgattaggt agttggtggg gtaaaggcct accaagccga cgatcagtag    300
ccgacctgag agggtgaccg gccacattgg gactgagaca cggcccaaac tcctacggga    360
ggcagcagtg ggaatattg cacaatgggg gaaaccctga tgcagcgacg ccgcgtgaag    420
gaagaagtat ttcggtatgt aaacttctat cagcagggaa agatgacgta cctgagt      480
aagaagcacc ggctaaatac gtgccagcag ccgcggtaat acgtatggtg caagcgttat    540
ccggatttac tgggtgtaaa gggagcgtag acgataggc aagtctggag tgaaaaccca    600
gggctcaacc ctgggactgc tttgaaact gcagatctgg agtgccggag aggtaagcgg    660
aattcctagt gtagcggtga aatgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcggt    840
gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catcggatg acgggcagt aatgtcgccg tcccttcggg    1020
gcatccgaga caggtggtgc atggttgtcg tcagctcgtg tcgtgagatg ttgggttaag    1080
```

```
tcccgcaacg agcgcaaccc ttatcttcag tagccagcat ataaggtggg cactctggag  1140
agactgccag ggagaacctg gaggaaggtg gggatgacgt caaatcatca tgccccttat  1200
ggccagggct acacacgtgc tacaatggcg taaacaaagg gaagcgagag ggtgacctgg  1260
agcgaatccc aaaaataacg tctcagttcg gattgtagtc tgcaactcga ctacatgaag  1320
ctggaatcgc tagtaatcgc ggatcagcat gccgcggtga atacgttccc gggtcttgta  1380
cacaccgccc gtcacaccat gggagtcagt aacgcccgaa gccagtgacc caaccttaga  1440
ggagggagct gtcgaaggcg ggacggataa ctggggtgaa gtcgtaacaa ggtagccgta  1500
tcggaaggtg cggctggatc acctcctttt                                   1529
```

SEQ ID NO: 16          moltype = DNA   length = 1527
FEATURE                Location/Qualifiers
misc_feature           1..1527
                       note = Synthetic Polynucleotide
source                 1..1527
                       mol_type = other DNA
                       organism = synthetic construct
SEQUENCE: 16
```
atgagagttt gatcctggct caggatgaac gctggcggcg tgcctaacac atgcaagtcg   60
aacgaagcga tttaacggaa gttttcggat ggaagttgaa ttgactgagt ggcggacggg  120
tgagtaacgc gtgggtaacc tgccttgtac tggggacaaa cagttagaaa tgactgctaa  180
taccgcataa gcgcacagta tcgcatgata cagtgtgaaa aactccggtg gtacaagatg  240
gacccgcgtc tgattagcta gttggtaagg taacggctta ccaaggcgac gatcagtagc  300
cgacctgaga gggtgaccgg ccacattggg actgagacac ggcccaaact cctacgggag  360
gcagcagtgg ggaatattgc acaatgggcg aaagcctgat gcagcgacgc cgcgtgagtg  420
aagaagtatt tcggtatgta aagctctatc agcagggaag aaaatgacgg tacctgacta  480
agaagccccg gctaactacg tgccagcccc gcggtaata cgtaggggc aagcgttatc  540
cggatttact gggtgtaaag ggagcgtaga cggtaaagca agtctgaagt gaaagcccg  600
ggctcaactg cgggactgct ttggaaactg tttaactgga gtgtcggaga ggtaagtgga  660
attcctagtg tagcggtgaa atgcgtagat attaggagga acaccagtgg cgaaggcgac  720
ttactggacg ataactgacg ttgaggctcg aaagcgtggg gagcaaacag gattagatac  780
cctggtagtc cacgccgtaa acgatgaata ctaggtgttg gggagcaaag ctcttcggtg  840
ccgtcgcaaa gcagtaagt attccacctg ggagtacgt tcgcaagaat gaaactcaaa  900
ggaattgacg gggacccgca caagcggtgg agcatgtggt ttaattcgaa gcaacgcgaa  960
gaaccttacc aggtcttgac atcgatccga cggggagta acgtccccttt cccttcgggg 1020
cggagaagac aggtggtgca tggttgtcgt cagctcgtgt cgtgagatgt tgggttaagt 1080
cccgcaacga gcgcaaccct tattctaagt agccagcggt tcggccggga actcttggga 1140
gactgccagg gataacctgg aggaaggtgg ggatgacgtc aaatcatcat gccccttatg 1200
atctgggcta cacacgtgct acaatggcgt aaacaaagag aagcaagacc gcgaggtgga 1260
gcaaatctca aaaataacgt ctcagttcgg actgcaggct gcaactcgcc tgcacgaagc 1320
tggaatcgct agtaatcgcg aatcagaatg tcgcggtga tacgttccg ggtcttgtac 1380
acaccgcccg tcacaccatg ggagtcagta acgcccgaag tcagtgacc aaccgcaagg 1440
agggagctgc cgaaggcggg accgataact ggggtgaagt cgtaacaagg tagccgtatc 1500
ggaaggtgcg gctggatcac ctccttt                                     1527
```

SEQ ID NO: 17          moltype = DNA   length = 1530
FEATURE                Location/Qualifiers
misc_feature           1..1530
                       note = Synthetic Polynucleotide
source                 1..1530
                       mol_type = other DNA
                       organism = synthetic construct
SEQUENCE: 17
```
atgagagttt gatcctggct caggatgaac gctggcggcg tgcctaacac atgcaagtcg   60
aacgaagcaa ttaaaatgaa gttttcggat ggattttga ttgactgagt ggcggacggg  120
tgagtaacgc gtggataacc tgcctcacac tggggataaa cagttagaaa tgactgctaa  180
taccgcataa gcgcacagta ccgcatggta cggtgtgaaa aactccggtg gtgtgagatg  240
gatccgcgtc tgattagcca gttggcgggg taacggccca ccaaagcgac gatcagtagc  300
cgacctgaga gggtgaccgg ccacattggg actgagacac ggcccaaact cctacggag  360
gcagcagtgg ggaatattgc acaatgggcg aaagcctgat gcagcgacgc cgcgtgagtg  420
aagaagtatt tcggtatgta agctctatc agcagggaag aaaatgacgg tacctgacta  480
agaagccccg gctaactacg tgccagcagc cgcggtaata cgtaggggc aagcgttatc  540
cggatttact gggtgtaaag ggagcgtaga cggcaagca agtctgaagt gaaacccag  600
ggctcaaccc tgggactgct ttggaaactg ttttgctaga gtgtcggaga ggtaagtgga  660
attcctagtg tagcggtgaa atgcgtagat attaggagga acaccagtgg cgaaggcgac  720
ttactggacg ataactgacg ttgaggctcg aaagcgtggg gagcaaacag gattagatac  780
cctggtagtc cacgccgtaa acgatgaatg ctaggtgttg ggggcaaag ccttcggtg  840
ccgtcgcaaa gcagtaagc attccacctg ggagtacgt tcgcaagaat gaaactcaaa  900
ggaattgacg gggacccgca caagcggtgg agcatgtggt ttaattcgaa gcaacgcgaa  960
gaaccttacc aagtcttgac atcctcttga ccggcgtgta acggcgcctt cccttcgggg 1020
caagagagac aggtggtgca tggttgtcgt cagctcgtgt cgtgagatgt tgggttaagt 1080
cccgcaacga gcgcaaccct tatcttagt agccagcagg taaagctggg cactctaggg 1140
agactgccag gataacctg gaggaaggtg gggatgacgt caaatcatca tgccccttat 1200
gatttgggct acacacgtgc tacaatggcg taaacaaagg gaagcaagac agtgatgtgg 1260
agcaaatccc aaaaataacg tcccagttcg gactgtagtc tgcaacccga ctacacgaag 1320
ctggaatcgc tagtaatcgc gaatcagaat gtcgcggtga atacgttccc ggtcttgta  1380
cacaccgccc gtcacaccat gggagtcagt aacgcccgaa gtcagtgacc caactcgcaa 1440
gagagggagc tgccgaaggc ggggcaggta actggggtga agtcgtaaca aggtagccgt 1500
atcggaaggt gcggctggat cacctccttt                                  1530
```

| SEQ ID NO: 18 | moltype = DNA length = 1528 |
|---|---|
| FEATURE | Location/Qualifiers |
| misc_feature | 1..1528 |
| | note = Synthetic Polynucleotide |
| source | 1..1528 |
| | mol_type = other DNA |
| | organism = synthetic construct |

SEQUENCE: 18

```
aacgagagtt tgatcctggc tcaggatgaa cgctggcggc gtgcttaaca catgcaagtc   60
gagcgaagca ctttggaaga ttcttcggat gaagacttt gtgactgagc ggcggacggg   120
tgagtaacgc gtgggtaacc tgcctcatac aggggaataa cagttagaaa tgactgctaa   180
taccgcataa gaccacggta ccgcatggta cagtggtaaa aactccggtg gtatgagatg   240
gacccgcgtc tgattaggta gttggtgggg taacggccta ccaagccgac gatcagtagc   300
cgacctgaga gggtgaccgg ccacattggg actgagacac ggcccagact cctacgggag   360
gcagcagtgg ggaatattgc acaatggagg aaactctgat gcagcgacgc cgcgtgaagg   420
atgaagtatt tcggtatgta aacttctatc agcagggaag aaaatgacgg tacctgacta   480
agaagccccg gctaactacg tgccagcagc cgcggtaata cgtaggggc aagcgttatc   540
cggatttact gggtgtaaag ggagcgtaga cggcacggca agccagatgt gaaagcccgg   600
ggctcaaccc cgggactgca tttgaactg ctgagctaga gtgtcggaga ggcaagtgga   660
attcctagtg tagcggtgaa atgcgtagat attaggagga acaccagtgg cgaaggcggc   720
ttgctggacg atgactgacg ttgaggctcg aaagcgtggg gagcaaacag gattagatac   780
cctggtagtc cacgccgtaa acgatgactg ctaggtgtcg ggtggcaaag ccattcggtg   840
ccgcagctaa cgcaataagc agtccacctg gggagtacgt tcgcaagaat gaaactcaaa   900
ggaattgacg gggacccgca caagcggtgg agcatgtggt ttaattcgaa gcaacgcgaa   960
gaaccttacc tgatcttgac atcccgatga ccgcttcgta atggaagctt ttcttcggaa  1020
catcggtgac aggtggtgca tggttgtcgt cagctcgtgt cgtgagatgt tgggttaagt  1080
cccgcaacga gcgcaacccc tatcttcagt agccagcagg ttaagctggg cactctggag  1140
agactgccag ggataacctg gaggaaggtg gggatgacgt caaatcatca tgcccttat   1200
gaccagggct acacacgtgc tacaatggcg taaacaaaga gaagcgaact cgcgagggta  1260
agcaaatctc aaaaataacg tctcagttcg gattgtagtc tgcaactcga ctacatgaag  1320
ctggaatcgc tagtaatcgc agatcagaat gctgcggtga atacgttccc gggtcttgta  1380
cacaccgccc gtcacaccat gggagtcagt aacgcccgaa gtcagtgacc caaccgtaag  1440
gagggagctg ccgaaggtgg gaccgataac tggggtgaag tcgtaacaag gtagccgtat  1500
cggaaggtgc ggctggatca cctcctt                                      1528
```

| SEQ ID NO: 19 | moltype = DNA length = 1531 |
|---|---|
| FEATURE | Location/Qualifiers |
| misc_feature | 1..1531 |
| | note = Synthetic Polynucleotide |
| source | 1..1531 |
| | mol_type = other DNA |
| | organism = synthetic construct |

SEQUENCE: 19

```
atcagagagt ttgatcctgg ctcaggatga acgctggcgg cgtgcttaac acatgcaagt   60
cgagcgaagc acttaagtgg atctcttcgg attgaaactt atttgactga gcggcggacg   120
ggtgagtaac gcgtgggtaa cctgcctcat acagggggat aacagttaga aatgactgct   180
aataccgcat aagcgcacag gaccgcatgg tctggtgtga aaaactccgg tggtatgaga   240
tggacccgcg tctgattagc tagttggagg ggtaacggcc caccaaggcg acgatcagta   300
gccgcctga gagggtgaac ggccacattg ggactgagac acggcccaga ctcctacggg   360
aggcagcagt ggggaatatt gcacaatggg ggaaacctg atgcagcgac gccgcgtgaa   420
ggaagaagta tctcggtatg taaacttcta tcagcaggga agaaaatgac ggtacctgac   480
taagaagccc cggctaacta cgtgccagca gccgcggtaa tacgtagggg gcaagcgtta   540
tccggattta ctgggtgtaa agggagcgta gacggaagag caagtctgat gtgaaaggct   600
ggggcttaac cccaggactg cattggaaac tgtttttcta gagtgccgga gaggtaagcg   660
gaattcctag tgtagcggtg aaatgcgtag atattaggag gaacaccagt ggcgaaggcg   720
gcttactgga cggtaactga cgttgaggct cgaaagcgtg gggagcaaac aggattagat   780
accctggtag tccacgccgt aaacgatgaa tactaggtgt cgggtggcaa agccattcgg   840
tgccgcagca aacgcaataa gtattccacc tggggagtac gttcgcaaga atgaaactca   900
aaggaattga cggggacccg cacaagcggt ggagcatgtg gtttaattcg aagcaacgcg   960
aagaaccttacc caagtcttg acatccctct gaccggcccg taacgggccc ttcccttcgg  1020
ggcagaggag acaggtggtg catggttgtc gtcagctcgt gtcgtgagat gttgggttaa   1080
gtcccgcaac gagcgcaacc cctatcctta gtagccagca ggtgaagctg gcactctag   1140
ggagactgcc ggggataacc cggaggaagg cggggacgac gtcaaatcat catgcccctt  1200
atgatttggg ctacacacgt gctacaatgg cgtaaacaaa gggaagcgag acagcgatgt  1260
tgagcaaatc ccaaaaataa cgtcccagtt cggactgcag tctgcaactc gactgcacga  1320
agctggaatc gctagtaatc gcgaatcaga atgtcgcggt gaatacgttc ccgggtcttg  1380
tacacaccgc ccgtcacacc atgggagtca gtaacgcccg aagtcagtga cccaaccctta  1440
caggagggag ctgccgaagg cgggaccgat aactggggtg aagtcgtaac aaggtagccg  1500
tatcggaagg tgcggctgga tcacctcctt t                                   1531
```

| SEQ ID NO: 20 | moltype = DNA length = 1528 |
|---|---|
| FEATURE | Location/Qualifiers |
| misc_feature | 1..1528 |
| | note = Synthetic Polynucleotide |
| source | 1..1528 |
| | mol_type = other DNA |
| | organism = synthetic construct |

```
SEQUENCE: 20
aacgagagtt tgatcctggc tcaggatgaa cgctggcggc gtgcttaaca catgcaagtc    60
gagcgaagca ctttggaaga ttcttcggat gatttccttt gtgactgagc ggcggacggg   120
tgagtaacgc gtgggtaacc tgcctcatac agggggataa cagttagaaa tgactgctaa   180
taccgcataa gaccacggta ccgcatggta cagtggtaaa aactccggtg gtatgagatg   240
gacccgcgtc tgattaggta gttggtgggg taacggccta ccaagccgac gatcagtagc   300
cgacctgaga gggtgaccgg ccacattggg actgagacac ggcccagact cctacgggag   360
gcagcagtgg ggaatattgc acaatggagg aaactctgat gcagcgacgc cgcgtgaagg   420
atgaagtatt tcggtatgta aacttctatc agcagggaag aaaatgacgg tacctgacta   480
agaagcccccg gctaactacg tgccagcagc cgcggtaata cgtaggggggc aagcgttatc   540
cggatttact gggtgtaaag ggagcgtaga cggcacggca agccagatgt gaaagcccgg   600
ggctcaaccc cgggactgca tttggaactg ctgagctaga gtgtcggaga ggcaagtgga   660
attcctagtg tagcggtgaa atgcgtagat attaggagga acaccagtgg cgaaggcggc   720
ttgctggacg atgactgacg ttgaggctcg aaagcgtggg gagcaaacag gattagatac   780
cctggtagtc cacgccgtaa acgatgactg ctaggtgtcg ggtggcaaag ccattcggtg   840
ccgcagctaa cgcaataagc agtccacctg ggagtacgt tcgcaagaat gaaactcaaa   900
ggaattgacg ggacccgca caagcggtgg agcatgtggt ttaattcgaa gcaacgcgaa   960
gaaccttacc tgatcttgac atcccgatga ccgcttcgta atggaagctt ttcttcggaa  1020
catcggtgac aggtggtgca tggttgtcgt cagctcgtgt cgtgagatgt tgggttaagt  1080
cccgcaacga gcgcaacccc tatcttcagt agccagcagg ttaagctggg cactctggag  1140
agactgccag ggataacctg gaggaaggtg gggatgacgt caaatcatca tgccccttat  1200
gaccagggct acacacgtgc tacaatggcg taaacaaaga cgcgaactt cgcgagggta  1260
agcaaatctc aaaaataacg tctcagttcg gattgtagtc tgcaactcga ctacatgaag  1320
ctggaatcgc tagtaatcgc agatcagaat gctgcggtga atacgttccc gggtcttgta  1380
cacaccgccc gtcacaccat gggagtcagt aacgcccgaa gtcagtgacc caaccgtaag  1440
gagggagctg ccgaaggtgg gaccgataac tgggggtgaag tcgtaacaag gtagccgtat  1500
cggaaggtgc ggctggatca cctcctttt                                    1528

SEQ ID NO: 21          moltype = DNA  length = 1537
FEATURE                Location/Qualifiers
misc_feature           1..1537
                       note = Synthetic Polynucleotide
source                 1..1537
                       mol_type = other DNA
                       organism = synthetic construct
SEQUENCE: 21
atggagagtt tgatcctggc tcaggatgaa cgctggcggc atgcctaata catgcaagtc    60
gaacgaagtt tcgaggaagc ttgcttccaa agagacttag tggcgaacgg gtgagtaaca   120
cgtaggtaac ctgcccatgt gtccgggata actgctggaa acggtagcta aaaccggata   180
ggtatacaga gcgcatgctc agtattatta agcgcccatc aaggcgtgaa catggatgga   240
cctgcggcgc attagctagt tggtgaggta acggcccacc aaggcgatga tgcgtagccg   300
gcctgagagg gtaaacggcc acattgggac tgagacacgg cccaaactcc tacgggaggc   360
agcagtaggg aattttcgtc aatggggaa acccctgaaca tgcggtgagt gaa         420
gaaggtcttc ggatcgtaaa gctctgttgt aagtgaagaa cggctcatag aggaaatgct   480
atgggagtga cggtagctta ccagaaagcc acgctaact acgtgccagc agccgcggta   540
atacgtaggt ggcaagcgtt atccggaatc attgggcgta aagggtgcgt aggtggcgta   600
ctaagtctgt agtaaaaggc aatggctcaa ccattgtaag ctatggaaac tggtatgctg   660
gagtgcagaa gagggcgatg gaattccatg tgtagcggga aaatgcgtag atatatggag   720
gaacaccagt ggcgaaggcg gtcgcctggt ctgtaactga cactgaggca cgaaagcgtg   780
gggagcaaat aggattagat accctagtag tccacgccgt aaacgatgag aactaagtgt   840
tggaggaatt cagtgctgca gttaacgcaa taagttctcc gcctggggag tatgcacgca   900
agtgtgaaac tcaaaggaat tgacggggggc ccgcacaagc ggtggagtat gtggtttaat   960
tcgaagcaac gcgaagaacc ttaccaggcc ttgacatgga aacaaatacc ctagatatag  1020
ggggataatt atggatcaca caggtggtgc atggttgtcg tcagctcgtg tcgtgagatg  1080
ttgggttaag tcccgcaacg agcgcaaccc ttgtcgcatg ttaccagcat caagttgggg  1140
actcatgcga gactgccggt gacaaaccgg aggaaggtgg ggatgacgtc aaatcatcat  1200
gccccttatg gcctgggcta cacacgtact acaatggcgg ccacaaagag cagcgacaca  1260
gtgatgtgaa gcgaatctca taaggtcgt ctcagttcgg attgaagtct gcaactcgac  1320
ttcatgaagt cggaatcgct agtaatcgca gatcagcatg ctgcggtgaa tacgttctcg  1380
ggccttgtac acaccgcccg tcaaaccatg ggagtcagta atacccgaag ccggtggcat  1440
aaccgtaagg agtgagccgt cgaaggtagg accgatgact gggggttaagt cgtaacaagg  1500
tatcccctacg gaacgtgggg gatggatcac ctccttt                          1537

SEQ ID NO: 22          moltype = DNA  length = 476
FEATURE                Location/Qualifiers
misc_feature           1..476
                       note = Synthetic Polynucleotide
source                 1..476
                       mol_type = other DNA
                       organism = synthetic construct
SEQUENCE: 22
agtaacgcgt gggtaacctg cctcatacag ggggataaca gttagaaatg actgctaata    60
ccgcataaga ccacggtacc gcatggtaca gtggtaaaaa ctccggtggt atgagatgga   120
cccgcgtctg attaggtagt tggtgggta acggcctacc aagccgacga tcagtagccg   180
acctgagagg gtgaccggcc acattgggac tgagacacgg cccagactcc tacgggaggc   240
agcagtgggg aatattgcac aatggaggaa actctgatgc agcgacgccg cgtgaaggat   300
gaagtatttc ggtatgtaaa cttctatcag caggaagaa aatgacgta cctgactaag    360
aagcccccggc taactacgtg ccagcagccg cggtaatacg taggggggcaa gcgttatccg   420
gatttactgg gtgtaaaggg agcgtagacg gcacggcaag ccagatgtga aagccc       476
```

```
SEQ ID NO: 23            moltype = DNA   length = 354
FEATURE                  Location/Qualifiers
misc_feature             1..354
                         note = Synthetic Polynucleotide
source                   1..354
                         mol_type = other DNA
                         organism = synthetic construct
SEQUENCE: 23
caggctggag tgcaggagag gtaagcggaa ttcctagtgt agcggtgaaa tgcgtagata    60
ttaggaggaa caccagtggc gaaggcggct tactggactg taactgacgt tgaggctcga   120
aagcgtgggg agcaaacagg attagatacc ctggtagtcc acgcggtaaa cgatgattgc   180
taggtgtagg tgggtatgga cccatcggtg ccgcagctaa cgcaataagc aatccacctg   240
gggagtacgt tcgcaagaat gaaactcaaa ggaattgacg ggacccgca caagcggtgg    300
agcatgtggt ttaattcgaa gcaacgcgaa gaaccttacc aagtcttgac atcc         354

SEQ ID NO: 24            moltype = DNA   length = 190
FEATURE                  Location/Qualifiers
misc_feature             1..190
                         note = Synthetic Polynucleotide
source                   1..190
                         mol_type = other DNA
                         organism = synthetic construct
SEQUENCE: 24
ccggggctca ccccgggact gcatttggaa ctgctgagct agagtgtcgg agaggcaagt    60
ggaattccta gtgtagcggt gaaatgcgta gatattagga ggaacaccag tggcgaaggc   120
ggcttgctgg acgatgactg acgttgaggc tcgaaagcgt ggggagcaaa caggattaga   180
taccctggta                                                          190

SEQ ID NO: 25            moltype = DNA   length = 190
FEATURE                  Location/Qualifiers
misc_feature             1..190
                         note = Synthetic Polynucleotide
source                   1..190
                         mol_type = other DNA
                         organism = synthetic construct
SEQUENCE: 25
agggtcaacc cctggactgc attggaaact gtcaggctgg agtgccggag aggtaagcgg    60
aattcctagt gtagcggtga aatgcgtaga tattaggagg aacaccagtg gcgaaggcgg   120
cttactggac ggtaactgac gttgatgctc gaaagcgtgg ggagcaaaca ggattagata   180
acctggtaaa                                                          190

SEQ ID NO: 26            moltype = DNA   length = 209
FEATURE                  Location/Qualifiers
misc_feature             1..209
                         note = Synthetic Polynucleotide
source                   1..209
                         mol_type = other DNA
                         organism = synthetic construct
SEQUENCE: 26
gggaagtcgg tcttaagtgc ggggcttaac cccgtgaggg gaccgaaact gtgaagctcg    60
agtgtcggag aggaaagcgg aattcctagt gtagcggtga aatgcgtaga tattaggagg   120
aacaccagtg gcgaaagcgg ctttctggac gacaactgac gctgaggcgc gaaagccagg   180
ggagcaaacg ggattagata ccccagtaa                                     209

SEQ ID NO: 27            moltype = DNA   length = 203
FEATURE                  Location/Qualifiers
misc_feature             1..203
                         note = Synthetic Polynucleotide
source                   1..203
                         mol_type = other DNA
                         organism = synthetic construct
SEQUENCE: 27
tagtctgagt gatgcgggc ttaacccgt atggcgttgg atactggaag tcttgagtgc     60
aggagaggaa aggggaattc ccagtgtagc ggtgaaatgc gtagatattg gggaacac     120
cagtggcgaa ggcgcctttc tggactgtgt ctgacgctga gatgcgaaag ccagggtagc   180
aaacgggatt agataccacg gta                                           203

SEQ ID NO: 28            moltype = DNA   length = 207
FEATURE                  Location/Qualifiers
misc_feature             1..207
                         note = Synthetic Polynucleotide
source                   1..207
                         mol_type = other DNA
                         organism = synthetic construct
```

```
SEQUENCE: 28
gatagtcggt cttaagtgcg gggcttaccc cgtgagggga ccgaaactgt gaagctcgag    60
tgtcggagag gaaagcggaa ttcctagtgt agcggtgaaa tgcgtagata ttaggaggaa   120
caccagtggc gaaagcggct ttctggacga caactgacgc tgaggcgcga aagccagggg   180
agcaaacggg attagatacc acggtaa                                      207

SEQ ID NO: 29           moltype = DNA   length = 424
FEATURE                 Location/Qualifiers
misc_feature            1..424
                        note = Synthetic Polynucleotide
source                  1..424
                        mol_type = other DNA
                        organism = synthetic construct
SEQUENCE: 29
cgtttgctcc acgctttcga gcctcacgtc agttaccgtc cagtaagccg ccttcgccac    60
tggtgttcct cctaatatct acgcatttca ccgctacact aggaattccg cttacctctc   120
cggtactcta gattgacagt ttccaatgca gtcccggggt tgagcccggg ttttcacat    180
cagacttgcc actccgtcta cgctcccttt acacccagta aatccggata acgcttgcac   240
catacgtatt accgcggctg ctggcacgta tttagccggt gcttcttagt caggtaccgt   300
cattttcttc cctgctgata gagctttaca taccgaaata cttcatcgct cacgcggcgt   360
cgctgcatca gggtttcccc cattgtgcaa tattccccac tgctgcctcc cgtaggagtt   420
tgga                                                               424

SEQ ID NO: 30           moltype = DNA   length = 441
FEATURE                 Location/Qualifiers
misc_feature            1..441
                        note = Synthetic Polynucleotide
source                  1..441
                        mol_type = other DNA
                        organism = synthetic construct
SEQUENCE: 30
tgtcacactt tcgagcatca gcgtcagtta cagtccagta agctgccttc gcaatcggag    60
ttcttcgtga tatctaagca tttcaccgct acaccacgaa ttccgcctac ctctactgca   120
ctcaagacga ccagtatcaa ctgcaatttt acggttgagc cgcaaacttt cacagctgac   180
ttaatagtcc gcctacgctc cctttaaacc caataaatcc ggataacgct tggatcctcc   240
gtattaccgc ggctgctggc acggagttag ccgatcctta ttcgtatggt acatacaaaa   300
agccacacgt ggctcacttt attcccatat aaaagaagtt tacaacccat agggcagtca   360
tccttcacgc tacttggctg gttcagactc tcgtccattg accaatattc ctcactgctg   420
cctcccgtag gtagtttgga a                                            441

SEQ ID NO: 31           moltype = DNA   length = 422
FEATURE                 Location/Qualifiers
misc_feature            1..422
                        note = Synthetic Polynucleotide
source                  1..422
                        mol_type = other DNA
                        organism = synthetic construct
SEQUENCE: 31
ccgttgtcac gctttcgtgc tcagtgtcag tttcagtcca gtaagccgcc ttcgccactg    60
atgttcctcc taatatctac gcatttcacc gctacactag gaattccgct tacctctcct   120
gcactccagt ctgacagttt caaaagcagt cccagagtta agccctgggt tttcacttct   180
gacttgccat accacctacg cacccttta acccagtaat tccggataac gcttgccccc   240
tacgtattac cgcggctgct ggcacggagt tagccggggc ttcttagtca ggtaccgtca   300
ttttcttccc tgctgataga gctttacata ccgaaatact tcttcactca cgcggcgtcg   360
ctgcatcagg gttccccca ttgtgcaata ttccccactg ctgcctcccg tggaagtttg   420
ga                                                                 422

SEQ ID NO: 32           moltype = DNA   length = 424
FEATURE                 Location/Qualifiers
misc_feature            1..424
                        note = Synthetic Polynucleotide
source                  1..424
                        mol_type = other DNA
                        organism = synthetic construct
SEQUENCE: 32
gcgaatgtca cgcattcgag cctcacgtca gttaccgtcc agtaagccgc cttcgccact    60
ggtgttcctc ctaatatcta cgcatttcac cgctacacta ggaattccgc ttacctctcc   120
ggcactcaag actaacagtt tccaatgcag tccaggggt gagccccgc ctttcacatc    180
agacttgcca gtccgtctac gctccctta cacccagtaa atccggataa cgcttgcccc   240
ctacgtatta ccgcggctgc tggcacgtag ttagccgggg cttcttagtc aggtaccgtc   300
actatcttcc ctgctgatag aagtttacat accgagatac ttcttccttc acgcggcgtc   360
gctgcatcag ggtttccccc attgtgcaat attccccact gctgcctccc gtgggagttt   420
ggaa                                                               424

SEQ ID NO: 33           moltype = DNA   length = 422
FEATURE                 Location/Qualifiers
misc_feature            1..422
                        note = Synthetic Polynucleotide
```

```
source                  1..422
                        mol_type = other DNA
                        organism = synthetic construct
SEQUENCE: 33
tgctcacgct ttcgcgctca gcgtcagtta ctgtccagca atccgccttc gccactggtg   60
ttcctccgta tatctacgca tttcaccgct acacacggaa ttccgattgc ctctccagca  120
ctcaagaact acagtttcaa atgcaggctg gaggttgagc cccagttttt cacatctgac  180
ttgcaatccc gcctacacgc cctttacacc cagtaaatcc ggataacgct tgccaccttac 240
gtattaccgc ggctgctggc acgtagttag ccgtggctta ttcgtcaggt accgtcattt  300
gtttcgtccc tgacaaaaga agtttacaac ccgaaagcct tcttccttca cgcggcgttg  360
ctgggtcagg cttgcgccca ttgccccaata ttccccactg ctgcctccg tggtagtttg   420
ga                                                                 422

SEQ ID NO: 34           moltype = DNA  length = 419
FEATURE                 Location/Qualifiers
misc_feature            1..419
                        note = Synthetic Polynucleotide
source                  1..419
                        mol_type = other DNA
                        organism = synthetic construct
SEQUENCE: 34
tgtccacgct ttcgagctca gcgtcagtta tcgtccagta agccgccttc gccactggtg   60
ttcctcctaa tatctacgca tttcaccgct acactaggaa ttccgcttac ccctccgaca  120
ctctagtacg acagtttcca atgcagtacc ggggttgagc cccgggcttt cacatcagac  180
ttgccgcacc gcctgcgctc cctttacacc cagtaaatcc ggataacgct tgcaccttac  240
gtattaccgc ggctgctggc acgtatttag ccggtgctta ttagtcaggt accgtcatta  300
tcttccctgc tgatagagct ttacataccg aaatacttct tcgctcacgc ggcgtcgctg  360
catcaggctt tcgcccattg tgcaatattc cccactgctg actccgtag gagtttggga  419

SEQ ID NO: 35           moltype = DNA  length = 424
FEATURE                 Location/Qualifiers
misc_feature            1..424
                        note = Synthetic Polynucleotide
source                  1..424
                        mol_type = other DNA
                        organism = synthetic construct
SEQUENCE: 35
cgtttctcca cgcttcgcgc tcagcgtcag ttactgtcca gcaatccgcc ttcgccactg   60
gtgttcctcc gtatatctac gcatttcacc gctacacacg gaattccgat tgcctctcca  120
gcactcaaga actacagttt caaatgcagg ctggaggttg agccccccagt tttcacatct 180
gacttgcaat cccgcctaca cgcctttac acccagtaaa tccggataac gcttgccacc  240
tacgtattac cgcggctgct ggcacgtagt tagccgtggc ttattcgtca ggtaccgtca  300
tttgtttcgt ccccgacaaa agaagtttac aacccgaaag ccttcttcct tcacgcggcg  360
ttgctgggtc aggcttgcgc ccattgccca atattcccca ctgctgcctc cctgggaagt  420
ttgg                                                               424

SEQ ID NO: 36           moltype = DNA  length = 445
FEATURE                 Location/Qualifiers
misc_feature            1..445
                        note = Synthetic Polynucleotide
source                  1..445
                        mol_type = other DNA
                        organism = synthetic construct
SEQUENCE: 36
atgtcctgac ttcgcgcctc agcgtcagtt gtcgtccaga aagccgcttt cgccactggt   60
gttcctccta atatctacgc atttcaccgc tacactagga attccgcttt cctctccgac  120
actcgagctt cacagtttcg gtcccctcac ggggttaagc cccgcacttt taagaccgac  180
ttgcgatgcc gcctgcgcgc cctttacgcc caataattcc ggacaacgct tgccaccttac 240
gtattaccgc ggctgctggc acgtagttag ccgtggcttc tcttacggtt accgtcaggg  300
ataacgggta ttgaccgcta tcctgttcgt cccatataac agaactttac aacccgaagg  360
ccgtcatcgt tcacgcggcg ttgctccgtc agactttcgt ccattgcgga agattcccca  420
ctgctgcctc cctgggaagt ttgga                                        445

SEQ ID NO: 37           moltype = DNA  length = 421
FEATURE                 Location/Qualifiers
misc_feature            1..421
                        note = Synthetic Polynucleotide
source                  1..421
                        mol_type = other DNA
                        organism = synthetic construct
SEQUENCE: 37
gtttgctcac gctttcgagc tcagcgtcag ttatcgtcca gtaagccgcc ttcgccactg   60
gtgttcctcc taatatctac gcatttcacc gctacactag gaattccgct taccctccg   120
acactctagt acgacagttt ccaatgcagt accggggttg agccccggc tttcacatca   180
gacttgccgc accgcctgcg ctccctttac acccagtaaa tccggataac gcttgcacca  240
tacgtattac cgcggctgct ggcacgtatt tagccggtgc ttcttagtca ggtaccgtca  300
ttatcttccc tgctgataga gctttacata ccgaaatact tcttcgctca cgcggcgtcg  360
ctgcatcagg ctttcgccca ttgtgcaata ttccccactg ctgcctccg taggagtttg   420
g                                                                  421
```

```
SEQ ID NO: 38            moltype = DNA  length = 424
FEATURE                  Location/Qualifiers
misc_feature             1..424
                         note = Synthetic Polynucleotide
source                   1..424
                         mol_type = other DNA
                         organism = synthetic construct
SEQUENCE: 38
cgttgctcac gcattcgagc ctcagcgtca gttaagccca gtaagccgcc ttcgccactg    60
atgttcctcc taatatctac gcatttcacc gctacactag gaattccgct tacctctact   120
tcactcaaga accacagttt caaatgcagt ttatgggtta agcccatagt tttcacatct   180
gacttgcgat cccgcctacg ctcccttac acccagtaat tccggacaac gctcgctccc    240
tacgtattac cgcggctgct ggcacgtagt tagccggagc ttcctcctca ggtaccgtc    300
tttttcgtcc ctgaagacag aggtttacaa tcctaaaacc ttcttccctc acgcggcatc   360
gctgcatcag agtttcctcc attgtgcaat attcccact gctgcctccc gtaggagttt    420
ggaa                                                                424

SEQ ID NO: 39            moltype = DNA  length = 189
FEATURE                  Location/Qualifiers
misc_feature             1..189
                         note = Synthetic Polynucleotide
source                   1..189
                         mol_type = other DNA
                         organism = synthetic construct
SEQUENCE: 39
tgggcttacc cataaactgc atttgaaact gtggttcttg agtgaagtag aggtaagcgg    60
aattcctagt gtagcggtga aatgcgtaga tattaggagg aacatcagtg gcgaaggcgg   120
cttactgggc tttaactgac gctgaggctc gaaagcgtgg ggagcaaaca ggattagata   180
cccaagtaa                                                           189

SEQ ID NO: 40            moltype = DNA  length = 414
FEATURE                  Location/Qualifiers
misc_feature             1..414
                         note = Synthetic Polynucleotide
source                   1..414
                         mol_type = other DNA
                         organism = synthetic construct
SEQUENCE: 40
gtcagcatcg agctcacgtc agttaccgtc cagtaagccg ccttcgccac tggtgttcct    60
cctaatatct acgcatttca ccgctacact aggaattccg cttactctc cggtactcta    120
gattgacagt ttccaatgca gtcccggggt tgagccccgg gttttcacat cagacttgcc   180
actccgtcta cgctcccttt acacccagta aatccggata acgcttgcac catacgtatt   240
accgcggctg ctggcacgta tttagccggt gcttcttagt caggtaccgt cattttcttc   300
cctgctgata gagctttaca taccgaaata cttcatcgct cacgcggcgt cgctgcatca   360
gggtttcccc cattgtgcaa tattccccac tgctgcctcc cgagggagtt tgga         414

SEQ ID NO: 41            moltype = DNA  length = 191
FEATURE                  Location/Qualifiers
misc_feature             1..191
                         note = Synthetic Polynucleotide
source                   1..191
                         mol_type = other DNA
                         organism = synthetic construct
SEQUENCE: 41
tcatcgctta cggtggatct gcgccgggta cgggcgggct ggagtgcggt aggggagact    60
ggaattcccg gtgtaacggt ggaatgtgta gatatcggga agaacaccga tgccgaaggc   120
aggtctctgg gccgtcactg acgctgagga gcgaaagcgt ggggagcgaa caggattaga   180
tacaacggta a                                                        191

SEQ ID NO: 42            moltype = DNA  length = 196
FEATURE                  Location/Qualifiers
misc_feature             1..196
                         note = Synthetic Polynucleotide
source                   1..196
                         mol_type = other DNA
                         organism = synthetic construct
SEQUENCE: 42
tgaacccagg gcttaactct gggactgctt tgaactgtc agactggagt gcaggagagg     60
taagcggaat tcctagtgta gcggtgaaat gcgtagatat taggaggaac atcagtggcg   120
aaggcggctt actggactga aactgacact gaggcacgaa agcgtgggga gcaaacagga   180
ttagatacca tggtaa                                                   196

SEQ ID NO: 43            moltype = DNA  length = 192
FEATURE                  Location/Qualifiers
misc_feature             1..192
                         note = Synthetic Polynucleotide
```

```
source                          1..192
                                mol_type = other DNA
                                organism = synthetic construct
SEQUENCE: 43
accagggctt aactctggga ctgcttttga actgtcagac tggagtgcag gagaggtaag    60
cggaattcct agtgtagcgg tgaaatgcgt agatattagg aggaacatca gtggcgaagg   120
cggcttactg gactgaaact gacactgagg cacgaaagcg tggggagcaa acaggattag   180
atacccctggt aa                                                      192

SEQ ID NO: 44                   moltype = DNA   length = 195
FEATURE                         Location/Qualifiers
misc_feature                    1..195
                                note = Synthetic Polynucleotide
source                          1..195
                                mol_type = other DNA
                                organism = synthetic construct
SEQUENCE: 44
gaacccaggg cttaactctg ggactgcttt tgaactgtca gactggagtg caggagaggt    60
aagcggaatt cctagtgtag cggtgaaatg cgtagatatt aggaggaaca tcagtggcga   120
aggcggctta ctggactgaa actgacactg aggcacgaaa gcgtggggag caaacaggat   180
tagatacccc ggtaa                                                    195

SEQ ID NO: 45                   moltype = DNA   length = 418
FEATURE                         Location/Qualifiers
misc_feature                    1..418
                                note = Synthetic Polynucleotide
source                          1..418
                                mol_type = other DNA
                                organism = synthetic construct
SEQUENCE: 45
gagtcagctt tcgagctcag cgtcagttat cgtccagtaa gccgccttcg ccactggtgt    60
tcctcctaat atctacgcat ttcaccgcta cactaggaat tccgcttacc cctccgacac   120
tctagtacga cagtttccaa tgcagtaccg gggttgagcc ccgggctttc acatcagact   180
tgccgcaccg cctgcgctcc ctttacaccc agtaaatccg gataacgctt gcaccatacg   240
tattaccgcg gctgctggca cgtatttagc cggtgcttct tagtcaggta ccgtcattat   300
cttccctgct gatagagctt tacataccga aatacttctt gctcacgcgg cgtcgctgc    360
atcaggcttt cgcccattgt gcaatattcc ccactgctgc ctcccgaggg agtttgga    418

SEQ ID NO: 46                   moltype = DNA   length = 416
FEATURE                         Location/Qualifiers
misc_feature                    1..416
                                note = Synthetic Polynucleotide
source                          1..416
                                mol_type = other DNA
                                organism = synthetic construct
SEQUENCE: 46
tgtcagcttt cgagctcacg tcagttaccg tccagtaagc cgccttcgcc actggtgttc    60
ctcctaatat ctacgcattt caccgctaca ctaggaattc cgcttacctc tccggtactc   120
tagattgaca cgtttccaatg cagtcccggg gttgagcccc gggttttcac atcagacttg   180
ccactccgtc tacgctccct ttacacccag taaatccgga taacgcttgc accatacgta   240
ttaccgcggc tgctggcacg tatttagccg gtgcttctta gtcaggtacc gtcatttct   300
tccctgctga tagagcttta cataccgaaa tacttcatcg ctcacgcggc gtcgctgcat   360
cagggttttc cccattgtgc aatattcccc actgctgcct cccgtaggag tttgga       416

SEQ ID NO: 47                   moltype = DNA   length = 400
FEATURE                         Location/Qualifiers
misc_feature                    1..400
                                note = Synthetic Polynucleotide
source                          1..400
                                mol_type = other DNA
                                organism = synthetic construct
SEQUENCE: 47
cacgtcagtt accgtccagt aagccgcctt cgccactggt gttcctccta atatctacgc    60
atttcaccgc tacactagga attccgctta cctctccggc actcaagacg ggcagtttcc   120
aatgcagtcc cggggttgag ccccagcctt tcacatcaga cttgtccatc cgtctacgct   180
cccttttacac ccagtaaatc cggataacgc ttgcccccta cgtattaccg cggctgctgg   240
cacgtagtta gccgggggctt cttagtcagg taccgtcatt ttcttccctg ctgatagaag   300
tttacatacc gagatacttc ttccttcacg cggcgtcgct gcatcagggt tcccccatt   360
gtgcaatatt ccccactgct gcctcccgta ggagtttggg                          400

SEQ ID NO: 48                   moltype = DNA   length = 416
FEATURE                         Location/Qualifiers
misc_feature                    1..416
                                note = Synthetic Polynucleotide
source                          1..416
                                mol_type = other DNA
                                organism = synthetic construct
```

```
SEQUENCE: 48
gtcagctttc gagctcacgt cagttaccgt ccagtaagcc gccttcgcca ctggtgttcc   60
tcctaatatc tacgcatttc accgctacac taggaattcc gcttacctct ccggtactct  120
agattgacga tttccaatgc agtcccgggg ttgagcccg gttttcaca tcagacttgc   180
cactccgtct acgctccctt tacacccagt aaatccggat aacgcttgca ccatacgtat  240
taccgcggct gctggcacgt atttagccgg tgcttcttag tcaggtaccg tcatttttctt 300
ccctgctgat agagctttac ataccgaaat acttcatcgc tcacgcggcg tcgctgcatc  360
agggtttccc ccattgtgca atattcccca ctgctgcctc ccgtggggag tttgga      416

SEQ ID NO: 49          moltype = DNA  length = 421
FEATURE                Location/Qualifiers
misc_feature           1..421
                       note = Synthetic Polynucleotide
source                 1..421
                       mol_type = other DNA
                       organism = synthetic construct
SEQUENCE: 49
gatgctcagc tttcgtgctc agtgtcagtt tcagtccagt aagccgcctt cgccactgat   60
gttcctccta atatctacgc atttcaccgc tacactagga attccgctta cctctcctgc  120
actccagtct gacagtttca aaagcagtcc cagagttaag ccctgggttt tcacttctga  180
cttgccatac cacctacgca cccttttacac ccagtaattc cggataacgc ttgcccccta 240
cgtattaccg cggctgctgg cacgtagtta gccggggcct cttagtcagg taccgtcatt  300
ttcttccctg ctgatagagc tttacatacc gagatacttc ttcactcacg cggcgtcgct  360
gcatcagggt ttcccccatt gtgcaatatt ccccactgct gcctccgaa ggaagtttgg  420
a                                                                   421

SEQ ID NO: 50          moltype = DNA  length = 418
FEATURE                Location/Qualifiers
misc_feature           1..418
                       note = Synthetic Polynucleotide
source                 1..418
                       mol_type = other DNA
                       organism = synthetic construct
SEQUENCE: 50
gtgtcagctt cgtgctcagt gtcagtttca gtccagtaag ccgccttcgc cactgatgtt   60
cctcctaata tctacgcatt tcaccgctac actaggaatt ccgcttacct ctcctgcact  120
ccagtctgac agtttcaaaa gcagtcccag agttaagccc tgggttttca cttctgactt  180
gccataccac ctacgcaccc tttacaccca gtaattccgg ataacgcttg cccctacgt  240
attaccgcgg ctgctggcac gtagttagcc ggggcttctt agtcaggtac cgtcattttc  300
ttccctgctg atagagcttt acataccgag atacttcttc actcacgcgg cgtcgctgca  360
tcagggtttc ccccattgtg caatattccc cactgctgcc tccgtaggg agtttgga    418

SEQ ID NO: 51          moltype = DNA  length = 415
FEATURE                Location/Qualifiers
misc_feature           1..415
                       note = Synthetic Polynucleotide
source                 1..415
                       mol_type = other DNA
                       organism = synthetic construct
SEQUENCE: 51
gtcagcttcg agcctcacgt cagttaccgt ccagtaagcc gccttcgcca ctggtgttcc   60
tcctaatatc tacgcatttc accgctacac taggaattcc gcttacctct ccggtactct  120
agattgacag tttccaatgc agtcccgggg ttgagcccg gttttcaca tcagacttgc   180
cactccgtct acgctccctt tacacccagt aaatccggat aacgcttgca ccatacgtat  240
taccgcggct gctggcacgt atttagccgg tgcttcttag tcaggtaccg tcatttttctt 300
ccctgctgat agagctttac ataccgaaat acttcatcgc tcacgcggcg tcgctgcatc  360
agggtttccc ccattgtgca atattcccca ctgctgcctc cgtaggagt ttgga       415

SEQ ID NO: 52          moltype = DNA  length = 418
FEATURE                Location/Qualifiers
misc_feature           1..418
                       note = Synthetic Polynucleotide
source                 1..418
                       mol_type = other DNA
                       organism = synthetic construct
SEQUENCE: 52
tgtcagcttt cgagctcagc gtcagttatc gtccagtaag ccgccttcgc cactggtgtt   60
cctcctaata tctacgcatt tcaccgctac actaggaatt ccgcttaccc ctccgacact  120
ctagtacgac agtttccaat gcagtaccgg ggttgagccc cggctttca catcagactt  180
gccgcaccgc ctgcgctccc tttacaccca gtaaatccgg ataacgcttg caccatacgt  240
attaccgcgg ctgctggcac gtatttagcc ggtgcttctt agtcaggtac cgtcattatc  300
ttccctgcta atagagcttt acataccgaa atacttcttc gctcacgcgg cgtcgctgca  360
tcaggctttc gcccattgtg caatattccc cactgctgcc tcccgaaggg agtttgga   418

SEQ ID NO: 53          moltype = DNA  length = 416
FEATURE                Location/Qualifiers
misc_feature           1..416
                       note = Synthetic Polynucleotide
```

```
source                  1..416
                        mol_type = other DNA
                        organism = synthetic construct
SEQUENCE: 53
ttcagctttc gagctcagcg tcagttatcg tccagtaagc cgccttcgcc actggtgttc    60
ctcctaatat ctacgcattt caccgctaca ctaggaattc cgcttacccc tccgacactc   120
tagtacgaca gtttccaatg cagtaccggg gttgagcccc gggctttcac atcgacttg    180
ccgcaccgcc tgcgctccct ttacacccag taaatccgga taacgcttgc accatacgta   240
ttaccgcggc tgctggcacg tatttagccg gtgcttctta gtcaggtacc gtcattatct   300
tccctgctga tagagcttta cataccgaaa tacttcttcg ctcacgcggg gtcgctgcat   360
caggctttcg cccattgtgc aatattcccc actgctgcct cccgaggga gtttgg        416

SEQ ID NO: 54           moltype = DNA  length = 435
FEATURE                 Location/Qualifiers
misc_feature            1..435
                        note = Synthetic Polynucleotide
source                  1..435
                        mol_type = other DNA
                        organism = synthetic construct
SEQUENCE: 54
ttcggtctgc tttcccttc tcgcgcctca gtgtcagttt ctgtctagta agccgccttc     60
gccactgatg ttcctcctaa tatctacgca cttcaccgct ccacaatgaa ttccgcttac   120
ccctcccgcg ctctagtctg acagttttaa aaaaactccc cgagagaaac cctgggtttt   180
ttcttctgac atgcgatatc ccacccccac ccttttataca cccaaaaatc ggataaaagg   240
tgcgacctac gtattatacc ggctgctggg gcgtagatag ccgggggttc ttatacaggg   300
accgtcattt tctttcccgc tgatacagct ttacataccg aaatacttct ttctcacgcg   360
gcgtcgctgc atcagggttt cccccattgt gcaatattcc ccactgctgc ctcccgaagg   420
ggaagttggg ggaaa                                                    435

SEQ ID NO: 55           moltype = DNA  length = 418
FEATURE                 Location/Qualifiers
misc_feature            1..418
                        note = Synthetic Polynucleotide
source                  1..418
                        mol_type = other DNA
                        organism = synthetic construct
SEQUENCE: 55
gttcagcttt cgagcctcac gtcagttacc gtccagtaag ccgccttcgc cactggtgtt    60
cctcctaata tctacgcatt tcaccgctac actaggaatt ccgcttacct ctccggtact   120
ctagattgac agtttccaat gcagtcccgg ggttgagccc cgggttttca catcagactt   180
gccactccgt ctacgctccc tttacaccca gtaaatccgg ataacgcttg caccatacgt   240
attaccgcgc tgctggcac gtatttagcc ggtgcttctt agtcaggtac cgtcattttc   300
ttccctgcta tagagctttt acataccgaa atacttcatc gctcacgcgg cgtcgctgca   360
tcagggtttc ccccattgtg caatattccc cactgctgcc tccgagggg agtttgga     418

SEQ ID NO: 56           moltype = DNA  length = 416
FEATURE                 Location/Qualifiers
misc_feature            1..416
                        note = Synthetic Polynucleotide
source                  1..416
                        mol_type = other DNA
                        organism = synthetic construct
SEQUENCE: 56
gtcagctttc gagctcacgt cagttaccgt ccagtaagcc gccttcgcca ctggtgttcc    60
tcctaatatc tacgcatttc accgctacac taggaattcc gcttacctct ccggtactct   120
agattgacag tttccaatgc agtcccgggg ttgagcccg gttttcaca tcagacttgc    180
cactccgtct acgctccctt tacacccagt aaatccggat aacgcttgca ccatacgtat   240
taccgcggct gctggcacgt atttagccgg tgcttcttag tcaggtaccg tcattttctt   300
ccctgctgat agagctttac ataccgaaat acttcatcgc tcacgcggcg tcgctgcatc   360
agggtttccc ccattgtgca atattcccca ctgctgcctc ccgagggag tttgga       416

SEQ ID NO: 57           moltype = DNA  length = 417
FEATURE                 Location/Qualifiers
misc_feature            1..417
                        note = Synthetic Polynucleotide
source                  1..417
                        mol_type = other DNA
                        organism = synthetic construct
SEQUENCE: 57
tctcacgctt tcgagctcac gtcagtcatc gtccagcaag ccgccttcgc cactggtgtt    60
cctcctaata tctacgcatt tcaccgctac actaggaatt ccacttgcct ctccgacact   120
ctagctcagc agtttccaaat gcagtcccgg ggttgagccc cgggctttca catctggctt   180
gccgtgccgt ctacgctccc tttacaccca gtaaatccgg ataacgcttg ccccctacgt   240
attaccgcgc tgctggcac gtagttagcc ggggcttctt agtcaggtac cgtcattttc   300
ttccctgctg atagaagttt acataccgaa atacttcatc cttcacgcgg cgtcgctgca   360
tcagagtttc ctccattgtg caatattccc cactgctgcc tccgtaggg agtttgg       417

SEQ ID NO: 58           moltype = DNA  length = 417
FEATURE                 Location/Qualifiers
```

```
misc_feature           1..417
                       note = Synthetic Polynucleotide
source                 1..417
                       mol_type = other DNA
                       organism = synthetic construct
SEQUENCE: 58
gtcagctttc gagctcagcg tcagttatcg tccagtaagc cgccttcgcc actggtgttc    60
ctcctaatat ctacgcattt caccgctaca ctaggaattc cacttacccc tccgacactc   120
tagtacgaca gtttccaatg cagtaccggg gttgagcccc gggctttcac atcagacttg   180
ccgcaccgcc tgcgctcccct ttacacccag taaatccgga taacgcttgc accatacgta   240
ttaccgcggc tgctggcacg tatttagccg gtgcttctta gtcaggtacc gtcattcttc   300
ttccctgctg atagagcttt acataccgaa atacttcttc gctcacgcgg cgtcgctgca   360
tcagggtttc ccccattgtg caatattccc cactgctgcc tcccgaggga gtttgga      417

SEQ ID NO: 59          moltype = DNA   length = 419
FEATURE                Location/Qualifiers
misc_feature           1..419
                       note = Synthetic Polynucleotide
source                 1..419
                       mol_type = other DNA
                       organism = synthetic construct
SEQUENCE: 59
agccccgctt tcgagcctca cgtcagttac cgtccagtaa gccgccttcg ccactggtgt    60
tcctcctaat atctacgcat ttcaccgcta cactaggaat tccgcttacc tctccggcac   120
tcaagacggg cagtttccaa tgcagtcccg gggttgagcc ccagccttc acatcagact   180
tgtccatccg tctacgctcc cttacaccc agtaaatccg gataacgctt gcccctacg    240
tattaccgcg gctgctggca cgtagttagc cggggcttct tagtcaggta ccgtcatttt   300
cttccctgct gatagaagtt tacataccga gatacttctt ccttcacgcg gcgtcgctgc   360
atcagggttt cccccattgt gcaatattcc ccactgctgc ctcccgaagg aagtttgga    419

SEQ ID NO: 60          moltype = DNA   length = 419
FEATURE                Location/Qualifiers
misc_feature           1..419
                       note = Synthetic Polynucleotide
source                 1..419
                       mol_type = other DNA
                       organism = synthetic construct
SEQUENCE: 60
tgctcagctt tcgagcctca cgtcagttac cgtccagtaa gccgccttcg ccactggtgt    60
tcttcctaat atctacgcat ttcaccgcta cactaggaat tccgcttacc tctccggcac   120
tcgagccaga cagtttccaa tgcagtccca gggttaagcc ctgggttttc acatcagact   180
tgccttgccg tctacgctcc ctttacaccc agtaaatccg gataacgctt gcccctacg    240
tattaccgcg gctgctggca cgtagttagc cggggcttct tagtcaggta ccgtcattat   300
cttccctgct gatagagctt tacataccga aatacttctt cgctcacgcg gcgtcgctgc   360
atcagggttt cccccattgt gcaatattcc ccactgctgc ctcccgaagg gagtttgga    419

SEQ ID NO: 61          moltype = DNA   length = 421
FEATURE                Location/Qualifiers
misc_feature           1..421
                       note = Synthetic Polynucleotide
source                 1..421
                       mol_type = other DNA
                       organism = synthetic construct
SEQUENCE: 61
gttgctcagc tttcgagctc acgtcagtta ccgtccagta agccgccttc gccactggtg    60
ttcttcctaa tatctacgca tttcaccgct acactaggaa ttccgcttac ctctccggca   120
ctcgagccag acagtttcca atgcagtccc agggttaagc cctgggtttt cacatcagac   180
ttgccttgcc gtctacgctc cctttacacc cagtaaatcc ggataacgct tgcccccctac   240
gtattaccgc ggctgctggc acgtagttag ccggggcttc ttagtcaggt accgtcatta   300
tcttccctgc tgatagagct ttacataccg aaatacttct tcgctcacgc ggcgtcgctg   360
catcagggtt tcccccattg tgcaatattc cccactgctg cctcccgaag gaaagtttgg   420
a                                                                   421

SEQ ID NO: 62          moltype = DNA   length = 420
FEATURE                Location/Qualifiers
misc_feature           1..420
                       note = Synthetic Polynucleotide
source                 1..420
                       mol_type = other DNA
                       organism = synthetic construct
SEQUENCE: 62
tgctcagctt tcgagctcag cgtcagttat cgtccagtaa gccgcttcg ccactggtgt    60
tcctcctaat atctacgcat ttcaccgcta cactaggaat tccacttacc cctccgacac   120
tctagtacga cagtttccaa tgcagtaccg gggttgagcc ccgggctttc acatcagact   180
tgccgcaccg cctgcgctcc ctttacaccc agtaaatccg gataacgctt gcaccatacg   240
tattaccgcg gctgctggca cgtatttagc cggtgcttct tagtcaggta ccgtcattct   300
tcttccctgc tgatagagct ttacataccg aaatacttct tcgctcacgc ggcgtcgctg   360
catcagggtt tcccccattg tgcaatattc cccactgctg cctcccgaag ggagtttgga   420
```

-continued

| | | |
|---|---|---|
| SEQ ID NO: 63 | moltype = DNA length = 446 | |
| FEATURE | Location/Qualifiers | |
| misc_feature | 1..446 | |
| | note = Synthetic Polynucleotide | |
| source | 1..446 | |
| | mol_type = other DNA | |
| | organism = synthetic construct | |

SEQUENCE: 63
```
gatgccctgg cttcgcgctc agcgtcagtt gtcgtccaga aagccgcttt cgccactggt    60
gttcctccta atatctacgc atttcaccgc tacactagga attccgcttt cctctccgac   120
actcgagctt cacagtttcg gtcccctcac ggggttaagc cccgcacttt taagaccgac   180
ttgcgatgcc gcctgcgcgc cctttacgcc caataattcc ggacaacgct tgccacctac   240
gtattaccgc ggctgctggc acgtagttag ccgtggcttt ctcttacggt accgtcaggg   300
ataacgggta ttgaccgcta tcctgttcgt cccatataac agaactttac aacccgaagg   360
ccgtcatcgt tcacgcggcg ttgctccgtc agactttcgt ccattgcgga agattcccca   420
ctgctgcctc ccggggggag tttgga                                        446
```

| | | |
|---|---|---|
| SEQ ID NO: 64 | moltype = DNA length = 419 | |
| FEATURE | Location/Qualifiers | |
| misc_feature | 1..419 | |
| | note = Synthetic Polynucleotide | |
| source | 1..419 | |
| | mol_type = other DNA | |
| | organism = synthetic construct | |

SEQUENCE: 64
```
gtcccgcttt cgagcctcag cgtcagttat cgtccagtaa gccgccttcg ccactggtgt    60
tcctcctaat atctacgcat ttcaccgcta cactaggaat tccgcttacc cctccgacac   120
tctagtacga cagtttccaa tgcagtaccg gggttgagcc ccgggctttc acatcagact   180
tgccgcaccg cctgcgctcc ctttacaccc agtaaatccg gataacgctt gcaccatacg   240
tattaccgcg gctgctggca cgtatttagc cggtgcttct tagtcaggta ccgtcattgc   300
cttccctgct gatagagctt tacataccga aatacttctc cgctcacgcg gcgtcgctgc   360
atcaggcttt cgcccattgt gcaatattcc ccactgctgc ctcccgaagg gaagtttgg    419
```

| | | |
|---|---|---|
| SEQ ID NO: 65 | moltype = DNA length = 418 | |
| FEATURE | Location/Qualifiers | |
| misc_feature | 1..418 | |
| | note = Synthetic Polynucleotide | |
| source | 1..418 | |
| | mol_type = other DNA | |
| | organism = synthetic construct | |

SEQUENCE: 65
```
tgtcagcttt cgagctcagc gtcagttatc gtccagtaag ccgccttcgc cactggtgtt    60
cctcctaata tctacgcatt tcaccgctac actaggaatt ccgcttaccc ctccgacact   120
ctagtacgac agtttccaat gcagtaccgg ggttgagccc cgggctttca catcagactt   180
gccgcaccgc ctgcgctccc tttacaccca gtaaatccgg ataacgcttg caccatacgt   240
attaccgcgc tgctggcacg tatttagccg gtgcttcttc agtcaggtac cgtcattatc   300
ttccctgctg atagagcttt acataccgaa atacttcttc gctcacgcgg cgtcgctgca   360
tcaggctttc gcccattgtg caatattccc cactgctgcc tcccgaaggg agtttgga     418
```

| | | |
|---|---|---|
| SEQ ID NO: 66 | moltype = DNA length = 420 | |
| FEATURE | Location/Qualifiers | |
| misc_feature | 1..420 | |
| | note = Synthetic Polynucleotide | |
| source | 1..420 | |
| | mol_type = other DNA | |
| | organism = synthetic construct | |

SEQUENCE: 66
```
tgctcagctt tcgagctcag cgtcagttat cgtccagtaa gccgccttcg ccactggtgt    60
tcctcctaat atctacgcat ttcaccgcta cactaggaat tccacttacc cctccgacac   120
tctagtacga cagtttccaa tgcagtaccg gggttgagcc ccgggctttc acatcagact   180
tgccgcaccg cctgcgctcc ctttacaccc agtaaatccg gataacgctt gcaccatacg   240
tattaccgcg gctgctggca cgtatttagc cggtgcttct tagtcaggta ccgtcattct   300
tcttccctgc tgatagagct ttacataccg aaatacttct cgctcacgcg ggcgtcgctg   360
catcagggtt tcccccattg tgcaatattc cccactgctg cctcccgaag ggagtttgga   420
```

| | | |
|---|---|---|
| SEQ ID NO: 67 | moltype = DNA length = 417 | |
| FEATURE | Location/Qualifiers | |
| misc_feature | 1..417 | |
| | note = Synthetic Polynucleotide | |
| source | 1..417 | |
| | mol_type = other DNA | |
| | organism = synthetic construct | |

SEQUENCE: 67
```
attcagcttt cgagctcacg tcagttaccg tccagtaagc cgccttcgcc actggtgttc    60
ctctaatat ctacgcattt caccgctaca ctaggaattc cgcttacccc tccggcactc   120
aagcatacca gttccaatg cagtccaggg gttaagcccc tgcctttcac atcagacttg   180
atacgccgtc tacgctccct ttacacccag taaatccgga taacgctcgc ccctacgta   240
ttaccgcggc tgctggcacg tagttagccg gggcttctta gtcaggtacc gtcattatct   300
```

```
tccctgctga tagaagttta cataccgaga tacttcttcc ttcacgcggc gtcgctgcat    360
cagggtttcc cccattgtgc aatattcccc actgctgcct cccgagggaa gtttgga       417

SEQ ID NO: 68          moltype = DNA   length = 416
FEATURE                Location/Qualifiers
misc_feature           1..416
                       note = Synthetic Polynucleotide
source                 1..416
                       mol_type = other DNA
                       organism = synthetic construct
SEQUENCE: 68
gtgtcagctt tcgagctcac gtcagttacc gtccagtaag ccgccttcgc cactggtgtt    60
cttcctaata tctacgcatt tcaccgctac actaggaatt ccgcttacct ctccggcact    120
cgagccagac agtttccaat gcagtcccag ggttaagccc tgggtttca catcagactt    180
gccttgccgt ctacgctccc tttacaccca gtaaatccgg ataacgcttg cccccctacgt   240
attaccgcgg ctgctggcac gtagttagcc ggggcttctt agtcaggtac cgtcattatc    300
ttccctgctg atagagcttt acataccgaa atacttcttc gctcacgcgg cgtcgctgca    360
tcagggtttc cccattgtg caatattccc cactgctgcc tcccgaggga gtttgg         416

SEQ ID NO: 69          moltype = DNA   length = 416
FEATURE                Location/Qualifiers
misc_feature           1..416
                       note = Synthetic Polynucleotide
source                 1..416
                       mol_type = other DNA
                       organism = synthetic construct
SEQUENCE: 69
gccagcttcg agcctcacgt cagtcatcgt ccagtaagcc gccttcgcca ctggtgttcc    60
tcctaatatc tacgcatttc accgctacac taggaattcc acttacctct ccgacactct    120
agctgcacag tttccaaagc agtccacagg ttgagcccgc cctttcact tcagacttgc     180
acagccgtct acgctccctt tacacccagt aaatccggat aacgcttgcc ccctacgtat    240
taccgcggct gctggcacgt agttagccgg ggcttcttag tcaggtaccg tcattttctt    300
ccctgctgat agaagtttac ataccgaaat acttcatcct tcacgcgcg tcgctgcatc     360
aggctttcgc ccattgtgca atattcccca ctgctgcctc ccgagggaag tttgga        416

SEQ ID NO: 70          moltype = DNA   length = 418
FEATURE                Location/Qualifiers
misc_feature           1..418
                       note = Synthetic Polynucleotide
source                 1..418
                       mol_type = other DNA
                       organism = synthetic construct
SEQUENCE: 70
tgatcagctt tcgagctcac gtcagttacc gtccagtaag ccgccttcgc cactggtgtt    60
cctcctaata tctacgcatt tcaccgctac actaggaatt ccgcttacct ctccggtact    120
ctagattgac agtttccaat gcagtcccgg ggttgagccc cgggttttca catcagactt    180
gccactccgt ctacgctccc tttacaccca gtaaatccgg ataacgcttg caccatacgt    240
attaccgcgg ctgctggcac gtatttagcc ggtgcttctt agtcaggtac cgtcattttc    300
ttccctgctg atagagcttt acataccgaa atacttcatc gctcacgcgg cgtcgctgca    360
tcagggtttc cccattgtg caatattccc cactgctgcc tcccggggg agtttgga        418

SEQ ID NO: 71          moltype = DNA   length = 420
FEATURE                Location/Qualifiers
misc_feature           1..420
                       note = Synthetic Polynucleotide
source                 1..420
                       mol_type = other DNA
                       organism = synthetic construct
SEQUENCE: 71
gatgatcagc tttcgagctc acgtcagtta ccgtccagta agccgccttc gccactggtg    60
ttcctcctaa tatctacgca tttcaccgct acactaggaa ttccgcttac ctctccggca    120
ctctagaaaa acagtttcca atgcagtcct ggggttaagc ccagcctttc acatcagac     180
ttgctcttcc gtctacgctc cctttacacc cagtaaatcc ggataacgct tgcccccctac   240
gtattaccgc ggctgctggc acgtagttag ccggggcttc ttagtcaggt accgtcattt     300
tcttccctgc tgatagaagt ttacataccg agatacttct tccttcacgc ggcgtcgctg    360
catcagggtt tccccattg tgcaatattc cccactgctg cctcccgggg gaagtttgga      420

SEQ ID NO: 72          moltype = DNA   length = 418
FEATURE                Location/Qualifiers
misc_feature           1..418
                       note = Synthetic Polynucleotide
source                 1..418
                       mol_type = other DNA
                       organism = synthetic construct
SEQUENCE: 72
ttgatcagct ttcgagctca cgtcagttac cgtccagtaa gccgccttcg ccactggtgt    60
tcctcctaat atctacgcat ttcaccgcta cactaggaat tccgcttacc tctccggcac    120
tctagaaaaa cagtttccaa tgcagtcctg ggggttaagcc ccagcctttc acatcagact   180
tgctcttccg tctacgctcc ctttacaccc agtaaatccg gataacgctt gcccccctacg   240
```

```
tattaccgcg gctgctggca cgtagttagc cggggcttct tagtcaggta ccgtcatttt    300
cttccctgct gatagaagtt tacataccga gatacttctt ccttcacgcg gcgtcgctgc    360
atcagggttt cccccattgt gcaatattcc ccactgctgc ctcccgaagg gagtttgg     418
```

SEQ ID NO: 73          moltype = DNA   length = 421
FEATURE                Location/Qualifiers
misc_feature           1..421
                       note = Synthetic Polynucleotide
source                 1..421
                       mol_type = other DNA
                       organism = synthetic construct
SEQUENCE: 73
```
gtatttcagc tttcgagctc agcgtcagtt atcgtccagt aagccgcctt cgccactggt     60
gttcctccta atatctacgc atttcaccgc tacactagga attccgctta ccctccgac    120
actctagtac gacagtttcc aatgcagtac cggggttgag ccccgggctt tcacatcaga   180
cttgccgcac cgcctgcgct ccctttacac ccagtaaatc cggataacgc ttgcaccata   240
cgtattaccg cggctgctgg cacgtattta gccggtgctt cttagtcagg taccgtcatt   300
atcttccctg ctgatagagc tttacatacc gaaatacttc ttcgctcacg cggcgtcgct   360
gcatcaggct ttcgcccatt gtgcaatatt ccccactgct gcctcccgaa gggagtttgg   420
a                                                                    421
```

SEQ ID NO: 74          moltype = DNA   length = 419
FEATURE                Location/Qualifiers
misc_feature           1..419
                       note = Synthetic Polynucleotide
source                 1..419
                       mol_type = other DNA
                       organism = synthetic construct
SEQUENCE: 74
```
gctcagcttt cgagctcagc gtcagttatc gtccagtaag ccgccttcgc cactggtgtt     60
cctcctaata tctacgcatt tcaccgctac actaggaatt ccacttaccc ctccgacact   120
ctagtacgac agtttccaat gcagtaccgg ggttgagccc cgggcttttca catcagactt   180
gccgcaccgc ctgcgctccc tttacaccca gtaaatccgg ataacgcttg caccatacgt   240
attaccgcgg ctgctggcac gtatttagcc ggtgcttctt agtcaggtac cgtcattctt   300
cttccctgct gatagagctt tacataccga aatacttctt cctcacgcg gcgtcgctgc    360
atcagggttt cccccattgt gcaatattcc ccactgctgc ctcccgaggg gagtttgga    419
```

SEQ ID NO: 75          moltype = DNA   length = 417
FEATURE                Location/Qualifiers
misc_feature           1..417
                       note = Synthetic Polynucleotide
source                 1..417
                       mol_type = other DNA
                       organism = synthetic construct
SEQUENCE: 75
```
tttcagcttc gagcctcagc gtcagttatc gtccagtaag ccgccttcgc cactggtgtt     60
cctcctaata tctacgcatt tcaccgctac actaggaatt ccgcttaccc ctccgacact   120
ctagtacgac agtttccaat gcagtaccgg ggttgagccc cgggcttttca catcagactt   180
gccgcaccgc ctgcgctccc tttacaccca gtaaatccgg ataacgcttg caccatacgt   240
attaccgcgg ctgctggcac gtatttagcc ggtgcttctt agtcaggtac cgtcattatc   300
ttccctgctg atagagcttt ataccgaa atacttcttc gctcacgcgg cgtcgctgca    360
tcaggctttc gcccattgtg caatattccc cactgctagc tcccgaagga gtttgga     417
```

SEQ ID NO: 76          moltype = DNA   length = 419
FEATURE                Location/Qualifiers
misc_feature           1..419
                       note = Synthetic Polynucleotide
source                 1..419
                       mol_type = other DNA
                       organism = synthetic construct
SEQUENCE: 76
```
agctcagctt tcgagctcag cgtcagttat cgtccagtaa gccgccttcg ccactggtgt     60
tcctcctaat atctacgcat ttcaccgcta cactaggaat tccgcttacc cctccgacac   120
tctagtacga cagtttccaa tgcagtaccg gggttgagcc ccgggctttc acatcagact   180
tgccgcaccg cctgcgctcc ctttacaccc agtaaatccg gataacgctt gcaccatacg   240
tattaccgcg gctgctggca cgtatttagc cggtgcttct tagtcaggta ccgtcattat   300
cttccctgct gatagagctt tacataccga aatacttctt cgctcacgcg gcgtcgctgc   360
atcaggcttt cgcccattgt gcaatattcc ccactgctgc ctcccgaagg gagtttgga   419
```

SEQ ID NO: 77          moltype = DNA   length = 418
FEATURE                Location/Qualifiers
misc_feature           1..418
                       note = Synthetic Polynucleotide
source                 1..418
                       mol_type = other DNA
                       organism = synthetic construct
SEQUENCE: 77
```
gtccagcttt cgagctcag cgtcagttat cgtccagtaa gccgccttcg ccactggtgt     60
tcctcctaat atctacgcat ttcaccgcta cactaggaat tccgcttacc cctccgacac   120
```

```
tctagtacga cagtttccaa tgcagtaccg gggttgagcc ccgggctttc acatcagact    180
tgccgcaccg cctgcgctcc ctttacaccc agtaaatccg gataacgctt gcaccatacg    240
tattaccgcg gctgctggca cgtatttagc cggtgcttct tagtcaggta ccgtcattat    300
cttccctgct gatagagctt tacataccga aatacttctt cgctcacgcg gcgtcgctgc    360
atcaggcttt cgcccattgt gcaatattcc ccactgctgc ctcccgaggg agtttgga     418

SEQ ID NO: 78           moltype = DNA   length = 193
FEATURE                 Location/Qualifiers
misc_feature            1..193
                        note = Synthetic Polynucleotide
source                  1..193
                        mol_type = other DNA
                        organism = synthetic construct
SEQUENCE: 78
tgagccgggc tcaccccggt actgcattgg aactgtcgta ctagagtgtc ggaggggtaa     60
gcggaattcc tagtgtagcg gtgaaatgcg tagatattag gaggaacacc agtggcgaag    120
gcggcttact ggacgataac tgacgctgag gctcgaaagc gtggggagca aacaggatta    180
gataccaccgg taa                                                     193

SEQ ID NO: 79           moltype = DNA   length = 424
FEATURE                 Location/Qualifiers
misc_feature            1..424
                        note = Synthetic Polynucleotide
source                  1..424
                        mol_type = other DNA
                        organism = synthetic construct
SEQUENCE: 79
cacgatgtca gctttcgagc tcagcgtcag ttatcgtcca gtaagccgcc ttcgccactg     60
gtgttcctcc taatatctac gcatttcacc gctacactag gaattccact taccccctccg   120
acactctagt acgacagttt ccaatgcagt accgggggttg agccccggcc tttcacatca    180
gacttgccgc accgcctgcg ctccctttac acccagtaaa tccggataac gcttgcacca    240
tacgtattac cgcggctgct ggcacgtatt tagccggtgc ttcttagtca ggtaccgtca    300
ttcttcttcc ctgctgatag agctttacat accgaaatac ttcttcgctc acgcggcgtc    360
gctgcatcag ggtttccccc attgtgcaat attcccccact gctgcctccc gagggagtt    420
tgga                                                                 424

SEQ ID NO: 80           moltype = DNA   length = 1524
FEATURE                 Location/Qualifiers
misc_feature            1..1524
                        note = Synthetic Polynucleotide
source                  1..1524
                        mol_type = other DNA
                        organism = synthetic construct
SEQUENCE: 80
atggagagtt tgatcctggc tcaggatgaa cgctggcggc gtgcctaata catgcaagtc     60
gaacgcgagc acttgtgctc gagtggcgaa cgggtgagta atacataagt aacctgccct    120
agacaggggg ataactattg gaaacgatag ctaagaccgc ataggtacgg acactgcatg    180
gtgaccgtat taaaagtgcc tcaaagcact ggtagaggat ggacttatgg cgcattagct    240
ggttggcggg gtaacggccc accaaggcga cgatgcgtag ccgacctgag agggtgaccg    300
gccacactgg gactgagaca cggcccagac tcctacggga ggcagcagta gggaattttc    360
ggcaatgggg gaaaccctga ccgagcaacg ccgcgtgaag gaagaaggtt ttcggattgt    420
aaacttctgt tataaaggaa gaacggcggc tacaggaaat ggtagccgaa tgacggtact    480
ttattagaaa gccacggcta actacgtgcc agcagccgcg gtaatacgta ggtggcaagc    540
gttatccgga attattgggc gtaaagaggg agcaggcggc agcaagggtc tgtggtgaaa    600
gcctgaagct taacttcagt aagccataga accaggcag ctagagtgca ggagaggatc     660
gtggaattcc atgtgtagcg gtgaaatgcg tagatatatg gaggaacacc agtggcgaag    720
gcgacgatct ggcctgcaac tgacgctcag tcccgaaagc gtggggagca aataggatta    780
gataccctag tagtccacgc cgtaaacgat gagtactaag tgttggatgt caaagttcag    840
tgctgcagtt aacgcaataa gtactccgcc tgagtagtac gttcgcaaga atgaaactca    900
aaggaattga cggggcccg cacaagcggt ggagcatgtg gtttaattcg aagcaacgcg     960
aagaaccctta ccaggtcttg acatactcat aaaggctcca gagatggaga gatagctata   1020
tgagatacag gtggtgcatg gttgtcgtca gctcgtgtcg tgagatgttg ggttaagtcc    1080
cgcaacgagc gcaaccctta tcgttagtta ccatcattaa gttgggact ctagcgagac     1140
tgccagtgac aagctggagg aaggcgggga tgacgtcaaa tcatcatgcc cttatgacc     1200
tgggctacac acgtgctaca atggatggtg cagagggaag cgaagccgcg aggtgaagca    1260
aaacccataa aaccattctc agttcggatt gtagtctgca actcgactac atgaagttgg    1320
aatcgctagt aatcgcgaat cagcatgtcg cggtgaatac gttctcgggc cttgtacaca    1380
ccgcccgtca caccacgaga gttgataaca cccgaagccg gtggcctaac cgcaaggaag    1440
gagctgtcta aggtgggatt gatgattggg gtgaagtcgt aacaaggtat ccctacggga    1500
acgtggggat ggatcacctc cttt                                          1524

SEQ ID NO: 81           moltype = DNA   length = 1528
FEATURE                 Location/Qualifiers
misc_feature            1..1528
                        note = Synthetic Polynucleotide
source                  1..1528
                        mol_type = other DNA
                        organism = synthetic construct
```

```
SEQUENCE: 81
atgagagttt gatcctggct caggatgaac gctggcggcg tgcctaacac atgcaagtcg    60
aacgaagcaa ttgaaggaag ttttcggatg gaattcgatt gactgagtgg cggacgggtg   120
agtaacgcgt ggataacctg cctcacactg ggggataaca gttagaaatg actgctaata   180
ccgcataagc gcacagtacc gcatgtgaaa ctcggtggt gtgagatgga   240
tccgcgtctg attagccagt tggcggggta acggcccacc aaagcgacga tcagtagccg   300
acctgagagg gtgaccggcc acattgggac tgagacacgg cccaaactcc tacgggaggc   360
agcagtgggg aatattgcac aatgggcgaa agcctgatgc agcgacgccg cgtgagtgaa   420
gaagtatttc ggtatgtaaa gctctatcag cagggaagaa aatgacggta cctgactaag   480
aagcccggc taactacgtg ccagcagccg cggtaatacg taggggggcaa gcgttatccg   540
gatttactgg gtgtaaaggg agcgtagacg gcgaagcaag tctgaagtga aaacccaggg   600
ctcaaccctg ggactgcttt ggaaactgtt ttgctagagt gtcggagagg taagtggaat   660
tcctagtgta gcggtgaaat gcgtagatat taggaggaac accagtggcg aaggcggctt   720
actgacgat aactgacgtt gaggctcgaa agcgtgggga gcaaacagga ttagataccc   780
tggtagtcca cgccgtaaac gatgaatgct aggtgttggg gggcaaagcc ttcggtgcc   840
gtcgcaaacg cagtaagcat tccacctggg gagtacgttc gcaagaatga aactcaaagg   900
aattgacggg gacccgcaca agcggtggag catgtggttt aattcgaagc aacgcgaaga   960
accttaccaa gtcttgacat cctcttgacc ggcgtgtaac ggcgccttcc cttcggggcga  1020
agagagacag gtggtgcatg gttgtcgtca gctcgtgtcg tgagatgttg ggttaagtcc   1080
cgcaacgagc gcaacccta tccttagtag ccagcaggta aagctgggca ctctaggag   1140
actgccaggg ataacctgga ggaaggtggg gatgacgtca aatcatcatg cccttatga   1200
tttgggctac acacgtgcta caatggcgta aacaaaggga agcaagaccg tgatgtggga   1260
caaatcccaa aaataacgtc ccagttcgga ctgtagtctg caacccgact acacgaagct   1320
ggaatcgcta gtaatcgcga atcagaatgt cgcggtgaat acgttcccgg gtcttgtaca   1380
caccgcccgt cacaccatgg gagtcagcaa cgcccgaagt cagtgaccca actcgcaaga   1440
gagggagctg ccgaaggcgg ggcaggtaac tgggtgaag tcgtaacaag gtagccgtat   1500
cggaaggtgc ggctggatca cctcctttt                                    1528

SEQ ID NO: 82         moltype = DNA  length = 385
FEATURE               Location/Qualifiers
misc_feature          1..385
                      note = Synthetic Polynucleotide
source                1..385
                      mol_type = other DNA
                      organism = synthetic construct
SEQUENCE: 82
aattcgacgt tgtccggatt actgggcgta aagggagcgt aggcggactt ttaagtgaga    60
tgtgaaatac ccgggctcaa cttgggtgct gcatttcaaa ctggaagtct agagtgcagg   120
agaggagaat ggaattccta gtgtagcggt gaaatgcgta gagatattagga agaacaccag   180
tggcgaaggc gattctctgg actgtaactg acgctgaggc tcgaaagcgt ggggagcaaa   240
caggattaga taccctggta gtccacgccg taaacgatga atactaggtg taggggttgt   300
catgacctct gtgccgccgc taacgcatta agtattccgc ctggggagta cggtcgcaag   360
attaaaactc aaagaaattg acgga                                         385

SEQ ID NO: 83         moltype = DNA  length = 434
FEATURE               Location/Qualifiers
misc_feature          1..434
                      note = Synthetic Polynucleotide
source                1..434
                      mol_type = other DNA
                      organism = synthetic construct
SEQUENCE: 83
acgagcgtat cggattattg ggtttaaggg agcgtaggtg gattgttaag tcagttgtga    60
aagtttgcgg ctcaaccgta aaattgcagt tgaaactggc agtcttgagt acagtagagg   120
tgggcggaat tcgtggtgta gcggtgaaat gcttagatat cacgaagaac tccgattcg   180
aaggcagctc actagactgt cactgacact gatgctcgaa agtgtgggta tcaaacagga   240
ttagataccc tggtagtcca cacagtaaac gatgaatact cgctgtttgc gatatacagt   300
aagcggccaa gcgaaagcat taagtattcc acctggggag tacgccggca acggtgaaac   360
tcaaagaaat tgacggaagc ccgccaggg ggaaaaaca tggggtttag ttggatgata   420
cggggaggaa cctc                                                     434

SEQ ID NO: 84         moltype = DNA  length = 1457
FEATURE               Location/Qualifiers
source                1..1457
                      mol_type = genomic DNA
                      organism = Ruminococcus obeum
SEQUENCE: 84
ggcggcgtgc ttaacacatg caagtcgaac gggaaacctt tcattgaagc ttcggcagat    60
ttggnntgtt tctagtggcg gacgggtgag taacgcgtgg gtaacctgcc ttatacaggg   120
ggataacaac cagaaatggt tgctaatacc gcataagcgc acaggaccgc atggtctggt   180
gtgaaaaact ccggtggtat aagatggacc cgcgttggat tagctagttg cagggtaac   240
ggcctaccaa ggcgacgatc catagccggc ctgagagggt gaacgccac attgggactg   300
agacacggcc cagactccta cgggaggcag cagtgggaa tattgcacaa tggggggaaac   360
cctgatgcag cgacgccgcg tgaaggaaga agtatctgga tgtaaactct atcatcaga   420
gggaagatag tgacggtacc tgactaagaa gccccggcta actacgtgcc agcagccgcg   480
gtaatacgta ggggcaagc gttatccgga tttactgggt gtaaagggag cgtagacgga   540
ctggcaagtc tgatgtgaaa ggcggggggct caaccctggg actgcattgg aaactgttag   600
tcttgagtgc cggagaggta agcggaattc ctagtgtagc ggtgaaatgc gtagatatta   660
ggaggaacac cagtggcgaa ggcggcttac tggacgtaa ctgacgttga ggctcgaaag   720
```

```
cgtggggagc aaacaggatt agatacccctg gtagtccacg ccgtaaacga tgattactag   780
gtgttgggga gcaaagctct tcggtgccgc cgcaaacgca ttaagtattc cacctgggga   840
gtacgttcgc aagaatgaaa ctcaaaggaa ttgacgggga cccgcacaag cggtggagca   900
tgtggtttaa ttcgaagcaa cgcgaagaac cttaccaagt cttgacatcc ctctgaccgn   960
cccttaaccg gatctttcct tcgggacagg ggagacaggt ggtgcatggt tgtcgtcagc  1020
tcgtgtcgtg agatgttggg ttaagtcccg caacgagcgc aaccccctatc cccagtagcc  1080
agcagtccgg ctgggcactc tgaggagact gccagggata acctggagga aggcggggat  1140
gacgtcaaat catcatgccc cttatgattt gggctacaca cgtgctacaa tggcgtaaac  1200
aaaggaagc aagcctgcga aggtaagcaa atcccaaaaa taacgtccca gttcggactg  1260
cagtctgcaa ctcgactgca cgaagctgga atcgctagta atcgcggatc agaatgccgc  1320
ggtgaatacg ttcccgggtc ttgtacacac cgcccgtcac accatgggag tcagtaacgc  1380
ccgaagtcag tgacctaact gcaaagaagg agctgccgaa ggcgggaccg atgactgggg  1440
tgaagtcgta acaaggt                                                 1457

SEQ ID NO: 85         moltype = DNA   length = 1398
FEATURE               Location/Qualifiers
source                1..1398
                      mol_type = genomic DNA
                      organism = Ruminococcus obeum
SEQUENCE: 85
ggcgtgctta acacatgcaa gtcgaacggg aaacttttca ttgaagcttc ggcagatttg   60
gtctgtttct agtggcggac gggtgagtaa cgcgtgggta acctgcctta tacaggggga  120
taacaaccag aaatggttgc taataccgca taagcgcaca ggaccgcatg gtctggtgtg  180
aaaaactccg gtggtataag atggaccccgc gttggattag ctagttgca gggtaacggc  240
ctaccaaggc gacgatccat agccggcctg agagggtgaa cggccacatt gggactgaga  300
cacgcccag actcctcggg aggcagcagt ggggaatatt gcacaatggg ggaaaccctg  360
atgcagcgac gccgcgtgaa ggaagaagta tctcggtatg taaacttcta tcagcaggga  420
agatagtgac ggtacctgac taagaagccc cgkctaacta cgtgccagca gccgcggtaa  480
tacgtagggg gcaagcgtta tccggattta ctgggtgtaa agggagcgta gacggactgg  540
caagtctgat gtgaaaggcg ggggctcaac ccctggctca cattggaaac tgttagtctt  600
gagtgccgga gaggtaagcg gaattcctag tgtagcggtg aaatgcgtag atattaggag  660
gaacaccagt ggcgaaggcg gcttactgga cggtaactga cgttgaggct cgaaagcgtg  720
gggagcaaac aggattagat accctggtag tccacgccgc aaacgatgaa tactaggtgt  780
tggggagcaa agctcttcgg tgccgccgca aacgcattaa gtattccacc tggggagtgg  840
gttcgcaaga atgaaactca aaggaattga cggggacccg cacaagcggt ggagcatgtg  900
gtttaattcg aagcaacgcg aagaaccttta ccaagtcttg acatccctct gaccgtccct  960
taaccggatc tttccttcgg gacagggggag acaggtggtg catggttgtc gtcagctcgt 1020
gtcgtgagat gttgggttaa gtcccgcaac gagcgcaacc cctatcccca gtagccagca 1080
gtncggcctgg gcactctgag gagactgcca gggataacct ggaggaaggc ggggatgcgg 1140
tcaaatcatc atgcccctta tgatttgggc tacacacgtg ctacaatggc gtaaacaaag 1200
ggaagcnagc ctkcgraggt aagcaaatcc canaaataac gtcccagttc ggactgcagt 1260
ctgcaactgc actgcacgaa gctggaatcg ctagtaatcg cggatcagaa tgccgcggtg 1320
aatacgttcc cgggtcttgt acacaccgcc cgtcacacca tgggagtcag taacgcccga 1380
agtcagtgac ctaactgc                                               1398

SEQ ID NO: 86         moltype = DNA   length = 1472
FEATURE               Location/Qualifiers
source                1..1472
                      mol_type = genomic DNA
                      organism = Clostridium disporicum
SEQUENCE: 86
gctcaggacg aacgctggcg gcgtgcctaa cacatgcaag tcgagcgagt tgattctctt   60
cggagatgaa gctagcggcg gacgggtgag taacacgtgg gcaacctgcc tcatagaggg  120
gaatagcctt ccgaaaggga gattaatacc gcataagatt gtagcttcgc atgaagtagc  180
aattaaagga gcaatccgct atgagatggg cccgcggcgc attagctagt tggtgaggta  240
acggctcacc aaggcgacga tgcgtagccg acctgagagg gtgatcggcc acattgggac  300
tgagacacgg cccagactcc tacgggaggc agcagtgggg aatattgcac aatggggaa  360
accctgatga gcaacgccg cgtgagtgat gacggccttc gggttgtaaa gctctgtctt  420
cagggacgat aatgacggta cctgaggagg aagccacggc taactacgtg ccagcagccg  480
cggtaatacg taggtggcga gcgttgtccg gatttactgg gcgtaaaggg agcgtaggcg  540
gacttttaag tgagatgtga atacccgggc tcaacttggt gctgcatt tcaaactgga  600
agtctagagt gcaggagagg agaatggaat tcctagtgta gcggtgaaat gcgtagagat  660
taggaagaac accagtggcg aaggcgatte tctggactgt aactgacgct gaggctcgaa  720
agcgtgggga gcaaacagga ttagataccc tggtagtcca cgccgtaaac gatgaatact  780
aggtgtaggg gttgtcatga cctctgtgcc gccgctaacg cattaagtat tccgcctggg  840
gagtacggtc gcaagattaa aactcaaagg aattgacggg ggcccgcaca agcagcggag  900
catgtggttt aattcgaagc aacgcgaaga accttaccta gacttgacat ctcctgaatt  960
acccgtaact ggggaagcca cttcggtggc aggaagacag gtggtgcatg gttgtcgtca 1020
gctcgtgtcg tgagatgttg ggttaagtcc cgcaacgage gcaaccccta ttgttagttg 1080
ctaccattta gttgagcact ctagcgagac tgcccggggtt aaccgggagg aaggtgggga 1140
tgacgtcaaa tcatcatgcc cctatgtct agggctacac acgtgctaca atggcaagta 1200
caaagagaag caagaccgcg aggtggagca aaactcaaaa acttgtctca gttcggattg 1260
taggctgaaa ctcgcctaca tgaagctgga gttgctagta atcgcgaatc agcatgtcgc 1320
ggtgaatacg ttcccgggcc ttgtacacac cgcccgtcac accatgagag ttggcaatac 1380
ccaacgtacg tgatctaacc cgcaaggggag gaagcgtcct aaggtagggt cagcgattgg 1440
ggtgaagtcg taacaaggta gccgtaggag aa                               1472

SEQ ID NO: 87         moltype = DNA   length = 1529
FEATURE               Location/Qualifiers
```

```
source                    1..1529
                          mol_type = genomic DNA
                          organism = Clostridium scindens
SEQUENCE: 87
gagagtttga tcctggctca ggatgaacgc tggcggcgtg cctaacacat gcaagtcgaa    60
cgaagcgcct ggccccgact tcttcggaac gaggagcctt gcgactgagt ggcggacggg   120
tgagtaacgc gtgggcaacc tgccttgcac tggggataaa cagccagaaa tggctgctaa   180
taccgcataa gaccgaagcg ccgcatggcg cggcggccaa agcccggcg gtgcaagatg    240
ggcccgcgtc tgattaggta gttggcgggg taacggccca ccaagccgac gatcagtagc   300
cgacctgaga gggtgaccgg ccacattggg actgagacac ggcccagact cctacgggag   360
gcagcagtgg ggaatattgc acaatggggg aaaccctgat gcagcgacgc cgcgtgaagg   420
atgaagtatt tcggtatgta aacttctatc agcagggaag aagatgacgg tacctgacta   480
agaagccccg gctaactacg tgccagcagc cgcggtaata cgtaggggc aagcgttatc    540
cggatttact gggtgtaaag ggagcgtaga cggcgatgca agccagatgt gaaagcccgg   600
ggctcaaccc cgggactgca tttgaactg cgtggctgaa gtgtcggaga ggcaggcgga    660
attcctagtg tagcggtgaa atgcgtagat attaggagga acaccagtgg cgaaggcggc   720
ctgctggacg atgactgacg ttgaggctcg aaagcgtggg gagcaaacag gattagatac   780
cctggtagtc cacgccgtaa acgatgacta ctaggtgtcg ggtggcaagg ccattcgggtg  840
ccgcagcaaa cgcaataagt agtccacctg gggagtacgt tcgcaagaat gaaactcaaa   900
ggaattgacg gggacccgca caagcggtgg agcatgtggt ttaattcgaa gcaacgcgaa   960
gaaccttacc tgatcttgac atcccgatgc caaagcgcgt aacgcgctct tcttcggaa    1020
catcggtgac aggtggtgca tggttgtcgt cagctcgtgt cgtgagatgt tgggttaagt   1080
cccgcaacga gcgcaacccc tatcttcagt agccagcatt ttggatgggc actctggaga   1140
gactgccagg gagaacctgg aggaaggtgg ggatgacgtc aaatcatcat gccccttatg   1200
accagggcta cacacgtgct acaatggcgt aaacaagggg aggcgaaccc gcgagggtgg   1260
gcaaatccca aaaataacgt ctcagttcgg atttgtagtct gcaactcgac tacatgaagt  1320
tggaatcgct agtaatcgcg aatcagaatg tcgcggtgaa tacgttcccg ggtcttgtac   1380
acaccgcccg tcacaccatg ggagtcagta acgcccgaag ccggtgaccc aacccgtaag   1440
ggagggagcc gtcgaaggtg ggaccgataa ctggggtgaa gtcgtaacaa ggtagccgta   1500
tcggaaggtg cggctggatc acctccttc                                    1529

SEQ ID NO: 88            moltype = DNA    length = 1456
FEATURE                  Location/Qualifiers
source                   1..1456
                         mol_type = genomic DNA
                         organism = Anaerostipes caccae
SEQUENCE: 88
gcgcttaata catgtcaagt cgaacgaagc atttaggatt gaagttttcg gatggatttc    60
ctatatgact gagtggcgga cgggtgagta acgcgtgggg aacctgccct atacaggggg   120
ataacagctg gaaacggctg ctaataccgc ataagcgcac agaatcgcat gattcagtgt   180
gaaaagccct ggcagtatag gatggtcccg cgtctgatta gctggttggt gaggtaacgg   240
ctcaccaagg cgacgatcag tagccggctt gagagagtga acggccacat gggactgag    300
acacgccca aactcctacg ggaggcagca gtgggaata ttgcacaatg ggggaaagc     360
ctgatgcagc gacgccgcgt gagtgaagaa gtatttcggt atgtaaagct ctatcagcag   420
ggaagaaaac agacggtacc tgactaagaa gccccggcta actacgtgcc agcagccgcg   480
gtaatacgta gggggcaagc gttatccgga attactgggt gtaaagggtg cgtaggtggc   540
atggtaagtc agaagtgaaa gcccgggggct taaccccggg actgcttttg aaactgtcat   600
gctggagtgc aggagaggta agcggaattc ctagtgtagc ggtgaaatgc gtagatatta   660
ggaggaacac cagtggcgaa ggcggcttac tggactgtca ctgacactga tgcacgaaag   720
cgtggggagc aaacaggatt agataccctg gtagtccacg ccgtaaacga tgaatactag   780
gtgtcgggg cgtagaggct tcggtgccgc agcaaacgca gtaagtattc cacctgggga   840
gtacgttcgc aagaatgaaa ctcaaaggaa ttgacgggga cccgcacaag cggtggagca   900
tgtggtttaa ttcgaagcaa cgcgaagaac cttacctggt cttgacatcc caatgaccga   960
accttaaccg gtttttcttt tcgagacatt ggagacaggt ggtgcatggt tgtcgtcagc  1020
tcgtgtcgtg agatgttggg ttaagtcccg caacgagcgc aaccctatc tttagtagcc   1080
agcatttaag gtgggcactc tagagagact gccaggggata acctggagga aggtgggac    1140
gacgtcaaat catcatgccc cttatggcca gggctacaca cgtgctacaa tggcgtaaac   1200
aaagggaagc gaagtcgtga ggcgaagcaa atcccagaaa taacgtctca gttcggattg   1260
tagtctgcaa ctcgactaca tgaagctgga atcgctagta atcgtgaatc agaatgtcac   1320
ggtgaatacg ttcccgggtc ttgtacacac cgcccgtcac accatgggag tcagtaacgc   1380
ccgaagtcag tgacccaacc gcaaggaggg agctgccgaa ggtgggaccg ataactgggg   1440
tgaagtcgta acaagg                                                  1456

SEQ ID NO: 89            moltype = DNA    length = 1456
FEATURE                  Location/Qualifiers
source                   1..1456
                         mol_type = genomic DNA
                         organism = Marvinbryantia formatexigens
SEQUENCE: 89
tggcggcgtg cttaacacat gcaagtcgag cgaagcattt taaatgaagt tttcggacgg    60
aatttaaaat gactgagcgg cggacgggtg agtaacgcgt ggataacctg ccttatacag   120
ggggataaca gccagaaatg ctgctaata ccgcataagc gcacggtacc gcatggtaca    180
gtgtgaaaaa ctccggtggt ataagatggg tccgcgttgc attaggcagt tggcgggta    240
aaggccacc aaaccgacga tccatagccg cctgagagg gtgacggc acattggga     300
tgagacacgg cccagactcc tacgggagg agcagtgggg aatattgcac aatgggggaa    360
accctgatgc agcgacgccg cgtggtgaa gaagtatttc ggtatgtaaa gcccatcag    420
caggaagaa aatgacggta cctgaccaag aagcccggc taactacgtg ccagcagccg    480
cggtaatacg tagggggcaa gcgttatccg gatttactgg gtgtaaaggg agcgtagacg   540
gccatgcaag tctggtgtga aaggcggggg ctcaacccc ggactgcatt ggaaactgta    600
```

```
tggcttgagt gccggagagg taagcggaat tcctggtgta gcggtgaaat gcgtagatat    660
caggaggaac accagtggcg aaggcggctt actggacggt aactgacgtt gaggctcgaa    720
agcgtgggga gcaaacagga ttagatacc  tggtagtcca cgccgtaaac gatgaatacc    780
aggtgtcggg ggacacggtc cttcggtgcc gcagcaaacg cactaagtat tccacctggg    840
gagtacgttc gcaagaatga aactcaaagg aattgacgg  gacccgcaca agcggtggag    900
catgtggttt aattcgaagc aacgcgaaga accttaccag gtcttgacat ccggacgacc    960
ggacagtaac gtgtccttcc cttcggggcg tccgagacag gtggtgcatg gttgtcgtca   1020
gctcgtgtcg tgagatgttg ggttaagtcc cgcaacgagc gcaaccctg  ttcccagtag   1080
ccagcattca ggatgggcac tctggggaga ctgccaggga taacctggag gaaggcgggg   1140
atgacgtcaa atcatcatgc cccttatgat ctgggctaca cacgtgctac aatggcgtga   1200
acagagggaa gcgaacccgc gaggggagc  aaatcccaga aataacgtcc cagttcggat   1260
tgtagtctgc aacccggcta catgaagctg gaatcgctag taatcgcgga tcagcatgcc   1320
gcggtgaata cgttcccggg tcttgtacac accgcccgtc acaccatggg agtcggaaat   1380
gcccgaagtc agtgacccaa ccggaaggag ggagctgccg aaggcgggc  cggtaactgg   1440
ggtgaagtcg taacaa                                                   1456

SEQ ID NO: 90          moltype = DNA  length = 1568
FEATURE                Location/Qualifiers
source                 1..1568
                       mol_type = genomic DNA
                       organism = Lactobacillus mucosae
SEQUENCE: 90
agagtttgat cctggctcag gatgaacgcc ggcggtgtgc ctaatacatg caagtcgaac     60
gcgttggccc aactgattga acgtgcttgc acggactga  cgttggttta ccagcgagtg    120
gcggacgggt gagtaacacg taggtaacct gccccaaagc ggggataac  atttggaaac    180
agatgctaat accgcataac aatttgaatc gcatgattca aatttaaaag atggcttcgg    240
ctatcacttt gggatggacc tgcggcgcat tagcttgttg gtagggtaac ggcctaccaa    300
ggctgtgatg cgtagccgag ttgagagact gatcggccac aatggaactg agacacggtc    360
catactccta cgggaggcag cagtaggaa  tcttccacaa tgggcgcaag cctgatggag    420
caacaccgcg tgagtgaaga agggtttcgg ctcgtaagac tctgttgtta gagaagaacg    480
tgcgtgagag caactgttca cgcagtgacg gtatctaacc agaaagtcac ggctaactac    540
gtgccagcag ccgcggtaat acgtaggtgg caagcgttat ccggatttat tgggcgtaaa    600
gcgagcgcag gcggtttgat aagtctgatg tgaaagcctt tggcttaacc aaagaagtgc    660
atcggaaact gtcagacttg agtgcagaag aggacagtgg aactccatgt gtagcggtgg    720
aatgcgtaga tatatggaag aacaccagtg gcgaaggcgg ctgtctggtc tgcaactgac    780
gctgaggctc gaaagcatgg gtagcgaaca ggattagata ccctggtagt ccatgccgta    840
aacgatgagt gctaggtgtt ggagggtttc cgcccttcag tgccgcagct aacgcattaa    900
gcactccgcc tggggagtac gaccgcaagg ttgaaactca aaggaattga cggggcccg    960
cacaaggcgg tggagcatgt ggtttaattc gaagctacgcg aagaacctta ccaggtcttg   1020
acatcttgcg ccaacccctag agataggggc ttccttcgg gaacgcaatg acaggtggtg   1080
catggtcgtc gtcagctcgt gtcgtgagat gttgggttaa gtcccgcaac gagcgcaacc   1140
cttgttacta gttgccagca ttcagttggg cactctagtg agactgccgg tgacaaaccg   1200
gaggaaggtg ggacgacgt  cagatcatca tgccccttat gacctgggct acacacgtgc   1260
tacaatggac ggtacaacga gtcgcgaact cgcgagggca agctaatctc ttaaaaccgt   1320
tctcagttcg gactgcaggc tgcaactcgc ctgcacgaag tcggaatcgc tagtaatcgc   1380
ggatcagcat gccgcggtga atacgttccc gggccttgta cacaccgccc gtcacaccat   1440
gagagtttgc aacacccaaa gtcggtgggg taacccttcg gggagctagc cgcctaaggt   1500
ggggcagatg attagggtga agtcgtaaca aggtagccgt aggagaacct gcggctggat   1560
cacctcct                                                            1568

SEQ ID NO: 91          moltype = DNA  length = 1508
FEATURE                Location/Qualifiers
source                 1..1508
                       mol_type = genomic DNA
                       organism = Turicibacter sanguinis
SEQUENCE: 91
agagtttgat catggctcag gatgaacgct ggcggcgtgc ctaatacatg caagtcgagc     60
gaaccacttc ggtggtgagc ggcgaacggg tgagtaacac gtaggttatc tgcccatcag    120
acggggacaa cgattggaaa cgatcgctaa taccggatag gacgaaagtt taaaggtgct    180
tcggcgaccac tgatggatga gcctgcggcg cattagctac ttggtagggt aaaggcctac    240
caaggcgacg atgcgtagcc gacctgagag ggtgaacggc cacactggga ctgagacacg    300
gcccagactc ctacgggagg cagcagtagg gaatcttcgg caatgggcga aagcctgacc    360
gagcaacgcc gcgtgaatga tgaaggcctt cgggttgtaa aattctgtta aggggaagaa    420
atggtctctag taggaaatgg ctagagtgtg acggtacctt atgagaaagc cacggctaaa    480
tacgtgccag cagccgcggt aatacgtagg tggcgagcgt tatccggaat tattgggcgt    540
aaagagcgcg caggtggttg attaagtctg atgtgaaagc ccacggctta accgtggagg    600
gtcattggaa actggtcaac ttgagtgcag aagagggaag tggaattcca tgtgtagcgg    660
tgaaatgcgt agagatatgg aggaacacca gtggcgaagg cggcttcctg gtctgtaact    720
gacactgagg cgcgaaagcg tgggagcaa  acaggttgat atacctgaag agtccaccgc    780
gtaaacgatg agtgctaagt gttggggtc  gaacctcagt gctgaagtta acgcattaag    840
cactccgcct ggggagtacg gtcgcaagac tgaaactcaa aggaattgac ggggacccgc    900
acaagcggtg gagcatgtgg tttaattcga agcaacgcga agaaccttac caggtcttga    960
cataccagta accgtcctag agataggatt ttcccttcgg gacaatgga  tacaggtggt   1020
gcatggttgt cgtcagctcg tgtcgtgaga gttgggttaa gtcccgcaac gagcgcaacc   1080
ccctgtcgtt agttgccagc attcagttgg ggactctaac gagactgcca gtgacaaact   1140
ggaggaaggt ggggatgacg tcaaatcatc atgcccctta tgacctgggc tacacacgtg   1200
ctacaatggt tggtacaaag agaagcgaag cggtgacgtg gagcaaacct cataagcca    1260
atctcagttc ggattgtagg ctgcaactcg cctacatgaa gttggaatcg ctagtaatcg   1320
cgaatcagca tgtcgcggtg aatacgttcc cgggtcttgt acacaccgcc cgtcacacca   1380
```

```
cgagagttta caacacccga agtcagtggc ctaaccgcaa ggagggagct gcctaaggtg   1440
gggtagatga ttggggtgaa gtcgtaacaa ggtatcccta ccggaaggtg gggttggatc   1500
acctcctt                                                            1508

SEQ ID NO: 92           moltype = DNA  length = 1456
FEATURE                 Location/Qualifiers
source                  1..1456
                        mol_type = genomic DNA
                        organism = Roseburia faecis
SEQUENCE: 92
gatgaacgct ggcggcgtgc ttaacacatg caagtcgaac gaagcactct atttgatttt    60
cttcggaaat gaagattttg tgactgagtg gcggacgggt gagtaacgcg tgggtaacct   120
gcctcataca gggggataac agttggaaac gactgctaat accgcataag cgcacaggat   180
cgcatgatcc ggtgtgaaaa actccggtgg tatgagatgg acccgcgtct gattagccag   240
ttggcagggt aacggcctac caaagcgacg atcagtagcc gacctgagag ggtgaccggc   300
cacattggga ctgagacacg gcccaaactc ctacgggagg cagcagtggg gaatattgca   360
caatggggga accctgatgc agcgacgccg cgtgagcga agaagtattt cggtatgtaa   420
agctctatca gcagggaaga agaatgacgg tacctgacta agaagcaccg gctaaatacg   480
tgccagcagc cgcggtaata cgtatgtgc aagcgttatc cggatttact gggtgtaaag   540
ggagcgcagg cggtgcggca agtctgatgt gaaagcccgg ggctcaaccc cggtactgca   600
ttggaaactg tcgtactaga gtgtcggagg ggtaagtgga attcctagtg tagcggtgaa   660
atgcgtagat attaggagga acaccagtgg cgaaggcggc ttactggacg ataactgacg   720
ctgaggctcg aaagcgtggg gagcaaacag gattagatac cctggtagtc cacgccgtaa   780
acgatgaata ctaggtgtcg gggagcattg ctcttcggtg ccgcagcaaa cgcaataagt   840
attccacctg gggagtacgt tcgcaagaat gaaactcaaa ggaattgacg ggacccgca    900
caagcggtgg agcatgtggt ttaattcgaa gcaacgcgaa gaaccttacc aagtcttga   960
atcccgatga cagagtatgt aatgtacytt ctcttcggag catcggtgac aggtggtgca  1020
tggttgtcgt cagctcgtgt cgtgagatgt tgggttaagt cccgcaacga gcgcaacccc  1080
tgtccttagt agccagcggt tcggccgggc actctaggga gactgccagg ataacctgg   1140
aggaaggcgg ggatgacgtc aaatcatcat gccccttatg acttgggcta cacacgtgct  1200
acaatggcgt aaacaaaggg aagcggagcc gtgaggccga gcaaatctca aaaataacgt  1260
ctcagttcgg actgtagtct gcaacccgac tacacgaagc tggaatcgct agtaatcgca  1320
gatcagaatg ctgcggtgaa tacgttcccg ggtcttgtac acaccgcccg tcacaccatg  1380
ggagttggaa atgcccgaag tcagtgaccc aaccgcaagg agggagctgc cgaaggcagg  1440
ttcgataact ggggtg                                                  1456

SEQ ID NO: 93           moltype = DNA  length = 1465
FEATURE                 Location/Qualifiers
source                  1..1465
                        mol_type = genomic DNA
                        organism = Flavonifractor plautii
SEQUENCE: 93
cgctggcggc gtgcttaaca catgcaagtc gaacgggtg ctcatgacgg aggattcgtc    60
caatggattg agttacctag tggcggacgg gtgagtaacg cgtgaggaac ctgccttgga   120
gaggggaata acactccgaa aggagtgcta ataccgcatg aagcagttgg gtcgcatggc   180
tctgactgcc aaagatttat cgctctgaga tggcctcgcg tctgattagc tagtaggcgg   240
ggtaacggcc cacctaggcg acgatcagta gccggactga gaggttgacc ggccacattg   300
ggactgagac acggcccaga ctcctacggg aggcagcagt ggggaatatt ggcaatggg   360
cgcaagcctg acccagcaac gccgcgtgaa ggaagaaggc tttcgggttg taaacttctt   420
ttgtcgggga cgaaacaaat gacggtaccc gacgaataag ccacggctaa ctacgtgcca   480
gcagccgcgg taatacgtag gtggcaagcg ttatccggat ttactgggtg taaagggcgt   540
gtaggcggaa ttgcaagtca gatgtgaaaa ctggggctc aacctccagc ctgcatttga   600
aactgtagtt cttgagtgct ggagaggcaa tcggaattcc gtgtgtagcg gtgaaatgcg   660
tagatatacg gaggaacacc agtggcgaag gcggattgct ggacagtaac tgacgctgag   720
gcgcgaaagc gtggggagca aacaggatta gataccctag tagtccacgc cgtaaacgat   780
ggatactagg tgtggggggt ctgacccct ccgtgccgca gttaacacaa taagtatccc    840
acctggggag tacgatcgca aggttgaaac tcaaaggaat tgacggggc ccgcacaagc   900
ggtggagtat gtggtttaat tcgaagcaac gcgaagaacc ttaccagggc ttgacatccc   960
actaacgagg cagagatgcg ttaggtgccc ttcgggaaa gtgagacaga gtggtgcatg   1020
gttgtcgtca gctcgtgtcg tgagatgttg gttaagtcc cgcaacgagc gcaaccctta  1080
ttgttagttg ctacgcaaga gcactctagc gagactgccg ttgacaaaac ggaggaaggt  1140
gggacgacg tcaaatcatc atgccccttat gtcctgggc cacacacgta ctacaatggt   1200
ggttaacaga gggaggcaat accgcgaggt ggagcaaatc cctaaaagcc atcccagttc  1260
ggattgcagg ctgaaacccg cctgtatgaa gttgaatcg ctagtaatcg cggatcagca   1320
tgccgcggtg aatacgttcc cgggccttgt acacaccgcc cgtcacacca tgagagtcgg  1380
gaacacccga agtccgtagc ctaaccgcaa ggagggcgcg gccgaaggtg gttcgataa   1440
ttggggtgaa gtcgtaacaa ggtag                                        1465

SEQ ID NO: 94           moltype = DNA  length = 1438
FEATURE                 Location/Qualifiers
source                  1..1438
                        mol_type = genomic DNA
                        organism = Blautia wexlerae
SEQUENCE: 94
caagtcgaac gggaattant ttattgaaac ttcggtcgat ttaatttaat tctagtggcg    60
gacgggtgag taacgcgtgg gtaacctgcc ttatacaggg ggataacagt cagaaatggc   120
tgctaatacc gcataagcgc acagagctgc atggctcagt gtgaaaaact ccggtggtat   180
aagatgacc cgcgttggat tagcttgttg gtggggtaac ggcccaccaa ggcgacgatc   240
catagccggc ctgagagggt gaacggccac attgggactg agacacggcc cagactccta   300
```

```
cgggaggcag cagtgggaa tattgcacaa tggggaaac cctgatgcag cgacgccgcg    360
tgaaggaaga agtatctcgg tatgtaaact tctatcagca gggaagatag tgacggtacc    420
tgactaagaa gccccggcta actacgtgcc agcagccgcg gtaatacgta ggggcaagc    480
gttatccgga tttactgggt gtaaaggag cgtagacggt gtggcaagtc tgatgtgaaa    540
ggcatgggct caacctgtgg actgcattgg aaactgtcat acttgagtgc cggaggggta    600
agcggaattc ctagtgtagc ggtgaaatgc gtagatatta ggaggaacac cagtggcgaa    660
ggcggcttac tggacggtaa ctgacgttga ggctcgaaag cgtggggagc aaacaggatt    720
agataccctg gtagtccacg ccgtaaacga tgaataacta ggtgtcgggt ggcaaagcca    780
ttcggtgccg tcgcaaacgc agtaagtatt ccacctgggg agtacgttcg caagaatgaa    840
actcaaagga attgacgggg acccgcacaa gcggtggagc atgtggttta attcgaagca    900
acgcgaagaa ccttaccaag tcttgacatc cgcctgaccg atccttaacc ggatctttcc    960
ttcgggacag gcgagacagg tggtgcatgg ttgtcgtcag ctcgtgtcgt gagatgttgg   1020
gttaagtccc gcaacgagcg caaccccctat cctcagtagc cagcatttaa ggtgggcact   1080
ctggggagac tgccagggat aacctggagg aaggcgggga tgacgtcaaa tcatcatgcc   1140
ccttatgatt tgggctacac acgtgctaca atggcgtaaa caaagggaag cgagattgtg   1200
agatggagca aatcccaaaa ataacgtccc agttcggact gtagtctgca acccgactac   1260
acgaagctgg aatcgctagt aatcgcggat cagaatgccg cggtgaatac gttcccgggt   1320
cttgtacaca ccgcccgtca ccatgggag tcagtaacg cccgaagtca gtgacctaac   1380
tgcaaagaag gagctgccga aggcgggacc gatgactggg gtgaagtcgt aacaaggt    1438

SEQ ID NO: 95          moltype = DNA   length = 1365
FEATURE                Location/Qualifiers
source                 1..1365
                       mol_type = genomic DNA
                       organism = Anaerotruncus colihominis
SEQUENCE: 95
aacggagctt acgttttgaa gttttcggat ggatgaatgt aagcttagtg gcggacgggt     60
gagtaacacg tgagcaacct gcctttcaga ggggataac agccggaaac ggctgctaat    120
accgcatgat gttgcggggg cacatgcccc tgcaaccaaa ggagcaatcc gctgaaagat    180
gggctcgcgt ccgattagcc agttggcggg gtaacggccc accaaagcga cgatcggtag    240
ccggactgag aggttgaacg gccacattgg gactgagaca cggcccagac tcctacggga    300
ggcagcagtg ggggatattg cacaatgggc gaaagcctga tgcagcgacg ccgcgtgagg    360
gaagacggtc ttcggattgt aaacctctgt ctttggggaa gaaaatgacg gtacccaaag    420
aggaagctcc ggctaactac gtgccagcag ccgcggtaat acgtagggag caagcgttgt    480
ccggaattac tgggtgtaaa gggagcgtag gcgggatgg aatagaatg ttaaatccat    540
cggctcaacc ggtggctgcg ttctaaactg ccgttcttga gtgaagtaga gcaggcggaa    600
attcctagtg tagcggtgaa atgcgtagat attaggagga acaccagtgg cgaaggcggc    660
ctgctgggct taactgacg ctgaggctcg aaagcgtggg gagcaaacag gattagatac    720
cctggtagtc cacgccgtaa acgatgatta ctaggtgtgg ggggactgac ccttccgtg    780
ccgcagttaa cacaataagt aatccacctg gggagtacgg ccgcaaggtt gaaactcaaa    840
ggaattgacg ggggccccgca caagcagtgg agtatgtggt ttaattcgaa gcaacgcgaa    900
gaaccttacc aggtcttgac atcggcgtaa tagcctagag agtaggtgaa gcccttcggg    960
gcatccagac aggtggtgca tggttgtcgt cagctcgtgt cgtgagatgt tgggttaagt   1020
cccgcaacga gcgcaaccct tattattagt tgctacgcaa gagcactcta atgagactgc   1080
cgttgacaaa acggaggaag gtgggggatga cgtcaaatca tcatgcccct tatgacctgg   1140
gctacacacg tactacaatg gcactaaaac agagggcgc gacaccgcga ggtgaagcga   1200
atcccagaaa aagtgtctca gttcagattg caggctgcaa cccgcctgca tgaagtcgga   1260
attgctagta atcgcggatc agcatgccgc ggtgaatacg ttcccgggcc ttgtacacac   1320
cgcccgtcac accatgggag tccgggtaac acccgaagcc agtag                   1365

SEQ ID NO: 96          moltype = DNA   length = 1404
FEATURE                Location/Qualifiers
source                 1..1404
                       mol_type = genomic DNA
                       organism = Ruminococcus faecis
SEQUENCE: 96
atgcaagtcg aacgaagcac cttgatttga ttcttcggat gaagatcttg gtgactgagt     60
ggcggacggg tgagtaacgc gtgggtaacc tgcctcatac aggggataaa cagttagaaa    120
tgactgctaa taccgcataa gaccacagca ccgcatggtg caggggtaaa aactccggtg    180
gtatgagatg gacccgcgtc tgattaggta gttggtgggg taacggccta ccaagccgac    240
gatcagtgac cgacctgaga gggtgaccgg ccacattggg actgagacac ggcccaaact    300
cctacgggag gcagcagtgg ggaatattgc acaatgggcg aaagcctgat gcagcgacgc    360
cgcgtgagcg atgaagtatt tcggtatgta aagctctatc agcagggaag aaaatgacgg    420
tacctgacta agaagcaccg gctaaatacg tgccagcagc cgcggtaata cgtatggtgc    480
aagcgttatc cggatttact gggtgtaaag ggagcgtaga cggagtggca agtctgatgt    540
gaaaacccgg ggctcaaccc cgggactgca ttggaaactg tcaatctaga gtaccggaga    600
ggtaagcgga attcctagtg tagcggtgaa atgcgtagat attaggagga acaccagtgg    660
cgaaggcggc ttactggacg gtaactgacg ttgaggctcg aaagcgtggg gagcaaacag    720
gattagatac cctggtagtc cacgccgtaa acgatgacta ctaggtgtcg ggcagcaaag    780
ctgttcggtg ccgcagcaaa cgcaataagt agtccacctg gggagtacgt tgcaagaat    840
gaaactcaaa ggaattgacg ggacccgca caagcggtgg agcatgtggt ttaattcgaa    900
gcaacgcgaa gaaccttacc tgctcttgac atctccccg gcaagta atgttgcctt    960
tccttcggga cagggatgac aggtggtgca tggttgtcgt cagctcgtgt cgtgagatgt   1020
tgggttaagt cccgcaacga gcgcaaccct tatctttagt agccagcggt ttggccgggc   1080
actctagaga gactgccagg gataacctgg aggaaggtgg ggatgacgtc aaatcatcat   1140
gccccttatg agcagggcta cacacgtgct acaatggcgt aaacaaaggg aggcagaacc   1200
gcgaggtcga gcaaatccca aaaataacgt ctcagttcgg attgtagtct gcaactcgac   1260
```

```
tacatgaagc tggaatcgct agtaatcgcg aatcagaatg tcgcggtgaa tacgttcccg   1320
ggtcttgtac acaccgcccg tcacaccatg ggagtcagta acgcccgaag tcagtgaccc   1380
aaccgtaagg aggagctgcc gaag                                          1404

SEQ ID NO: 97           moltype = DNA   length = 1316
FEATURE                 Location/Qualifiers
source                  1..1316
                        mol_type = genomic DNA
                        organism = Dorea longicatena
SEQUENCE: 97
taacgcgtgg gtaacctgcc tcatacaggg ggataacagt tagaaatgac tgctaatacc   60
gcataagacc acgtaccgca tggtacagtg gtaaaaactc cggtggtatg agatggaccc   120
gcgtctgatt aggtagttgg tggggtaacg gcctaccaag ccgacgatca gtagccgacc   180
tgagagggtg accggccaca ttgggactga gacacggccc agactcctac ggaggcagc   240
agtggggaat attgcacaat ggaggaaact ctgatgcagc gacgccgcgt gaaggatgaa   300
gtatttcggt atgtaaactt ctatcagcag ggaagaaaat gacggtacct gactaagaag   360
ccccggctaa ctacgtgcca gcagccgcgg taatacgtag gggcaagcg ttatccggat   420
ttactgggtg taaagggagc gtagacggca cggcaagcca gatgtgaaaa gcccgggct   480
caaccccggg actgcatttg gaactgctga gctagagtgt cggagaggca agtggaattc   540
ctagtgtagc ggtgaaatgc gtagatatta ggaggaacac cagtggcgaa ggcggcttgc   600
tggacgatga ctgacgttga ggctcgaaag cgtggggagc aaacaggatt agataccctg   660
gtagtccacg ccgtaaacga tgactgctca gtgtcgggag cagagccgac tcggtgccgc   720
agctaacgca ataagcagtc cacctgggga gtacgttcgc aagaatgaaa ctcaaaggaa   780
ttgacgggga cccgcacaag cggtggagca tgtggtttaa ttcgaagcaa cgcgaagaac   840
cttacctgat cttgacatcc cgatgaccgc ttcgtaatgg aagttttcct tcggaacatc   900
ggtgacaggt ggtgcatggt tgtcgtcagc tcgtgtcgtg agatgttggg ttaagtcccg   960
caacgagcgc aacccctatc ttcagtagcc agcaggttaa gctgggcact ctggagagac   1020
tgccagggat aacctggagg aaggtgggga tgacgtcaaa tcatcatgcc ccttatgacc   1080
agggctacac acgtgctaca atggcgtaaa caaagagaag cgaactcgcg agggtaagca   1140
aatctcaaaa ataacgtctc agttcggatt gtagtctgca actcgactac atgaagctgg   1200
aatcgctagt aatcgcagat cagaatgctg cggtgaatac gttcccgggt cttgtacaca   1260
ccgcccgtca caccatggga gtcataacgc ccgaagtcag tgacccaacc gtaagg       1316

SEQ ID NO: 98           moltype = DNA   length = 1475
FEATURE                 Location/Qualifiers
source                  1..1475
                        mol_type = genomic DNA
                        organism = Clostridium innocuum
SEQUENCE: 98
atggagagtt tgatcctggc tcaggatgaa cgctggcggc atgcctaata catgcaagtc   60
gaacgaagtc ttcaggaagc ttgcttccaa aaagacttag tggcgaacgg gtgagtaaca   120
cgtaggtaac ctgcccatgt gtccgggata actgctggaa acggtagcta aaccggata   180
ggtatacgga gcgcatgctc tgtatattaa agcgcccttc aaggcgtgaa catggatgga   240
cctgcgacgc attagctagt tggtgaggta acggcccacc aaggcgatga tgcgtagccg   300
gcctgagagg gtaaacggcc acattgggac tgagacacgg cccaaactcc tacgggaggc   360
agcagtaggg aattttcgtc aatggggaa accctgaacg agcaatgccg cgtgagtgaa   420
gaaggtcttc ggatcgtaaa gctctgttgt aagtgaagaa cggctcatag aggaaatgct   480
atggagagtga cggtagctta ccagaaagcc acggctaact acgtgccagy agccgcggta   540
atacgtaggt ggcaagcgtt atccggaatc attgggcgta aagggcgcgt aggtggcgta   600
ctaagtctgt agtaaaaggc aatggctcaa ccattgtaag ctatgaaac tggtatgctg   660
gagtgcagaa gagggcgatg gaattccatg tgtagcggta aaatgcgtag atatatggag   720
gaacaccagt ggcgaaggcg tcgcctggt ctgtaactga cactgaggca cgaaagcgtg   780
gggagcaaat aggattagat accctagtag tccacgccgt aaacgatgag aactaagtgt   840
tggagaaatt cagtgctgca gttaacgcaa taagttctcc gcctgggag tatgcacgca   900
agttngaaac tcaaaggaat tgacggggc ccgcacaagc gntggagtat gtggtttaat   960
tcgaagcaac gcgaagaacc ttaccaggcc ttgacatgca aacaaatacc ctagagatag   1020
ggggataatt atggatcaca caggtggtgc atggttgtcg tcagctcgtg tcgtgagatg   1080
ttgggttaag tccgcaacg agcgcaaccc ttgtcgcatg ttaccagcat caagttgggg   1140
actcatgcga gactgccggt gacaaaccgg aggaaggtgg ggatgacgtc aaatcatcat   1200
gccccttatg gcctgggcta cacacgtact acaatggca ccacaaagag cagcgacttg   1260
gtgacaagaa gcgaatctca taaagatcgt ctcagttcgg attgaagtct gcaactcgac   1320
ttcatgaagt cggaatcgct agtaatcgca gatcagcatg ctgcggtgaa tacgttctcg   1380
ggccttgtac acaccgcccg tcaaaccatg ggagtcagta atacccgaag ccggtggcat   1440
aaccgtaagg agtgagccgt cgaaggtagg accga                              1475

SEQ ID NO: 99           moltype = DNA   length = 1492
FEATURE                 Location/Qualifiers
source                  1..1492
                        mol_type = genomic DNA
                        organism = Blautia hansenii
SEQUENCE: 99
agagtttgat cctggctcag gatgaacgct ggcggcgtgc ttaacacatg caagtcgagc   60
gaagcactta tcattgactc ttcggaagat ttgatatttg actgagcggc ggacgggtga   120
gtaacgcgtg gtaacctgc ctcatacagg ggaataacta ttagaaatgg ctgctaatgc   180
cgcataagcg cacaggaccg catggtctgt gtgaaaaac tgaggtggta tgagatggac   240
ccgcgtctga ttaggtagtt ggtgggtaa cggcctacca agccgacgat cagtagccgg   300
cctgagaggg tgaacggcca cattgggact gagacacggc ccagactcct acggaggca   360
gcagtgggga atattgcaca atgggggaaa ccctgatgca gcgacgccgc gtgaaggaag   420
aagtatctcg gtatgtaaac ttctatcagc agggaagaaa atgacggtac ctgactaaga   480
```

```
agccccggct aactacgtgc cagcagccgc ggtaatacgt aggggggcaag cgttatccgg    540
atttactggg tgtaaaggga gcgtagacgg aagagcaagt ctgatgtgaa aggctgggc     600
ttaaccccag gactgcattg gaaactgttt ttctagagtg ccggagaggt aagcggaatt    660
cctagtgtat cggtgaaatg cgtagatatt aggaggaaca ccagtggcga aggcggctta    720
ctggacggta actgacgttg aggctcgaaa gcgtggggag caaacaggat tagatacct    780
ggtagtccac gccgtaaacg atgaatacta ggtgtcgggg tgcaaagcag ttcggtgccg    840
cagcaaacgc aataagtatt ccacctgggg agtacgttcg caagaatgaa actcaaagga    900
attgacgggg acccgcacaa gcggtggagc atgtggttta attcgaagca acgcgaagaa    960
ccttaccaag tcttgacatc tgcctgaccg ttccttaacc ggagctttcc ttcgggacag   1020
gcaagacagt tggtgcatgg ttgtcgtcag ctcgtgtcgt gagatgttgg gttaagtccc   1080
gcaacgagcg caaccctat ccttagtagc cagcagtccg gctgggcact ctagggagac    1140
tgccggggat aacccggagg aaggcgggga cgacgtcaaa tcatcatgcc cttatgatt    1200
tgggctacac acgtgctaca atggcgtaaa caaagggaag cgaagcggtg acgcttagca   1260
aatctcaaaa ataacgtccc agttcggact gcagtcgcaa actcgactgc acgaagctgg   1320
aatcgctagt aatcgcgaat cagaatgtcg cggtgaatac gttcccgggt cttgtacaca   1380
ccgcccgtca caccatggga gtcagtaacg cccgaagtca gtgacccaac cttatggagg   1440
gagctgccga aggcgggacc gataactggg gtgaagtcgt aacaaggtaa cc            1492

SEQ ID NO: 100        moltype = DNA   length = 1473
FEATURE               Location/Qualifiers
source                1..1473
                      mol_type = genomic DNA
                      organism = Bacteroides cellulosilyticus
SEQUENCE: 100
agagtttgat cctggctcag gatgaacgct agctacaggc ttaacacatg caagtcgagg    60
ggcagcatga cctagcaata ggttgatggc gaccggcgca cgggtgagta acacgtatcc   120
aacctaccgg ttattccggg atagcctttc gaaagaaaga ttaataccgg atagtataac   180
gagaaggcat cttttgtta ttaaagaatt tcgataaccg atgggatgc gttccattag     240
tttgttggcg gggtaacggc ccaccaagac atcgatggat aggggttctg agaggaaggt   300
cccccacatt ggaactgaga cacggtccaa actcctagga ggcagcag tgaggaatat     360
tggtcaatgg acgagagtct gaaccagcca gtagcgtga aggatgactg ccctatgggt    420
tgtaaacttc ttttatatgg gaataaagtg agccacgtgt ggcttttgt atgtaccata    480
cgaataagga tcggctaact ccgtgccagc agccgcggta atacgagga tccgagcgtt    540
atccggattt attgggttta aagggagcgt aggcggata ttaagtcagc tgtgaaagtt    600
tgcggctcaa ccgtaaaatt gcagttgata ctggtcgtct tgagtgcagt agaggtaggc   660
ggaattcgtg tgtagcggt gaaatgctta gatatcacga agaactccga ttgcgaaggc    720
agcttactgg actgtaactg acgctgatgc tcgaaagtgt gggtatcaaa caggattaga    780
taccctggta gtccacacag taaacgatga atactcgctg tttgcgatat acagcaagcg   840
gccaagcgaa agcattagt attccacctg ggagtgccg cggcaacgt gaaactcaaa      900
ggaattgacg gggccccgca caagcggagg aacatgtggt ttaattcgat gatacgcgag   960
gaaccttacc cgggcttaaa ttgcatctga ataaatttgga aacagattag ccgcaagcga  1020
gatgtgaagg tgctgcatgg ttgtcgtcag ctcgtgccgt gaggtgtcgg cttaagtgcc   1080
ataacgagcg caacccctat ctttagttac taacaggtca tgctgaggac tctagagaga   1140
ctgccgtcgt aagatgtgag gaaggtgggg atgacgtcaa atcagcacgg cccttacgtc   1200
cggggctaca cacgtgttac aatgggggt acagaaggca gctacacagc gatgtgatgc    1260
taatcccaaa agcctctctc agttcggatt ggagtctgca cccgactcc atgaagctgg    1320
attcgctagt aatcgcgcat cagccacggc gcggtgaata cgttcccggg ccttgtacac   1380
accgcccgtc aagccatgaa agccgggggt acctgaagtc cgtaaccgca aggagcggcc   1440
tagggtaaaa ctggtaattg gggctaagtc gta                                1473

SEQ ID NO: 101        moltype = DNA   length = 1459
FEATURE               Location/Qualifiers
source                1..1459
                      mol_type = genomic DNA
                      organism = Bacteroides ovatus
SEQUENCE: 101
ggctcaggat gaacgctagc tacaggctta acacatgcaa gtcgaggggc agcatttag     60
tttgcttgca aactgaagat ggcgaccggc gcacgggtga gtaacacgta tccaacctgc   120
cgataactcc ggaatagcct tcgaaagaa agattaatac cggatagcat acgaatatcg    180
catgatattt ttattaaaga atttcggtta tcgatggga tgcgttccat tagtttgttg    240
gcggggtaac ggcccaccaa gactacgatg gataggggtt ctgagaggaa ggtccccac    300
attggaactg agacacggtc caaactccta cgggaggcag cagtgaggaa tattggtcaa   360
tgggcgagag cctgaaccag ccaagtagcg tgaaggatga aggctctatg ggtcgtaaac   420
ttcttttata tgggaataaa gttttccacg tgtgtgaatt tgtatgtacc atagtaataa   480
ggatcggcta actccgtgcc agcagccgcg gtaatacgga ggatccgagc gttatccgga   540
tttattgggt ttaagggag cgtaggtgga ttgttaagtc agttgtgaaa gtttgcggct    600
caaccgtaaa attgcagttg aaactggcag tcttgagtac agtagaggtg gcggaattc    660
gtggtgtagc ggtgaaatgc ttagatatca cgaagaactc cgattgcgaa ggcagctcac   720
tagactgtta ctgacactga tgctcgaaag tgtgggtatc aaacaggatt agataccctg   780
gtagtccaca cagtaaacga tgaatactcg ctgtttgcga tatacagtaa gcggccaagc   840
gaaagcatta gtattccac ctggggagta cgccggcaac ggtgaaactc aaaggaattg    900
acggggcccc gcacaagcgg aggaacatgt ggtttaattc gatgatacgc gaggaacctt   960
acccgggctt aaattgcaac agaatatatt ggaaacagta tagccgtaag ctgttgtga   1020
aggtgctgca tggttgtcgt cagctcgtgc cgtgagggtgc cttaagt gccataacga    1080
gcgcaaccct atctttagt tactaacagg ttatgctgag gactctagag agactgccgt   1140
cgtaagatgt gaggaaggtg gggatgacgt caaatcagca cggcccttac gtccgggct   1200
acacgtgt acaatggggg gtacagaag gcagctacct ggcgacagga tgctaatccc    1260
aaaaacctct ctcagttcgg atcgaagtct gcaacccgac ttcgtgaagc tggattcgct   1320
agtaatcgcg catcagccat ggcgcggtga atacgttccc gggccttgta cacccgccc   1380
```

```
gtcaagccat gaaagccggg ggtacctgaa gtacgtaacc gcaaggagcg tcctagggta   1440
aaactggtaa ttggggcta                                                1459

SEQ ID NO: 102         moltype = DNA  length = 1526
FEATURE                Location/Qualifiers
source                 1..1526
                       mol_type = genomic DNA
                       organism = Eubacterium fissicatena
SEQUENCE: 102
tagagtttga tcctggctca ggatgaacgc tggcggcgtg cttaacacat gcaagtcgag     60
cgaagcgctt tacttagatt tcttcggatt gaagagtttt gcgactgagc ggcggacggg    120
tgagtaacgc gtgggtaacc tgcctcatac aggggataaa cagttagaaa tgactgctaa    180
taccgcataa gaccacagta ccgcatggta cagtgggaaa aactccggtg gtatgagatg    240
gacccgcgtc tgattagcta gttggtaagg taacggctta ccaaggcgac gatcagtagc    300
cgacctgaga gggtgaccgg ccacattggg actgagacac ggcccaaact cctacggag    360
gcagcagtgg ggaatattgc acaatggggg aaaccctgat gcagcgacgc cgcgtgaagg    420
atgaagtatt tcggtatgta aacttctatc agcagggaag aaaatgacgg tacctgacta    480
agaagcgccg gctaactacg tgccagcagc cgcggtaata cgtagggggc aagcgttatc    540
cggatttact gggtgtaaag ggagcgtaga cggttatgta agtctgatgt gaaaacccgg    600
ggctcaaccc cgggactgca ttggaaacta tgtaactaga gtgtcggaga ggtaagtgga    660
attcctagtg tagcggtgaa atgcgtagat attaggagga acaccagtgg cgaaggcggc    720
ttactggacg atcactgacg ttgaggctcg aaagcgtggg gagcaaacag gattagatac    780
cctggtagtc cacgccgtaa acgatgaata ctaggtgtcg ggtggcaaag ccattcggtg    840
ccgcagcaaa cgcaataagt attccacctg gggagtacgt tcgcaagaat gaaactcaaa    900
ggaattgacg ggacccgca caagcggtgg agcatgtggt ttaattcgaa gcaacgcgaa    960
gaaccttacc tgctcttgac atcccactga ccggcgttca atgtcgtgaa tgcttgaagt 1020
[continuation with slightly unclear readings — best-effort above]
cagtggagac aggtggtgca tggttgtcgt cagctcgtgt cgtgagatgt tgggttaagt   1080
cccgcaacga gcgcaaccct tatctttagt agccagcggt ttggccgggc actctagaga   1140
gactgccagg ataacctgg aggaaggtgg ggatgacgtc aaatcatcat gccccttatg    1200
agcagggcta cacacgtgct acaatggcgt aaacaaaggg aggcaataacc gcgaggttga  1260
gcaaatccca aaaataacgt ctcagttcgg attgtagtct gcaactcgac tacatgaagc   1320
tggaatcgct agtaatcgcg aatcagaatg tcgcggtgaa tacgttcccg ggtcttgtac   1380
acaccgcccg tcacaccatg ggagttggta acgcccgaag tcagtgaccc aaccgtaagg   1440
agggagctgc cgaaggcggg atcgataact ggggtgaagt cgtaacaagg tagccgtatc   1500
ggaaggtgcg gctggatcac ctcctt                                       1526

SEQ ID NO: 103         moltype = DNA  length = 1493
FEATURE                Location/Qualifiers
source                 1..1493
                       mol_type = genomic DNA
                       organism = Blautia coccoides
SEQUENCE: 103
agagtttgat cctggctcag gatgaacgct ggcggcgtgc ttaacacatg caagtcgagc     60
gaagcgctaa gacagatttc ttcggattga agtctttgtg actgagcggc ggacgggtga    120
gtaacgcgtg gtaacctgcc tcatacaggg ggataacag ttagaaatga ctgctaatac    180
cgcataagcg cacaggaccg catggtctgg tgtgaaaaac tccggtggta tgagatggac    240
ccgcgtctga ttagctagtt ggaggggtaa cggcccacca aggcgacgat cagtagccgg    300
cctgagaggg tgaacggcca cattgggact gagacacggc ccagactcct acggaggca    360
gcagtgggga atattgcaca atgggggaaa ccctgatgca gcgacgccgc gtgaaggaag   420
aagtatctcg gtatgtaaac ttctatcagc agggaagaaa atgacggtac ctgactaaga   480
agcccggct aactacgtgc cagcagccgc ggtaatacg aggggcaag cgttatccgg     540
atttactggg tgtaaaggga gcgtagacgg aagagcaagt ctgatgtgaa aggctgggc    600
ttaaccccag gactgcattg gaaactgttg ttctagagtg ccggagaggt aagcggaatt   660
cctagtgtag cggtgaaatg cgtagatatt aggaggaaca ccagtggcga aggcggctta   720
ctggacggta actgacgttg aggctcgaaa gcgtggggga caaacaggat tagataccct   780
ggtagtccac gccgtaaacg atgaatacta ggtgtcgggt ggcaaagcca ttcggtgccg   840
cagcaaacgc aataagtatt ccacctgggg agtacgttcg caagaatgaa actcaaagga   900
attgacgggg acccgcacaa gcggtggagc atgtggttta ttcgaagca acgcgaagaa    960
ccttaccaag tcttgacatc cctctgaccg tcccgtaacg ggggcttccc ttcggggcag  1020
aggagacagg tggtgcatgg ttgtcgtcag ctcgtgtcgt gagatgttgg gttaagtcc   1080
gcaacgagcg caacccttat ccttagtagc cagcacatga tggtgggcac tctagggaga  1140
ctgccgggga taacccggag gaaggcgggg acgacgtcaa atcatcatgc ccttatgat   1200
ttgggctaca cacgtgctac aatggcgtaa acaaagggag cgagacagc gatgttgagc   1260
gaatcccaaa aataacgtcc cagttcggac tgcagtctgc aactcgactg cacgaagctg  1320
gaatcgctag taatcgcgga tcagaatgcc gcggtgaata cgttcccggg tcttgtacac   1380
cgcccgtc acaccatggg agtcagtaac gcccgaagtc agtgacctaa ccgaaaggaa    1440
ggagctgccg aaggcgggac cgataactgg ggtgaagtcg taacaaggta acc          1493

SEQ ID NO: 104         moltype = DNA  length = 1262
FEATURE                Location/Qualifiers
source                 1..1262
                       mol_type = other DNA
                       note = Blautia faecis
                       organism = unidentified
SEQUENCE: 104
ataacagcca gaaatgactg ctaataccgc ataagcgcac agaaccgcat ggttcggtgt     60
gaaaaactcc ggtggtataa gatgacccg cgttggatta gctagttggc agggcagcgg    120
cctaccaagg cgacgatcca tagccggcct gagagggtga acggcacat gggactgag    180
acacggccca gactcctacg ggaggcagca gtggggaata ttgcacaatg ggggaaaccc   240
```

-continued

```
tgatgcagcg acgccgcgtg aaggaagaag tatctcggta tgtaaacttc tatcagcagg    300
gaagataatg acggtacctg actaagaagc cccggctaac tacgtgccag cagccgcggt    360
aatacgtagg gggcaagcgt tatccggatt tactgggtgt aaagggagcg tagacggcgc    420
agcaagtctg atgtgaaagg cagggggctta accctggac tgcattggaa actgctgtgc    480
ttgagtgccg gagggtaag cggaattcct agtgtagcgg tgaaatgcgt agatattagg    540
aggaacacca gtggcgaagg cggcttactg gacggtaact gacgttgagg ctcgaaagcg    600
tggggagcaa acaggattag ataccctggt agtccacgcc gtaaacgatg aatactaggt    660
gtcagggagc acagctcttt ggtgccgccg caaacgcatt aagtattcca cctggggagt    720
acgttcgcaa gaatgaaact caaaggaatt gacggggacc cgcacaagcg gtggagcatg    780
tggtttaatt cgaagcaacg cgaagaacct taccaaatct tgacatccct ctgaccggga    840
cttaaccgtc cctttccttc gggacagggg agacaggtgg tgcatggttg tcgtcagctc    900
gtgtcgtgag atgttgggtt aagtcccgca acgagcgcaa ccctatcct tagtagccag    960
cacgcartgg tgggcactct gaggagactg ccagggataa cctggaggaa ggcggggatg   1020
acgtcaaatc atcatgcccc ttatgatttg ggctacacac gtgctacaat ggcgtaaaca   1080
aagggaagcg aacccgcgag ggtgggcaaa tctcaaaaat aacgtcccag ttcggactgc   1140
agtctgcaac tcgactgcac gaagctgaa tcgctagtaa tcgcggatca gaatgccgcg   1200
gtgaatacgt tcccgggtct tgtacacacc gcccgtcaca ccatgggagt cagtaacgcc   1260
cg                                                                  1262

SEQ ID NO: 105         moltype = DNA   length = 1431
FEATURE                Location/Qualifiers
source                 1..1431
                       mol_type = genomic DNA
                       organism = Clostridium hathewayi
SEQUENCE: 105
ctcaggatga acgctggcgg cgtgcttaac acatgcaagt cgagcgaagc ggtttcaatg     60
aagttttcgg atggatttga aattgactta gcggcggacg ggtgagtaac gcgtgggtaa    120
cctgccttac actgggggat aacagttaga atgactgct aataccgcat aagcgcacag    180
ggccgcatgg nctggtgtga aaactccgg nggtgtaaga tggacccgcg tctgattagg    240
tagttggngg ggtaacggcc caccaagcc acgatccagta gccgacctga gagggtgacc    300
ggccacattg ggactgagac acggcccaaa ctcctacggg aggcagcagt ggggaatatt    360
ggacaatggg cgaaagcctg atccagcgac gccgcgtgag tgaagaagta tttcggtatg    420
taaagctcta tcagcaggga agaaaatgac ggtacctgac taagaagccc cggctaacta    480
cgtgccagca gccgcggtaa tacgtagggg gcaagcgtta tccggattta ctgggtgtaa    540
agggagcgta gacggtttag caagtctgaa gtgaaagccc gggctcaac cccggtactg    600
ctttggaaac tgtagacttg agtgcagga gaggtaagtg gaattcctag tgtagcggtg    660
aaatgcgtag atattaggag gaacaccagt ggcgaaggcg gcttactgga ctgtaactga    720
cgttgaggct cgaaagcgtg gggagcaaac aggattagat accctggtag tccacgccgt    780
aaacgatgaa tactaggtgt cgggggggcaa agcccttcgg tgccgccgca aacgcaataa    840
gtattccacc tggggagtac gttcgcaaga tgaaactca aaggaattga cggggacccg    900
cacaagcggt ggagcatgtg gtttaattcg aagcaacgcg aagaaccttat ccaagtcttg    960
acatcccact gaaaacacnt taaccgtgat ccctcttcgg agcagtggag acaggtggtg   1020
catggttgtc gtcagctcgt gtcgtgagat gttgggttaa gtcccgcaac gagcgcaacc   1080
cttatcctta gtagccagcg agtagagtcg ggcactctgg ggagactgcc agggataacc   1140
tggaggaagg tggggatgac gtcaaatcat catgcccctt atgatttggg ctacacacgt   1200
gctacaatgg cgtaaacaaa gggaggcaaa ggagcgatct ggagcaaacc ccaaaaataa   1260
cgtctcagtt cggattgcag gctgcaactc gcctgcatga agctggaatc gctagtaatc   1320
gcgaatcaga atgtcgcggt gaatacgttc ccggtcttg tacacaccgc ccgtcacacc   1380
atgggagttg gtaacgcccg aagtcagtga cccaaccgaa aggagggagc t            1431

SEQ ID NO: 106         moltype = DNA   length = 1493
FEATURE                Location/Qualifiers
source                 1..1493
                       mol_type = genomic DNA
                       organism = Blautia producta
SEQUENCE: 106
agagtttgat cctggctcag gatgaacgct ggcggcgtgc ttaacacatg caagtcgagc     60
gaagcactaa gacggatttc ttcggattga agtctttgtg actgagcggc ggacgggtga    120
gtaacgcgtg ggtaacctgc ctcatacagg gggataacag ttagaaatga ctgctaatac    180
cgcataagcg cacaggaccg catggtctgg tgtgaaaaac tccgtggta tgagatggac    240
ccgcgtctga ttagctagtt ggaggggtaa cggcccacca aggcgacgat cagtagccgg    300
cctgagaggg tgaacggcca cattgggact gagacacggc ccagactcct acgggaggca    360
gcagtgggga atattgcaca atgggggaaa ccctgatgca gcgacgccgc gtgaaggaag    420
aagtatctcg gtatgtaaac ttctatcagc agggaagaaa atgacggtac ctgactaaga    480
agccccggct aactacgtgc cagcagccgc ggtaatacgt aggggggcaag cgttatccgg    540
atttactggg tgtaaaggga gcgtagacgg aagagcaagt ctgatgtgaa aggctggggc    600
ttaaccccag gactgcattg gaaactgttt ttctagagtg ccgagaggt aagcggaatt    660
cctagtgtag cggtgaaatg cgtagatatt aggaggaaca ccagtggcga aggcggctta    720
ctggacgttg actgacgttg aaacgtgaaa cgtagacgg caaacaggat tagataccct    780
ggtagtccac gccgtaaacg atgaatacta ggtgtcgggg ggcaaagcca ttcggtgccg    840
cagcaaacgc aataagtatt ccacctgggg agtacgttcg caagaatgaa actcaaagga    900
attgacgggg acccgcacaa gcggtggagc atgtggttta ttcgaagca acgcgaagaa    960
ccttaccaag tcttgacatc cctctgaccg tcccgtaacg ggacttccc ttcggggcag   1020
aggagacagg tggtgcatgg ttgtcgtcag ctcgtgtcgt gagatgttgg gttaagtccc   1080
gcaacgagcg caacccttat ccttagtagc cagcacatga tggtgggcac tctagggaga   1140
ctgccgggga taacccggag gaaggcgggg acgacgtcaa atcatcatgc ccttatgat   1200
ttgggctaca cacgtgctac aatggcgtaa acaaagggaa gcgagacagc gatgttgagc   1260
gaatcccaaa aataacgtcc cagttcggac tgcagtctgc aactcgactg cacgaagctg   1320
gaatcgctag taatcgcgga tcagaatgcc gcggtgaata cgttcccggg tcttgtacac   1380
```

```
accgcccgtc acaccatggg agtcagtaac gcccgaagtc agtgacctaa ccgaaaggaa  1440
ggagctgccg aaggcgggac cgataactgg ggtgaagtcg taacaaggta acc          1493
```

| SEQ ID NO: 107 | moltype = DNA   length = 1515 |
|---|---|
| FEATURE | Location/Qualifiers |
| source | 1..1515 |
| | mol_type = other DNA |
| | note = Anaerostipes hadrus |
| | organism = unidentified |

SEQUENCE: 107
```
tggctcagga tgaacgctgg cggcgtgctt aacacatgca agtcgaacga agctgcttaa   60
ctgatcttct tcggaattga cgttttgtag actgagtggc ggacgggtga gtaacgcgtg  120
ggcaacctgc cctgtacagg gggataacag tcagaaatga ctgctaatac cgcataagac  180
cacagcaccg catggtgcag gggtaaaaac tccggtggta caggatggac ccgcgtctga  240
ttagctggtt ggtgaggtaa cggctcacca aggcgacgat cagtagccgg cttgagagag  300
tgaacggcca cattgggact gagacacggc ccaaactcct acgggaggca gcagtgggga  360
atattgcaca atgggggaaa ccctgatgca gcgacgccgc gtgagtgaag aagtatctcg  420
gtatgtaaag ctctatcagc agggaagaaa atgacggtac ctgactaaga agccccggct  480
aactacgtgc cagcagccgc ggtaatacgt aggggggcaag cgttatccgg aattactggg  540
tgtaaagggt gcgtaggtgg tatggcaagt cagaagtgaa acccagggc ttaactctgg  600
gactgctttt gaaactgtca gactggagtg caggagaggt aagcggaatt cctagtgtag  660
cggtgaaatg cgtagatatt aggaggaaca tcagtgggta agcggctta ctggactgaa  720
actgacactg aggcacgaaa gcgtggggag caaacaggat tagataccct ggtagtccac  780
gccgtaaacg atgaatacta ggtgtcgggg ccgtagaggc ttcggtgccg cagccaacgc  840
agtaagtatt ccacctgggg agtacgttcg caagaatgaa actcaaagga attgacgggg  900
acccgcacaa gcggtggagc atgtggttta attcgaagca acgcgaagaa ccttacctgg  960
tcttgacatc cttctgaccg gtccttaacc ggaccttttcc ttcgggacag gagagacagg 1020
tggtcatggt tgtcgtcag ctcgtgtcgt gagatgttgg gttaagtccc gcaacgagcg 1080
caaccctat cttagtgagc cagcattca ggtggcact ctagagagac tgccagggat 1140
aacctgggagg aaggtggga cgacgtcaaa tcatcatgc ccttatgacc agggctacac 1200
acgtgctaca atggcgtaaa cagagggaag cagcctcgtg agagtgagca aatcccaaaa 1260
ataacgtctc agttcggatt gtagtctgca actcgactac atgaagctgg aatcgctagt 1320
aatcgcgaat cagaatgtcg cggtgaatac gttcccgggt cttgtacaca ccgcccgtca 1380
caccatggga gtcagtaacg cccgaagtca gtgacccaac cgtaaggagg gagctgccga 1440
aggcgggacc gataactggg gtgaagtcgt aacaaggtag ccgtatcgga aggtgcggct 1500
ggatcacctc ctttc                                                  1515
```

| SEQ ID NO: 108 | moltype = DNA   length = 1523 |
|---|---|
| FEATURE | Location/Qualifiers |
| source | 1..1523 |
| | mol_type = genomic DNA |
| | organism = Eubacterium fissicatena |

SEQUENCE: 108
```
gtttgatcct ggctcaggat gaacgctggc ggcgtgctta acacatgcaa gtcgagcgaa   60
gcgcttact tagatttctt cggattgaag agttttgcga ctgagcggcg gacgggtgag  120
taacgcgtgg gtaacctgcc tcatacaggg ggataacagt tagaaatgac tgctaatacc  180
gcataagacc acagtaccgc atggtacagt gggaaaaact ccggtggtat gagatggacc  240
cgcgtctgat tagctagttg gtaaggtaac ggcttaccaa ggcaacgatc agtagccgac  300
ctgagagggt gaccggccac attgggactg agacacggcc caaactccta cgggaggcag  360
cagtggggaa tattgcacaa tgggggaaac cctgatgcag cgacgccgcg tgaaggatga  420
agtatttcgg tatgtaaact tctatcagca gggaagaaaa tgacggtacc tgactaagaa  480
gccccggcta actacgtgcc agcagccgcg gtaatacgta gggggcaagc gttatccgga  540
tttactgggt gtaaagggag cgtagacggt tatgtaagtc tgatgtgaaa acccggggct  600
caacccggg actgcattgg aaactatgta actagagtgt cggagaggta agtggaattc  660
ctagtgtagc ggtgaaatgc gtagatatta ggaggaacac cagtgggcga agcggcttac  720
tggacgatca ctgacgttga ggctcgaaag cgtggggagc aaacaggatt agataccctg  780
gtagtccacg ccgtaaacga tgaatactag gtgtcgggtg gcaaagccat tcggtgccgc  840
agcaaacgca ataagtattc cacctgggga gtacgttcgc aagaatgaaa ctcaaaggaa  900
ttgacgggga cccgcacaag cggtggagca tgtggtttaa ttcgaagcaa cgcgaagaac  960
cttaccctgct cttgacatcc cactgaccgg cgtgtaatgg cgccttcctt tcgggtgcagt 1020
ggagacaggt ggtgcatggt tgtcgtcagc tcgtgtcgtg agatgttggg ttaagtcccg 1080
caacgagcgc aacccttatc tttagtagcc agcggtttgg ccgggcactc tagagagact 1140
gccaggata acctggagga aggtgggat gacgtcaaat catcatgccc cttatgagca 1200
gggctacaca cgtgctacaa tggcgtaaac aaagggagcc aataccgcga ggttagccaa 1260
atcccaaaaa taacgtctca gttcggatt tagtctgcaa ctcgactaca tgaagctgga 1320
atcgctagta atcgcgaatc agaatgtcgc ggtgaatacg ttcccgggtc ttgtacacac 1380
cgcccgtcac accatgggag ttggtaacgc ccgaagtcag tgacccaacc gtaaggaggg 1440
agctgccgaa ggcgggatcg ataactgggg tgaagtcgta acaaggtagc cgtatcggaa 1500
ggtgcggctg atcacctcc ttt                                          1523
```

| SEQ ID NO: 109 | moltype = DNA   length = 1524 |
|---|---|
| FEATURE | Location/Qualifiers |
| source | 1..1524 |
| | mol_type = genomic DNA |
| | organism = Eubacterium contortum |

SEQUENCE: 109
```
tttgatcctg gctcaggatg aacgctggcg acgtgcttaa cacatgcaag tcgagcgaag   60
cactttactt tgatttcttc ggaatgaaag gttttgtgac tgagcggcgg acgggtgagt  120
aacgcgtggg taacctgcct catacagggg gataacagtt agaaatgact gctaataccg  180
```

```
cataagacca cagtaccgca tggtacagtg ggaaaaactc cggtggtatg agatggaccc   240
gcgtctgatt agctagttgg taaggtaacg gcttaccaag gcgacgatca gtagccgacc   300
tgagagggtg accggccaca ttgggactga gacacggccc aaactcctac ggggaggcag   360
agtggggaat attgcacaat gggggaaacc ctgatgcagc gacgccgcgt gaaggatgaa   420
gtatttcggt atgtaaactt ctatcagcag ggaagaaaat ggtgtacct gactaagaag   480
ccccggctaa ctacgtgcca gcagccgcgg taatacgtag ggggcaagcg ttatccggat   540
ttactgggtg taaagggagc gtagacggtt atgtaagtct gatgtgaaaa cccgggctc    600
aaccccggga ctgcattgga aactatgtaa ctagagtgtc ggagaggtaa gtggaattcc   660
tagtgtagcg gtgaaatgcg tagatattag gaggaacacc agtggcgaag gcggcttact   720
ggacgatgac tgacgttgag gctcgaaagc gtggggagca aacaggatta gataccctgg   780
tagtccacgc cgtaaacgat gaatactagg tgtcggtgg caaagccatt cggtgccgca    840
gcaaacgcaa taagtattcc acctggggag tacgttcgca agaatgaaac tcaaaggaat   900
tgacgggggac ccgcacaagc ggtggagcat gtggtttaat tcgaagcaac gcgaagaacc   960
ttacctgctc ttgacatccc cctgaccggc gtgtaatggt gcctttcctt cgggacaggg  1020
gagacaggtg gtgcatggtt gtcgtcagct cgtgtcgtga gatgttgggt taagtcccgc  1080
aacgagcgca acccttatct ttagtagcca gcggtttggc cgggcactct agagagactg  1140
ccagggataa cctggaggaa ggtggggatg acgtcaaatc atcatgcccc ttatgagcag  1200
ggctacacac gtgctacaat ggcgtaaaca aagggaggcg aagccgtgag gtggagcaaa  1260
tcccaaaaat aacgtctcag ttcggattgt agtctgcaac tcgactacat gaagctggaa  1320
tcgctagtaa tcgcgaatca gaatgtcgcg gtgaatacgt tcccgggtct tgtacacacc  1380
gcccgtcaca ccatggagt tggtaacgcc cgaagtcagt gacccaaccg caaggaggga  1440
gctgccgagg gtgggaccga taactggggt gaagtcgtaa caaggtagcc gtatcggaag  1500
gtgcggctgg atcacctcct ttct                                         1524

SEQ ID NO: 110          moltype = DNA  length = 1390
FEATURE                 Location/Qualifiers
source                  1..1390
                        mol_type = genomic DNA
                        organism = Clostridium bolteae
SEQUENCE: 110
tttaattga ctgagtggcg gacgggtgag taacgcgtgg ataacctgcc tcacactggg    60
ggataacagt tagaaatgac tgctaatacc gcataagcgc acagtaccgc atggtacagt  120
gtgaaaaact ccggtggtgt gagatggatc cgcgtctgat tagccagttg gcggggtaac  180
ggcccaccaa agcgacgatc agtagccgac ctgagagggt gaccggccac attgggactg  240
agacacggcc caaactccta cgggaggcag cagtgggga tattgcacaa tggcgaaag   300
cctgatgcag cgacgccgcg tgagtgaaga agtatttcgg tatgtaaagc tctatcagca  360
gggaagaaaa tgacggtacc tgactaagaa gccccggcta actacgtgcc agcagccgcg  420
gtaatacgta ggggcaagc gttatccgga tttactgggt gtaaagggag cgtagacggc   480
gaagcagtc tgaagtgaaa acccagggct caaccctggg actgcttttgg aaactgtttt  540
gctagagtgt cggagaggta agtggaattc ctagtgtagc ggtgaaatgc gtagatatta  600
ggaggaacac cagtggcgaa ggcggcttac tggacgataa ctgacgttga ggctcgaaag  660
cgtggggagc aaacaggatt agataccctg gtagtccacg ccgtaaacga tgaatgctag  720
gtgttggggg gcaaagccct tcggtgccgt cgcaaacgca gtaagcattc cacctggga   780
gtacgttcgc aagaatgaaa ctcaaaggaa ttgacgggga cccgcacaag cggtggagca  840
tgtggtttaa ttcgaagcaa cgcgaagaac cttaccaagt cttgacatcc tcttgaccgg  900
cgtgtaacgg cgccttccct tcggggcaag agagacaggt ggtgcatggt tgtcgtcagc  960
tcgtgtcgtg agatgttggg ttaagtcccg caacgagcgc aacccttatc cttagtagcc  1020
agcaggtaaa gctgggcact ctagggagac tgccagggat aacctggagg aaggtgggga  1080
tgacgtcaaa tcatcatgcc ccttatgatt tgggctacac acgtgctaca atggcgtaaa  1140
caaagggaag caagacagtg atgtggagca aatcccaaaa ataacgtccc agttcggact  1200
gtagtctgca acccgactac acgaagctgg aatcgctagt aatcgcgaat cagaatgtcg  1260
cggtgaatac gttcccgggt cttgtacaca ccgcccgtca ccatggga gtcagcaacg   1320
cccgaagtca gtgacccaac tcgcaagaga gggagctgcc gaaggcgggg caggtaactg  1380
gggtgaagtc                                                        1390

SEQ ID NO: 111          moltype = DNA  length = 1308
FEATURE                 Location/Qualifiers
source                  1..1308
                        mol_type = genomic DNA
                        organism = Blautia luti
SEQUENCE: 111
gtgggtaacc tgcctatac aggggggataa cagtcagaaa tgactgctaa taccgcataa   60
gcgcacagag ctgcatggct ccggtgtgaa aaactccggt ggtataagat ggacccgcgt  120
tggattagct agttggtgag gtaacggccc accaaggcga cgatccatag ccggcctgag  180
agggtgaacg gccacattgg gactgagaca cggcccagas tcctacggga ggcagcagtg  240
gggaatattg cacaatgggg gaaaccctga tgcagcgacg ccgcgtgaag gaagaagtat  300
ctcggtatgt aaacttctat cagcaggaa gaaaatgacg gtacctgact aagaagcccc  360
ggctaactac gtgccagcag ccgcggtaat acgtagggg caagcgttat ccggatttac   420
tgggtgtaaa gggagcgtag acggcatgga caagtcgtat gtgaaaggct gggggctcaac  480
cccgggactg cattggaaac tgcccgtctt gagtgccgga gaggtaagcg gaattcctag  540
tgtagcggtg aaatgcgtag atattaggag gaacaccagt ggcgaaggcg gcttactgga  600
cggtaactga cgttgaggct cgaaagcgtg ggagcaaac aggattagat accctggtag   660
tccacgcggt aaacgatgaa tcctaggtgt cggggagcaa annnnttcgg tgccgccgca  720
aacgcattaa gcattccacc tggggagtac gttcgcaaga atgaaactca aaggaattga  780
cggggacccg cacaagcggt ggagcatgtg gtttaattcg aagcaacgcg aagaaccta   840
ccaagtcttg acatccctct gaccgagtat gtatggtact tttccttcgg gagagagagg  900
agacaggtgg tgcatggttg tcgtcagctc gtgtcgtgag atgttgggtt aagtcccgca  960
acgagcgcaa ccctatccc cagtagccag cggttcggcc gggcactct aggagactgc   1020
cagggataac ctggaggaag gcggggatga cgtcaaatca tcatgcccct tatgatttgg  1080
```

```
gctacacacg tgctacaatg gcgtaaacaa agggaagcaa gcctgcgagg gtgggcaaat    1140
cccaaaaata acgtcccagt tcggactgta gtctgcaacc cgactacacg aagctggaat    1200
cgctagtaat cgcggatcag aatgccgcgg tgaatacgtt cccgggtctt gtacacaccg    1260
cccgtcacac catgggagtc agtaacgccc gaagtcagtg acctaact                 1308

SEQ ID NO: 112          moltype = DNA   length = 1489
FEATURE                 Location/Qualifiers
source                  1..1489
                        mol_type = genomic DNA
                        organism = Acidaminococcus intestini
SEQUENCE: 112
ctggcggcgt gcttaacaca tgcaagtcga acgagaact tatttcggta agttcttagt     60
ggcgaacggg tgagtaacgc gtgggcaacc tgccctccag ttggggacaa cattccgaaa    120
gggatgctaa taccgaatgt cctccctcct ccgcatggag gagggaggaa agatggcctc    180
tgcttgcaag ctatcgctgg aagatgggcc cgcgtctgat tagctagttg gtggggtaac    240
ggctcaccaa ggcgatgatc agtagccggt ctgagaggat gaacgccac attgggactg     300
agacacggcc caaactccta cgggaggcag cagtgggaa tcttccgcaa tggacgaaag    360
tctgacggag caacgccgcg tgagtgatga aggtcttcgg attgtaaaac tctgttgtta    420
gggacgaaag caccgtgttc gaacaggtca tggtgttgac ggtacctaac gaggaagcca    480
cggctaacta cgtgccagca gccgcggtaa tacgtaggtg gcaagcgttg tccggaatta    540
ttgggcgtaa agagcatgta ggcgggcttt taagtctgac gtgaaaatgc ggggcttaac    600
cccgtatggc gttggatact ggaagtcttg agtgcaggag aggaaaggga aattcccagt    660
gtagcggtga aatgcgtaga tattgggagg aacaccagtg gcgaaggcgc ctttctggac    720
tgtgtctgac gctgagatgc gaaagccagg gtagcaaacg ggattagata ccccggtagt    780
cctggccgta aacgatggat actaggtgta ggaggtatcg acccttctg tgccggagtt    840
aacgcaataa gtatcccgcc tggggactac gatcgcaaga ttgaaactca aaggaattga    900
cggggccccg cacaagcggt ggagtatgtg gtttaattcg acgcaacgcg aagaaccta   960
ccaaggcttg acattgagtg aaagaccctag agataggtcc ctccctcgg ggacacgaaa   1020
acaggtggtg catggctgtc gtcagctcgt gtcgtgagat gttgggttaa gtcccgcaac    1080
gagcgcaacc cctatcctat gttaccagcg cgtaaaggcg ggactcata gagactgcc    1140
agggataact ggaggaagg cggggatgac gtcaagtcat catgcccctt atgtcttggg    1200
ctacacacgt actacaatgg tcggcaacaa agggcagcga aaccgcgagg tggagcaaat    1260
cccagaaaacc cgaccccagt tcggatcgta ggctgcaacc cgcctacgtg aagttggaat    1320
cgctagtaat cgcaggtcag catactgcgg tgaatacgtt cccgggcctt gtacacaccg    1380
cccgtcacac cacgaaagtt ggtaacaccc gaagccggtg agataacctt ttaggagtca    1440
gctgtctaag gtgggccga tgattggggt gaagtcgtaa caaggtagc                 1489

SEQ ID NO: 113          moltype = DNA   length = 1500
FEATURE                 Location/Qualifiers
source                  1..1500
                        mol_type = genomic DNA
                        organism = Ruminococcus albus
SEQUENCE: 113
agagtttgat cctggctcag gacgaacgct ggcggcacgc ttaacacatg caagtcgaac    60
gagcgaaaga gtgcttgcac tctctagcta gtggcggacg ggtgagtaac acgtgagcaa    120
tctgcctttc ggagagggat accaattgga aacgattgtt aatacctcat aacataacga    180
agccgcatga ctttgttatc aaatgaattt cgccgaaaga tgagctcgcg tctgattagg    240
tagttggtga ggtaacggcc caccaagccg acgatcagta gccggactga gaggttgaac    300
ggccacattg gactgagac acggcccaga ctcctacggg aggcagcagt ggggaatatt    360
gcacaatggg cgaaagcctg atgcagcgat gccgcgtgag ggaagaaggt tttaggattg    420
taaacctctg tcttttgggga cgataatgac ggtacccaag gaggaagctc cggctaacta    480
cgtgccagca gccgcggtaa tacgtaggga gcgagcgttg tccggaatta ctgggtgtaa    540
agggagcgta ggcgggattg caagtcaggt gtgaaattta ggggcttaac ccctgaactg    600
cacttgaaac tgtagttctt gagtgaagta gaggtaagcg gaattcctag tgtagcggtg    660
aaatgcgtag atattaggag gaacatcagt ggcgaaggcg gcttactggg ctttaactga    720
cgctgaggct cgaaagcgtg gggagcaaac aggattagat accctggtag tccacgccgt    780
aaacgatgat tactaggtgt gggggactg ccccctccg tgccgcagtt aacacaataa    840
gtaatccacc tggggagtac ggccgcaagg ctgaaactca aaggaattga cggggaccccg   900
cacaagcagt ggagtatgtg gtttaattcg aagcaacgcg aagaaccta ccaggtcttg    960
acatcgtacg catagcatag agatatgtga aatccctcg gggacgtata gacaggtggt    1020
gcatggttgt cgtcagctcg tgtcgtgaga tgttgggtt aagtcccgca acgagcgcaa    1080
cccttactgt tagttgctac gcaagagcac tctagcagga ctgccgttga caaacgagg    1140
gaaggtgggg atgacgtcaa atcatcatgc cccttatgac ctgggctaca cacgtactac    1200
aatggctgtt aacagaggga agcaaaacag tgatgtgaaga caaaccccta aaagcagtct    1260
tagttcggat tgtaggctgc aacccgccta catgaagtcg gaattgctag taatcgcgga    1320
tcagcatgcc gcggtgaata cgttcccggg ccttgtacac accgcccgtc acgccatggg    1380
agtcggtaac acccgaagcc tgtgttctaa ccgcaaggag gaagcagtcg aaggtgggat    1440
tgatgactgg ggtgaagtcg taacaaggta gccgtatcgg aaggtgcggc tggatcacct    1500

SEQ ID NO: 114          moltype = DNA   length = 1521
FEATURE                 Location/Qualifiers
source                  1..1521
                        mol_type = genomic DNA
                        organism = Eubacterium rectale
SEQUENCE: 114
agagtttgat cctggctcag gatgaacgct ggcggcgtgc ttaacacatg caagtcgaac    60
gaagcacttt atttgatttc cttcgggact gattattttg tgactgagtg gcggacgggt    120
gagtaacgcg tgggtaacct gccttgtaca ggggataac agttggaaac ggctgctaat    180
accgcataag cgcacggcat cgcatgatgc agtgtgaaaa actccggtgg tataagatgg    240
```

```
acccgcgttg gattagctag ttggtgaggt aacggcccac caaggcgacg atccatagcc  300
gacctgagag ggtgaccggc cacattggga ctgagacacg gcccaaactc ctacgggagg  360
cagcagtggg gaatattgca caatgggcga agcctgatg cagcgacgcc gcgtgagcga  420
agaagtattt cggtatgtaa agctctatca gcagggaaga taatgacggt acctgactaa  480
gaagcaccgg ctaaatacgt gccagcagcc gcggtaatac gtatggtgca agcgttatcc  540
ggatttactg ggtgtaaagg gagcgcaggc ggtgcggcaa gtctgatgtg aaagcccggg  600
gctcaacccc ggtactgcat tggaaactgt cgtactagag tgtcggaggg gtaagcggaa  660
ttcctagtgt agcggtgaaa tgcgtagata ttaggaggaa caccagtggc gaaggcggct  720
tactgacga taactgacgc tgaggctcga aagcgtgggg agcaaacagg attagatacc  780
ctggtagtcc acgccgtaaa cgatgaatac taggtgttgg gaagcattgc ttctcggtgc  840
cgtcgcaaac gcagtaagta ttccacctgg ggagtacgtt cgcaagaatg aaactcaaag  900
gaattgacgg ggacccgcac aagcggtgga gcatgtggtt taattcgaag caacgcgaag  960
aaccttacca agtcttgaca tccttctgac cggtacttaa ccgtaccttc tcttcggagc 1020
aggagtgaca ggtggtgcat ggttgtcgtc agctcgtgtc gtgagatgtt gggttaagtc 1080
ccgcaacgag cgcaacccct atctttagta gccagcggtt cggccgggca ctctagagag 1140
actgccaggg ataacctgga ggaaggcggg gatgacgtca aatcatcatg ccccttatga 1200
cttgggctac acacgtgcta caatggcgta aacaaaggga gcaaagctg tgaagccgag 1260
caaatctcaa aaataacgtc tcagttcgga ctgtagtctg caacccgact acacgaagct 1320
ggaatcgcta gtaatcgcag atcagaatgc tgccggtgaat acgttcccgg gtcttgtaca 1380
caccgcccgt cacaccatgg gagttgggaa tgcccgaagc cagtgaccta accgaaagga 1440
aggagctgtc gaaggcaggc tcgataactg gggtgaagtc gtaacaaggt agccgtatcg 1500
gaaggtgcgg ctggatcacc t                                          1521

SEQ ID NO: 115           moltype = DNA  length = 1545
FEATURE                  Location/Qualifiers
source                   1..1545
                         mol_type = genomic DNA
                         organism = Acidaminococcus fermentans
SEQUENCE: 115
agagtttgat cctggctcag gacgaacgct ggcggcgtgc ttaacacatg caagtcgaac   60
ggagaacttt cttcggaatg ttcttagtgg cgaacgggtg agtaacgcgt aggcaacctg  120
ccctctggtt ggggacaaca ttccgaaagg gatgctaata ccgaatgaga tcctctttcc  180
gcatggagag aggatgaaag atggcctcta cttgtaagct atcgcagaa gatgggcctg  240
cgtctgatta gctagtaggt gaggtaacgg ctcacctagg cgatgatcag tagccggtct  300
gagaggatga acggccacat tgggactgag acacggccca aactcctacg ggaggcagca  360
gtggggaatc ttccgcaatg gacgaaagtc tgacggagca acgccgcgtg agtgatgaag  420
gccttcgggt tgtaaaactc tgttgtcagg acgaaagca ccgatctata atacattttg  480
gtgttgacgg tacctgacga ggaagccacg gctaactacg tgccagcagc cgcggtaata  540
cgtaggtggc aagcgttgtc cggaattatt gggcgtaaag agcatgtagg cgggcttta  600
agtccgacgt gaaaatgcgg ggcttaaccc cgtatggcgt tggatactgg aagtcttgag  660
tgcaggagag gaaaggggaa ttcccagtgt agcggtgaaa tgcgtagata ttgggaggaa  720
caccagtggc gaaggcgcct ttctggactg tgtctgacgc tgagatgcga aagccagggt  780
agcaaacgg attagatacc ccggtagtcc tggccgtaaa cgatgggtac taggtgtagg  840
aggtatcgac cccttctgtg ccggagttaa cgcaataagt accccgcctg gggactacga  900
tcgcaagatt gaaactcaaa ggaattgacg ggggcccgca caagcggtgg agtatgtggt  960
ttaattcgac gcaacgcgaa gaaccttacc aaggcttgac attgagtgaa agacccgag  1020
atgggtcccc ttcttcggaa gcacgaaaac aggtggtgca tggctgtcgt cagctcgtgt  1080
cgtgagatgt tgggttaagt cccgcaacga gcgcaaccct atcctatgt taccagcacg  1140
taatggtggg gactcatagg agactgccag ggataacctg gaggaaggcg gggatgacgt  1200
caagtcatca tgccccttat gtcttgggct acacacgtac taatggtc ggcaacaaag   1260
ggcagcgaag ccgcgaggcg gagccaatca cagaaacccg accccagttc ggatcgcag  1320
ctgcaacccg cctgcgtgaa gttgaatcg ctagtaatcg caggtcagca tactgcggtg  1380
aatacgttcc cgggccttgt acaccgccc cgtcacacca cgaaagttgg taacacccga  1440
agccggtgag ataacctttt aggagtcagc tgtctaaggt ggggccgatg attgggtgaa  1500
agtcgtaaca aggtagccgt tcgagaacga gcggctggat cacct                 1545

SEQ ID NO: 116           moltype = DNA  length = 1423
FEATURE                  Location/Qualifiers
source                   1..1423
                         mol_type = genomic DNA
                         note = Fusicatenibacter saccharivorans
                         organism = unidentified
SEQUENCE: 116
tggctcagga tgaacgctgg cggcgtgctt aacacatgca agtcgagcga agcagttaag   60
aagattyttc ggatgattct tgactgactg agcggcggac gggtgagtaa cgcgtgggtg  120
acctgcccca taccggggga taacagctgg aaacggctgc taataccgca taagcgcaca  180
gagctgcatg gctcggtgtg aaaaactccg gtggtatggg atgggcccgc gtctgattag  240
gcagttggcg gggtaacggc ccaccaaacc gacgatcagt agccggcctg agagggcgac  300
cggccacatt gggactgaga cacggcccaa actcctacg gaggcagcag tgggaatat  360
tgcacaatgg gggaaaccct gatgcagcga cgccgcgtga gcgaagaagt atttcggtat  420
gtaaagctct atcagcaggg aagataatga cggtacctga ctaagaagcc ccggctaact  480
acgtgccagc agccgcggta atacgtaggg ggcaagcgtt atccggattt actgggtgta  540
aagggagcgt agacggcaag gcaagtctga tgtgaaaacc cagggcttaa ccctgggact  600
gcattggaaa ctgtctgct cgagtgccgg agaggtaagc ggaattccta gtgtagcggt  660
gaaatgcgta gatattagga agaacaccag tggcgaaggc ggcttactgg acggtaactg  720
acgttgaggc tcgaaagcgt ggggagcaaa caggattaga taccctggta gtccacgccg  780
taacgatga atgctaggtg ttggggagca agctcttcg gtgccgccgc aaacgcatta  840
agcattccac ctgggagta cgttcgcaag aatgaaactc aaaggaattg acggggaccc  900
gcacaagcgg tggagcatgt ggtttaattc gaagcaacgc gaagaacctt accaggtctt  960
```

-continued

```
gacatcccga tgaccggccc gtaacgggc cttctcttcg gagcattgga gacaggtggt   1020
gcatggttgt cgtcagctcg tgtcgtgaga tgttgggtta agtcccgcaa cgagcgcaac   1080
ccttatcctc agtagccagc aggtaaagct gggcactctg tggagactgc cagggataac   1140
ctggaggaag gtgggatga cgtcaaatca tcatgcccct tatgatctgg gctacacacg   1200
tgctacaatg gcgtaaacaa agggaggcaa agccgcgagg tggagcaaat cccaaaaata   1260
acgtctcagt tcggactgca gtctgcaact cgactgcacg aagctggaat cgctagtaat   1320
cgcgaatcag aatgtcgcgg tgaatacgtt cccgggtctt gtacacaccg cccgtcacac   1380
catgggagtt ggtaacgccc gaagtcagtg acccaacctt tta                    1423

SEQ ID NO: 117         moltype = DNA  length = 1494
FEATURE                Location/Qualifiers
source                 1..1494
                       mol_type = genomic DNA
                       organism = Ruminococcus champanellensis SEQUENCE: 117
agagtttgat cctggctcag gacgaacgct ggcggcacgc ctaacacatg caagtcgaac    60
gggagataaag acttcggttt ttatcttagt ggcgacggtg tgagtaacac gtgagcaacc   120
tgcctctgag agagggatag cttctggaaa cggatggtaa tacctcataa catagccgta   180
ccgcatgata ctgctatcaa agatttatcg ctcagagatg gctcgcgtc tgattagcta    240
gatggtgagg taacggctca ccatggcgac gatcagtagc cggactgaga ggttgaacgg   300
ccacattggg actgagacac ggcccagact cctacggga gcagcagtgg ggaatattgc    360
acaatgggcg caagcctgat gcagcgatgc cgcgtgagg aagaaggttt tcggattgta    420
aactcctgtc ttaagggacg ataatgacgg taccttagga ggaagctccg gctaactacg    480
tgccagcagc cgcggtaata cgtagggagc gagcgttgtc cggaattact gggtgtaaag   540
ggagcgtagg cgggattgca agtcagatgt gaaaactatg ggcttaaccc atagactgca   600
tttgaaactg tagttcttga gtgaagtaga ggtaagcgga attcctagtg tagcggtgta   660
atgcgtagat attaggagga acatcggtgg cgaaggcggc ttactgggct tttactgacg    720
ctgaggctcg aaagcgtggg gagcaaacag gattagatac cctggtagtc cacgctgtaa   780
acgatgatta ctaggtgtgg ggggactgac ccctttccgtg ccgcagttaa cacaataagt   840
aatccacctg gggagtacgg ccgcaaggtt gaaactcaaa ggaattgacg ggggcccgca    900
caagcagtgg agtatgtggt ttaattcgaa gcaacgcgaa aaaccttacc aggtcttgac    960
atcgagtgaa tgatctagag atagatcagt ccttcgggac acaaagacag gtggtgcatg    1020
gttgtcgtca gctcgtgtcg tgagatgttg ggttaagtcc cgcaacgagc gcaaccctta   1080
cctttagttg ctacgcaaga gcactctaga gggactgccg ttgacaaaac ggaggaaggt   1140
ggggatgacg tcaaatcatc atgcccctta tgacctgggc tacacacgta ctacaatgga   1200
aatgaacaga gggaagcaat acagtgatgt ggagcaaatc cccaaaaatt gtcccagttc    1260
agattgtagg ctgcaactcg cctacatgaa gtcggaattg ctagtaatcg cagatcagca    1320
tgctgcggtg aatacgttcc cgggccttgt acacaccgcc cgtcacacca tgggagtcgg   1380
taacacccga agccagtagc ctaacgcaa ggagggcgct gtcgaaggtg ggattgatga   1440
ctggggtgaa gtcgtaacaa ggtagccgta tcggaaggtg cggctggatc acct          1494

SEQ ID NO: 118         moltype = DNA  length = 1533
FEATURE                Location/Qualifiers
source                 1..1533
                       mol_type = genomic DNA
                       organism = Bifidobacterium bifidum SEQUENCE: 118
tttttgtgga gggttcgatt ctggctcagg atgaacgctg gcggcgtgct taacacatgc    60
aagtcgaacg ggatccatcg ggctttgctt ggtggtgaga gtggcgaacg ggtgagtaat   120
gcgtgaccga cctgccccat gctccggaat agctcctgga acgggtggt aatgccggat    180
gttccacatg atcgcatgtg atttgtggaa agattctatc ggcgtgggat ggggtcgcgt   240
cctatcagct tgttggtgag gtaacggctc accaaggctt cgacgggtag ccggcctgag   300
agggcgaccg gccacattgg gactgagata cggcccagac tcctacggga ggcagcagtg   360
gggaatattg cacaatgggc gcaagcctga tgcagcgacg ccgcgtgagg gatggaggcc   420
ttcgggttgt aaacctcttt tgtttgggag caagccttcg gtgagtgta cctttcgaat   480
aagcgccggc taactacgtg ccagcagccg cggtaatacg tagggcgcaa cgttatccgg   540
gatttattgg gcgtaaaggg ctcgtaggcg gctcgtcgcg tccggtgtga aagtccatcg   600
cttaacggtg gatctgcgcc gggtacgggc gggctggagt gcggtagggg agactggaat   660
tcccggtgta acggtggaat gtgtagatat cgggaagaac accgatggcg aaggcaggtc   720
tctgggccgt cactgacgct gaggagcgaa agcgtgggga gcgaacagga ttagataccc   780
tggtagtcca cgccgtaaac ggtggacgct ggatgtgggg cacgttccac gtgttccgtg   840
tcggagctaa cgcgttaagc gtcccgcctg gggagtacgg ccgcaaggct aaaactcaaa   900
gaaattgacg ggggcccgca caagcggcgg agcatgcgga ttaattcgat gcaacgcgaa    960
gaaccttacc tgggcttgac atgttcccga cgacgccaga gatgcgtttc ccttcgggga   1020
cgggttcaca ggtggtgcat ggtcgtcgtc agctcgtgtc gtgagatgtt gggttaagtc   1080
ccgcaacgag cgcaaccctc gccccgtgtt gccagcacgt tatggtggga actcacgggg   1140
gaccgccggg gttaactcgg aggaaggtgg ggatgacgtc agatcatcat gcccttacg    1200
tccagggctt cacgcatgct acaatggccg gtacagcggg atgcgacatg cgacatgga   1260
gcggatccct gaaaactggt ctcagttcgg atcggagtct gcaaccccg tccgtgaagg   1320
cggagtcgct agtaatcgcg gatcagcaac gccgcggtga atgcgttccc ggccttgta    1380
cacaccgccc gtcaagtcat gaaagtgggc agcacccgaa gccggtggcc taaccccttg   1440
tgggatggag ccgtctaagg tgaggctcgt gattgggact aagtcgtaac aaggtagccg   1500
taccggaagg tgcggctgga tcacctcctt tct                                1533

SEQ ID NO: 119         moltype = DNA  length = 1552
FEATURE                Location/Qualifiers
source                 1..1552
                       mol_type = genomic DNA
                       organism = Megasphaera elsdenii
```

```
SEQUENCE: 119
agagtttgat cctggctcag gacgaacgct ggcggcgtgc ttaacacatg caagtcgaac    60
gagaagagat gagaagcttg cttcttatca attcgagtgg caaacgggtg agtaacgcgt   120
aagcaacctg cccttcagat ggggacaaca gctggaaacg gctgctaata ccgaatacgt   180
tcttttttgtc gcatggcaga gggaagaaag ggaggctctt cggagctttc gctgaaggag   240
gggcttgcgt ctgattagct agttggaggg gtaacggccc accaaggcga cgatcagtag   300
ccggtctgag aggatgaacg gccacattgg gactgagaca cggcccagac tcctacggga   360
ggcagcagtg gggaatcttc cgcaatggac gaaagtctga cggagcaacg ccgcgtgaac   420
gatgacggcc ttcgggttgt aaagttctgt tatacgggac gaatggcgta gcggtcaata   480
cccgttacga gtgacggtac cgtaagagaa agccacggct aactacgtgc cagcagccgc   540
ggtaatacgt aggtggcaag cgttgtccgg aattattggg cgtaaagggc gcgcaggcgg   600
cgtcgtaagt cggtcttaaa agtgcgggc ttaaccccgt gaggggaccg aaactgcgat   660
gctagagtat cggagaggaa agcggaattc ctagtgtagc ggtgaaatgc gtagatatta   720
ggaggaacac cagtggcgaa agcggcttc tggacgacaa ctgacgctga ggcgcgaaag   780
ccaggggagc aaacgggatt agataccccg gtagtcctgg ccgtaaacga tggatactag   840
gtgtaggagg tatcgacccc ttctgtgccg gagttaacgc aataagtatc ccgcctgggg   900
agtacgccg caaggctgaa actcaaagga attgacgggg cccgcacaa gcggtggagt   960
atgtggttta attcgacgca acgcgaagaa ccttaccaag ccttgacatt gattgctatg  1020
gatagagata tccagttcct cttcggagga caagaaaaca ggtggtgcac ggctgtcgtc  1080
agctcgtgtc gtgagatgtt gggttaagtc ccgcaacgag cgcaacccct atcttctgtt  1140
accagcggtt cggccgggga ctcaggagag actgccgcag acaatgcgga ggaaggcggg  1200
gatgacgtca agtcatcatg cccttatgg cttgggctac acacgtacta caatggctct  1260
taatagaggg aagcgaagga gcgatccgga gcaaacccca aaaacagagt cccagttcgg  1320
attgcaggct gcaactcgcc tgcatgaagc aggaatcgct agtaatcgca ggtcagcata  1380
ctgccggtgaa tacgttcccg ggccttgtac acaccgcccg tcacaccacg aaagtcattc  1440
acacccgaag ccggtgaggt aacctttttgg agccagccgt cgaaggtggg ggcgatgatt  1500
ggggtgaagt cgtaacaagg tagccgtatc ggaaggtgcg gctggatcac ct           1552

SEQ ID NO: 120         moltype = DNA    length = 1479
FEATURE                Location/Qualifiers
source                 1..1479
                       mol_type = genomic DNA
                       organism = Dorea formicigenerans
SEQUENCE: 120
ttaaacgaga gtttgatcct ggctcaggat gaacgctggc ggcgtgctta acacatgcaa    60
gtcgagcgaa gcacataagt ttgattcttc ggatgaagac ttttgtgact gagcggcgga   120
cgnnngagta acgcgtgggt aacctgcctc atacaggggg ataacagyta gaaatgcctg   180
ctaataccgc ataagaccac agtactgcat ggtacagtgn nnaaaactcc ggtggtatga   240
gatggaacccg cgtctgatta ggtagttggt gaggtaacgg cccaccnage ccgacgatcag   300
tagccgacct gagagggtga ccggccacat tgggactgag acacggccnn gactcctacg   360
ggaggcagca gtgggaata ttgcacaatg ggcgaaagcc tgatgcagcg acgccgcgtg   420
aaggatgaag tatttcggta tgtaaacttc tatcagcagg gaagaaaatg acggtacctg   480
actaagaagc cccggctaac tacgtgccag cagccgnggt aatacgtagg gggnnagcgt   540
tatccggatt tactgggtgt aaagggagcg tagacggctg tgcaagtctg aagtgaaagg   600
catgggctca acctgtggac tgctttggaa actgtgcagc tagagtgtcg gagaggtaag   660
tggaattcct agtgtagcgg tgaaatgcgt agatattagg aggaacacca gtggcgaagg   720
cggcntactg gacgatgact gacgttgagg ctcgaaacgt ggggagcaa acaggattag   780
ataccctggt agtccacgcc gtaaacgatg actgctaggt gtcgggtagc aaagctattc   840
ggtgccgcag ctaacgcaat aagcagtcca cctggggagt acgttcgcaa gaatgaaact   900
caaaggaatt gacgggggncc ncgcacaagcg gtggagcatg tggtttaatt cgaannaacg   960
cgaagaacct tacctgatct tgacatcccg atgaccgctt cgtaatggaa gyttttcttc  1020
ggaacatcgg tgacaggtgg tgcatggttg tcgtcagctc gtgtcgtgag atgttgggtt  1080
aagtcccgca acgagcgcaa cccttatctt cagtagccag catttaggat gggcactctg  1140
gagagactgc cagggataac ctggaggaag gtggggatga cgtnnaatca tcatgcccct  1200
tatgaccagg gctacacacg tgctacaatg gcgtaaacag agggaggcaa agccgcgagg  1260
ccgagcaaat ctcaaaaata acgtctcagt tcggattgta gtctgcaact cgactacatg  1320
aagctggaat cgctagtaat cgcagatcag aatgctgcgg tgaatacgtt cccgggtctt  1380
gtacacaccg cccgtcacac catgggagtc agtaacgccc gaagtcagtg acccaaccga  1440
aaggaggag ctgccgaagg tgggaccgat aactgggt                            1479

SEQ ID NO: 121         moltype = DNA    length = 1390
FEATURE                Location/Qualifiers
source                 1..1390
                       mol_type = genomic DNA
                       note = Eisenbergiella tayi
                       organism = unidentified
SEQUENCE: 121
ggtataactt agtggcggac gggtgagtaa cgcgtgggaa acctgccctg taccggggga    60
taacttag aaataggtgc taataccgca taagcgcacg gaaccgcatg gttccgtgtg   120
aaaaactccg gtggtacagg atggtcccgc gtctgattag ccagttggca gggtaacggc   180
ctaccaaagc gacgatcagt agccggcctg agagggtgaa cggccacatt gggactgaga   240
cacgcccaa actcctacgg gaggcagcag tggggaatat tgcacaatgg gggaaaccct   300
gatgcagcga cgccgcgtga gtgaagaagt atttcggtat gtaaagctct atcagcaggg   360
aagaaaatga cggtacctga ctaagaagcc ccggctaact acgtgccagc agccgcggta   420
atacgtaggg ggcaagcgtt atccggattt actgggtgta aagggagcgt agacggcatg   480
gcaagccaga tgtgaaaacc cagggctcaa ccttgggatt gcatttggaa ctgccaggct   540
ggagtgcagg agaggtaagc ggaattccta gtgtagcggt gaaatgcgta gatattagga   600
ggaacaccag tggcgaaggc ggcttactgg actgtaactg acgttgaggc tcgaaagcgt   660
ggggagcaaa caggattaga taccctggta gtccacgcgg taaacgatga ttgctaggtg   720
```

```
taggtgggta tggacccatc ggtgccgcag ctaacgcaat aagcaatcca cctggggagt    780
acgttcgcaa gaatgaaact caaaggaatt gacggggacc cgcacaagcg gtggagcatg    840
tggtttaatt cgaagcaacg cgaagaacct taccaagtct tgacatccca atgacgcacc    900
tgtaaagagg tgttcccttc ggggcattgg agacaggtgg tgcatggttg tcgtcagctc    960
gtgtcgtgag atgttgggtt aagtcccgca acgagcgcaa cccttattct tagtagccag   1020
caggtaaagc tgggcactct aaggagactg ccggggataa cccggaggaa ggcggggatg   1080
acgtcaaatc atcatgcccc ttatgatttg ggctacacac gtgctacaat ggcgtaaaca   1140
aagggaagcg agacagtgat gtggagcaaa tcycagaaat aacgtctcag ttcggattgt   1200
agtctgcaac tcgactacat gaagctggaa tcgctagtaa tcgcgaatca gcatgtcgcg   1260
gtgaatacgt tcccgggtct tgtacacacc gcccgtcaca ccatgggagt tggaaatgcc   1320
cgaagtctgt gacctaaccg aaagggagga gcagccgaag gcaggtctga taactggggt   1380
gaagtcgtaa                                                          1390

SEQ ID NO: 122        moltype = DNA   length = 1478
FEATURE               Location/Qualifiers
source                1..1478
                      mol_type = genomic DNA
                      organism = Clostridium symbiosum
SEQUENCE: 122
aaacatgaga gtttgatcct ggctcaggat gaacgctggc ggcgtgccta acacatgcaa     60
gtcgaacgaa gcgatttaac ggaagttttc ggatggaagt tgaattgact gagtggcgga    120
cgggtgagta acgcgtgggt aacctgcctt gtactgggga acaacagtta gaaatgactg    180
ctaataccgc ataagcgcac agtattgcat gatacagtgt gaaaaactcc ggtggtacaa    240
gatggacccg cgtctgatta gctagttggt aaggtaacgg cttaccaagg cgacgatcag    300
tagccgacct gagagggtga ccggccacat tgggactgag acacggccnn aactcctacg    360
ggaggcagca gtggggaata ttgcacaatg ggcgaaagcc tgatgcagcg acgccgcgtg    420
agtgaagaag tatttcggta tgtaaagctc tatcagcagg gaagaaaatg acggtacctg    480
actaagaagc cccggctaac tacgtgccag cagccgcggt aatacgtagg gggnnagcgt    540
tatccggatt tactgggtgt aaaggggcgc tagacggtaa agcaagtctg aagtgaaagc    600
ccgcgnctca actgcggnnc tgctttggaa actgtttaac tggagtgtcg gagaggtaag    660
tggaattcct agtgtagcgg tgaaatgcgt agatattagg aggaacacna gtggcgaagg    720
cgacttactg gacgataact gacgttgagg ctcgaaagcg tggggagcaa acaggattag    780
ataccctggt agtccacgcc gtaaacgatg aatactaggt gttggggagc aaagctcttc    840
ggtgccgtcg caaacgcagt aagtattcca cctggggagt acgttcgcaa gaatgaaact    900
caaaggaatt gacggggacc ngcacaagcg gtggagcatg tggtttaatt cgaannaacg    960
cgaagaacct taccaggtct tgacatcgac tcgacggggg agtaacgtcc cnntnccttc   1020
ggggcggaga agacaggtgg tgcatggttg tcgtcagctc gtgtcgtgag atgttgggtt   1080
nagtcccgca acgagcgcaa cccttattct aagtagccag cggttcggcc gggaactctt   1140
gggagactgc cagggataac ctggaggaag tgggggatga cgtcnaatca tcatgcccct   1200
tatgatctgg gctacacacg tgctacaatg gcgtaaacan agagaagcaa gaccgcgagg   1260
tggagcaaat ctcaaaaata acgtctcagt tcggactgca ggctgcaact cgcctgcacg   1320
aagctggaat cgctagtaat cgcgaatcag aatgtcgcgg tgaatacgtt cccgggtctt   1380
gtacacaccg nncgtcacac catggagtc agtaacgccc gaagtcagtg acccaaccgc   1440
aagagggag ctgccgaagg cgggaccgan aacnnggg                            1478

SEQ ID NO: 123        moltype = DNA   length = 1488
FEATURE               Location/Qualifiers
source                1..1488
                      mol_type = genomic DNA
                      note = Erysipelatoclostridium ramosum
                      organism = unidentified
SEQUENCE: 123
agagtttgat cctggctcag gatgaacgct ggcggcgtgc ctaatacatg caagtcgaac     60
gcgagcactt gtgctcgagt ggcgaacggg tgagtaatac ataagtaacc tgccctagac    120
aggggataa ctattggaaa cgatagctaa gaccgacgac gtacggacac tgcatggtga    180
ccgtattaaa agtgcctcaa agcactggta gaggatggac ttatggcgca ttagctggtt    240
ggcggggtaa cggcccacca aggcgacgat gcgtagccga cctgagaggg tgaccggcca    300
cactgggact gagacacggc ccagactcct acggaggca gcagtaggga atttttcggca    360
atggggaaa ccctgaccga gcaacgccgc gtgaaggaag aaggtttttcg gattgtaaac    420
ttctgttata aaggaagaac ggcggtcaca ggaaatgtca gccgagtgac ggtactttat    480
tagaaagcca cggctaacta cgtgccagca gccgcggtaa tacgtaggtg gcaagcgtta    540
tccgaattat tgggcgtaaa gagggagca ggcggcagca agggtctgtg gtgaaagcct    600
gaagcttaac ttcagtaagc catagaaacc aggcagctag agtgcaggag aggatcgtgg    660
aattccatgt gtagcggtga aatgctaga tatatgaaga aacaccagtg gcgaaggcga    720
tgatctggcc tgcaactgac gctcagtccc gaaagcgtgg ggagcaaata ggattagata    780
ccctagtagt ccacgccgta aacgatgagt actaagtgtt ggatgtcaaa gttcagtgct    840
gcagttaacg caataagtac tccgcctgag tagtacgttc gcaagaatga aactcaaagg    900
aattgacggg gccccgcaca agcggtggag catgtggttt aattcgaagc aacgcgaaga    960
accttaccag gtcttgacat actcataaag gctccagaga tggagataga ctatatgag   1020
atacaggtgg tgcatggttg tcgtcagctc gtgtcgtgag atgttgggtt aagtcccgca   1080
acgagcgcaa cccttatcgt tagttaccat cattaagttg gggactctag cgagactgcc   1140
agtgacaagc tggaggaagg cgggatgac gtcaaatcat catgcccctt atgacctggg   1200
ctacacacgt gctacaatgg atggtgcaga gggaagcgaa gccgcgaggt gaagcaaaac   1260
ccataaaacc attctcagtt cggattgtag tctgcaactc gactacatga agttgaatc   1320
gctagtaatc gcgaatcagc atgtcgcggt gaatacgttc tcgggccttg tacacaccg   1380
ccgtcacacc acgagagttg ataacacccg aagccggtgg cctaaccgca aggaaggagc   1440
tgtctaaggt gggattgatg attggggtga agtcgtaaca aggtaacc                1488

SEQ ID NO: 124        moltype = DNA   length = 1528
```

```
FEATURE              Location/Qualifiers
misc_feature         1..1528
                     note = Synthetic Polynucleotide
source               1..1528
                     mol_type = other DNA
                     organism = synthetic construct
SEQUENCE: 124
atgagagttt gatcctggct caggatgaac gctggcggcg tgcctaacac atgcaagtcg    60
aacgaagcaa ttaaaggaag ttttcggatg gaatttgatt gactgagtgg cggacgggtg   120
agtaacgcgt ggataaacctg cctcacactg ggggataaca gttagaaatg actgctaata  180
ccgcataagc gcacagtacc gcatggtacg gtgtgaaaaa ctccggtggt gtgagatgga   240
tccgcgtctg attagccagt tggcggggta acggcccacc aaagcgacga tcagtagccg   300
acctgagagg gtgaccggcc acattgggac tgagacacgg cccaaactcc tacgggaggc   360
agcagtgggg aatattgcac aatgggcgaa agcctgatgc agcgacgccg cgtgagtgaa   420
gaagtatttc ggtatgtaaa gctctatcag cagggaagaa aatgacggta cctgactaag   480
aagcccggc taactacgtg ccagcagccg cggtaatacg tagggggcaa gcgttatccg    540
gattcactgg gtgtaaaggg agcgtagacg gcgaagcaag tctgaagtga aacccaggg    600
ctcaaccctg ggactgcttt ggaaactgtt tgctagagt gtcggagagg taagtggaat    660
tcctagtgta gcggtgaaat gcgtagatat taggaggaac accagtggcg aaggcggctt   720
actgacgat aactgacgtt gaggctcgaa agcgtgggga gcaaacagga ttagataccc    780
tggtagtcca cgccgtaaac gatgaatgct aggtgttggg gggcaaagcc cttcggtgcc   840
gtcgcaaacg cagtaagcat tccacctggg gagtacgttc gcaagaatga aactcaaagg   900
aattgacggg gacccgcaca gcggtggag catgtggttt aattcgaagc aacgcgaaga    960
accttaccaa gtcttgacat cctcttgacc ggcgtgtaac ggcgcttcc cttcgggca   1020
agagagacag gtggtgcatg gttgtcgtca gctcgtgtcg tgagatgttg ggttaagtcc   1080
cgcaacgagc gcaacccctta tccttagtag ccagcagta gagctgggca ctctagggag  1140
actgccaggg ataacctgga ggaaggtggg gatgacgtca aatcatcatg ccccttatga   1200
tttgggctac acacgtgcta caatggcgta aacaaaggga agcaagacag tgatgtggag   1260
caaatcccaa aaataacgtc ccagttcgga ctgtagtctg caacccgact acacgaagct   1320
ggaatcgcta gtaatcgcga atcagaatgt cgcggtgaat acgttcccgg gtcttgtaca   1380
caccgcccgt cacaccatgg gagtcagcaa cgcccgaagt cagtgaccca actcgcaaga   1440
gagggagctg ccgaaggcgg ggcaggtaac tggggtgaag tcgtaacaag gtagccgtat   1500
cggaaggtgc ggctggatca cctcctttt                                    1528

SEQ ID NO: 125       moltype = DNA  length = 1530
FEATURE              Location/Qualifiers
misc_feature         1..1530
                     note = Synthetic Polynucleotide
source               1..1530
                     mol_type = other DNA
                     organism = synthetic construct
SEQUENCE: 125
atgagagttt gatcctggct caggatgaac gctggcggcg tgcctaacac atgcaagtcg    60
aacgaagcaa ttaaaatgaa gttttcggat ggatttttga ttgactgagt ggcggacggg   120
tgagtaacgc gtggataacc tgcctcacac tgggggataa cagttagaaa tgactgctaa   180
taccgcataa gcgcacagta ccgcatggta cggtgtgaaa aactccggtg gtgtgggatg   240
gatccgcgtc tgattagcca gttggcgggg taacggccca ccaaagcgac gatcagtagc   300
cgacctgaga gggtgaccgg ccacattggg actgagacac ggcccaaact cctacgggag   360
gcagcagtgg gaatattgc acaatgggcg aaagcctgat gcagcgacgc cgcgtgagtg   420
aagaagtatt tcggtatgta aagctctatc agcagggaag aaaatgacgg tacctgacta   480
agaagccccg gctaactacg tgccagcagc cgcggtaata cgtaggggc aagcgttatc    540
cggatttact gggtgtaaag ggagcgtaga cggcgaagca agtctgaagt gaaaacccag   600
ggctcaaccc tgggactgct tttggaaact gttttgctaga gtgtcggaga ggtaagtgga   660
attcctagtg tagcggtgaa atgcgtagat attaggagga caccagtggc gaaggcggc    720
ttactggacg ataactgacg ttgaggctcg aaagcgtggg gagcaaacag gattagatac   780
cctggtagtc cacgccgtaa acgatgaatg ctaggtgttg gggggcaaag cccttcggtg   840
ccgtcgcaaa cgcagtaagc attccacctg gggagtacgt tcgcaagaat gaaactcaaa   900
ggaattgacg gggacccgca caagcggtgg agcatgtggt ttaattcgaa gcaacgcgaa   960
gaaccttacc aagtcttgac atcctcttga ccggcgtgta acggcgcctt cccttcggtg  1020
caagagagac aggtggtgca tggttgtcgt cagctcgtgt cgtgagatgt tgggttaagt  1080
cccgcaacga gcgcaaccct tatccttagt agccagcagg taaagctggg cactctaggg  1140
agactgccag gataacctg gaggaaggtg gggatgacgt caaatcatca tgccccttat   1200
gatttgggct acacacgtgc tacaatggcg taaacaaagg gaagcaagac agtgatgtgg   1260
agcaaatccc aaaaataacg tcccagttcg gactgtagtc tgcaacccga ctacacgaag   1320
ctggaatcgc tagtaatcgc gaatcagaat gtcgcggtga atacgttccc gggtcttgta   1380
cacaccgccc gtcacaccat gggagtcagc aacgcccgaa gtcagtgacc caactcgcaa   1440
gagggagc tgccgaaggc ggggcaggta actggggtga agtcgtaaca aggtagccgt   1500
atcggaaggt gcggctggat cacctccttt                                   1530

SEQ ID NO: 126       moltype = DNA  length = 1528
FEATURE              Location/Qualifiers
misc_feature         1..1528
                     note = Synthetic Polynucleotide
source               1..1528
                     mol_type = other DNA
                     organism = synthetic construct
SEQUENCE: 126
atgagagttt gatcctggct caggatgaac gctggcggcg tgcctaacac atgcaagtcg    60
aacgaagcaa ttaaaatgaa gttttcggat ggatttttga ttgactgagt ggcggacggg   120
```

```
tgagtaacgc gtggataacc tgcctcacac tggggataaa cagttagaaa tgactgctaa    180
taccgcataa gcgcacagta ccgcatggta cggtgtgaaa aactccggtg gtgtgagatg    240
gatccgcgtc tgattagcca gttggcgggg taacggccca ccaaagcgac gatcagtagc    300
cgacctgaga gggtgaccgg ccacattggg actgagacac ggcccaaact cctacggag    360
gcagcagtgg ggaatattgc acaatggcg aaagcctgat gcagcgacgc cgcgtgagtg    420
aagaagtatt tcggtatgta aagctctatc agcaggaag aaatgacggt acctgactaa    480
gaagccccgg ctaactacgt gccagcagcc gcggtaatac gtaggggca agcgttatcc    540
ggatttactg ggtgtaaagg gagcgtagac ggcgaagcaa gtctgaagtg aaaacccagg    600
gctcaacccct gggactgctt tggaaactgt tttgctagag tgtcggagag gtaagtggaa    660
ttcctagtgt agcggtgaaa tgcgtagata ttaggaggaa caccagtggc gaaggcggct    720
tactggacga taactgacgt tgaggctcga aagcgtgggg agcaaacagg attagatacc    780
ctggtagtcc acgccgtaaa cgatgaatgc taggtgttgg gggcaaagcc cttcggtgcc    840
gtcgcaaacg cagtaagcat tccacctggg gagtacgttc gcaagaatga aactcaaagg    900
aattgacggg gacccgcaca agcggtggag catgtggttt aattcgaagc aacgcgaaga    960
accttaccaa gtcttgacat cctcttgacc ggcgtgtaac ggcgccttcc cttcgggga   1020
agagagacag gtggtgcatg gttgtcgtca gctcgtgtcg tgagatgttg ggttaagtcc   1080
cgcaacgagc gcaacccta tccttagtag ccagcaggta aagctgggca ctctaggag   1140
actgccaggg ataacctgga ggaaggtggg gatgacgtca aatcatcatc ccccttatga   1200
tttgggctac acacgtgcta caatggcgta aacaaggga agcaagacag tgatgtggag   1260
caaatcccaa aaataacgtc ccagttcgga ctgtagtctg caacccgact acacgaagct   1320
ggaatcgcta gtaatcgcga atcagaatgt cgcggtgaat acgttccgg gtcttgtaca   1380
caccgcccgt cacaccatgg gagtcagcaa cgcccgaagt cagtgaccca actcgcaaga   1440
gagggagctg ccgaaggcgg ggcaggtaac tggggtgaag tcgtaacaag gtagccgtat   1500
cggaaggtgc ggctggatca cctcctttt                                     1528

SEQ ID NO: 127         moltype = DNA  length = 1528
FEATURE                Location/Qualifiers
misc_feature           1..1528
                       note = Synthetic Polynucleotide
source                 1..1528
                       mol_type = other DNA
                       organism = synthetic construct
SEQUENCE: 127
atgagagttt gatcctggct caggatgaac gctggcggcg tgcctaacac atgcaagtcg     60
aacgaagcaa ttaaaatgaa gttttcggat ggattttga ttgactgagt ggcggacggg    120
tgagtaacgc gtggataacc tgcctcacac tggggataaa cagttagaaa tgactgctaa    180
taccgcataa gcgcacagta ccgcatggta cggtgtgaaa aactccggtg gtgtgagatg    240
gatccgcgtc tgattagcca gttggcgggg taacggccca ccaaagcgac gatcagtagc    300
cgacctgaga gggtgaccgg ccacattggg actgagacac ggcccaaact cctacgggag    360
gcagcagtgg ggaatattgc acaatgggcg aaagcctgat gcagcgacgc cgcgtgagtg    420
aagaagtatt tcggtatgta agctctatc agcaggaag aaaatgacgg tacctgacta    480
agaagccccg gctaactacg tgccagcagc cgcggtaata cgtaggggc aagcgttatc    540
cggatttact gggtgtaaag ggagcgtaga cggcgaagca agtctgaagt gaaaacccag    600
ggctcaaccc tgggactgct tggaaactgt ttttgctaga gtgtcggaga ggtaagtgga    660
attcctagtg tagcggtgaa atgcgtagat attaggagga acaccagtgg cgaaggcggc    720
ttactggacg ataactgacg ttgaggctcg aaagcgtggg gagcaaacag gattagatac    780
cctggtagtc cacgccgtaa acgatgaatg ctaggtgttg gggcaaagcc cttcggtgc    840
cgtcgcaaac gcagtaagca ttccacctgg ggagtacgtt cgcaagaatg aaactcaaag    900
gaattgacgg ggacccgcac aagcggtgga gcatgtggtt taattcgaag caacgcgaag    960
aaccttacca agtcttgaca tcctcttgac cggcgtgtaa cggcgccttc ccttcgggc   1020
aggagagaca ggtggtgcat ggttgtcgtc agctcgtgtc gtgagatgtt ggttaagtcc   1080
ccgcaacgag cgcaaccctt atccttagta gccagcaggt agagctgggc actctaggga   1140
gactgccagg gataacctgg aggaaggtgg ggatgacgtc aaatcatcat gccccttatg   1200
atttgggcta cacacgtgct acaatggcgt aaacaaaggg aagcaagaca gtgatgtgga   1260
gcaaatccca aaataacgtc ccagttcgga ctgtagtctg caacccgact acacgaagct   1320
ggaatcgcta gtaatcgcga atcagaatgt cgcggtgaat acgttccgg gtcttgtaca   1380
caccgcccgt cacaccatgg gagtcagcaa cgcccgaagt cagtgaccca actcgcaaga   1440
gagggagctg ccgaaggcgg ggcaggtaac tggggtgaag tcgtaacaag gtagccgtat   1500
cggaaggtgc ggctggatca cctccttt                                     1528

SEQ ID NO: 128         moltype = DNA  length = 1528
FEATURE                Location/Qualifiers
misc_feature           1..1528
                       note = Synthetic Polynucleotide
source                 1..1528
                       mol_type = other DNA
                       organism = synthetic construct
SEQUENCE: 128
atgagagttt gatcctggct caggatgaac gctggcggcg tgcctaacac atgcaagtcg     60
aacgaagcaa ttaaaatgaa gttttcggat ggatttaat tgactgagtg gcggacgggt    120
gagtaacgcg tggataacct gcctcacact ggggataaac agttagaaat gactgctaat    180
accgcataag cgcacagtac cgcatggtac ggtgtgaaaa actccggtgg tgtgagatgg    240
atccgcgtct gattagccag ttggcggggt aacggcccac caaagcgacg atcagtagcc    300
gacctgagag ggtgaccggc cacattggga ctgagacacg gcccaaactc ctacgggagg    360
cagcagtggg gaatattgca caatgggcga aagcctgatg cagcgacgcc gcgtgagtgg    420
agaagtattt cggtatgtaa gctctatcg cagggaaga aaatgacggt acctgactaa    480
gaagccccgg ctaactacgt gccagcagcc gcggtaatac gtaggggca agcgttatcc    540
ggatttactg ggtgtaaagg gagcgtagac ggcgaagcaa gtctgaagtg aaaacccagg    600
gctcaacccct gggactgctt tggaaactgt tttgctagag tgtcggagag gtaagtggaa    660
```

```
ttcctagtgt agcggtgaaa tgcgtagata ttaggaggaa caccagtggc gaaggcggct    720
tactggacga taactgacgt tgaggctcga agcgtgggg agcaaacagg attagatacc    780
ctggtagtcc acgccgtaaa cgatgaatgc taggtgttgg ggggcaaagc ccttcggtgc    840
cgtcgcaaac gcagtaagca ttccacctgg ggagtacgtt cgcaagaatg aaactcaaag    900
gaattgacgg gacccgcac aagcggtgga gcatgtggtt taattcgaag caacgcgaag    960
aaccttacca agtcttgaca tcctcttgac cggcgtgtaa cggcgccttc ccttcggggc   1020
aagagagaca ggtggtgcat ggttgtcgtc agctcgtgtc gtgagatgtt gggttaagtc   1080
ccgcaacgag cgcaacccttt atccttagta gccagcaggt aaagctgggc actctaggga   1140
gactgccagg gataacctgg aggaaggtgg ggatgacgtc aaatcatcat gccccttatg   1200
atttgggcta cacacgtgct acaatggcgt aaacaaaggg aagcaagaca gtgatgtgga   1260
gcaaatccca aaataacgtc ccagttcgga ctgtagtctg caacccgact acacgaagct   1320
ggaatcgcta gtaatcgcga atcagaatgt cgcggtgaat acgttccgg gtcttgtaca   1380
caccgcccgt cacaccatgg gagtcagcaa cgcccgaagt cagtgaccca actcgcaaga   1440
gagggagctg ccgaaggcgg ggcaggtaac tggggtgaag tcgtaacaag gtagccgtat   1500
cggaaggtgc ggctggatca cctcctttt                                     1528

SEQ ID NO: 129            moltype = DNA   length = 1522
FEATURE                   Location/Qualifiers
misc_feature              1..1522
                          note = Synthetic Polynucleotide
source                    1..1522
                          mol_type = other DNA
                          organism = synthetic construct
SEQUENCE: 129
tcaaagagtt tgatcctggc tcaggacgaa cgctggcggc gcgcctaaca catgcaagtc     60
gaacggagct tacgttttga agttttcgga tggatgaatg taagcttagt ggcggacggg    120
tgagtaacac gtgagcaacc tgcctttcag aggggataa cagccggaaa cggctgctaa    180
taccgcatga tgttgcgggg gcacatgccc ctgcaaccaa aggagcaatc cgctgaaaga    240
tgggctcgcg tccgattagc cagttggcgg ggtaacggcc caccaaagcg acgatcggta    300
gccggactga gaggttgaac ggccacattg ggactgagac acggcccaga ctcctacggg    360
aggcagcagt ggggggatatt gcacaatggg cgaaagcctg atgcagcgac gccgcgtgag    420
ggaagacggt cttcggattg taaacctctg tctttgggga agaaaatgac ggtacccaaa    480
gaggaagctc cggctaacta cgtgccagca gccgcggtaa tacgtaggga caagcgttg    540
tccggaatta ctgggtgtaa agggagcgta ggcgggatgg caagtagaat gttaaatcca    600
tcggctcaac cggttggctgc gttctaaact gccgttcttg agtgaagtag aggcaggcgg    660
aattcctagt gtagcggtga aatgcgtaga tattaggagg aacaccagtg gcgaaggcgg    720
cctgctgggc tttaactgac gctgaggctc gaaagcgtgg ggagcaaaca ggattagata    780
ccctggtagt ccacgccgta aacgatgatt actaggtgtg gggggactga ccccttccgt    840
gccgcagtta acacaataag taatccacct ggggagtacg ccgcaaggt tgaaactcaa    900
aggaattgac gggggcccgc acaagcagtg gagtatgtgg tttaattcga gcaacgcga    960
agaaccttac caggtcttga catcggatgc atagcctaga gataggtgaa gcccttcggg   1020
gcatccagac aggtggtgca tggttgtcgt cagctcgtgt cgtgagatgt gggttaagt   1080
cccgcaacga gcgcaaccct tattattagt tgctacgcaa gagcactcta atgagactgcc   1140
cgttgacaaa acgaggaag gtggggatga cgtcaaatca tcatgcccct tatgacctgg   1200
gctacacacg tactacaatg gcactaaaac agagggcggc gacaccgcga ggtgaagcga   1260
atcccgaaaa agtgtctcag ttcagattgc aggctgcaac ccgcctgcat gaagtcgaa   1320
ttgctagtaa tcgcggatca gcatgccgcg gtgaatacgt tcccgggcct tgtacacacc   1380
gcccgtcaca ccatgggagt cggtaacacc cgaagccagt agcctaaccg caaggggggc   1440
gctgtcgaag gtgggattga tgactggggt gaagtcgtaa caaggtagcc gtatcggaag   1500
gtgcggctgg atcacctcct tt                                            1522

SEQ ID NO: 130            moltype = DNA   length = 1521
FEATURE                   Location/Qualifiers
misc_feature              1..1521
                          note = Synthetic Polynucleotide
source                    1..1521
                          mol_type = other DNA
                          organism = synthetic construct
SEQUENCE: 130
tcaaagagtt tgatcctggc tcaggacgaa cgctggcggc gcgcctaaca catgcaagtc     60
gaacggagct tacgttttga agttttcgga tggacgaatg taagcttagt ggcggacggg    120
tgagtaacac gtgagcaacc tgcctttcag agggataac agccgaaac ggctgctaat    180
accgcatgat gttgcggggg cacatgcccc tgcaaccaaa ggagcaatcc gctgaaagat    240
gggctcgcgt ccgattagcc agttggcggg gtaacggccc accaaagcga cgatcgtag    300
ccggactgag aggttgaacg gccacattgg gactgagaca cggcccagac tcctacggga    360
ggcagcagtg ggggatattg cacaatgggc gaaagcctga tgcagcgacg ccgcgtgagg    420
gaagacggtt tcggattgt aaacctctgt ctttgggga gaaaatgacg gtacccaaag    480
aggaagctcc ggctaactac gtgccagcag ccgcggtaat acgtagggga caagcgttgt    540
ccggaattac tgggtgtaaa gggagcgtag gcgggatgag aagtagaatg ttaaatccat    600
cggctcaacc ggtggctgcg ttctaaactg ccgttcttga gtgaagtaga ggcaggcgga    660
attcctagtg tagcggtgaa atgcgtagat attaggagga acaccagtgg cgaaggcggc    720
ctgctgggct taactgacg ctgaggctcg aaagcgtggg gagcaaacag gattagatac    780
cctggtagtc cacgccgtaa acgatgatta ctaggtgtgg ggggactgac cccttccgtg    840
ccgcagttaa cacaataagt aatccacctg gggagtacgc cgcaaggttg aaactcaaa    900
ggaattgacg ggggcccgca caagcagtgg agtatgtggt ttaattcgaa gcaacgcgaa    960
gaaccttacc aggtcttgac atcggatgca tagcctagag ataggtgaag cccttcgggg   1020
catccagaca ggtggtgcat ggttgtcgtc agctcgtgtc gtgagatgtt gggttaagtc   1080
ccgcaacgag cgcaaccctt attattagtt gctacgcaag agcactctaa tgagactgcc   1140
gttgacaaaa cggaggaagg tggggatgac gtcaaatcat catgccccctt atgacctggg   1200
```

```
ctacacacgt actacaatgg cactaaaaca gagggcggcg acaccgcgag gtgaagcgaa   1260
tcccgaaaaa gtgtctcagt tcagattgca ggctgcaacc cgcctgcatg aagtcggaat   1320
tgctagtaat cgcggatcag catgccgcgg tgaatacgtt cccgggcctt gtacacaccg   1380
cccgtcacac catgggagtc ggtaacaccc gaagccagta gcctaaccgc aagggggcg    1440
ctgtcgaagg tgggattgat gactggggtg aagtcgtaac aaggtagccg tatcggaagg   1500
tgcggctgga tcacctcctt t                                              1521
```

SEQ ID NO: 131          moltype = DNA  length = 1522
FEATURE                 Location/Qualifiers
misc_feature            1..1522
                        note = Synthetic Polynucleotide
source                  1..1522
                        mol_type = other DNA
                        organism = synthetic construct
SEQUENCE: 131
```
tcaaagagtt tgatcctggc tcaggacgaa cgctggcggc gcgcctaaca catgcaagtc    60
gaacggagct tacgttttga agttttcgga tggatgaatg taagcttagt ggcggacggg   120
tgagtaacac gtgagcaacc tgcctttcag aggggggataa caccgcgaaa cggctgctaa   180
taccgcatga tgttgcgggg gcacatgccc ctgcaaccaa aggagcaatc cgctgaaaga   240
tgggctcgcg tccgattagc cagttggcgg ggtaacggcc caccaaagcg acgatcggta   300
gccggactga gaggttgaac ggccacattg gactgagaca cggcccaga ctcctacggg    360
aggcagcagt ggggggatatt gcacaatggg cgaaagcctg atgcagcgac gccgcgtgag   420
ggaagacggt cttcggattg taaaccctctg tctttgggga agaaaatgac ggtacccaaa   480
gaggaagctc cggctaacta cgtgccagca gccgcggtaa tacgtaggga gcaagcgttg   540
tccggaatta ctgggtgtaa agggagcgta ggcgggatgg caagtagaat gttaaatcca   600
tcggctcaac cggttggctgc gttctaaact gccgttcttg agtgaagtag aggcaggcga   660
aattcctagt gtagcggtga aatgcgtaga tattaggagg aacaccagtg gcgaaggcgg   720
cctgctgggc tttaactgac gctgaggctc gaaagcgtgg ggagcaaaca ggattagata   780
ccctggtagt ccacgccgta aacgatgatt actaggtgtg gggggactga ccccttccgt   840
gccgcagtta acacaataag taatccacct ggggagtacg ccgcaaggt tgaaactcaa    900
aggaattgac ggggccccgc acaagcagtg gagtatgtgg tttaattcga agcaacgcga   960
agaaccttac caggtcttga catcggatgc atagcctaga gataggtgaa gcccttcggg   1020
gcatccgac aggtggtgca tggttgtcgt cagctcgtgt cgtgagatgt tgggttaagt    1080
cccgcaacga gcgcaaccct tattattagt tgctacgcaa gagcactcta atgagactcg   1140
cgttgacaaa acggaggaag gtggggatga cgtcaaatca tcatgcccct tatgacctgg   1200
gctacacacg tactacaatg gcactaaaac agagggcggc gacaccgcga ggtgaagcga   1260
atcccgaaaa agtgtctcag ttcagattgc aggctgcaac cgcctgcat gaagtcggaa    1320
ttgctagtaa tcgcggatca gcatgccgcg gtgaatacgt tcccgggcct tgtacacacc   1380
gcccgtcaca ccatgggagt cggtaacacc cgaagccagt agcctaaccg caaggggggc   1440
gctgtcgaag gtgggattga tgactggggt gaagtcgtaa caaggtagcc gtatcggaag   1500
gtgcggctgg atcacctcct tt                                             1522
```

SEQ ID NO: 132          moltype = DNA  length = 1529
FEATURE                 Location/Qualifiers
misc_feature            1..1529
                        note = Synthetic Polynucleotide
source                  1..1529
                        mol_type = other DNA
                        organism = synthetic construct
SEQUENCE: 132
```
tacgagagtt tgatcctggc tcaggatgaa cgctggcggc gtgcctaaca catgcaagtc    60
gagcgaagcg ctgttttcag aatcttcgga ggaagaggac agtgactgag cggcggacgg   120
gtgagtaacg cgtgggcaac ctgcctcata caggggata acagttagaa atgactgcta    180
ataccgcata agcgcacagg accgcatggt gtagtgtgaa aaactccggt ggtatgagat   240
ggaccgcgcgt ctgattaggt agttggtggg gtaaaggcct accaagccga cgatcagtag   300
ccgacctgag agggtgaccg gccacattgg gactgagaca cggcccaaac tcctacggga   360
ggcagcagtg gggaatattg cacaatgggg gaaaccctga tgcagcgacg ccgcgtgaag   420
gaagaagtat tcggtatgt aaacttctat cagcagggaa gaaaatgacg gtacctgagt     480
aagaagcacc ggctaaatac gtgccagcag ccgcggtaat acgtatggtg caagcgttat   540
ccggatttac tgggtgtaaa gggagcgtag acggatagc aagtctggag tgaaaaccca    600
gggctcaacc ctgggactgc tttgaaact gcagatctgg agtgccggag aggtaagcgg    660
aattcctagt gtagcggtga aatgcgtaga tattaggagg aacaccagtg gcgaaggcgg   720
cttactggac ggtgactgac gttgaggctc gaaagcgtgg ggagcaaaca ggattagata   780
ccctggtagt ccacgccgta aacgatgact actaggtgtc ggtgtgcaaa gcacatcggt   840
gccgcagcaa acgcaataag tagtccacct ggggagtacg ttcgcaagaa tgaaactcaa   900
aggaattgac ggggacccgc acaagcggtg gagcatgtgg tttaattcga agcaacgcga   960
agaaccttac ctggtcttga catccggatg acgggcgagt aatgtcgccg tcccttcggg   1020
gcgtccgaga caggtggtgc atggttgtcg tcagctcgtg tcgtgagatg ttgggttaag   1080
tcccgcaacg agcgcaaccc ttatcttcag tagccagcat ataaggtggc cactctggag   1140
agactgccag ggagaacctg gaggaaggtg gggatgacgt caaatcatca tgccccttat   1200
ggccagggct acacacgtgc tacaatgcgt aaacaaagg gaagcgagag ggtgacctgg    1260
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc caaccttaga   1440
ggagggagct gtccaaggcg gacggataaa ctggggtgaa gtcgtaacaa ggtagccgta   1500
tcggaaggtg cggctggatc acctcctt                                       1529
```

SEQ ID NO: 133          moltype = DNA  length = 1529
FEATURE                 Location/Qualifiers

```
misc_feature           1..1529
                       note = Synthetic Polynucleotide
source                 1..1529
                       mol_type = other DNA
                       organism = synthetic construct
SEQUENCE: 133
tacgagagtt tgatcctggc tcaggatgaa cgctggcggc gtgcctaaca catgcaagtc    60
gagcgaagcg ctgttttcag aatcttcgga ggaagaggac agtgactgag cggcggacgg   120
gtgagtaacg cgtgggcaac ctgcctcata caggggata acagttagaa atgactgcta    180
ataccgcata agcgcacagg accgcatggt gtagtgtgaa aaactccggt ggtatgagat   240
ggacccgcgt ctgattaggt agttggtggg gtaaaggcct accaagccga cgatcagtag   300
ccgacctgag agggtgaccg gccacattgg gactgagaca cggcccaaac tcctacggga   360
ggcagcagtg gggaatattg cacaatgggg gaaaccctga tgcagcgacg ccgcgtgaag   420
gaagaagtat ttcggtatgt aaacttctat cagcagggaa gaagatgacg gtacctgagt   480
aagaagcacc ggctaaatac gtgccagcag ccgcggtaat acgtatggtg caagcgttat   540
ccggatttac tgggtgtaaa gggagcgtag acggataggc aagtctggag tgaaaaccca   600
gggctcaacc ctgggactgc tttggaaact gcagatctgg agtgccggag aggtaagcgg   660
aattcctagt gtagcggtga atgcgtaga tattaggagg aacaccagtg gcgaaggcgg   720
cttactggac ggtgactgac gttgaggctc gaaagcgtgg ggagcaaaca ggattagata   780
ccctggtagt ccacgccgta aacgatgact actaggtgtc ggtgtgcaaa gcacatcggt   840
gccgcagcaa acgcaataag tagtccacct ggggagtacg ttcgcaagaa tgaaactcaa   900
aggaattgac ggggacccgc acaagcggtg gagcatgtgg tttaattcga gcaacgcga    960
agaaccttac ctggtcttga catccggatg acgggcgagt aatgtcgccg tcccttcggg  1020
gcatccgaga caggtggtgc atggttgtcg tcagctcgtg tcgtgagatg ttgggttaag  1080
tcccgcaacg agcgcaaccc ttatcttcag tagccagcat ataaggtggg cactctggag  1140
agactgccag ggagaacctg gaggaaggtg gggatgacgt caaatcatca tgccccttat  1200
ggccagggct acacacgtgc tacaatggcg taaacaaagg gaagcgagag ggtgacctga  1260
agcgaatccc aaaaataacg tctcagttcg gattgtagtc tgcaactcga ctacatgaag  1320
ctggaatcgc tagtaatcgc ggatcagcat gccgcggtga atacgttccc gggtcttgta  1380
cacaccgccc gtcacaccat gggagtcagt aacgcccgaa gccagtgacc aaccttaga   1440
ggagggagct gtcgaaggcg ggacggataa ctggggtgaa gtcgtaacaa ggtagccgta  1500
tcggaaggtg cggctggatc acctcctttt                                   1529

SEQ ID NO: 134         moltype = DNA  length = 1529
FEATURE                Location/Qualifiers
misc_feature           1..1529
                       note = Synthetic Polynucleotide
source                 1..1529
                       mol_type = other DNA
                       organism = synthetic construct
SEQUENCE: 134
tacgagagtt tgatcctggc tcaggatgaa cgctggcggc gtgcctaaca catgcaagtc    60
gagcgaagcg ctgttttcag aatcttcgga ggaagaggac agtgactgag cggcggacgg   120
gtgagtaacg cgtgggcaac ctgcctcata caggggata acagttagaa atgactgcta    180
ataccgcata agcgcacagg accgcatggt gtagtgtgaa aaactccggt ggtatgagat   240
ggacccgcgt ctgattaggt agttggtggg gtaaaggcct accaagccga cgatcagtag   300
ccgacctgag agggtgaccg gccacattgg gactgagaca cggcccaaac tcctacggga   360
ggcagcagtg gggaatattg cacaatgggg gaaaccctga tgcagcgacg ccgcgtgaag   420
gaagaagtat ttcggtatgt aaacttctat cagcagggaa gaagatgacg gtacctgagt   480
aagaagcacc ggctaaatac gtgccagcag ccgcggtaat acgtatggtg caagcgttat   540
ccggatttac tgggtgtaaa gggagcgtag acggataggc aagtctggag tgaaaaccca   600
gggctcaacc ctgggactgc tttggaaact gcagatctgg agtgccggag aggtaagcgg   660
aattcctagt gtagcggtga atgcgtaga tattaggagg aacaccagtg gcgaaggcgg   720
cttactggac ggtgactgac gttgaggctc gaaagcgtgg ggagcaaaca ggattagata   780
ccctggtagt ccacgccgta aacgatgact actaggtgtc ggtgtgcaaa gcacatcggt   840
gccgcagcaa acgcaataag tagtccacct ggggagtacg ttcgcaagaa tgaaactcaa   900
aggaattgac ggggacccgc acaagcggtg gagcatgtgg tttaattcga gcaacgcga    960
agaaccttac ctggtcttga catccggatg acgggcgagt aatgtcgccg tcccttcggg  1020
gcatccgaga caggtggtgc atggttgtcg tcagctcgtg tcgtgagatg ttgggttaag  1080
tcccgcaacg agcgcaaccc ttatcttcag tagccagcat ataaggtggg cactctggag  1140
agactgccag ggagaacctg gaggaaggtg gggatgacgt caaatcatca tgccccttat  1200
ggccagggct acacacgtgc tacaatgcg taaacaaagg gaagcgagag ggtgacctgg   1260
agcgaatccc aaaaataacg tctcagttcg gattgtagtc tgcaactcga ctacatgaag  1320
ctggaatcgc tagtaatcgc ggatcagcat gccgcggtga atacgttccc gggtcttgta  1380
cacaccgccc gtcacaccat gggagtcagt aacgcccgaa gccagtgacc aaccttaga   1440
ggagggagct gtcgaaggcg ggacggataa ctggggtgaa gtcgtaacaa ggtagccgta  1500
tcggaaggtg cggctggatc acctcctttt                                   1529

SEQ ID NO: 135         moltype = DNA  length = 1529
FEATURE                Location/Qualifiers
misc_feature           1..1529
                       note = Synthetic Polynucleotide
source                 1..1529
                       mol_type = other DNA
                       organism = synthetic construct
SEQUENCE: 135
tacgagagtt tgatcctggc tcaggatgaa cgctggcggc gtgcctaaca catgcaagtc    60
gagcgaagcg ctgttttcag aatcttcgga ggaagaggac agtgactgag cggcggacgg   120
gtgagtaacg cgtgggcaac ctgcctcata caggggata acagttagaa atgactgcta    180
```

```
ataccgcata agcgcacagg accgcatggt gtagtgtgaa aaactccggt ggtatgagat    240
ggacccgcgt ctgattaggt agttggtggg gtaaaggcct accaagccga cgatcagtag    300
ccgacctgag agggtgaccg gccacattgg gactgagaca cggcccaaac tcctacggga    360
ggcagcagtg gggaatattg cacaatgggg gaaaccctga tgcagcgacg ccgcgtgaag    420
gaagaagtat ttcggtatgt aaacttctat cagcagggaa gaagatgacg gtacctgagt    480
aagaagcacc ggctaaatac gtgccagcag ccgcggtaat acgtatggtg caagcgttat    540
ccggatttac tgggtgtaaa gggagcgtag acggataggc aagtctggag tgaaaaccca    600
gggctcaacc ctgggactgc tttggaaact gcagatctgg agtgccggag aggtaagcgg    660
aattcctagt gtagcggtga aatgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcggt    840
gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcatccgaga caggtggtgc atggttgtcg tcagctcgtg tcgtgagatg ttgggttaag   1080
tcccgcaacg agcgcaaccc ttatcttcag tagccagcat ataaggtggg cactctggag   1140
agactgccag ggagaacctg gaggaaggtg gggatgacgt caaatcatca tgccccttat   1200
ggccagggct acacacgtgc tacaatggcg taaacaaagg gaagcgagag ggtgacctga   1260
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc aaccttaga    1440
ggagggagct gtcgaaggcg ggacggataa ctggggtgaa gtcgtaacaa ggtagccgta    1500
tcggaaggtg cggctggatc acctcctttt                                    1529

SEQ ID NO: 136             moltype = DNA  length = 1529
FEATURE                    Location/Qualifiers
misc_feature               1..1529
                           note = Synthetic Polynucleotide
source                     1..1529
                           mol_type = other DNA
                           organism = synthetic construct
SEQUENCE: 136
tacgagagtt tgatcctggc tcaggatgaa cgctggcggc gtgcctaaca catgcaagtc     60
gagcgaagcg ctgttttcag aatcttcgga ggaagaggac agtgactgag cggcggacgg    120
gtgagtaacg cgtgggcaac ctgcctcata caggggdata acagttagaa atgactgcta    180
ataccgcata agcgcacagg accgcatggt gtagtgtgaa aaactccggt ggtatgagat    240
ggacccgcgt ctgattaggt agttggtggg gtaaaggcct accaagccga cgatcagtag    300
ccgacctgag agggtgaccg gccacattgg gactgagaca cggcccaaac tcctacggga    360
ggcagcagtg gggaatattg cacaatgggg gaaaccctga tgcagcgacg ccgcgtgaag    420
gaagaagtat ttcggtatgt aaacttctat cagcagggaa gaagatgacg gtacctgagt    480
aagaagcacc ggctaaatac gtgccagcag ccgcggtaat acgtatggtg caagcgttat    540
ccggatttac tgggtgtaaa gggagcgtag acggataggc aagtctggag tgaaaaccca    600
gggctcaacc ctgggactgc tttggaaact gcagatctgg agtgccggag aggtaagcgg    660
aattcctagt gtagcggtga aatgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcggt    840
gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcatccgaga caggtggtgc atggttgtcg tcagctcgtg tcgtgagatg ttgggttaag   1080
tcccgcaacg agcgcaaccc ttatcttcag tagccagcat ataaggtggg cactctggag   1140
agactgccag ggagaacctg gaggaaggtg gggatgacgt caaatcatca tgccccttat   1200
ggccagggct acacacgtgc tacaatggcg taaacaaagg gaagcgagag ggtgacctga   1260
agcgaatccc aaaaataacg tctcagttcg gattgtagtc tgcaactcga ctacatgaag   1320
ctggaatcgc tagtaatcgc ggatcagcat gccgcggtga atacgttccc gggtcttgta   1380
cacaccgccc gtcacaccat gggagtcagt aacgcccgaa gccagtgacc aaccttaga    1440
ggagggagct gtcgaaggcg ggacggataa ctggggtgaa gtcgtaacaa ggtagccgta    1500
tcggaaggtg cggctggatc acctcctttt                                    1529

SEQ ID NO: 137             moltype = DNA  length = 1527
FEATURE                    Location/Qualifiers
misc_feature               1..1527
                           note = Synthetic Polynucleotide
source                     1..1527
                           mol_type = other DNA
                           organism = synthetic construct
SEQUENCE: 137
atgagagttt gatcctagct caggatgaac gctggcggcg tgcctaacac atgcaagtcg     60
aacgaagcaa tttaacgaa gttttcggat ggaagttgaa ttgactgagt ggcggacggg    120
tgagtaacgc gtgggtaacc tgccttgtac tggggdacaa cagttagaaa tgactgctaa    180
taccgcataa gcgcacagta tcgcatgata cagtgtgaaa aactccggtg tacaagatg    240
gacccgcgtc tgattagcta gttggtaagg taacggctta ccaaggcgac gatcagtagc    300
cgacctgaga gggtgaccgg ccacattggg actgagacac ggcccaaact cctacggagg    360
gcagcagtgg ggaatattgc acaatgggcg aaagcctgat gcagcgacgc cgcgtgagtg    420
aagaagtatt tcggtatgta aagctctatc agcagggaag aaaatgacgg tacctgacta    480
agaagccccg gctaactacg tgccagcagc cgcggtaata cgtaggggc aagcgttatc    540
cggatttact gggtgtaaag ggagcgtaga cggtaaagca agtctgaagt gaaagcccgc    600
ggctcaactg cgggactgct ttggaaactg tttaactgga gtcggagag gtaagtgga    660
attcctagtg tagcggtgaa atgcgtagat attaggagga acaccagtgg cgaaggcgac    720
```

```
ttactggacg ataactgacg ttgaggctcg aaagcgtggg gagcaaacag gattagatac   780
cctggtagtc cacgccgtaa acgatgaata ctaggtgttg gggagcaaag ctcttcggtg   840
ccgtcgcaaa cgcagtaagt attccacctg gggagtacgt tcgcaagaat gaaactcaaa   900
ggaattgacg gggacccgca caagcggtgg agcatgtggt ttaattcgaa gcaacgcgaa   960
gaaccttacc aggtcttgac atcgatccga cggggagta acgtcccctt ccctttcgggg  1020
cggagaagac aggtggtgca tggttgtcgt cagctcgtgt cgtgagatgt tgggttaagt  1080
cccgcaacga gcgcaaccct tattctaagt agccagcggt tcggccggga actcttggga  1140
gactgccagg gataacctgg aggaaggtgg ggatgacgtc aaatcatcat gccccttatg  1200
atctgggcta cacacgtgct acaatggcgt aaacaaagag aagcaagacc gcgaggtgga  1260
gcaaatctca aaaataacgt ctcagttcgg actgcaggct gcaactcgcc tgcacgaagc  1320
tggaatcgct agtaatcgcg aatcagaatg tcgcggtgaa tacgttcccg ggtcttgtac  1380
acaccgcccg tcacaccatg ggagtcagta acgcccgaag tcagtgaccc aaccgcaagg  1440
agggagctgc cgaaggcggg accgataact ggggtgaagt cgtaacaagg tagccgtatc  1500
ggaaggtgcg gctggatcac ctccttt                                     1527

SEQ ID NO: 138         moltype = DNA  length = 1527
FEATURE                Location/Qualifiers
misc_feature           1..1527
                       note = Synthetic Polynucleotide
source                 1..1527
                       mol_type = other DNA
                       organism = synthetic construct
SEQUENCE: 138
atgagagttt gatcctggct caggatgaac gctggcggcg tgcctaacac atgcaagtcg   60
aacgaagcga tttaacggaa attttcggat ggaagttgaa ttgactgagt ggcggacggg  120
tgagtaacgc gtgggtaacc tgccttgtac tggggacaa cagttagaaa tgactgctaa  180
taccgcataa gcgcacagta tcgcatgata cagtgtgaaa aactccggtg gtacaagatg  240
gacccgcgtc tgattagcta gttggtaagg taacggctta ccaaggcgac gatcagtagc  300
cgacctgaga gggtgaccgg ccacattggg actgagacac ggcccaaact cctacgggag  360
gcagcagtgg ggaatattgc acaatgggcg aaagcctgat gcagcgacgc cgcgtgagtg  420
aagaagtatt tcggtatgta aagctctatc agcaggaag aaaatgacgg tacctgacta  480
agaagccccg gctaactacg tgccagcagc cgcggtaata cgtaggggc aagcgttatc  540
cggatttact gggtgtaaag ggagcgtaga cggtaaagca agtctgaagt gaaagcccgc  600
ggctcaactg cgggactgct ttgaaactg tttaactgga gtgtcggaga ggtaagtgga  660
attcctagtg tagcggtgaa atgcgtagat attaggagga acaccagtgg cgaaggcgac  720
ttactggacg ataactgacg ttgaggctcg aaagcgtggg gagcaaacag gattagatac  780
cctggtagtc cacgccgtaa acgatgaata ctaggtgttg gggagcaaag ctcttcggtg  840
ccgtcgcaaa cgcagtaagt attccacctg gggagtacgt tcgcaagaat gaaactcaaa  900
ggaattgacg gggacccgca caagcggtgg agcatgtggt ttaattcgaa gcaacgcgaa  960
gaaccttacc aggtcttgac atcgatccga cggggagta acgtcccctt ccctttcgggg 1020
cggagaagac aggtggtgca tggttgtcgt cagctcgtgt cgtgagatgt tgggttaagt 1080
cccgcaacga gcgcaaccct tattctaagt agccagcggt tcggccggga actcttggga 1140
gactgccagg gataacctgg aggaaggtgg ggatgacgtc aaatcatcat gccccttatg 1200
atctgggcta cacacgtgct acaatggcgt aaacaaagag aagcaagacc gcgaggtgga 1260
gcaaatctca aaaataacgt ctcagttcgg actgcaggct gcaactcgcc tgcacgaagc 1320
tggaatcgct agtaatcgcg aatcagaatg tcgcggtgaa tacgttcccg ggtcttgtac 1380
acaccgcccg tcacaccatg ggagtcagta acgcccgaag tcagtgaccc aaccgcaagg 1440
agggagctgc cgaaggcggg accgataact ggggtgaagt cgtaacaagg tagccgtatc 1500
ggaaggtgcg gctggatcac ctccttt                                    1527

SEQ ID NO: 139         moltype = DNA  length = 1527
FEATURE                Location/Qualifiers
misc_feature           1..1527
                       note = Synthetic Polynucleotide
source                 1..1527
                       mol_type = other DNA
                       organism = synthetic construct
SEQUENCE: 139
atgagagttt gatcctggct caggatgaac gctggcggcg tgcctaacac atgcaagtcg   60
aacgaagcga tttaacggaa gttttcggat ggaagttgaa ttgactgagt ggcggacggg  120
tgagtaacgc gtgggtaacc tgccttgtac tggggacaa cagttagaaa tgactgctaa  180
taccgcataa gcgcacagta tcgcatgata cagtgtgaaa aactccggtg gtacaagatg  240
gacccgcgtc tgattagcta gttggtaagg taacggctta ccaaggcgac gatcagtagc  300
cgacctgaga gggtgaccgg ccacattggg actgagacac ggcccaaact cctacgggag  360
gcagcagtgg ggaatattgc acaatgggcg aaagcctgat gcagcgacgc cgcgtgagtg  420
aagaagtatt tcggtatgta aagctctatc agcaggaag aaaatgacgg tacctgacta  480
agaagccccg gctaactacg tgccagcagc cgcggtaata cgtaggggc aagcgttatc  540
cggatttact gggtgtaaag ggagcgtaga cggtaaagca agtctgaagt gaaagcccgc  600
ggctcaactg cgggactgct ttgaaactg tttaactgga gtgtcggaga ggtaagtgga  660
attcctagtg tagcggtgaa atgcgtagat attaggagga acaccagtgg cgaaggcgac  720
ttactggacg ataactgacg ttgaggctcg aaagcgtggg gagcaaacag gattagatac  780
cctggtagtc cacgccgtaa acgatgaata ctaggtgttg gggagcaaag ctcttcggtg  840
ccgtcgcaaa cgcagtaagt attccacctg gggagtacgt tcgcaagaat gaaactcaaa  900
ggaattgacg gggacccgca caagcggtgg agcatgtggt ttaattcgaa gcaacgcgaa  960
gaaccttacc aggtcttgac atcgatccga cggggagta acgtcccctt ccctttcgggg 1020
cggagaagac aggtggtgca tggttgtcgt cagctcgtgt cgtgagatgt tgggttaagt 1080
cccgcaacga gcgcaaccct tattctaagt agccagcggt tcggccggga actcttggga 1140
gactgccagg gataacctgg aggaaggtgg ggatgacgtc aaatcatcat gccccttatg 1200
atctgggcta cacacgtgct acaatggcgt aaacaaagag aagcaagacc gcgaggtgga 1260
```

```
gcaaatctca aaaataacgt ctcagttcgg actgcaggct gcaactcgcc tgcacgaagc  1320
tggaatcgct agtaatcgcg aatcagaatg tcgcggtgaa tacgttcccg ggtcttgtac  1380
acaccgcccg tcacaccatg ggagtcagta acgcccgaag tcagtgaccc aaccgcaagg  1440
agggagctgc cgaaggcggg accgataact gggggtgaagt cgtaacaagg tagccgtatc  1500
ggaaggtgcg gctggatcac ctccttt                                       1527

SEQ ID NO: 140         moltype = DNA   length = 1527
FEATURE                Location/Qualifiers
misc_feature           1..1527
                       note = Synthetic Polynucleotide
source                 1..1527
                       mol_type = other DNA
                       organism = synthetic construct
SEQUENCE: 140
atgagagttt gatcctggct caggatgaac gctggcggcg tgcctaacac atgcaagtcg  60
aacgaagcga tttaacggaa gttttcggat ggaagttgga ttgactgagt ggcggacggg  120
tgagtaacgc gtgggtaacc tgccttgtac tgggggacaa cagttagaaa tgactgctaa  180
taccgcataa gcgcacagta tcgcatgata cagtgtgaaa aactccggtg gtacaagatg  240
gacccgcgtc tgattagcta gttggtaagg taacggctta ccaaggcgac gatcagtagc  300
cgacctgaga gggtgaccgg ccacattggg actgagacac ggcccaaact cctacgggag  360
gcagcagtgg ggaatattgc acaatgggcg aaagcctgat gcagcgacgc cgcgtgagtg  420
aagaagtatt tcggtatgta aagctctatc agcagggaga agaaatgacg tacctgacta  480
agaagcgccg gctaactacg tgccagcagc cgcggtaata cgtaggggc aagcgttatc  540
cggatttact gggtgtaaag ggagcgtaga cggtaaagca agtctgaagt gaaagcccgc  600
ggctcaactg cgggactgct ttggaaactg tttaactgga gtgtcggaga ggtaagtgga  660
attcctagtg tagcggtgaa atgcgtagat attaggagga acaccagtgg cgaaggcgac  720
ttactggacg ataactgacg ttgaggctcg aaagcgtggg gagcaaacag gattagatac  780
cctggtagtc cacgccgtaa acgatgaata ctaggtgttg gggagcaaag ctcttcggtg  840
ccgtcgcaaa gcagtaagt attccacctg gggagtacgt tcgcaagaat gaaactcaaa  900
ggaattgacg gggacccgca caagcggtgg agcatgtggt ttaattcgaa gcaacgcgaa  960
gaaccttacc aggtcttgac atcgatccga cggggagta acgtcccctt ccctttcggg  1020
cggagaagac aggtggtgca tggttgtcgt cagctcgtgt cgtgagatgt tgggttaagt  1080
cccgcaacga gcgcaaccct tattctaagt agccagcggt tcggccggga actcttggga  1140
gactgccagg gataacctgg aggaaggtgg ggatgacgtc aaatcatcat gccccttatg  1200
atctgggcta cacacgtgct acaatggcgt aaacaaagag aagcaagacc gcgaggtgca  1260
gcaaatctca aaaataacgt ctcagttcgg actgcaggct gcaactcgcc tgcacgaagc  1320
tggaatcgct agtaatcgcg aatcagaatg tcgcggtgaa tacgttcccg ggtcttgtac  1380
acaccgcccg tcacaccatg ggagtcagta acgcccgaag tcagtgaccc aaccgcaagg  1440
agggagctgc cgaaggcggg accgataact gggggtgaagt cgtaacaagg tagccgtatc  1500
ggaaggtgcg gctggatcac ctccttt                                       1527

SEQ ID NO: 141         moltype = DNA   length = 1531
FEATURE                Location/Qualifiers
misc_feature           1..1531
                       note = Synthetic Polynucleotide
source                 1..1531
                       mol_type = other DNA
                       organism = synthetic construct
SEQUENCE: 141
atcagagagt ttgatcctgg ctcaggatga acgctggcgg cgtgcttaac acatgcaagt  60
cgagcgaagc acttaagtgg atctcttcgg attgaaactt atttgactga gcggcggacg  120
ggtgagtaac gcgtgggtaa cctgcctcat acagggggat aacagttaga aatgctgct  180
aataccgcat aagcgcacag gaccgcatgt tctggtgtga aaaactccgg tggtatgaga  240
tggacccgcg tctgattagc tagttggagg ggtaacggcc caccaaggcg acgatcagta  300
gccggcctga gagggtgaac ggccacattg gactgagaca cggcccaga ctcctacggg  360
aggcagcagt ggggaatatt gcacaatggg ggaaaccctg atgcagcgac gccgcgtgaa  420
ggaagaagta tctcggtatg taaacttcta tcagcaggga agaaaatgac ggtacctgac  480
taagaagccc cggctaacta cgtgccagca gccgcggtaa tacgtagggg gcaagcgtta  540
tccggattta ctgggtgtaa agggagcgta gacggaagag caagtctgat gtgaaaggct  600
ggggcttaac cccaggactg cattggaaac tgttttccta gagtgccgga gaggtaagcg  660
gaattcctag tgtagcggtg aaatgcgtag atattaggag gaacaccagt ggcgaaggcg  720
gcttactgga cggtaactga cgttgaggct cgaaagcgtg gggagcaaac aggattagat  780
accctggtag tccacgccgt aaacgatgaa tactaggtgt cgggtggcaa agccattcgg  840
tgccgcagca aacgcaataa gtattccacc tggggagtac gttcgcaaga tgaaactca  900
aaggaattga cggggacccg cacaagcggt ggagcatgtg gtttaattcg aagcaacgcg  960
aagaacctta ccaagtcttg acatccctct gaccggcccg taacgggcc ttcccttcgg  1020
ggcagaggag acaggtggtg catggttgtc gtcagctcgt gtcgtgagat gttgggttaa  1080
gtcccgcaac gagcgcaacc cctatcctta gtagccagca ggtgaagctg ggcactcgta  1140
ggagactgcc ggggataacc cggaggaagg cggggacgac gtcaaatcat catgcccctt  1200
atgatttggg ctacacacgt gctacaatgg cgtaaacaaa gggaagcgag acagcgatgt  1260
tgagcaaatc ccaaaaataa cgtcccagtt cggactgcag tctgcaactc gactgcacga  1320
agctggaatc gctagtaatc gcgaatcaga atgtcgcggt gaatacgttc ccgggtcttg  1380
tacacaccgc ccgtcacacc atgggagtca gtaacgcccg aagtcagtga cccaacctttt  1440
taggagggag ctgccgaagg cgggaccgat aactggggtg aagtcgtaac aaggtagccg  1500
tatcggaagg tgcggctgga tcacctcctt t                                  1531

SEQ ID NO: 142         moltype = DNA   length = 1531
FEATURE                Location/Qualifiers
```

| misc_feature | 1..1531 |
| | note = Synthetic Polynucleotide |
| source | 1..1531 |
| | mol_type = other DNA |
| | organism = synthetic construct |

SEQUENCE: 142

```
atcagagagt tgatcctgg ctcaggatga acgctggcgg cgtgcttaac acatgcaagt   60
cgagcgaagc acttaagtgg atctcttcgg attgaaactt atttgactga gcggcggacg  120
ggtgagtaac gcgtgggtaa cctgcctcat acaggggat  aacagttaga aatggctgct  180
aataccgcat aagcgcacag gaccgcatgg tctggtgtga aaaactccgg tggtatgaga  240
tggacccgcg tctgattagc tagttggagg ggtaacggcc caccaaggcg acgatcagta  300
gccggcctga gagggtgaac ggccacattg gactgagac  acgggccaga ctcctacggg  360
aggcagcagt ggggaatatt gcacaatggg ggaaaccctg atgcagcgac gccgcgtgaa  420
ggaagaagta tctcggtatg taaacttcta tcagcaggga agaaaatgac ggtacctgac  480
taagaagccc cggctaacta cgtgccagca gccgcggtaa tacgtagggg gcaagcgtta  540
tccggattta ctgggtgtaa agggagcgta gacggaagag caagtctgat gtgaaaggct  600
ggggcttaac cccaggactg cattggaaac tgttttcta  gagtgccgga gaggtaagtg  660
gaattcctag tgtagcggtg aaatgcgtag atattaggag gaacaccagt ggcgaaggcg  720
gcttactgga cggtaactga cgttgaggct cgaaagcgtg gggagcaaac aggattagat  780
accctggtag tccacgccgt aaacgatgaa tactaggtgt cgggtggcaa agccattcgg  840
tgccgcagca aacgcaataa gtattccacc tggggagtac gttcgcaaga atgaaactca  900
aaggaattga cggggaccccg cacaagcggt ggagcatgtg gtttaattcg aagcaacgcg  960
aagaaccta  ccaagtcttg acatccctct gaccggcccg taacgggcc  ttcccttcgg 1020
ggcagaggag acaggtggtg catggttgtc gtcagctcgt gtcgtgagat gttgggttaa 1080
gtcccgcaac gagcgcaacc cctatcctta gtagccagca ggtgaagctg gcactctag  1140
ggagactgcc ggggataacc cggaggaagg cggggacgac gtcaaatcat catgcccctt 1200
atgatttggg ctacacacgt gctacaatgg cgtaaacaaa gggaagcggg acagcgatgt 1260
tgagcaaatc ccaaaaataa cgtcccagtt cggactgcag tctgcaactc gactgcacga 1320
agctggaatc gctagtaatc gcgaatcaga atgtcgcggt gaatacgttc ccgggtcttg 1380
tacacaccgc ccgtcacacc atgggagtca gtaacgcccg aagtcagtga cccaaccta  1440
caggaggag  ctgccgaagg cgggaccgat aactggggtg aagtcgtaac aaggtagccg 1500
tatcggaagg tgcggctgga tcacctcctt t                                1531
```

| SEQ ID NO: 143 | moltype = DNA length = 1531 |
| FEATURE | Location/Qualifiers |
| misc_feature | 1..1531 |
| | note = Synthetic Polynucleotide |
| source | 1..1531 |
| | mol_type = other DNA |
| | organism = synthetic construct |

SEQUENCE: 143

```
atcagagagt tgatcctgg ctcaggatga acgctggcgg cgtgcttaac acatgcaagt   60
cgagcgaagc acttaagtgg atctcttcgg attgaagctt atttgactga gcggcggacg  120
ggtgagtaac gcgtgggtaa cctgcctcat acaggggat  aacagttaga aatggctgct  180
aataccgcat aagcgcacag gaccgcatgg tctggtgtga aaaactccgg tggtatgaga  240
tggacccgcg tctgattagc tagttggagg ggtaacggcc caccaaggcg acgatcagta  300
gccggcctga gagggtgaac ggccacattg gactgagac  acgggccaga ctcctacggg  360
aggcagcagt ggggaatatt gcacaatggg ggaaaccctg atgcagcgac gccgcgtgaa  420
ggaagaagta tctcggtatg taaacttcta tcagcaggga agaaaatgac ggtacctgac  480
taagaagccc cggctaacta cgtgccagca gccgcggtaa tacgtagggg gcaagcgtta  540
tccggattta ctgggtgtaa agggagcgta gacggaagag caagtctgat gtgaaaggct  600
ggggcttaac cccaggactg cattggaaac tgttttcta  gagtgccgga gaggtaagcg  660
gaattcctag tgtagcggtg aaatgcgtag atattaggag gaacaccagt ggcgaaggcg  720
gcttactgga cggtaactga cgttgaggct cgaaagcgtg gggagcaaac aggattagat  780
accctggtag tccacgccgt aaacgatgaa tactaggtgt cgggtggcaa agccattcgg  840
tgccgcagca aacgcaataa gtattccacc tggggagtac gttcgcaaga atgaaactca  900
aaggaattga cggggacccg cacaagcggt ggagcatgtg gtttaattcg aagcaacgcg  960
aagaaccta  ccaagtcttg acatccctct gaccggcccg taacgggcc  ttcccttcgg 1020
ggcagaggag acaggtggtg catggttgtc gtcagctcgt gtcgtgagat gttgggttaa 1080
gtcccgcaac gagcgcaacc cctatcctta gtagccagca ggtgaagctg ggcactctag 1140
ggagactgcc ggggataacc cggaggaagg cggggacgac gtcaaatcat catgcccctt 1200
atgatttggg ctacacacgt gctacaatgg cgtaaacaaa gggaagcgag acagcgatgt 1260
tgagcaaatc ccaaaaataa cgtcccagtt cggactgcag tctgcaactc gactgcacga 1320
agctggaatc gctagtaatc gcgaatcaga atgtcgcggt gaatacgttc ccgggtcttg 1380
tacacaccgc ccgtcacacc atgggagtca gtaacgcccg aagtcagtga cccaaccta  1440
caggaggag  ctgccgaagg cgggaccgat aactggggtg aagtcgtaac aaggtagccg 1500
tatcggaagg tgcggctgga tcacctcctt t                                1531
```

| SEQ ID NO: 144 | moltype = DNA length = 1531 |
| FEATURE | Location/Qualifiers |
| misc_feature | 1..1531 |
| | note = Synthetic Polynucleotide |
| source | 1..1531 |
| | mol_type = other DNA |
| | organism = synthetic construct |

SEQUENCE: 144

```
atcagagagt tgatcctgg ctcaggatga acgctggcgg cgtgcttaac acatgcaagt   60
cgagcgaagc acttaagcgg atctcttcgg attgaaactt atttgactga gcggcggacg  120
ggtgagtaac gcgtgggtaa cctgcctcat acaggggat  aacagttaga aatggctgct  180
```

```
aataccgcat aagcgcacag gaccgcatgg tctggtgtga aaaactccgg tggtatgaga    240
tggacccgcg tctgattagc tagttggagg ggtaacggcc caccaaggcg acgatcagta    300
gccggcctga gagggtgaac ggccacattg ggactgagac acggcccaga ctcctacggg    360
aggcagcagt ggggaatatt gcacaatggg ggaaaccctg atgcagcgac gccgcgtgaa    420
ggaagaagta tctcggtatg taaacttcta tcagcaggga agaaaatgac ggtacctgac    480
taagaagccc cggctaacta cgtgccagca gccgcggtaa tacgtagggg gcaagcgtta    540
tccggattta ctgggtgtaa agggagcgta gacggaagag caagtctgat gtgaaaggct    600
ggggcttaac cccaggactg cattggaaac tgttttcta gagtgccgga gaggtaagcg    660
gaattcctag tgtagcggtg aaatgcgtag atattaggag gaacaccgtg gcgaaggcg    720
gcttactgga cggtaactga cgttgaggct cgaaagcgtg gggagcaaac aggattagat    780
accctggtag tccacgccgt aaacgatgaa tactaggtgt cgggtggcaa agccattcgg    840
tgccgcagca aacgcaataa gtattccacc tggggagtac gttcgcaaga atgaaactca    900
aaggaattga cggggacccg cacaagcggt ggagcatgtg gtttaattcg aagcaacgcg    960
aagaaccta ccaagtcttg acatccctct gaccggccgt taacggggcc ttcccttcgg   1020
ggcagaggag acaggtggtg catggttgtc gtcagctcgt gtcgtgagat gttgggttaa   1080
gtcccgcaac gagcgcaacc cctatcctta gtagccagca ggtgaagctg ggcactctag   1140
ggagactgcc ggggataacc cggaggaagg cggggacgac gtcaaatcat catgcccctt   1200
atgatttggg ctacacacgt gctacaatgg cgtaaacaaa gggaagcgag acagcgatgt   1260
tgagcaaatc ccaaaaataa cgtcccagtt cggactgcag tctgcaactc gactgcacga   1320
agctggaatc gctagtaatc gcgaatcaga atgtcgcggt gaatacgttc ccgggtcttg   1380
tacacaccgc ccgtcacacc atgggagtca gtaacgcccg aagtcagtga cccaaccta    1440
caggagggag ctgccgaagg cgggaccgat aactggggtg aagtcgtaac aaggtagccg   1500
tatcggaagg tgcggctgga tcacctcctt t                                   1531

SEQ ID NO: 145          moltype = DNA  length = 1531
FEATURE                 Location/Qualifiers
misc_feature            1..1531
                        note = Synthetic Polynucleotide
source                  1..1531
                        mol_type = other DNA
                        organism = synthetic construct
SEQUENCE: 145
atcagagagt ttgatcctgg ctcaggatga acgctggcgg cgtgcttaac acatgcaagt    60
cgagcgaagc acttaagtgg atctcttcgg attgaaactt atttgactga gcggcggacg   120
ggtgagtaac gcgtgggtaa cctgcctcat acaggggata acagttttaga aatgactgct   180
aataccgcat aagcgcacag gaccgcatgg tctggtgtga aaaactccgg tggtatgaga   240
tggacccgcg tctgattagc tagttggagg ggtaacggcc caccaaggcg acgatcagta   300
gccggcctga gagggtgaac ggccacattg ggactgagac acggcccaga ctcctacggg   360
aggcagcagt ggggaatatt gcacaatggg ggaaaccctg atgcagcgac gccgcgtgaa   420
ggaagaagta tctcggtatg taaacttcta tcagcaggga agaaaatgac ggtacctgac   480
taagaagccc cggctaacta cgtgccagca gccgcggtaa tacgtagggg gcaagcgtta   540
tccggattta ctgggtgtaa agggagcgta gacggaagag caagtctgat gtgaaaggct   600
ggggcttaac cccaggactg cattggaaac tgttttcta gagtgccgga gaggtaagcg   660
gaattcctag tgtagcggtg aaatgcgtag atattaggag gaacatcagt ggcgaaggcg   720
gcttactgga cggtaactga cgttgaggct cgaaagcgtg gggagcaaac aggattagat   780
accctggtag tccacgccgt aaacgatgaa tactaggtgt cgggtggcaa agccattcgg   840
tgccgcagca aacgcaataa gtattccacc tggggagtac gttcgcaaga atgaaactca   900
aaggaattga cggggacccg cacaagcggt ggagcatgtg gtttaattcg aagcaacgcg   960
aagaaccta ccaagtcttg acatccctct gaccggccgt taacggggcc ttcccttcgg   1020
ggcagaggag acaggtggtg catggttgtc gtcagctcgt gtcgtgagat gttgggttaa   1080
gtcccgcaac gagcgcaacc cctatcctta gtagccagca ggtgaagctg ggcactctag   1140
ggagactgcc ggggataacc cggaggaagg cggggacgac gtcaaatcat catgcccctt   1200
atgatttggg ctacacacgt gctacaatgg cgtaaacaaa gggaagcgag acagcgatgt   1260
tgagcaaatc ccaaaaataa cgtccctagtt cggactgcag tctgcaactc gactgcacga   1320
agctggaatc gctagtaatc gcgaatcaga atgtcgcggt gaatacgttc ccgggtcttg   1380
tacacaccgc ccgtcacacc atgggagtca gtaacgcccg aagtcagtga cccaaccta    1440
caggagggag ctgccgaagg cgggaccgat aactggggtg aagtcgtaac aaggtagccg   1500
tatcggaagg tgcggctgga tcacctcctt t                                   1531

SEQ ID NO: 146          moltype = DNA  length = 1529
FEATURE                 Location/Qualifiers
misc_feature            1..1529
                        note = Synthetic Polynucleotide
source                  1..1529
                        mol_type = other DNA
                        organism = synthetic construct
SEQUENCE: 146
aacgagagtt tgatcctggc tcaggatgaa cgctggcggc gtgcttaaca catgcaagtc    60
gagcgaagca cttaagtttt attcttcgga tgaagacttt tgtgactgag cggcggacgg   120
gtgagtaacg cgtgggtaac ctgcctcata caggggggata acagttagaa atgactgcta   180
ataccgcata agaccacggt accgcatggt acagtggtaa aaactccggt ggtatgagat   240
ggacccgcgt ctgattaggt agttggtggg gtaacgcct accaagccga cgatcagtag   300
ccgacctgag agggtgaccg gccacattgg gactgagaca cggcccagac tcctacggga   360
ggcagcagtg gggaattgc acaatggagg aaacctgac tgcagcgacg ccgcgtgaag   420
gatgaagtat ttcggtatgt aaacttctat cagcagggaa gaaaatgacg gtacctgact   480
aagaagcccc ggctaactac gtgccagcag ccgcggtaat acgtagggggg caagcgttat   540
ccggatttac tgggtgtaaa gggagcgtag acggacggc aagccagatg tgaaagcccg   600
gggctcaacc ccgggactgc atttggaact gctgagctag agtgtcggag aggcaagtgg   660
aattcctagt gtagcggtga aatgcgtaga tattaggagg aacaccagtg gcgaaggcgg   720
```

```
cttgctggac gatgactgac gttgaggctc gaaagcgtgg ggagcaaaca ggattagata    780
ccctggtagt ccacgccgta aacgatgact gctaggtgtc gggtggcaaa gccattcggt    840
gccgcagcta acgcaataag cagtccacct ggggagtacg ttcgcaagaa tgaaactcaa    900
aggaattgac ggggacccgc acaagcggtg gagcatgtgg tttaattcga agcaacgcga    960
agaaccttac ctgatcttga catcccgatg accgcttcgt aatggaagtt tttcttcgga   1020
acatcggtga caggtggtgc atggttgtcg tcagctcgtg tcgtgagatg ttgggttaag   1080
tcccgcaacg agcgcaaccc ctatcttcag tagccagcag gttaagctgg cactctgga   1140
gagactgcca gggataacct ggaggaaggt ggggatgacg tcaaatcatc atgcccctta   1200
tgaccagggc tacacacgtg ctacaatggc gtaaacaaag agaagcgaac tcgcgagggt   1260
aagcaaatct caaaaataac gtctcagttc ggattgtagt ctgcaactcg actacatgaa   1320
gctggaatcg ctagtaatcg cagatcagaa tgctgcggtg aatacgttcc cgggtcttgt   1380
acacaccgcc cgtcacacca tgggagtcag taacgcccga agtcagtgac caaccgtaa    1440
ggagggagct gccgaaggtg ggaccgataa ctggggtgaa gtcgtaacaa ggtagccgta   1500
tcggaaggtg cggctggatc acctcctttt                                    1529

SEQ ID NO: 147         moltype = DNA  length = 1528
FEATURE                Location/Qualifiers
misc_feature           1..1528
                       note = Synthetic Polynucleotide
source                 1..1528
                       mol_type = other DNA
                       organism = synthetic construct
SEQUENCE: 147
aacgagagtt tgatcctggc tcaggatgaa cgctggcggc gtgcttaaca catgcaagtc     60
gagcgaagca ctttggaaag attcttcgga tgatttcctt tgtgactgag cggcggacgg    120
gtgagtaacg cgtgggtaac ctgcctcata caggggata acagttagaa atgactgcta    180
ataccgcata agaccacggt accgcatggt acagtggtaa aaactccggt ggtatgagat    240
ggacccgcgt ctgattaggt agttggtggg gtaacggcct accaagccga cgatcagtag    300
ccgacctgag agggtgaccg gccacattgg gactgagaca cggcccagac tcctacggga    360
ggcagcagtg gggaatattg cacaatggag gaaactctga tgcagcgacg tcgcgtgaa    420
gatgaagtat ttcggtatgt aaacttctat cagcagggaa gaaaatgacg gtacctgact    480
aagaagcccc ggctaactac gtgccagcag ccgcggtaat acgtaggggg caagcgttat    540
ccggatttac tgggtgtaaa gggagcgtag acggcacggc aagccagatg tgaaagcccg    600
gggctcaacc ccgggactgc atttggaactg ctgagctaga gtgtcggaga ggcaagtgga   660
attcctagtg tagcggtgaa atgcgtagat attaggagga acaccagtgg cgaaggcgt    720
ttgctggacg atgactgacg ttgaggctcg aaagcgtggg gagcaaacag gattagatac    780
cctggtagtc cacgccgtaa acgatgactg ctaggtgtcg ggtggcaaag ccattcggtg    840
ccgcagctaa cgcaataagc agtccacctg gggagtacgt tcgcaagaat gaaactcaaa    900
ggaattgacg ggacccgca caagcggtgg agcatgtgg ttaattcgaa gcaacgcgaa      960
gaaccttacc tgatcttgac atcccgatga ccgcttcgta atggaagctt ttcttcggaa   1020
catcggtgac aggtggtgca tggttgtcgt cagctcgtgt cgtgagatgt tgggttaagt   1080
cccgcaacga gcgcaacccc tatcttcagt agccagcagg ttaagctggg cactctgag    1140
agactgccag ggataacctg gaggaaggtg gggatgacgt caaatcatc tgcccctat     1200
gaccagggct acacacgtgc tacaatggcg taaacaaaga agcgaact cgcgagggta     1260
agcaaatctc aaaaataacg tctcagttcg gattgtagtc tgcaactcga ctacatgaag   1320
ctggaatcgc tagtaatcgc agatcagaat gctgcggtga atacgttccc gggtcttgta   1380
cacaccgccc gtcacaccat gggagtcagt aacgcccgaa gtcagtgacc caaccgtaag   1440
gagggagctg ccgaaggtgg gaccgataac tggggtgaag tcgtaacaag gtagccgtat   1500
cggaaggtgc ggctggatca cctccttt                                      1528

SEQ ID NO: 148         moltype = DNA  length = 1529
FEATURE                Location/Qualifiers
misc_feature           1..1529
                       note = Synthetic Polynucleotide
source                 1..1529
                       mol_type = other DNA
                       organism = synthetic construct
SEQUENCE: 148
aacgagagtt tgatcctggc tcaggatgaa cgctggcggc gtgcttaaca catgcaagtc     60
gagcgaagca cttaagtttg attcttcgga tgaagacttt tgtgactgag cggcggacgg    120
gtgagtaacg cgtgggtaac ctgcctcata caggggata acagttagaa atgactgcta    180
ataccgcata agaccacggt accgcatggt acagtggtaa aaactccggt ggtatgagat    240
ggacccgcgt ctgattaggt agttggtggg gtaacggcct accaagccga cgatcagtag    300
ccgacctgag agggtgaccg gccacattgg gactgagaca cggcccagac tcctacggga    360
ggcagcagtg gggaatattg cacaatggag gaaactctga tgcagcgacg ccgcgtgaag    420
gatgaagtat ttcggtatgt aaacttctat cagcagggaa gaaaatgacg gtacctgact    480
aagaagcccc ggctaactac gtgccagcag ccgcggtaat acgtaggggg caagcgttat    540
ccggatttac tgggtgtaaa gggagcgtag acggcacggc aagccagatg tgaaagcccg    600
gggctcaacc ccgggactgc atttggaact gctgagctag agtgtcggag aggcaagtgg    660
aattcctagt gtagcggtga atgcgtaga tattaggagg aacaccagtg gcgaaggcgg    720
cttgctggac gatgactgac gttgaggctc gaaagcgtgg ggagcaaaca ggattagata    780
ccctggtagt ccacgccgta aacgatgact gctaggtgtc gggtggcaaa gccattcggt    840
gccgcagcta acgcaataag cagtccacct ggggagtacg ttcgcaagaa tgaaactcaa    900
aggaattgac ggggacccgc acaagcggtg gagcatgtgg tttaattcga agcaacgcga    960
agaaccttac ctgatcttga catcccgatg accgcttcgt aatggaagct tttcttcgga   1020
acatcggtga caggtggtgc atggttgtcg tcagctcgtg tcgtgagatg ttgggttaag   1080
tcccgcaacg agcgcaaccc ctatcttcag tagccagcag gttaagctgg cactctgga   1140
gagactgcca gggataacct ggaggaaggt ggggatgacg tcaaatcatc atgcccctta   1200
tgaccagggc tacacacgtg ctacaatggc gtaaacaaag agaagcgaac tcgcgagggt   1260
```

```
aagcaaatct caaaaataac gtctcagttc ggattgtagt ctgcaactcg actacatgaa  1320
gctggaatcg ctagtaatcg cagatcagaa tgctgcggtg aatacgttcc cgggtcttgt  1380
acacaccgcc cgtcacacca tgggagtcag taacgcccga agtcagtgac ccaaccgtaa  1440
ggagggagct gccgaaggtg ggaccgataa ctggggtgaa gtcgtaacaa ggtagccgta  1500
tcggaaggtg cggctggatc acctccttt                                   1529

SEQ ID NO: 149         moltype = DNA  length = 1529
FEATURE                Location/Qualifiers
misc_feature           1..1529
                       note = Synthetic Polynucleotide
source                 1..1529
                       mol_type = other DNA
                       organism = synthetic construct
SEQUENCE: 149
aacgagagtt tgatcctggc tcaggatgaa cgctggcggc gtgcttaaca catgcaagtc   60
gagcgaagca ctttggaaag attcttcgga tgatttcctt tgtgactgag cggcggacgg  120
gtgagtaacg cgtgggtaac ctgcctcata caggggata acagttagaa atgactgcta   180
ataccgcata agaccacggt accgcatggt acagtggtaa aaactccggt ggtatgagat  240
ggacccgcgt ctgattaggt agttggtggg gtaacggcct accaagccga cgatcagtag  300
ccgacctgag agggtgaccg gccacattgg gactgagaca cggcccagac tcctacggga  360
ggcagcagtg gggaatattg cacaatggag gaaactctga tgcagcgacg ccgcgtgaag  420
gatgaagtat ttcggtatgt aaacttctat cagcagggaa gaaaatgacg gtacctgact  480
aagaagcccc ggctaactac gtgccagcag ccgcggtaat acgtaggggg caagcgttat  540
ccggatttac tgggtgtaaa gggagcgtag acggcacggc aagccagatg tgaaagcccg  600
gggctcaacc ccgggactgc atttggaact gctgagctag agtgtcggag aggcaagtgg  660
aattcctagt gtagcggtga aatgcgtaga tattaggagg acaccagtgg cgaaggcgcg  720
cttgctggac gatgactgac gttgaggctc gaaagcgtgg ggagcaaaca ggattagata  780
ccctggtagt ccacgccgta acgatgact gctaggtgtc gggtggcaaa gccattcggt  840
gccgcagcta acgcaataag cagtccacct ggggagtacg ttcgcaagaa tgaaactcaa  900
aggaattgac ggggacccgc acaagcggtg gagcatgtgg tttaattcga agcaacgcga  960
agaaccttac ctgatcttga catcccgatg accgcttcgt aatggaagct ttcttcgga  1020
acatcggtga caggtggtgc atggttgtcg tcagctcgtg tcgtgagatg ttgggttaag  1080
tcccgcaacg agcgcaaccc ctatcttcag tagccagcag gttaagctgg cactctgga   1140
gagactgcca gggataaacct ggaggaaggt ggggatgacg tcaaatcatc atgccccta   1200
tgaccaggc tacacacgtg ctacaatggc gtaaacaaag aagcgaac tcgcgagggt  1260
aagcaaatct caaaaataac gtctcagttc ggattgtagt ctgcaactcg actacatgaa  1320
gctggaatcg ctagtaatcg cagatcagaa tgctgcggtg aatacgttcc cgggtcttgt  1380
acacaccgcc cgtcacacca tgggagtcag taacgcccga agtcagtgac ccaaccgtaa  1440
ggagggagct gccgaaggtg ggaccgataa ctggggtgaa gtcgtaacaa ggtagccgta  1500
tcggaaggtg cggctggatc acctccttt                                   1529

SEQ ID NO: 150         moltype = DNA  length = 1528
FEATURE                Location/Qualifiers
misc_feature           1..1528
                       note = Synthetic Polynucleotide
source                 1..1528
                       mol_type = other DNA
                       organism = synthetic construct
SEQUENCE: 150
aacgagagtt tgatcctggc tcaggatgaa cgctggcggc gtgcttaaca catgcaagtc   60
gagcgaagcg cttaagtttg attcttcgga tgaagacttt tgtgactgag cggcggacgg  120
gtgagtaacg cgtgggtaac ctgcctcata caggggata acagttagaa atgactgcta   180
ataccgcata agaccacggt accgcatggt acagtggtaa aaactccggt ggtatgagat  240
ggacccgcgt ctgattaggt agttggtggg gtaacggcct accaagccga cgatcagtag  300
ccgacctgag agggtgaccg gccacattgg gactgagaca cggcccagac tcctacggga  360
ggcagcagtg gggaatattg cacaatggag gaaactctga tgcagcgacg ccgcgtgaag  420
gatgaagtat ttcggtatgt aaacttctat cagcagggaa gaaaatgacg gtacctgact  480
aagaagcccc ggctaactac gtgccagcag ccgcggtaat acgtaggggg caagcgttat  540
ccggatttac tgggtgtaaa gggagcgtag acggcacggc aagccagatg tgaaagcccg  600
ggctcaaccc cgggactgca tttggaactg ctgagctaga gtgtcggaga ggcaagtgga  660
attcctagtg tagcggtgaa atgcgtagat attaggagga caccagtggc gaaggcggc   720
ttgctggacg atgactgacg ttgaggctcg aaagcgtggg gagcaaacag gattagatac  780
cctggtagtc cacgccgtaa acgatgactg ctaggtgtcg ggtggcaaag ccattcggt   840
ccgcagctaa cgcaataagc agtccacctg gggagtacgt tcgcaagaat gaaactcaaa   900
ggaattgacg ggacccgca caagcggtgg agcatgtgg ttaattcgaa gcaacgcgaa   960
gaaccttacc tgatcttgac atcccgatga ccgcttcgta atggaagttt ttcttcgaa  1020
catcggtgac aggtggtgca tggttgtcgt cagctcgtgt cgtgagatgt tgggttaagt  1080
cccgcaacga gcgcaacccc tatcttcagt agccagcagg ttaagctggc actctggaa  1140
agactgccag ggataacctg gaggaaggtg gggatgacgt caaatcatca tgccccttat  1200
gaccagggct acacacgtgc tacaatgcgt aaacaaagga ggcaaact cgcgagggta  1260
agcaaatcgc aaaaataacg tctcagttcg gattgtagtc tgcaactcga ctacatgaag  1320
ctggaatcgc tagtaatcgc agatcagaat gctgcggtga atacgttccc gggtcttgta  1380
cacaccgccc gtcacaccat gggagtcagt aacgcccgaa gtcagtgacc caaccgtaag  1440
gagggagctg ccgaaggtgg gaccgataac tggggtgaag tcgtaacaag gtagccgtat  1500
cggaaggtgc ggctggatca cctccttt                                    1528

SEQ ID NO: 151         moltype = DNA  length = 1529
FEATURE                Location/Qualifiers
```

```
misc_feature            1..1529
                        note = Synthetic Polynucleotide
source                  1..1529
                        mol_type = other DNA
                        organism = synthetic construct
SEQUENCE: 151
aacgagagtt tgatcctggc tcaggatgaa cgctggcggc gtgcttaaca catgcaagtc    60
gagcgaagcg ctttgggaag attcttcgga tgatttcctt tgtgactgag cggcggacgg   120
gtgagtaacg cgtgggtaac ctgcctcata caggggata acagttagaa atgactgcta    180
ataccgcata agaccacggt accgcatggt acagtggtaa aaactccggt ggtatgagat   240
ggacccgcgt ttgattaggt agttggtggg gtaacggcct accaagccga cgatcagtag   300
ccgacctgag agggtgaccg gccacattgg gactgagaca cggcccagac tcctacggga   360
ggcagcagtg gggaatattg cacaatggag gaaactctga tgcagcgacg ccgcgtgaag   420
gatgaagtat ttcggtatgt aaacttctat cagcagggaa gaaatgtacc tgact         480
aagaagcccc ggctaactac gtgccagcag ccgcggtaat acgtaggggg caagcgttat    540
ccggatttac tgggtgtaaa gggagcgtag acggcacggc aagccagatg tgaaagcccg    600
gggctcaacc ccgggactgc atttggaact gctgagctag agtgtcggag aggcaagtgg    660
aattcctagt gtagcggtga aatgcgtaga tattaggagg aacaccagtg gcgaaggcgt    720
cttgctggac gatgactgac gttgaggctc gaaagcgtgg ggagcaaaca ggattagata    780
ccctggtagt ccacgccgta aacgatgact gctaggtgtc gggtggcaaa gccattcggt    840
gccgcagcta acgcaataag cagtccacct ggggagtacg ttcgcaagaa tgaaactcaa    900
aggaattgac ggggacccgc acaagcggtg gagcatgtgg tttaattcga acgcaacgcg    960
agaaccttac ctgatcttga catcccgatg actgcttcgt aatggaagtt tttcttcgga   1020
acatcggtga caggtggtgc atggttgtcg tcagctcgtg tcgtgagatg ttgggttaag   1080
tcccgcaacg agcgcaaccc ctatcttcag tagccagcag gttaagctgg cactctgga    1140
gagactgcca gggataacct ggaggaaggt gggatgacg tcaaatcatc atgccctta      1200
tgaccagggc tacacacgtg ctacaatggc gtaaacaaag agaagcgaac tcgcgagggt   1260
aagcaaatct caaaaataac gtctcagttc ggattgtagt ctgcaactcg actacatgaa   1320
gctgaatcg ctagtaatcg cagatcagaa tgctgcggtg aatacgttcc cgggtcttgt    1380
acacaccgcc cgtcacacca tgggagtcag taacgcccga agtcagtgac caaccgtaa    1440
ggagggagct gccgaaggtg ggaccgataa ctggggtgaa gtcgtaacaa ggtagccgta   1500
tcggaaggtg cggctggatc acctcctttt                                    1529

SEQ ID NO: 152         moltype = DNA   length = 1537
FEATURE                Location/Qualifiers
misc_feature           1..1537
                       note = Synthetic Polynucleotide
source                 1..1537
                       mol_type = other DNA
                       organism = synthetic construct
SEQUENCE: 152
atggagagtt tgatcctggc tcaggatgaa cgctggcggc atgcctaata catgcaagtc    60
gaacgaagtt tcgaggaagc ttgcttccaa agagacttag tggcgaacgg gtgagtaaca   120
cgtaggtaac ctgcccatgt gtccgggata actgctggaa acggtagcta aaaccggata   180
ggtatacaga gcgcatgctc agtatattaa agcgcccatc aaggcgtgaa catggatgga   240
cctgcggcgc attagctagt tggtgaggta acggctcacc aaggcgatga tgcgtagccg   300
gcctgcgagg gtaaacggcc acattgggac tgagacaccc caaactcc tacgggaggc     360
agcagtaggg aattttcgtc aatggggaa accctgaacg agcaatgccg cgtgagtgaa    420
gaaggtcttc ggatcgtaaa gctctgttgt aagtgaagaa cggctcatag aggaaatgct   480
atgggagtga cggtagctta ccagaaagcc acggctaact acgtgccagc agccgcggta   540
atacgtaggt ggcaagcgtt atccggaatc atttgggcgta aagggtgcgt aggtggcgta   600
ctaagtctgt agtaaaaggc aatggctcaa ccattgtaag ctatggaaac tggtatgctg    660
gagtgcagaa gagggcgatg gaattccatg tgtagcggta aaatgcgtag atatatggag   720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctgggag tatgcacgca     900
agtgtgaaac tcaaaggaat tgacgggggc ccgcacaagc ggtggagtat gtggtttaat   960
tcgaagcaac gcgaagaacc ttaccaggcc ttgacatgga aacaaatacc ctagatatag   1020
ggggataatt atggatcaca caggtggtgc atggttgtcg tcagctcgt tcgtgagatg    1080
ttgggttaag tcccgcaacg agcgcaaccc ttgtcgcatg ttaccagcat caagttgggg   1140
actcatgcga gactgccggt gacaaaccgg aggaaggtgg ggatgacgtc aaatcatcat   1200
gccccttatg gcctgggcta cacacgtact acaatgcgg ccacaaagag cagcgacaca    1260
gtgatgtgaa gcgaatctca taaggtcgt ctcagttcgg attgaagtct gcaactcgac    1320
ttcatgaagt cggaatcgct agtaatcga gatcagcatg ctgcggtgaa tacgttctcg    1380
ggccttgtac acaccgcccg tcaaaccatg ggagtcagta atacccgaag ccggtggcat    1440
aaccgtaagg agtgagccgt cgaaggtagg accgatgact ggggttaagt cgtaacaagg   1500
tatcccctacg gaacgtgggg gatggatcac ctccttt                             1537

SEQ ID NO: 153         moltype = DNA   length = 1537
FEATURE                Location/Qualifiers
misc_feature           1..1537
                       note = Synthetic Polynucleotide
source                 1..1537
                       mol_type = other DNA
                       organism = synthetic construct
SEQUENCE: 153
atggagagtt tgatcctggc tcaggatgaa cgctggcggc atgcctaata catgcaagtc    60
gaacgaagtt tcgaggaagc ttgcttccaa agagacttag tggcgaacgg gtgagtaaca   120
cgtaggtaac ctgcccatgt gtccgggata actgctggaa acggtagcta aaaccggata   180
```

-continued

```
ggtatacaga gcgcatgctc agtatattaa agcgcccatc aaggcgtgaa catggatgga    240
cctgcggcgc attagctagt tggtgaggta acggcccacc aaggcgatga tgcgtagccg    300
gcctgagagg gtaaacggcc acattgggac tgagacacgg cccaaactcc tacgggaggc    360
agcagtaggg aattttcgtc aatggggaa acccctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatgaaac tggtatgctg    660
gagtgcagaa gagggcgatg gaattccatg tgtagcggta aaatgcgtag atatatggag    720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctggggag tatgcacgca    900
agtgtgaaac tcaaaggaat tgacggggggc ccgcacaagc ggtggagtat gtggtttaat    960
tcgaagcaac gcgaagaacc ttaccaggcc ttgacatgga aacaaatacc ctagagatag   1020
ggggataatt atgatcaca caggtggtgc atggttgtcg tcagctcgtg tcgtgagatg    1080
ttgggttaag tcccgcaacg agcgcaaccc ttgtcgcatg ttaccagcat caagttgggg   1140
actcatgcga gactgccggt gacaaaccgg aggaaggtgg ggatgacgtc aaatcatcat    1200
gccccttatg gcctgggcta cacacgtact acaatggcgg ccacaaagag cagcgacaca   1260
gtgatgtgaa gcgaatctca taaaggtcgt ctcagttcgg attgaagtct gcaactcgac   1320
ttcatgaagt cggaatcgct agtaatcgca gatcagcatg ctgcggtgaa tacgttctcg    1380
ggccttgtac acaccgcccg tcaaaccatg ggagtcagta atacccgaag ccggtggcat    1440
aaccgtaagg agtgagccgt cgaaggtagg accgatgact ggggttaagt cgtaacaagg   1500
tatccctacg gaacgtgggg gatggatcac ctccttt                           1537

SEQ ID NO: 154            moltype = DNA   length = 1537
FEATURE                   Location/Qualifiers
misc_feature              1..1537
                          note = Synthetic Polynucleotide
source                    1..1537
                          mol_type = other DNA
                          organism = synthetic construct
SEQUENCE: 154
atggagagtt tgatcctggc tcaggatgaa cgctggcggc atgcctaata catgcaagtc     60
gaacgaagtt tcgaggaagc ttgcttccaa agagacttag tggcgaacgg gtgagtaaca    120
cgtaggtaac ctgcccatgt gtccgggata actgctggaa acggtagcta aaaccggata    180
ggtatacaga gcgcatgctc agtatattaa agcgcccatc aaggcgtgaa catggatgga    240
cctgcggcgc attagctagt tggtgaggta acggctcacc aaggcgatga tgcgtagccg    300
gcctgagagg gtaaacggcc acattgggac tgagacacgg cccaaactcc tacgggaggc    360
agcagtaggg aattttcgtc aatggggaa acccctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatgaaac tggtatgctg    660
gagtgcagaa gagggcgatg gaattccatg tgtagcggta aaatgcgtag atatatggag    720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctggggag tatgcacgca    900
agtgtgaaac tcaaaggaat tgacggggggc ccgcacaagc ggtggagtat gtggtttaat    960
tcgaagcaac gcgaagaacc ttaccaggcc ttgacatgga aacaaatacc ctagagatag   1020
ggggataatt atgatcaca caggtggtgc atggttgtcg tcagctcgtg tcgtgagatg    1080
ttgggttaag tcccgcaacg agcgcaaccc ttgtcgcatg ttaccagcat caagttgggg   1140
actcatgcga gactgccggt gacaaaccgg aggaaggtgg ggatgacgtc aaatcatcat    1200
gccccttatg gcctgggcta cacacgtact acaatggcgg ccacaaagag cagcgacaca   1260
gtgatgtgaa gcgaatctca taaaggtcgt ctcagttcgg attgaagtct gcaactcgac   1320
ttcatgaagt cggaatcgct agtaatcgca gatcagcatg ctgcggtgaa tacgttctcg    1380
ggccttgtac acaccgcccg tcaaaccatg ggagtcagta atacccgaag ccggtggcat    1440
aaccgtaagg agtgagccgt cgaaggtagg accgatgact ggggttaagt cgtaacaagg   1500
tatccctacg gaacgtgggg gatggatcac ctccttt                           1537

SEQ ID NO: 155            moltype = DNA   length = 1537
FEATURE                   Location/Qualifiers
misc_feature              1..1537
                          note = Synthetic Polynucleotide
source                    1..1537
                          mol_type = other DNA
                          organism = synthetic construct
SEQUENCE: 155
atggagagtt tgatcctggc tcaggatgaa cgctggcggc atgcctaata catgcaagtc     60
gaacgaagtt tcgaggaagc ttgcttccaa agagacttag tggcgaacgg gtgagtaaca    120
cgtaggtaac ctgcccatgt gtccgggata actgctggaa acggtagcta aaaccggata    180
ggtatacaga gcgcatgctc agtatattaa agcgcccatc aaggcgtgaa catggatgga    240
cctgcggcgc attagctagt tggtgaggta acggcccacc aaggcgatga tgcgtagccg    300
gcctgagagg gtaaacggcc acattgggac tgagacacgg cccaaactcc tacgggaggc    360
agcagtaggg aattttcgtc aatggggaa acccctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatgaaac tggtatgctg    660
gagtgcagaa gagggcgatg gaattccatg tgtagcggta aaatgcgtag atatatggag    720
```

```
gaacaccagt ggcgaaggcg gtcgcctggt ctgtaactga cactgaggca cgaaagcgtg   780
gggagcaaat aggattagat accctagtag tccacgccgt aaacgatgag aactaagtgt   840
tggaggaatt cagtgctgca gttaacgcaa taagttctcc gcctgggag tatgcacgca    900
agtgtgaaac tcaaaggaat tgacggggc ccgcacaagc ggtggagtat gtggtttaat    960
tcgaagcaac gcgaagaacc ttaccaggcc ttgacatgaa aacaaatacc ctagagatag  1020
ggggataatt atggatcaca caggtggtgc atggttgtcg tcagctcgtg tcgtgagatg  1080
ttgggttaag tcccgcaacg agcgcaaccc ttgtcgcatg ttaccagcat caagttgggg  1140
actcatgcga gactgccggt gacaaacgg aggaaggtgg ggatgacgtc aaatcatcat   1200
gccccttatg gcctgggcta cacacgtact acaatggcgg ccacaaagag cagcgacaca  1260
gtgatgtgaa gcgaatctca taaaggtcgt ctcagttcgg attgaagtct gcaactcgac  1320
ttcatgaagt cggaatcgct agtaatcgca gatcagcatg ctgcggtgaa tacgttctcg  1380
ggccttgtac acaccgcccg tcaaaccatg ggagtcagta atacccgaag ccggtggcat  1440
aaccgcaagg agtgagccgt cgaaggtagg accgatgact ggggttaagt cgtaacaagg  1500
tatccctacg ggaacgtggg gatggatcac ctcctttt                           1537

SEQ ID NO: 156           moltype = DNA   length = 1537
FEATURE                  Location/Qualifiers
misc_feature             1..1537
                         note = Synthetic Polynucleotide
source                   1..1537
                         mol_type = other DNA
                         organism = synthetic construct
SEQUENCE: 156
atggagagtt tgatcctggc tcaggatgaa cgctggcggc atgcctaata catgcaagtc    60
gaacgaagtt tcgaggaagc ttgcttccaa agagacttag tggcgaacgg gtgagtaaca   120
cgtaggtaac ctgcccatgt gtccgggata actgctggaa acggtagcta aaaccggata   180
ggtatacaga gcgcatgctc agtatattaa agcgcccatc aaggcgtgaa catggatgga   240
cctgcggcgc attagctagt tggtgaggta acggcccacc aaggcgatga tgcgtagccg   300
gcctgagagg gtaaacggcc acattgggac tgagacacgg cccaaactcc tacgggaggc   360
agcagtaggg aattttcgtc aatggggga accctgaaca gcaatgccg cgtgagtgaa    420
gaaggtcttc ggatcgtaaa gctctgttgt aagtgaagaa cggctcatag aggaaatgct   480
atgggagtga cggtagctta ccagaaagcc acggctaact acgtgccagc agccgcggta   540
atacgtaggt ggcaagcgtt atccggaatc attgggcgta aagggtgcgt aggtggcgta   600
ctaagtctgt agtaaaagc aatggctcaa ccattgtaag ctatggaaac tggtatgctg   660
gagtgcagaa gagggcgatg gaattccatg tgtagcggta aaatgcgtag atatatgg    720
gaacaccagt ggcgaaggcg gtcgcctggt ctgtaactga cactgaggca cgaaagcgtg   780
gggagcaaat aggattagat accctagtag tccacgccgt aaacgatgag aactaagtgt   840
tggaggaatt cagtgctgca gttaacgcaa taagttctcc gcctgggag tatgcacgca    900
agtgtgaaac tcaaaggaat tgacggggc ccgcacaagc ggtggagtat gtggtttaat    960
tcgaagcaac gcgaagaacc ttaccaggcc ttgacatgaa aacaaatacc ctagagatag  1020
ggggataatt atggatcaca caggtggtgc atggttgtcg tcagctcgtg tcgtgagatg  1080
ttgggttaag tcccgcaacg agcgcaaccc ttgtcgcatg ttaccagcat caagttgggg  1140
actcatgcga gactgccggt gacaaacgg aggaaggtgg ggatgacgtc aaatcatcat   1200
gccccttatg gcctgggcta cacacgtact acaatggcgg ccacaaagag cagcgacaca  1260
gtgatgtgaa gcgaatctca taaaggtcgt ctcagttcgg attgaagtct gcaactcgac  1320
ttcatgaagt cggaatcgct agtaatcgca gatcagcatg ctgcggtgaa tacgttctcg  1380
ggccttgtac acaccgcccg tcaaaccatg ggagtcagta atacccgaag ccggtggcat  1440
aaccgtaagg agtgagccgt cgaaggtagg accgatgact ggggttaagt cgtaacaagg  1500
tatccctacg ggaacgtggg gatggatcac ctcctttt                           1537

SEQ ID NO: 157           moltype = DNA   length = 1529
FEATURE                  Location/Qualifiers
misc_feature             1..1529
                         note = Synthetic Polynucleotide
source                   1..1529
                         mol_type = other DNA
                         organism = synthetic construct
SEQUENCE: 157
tattgagagt ttgatcctgg ctcaggatga acgctggcgg cgtgcttaac acatgcaagt    60
cgaacggggt gctcatgacg gaggattcgt ccaacggatt gagttaccta gtggcggacg   120
ggtgagtaac gcgtgaggaa cctgccttgg agagggaat aacactccga aaggagtgct   180
aataccgcat gatgcagttg ggtcgcatgg ctctgactgc caaagattta tcgctctgag   240
atggcctcgt gtctgattag ctagtaggcg gggtaacggc ccacctaggc gacgatcagt   300
agccggactg agaggttgac cggccacatt ggactgagac actccggccc   360
gaggcagcag tggggaatat tgggcaatgg gcgcaagcct gacccagcaa cgccgcgtga   420
aggaagaagg ctttcgggtt gtaaacttct tttgtcgggg acgaaacaaa tgacggtacc   480
cgacgaataa gccacggcta actacgtgcc agcagccgcg gtaatacgta ggtggcaagc   540
gttatccgga tttactgggt gtaaagggcg tgtaggcggg attgcaagtc agatgtgaaa   600
actgggggct caacctccag cctgcatttg aaactgttgt tcttgagtgt tggagaggca   660
atcggaattc cgtgtgtagc ggtgaaatgc gtagatatac ggaggaacac cagtggcgaa   720
ggcggattgc tggacagtaa ctgacgctga ggcgcgaaag cgtggggagc aaacaggatt   780
agataccctg gtagtccacg ccgtaaacga tggatactag gtgtgggggt ctgccccct    840
ccgtgccgca gttaacacaa taagtatccc acctggggag tacgatcgca aggttgaaac   900
tcaaaggaat tgacggggc ccgcacaagc ggtggagtat gtggtttaat tcgaagcaac   960
gcgaagaacc ttaccagggc ttgacatccc actaacgaag cagagatgca ttaggtgccc  1020
ttcggggaaa gtggagacag gtggtgcatg gttgtcgtca gctcgtgtcg tgagatgttg  1080
ggttaagtcc cgcaacgagc gcaaccctta ttgttagttg ctacgcaaga gcactctagc  1140
gagactgccg ttgacaaaac ggaggaaggt ggggacgacg tcaaatcatc atgccccctta 1200
tgtcctgggc cacacacgta ctacaatggg ggttaacaga gggaggcaat accgcgaggt  1260
```

```
ggagcaaatc cctaaaagcc atcccagttc ggattgcagg ctgaaacccg cctgtatgaa    1320
gttggaatcg ctagtaatcg cggatcagca tgccgcggtg aatacgttcc cgggccttgt    1380
acacaccgcc cgtcacacca tgagagtcgg gaacacccga agtccgtagc ctaaccgcaa    1440
ggagggcgcg gccgaaggtg ggttcgataa ttggggtgaa gtcgtaacaa ggtagccgta    1500
tcggaaggtg cggctggatc acctcctttt                                    1529
```

SEQ ID NO: 158            moltype = DNA  length = 1530
FEATURE                   Location/Qualifiers
misc_feature              1..1530
                          note = Synthetic Polynucleotide
source                    1..1530
                          mol_type = other DNA
                          organism = synthetic construct
SEQUENCE: 158
```
tattgagagt ttgatcctgg ctcaggatga acgctggcgg cgtgcttaac acatgcaagt    60
cgaacggggt gctcatgacg gaggattcgt ccaacggatt gagttaccta gtggcggacg    120
ggtgagtaac gcgtgaggaa cctgccttgg agagggggaat aacactccga aaggagtgct   180
aataccgcat gatgcagttg ggtcgcatgg ctctgactgc caaagattta cgctctgag    240
atggcctcgc gtctgattag ctagtaggcg gggtaacggc ccacctaggc gacgatcagt    300
agccggactg agaggttgac cggccacatt gggactgaga cacggcccag actcctacgg   360
gaggcagcag tggggaatat tgggcaatgg gcgcaagcct gacccagcaa cgccgcgtga    420
aggaagaagg ctttcgggtt gtaaacttct tttgtcgggg acgaaacaaa tgacggtacc    480
cgacgaataa gccacggcta actacgtgcc agcagccgcg gtaatacgta ggtggcaagc    540
gttatccgga tttactgggt gtaaagggcg tgtaggcggg attgcaagtc agatgtgaaa    600
actgggggct caacctccag cctgcatttg aaactgtagt tcttgagtgc tggagaggca    660
atcggaattc cgtgtgtagc ggtgaaatgc gtagatatac ggaggaacac cagtggcgaa    720
ggcggattgc tggacagtaa ctgacgctga ggcgcgaaag cgtggggagc aaacaggatt    780
agataccctg gtagtccacg ccgtaaacga tggatactag gtgtgggggg tctgaccccc    840
tccgtgccgc agttaacaca taagtatccc cacctgggga gtacgatcgc aaggttgaaa    900
ctcaaaggaa ttgacggggg cccgcacaag cggtggagta tgtggtttaa ttcgaagcaa    960
cgcgaagaac cttaccaggg cttgacatcc cactaacgaa gcagagatgc attaggtgcc    1020
cttcggggaa agtggagaca ggtggtgcat ggttgtcgtc agctcgtgtc gtgagatgtt    1080
gggttaagtc ccgcaacgag cgcaaccctt attgttagtt gctacgcaag agcactctag    1140
cgagactgcc gttgacaaaa cggaggaagg tgggggacgac gtcaaatcat catgccccctt   1200
atgtcctggg ccacacacgt actacaatgg tggttaacag agggaggcaa taccgcgagg    1260
tggagcaaat ccctaaaagc catcccagtt cggattgcag gctgaaaccc gcctgtatga    1320
agttggaatc gctagtaatc gcggatcagc atgccgcggt gaatacgttc cgggccttg    1380
tacacaccgc ccgtcacacc atgagagtcg gaacacccg aagtccgtag cctaaccgca    1440
aggagggcgc ggccgaaggt gggttcgata ttggggtga gtcgtaaca aggtagccgt    1500
atcggaaggt gcggctggat cacctcctttt                                   1530
```

SEQ ID NO: 159            moltype = DNA  length = 1529
FEATURE                   Location/Qualifiers
misc_feature              1..1529
                          note = Synthetic Polynucleotide
source                    1..1529
                          mol_type = other DNA
                          organism = synthetic construct
SEQUENCE: 159
```
tattgagagt ttgatcctgg ctcaggatga acgctggcgg cgtgcttaac acatgcaagt    60
cgaacggggt gctcatgacg gaggattcgt ccaacggatt gagttaccta gtggcggacg    120
ggtgagtaac gcgtgaggaa cctgccttgg agagggggaat aacactccga aaggagtgct   180
aataccgcat aatgcagttg ggtcgcatgg ctctgactgc caaagattta cgctctgag    240
atggcctcgc gtctgattag ctagtaggcg gggtaacggc ccacctaggc gacgatcagt    300
agccggactg agaggttgac cggccacatt gggactgaga cacggcccag actcctacgg   360
gaggcagcag tggggaatat tgggcaatgg gcgcaagcct gacccagcaa cgccgcgtga    420
aggaagaagg ctttcgggtt gtaaacttct tttgtcaggg acgaaacaaa tgacggtacc    480
tgacgaataa gccacggcta actacgtgcc agcagccgcg gtaatacgta ggtggcaagc    540
gttatccgga tttactgggt gtaaagggcg tgtaggcggg attgcaagtc agatgtgaaa    600
actgggggct caacctccag cctgcatttg aaactgtagt tcttgagtgc tggagaggca    660
atcggaattc cgtgtgtagc ggtgaaatgc gtagatatac ggaggaacac cagtggcgaa    720
ggcggattgc tggacagtaa ctgacgctga ggcgcgaaag cgtggggagc aaacaggatt    780
agataccctg gtagtccacg ccgtaaacga tggatactag gtgtgggggg tctgacccct    840
ccgtgccgca gttaacacaa taagtatccc acctggggag tacgatcgca aggttgaaac    900
tcaaaggaat tgacggggggc ccgcacaagc ggtggagtat gtggtttaat tcgaagcccc    960
gcgaagaacc ttaccagggc ttgacatccc actaacgaag cagagatgca ttaggtgccc    1020
ttcggggaaa gtggagacag gtggtgcatg gttgtcgtca gctcgtgtcg tgagatgttg    1080
ggttaagtcc cgcaacgagc gcaacccttta ttgttagttg ctacgcaaga gcactctagc    1140
gagactgccc ttgacaaaac ggaggaaggt ggggacgacg tcaaatcatc atgcccctta    1200
tgtcctgggc acacacgta ctacaatggt ggttaacaga gggaggcaat accgcgaggt    1260
ggagcaaatc cctaaaagcc atcccagttc ggattgcagg ctgaaacccg cctgtatgaa    1320
gttggaatcg ctagtaatcg cggatcagca tgccgcggtg aatacgttcc cgggccttgt    1380
acacaccgcc cgtcacacca tgagagtcgg gaacacccga agtccgtagc ctaaccgcaa    1440
ggagggcgcg gccgaaggtg ggttcgataa ttggggtgaa gtcgtaacaa ggtagccgta    1500
tcggaaggtg cggctggatc acctcctttt                                    1529
```